US012564638B2

(12) United States Patent
Yang et al.

(10) Patent No.: US 12,564,638 B2

(45) Date of Patent: Mar. 3, 2026

(54) EGFR PROTEIN DEGRADANT AND ANTI-TUMOR APPLICATION THEREOF

(71) Applicant: SHANGHAITECH UNIVERSITY, Shanghai (CN)

(72) Inventors: Xiaobao Yang, Shanghai (CN); Biao Jiang, Shanghai (CN); Xiaoling Song, Shanghai (CN); Ning Sun, Shanghai (CN); Chaowei Ren, Shanghai (CN); Renhong Sun, Shanghai (CN); Xiaojuan Qu, Shanghai (CN); Haixia Liu, Shanghai (CN); Xing Qiu, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 881 days.

(21) Appl. No.: 17/632,612

(22) PCT Filed: Aug. 5, 2020

(86) PCT No.: PCT/CN2020/107177

§ 371 (c)(1),
(2) Date: Feb. 3, 2022

(87) PCT Pub. No.: WO2021/023233

PCT Pub. Date: Feb. 11, 2021

(65) Prior Publication Data

US 2022/0313829 A1 Oct. 6, 2022

(30) Foreign Application Priority Data

Aug. 5, 2019 (CN) ......................... 201910717328.8

(51) Int. Cl.
*A61K 47/55* (2017.01)
*A61K 47/54* (2017.01)
*A61P 35/00* (2006.01)

(52) U.S. Cl.
CPC ............ *A61K 47/55* (2017.08); *A61K 47/545* (2017.08); *A61P 35/00* (2018.01)

(58) Field of Classification Search
CPC ........ A61K 47/55; A61K 47/545; A61P 35/00
See application file for complete search history.

(56) References Cited

U.S. PATENT DOCUMENTS

| | | | | |
|---|---|---|---|---|
| 9,993,514 | B2 * | 6/2018 | Campos ............. | C07K 5/06043 |
| 10,385,037 | B2 | 8/2019 | Ruchelman et al. | |
| 10,759,808 | B2 | 9/2020 | Wang et al. | |
| 11,104,666 | B2 | 8/2021 | Crew et al. | |
| 12,226,424 | B2 | 2/2025 | Yang et al. | |
| 2002/0177601 | A1 * | 11/2002 | Himmelsbach ......... | A61P 29/00 546/159 |
| 2006/0063926 | A1 | 3/2006 | Ma et al. | |
| 2006/0211728 | A1 | 9/2006 | Greig et al. | |
| 2008/0167345 | A1 | 7/2008 | Jones et al. | |
| 2010/0099658 | A1 | 4/2010 | Kondoh et al. | |
| 2010/0204196 | A1 | 8/2010 | Chamberlain et al. | |
| 2012/0028924 | A1 | 2/2012 | Aquila et al. | |
| 2012/0083488 | A1 | 4/2012 | Kinoshita et al. | |
| 2012/0202776 | A1 | 8/2012 | Wang et al. | |
| 2013/0143922 | A1 | 6/2013 | Greig et al. | |
| 2013/0190298 | A1 | 7/2013 | Liang et al. | |
| 2015/0291562 | A1 | 10/2015 | Crew et al. | |
| 2016/0022642 | A1 * | 1/2016 | Crews .................... | A61K 47/54 514/391 |
| 2017/0121321 | A1 * | 5/2017 | Crews .................... | A61K 47/55 |
| 2018/0099940 | A1 | 4/2018 | Crew | |
| 2022/0041576 | A1 | 2/2022 | Chen et al. | |
| 2022/0041578 | A1 | 2/2022 | Chen et al. | |
| 2022/0117982 | A1 | 4/2022 | Yang et al. | |
| 2022/0143002 | A1 | 5/2022 | Yang et al. | |
| 2022/0313829 | A1 | 10/2022 | Yang | |
| 2023/0096517 | A1 | 3/2023 | Yang | |
| 2023/0203022 | A1 | 6/2023 | Yang | |

FOREIGN PATENT DOCUMENTS

| | | |
|---|---|---|
| CN | 1867331 | 11/2006 |
| CN | 101679380 | 3/2010 |
| CN | 102822165 | 12/2012 |
| CN | 103396397 | 11/2013 |
| CN | 103787802 | 5/2014 |
| CN | 106432104 | 2/2017 |
| CN | 106458993 | 2/2017 |
| CN | 108136044 | 6/2018 |
| CN | 108366992 | 8/2018 |

(Continued)

OTHER PUBLICATIONS

Yamazoe et al, Heterobifunctional molecules induce dephosphorylation of kinases—a proof of concept study, ChemRxiv, Jul. 31, 2019, doi.org/10.26434/chemrxiv.9177878.v1 (Year: 2019).*
International Search Report for PCT/CN2020/107177 dated Oct. 28, 2020, 10 pages.
Steinebach "A MedChem toolbox for cereblon-directed PROTACs" Med. Chem. Commun., 2019, 10, 1037-1041 (Year: 2019).
International Search Report for PCT/CN2020/076578 mailed Mar. 30, 2020, 9 pages.
Written Opinion of the ISA for PCT/CN2020/076578 mailed Mar. 30, 2020, 12 pages.
International Search Report for PCT/CN2021/077793, mailed May 26, 2021, 14 pages.
Written Opinion of the ISA for PCT/CN2021/077793, mailed May 26, 2021, 19 pages.

(Continued)

*Primary Examiner* — Andrew D Kosar
*Assistant Examiner* — Phillip Matthew Rzeczycki
(74) *Attorney, Agent, or Firm* — NIXON & VANDERHYE, PC

(57) ABSTRACT

A bifunctional compound, or a pharmaceutically acceptable salt, an isomer, a prodrug, a polymorphic substance or a solvate thereof. The chemical structural formula of the bifunctional compound is represented as formula I, and the bifunctional compound can be used for preventing or treating cancers.

16 Claims, 2 Drawing Sheets

(56) References Cited

FOREIGN PATENT DOCUMENTS

| | | | | |
|---|---|---|---|---|
| CN | 109311900 | | 2/2019 | |
| CN | 109475528 | | 3/2019 | |
| CN | 105566290 | | 5/2019 | |
| CN | 109912655 | | 6/2019 | |
| CN | 109928956 | | 6/2019 | |
| CN | 110204532 | | 9/2019 | |
| CN | 110291087 | | 9/2019 | |
| CN | 110357889 | | 10/2019 | |
| CN | 110506039 | | 11/2019 | |
| CN | 11051298 | | 4/2020 | |
| CN | 110963994 | | 4/2020 | |
| CN | 111606883 | | 9/2020 | |
| JP | H02-184659 | | 7/1990 | |
| JP | 2006519827 | | 8/2006 | |
| JP | 2008513538 | | 5/2008 | |
| JP | 2010515715 | | 5/2010 | |
| JP | 2010522170 | | 7/2010 | |
| JP | 2010535798 | | 11/2010 | |
| JP | 2011523646 | | 8/2011 | |
| JP | 2013534221 | | 9/2013 | |
| JP | 2013539765 | | 10/2013 | |
| JP | 2017513862 | | 6/2017 | |
| JP | 2019513746 | | 5/2019 | |
| JP | 2020504089 | | 2/2020 | |
| JP | 2022503942 | | 1/2022 | |
| JP | 2022521746 | | 4/2022 | |
| WO | 2004080976 | | 9/2004 | |
| WO | WO-2005030765 | A1 * | 4/2005 | ........... A61K 31/517 |
| WO | 2008115516 | | 9/2008 | |
| WO | WO-2008150118 | A2 * | 12/2008 | .............. A61P 35/00 |
| WO | 2009008371 | | 1/2009 | |
| WO | 2010143664 | | 12/2010 | |
| WO | 2016065980 | | 5/2016 | |
| WO | 2016197032 | | 12/2016 | |
| WO | 2017079267 | | 5/2017 | |
| WO | 2017/117474 | | 7/2017 | |
| WO | WO-2017117474 | A1 * | 7/2017 | ........... C07D 401/14 |
| WO | 2017176957 | | 10/2017 | |
| WO | 2017176958 | | 10/2017 | |
| WO | 2017185031 | | 10/2017 | |
| WO | WO-2017176958 | A1 * | 10/2017 | ........... C07D 487/04 |
| WO | WO-2017185036 | A1 * | 10/2017 | ............. A61K 47/18 |
| WO | 2017197051 | | 11/2017 | |
| WO | 2017197056 | | 11/2017 | |
| WO | 2018052945 | | 3/2018 | |
| WO | 2018052949 | | 3/2018 | |
| WO | 2018071606 | | 4/2018 | |
| WO | 2018/098288 | | 5/2018 | |
| WO | 2018102067 | | 6/2018 | |
| WO | 2018102725 | | 6/2018 | |
| WO | 2018119441 | | 6/2018 | |
| WO | 2018119448 | | 6/2018 | |
| WO | 2018140809 | | 8/2018 | |
| WO | 2019038717 | | 2/2019 | |
| WO | 2019079569 | | 4/2019 | |
| WO | 2019133531 | | 7/2019 | |
| WO | 2019195609 | | 10/2019 | |
| WO | 2019196812 | | 10/2019 | |
| WO | 2020006264 | | 1/2020 | |
| WO | 2020114482 | | 6/2020 | |
| WO | 2020173426 | | 9/2020 | |
| WO | 2020198435 | | 10/2020 | |
| WO | 2021113557 | | 6/2021 | |
| WO | 2021118629 | | 6/2021 | |

OTHER PUBLICATIONS

Donghuai Xiao et al., "Design, synthesis and biological evaluation of the thioether-containing lenalidomide analogs with anti-proliferative activities", Science Direct, European Journal of Medicinal Chemistry 176 (available on line May 15, 2019), pp. 419-430 (12 pages).

Yiming Li et al., "A Highly Efficient Cu-Catalyzed S-Transfer Reaction: From Amine to Sulfide", Organic Letters, pubs.acs.org/OrgLett, ASC Publications, 2014 American Chemical Society, dx.doi.org/10.1021/ol5009747, pp. 2692-2695, Downloaded via Shanghai Advanced Research Inst on Aug. 30, 2021 at 00:30:59 (UTC). See https://pubs.acs.org/sharingguidelines for options on how to legitimately share published articles. (4 pages).

Yiming Li et al., "Selective Late-Stage Oxygenation of Sulfides with Ground-State Oxygen by Uranyl Photocatalysis", Angewandte Chem. Int. Ed. 2019, first published Jul. 2019, 58, pp. 13499-13506, DOI: 10.1002/anie.201906080, Wiley Online Library (8 pages).

Turk, et. al., Proceedings of the National Academy of Sciences of the United States of America (1996), 93(15), 7552-7556.

Ishoey, Mette, Translation Termination Factor GSPT1 Is a Phenotypically Relevant Off-Target of Heterobifunctional Phthalimide Degraders, A CS Chemical Biology , 2018, 13(3), 553-560.

Zhang, Chengwei, Proteolysis Targeting Chimeras (PROTACs) of Anaplastic Lymphoma Kinase (ALK), European Journal of Medicinal Chemistry, 2018, 151, 304-314.

Lai, Ashton C., Modular PROTAC Design for the Degradation of Oncogenic BCR-ABL, Angewandte Chemie, International Edition, 2016, 55(2), 807-810.

Restriction Requirement issued in U.S. Appl. No. 17/433,462 dated Jul. 30, 2024, 13 pages.

Non-Final Office Action issued in U.S. Appl. No. 17/433,462 dated Dec. 13, 2024, 19 pages.

Restriction Requirement issued in U.S. Appl. No. 17/046,690 dated May 24, 2022, 11 pages.

Non-Final Office Action issued in U.S. Appl. No. 17/046,690 dated Sep. 14, 2022, 31 pages.

Non-Final Office Action issued in U.S. Appl. No. 17/046,690 dated May 24, 2023, 19 pages.

Non-Final Office Action issued in U.S. Appl. No. 17/046,690 dated Mar. 25, 2024, 21 pages.

Restriction Requirement issued in U.S. Appl. No. 17/801,953 dated Feb. 5, 2025, 11 pages.

U.S. Appl. No. 17/922,124, filed Oct. 28, 2022, 89 pages.

U.S. Appl. No. 17/801,953, filed Aug. 24, 2022, 103 pages.

U.S. Appl. No. 17/433,462, filed Aug. 24, 2021, 282 pages.

* cited by examiner

EGFR PROTEIN DEGRADANT AND ANTI-TUMOR APPLICATION THEREOF

This application is the U.S. national phase of International Application No. PCT/CN2020/107177 filed Aug. 5, 2020 which designated the U.S. and claims priority to CN Patent Application No. 201910717328.8 filed Aug. 5, 2019, the entire contents of each of which are hereby incorporated by reference.

TECHNICAL FIELD

The present invention is in the field of medicinal chemistry and particularly relates to a bifunctional compound, preparation method and use thereof. The bifunctional compound can be used to prevent or treat cancers, especially cancers harboring abnormal expression of EGFR, Her2, Her3 or Her4 proteins etc.

BACKGROUND

Lung cancer is the leading cause of cancer death and the most commonly diagnosed cancer not only in China but in the worldwide. According to the latest epidemiological data of the Chinese oncology in 2019, there are 572.6 thousand new cases and 458.7 thousand deaths of lung cancer each year in China. Currently, the 5-year survival rate of lung cancer is only 17%, which has changed little since 1970s. The most important reason is that the conventional radiotherapy and chemotherapy with strong toxic and side effects, which not only kill cancer cells, but also normal cells in patients, could not prevent the progress of lung cancer. It's urgent to explore a new way for improving the survival rate and quality of life of patients with lung cancer.

Targeted therapy can reduce the toxic and side effects compared to chemotherapy or radiotherapy in patients harboring special oncogenes. The use of tyrosine kinase inhibitors (TKIs), for instance, can increase the therapy effect from 40% of the chemotherapy up to 70%, and the PFS (progress free survival) will raise to about 10 months from 5 months in patients with aberrant epidermal growth factor receptor (EGFR). EGFR is one of the family members of epidermal growth factor receptor tyrosine kinase, and the morbidity of lung cancers with abnormal EGFR expression is higher amongst eastern populations which accounts for 50% of lung adenocarcinoma, than that in western populations with the morbidity of 15%, which means that the targeted drugs for EGFR will benefit Asian patients well. However, almost all of the patients will develop resistance to the targeted drugs at about 1 year after treatment, causing tumor progress again. Researches on the drug resistant mechanisms against the $1^{st}$ and $2^{nd}$ EGFR TKIs showed that about 60% of these lung cancer patients acquired the secondary EGFR mutation T790M. These findings promote the development of the next EGFR targeted drugs and are expected to improve the life quality of patients. The first generation EGFR TKIs such as Erlotinib (trade name "Tarceva") and Gefitinib (trade name "Iressa"), which can combine with EGFR tyrosine kinase domain on the ATP binding pocket reversibly, and the second generation irreversible EGFR TKI Afatinib (approved by FDA in July 2013), have been approved by FDA for clinical use at present. The second generation EGFR TKI Dacomitinib, approved by FDA in 2018, was used for the first line treatment on the locally advanced or metastatic non-small cell lung cancer (NSCLC) patients harboring EGFR activation mutations. The third generation EGFR TKI Osimertinib (AZD9291), approved by FDA at the end of 2015, can specifically kill cancer cells with EGFR activating mutations (EGFR exon 19del or EGFR exon 20 L858R) and T790M, the drug resistance mutation, and can extend the PFS of the lung cancer patients with T790M mutation about one year. However, research found that the acquired resistance against AZD9291 was developed inevitably due to some complicated reasons including the incidence of the tertiary mutation C797S. The recurrence of tumors and their resistance to targeted drugs indicated that the small molecular inhibitors, without a long-term efficacy, couldn't improve the quality of survival for patients or meet the need of social development. Patients of lung cancer with EGFR mutations account for a high proportion of Chinese lung cancer patients, and the rate are still increasing year by year. Thus, it's necessary to explore new therapies and drugs for lung cancers to overcome drug resistance problems on small molecular targeted compounds.

We have developed a brand-new technology for targeted drugs called PROTAD:PROteolysis TArgeting Drug, which aimed to change the fate of those disease proteins by using the ubiquitination/proteasome system, the intracellular protein degradation machine. PROTAD is composed of two ligands, one of which can target the disease protein and the other can bind with ubiquitin-protein ligase (E3), connected by a linker. The bi-functional small molecular can compel the proteins of interest ubiquitinated, and then transfer them to the degradation machine. Compared with the traditional small molecule drug design, the biggest difference of PROTAD is that it mobilizes the whole cell as the drug effector unit. The PROTAD only need a transient combination with targets to tag the proteins as "to be cleaned", and then the compounds can be recycled, which means can a low PROTAD dosage not only meet the need of therapy, but reduce the off-target risk. Due to the above advantages, PROTAD, potential to eliminate the tumor progress caused by oncogenes and the acquired drug resistance, is expected to conquer the difficulties in tumor targeted therapy.

SUMMARY OF THE INVENTION

It is an objective of the present invention to provide a bifunctional compound, preparation method and use thereof to overcome the above mentioned disadvantages and solve the problems in the prior art.

In order to achieve the above-mentioned objectives and other related objectives, in one aspect of the present invention, there is provided a bifunctional compound of Formula I:

Formula I

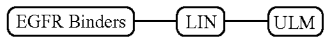

or a pharmaceutically acceptable salt, an isomer, a prodrug, a polymorph, or a solvate thereof, wherein EGFR Binders can bind to EGFR protein;

ULM represents:

Formula II

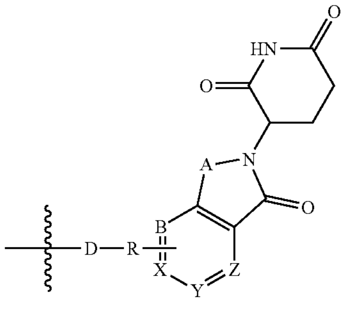

wherein A is selected from —$CH_2$— and —(C═O)—;

B, X, Y, and Z are each independently selected from CH and N;

is selected from —S—, —SO—, —$SO_2$—,

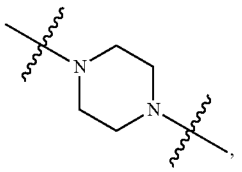 [SMILES: *N1CCN(*)CC1]

—$CH_2$—, —(C═O)—, —NH—, —O—, and ethynylene, or R is absent;

D is selected from —(C═O)—, or D is absent;

or, ULM represents:

Formula III

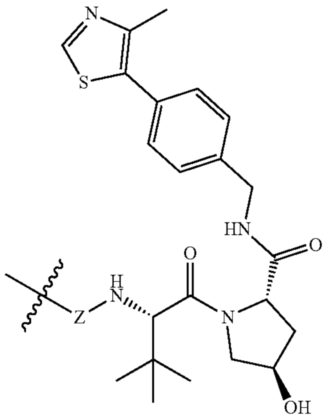

wherein Z is selected from —(C═O)—, or Z is absent;

or, ULM represents:

Formula IV

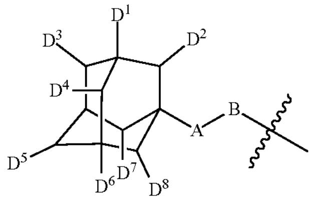

wherein A is selected from —$CH_2$—, —NR'—, —O—, —S—, and —(C═O)—, wherein R' is selected from H, linear or branched $C_1$-$C_{10}$ alkyl, or $C_3$-$C_{10}$ cycloalkyl;

B is selected from —(C═O)—, or B is absent;

$D_1$, $D_2$, $D_3$, $D_4$, $D_5$, $D_6$, $D_7$, and $D_8$ are each independently selected from F, Cl, Br, OH, Me, Et, iPr, H, and D; and LIN represents a linking group covalently bonded to the EGFR Binders and ULM, respectively.

In another aspect of the present invention, there is provided the use of the bifunctional compound in the manufacture of a medicament.

In another aspect of the present invention, there is provided a pharmaceutical composition, comprising the bifunctional compound or a pharmaceutically acceptable salt, an isomer, a prodrug, a polymorph, or a solvate thereof, and at least one pharmaceutically acceptable carrier, an additive, an adjuvant, or an excipient.

DETAILED DESCRIPTION OF THE INVENTION

Figure 1:
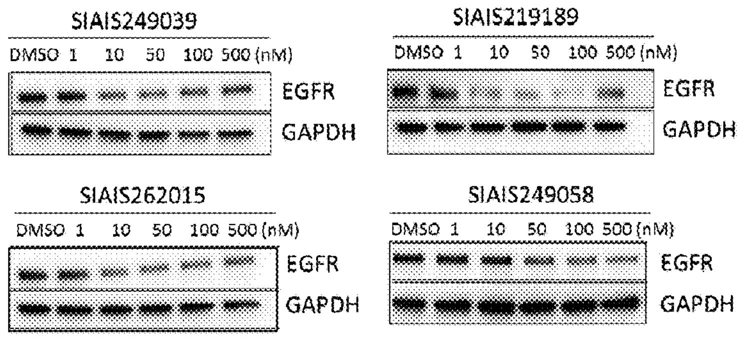
FIG. 1 shows the study on the compounds of the present invention based on dacomitinib derivative A (lung cancer cell line HCC827).

As a result of extensive studies, the present inventors synthesized and developed a new class of bifunctional compounds based on different EGFR-related drugs, e.g., EGFR inhibitors, e.g., Dacomitinib, Poziotinib, Gefitinib, Afatinib, Sapitinib, Canertinib, Osimertinib, and EAI045, etc. The bifunctional compounds of the present invention show different degrees of regulatory effects on EGFR protein, which can not only promote the degradation of EGFR protein, but also inhibit the activity of EGFR kinase and the proliferation of EGFR mutation-positive cells, and thus can be used as a therapeutic agent for tumor patients. In view of the above, the present invention has been completed.

Designing degraders that target specific proteins is a new mode of drug development. In the present invention, the present inventors designed special bispecific protein modulators by using the Proteolysis Targeting Drug (PROTAD) technology platform, which can tag the target proteins as "to be degraded", and degrade them by activating the protein degradation pathway inside the cell. Compared with traditional small molecule drug design, the proteins-targeted small molecule modulators of the present invention can induce the degradation of the target proteins, which is essentially different from the traditional small molecule inhibitor in mechanism.

In one aspect of the present invention, there is provided a bifunctional compound of Formula I:

Formula I

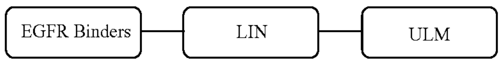

or a pharmaceutically acceptable salt, an isomer, a prodrug, a polymorph, or a solvate thereof, wherein EGFR Binders can bind to EGFR protein;

ULM represents:

Formula II

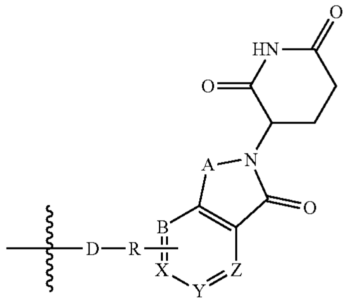

wherein A is selected from —$CH_2$— and —(C═O)—;

B, X, Y, and Z are each independently selected from CH and N;

R is selected from —S—, —SO—, —$SO_2$—,

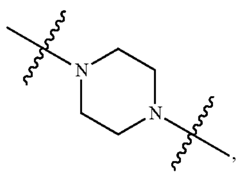 [SMILES: *N1CCN(*)CC1]

—$CH_2$—, —(C═O)—, —NH—, —O—, ethynylene, or R is absent;

D is selected from —(C═O)—, or D is absent;

or, ULM represents:

Formula III

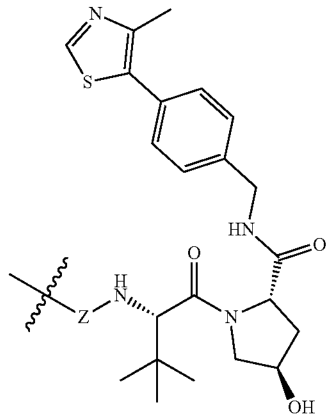

wherein Z is selected from —(C═O)—, or Z is absent;

or, ULM represents:

Formula IV

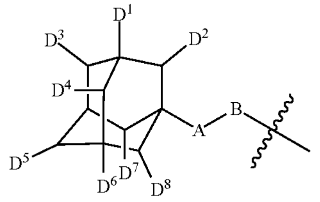

wherein A is selected from —$CH_2$—, —NR'—, —O—, —S—, and —(C═O)—, wherein R' is selected from H, linear or branched $C_1$-$C_{10}$ alkyl, or $C_3$-$C_{10}$ cycloalkyl;

B is selected from —(C═O)—, or B is absent;

$D_1$, $D_2$, $D_3$, $D_4$, $D_5$, $D_6$, $D_7$, and $D_8$ are each independently selected from F, Cl, Br, OH, Me, Et, iPr, H, and D; and LIN represents a linking group covalently bonded to the EGFR Binders and ULM, respectively.

Unless otherwise specified, the isotope-labeled forms of the compounds of the present invention are also encompassed within the scope of the present invention. For example, in the compounds of the present invention with the structure/formula given above, at least one hydrogen atom is replaced by deuterium or tritium, or at least one carbon atom is replaced by $^{13}C$- or $^{14}C$-enriched carbon, or at least one nitrogen atom is replaced by $^{15}N$-enriched nitrogen.

In the present invention, the term "salt" should be understood as any form of active compounds used in the present invention, wherein the compounds may be in ionic form or charged or coupled to a counter-ion (cation or anion) or in solution. The term "salt" can also include quaternary ammonium salts and complexes of the active compounds with other molecules and ions, especially complexes through ionic interactions. The term "salt" especially includes physiologically acceptable salts, and can be understood to be equivalent to "pharmacologically acceptable salts".

In the present invention, the term "pharmaceutically acceptable salt" generally refers to any salt that is physiologically tolerable (generally speaking, this means that it is non-toxic, especially as a result of counter-ion is non-toxic) when used in a suitable manner for treatment (especially when applied or used in humans and/or mammals). These physiologically acceptable salts may be formed with cations or bases, and in the context of the present invention, especially when administered in humans and/or mammals, they should be understood to be a salt formed by at least one compound provided in accordance with the invention (usually a (deprotonated) acid), such as an anion, and at least one physiologically tolerable cation (preferably an inorganic cation). In the context of the present invention, it may specifically include salts formed with alkali metals and alkaline earth metals, and salts formed with ammonium cations ($NH_4^+$), specifically including but not limited to (mono) or (di) sodium, (mono) or (di) potassium, magnesium or calcium salts. These physiologically acceptable salts can also be formed with anions or acids, and in the context of the present invention, especially when administered in humans and/or mammals, they should be understood as a salt formed by at least one compound provided in accordance with the present invention (usually protonated (for example on nitrogen)), such as a cation and at least one physiologically tolerable anion. In the context of the present invention, it may specifically include a salt formed by a physiologically tolerable acid, that is, a salt formed by a specific active compound and a physiologically tolerable organic or inorganic acid, and specifically may include but not limited to salts formed with hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, or citric acid.

The compound of formula I of the present invention may include an enantiomer depending on the presence of a chiral center or an isomer depending on the presence of a double bond (for example, Z, E). Single isomer, enantiomers, diastereomers, or cis-trans isomers, and mixtures thereof are also encompassed within the scope of the present invention.

In the present invention, the term "prodrug" is used in its broadest sense and includes those derivatives that can be converted into the compounds of the present invention in vivo. Methods for preparing the prodrugs of a designated active compound should be known to those skilled in the art. For example, one can refer to related content disclosed in Krogsgaard-Larsen et al., "Textbook of Drug design and Discovery", published by Taylor & Francis (April 2002).

In the present invention, the term "solvate" generally refers to any form of the active compound according to the present invention bonded to another molecule (usually a polar solvent) through a non-covalent bond, and the obtained substance may specifically include but not limited to hydrates and alcoholates, such as methanolates.

The bifunctional compounds of the present invention can comprise an EGFR Binders moiety, which is usually covalently bonded to LIN and can usually bind to EGFR protein. In the present invention, the EGFR Binders can be any molecule that can bind to EGFR protein, more specifically EGFR TKIs. The EGFR TKIs (epidermal growth factor receptor (EGFR) tyrosine kinase inhibitors) can act on intracellular protein tyrosine kinase domain of EGFR; the epidermal growth factor receptor tyrosine kinase inhibitor can usually bind to the tyrosine kinase functional domain competitively with ATP, and can reversibly or irreversibly inhibit tyrosine kinase phosphorylation. The EGFR TKIs part is usually used as the protein target binding moiety (PTM, protein target moiety), which can be linked to the ULM moiety (E3 ubiquitin ligase binding moiety) via LIN, thereby leading to the ubiquitination of the target proteins, and the activation of the intracellular proteasome system for targeted degradation of the target proteins. The ubiquitination degradation pathway can degrade most of the ubiquitinated proteins in the cells, e.g., 80% to 90% or higher of the ubiquitinated proteins in the cells. If this system can be activated to specifically clean up the carcinogen proteins, which restores the cellular protein homeostasis, it is likely to alleviate or treat cancers. The PROTAD technology takes advantage of this, and uses the specially designed dual-specific degraders to tag the target proteins as "to be ubiquitined" to achieve targeted degradation.

In the bifunctional compounds of the present invention, the EGFR TKIs can specifically represents a group as shown by the following formula:

Formula V

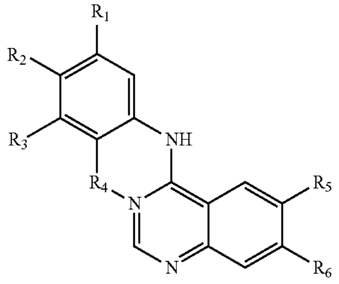

wherein $R_1$, $R_2$, $R_3$, and $R_4$ are each independently selected from H, halogen, Cl, F, $C_{1-10}$ alkyl, $C_{1-10}$ haloalkyl, $C_{1-10}$ alkynyl, $C_{1-10}$ alkoxy, arylmethoxy, and heteroarylmethoxy, wherein the aryl of the arylmethoxy and the heteroaryl of the heteroarylmethoxy are unsubstituted or are substituted by 1-2 substituent(s) selected from $C_{1-10}$ alkyl, halogen, and $C_{1-10}$ haloalkyl;

one of $R_5$ and $R_6$ is covalently bonded to LIN, and forms —NR"—, where R" is selected from H, linear or branched $C_1$-$C_{10}$ alkyl, or $C_3$-$C_9$ cycloalkyl, or forms a group as shown by the following formulas:

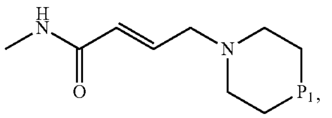

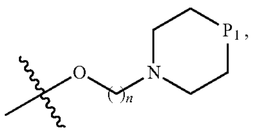

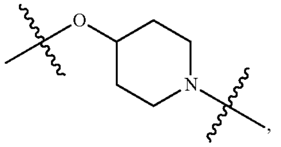

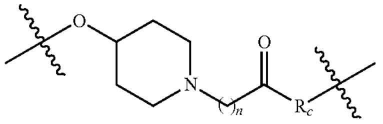

wherein $P_1$ is selected from

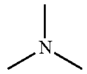

and $CHR_b$, where $R_b$ is selected from —NH— and piperazinylene, n=0-3, 0, 1, 2, or 3, and $R_c$ represents vinylidene or $R_c$ is absent;

one of $R_5$ and $R_6$ is selected from H, N, halogen, $C_{1-10}$ alkyl, $C_{1-10}$ haloalkyl, $C_{1-10}$ alkoxy, amino, acylamino, alkylamino, di-$C_{1-10}$alkylamino, cyano, aryl, heteroaryl, furyl, pyrrolyl, imidazolyl, oxazolyl, isoxazolyl, triazolyl, $C_{3-9}$ cycloalkyl, $C_{3-9}$ cycloalkyloxy, heterocyclyl, heterocyclyloxy, and —NHC(O)$R_4$, wherein the aryl and the heteroaryl are unsubstituted or are substituted by 1-2 substituent(s) selected from $C_{1-10}$ alkyl, halogen, $C_{1-10}$ haloalkyl, cyano, $R_7SO_2(CH_2)_s$NHCH$_2$—, —$OR_8$, and —NHC(O)$R_9$, wherein $R_7$ is selected from $C_{1-10}$ alkyl and s is 0, 1, 2, or 3; and $R_8$ is selected from $C_{1-10}$ alkyl which is optionally mono- or multi-substituted by the groups independently selected from hydroxyl, $C_{1-10}$ alkoxy, amino, $C_{1-10}$ alkylamino, and di-$C_{1-10}$alkylamino; and $R_9$ is selected from the following groups:

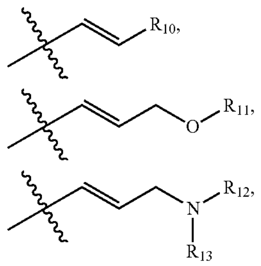

$R_{10}$ and $R_{11}$ are each independently selected from H and $C_{1-10}$ alkyl;

$R_{12}$ and $R_{13}$ are each independently selected from H and $C_{1-10}$ alkyl, or $R_{12}$ and $R_{13}$ together with the adjacent nitrogen atom to which they are attached form a heterocyclyl; and $R_{14}$ is selected from $C_{1-10}$ alkyl and alkenyl.

In the present invention, the term "halogen" or "halo" or "halogenated" generally refers to fluorine, chlorine, bromine or iodine.

In the present invention, the term "alkyl" generally refers to saturated aliphatic groups, which can be linear or branched. For example, $C_{1-10}$ alkyl generally refers to an alkyl group including 1, 2, 3, 4, 5, 6, 7, 8, 9, or 10 carbon atoms, and may specifically include, but is not limited to, methyl, ethyl, propyl, butyl, pentyl, hexyl, heptyl, octyl, nonyl, decyl, etc. Again for example, $C_{1-30}$ alkylene generally refers to an alkylene group including 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, and may specifically include, but is not limited to, methylene, ethylene, propylene, butylene, pentylene, hexylene, heptylene, octylene, nonylene, and decylene, etc.

In the present invention, the term "haloalkyl" generally refers to halogenated saturated aliphatic groups, which can be linear or branched, and are optionally independently mono- or multi-substituted by the group selected from fluorine, chlorine, bromine, or iodine. For example, $C_{1-10}$ haloalkyl generally refers to a haloalkyl group including 1, 2, 3, 4, 5, 6, 7, 8, 9, or 10 carbon atoms, and may specifically include, but is not limited to, halomethyl, haloethyl, halopropyl, halobutyl, halopentyl, halohexyl, haloheptyl, halooctyl, halononyl, halodecyl, etc.

In the present invention, the term "$C_{3-9}$ cycloalkyl" generally refers to a saturated or unsaturated (but not aromatic) cyclic hydrocarbon having from 3 to 9 carbon atoms. The cycloalkyl group may specifically include, but is not limited to, cyclopropyl, 2-methylcyclopropyl, cyclopropylmethyl, cyclobutyl, cyclopentyl, cyclopentylmethyl, cyclohexyl, cycloheptyl, cyclooctyl, adamantanyl, noradamantanyl, etc.

In the present invention, the term "heterocyclyl" generally refers to a saturated or unsaturated (but not aromatic) cyclic hydrocarbon, containing at least one heteroatoms selected from N, O or S. The heterocyclyl group may specifically include, but are not limited to, pyrrolinyl, pyrrolidinyl, pyrazolinyl, aziridinyl, azetidinyl, tetrahydropyrrolyl, oxiranyl, oxetanyl, dioxetanyl, tetrahydropyranyl, tetrahydrofuranyl, dioxanyl, dioxolanyl, oxazolidinyl, piperidinyl, piperazinyl, morpholinyl, azepanyl or diazepanyl, etc. Preferably, the heterocyclyl group in the present invention is usually a 5- or 6-membered ring system.

In the present invention, the term "aryl" generally refers to a group having at least one aromatic ring but no heteroatoms. The aryl group may optionally be mono- or multi-substituted with substituents independently selected from alkyl, halogen, haloalkyl, cyano, $R_7SO_2(CH_2)$sNHCH$_2$—, —$OR_8$, —NHC(O)$R_9$. The aryl group may specifically include, but is not limited to, phenyl, naphthyl, fluoranthenyl, fluorenyl, tetrahydronaphthyl, indanyl, anthracyl, etc. Preferably, the aryl group in the present invention is a 5- or 6-membered ring system which is optionally at least mono-substituted.

In the present invention, the term "heteroaryl" generally refers to a heterocyclic ring system having at least one aromatic ring and optionally containing one or more heteroatoms selected from N and O, and may optionally be mono- or multi-substituted by the substituents independently selected from alkyl, halogen, haloalkyl, cyano, $R_7SO_2(CH_2)$sNHCH$_2$—, —$OR_8$, and —NHC(O)$R_9$. The heteroaryl group may specifically include, but is not limited to, furanyl, benzofuranyl, pyrrolyl, pyridinyl, pyrimidinyl, pyridazinyl, pyrazinyl, quinolinyl, isoquinolinyl, phthalazinyl, triazolyl, pyrazolyl, isoxazolyl, indolyl, benzotriazolyl, benzodioxolanyl, benzodioxanyl, benzimidazolyl, carbazolyl, quinazolinyl, etc. Preferably, the heteroaryl group in the present invention is a 5- or 6-membered ring system which is optionally at least mono-substituted.

In the present invention, the term "alkenyl" generally refers to an unsaturated aliphatic group including at least one C═C double bond. The alkenyl group may specifically include, but is not limited to, vinyl, propenyl, butenyl, etc.

In some preferred embodiments of the present invention, in the formula V, $R_1$, $R_2$, $R_3$, and $R_4$ are each independently selected from H, halogen, Cl, and F.

In a more preferred embodiment of the present invention, in the formula V, $R_1$ is selected from Cl, $R_2$ is selected from F, $R_3$ and $R_4$ are each independently selected from H; or, $R_1$ is selected from H, $R_2$ is selected from Cl, $R_3$ is selected from Cl, and $R_4$ is selected from F.

In some preferred embodiments of the present invention, in the formula V, one of $R_5$ and $R_6$ may be covalently bonded to LIN, and form —NR"—, where R" is selected from H, linear or branched $C_1$-$C_{10}$ alkyl, or $C_3$-$C_{10}$ cycloalkyl; or form a group as shown by the following formulas:

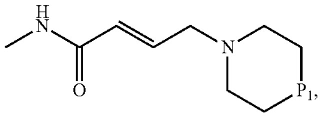

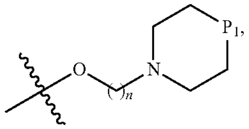

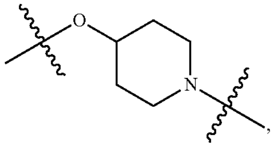

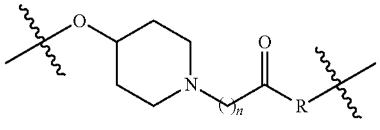

wherein $P_1$ is selected from

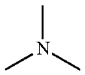

and $CHR_b$, where $R_b$ is selected from —NH— and piperazinylene, n=0-3, 0, 1, 2, or 3, $R_c$ represents vinylidene or $R_c$ is absent;

one of $R_5$ and $R_6$ is selected from $C_1$-$C_{10}$ alkoxy, heterocyclyloxy, and —NHC(O)$R_{14}$, wherein $R_{14}$ is selected from $C_1$-$C_{10}$ alkyl and alkenyl.

In a more preferred embodiment of the present invention, in the formula V, $R_5$ can be covalently bonded to LIN, and forms —NH—, or forms a group as shown by the following formulas:

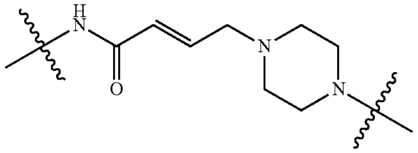

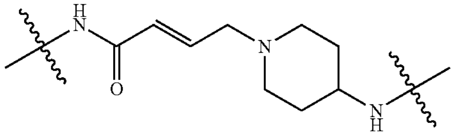

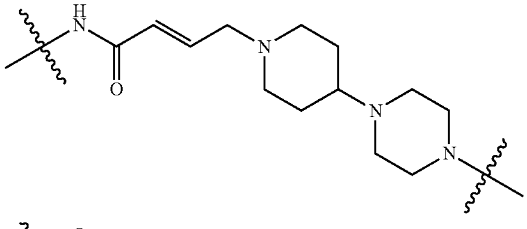

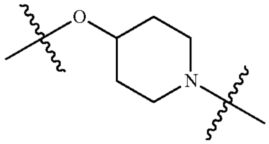

-continued

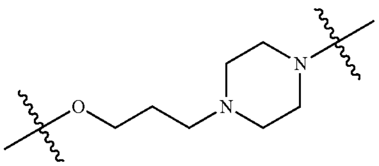

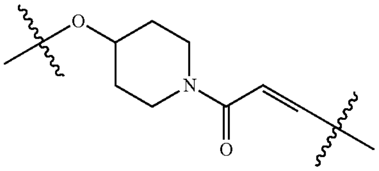

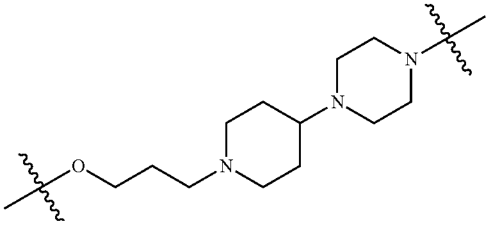

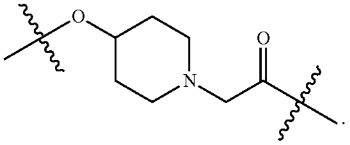

In a more preferred embodiment of the present invention, in the formula V, $R_6$ may be selected from methoxy, or a group as shown by the following formula:

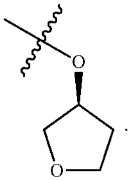 [SMILES: *O[C@H]1CCOC1]

In a more preferred embodiment of the present invention, in the formula V, $R_5$ can be selected from —NHC(O)$R_{14}$, where $R_{14}$ is selected from vinyl.

In a more preferred embodiment of the present invention, in the formula V, $R_6$ can be covalently bonded to LIN, and represents a group shown by one of the following formulas:

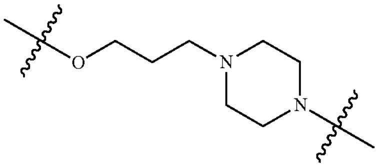

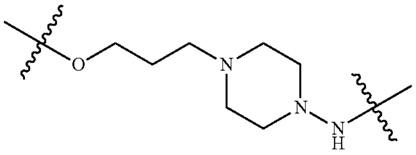

-continued
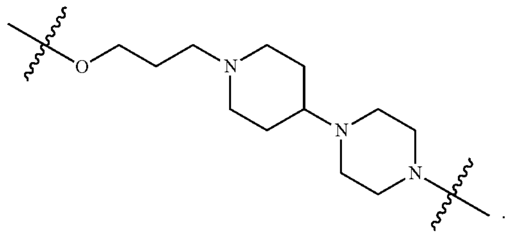
In a further preferred embodiment of the present invention, the EGFR TKIs represents a group shown by one of the following formulas:
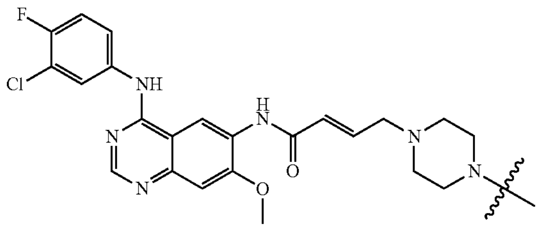
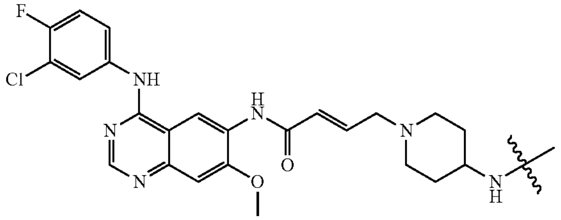
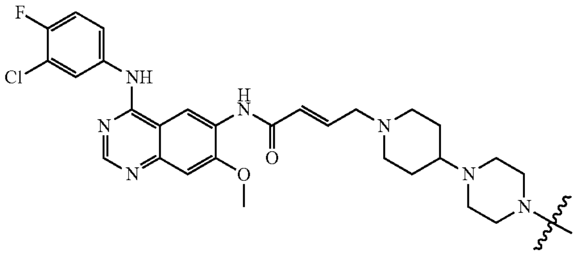
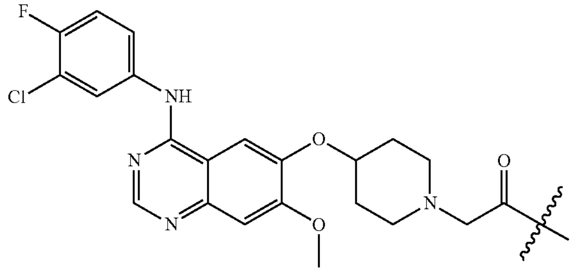
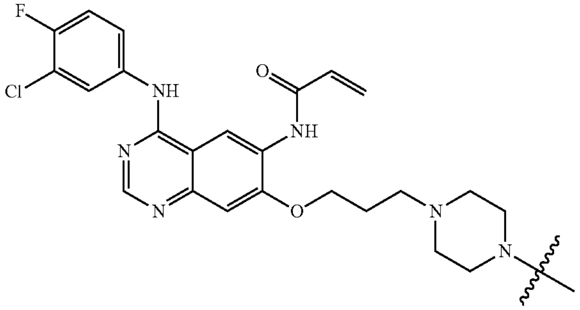
-continued
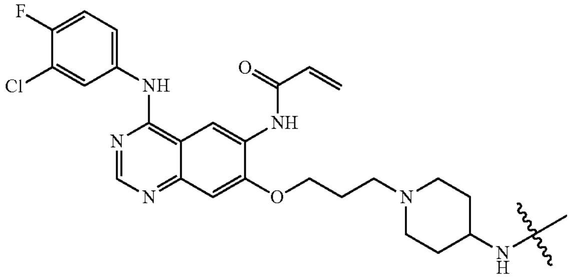
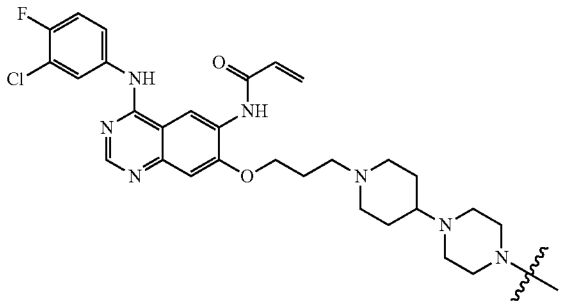
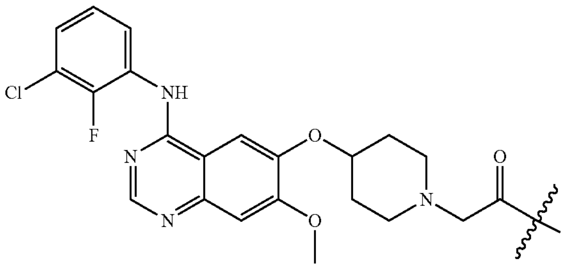
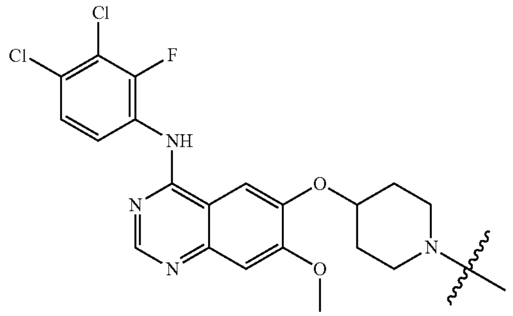
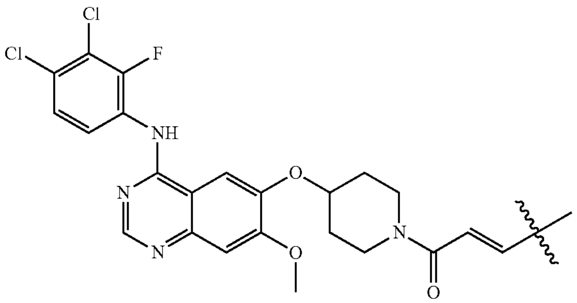
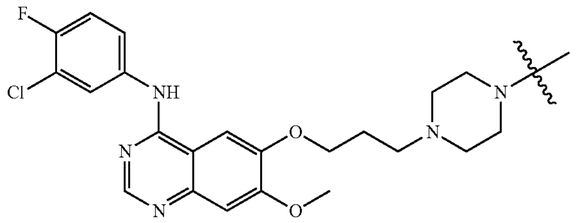

-continued

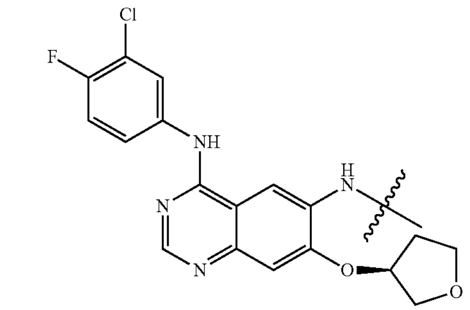

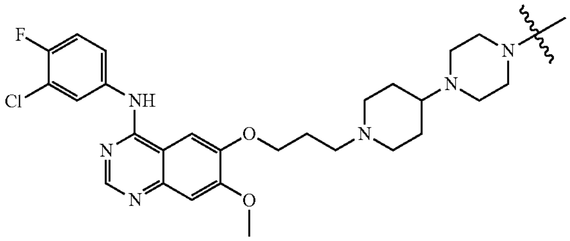

.

In the bifunctional compounds of the present invention, the EGFR TKIs can also specifically represent the group shown by the following formula:

Formula VI

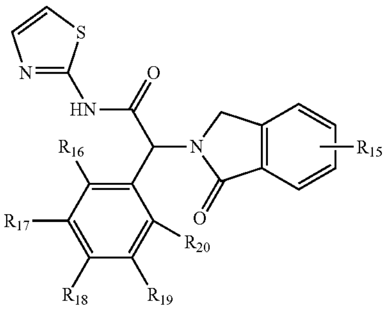

wherein $R_{16}$, $R_{17}$, $R_{18}$, $R_{19}$, and $R_{20}$ are each independently selected from H, OH, F, Br, Cl, and OMe;

$R_{15}$ is covalently bonded to LIN, and forms a group selected from ones shown by the following formulas:

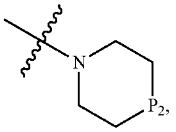

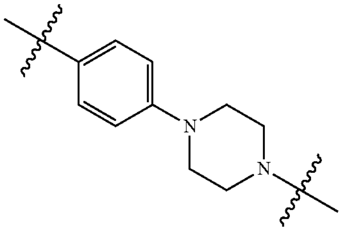

,

-continued

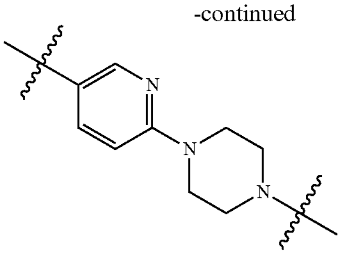

, wherein $P_2$ is selected from

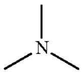

and $CHR_d$, where $R_d$ is selected from —NH— and piperazinylene.

In some preferred embodiments of the present invention, in the formula VI, $R_{16}$, $R_{17}$, $R_{18}$, $R_{19}$, and $R_{20}$ are each independently selected from H, OH, and F;

In a more preferred embodiment of the present invention, in the formula VI, $R_{16}$ is selected from H and OH; $R_{17}$ is selected from H; $R_{18}$ is selected from H; $R_{19}$ is selected from H and F; $R_{20}$ is selected from H;

In some preferred embodiments of the present invention, $R_{15}$ is covalently bonded to LIN, and forms a group selected from ones shown by the following formulas:

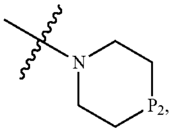

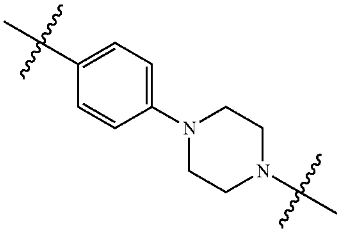

,

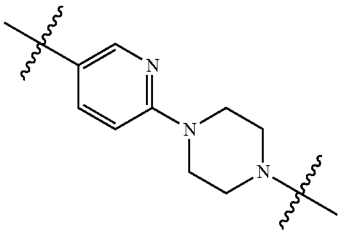

, wherein $P_2$ is selected from

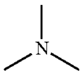

and $CHR_d$, where $R_d$ is selected from —NH— and piperazinylene.

In a further preferred embodiment of the present invention, the EGFR TKIs represent a group shown by the following formulas:
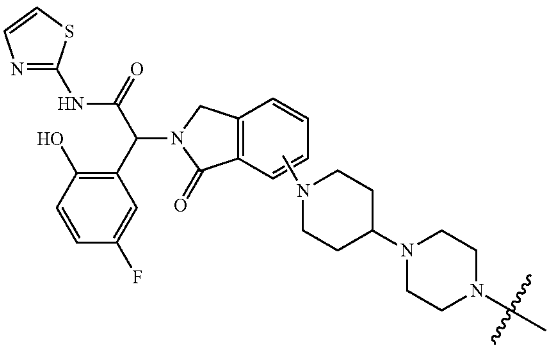
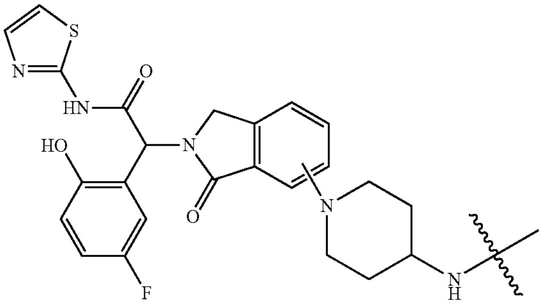
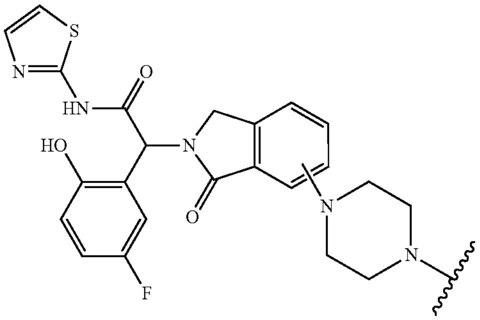
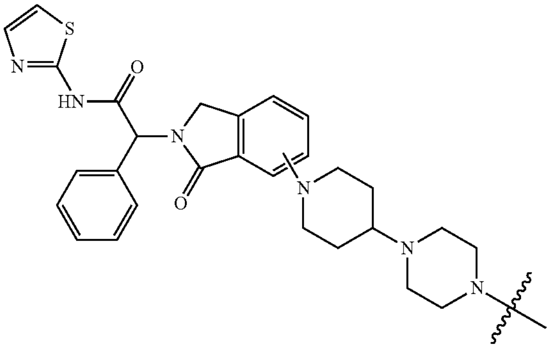
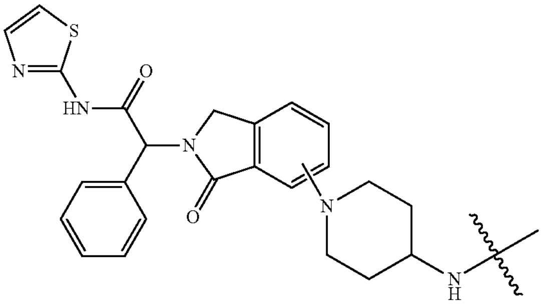
-continued
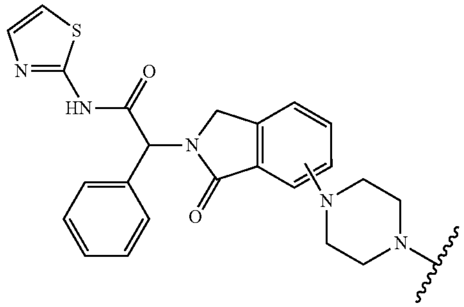
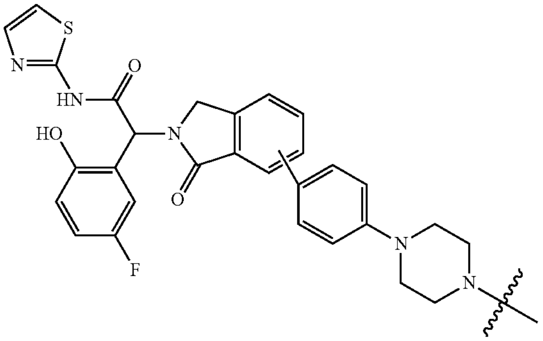
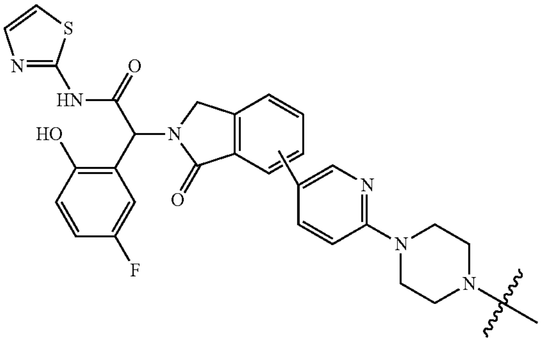
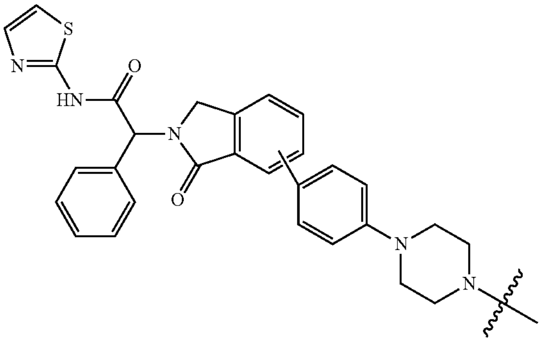
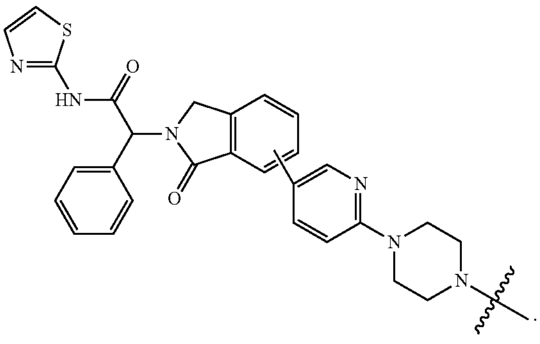

In the bifunctional compounds of the present invention, the EGFR TKIs can also specifically represent a group shown by the following formula:

Formula VII

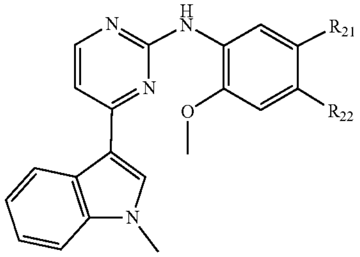

one of $R_{21}$ and $R_{22}$, which is covalently bonded to LIN, forms —NR'''—, where R''' is selected from H, linear or branched $C_1$-$C_{10}$ alkyl, or $C_3$-$C_9$ cycloalkyl; or forms a group as shown by the following formulas:

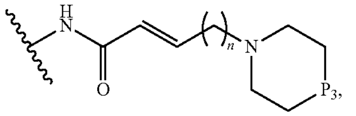

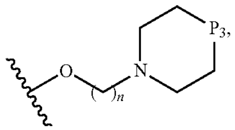

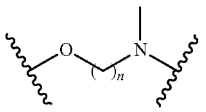

,

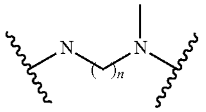

,

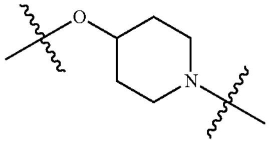

,

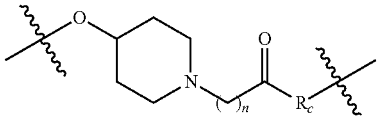

;

wherein $P_3$ is selected from

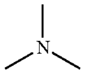

and $CHR_e$, where $R_e$ is selected from —NH— and piperazinylene, n=0, 1, 2, or 3, and $R_e$ represents vinylidene or $R_c$' is absent;

one of $R_{21}$ and $R_{22}$ is selected from H, N, halogen, $C_{1-10}$ alkyl, $C_{1-10}$ haloalkyl, $C_{1-10}$ alkoxy, amino, acylamino, alkylamino, di-$C_{1-10}$alkylamino, cyano, aryl, heteroaryl, furyl, pyrrolyl, imidazolyl, oxazolyl, isoxazolyl, triazolyl, $C_{3-9}$ cycloalkyl, $C_{3-9}$ cycloalkyloxy, heterocyclyl, heterocyclyloxy, $—NHC(O)R_{31}$, where the aryl and heteroaryl are unsubstituted or are substituted by 1-2 substituent(s) selected from $C_{1-10}$ alkyl, halogen, $C_{1-10}$ haloalkyl, cyano, $R_{24}SO_2(CH_2)_s NHCH_2—$, $—OR_{25}$, and $—NHC(O)R_{26}$, wherein $R_{24}$ is selected from $C_{1-10}$ alkyl and s is 0, 1, 2, or 3; and $R_{25}$ is selected from $C_{1-10}$ alkyl which is optionally mono- or multi-substituted by the groups independently selected from hydroxyl, $C_{1-10}$ alkoxy, amino, $C_{1-10}$ alkylamino, and di-$C_{1-10}$alkylamino; and $R_{26}$ is selected from the following groups:

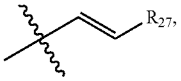

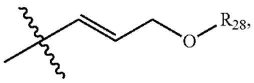

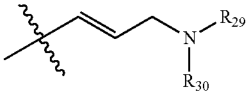

$R_{27}$ and $R_{28}$ are each independently selected from H and $C_{1-10}$ alkyl;

$R_{29}$ and $R_{30}$ are each independently selected from H and $C_{1-10}$ alkyl, or $R_{29}$ and $R_{30}$ together with the adjacent nitrogen atom to which they are attached form heterocyclyl;

$R_{31}$ is selected from $C_{1-10}$ alkyl and alkenyl.

In some preferred embodiments of the present invention, in the formula VII, one of $R_{21}$ and $R_{22}$, which is covalently bonded to LIN, forms —NR'''—, where R''' is selected from H, linear or branched $C_1$-$C_{10}$ alkyl, or $C_3$-$C_9$ cycloalkyl; or forms a group as shown by the following formulas:

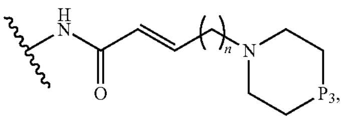

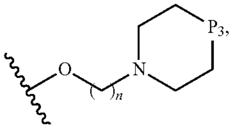

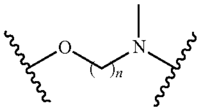

,

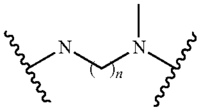

,

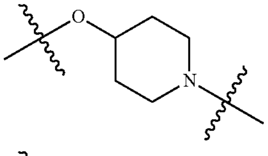

,

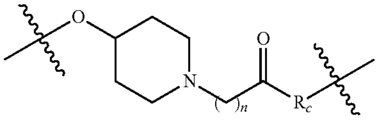

, wherein $P_3$ is selected from

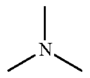

or $CHR_c$, where $R_c$ is selected from —NH— and piperazinylene, n=0, 1, 2, or 3, and $R_c'$ represents vinylidene or is absent;

one of $R_{21}$ and $R_{22}$ is selected from $C_1$-$C_{10}$ alkoxy, heterocyclyloxy, and —NHC(O)$R_{23}$, where $R_{23}$ is selected from $C_1$-$C_{10}$ alkyl, alkenyl,

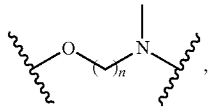

, and

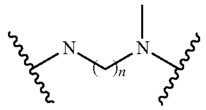

, wherein n=0, 1, 2, or 3.

In a further preferred embodiment of the present invention, the EGFR TKIs represents a group as shown by one of the following formulas:

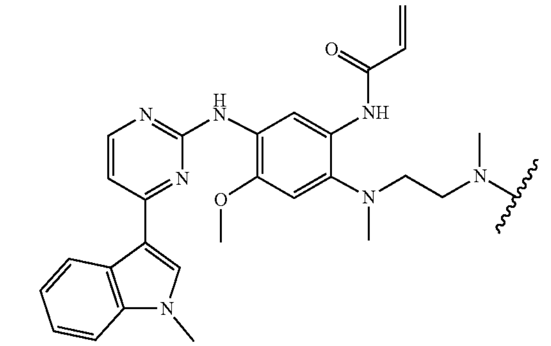

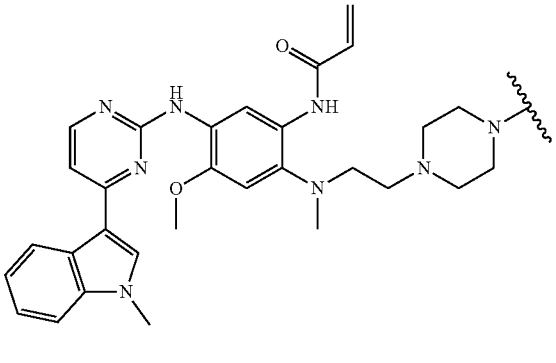

-continued

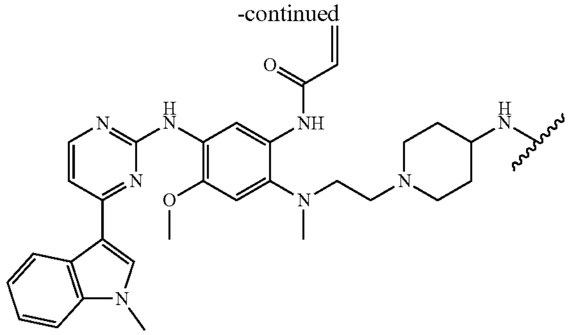

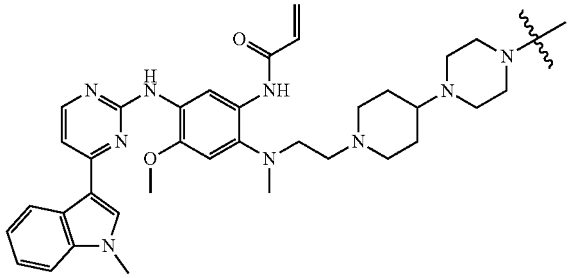

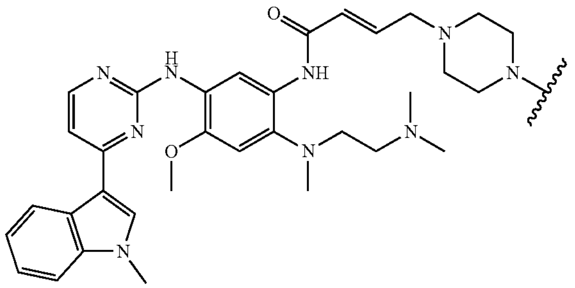

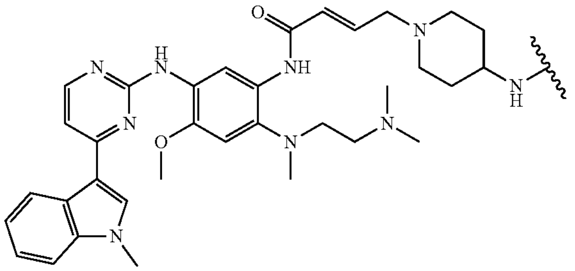

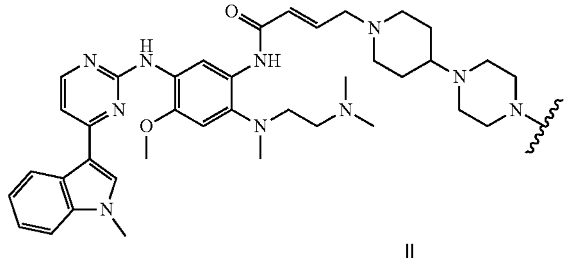

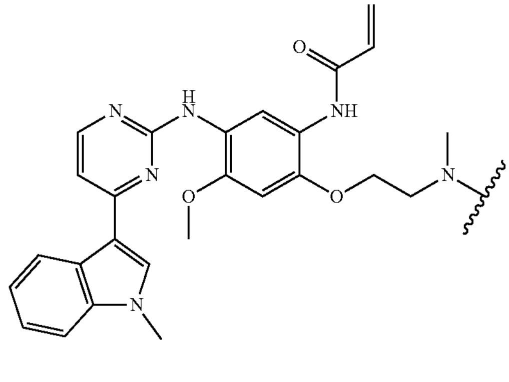

-continued

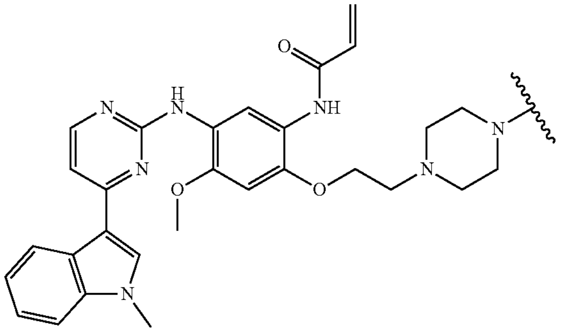

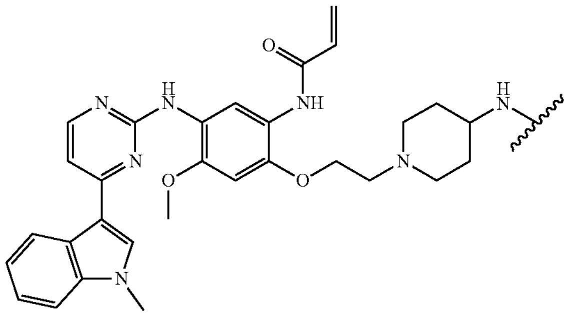

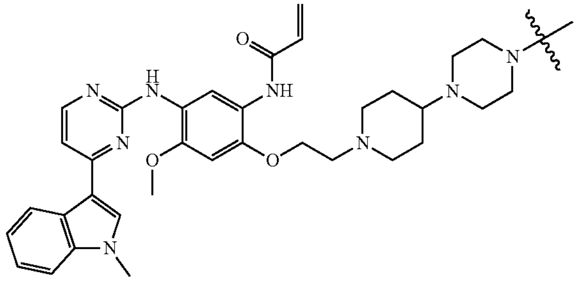

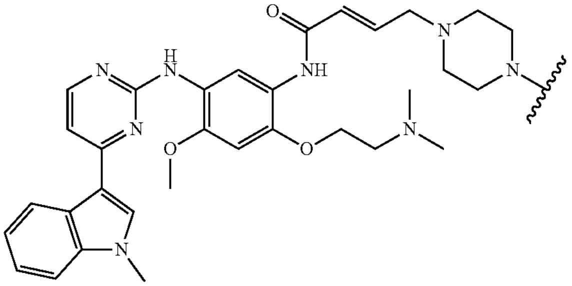

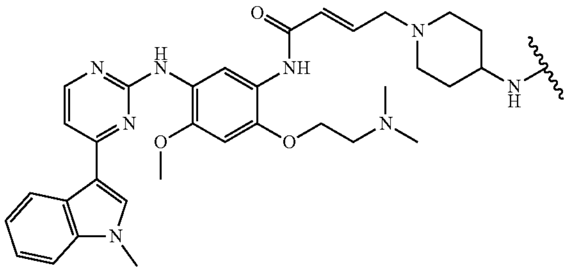

-continued

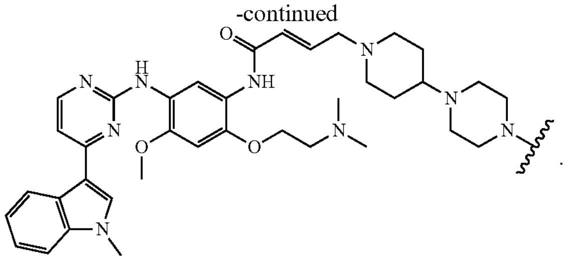

The bifunctional compound of the present invention may include a ULM moiety usually covalently bonded to LIN, which is mainly used to bind to E3 ubiquitin ligase as a ligand of E3 ubiquitin ligase.

In some preferred embodiments of the present invention, ULM can represent a group as shown by the following formula:

Formula II

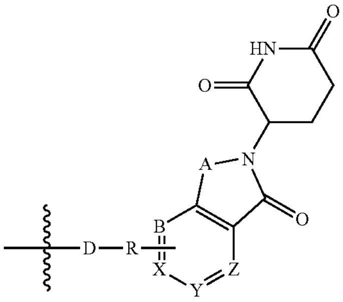

wherein A is selected from —$CH_2$— and —(C═O)—;

B, X, Y, and Z are each independently selected from CH and N;

R is selected from —S—, —SO—, —$SO_2$—,

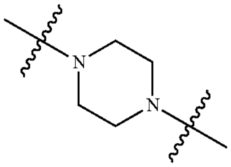

,

—$CH_2$—, —(C═O)—, —NH—, —O—, and ethynylene;

D is selected from —(C═O)—; or D is absent.

In a more preferred embodiment of the present invention, in the formula II, A is selected from —$CH_2$— and —(C═O)—; B is selected from C and N; and X, Y, and Z are each independently selected from CH and N;

In a more preferred embodiment of the present invention, in the formula II, R is selected from —S—, —NH—, and ethynylene; or R is absent; D is selected from —(C═O)—; or D is absent.

In a further preferred embodiment of the present invention, ULM can represent a group as shown by the following formulas:

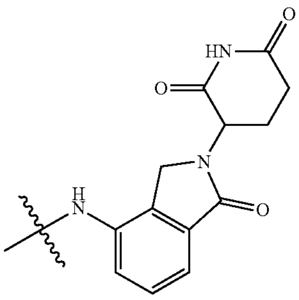
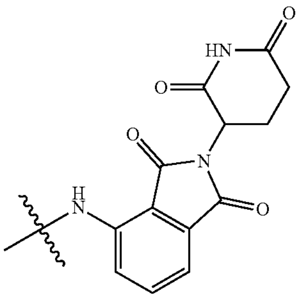
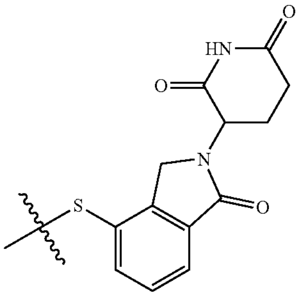
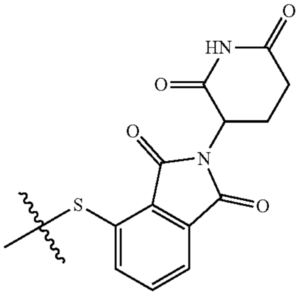
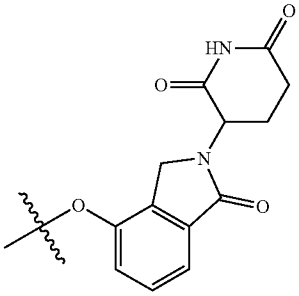
-continued
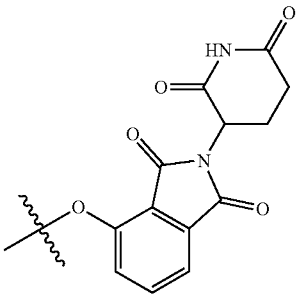
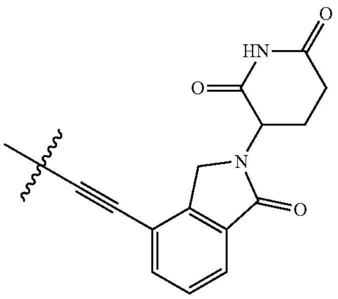
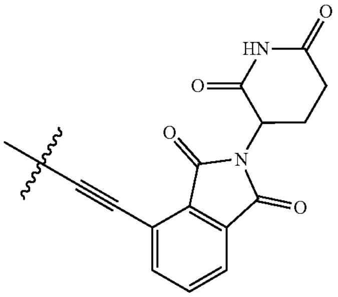
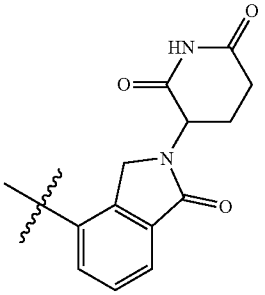
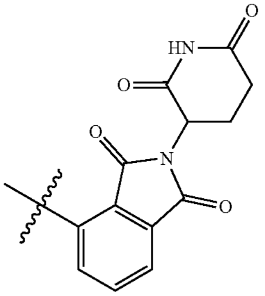

-continued
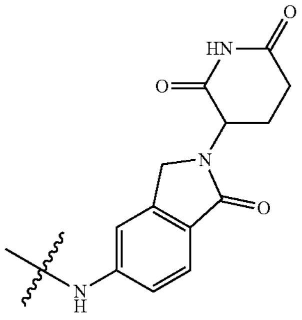
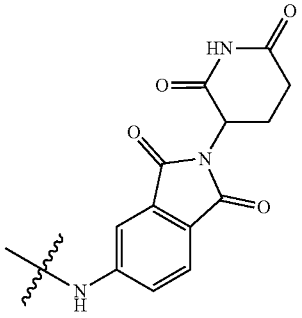
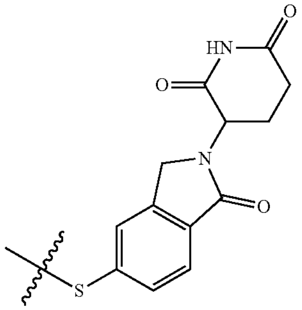
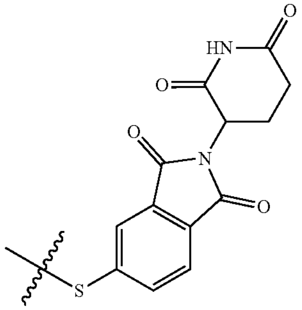
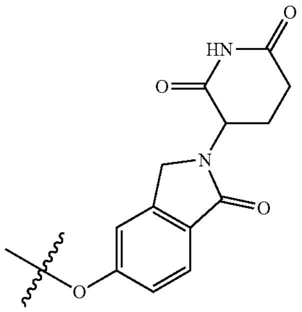
-continued
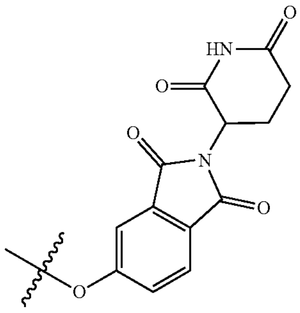
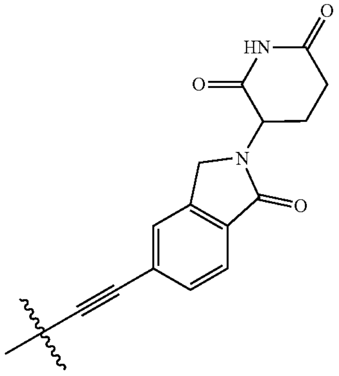
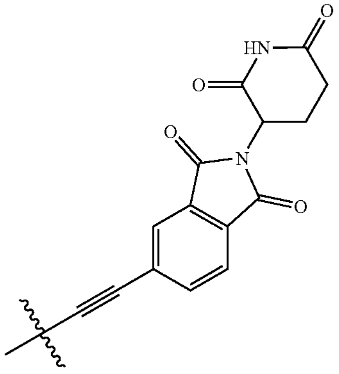
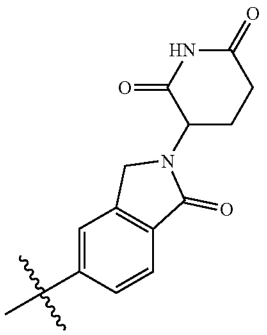

-continued

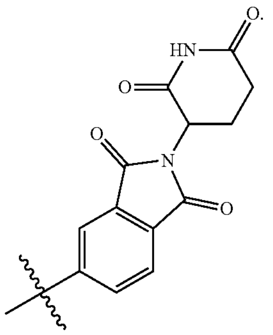

In some preferred embodiments of the present invention, ULM can represent a group as shown by the following formula:

Formula III

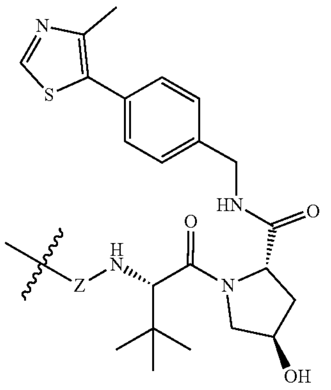

wherein Z is selected from —(C═O)—, or Z is absent;

In a more preferred embodiment of the present invention, in the formula III, Z is selected from —(C═O)—.

In a further preferred embodiment of the present invention, ULM can represent a group as shown by the following formula:

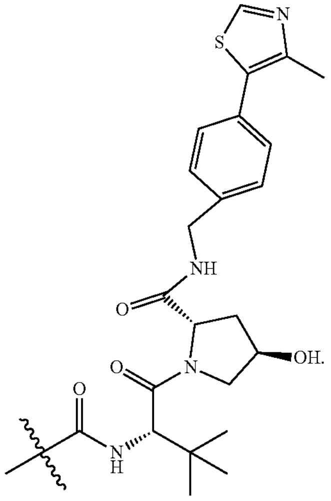 [SMILES: *C(=O)N[C@H](C(=O)N1C[C@H](O)C[C@H]1C(=O)NCc1ccc(-c2scnc2C)cc1)C(C)(C)C]

In some preferred embodiments of the present invention, ULM can represent a group as shown by the following formula:

Formula IV

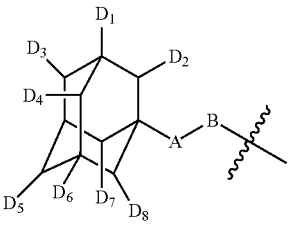

wherein A is selected from —$CH_2$—, —NR'—, —O—, —S—, and —(C═O)—, wherein R' is selected from H, linear or branched $C_1$-$C_{10}$ alkyl group, or $C_3$-$C_{10}$ cycloalkyl;

B is selected from —(C═O)—, or B is absent;

$D_1$, $D_2$, $D_3$, $D_4$, $D_5$, $D_6$, $D_7$, and $D_8$ are each independently selected from F, Cl, Br, OH, Me, Et, iPr, H, and D.

The bifunctional compound of the present invention may include a LIN moiety usually covalently bonded to the EGFR TKIs moiety and the ULM moiety, which is mainly used to connect two key parts, namely the target protein and the ligand of E3 ubiquitin ligase. The length, type, and hydrophobicity of the LIN moiety usually have an impact on the stability of the finally formed target protein-PROTAD-E3 ligase ternary complex, which in turn affects its inhibitory and degradation activities. The LIN moiety suitable for connecting PTM (protein target binding portion) and ULM (E3 ubiquitin ligase binding moiety) should be known to those skilled in the art (see, e.g., contents described in Org. Lett. 2019, 21, 3838-3841; and Bioorg. Med. Chem. Lett. 2016; 26:5260-5262). In the present invention, the LIN can specifically represent:

—W-alkylene-;

wherein the alkylene group is a linear or branched alkylene group optionally interrupted one or more times by one or more groups selected from: —O—, —CONH—, —NHCO—, —NH—, —NHCONH—, —S—, sulfinyl, sulfonyl, alkynylene, alkenylene, cycloalkylene, arylene, heterocyclylene, heteroarylene, or any combination thereof, wherein the linear or branched alkylene group is optionally substituted with one or more substituents;

W is selected from —(C═O)—, —(C═O)O—, and —NR'''—, where R'''' is selected from H, linear or branched $C_1$-$C_{10}$ alkylene, or $C_3$-$C_{10}$ cycloalkylene; or W is absent.

In a more preferred embodiment of the present invention, the substituents of the linear or branched alkylene are each independently selected from hydroxyl, amino, mercapto, and halogen.

In a more preferred embodiment of the present invention, the alkylene is $C_{1-30}$ alkylene.

In a more preferred embodiment of the present invention, the LIN represents:

—W—$C_{1-30}$ alkylene-, —W—$(CH_2)_{n1}$—$(O(CH_2)_{n2})_{m1}$—, —W—$(CH_2)_{n1}$—$(O(CH_2)_{n2})_{m1}$—$(O(CH_2)_{n3})_{m2}$—, —W—$(CR_{a1}R_{a2})_{n1}$—$(O(CR_{a3}R_{a4})_{n2})_{m1}$—, —W—$(CR_{a5}R_{a6})_{n1}$—$(O(CR_{a7}R_{a8})_{n2})_{m1}$—$(O(CR_{a9}R_{a10})_{n3})_{m2}$—, —W—$(CH_2)_{n1}$—(CONH—$(CH_2)_{n2})_{m1}$—, —W—$(CH_2)_{n1}$—(CONH—$(CH_2)_{n2})_{m1}$—$(CH_2)_{n3}$—, —W—$(CH_2)_{n1}$—(CONH—$(CH_2)_{n2})_{m1}$—

$(O(CH_2)_{n3})_{m2}$—, —W—$(CH_2)_{n1}$—$(O(CH_2)_{n2})_{m1}$—O—$(CH_2)_{n3}$—CONH—$(CH_2)_{n4}$—$(O(CH_2)_{n5})_{m2}$—O—$(CH_2)_{n6}$—, —W—$(CR_{a11}R_{a12})_{n1}$—$(O(CR_{a13}R_{a14})_{n2})_{m1}$—O—$(CR_{a15}R_{a16})_{n3}$—CONH—$(CR_{a17}R_{a18})_{n4}$—$(O(CR_{a19}R_{a20})_{n5})_{m2}$—O—$(CR_{a21}R_{a22})_{n6}$—, —W—$(CR_{a23}R_{a24})_{n1}$—CONH—$(O(CR_{a25}R_{a26})_{n2})_{m1}$—, —W—$(CH_2)_{n1}$—(NHCO—$(CH_2)_{n2})_{m1}$—, —W—$(CH_2)_{n1}$—(NHCO—$(CH_2)_{n2})_{m1}$—$(O(CH_2)_{n3})_{n2}$—, —W—$(CH_2)_{n1}$—CONH—$(O(CR_{a27}R_{a28})_{n2})_{m1}$—, —$(CH_2)_{n1}$—NHCONH—$(CH_2)_{n2}$—, —$(CH_2)_{n1}$—S—$(CH_2)_{n2}$—, —$(CH_2)_{n1}$—SO—$(CH_2)_{n2}$—, —$(CH_2)_{n1}$—$SO_2$—$(CH_2)_{n2}$—, —$(CH_2)_{n1}$—CH═CH—$(CH_2)_{n2}$—, —$(CH_2)_{n1}$—C≡C—$(CH_2)_{n2}$—, —$(CH_2)_{n1}$—C≡C—C≡C—$(CH_2)_{n2}$—, —$(CH_2)_{n1}$-piperazinylene-$(CH_2)_{n2}$—, —$(CH_2)_{n1}$-phenylene-$(CH_2)_{n2}$—, and —W—$(CH_2)_{n1}$—$(O(CH_2)_{n2})_{m1}$— in which backbone carbon chain is interrupted one or more times by one or more group(s) selected from the group consisting of arylene, heterocyclylene, heteroarylene, or any combination thereof;

$R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$, $R_{a27}$, and $R_{a28}$ are each independently selected from H, linear or branched $C_1$-$C_{10}$ alkyl, or $C_3$-$C_{10}$ cycloalkyl, wherein in the same group LIN, $R_{a1}$, $R_{a2}$, $R_{a3}$, and $R_{a4}$ are not H at the same time; or $R_{a5}$, $R_{a6}$, $R_{a7}$, $R_{a8}$, $R_{a9}$, and $R_{a10}$ are not H at the same time; or $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, and $R_{a22}$ are not H at the same time; or $R_{a23}$, $R_{a24}$, $R_{a25}$, and $R_{a26}$ are not H at the same time; or $R_{a27}$ and $R_{a28}$ are not H at the same time;

n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19, or 20.

In a further preferred embodiment of the present invention, the LIN represents:

—W—$CH_2$—, —W—$(CH_2)_2$—, —W—$(CH_2)_3$—, —W—$(CH_2)_4$—, —W—$(CH_2)_5$—, —W—$(CH_2)_6$—, —W—$(CH_2)_7$—, —W—$(CH_2)_8$—, —W—$(CH_2)_9$—, —W—$(CH_2)_{10}$—, —W—$(CH_2)_{11}$—, —W—$(CH_2)_{12}$—, —W—$(CH_2)_{13}$—, —W—$(CH_2)_{14}$—, —W—$(CH_2)_{15}$—, —W—$(CH_2)_{16}$—, —W—$(CH_2)_{17}$—, —W—$(CH_2)_{18}$—, —W—$(CH_2)_{19}$—, —W—$(CH_2)_{20}$—, —W—$(CH_2)_{21}$—, —W—$(CH_2)_{22}$—, —W—$(CH_2)_{23}$—, —W—$(CH_2)_{24}$—, —W—$(CH_2)_{25}$—, —W—$(CH_2)_{26}$—, —W—$(CH_2)_{27}$—, —W—$(CH_2)_{28}$—, —W—$(CH_2)_{29}$—, or —W—$(CH_2)_{30}$—.

In a further preferred embodiment of the present invention, the LIN represents:

—W—$CH_2$—O—$(CH_2)_2$—, —W—$CH_2$—$(O(CH_2)_2)_2$—, —W—$CH_2$—$(O(CH_2)_2)_3$—, —W—$CH_2$—$(O(CH_2)_2)_4$—, —W—$CH_2$—$(O(CH_2)_2)_5$—, —W—$CH_2$—$(O(CH_2)_2)_6$—, —W—$CH_2$—$(O(CH_2)_2)_7$—, —W—$CH_2$—$(O(CH_2)_2)_8$—, —W—$CH_2$—$(O(CH_2)_2)_9$—, —W—$CH_2$—$(O(CH_2)_2)_{10}$—, —W—$(CH_2)_2$—O—$(CH_2)_2$—, —W—$(CH_2)_2$—$(O(CH_2)_2)_2$—, —W—$(CH_2)_2$—$(O(CH_2)_2)_3$—, —W—$(CH_2)_2$—$(O(CH_2)_2)_4$—, —W—$(CH_2)_2$—$(O(CH_2)_2)_5$—, —W—$(CH_2)_2$—$(O(CH_2)_2)_6$—, —W—$(CH_2)_2$—$(O(CH_2)_2)_7$—, —W—$(CH_2)_2$—$(O(CH_2)_2)_8$—, —W—$(CH_2)_2$—$(O(CH_2)_2)_9$—, —W—$(CH_2)_2$—$(O(CH_2)_2)_{10}$—, —W—$(CH_2)_3$—O—$(CH_2)_2$—, —W—$(CH_2)_3$—$(O(CH_2)_2)_2$—, —W—$(CH_2)_3$—$(O(CH_2)_2)_3$—, —W—$(CH_2)_3$—$(O(CH_2)_2)_4$—, —W—$(CH_2)_3$—$(O(CH_2)_2)_5$—, —W—$(CH_2)_3$—$(O(CH_2)_2)_6$—, —W—$(CH_2)_3$—$(O(CH_2)_2)_7$—, —W—$(CH_2)_3$—$(O(CH_2)_2)_8$—, —W—$(CH_2)_3$—$(O(CH_2)_2)_9$—, —W—$(CH_2)_3$—$(O(CH_2)_2)_{10}$—, —W—$(CH_2)_4$—O—$(CH_2)_2$—, —W—$(CH_2)_4$—$(O(CH_2)_2)_2$—, —W—$(CH_2)_4$—$(O(CH_2)_2)_3$—, —W—$(CH_2)_4$—$(O(CH_2)_2)_4$—, —W—$(CH_2)_4$—$(O(CH_2)_2)_5$—, —W—$(CH_2)_4$—$(O(CH_2)_2)_6$—, —W—$(CH_2)_4$—$(O(CH_2)_2)_7$—, —W—$(CH_2)_4$—$(O(CH_2)_2)_8$—, —W—$(CH_2)_4$—$(O(CH_2)_2)_9$—, —W—$(CH_2)_4$—$(O(CH_2)_2)_{10}$—, —W—$CH_2$—O—$(CH_2)_3$—, —W—$CH_2$—$(O(CH_2)_3)_2$—, —W—$CH_2$—$(O(CH_2)_3)_3$—, —W—$CH_2$—$(O(CH_2)_3)_4$—, —W—$CH_2$—$(O(CH_2)_3)_5$—, —W—$CH_2$—$(O(CH_2)_3)_6$—, —W—$CH_2$—$(O(CH_2)_3)_7$—, —W—$CH_2$—$(O(CH_2)_3)_8$—, —W—$CH_2$—$(O(CH_2)_3)_9$—, —W—$CH_2$—$(O(CH_2)_3)_{10}$—, —W—$(CH_2)_2$—O—$(CH_2)_3$—, —W—$(CH_2)_2$—$(O(CH_2)_3)_2$—, —W—$(CH_2)_2$—$(O(CH_2)_3)_3$—, —W—$(CH_2)_2$—$(O(CH_2)_3)_4$—, —W—$(CH_2)_2$—$(O(CH_2)_3)_5$—, —W—$(CH_2)_2$—$(O(CH_2)_3)_6$—, —W—$(CH_2)_2$—$(O(CH_2)_3)_7$—, —W—$(CH_2)_2$—$(O(CH_2)_3)_8$—, —W—$(CH_2)_2$—$(O(CH_2)_3)_9$—, —W—$(CH_2)_2$—$(O(CH_2)_3)_{10}$—, —W—$(CH_2)_3$—O—$(CH_2)_3$—, —W—$(CH_2)_3$—$(O(CH_2)_3)_2$—, —W—$(CH_2)_3$—$(O(CH_2)_3)_3$—, —W—$(CH_2)_3$—$(O(CH_2)_3)_4$—, —W—$(CH_2)_3$—$(O(CH_2)_3)_5$—, —W—$(CH_2)_3$—$(O(CH_2)_3)_6$—, —W—$(CH_2)_3$—$O(CH_2)_3)_7$—, —W—$(CH_2)_3$—$(O(CH_2)_3)_8$—, —$(CH_2)_3$)—$(O(CH_2)_3)_9$—, —W—$(CH_2)_3$—$(O(CH_2)_3)_{10}$—, —W—$CH_2$—O—$(CH_2)_2$—O—$(CH_2)_3$—, —W—$CH_2$—$(O(CH_2)_2)_2$—$(O(CH_2)_3)_2$—, —W—$CH_2$—$(O(CH_2)_2)_3$—$(O(CH_2)_3)_3$—, —W—$CH_2$—$(O(CH_2)_2)_4$—$(O(CH_2)_3)_4$—, —W—$CH_2$—$(O(CH_2)_2)_5$—$(O(CH_2)_3)_5$—, —W—$CH_2$—$(O(CH_2)_2)_6$—$(O(CH_2)_3)_6$—, —W—$(CH_2)_2$—O—$(CH_2)_2$—O—$(CH_2)_3$—, —W—$(CH_2)_2$—$(O(CH_2)_2)_2$)—$(O(CH_2)_3)_2$—, —W—$(CH_2)_2$—$(O(CH_2)_2)_3$—$(O(CH_2)_3)_3$—, —W—$(CH_2)_2$—$(O(CH_2)_2)_4$—$(O(CH_2)_3)_4$—, —W—$(CH_2)_2$—$(O(CH_2)_2)_5$—$(O(CH_2)_3)_5$—, —W—$(CH_2)_2$—$(O(CH_2)_2)_6$—$(O(CH_2)_3)_6$—, —W—$(CH_2)_3$—O—$(CH_2)_2$—O—$(CH_2)_3$—, —W—$(CH_2)_3$—$(O(CH_2)_2)_2$—$(O(CH_2)_3)_2$—, —W—$(CH_2)_3$—$(O(CH_2)_2)_3$—$(O(CH_2)_3)_3$—, —W—$(CH_2)_3$—$(O(CH_2)_2)_4$—$(O(CH_2)_3)_4$—, —W—$(CH_2)_3$—$(O(CH_2)_2)_5$—$(O(CH_2)_3)_5$—, —W—$(CH_2)_3$—$(O(CH_2)_2)_6$—$(O(CH_2)_3)_6$—, —W—$CH_2$—O—$(CH_2)_3$—O—$(CH_2)_2$—, —W—$CH_2$—$(O(CH_2)_3)_2$—$(O(CH_2)_2)_2$—, —W—$CH_2$—$(O(CH_2)_3)_3$—$(O(CH_2)_2)_3$—, —W—$CH_2$—$(O(CH_2)_3)_4$—$(O(CH_2)_2)_4$—, —W—$CH_2$—$(O(CH_2)_3)_5$—$(O(CH_2)_2)_5$—, —W—$CH_2$—$(O(CH_2)_3)_6$—$(O(CH_2)_2)_6$—, —W—$(CH_2)_2$—O—$(CH_2)_3$—O—$(CH_2)_2$—, —W—$(CH_2)_2$—$(O(CH_2)_3)_2$—$(O(CH_2)_2)_2$—, —W—$(CH_2)_2$—$(O(CH_2)_3)_3$—$(O(CH_2)_2)_3$—, —W—$(CH_2)_2$—$(O(CH_2)_3)_4$—$(O(CH_2)_2)_4$—, —W—$(CH_2)_2$—$(O(CH_2)_3)_5$—$(O(CH_2)_2)_5$—, —W—$(CH_2)_2$—$(O(CH_2)_3)_6$—$(O(CH_2)_2)_6$—, —W—$(CH_2)_3$—O—$(CH_2)_3$—O—$(CH_2)_2$—, —W—$(CH_2)_3$—$(O(CH_2)_3)_2$—$(O(CH_2)_2)_2$—, —W—$(CH_2)_3$—$(O(CH_2)_3)_3$—$(O(CH_2)_2)_3$—, —W—$(CH_2)_3$—$(O(CH_2)_3)_4$—$(O(CH_2)_2)_4$—, —W—$(CH_2)_3$—$(O(CH_2)_3)_5$—$(O(CH_2)_2)_5$—, —W—$(CH_2)_3$—$(O(CH_2)_3)_6$—$(O(CH_2)_2)_6$—, —W—$CH_2$—O—$(CH_2)_2$O—$CH_2$—, —W—$(CH_2)_2$—O—$(CH_2)_2$O—$CH_2$—, —W—$(CH_2)_2$—$(O(CH_2)_2)_2$—O—$(CH_2)_3$—, —W—$(CH_2)_2$—$(O(CH_2)_2)_3$—O—$(CH_2)_3$—, —W—$(CH_2)_2$—$(O(CH_2)_2)_4$—O—$(CH_2)_3$—, —W—$(CH_2)_5$—$(O(CH_2)_2)_2$—O—$(CH_2)_5$—, or —W—$(CH_2)_5$—$(O(CH_2)_2)_2$—O—$(CH_2)_6$—.

In a further preferred embodiment of the present invention, the LIN represents: —W—$(CH_2)_3$CH(OH)CH(OH)$(CH_2)_4$—.

In a more preferred embodiment of the present invention, the LIN represents:

—W—$(CH_2)_{n1}$-triazolylene-$(CH_2)_{n2}$—, —W—$(CH_2)_{n1}$-triazolylene-$(CH_2)_{n2}$—$(O(CH_2)_{n3})_{m1}$—, —W—$(CH_2)_{n1}$—$(O(CH_2)_{n2})_{m1}$—O—$(CH_2)_{n3}$-triazolylene-$(CH_2)_{n4}$—$(O(CH_2)_{n5})_{m2}$—O—$(CH_2)_{n6}$—, —W—$(CH_2)_{n1}$-triazolylene-$(CH_2)_{n2}$—$(O(CH_2)_{n3})_{m1}$—O—$(CH_2)_{n4}$—, —W—$(CH_2)_{n1}$—$(O(CH_2)_{n2})_{m1}$—O—$(CH_2)_{n3}$-triazolylene-$(CH_2)_{n4}$—;

wherein n1, n2, n3, n4, n5, n6, m1, and m2 are independently selected from 1, 2, 3, 4, 5, 6, 7, 8, 9, 10, 11, 12, 13, 14, 15, 16, 17, 18, 19, or 20.

In a further preferred embodiment of the present invention, the LIN represents: —W—$(CH_2)_3$-triazolylene-$(CH_2)_5$—, —W—$(CH_2)_2$-triazolylene-$(CH_2)_5$—, —W—$CH_2$-triazolylene-$(CH_2)_5$—, —W—$(CH_2)_2$-triazolylene-$(CH_2)_4$—, —W—$(CH_2)_3$-triazolylene-$(CH_2)_3$—, —W—$(CH_2)_5$-triazolylene-$(CH_2)_5$—, —W—$(CH_2)_5$-triazolylene-$(CH_2)_8$—, —W—$(CH_2)_3$-triazolylene-$(CH_2)_2$—$O(CH_2)_2$—, —W—$(CH_2)_2$-triazolylene-$(CH_2)_2$—$O(CH_2)_2$—, W—$CH_2$-triazolylene-$(CH_2)_2$—$O(CH_2)_2$.

In a further preferred embodiment of the present invention, the LIN represents:

—W—$CH_2CONHCH_2$—, —W—$(CH_2)_2CONH(CH_2)_2$—, —W—$(CH_2)_3CONH(CH_2)_3$—, —W—$(CH_2)_3CONH(CH_2)_4$—, —W—$(CH_2)_4CONH(CH_2)_4$—, —W—$(CH_2)_5CONH(CH_2)_5$—, —W—$(CH_2)_6CONH(CH_2)_7$—, —W—$(CH_2)_6CONH(CH_2)_6$—, —W—$(CH_2)_7CONH(CH_2)_7$—, —W—$(CH_2)_8CONH(CH_2)_8$, W—$(CH_2)_9CONH(CH_2)_9$—, —W—$(CH_2)_{10}CONH(CH_2)_{10}$—, —W—$(CH_2)_2CONH(CH_2)_5$—, —W—$(CH_2)_2CONH(CH_2)_3$—, —W—$(CH_2)_2CONH(CH_2)_4$—, —W—$(CH_2)_2CONH(CH_2)_2$—O—$(CH_2)_2$—.

In a further preferred embodiment of the present invention, the LIN represents:

—W—$CH_2NHCOCH_2$—, —W—$(CH_2)_2NHCO(CH_2)_2$—, —W—$(CH_2)_3NHCO(CH_2)_3$—, —W—$(CH_2)_3NHCO(CH_2)_4$—, —W—$(CH_2)_4NHCO(CH_2)_4$—, —W—$(CH_2)_5NHCO(CH_2)_5$—, —W—$(CH_2)_6NHCO(CH_2)_7$—, —W—$(CH_2)_6NHCO(CH_2)_6$—, —W—$(CH_2)_7NHCO(CH_2)_7$—, —W—$(CH_2)_8NHCO(CH_2)_8$, —W—$(CH_2)_9NHCO(CH_2)_9$—, —W—$(CH_2)_{10}NHCO(CH_2)_{10}$—, —W—$(CH_2)_2NHCO(CH_2)_5$—, —W—$(CH_2)_2NHCO(CH_2)_3$—, —W—$(CH_2)_2NHCO(CH_2)_4$—, —W—$(CH_2)_4NHCO(CH_2)_8$—, —W—$(CH_2)_2NHCO(CH_2)_2$—O—$(CH_2)_2$—, —W—$(CH_2)_4NHCOCH_2$—.

In a further preferred embodiment of the present invention, the LIN represents: —W—$(CH_2)_4NHCONH(CH_2)_4$—.

In a further preferred embodiment of the present invention, the LIN represents: —W—$(CH_2)_5S(CH_2)_5$—, —W—$(CH_2)_6S(CH_2)_5$—.

In a further preferred embodiment of the present invention, the LIN represents: —W—$(CH_2)_5SO(CH_2)_5$—, —W—$(CH_2)_6SO(CH_2)_5$—.

In a further preferred embodiment of the present invention, the LIN represents: —W—$(CH_2)_5SO_2(CH_2)_5$—, —W—$(CH_2)_6SO_2(CH_2)_5$—.

In a further preferred embodiment of the present invention, the LIN represents: —W—$(CH_2)_4CH{=}CH(CH_2)_3$—.

In a further preferred embodiment of the present invention, the LIN represents: —W—$(CH_2)_2C{\equiv}C(CH_2)_2$—, —W—$(CH_2)_5C{\equiv}C(CH_2)_4$—.

In a further preferred embodiment of the present invention, the LIN represents:

—W—$CH_2$-piperazinylene-$CH_2$—, —W—$(CH_2)_2$-piperazinylene-$(CH_2)_2$—, —W—$(CH_2)_3$-piperazinylene-$(CH_2)_3$—, —W—$(CH_2)_2$-piperazinylene-$(CH_2)_3$—, —W—$CH_2$-piperazinylene-$(CH_2)_2$—, —W—$CH_2$-piperazinylene-$(CH_2)_3$—, —W—$(CH_2)_2$-piperazinylene-$(CH_2)_3$—.

In a further preferred embodiment of the present invention, the LIN represents:

—W—$CH_2$-phenylene-$CH_2$—, —W—$(CH_2)_2$-phenylene-$(CH_2)_2$—, —W—$CH_2$-phenylene-$(CH_2)_2$—, —W—$(CH_2)_2$-phenylene-$CH_2$—, —W—$(CH_2)_3$-phenylene-$(CH_2)_3$—, —W—$CH_2$-phenylene-$(CH_2)_3$—, —W—$(CH_2)_2$-phenylene-$(CH_2)_3$—, —W—$(CH_2)_3$-phenylene-$(CH_2)_2$—, —W—$(CH_2)_3$-phenylene-$CH_2$—, —W—$(CH_2)_2O$—$CH_2$-phenylene-$CH_2$—O—$(CH_2)_2$—.

In a further preferred embodiment of the present invention, the LIN represents: —W-piperazinylene-, —W-spirocycloalkylene, —W-phenylene-, —W—C≡C—C≡C—. Specifically, the LIN can be a group as shown by the following formulas:

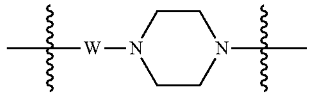
,

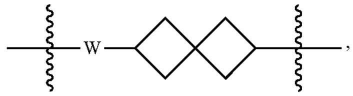
, or

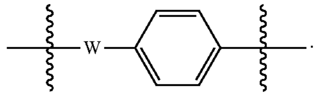
.

In a further preferred embodiment of the present invention, the bifunctional compound is selected from the compounds shown in Table 1 or Table 2:

TABLE 1

| | Compound No. | The compounds' name | Structure of the compounds |
|---|---|---|---|
| 1 | SIAIS249046 | (E)-N-(4-((3-chloro-4-fluorophenyl)amino)-7-methoxyquinazolin-6-yl)-4-(4-(3-(2-((2-(2,6-dioxopiperidin-3-yl)-1,3-dioxoisoindolin-4-yl)amino)ethoxy)propanoyl)piperazin-1-yl)but-2-enamide | 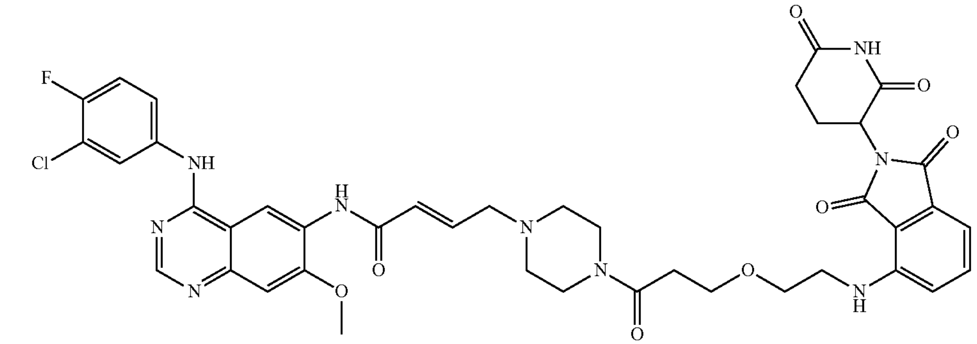 [SMILES: COc1cc2ncnc(Nc3ccc(F)c(Cl)c3)c2cc1NC(=O)/C=C/CN1CCN(C(=O)CCOCCNc2cccc3c2C(=O)N(C2CCC(=O)NC2=O)C3=O)CC1] |
| 2 | SIAIS262013 | (E)-N-(4-((3-chloro-4-fluorophenyl)amino)-7-methoxyquinazolin-6-yl)-4-(4-(3-(2-(2-((2-(2,6-dioxopiperidin-3-yl)-1,3-dioxoisoindolin-4-yl)amino)ethoxy)ethoxy)propanoyl)piperazin-1-yl)but-2-enamide— | 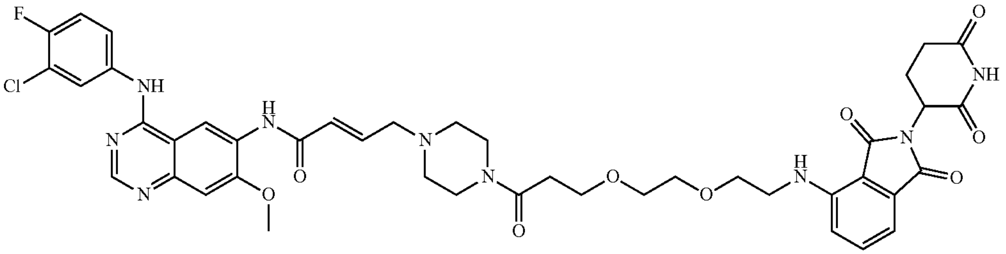 [SMILES: COc1cc2ncnc(Nc3ccc(F)c(Cl)c3)c2cc1NC(=O)/C=C/CN1CCN(C(=O)CCOCCOCCNc2cccc3c2C(=O)N(C2CCC(=O)NC2=O)C3=O)CC1] |
| 3 | SIAIS249047 | (E)-N-(4-((3-chloro-4-fluorophenyl)amino)-7-methoxyquinazolin-6-yl)-4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)but-2-enamide | 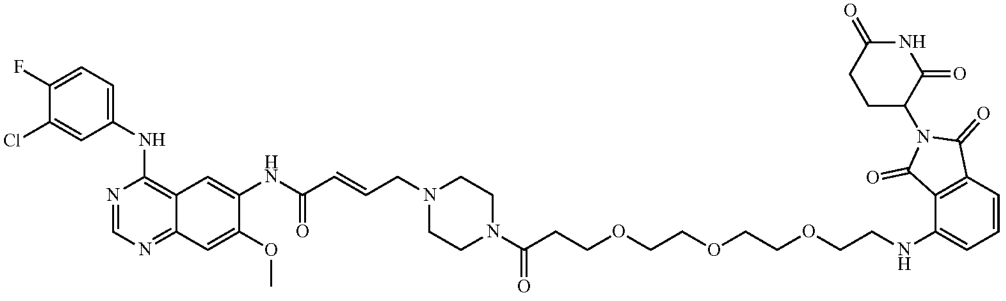 [SMILES: COc1cc2ncnc(Nc3ccc(F)c(Cl)c3)c2cc1NC(=O)/C=C/CN1CCN(C(=O)CCOCCOCCOCCNc2cccc3c2C(=O)N(C2CCC(=O)NC2=O)C3=O)CC1] |

TABLE 1-continued

| Compound No. | | The compounds' name | Structure of the compounds |
|---|---|---|---|
| 4 | SIAIS262014 | (E)-N-(4-((3-chloro-4-fluorophenyl)amino)-7-methoxyquinazolin-6-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)but-2-enamide | 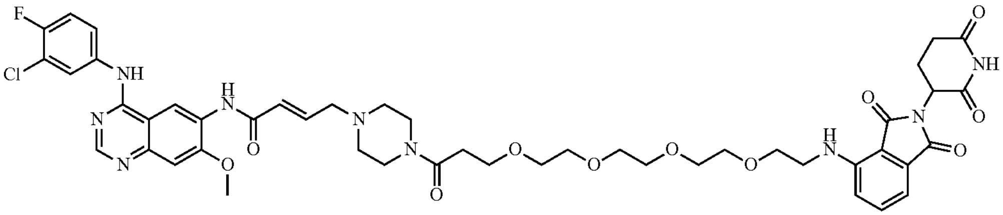 [SMILES: COc1cc2ncnc(Nc3ccc(F)c(Cl)c3)c2cc1NC(=O)/C=C/CN1CCN(C(=O)CCOCCOCCOCCOCCNc2cccc3c2C(=O)N(C2CCC(=O)NC2=O)C3=O)CC1] |
| 5 | SIAIS219194 | (E)-N-(4-((3-chloro-4-fluorophenyl)amino)-7-methoxyquinazolin-6-yl)-4-(4-(2-((2-(2,6-dioxopiperidin-3-yl)-1,3-dioxoisoindolin-4-yl)amino)acetyl)piperazin-1-yl)but-2-enamide | 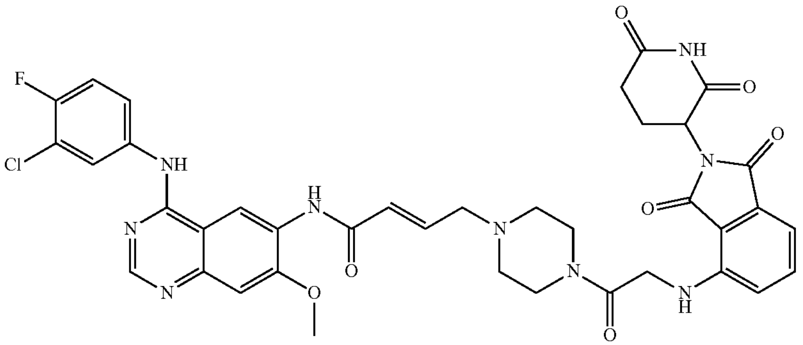 [SMILES: COc1cc2ncnc(Nc3ccc(F)c(Cl)c3)c2cc1NC(=O)/C=C/CN1CCN(C(=O)CNc2cccc3c2C(=O)N(C2CCC(=O)NC2=O)C3=O)CC1] |
| 6 | SIAIS262016 | (E)-N-(4-((3-chloro-4-fluorophenyl)amino)-7-methoxyquinazolin-6-yl)-4-(4-(3-((2-(2,6-dioxopiperidin-3-yl)-1,3-dioxoisoindolin-4-yl)amino)propanoyl)piperazin-1-yl)but-2-enamide | 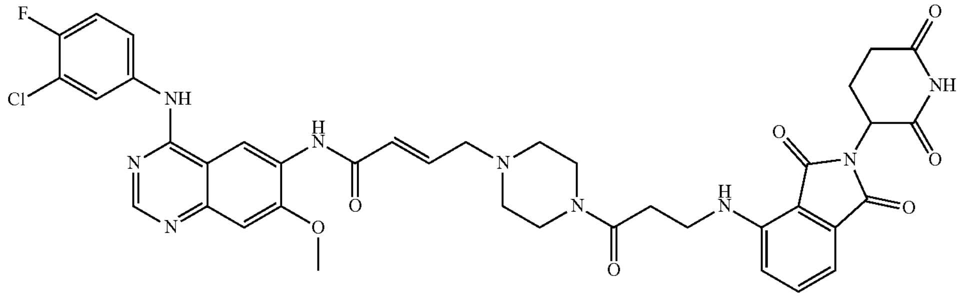 [SMILES: COc1cc2ncnc(Nc3ccc(F)c(Cl)c3)c2cc1NC(=O)/C=C/CN1CCN(C(=O)CCNc2cccc3c2C(=O)N(C2CCC(=O)NC2=O)C3=O)CC1] |

TABLE 1-continued

| Compound No. | | The compounds' name | Structure of the compounds |
|---|---|---|---|
| 7 | SIAIS249062 | (E)-N-(4-((3-chloro-4-fluorophenyl)amino)-7-methoxyquinazolin-6-yl)-4-(4-(4-((2-(2,6-dioxopiperidin-3-yl)-1,3-dioxoisoindolin-4-yl)amino)butanoyl)piperazin-1-yl)but-2-enamide | 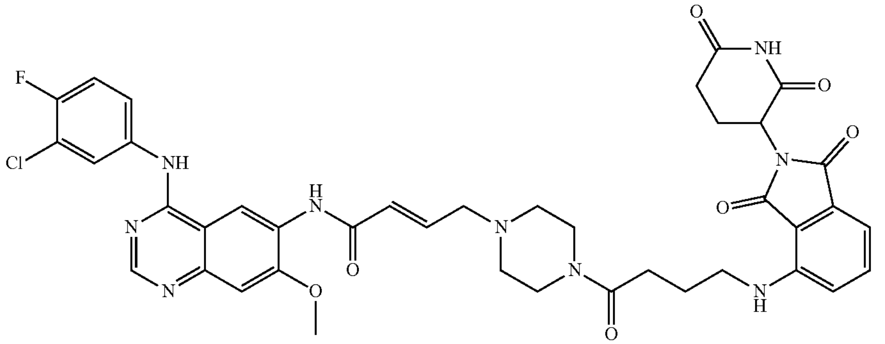 [SMILES: COc1cc2ncnc(Nc3ccc(F)c(Cl)c3)c2cc1NC(=O)/C=C/CN1CCN(C(=O)CCCNc2cccc3c2C(=O)N(C2CCC(=O)NC2=O)C3=O)CC1] |
| 8 | SIAIS249048 | (E)-N-(4-((3-chloro-4-fluorophenyl)amino)-7-methoxyquinazolin-6-yl)-4-(4-(5-((2-(2,6-dioxopiperidin-3-yl)-1,3-dioxoisoindolin-4-yl)amino)pentanoyl)piperazin-1-yl)but-2-enamide | 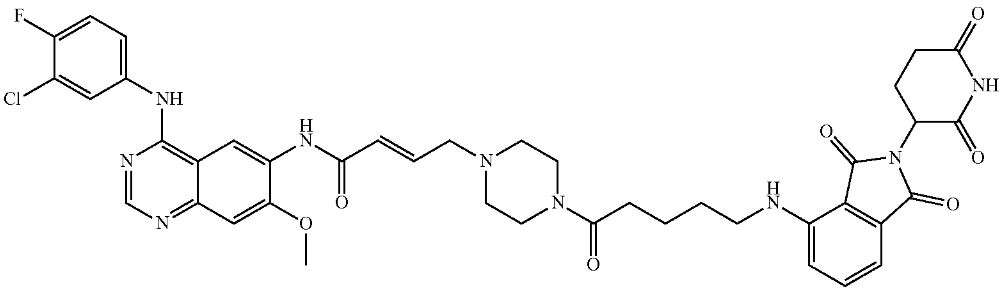 [SMILES: COc1cc2ncnc(Nc3ccc(F)c(Cl)c3)c2cc1NC(=O)/C=C/CN1CCN(C(=O)CCCCNc2cccc3c2C(=O)N(C2CCC(=O)NC2=O)C3=O)CC1] |
| 9 | SIAIS249049 | (E)-N-(4-((3-chloro-4-fluorophenyl)amino)-7-methoxyquinazolin-6-yl)-4-(4-(6-((2-(2,6-dioxopiperidin-3-yl)-1,3-dioxoisoindolin-4-yl)amino)hexanoyl)piperazin-1-yl)but-2-enamide | 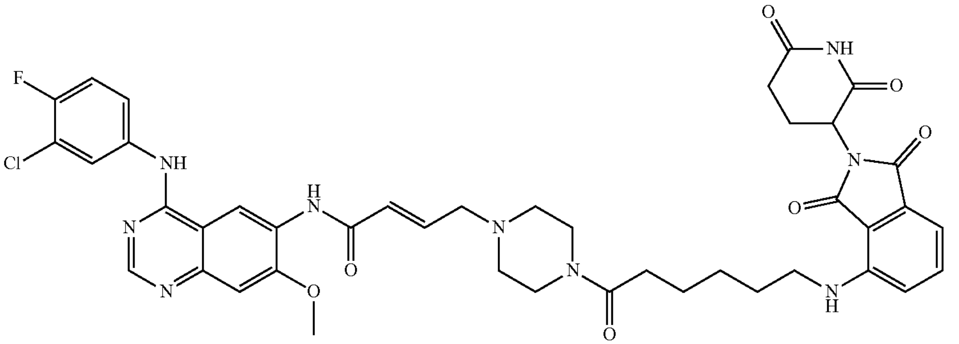 |

TABLE 1-continued

| Compound No. | | The compounds' name | Structure of the compounds |
|---|---|---|---|
| 10 | SIAIS262015 | (E)-N-(4-((3-chloro-4-fluorophenyl)amino)-7-methoxyquinazolin-6-yl)-4-(4-(7-((2-(2,6-dioxopiperidin-3-yl)-1,3-dioxoisoindolin-4-yl)amino)heptanoyl)piperazin-1-yl)but-2-enamide | 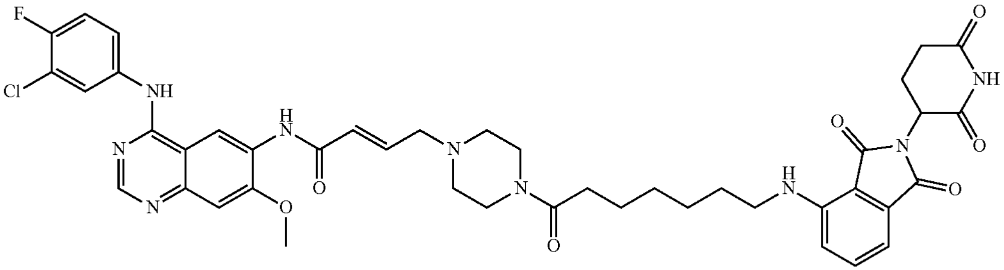 [SMILES: COc1cc2ncnc(Nc3ccc(F)c(Cl)c3)c2cc1NC(=O)/C=C/CN1CCN(C(=O)CCCCCCNc2cccc3c2C(=O)N(C2CCC(=O)NC2=O)C3=O)CC1] |
| 11 | SIAIS249056 | (E)-N-(4-((3-chloro-4-fluorophenyl)amino)-7-methoxyquinazolin-6-yl)-4-(4-(2-((2-(2,6-dioxopiperidin-3-yl)-1-oxoisoindolin-4-yl)amino)acetyl)piperazin-1-yl)but-2-enamide | 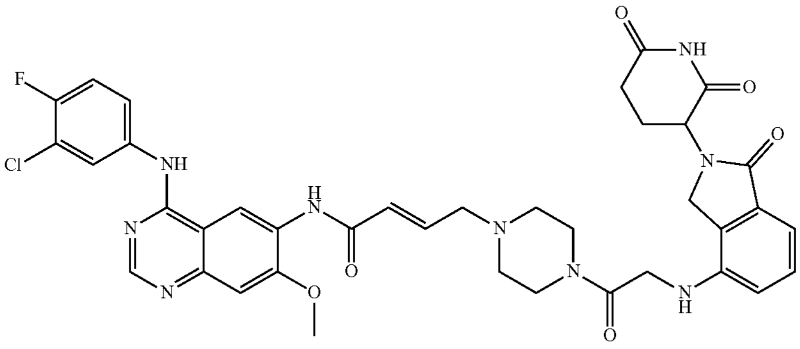 [SMILES: COc1cc2ncnc(Nc3ccc(F)c(Cl)c3)c2cc1NC(=O)/C=C/CN1CCN(C(=O)CNc2cccc3c2CN(C2CCC(=O)NC2=O)C3=O)CC1] |
| 12 | SIAIS249057 | (E)-N-(4-((3-chloro-4-fluorophenyl)amino)-7-methoxyquinazolin-6-yl)-4-(4-(4-((2-(2,6-dioxopiperidin-3-yl)-1-oxoisoindolin-4-yl)amino)butanoyl)piperazin-1-yl)but-2-enamide | 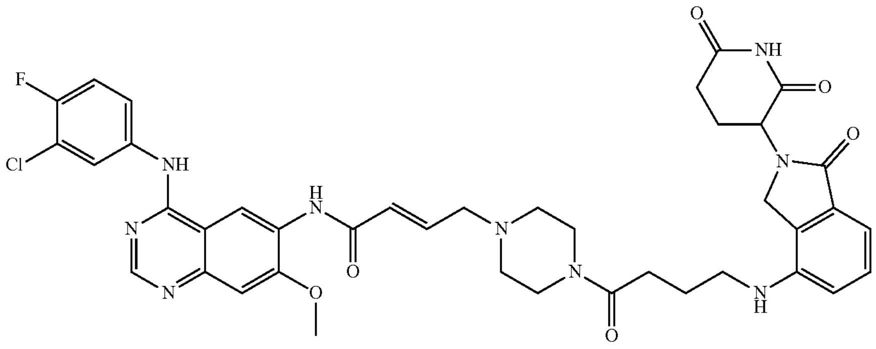 [SMILES: COc1cc2ncnc(Nc3ccc(F)c(Cl)c3)c2cc1NC(=O)/C=C/CN1CCN(C(=O)CCCNc2cccc3c2CN(C2CCC(=O)NC2=O)C3=O)CC1] |

TABLE 1-continued

| Compound No. | | The compounds' name | Structure of the compounds |
|---|---|---|---|
| 13 | SIAIS249058 | (E)-N-(4-((3-chloro-4-fluorophenyl)amino)-7-methoxyquinazolin-6-yl)-4-(4-(5-((2-(2,6-dioxopiperidin-3-yl)-1-oxoisoindolin-4-yl)amino)pentanoyl)piperazin-1-yl)but-2-enamide | 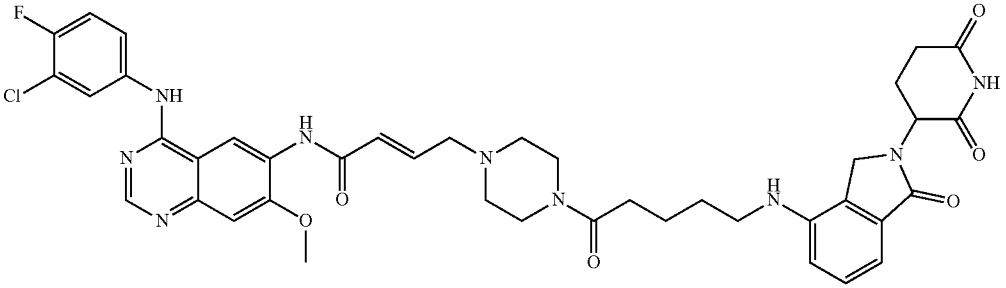 [SMILES: COc1cc2ncnc(Nc3ccc(F)c(Cl)c3)c2cc1NC(=O)/C=C/CN1CCN(C(=O)CCCCNc2cccc3c2CN(C2CCC(=O)NC2=O)C3=O)CC1] |
| 14 | SIAIS249059 | (E)-N-(4-((3-chloro-4-fluorophenyl)amino)-7-methoxyquinazolin-6-yl)-4-(4-(6-((2-(2,6-dioxopiperidin-3-yl)-1-oxoisoindolin-4-yl)amino)hexanoyl)piperazin-1-yl)but-2-enamide | 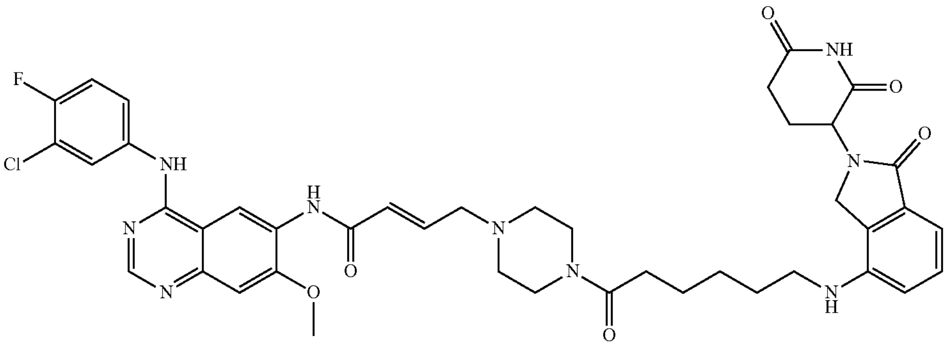 [SMILES: COc1cc2ncnc(Nc3ccc(F)c(Cl)c3)c2cc1NC(=O)/C=C/CN1CCN(C(=O)CCCCCNc2cccc3c2CN(C2CCC(=O)NC2=O)C3=O)CC1] |
| 15 | SIAIS249060 | (E)-N-(4-((3-chloro-4-fluorophenyl)amino)-7-methoxyquinazolin-6-yl)-4-(4-(7-((2-(2,6-dioxopiperidin-3-yl)-1-oxoisoindolin-4-yl)amino)heptanoyl)piperazin-1-yl)but-2-enamide | 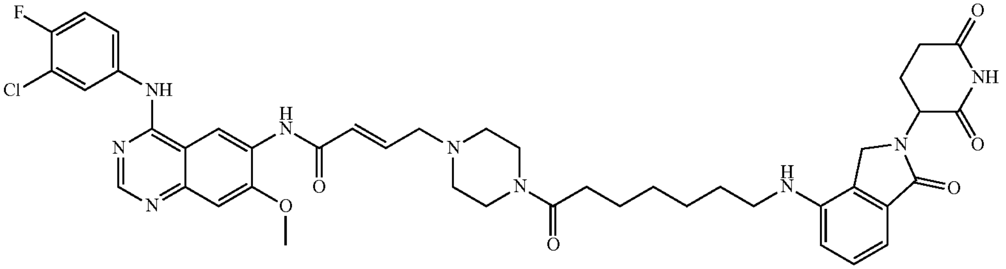 [SMILES: COc1cc2ncnc(Nc3ccc(F)c(Cl)c3)c2cc1NC(=O)/C=C/CN1CCN(C(=O)CCCCCCNc2cccc3c2CN(C2CCC(=O)NC2=O)C3=O)CC1] |

TABLE 1-continued

| | Compound No. | The compounds' name | Structure of the compounds |
|---|---|---|---|
| 16 | SIAIS249034 | (E)-N-(4-((3-chloro-4-fluorophenyl)amino)-7-methoxyquinazolin-6-yl)-4-(4-(2-((2-(2,6-dioxopiperidin-3-yl)-1,3-dioxoisoindolin-4-yl)thio)acetyl)piperazin-1-yl)but-2-enamide | 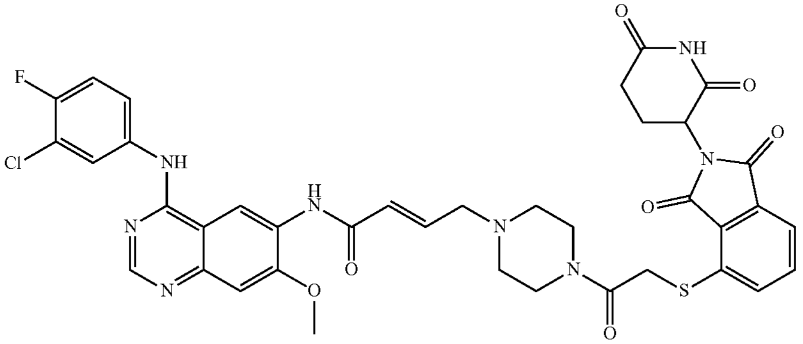 [SMILES: COc1cc2ncnc(Nc3ccc(F)c(Cl)c3)c2cc1NC(=O)/C=C/CN1CCN(C(=O)CSc2cccc3c2C(=O)N(C2CCC(=O)NC2=O)C3=O)CC1] |
| 17 | SIAIS249035 | (E)-N-(4-((3-chloro-4-fluorophenyl)amino)-7-methoxyquinazolin-6-yl)-4-(4-(3-((2-(2,6-dioxopiperidin-3-yl)-1,3-dioxoisoindolin-4-yl)thio)propanoyl)piperazin-1-yl)but-2-enamide | 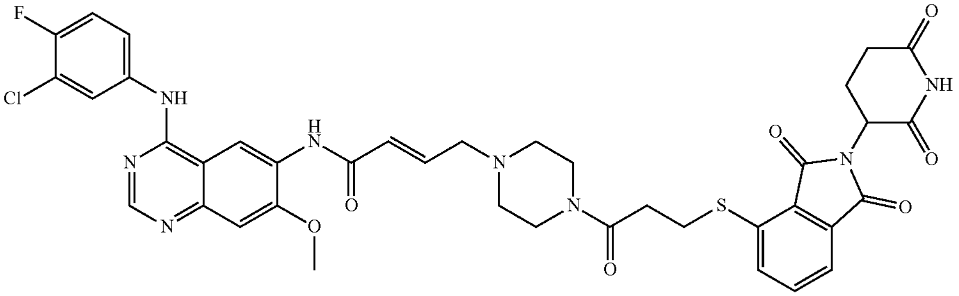 [SMILES: COc1cc2ncnc(Nc3ccc(F)c(Cl)c3)c2cc1NC(=O)/C=C/CN1CCN(C(=O)CCSc2cccc3c2C(=O)N(C2CCC(=O)NC2=O)C3=O)CC1] |
| 18 | SIAIS249036 | (E)-N-(4-((3-chloro-4-fluorophenyl)amino)-7-methoxyquinazolin-6-yl)-4-(4-(4-((2-(2,6-dioxopiperidin-3-yl)-1,3-dioxoisoindolin-4-yl)thio)butanoyl)piperazin-1-yl)but-2-enamide | 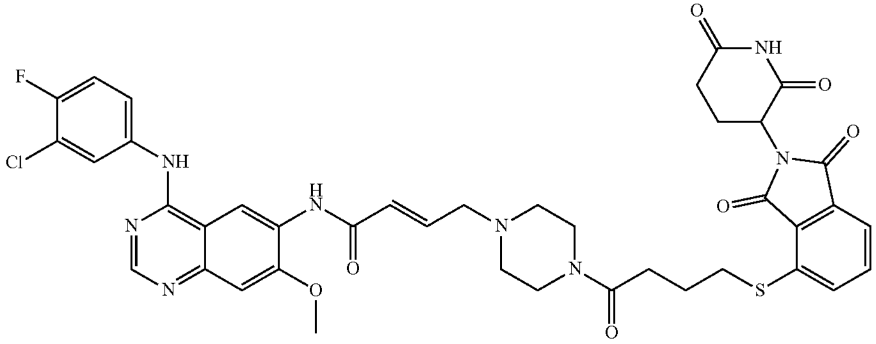 [SMILES: COc1cc2ncnc(Nc3ccc(F)c(Cl)c3)c2cc1NC(=O)/C=C/CN1CCN(C(=O)CCCSc2cccc3c2C(=O)N(C2CCC(=O)NC2=O)C3=O)CC1] |

TABLE 1-continued

| Compound No. | | The compounds' name | Structure of the compounds |
|---|---|---|---|
| 19 | SIAIS249037 | (E)-N-(4-((3-chloro-4-fluorophenyl)amino)-7-methoxyquinazolin-6-yl)-4-(4-(5-((2-(2,6-dioxopiperidin-3-yl)-1,3-dioxoisoindolin-4-yl)thio)pentanoyl)piperazin-1-yl)but-2-enamide | 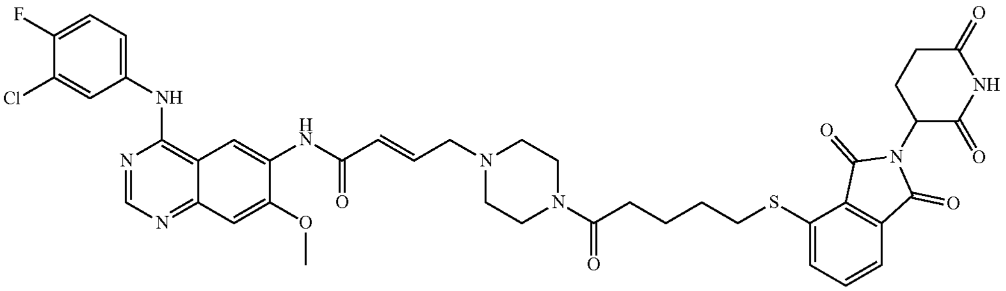 [SMILES: COc1cc2ncnc(Nc3ccc(F)c(Cl)c3)c2cc1NC(=O)/C=C/CN1CCN(C(=O)CCCCSc2cccc3c2C(=O)N(C2CCC(=O)NC2=O)C3=O)CC1] |
| 20 | SIAIS249038 | (E)-N-(4-((3-chloro-4-fluorophenyl)amino)-7-methoxyquinazolin-6-yl)-4-(4-(6-((2-(2,6-dioxopiperidin-3-yl)-1,3-dioxoisoindolin-4-yl)thio)hexanoyl)piperazin-1-yl)but-2-enamide | 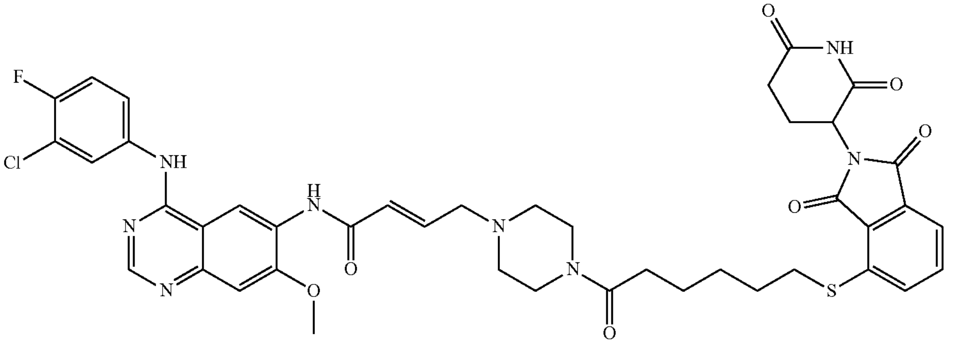 [SMILES: COc1cc2ncnc(Nc3ccc(F)c(Cl)c3)c2cc1NC(=O)/C=C/CN1CCN(C(=O)CCCCCSc2cccc3c2C(=O)N(C2CCC(=O)NC2=O)C3=O)CC1] |
| 21 | SIAIS249039 | (E)-N-(4-((3-chloro-4-fluorophenyl)amino)-7-methoxyquinazolin-6-yl)-4-(4-(7-((2-(2,6-dioxopiperidin-3-yl)-1,3-dioxoisoindolin-4-yl)thio)heptanoyl)piperazin-1-yl)but-2-enamide | 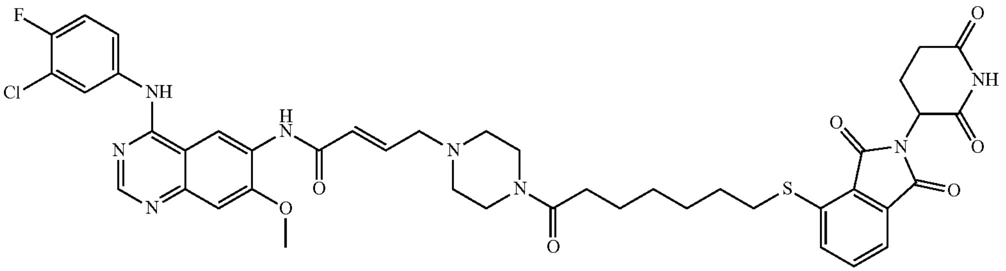 [SMILES: COc1cc2ncnc(Nc3ccc(F)c(Cl)c3)c2cc1NC(=O)/C=C/CN1CCN(C(=O)CCCCCCSc2cccc3c2C(=O)N(C2CCC(=O)NC2=O)C3=O)CC1] |

TABLE 1-continued

| | Compound No. | The compounds' name | Structure of the compounds |
|---|---|---|---|
| 22 | SIAIS219192 | (E)-N-(4-((3-chloro-4-fluorophenyl)amino)-7-methoxyquinazolin-6-yl)-4-(4-(2-(2-((2-(2,6-dioxopiperidin-3-yl)-1,3-dioxoisoindolin-4-yl)thio)ethoxy)acetyl)piperazin-1-yl)but-2-enamide | 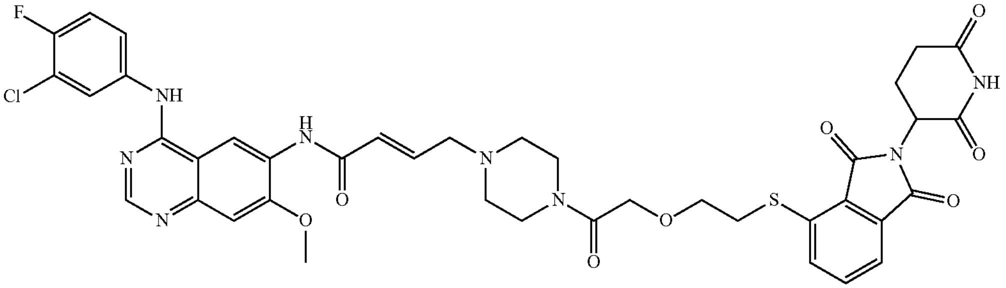 [SMILES: COc1cc2ncnc(Nc3ccc(F)c(Cl)c3)c2cc1NC(=O)/C=C/CN1CCN(C(=O)COCCSc2cccc3c2C(=O)N(C2CCC(=O)NC2=O)C3=O)CC1] |
| 23 | SIAIS262005 | (E)-N-(4-((3-chloro-4-fluorophenyl)amino)-7-methoxyquinazolin-6-yl)-4-(4-(2-(2-(2-((2-(2,6-dioxopiperidin-3-yl)-1,3-dioxoisoindolin-4-yl)thio)ethoxy)ethoxy)acetyl)piperazin-1-yl)but-2-enamide | 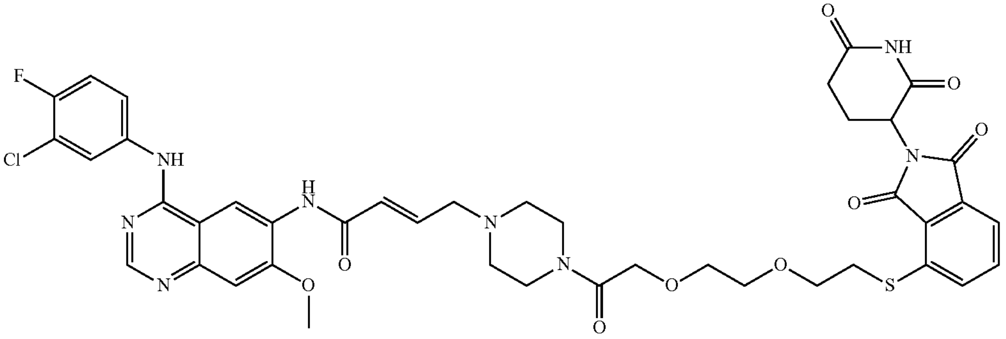 [SMILES: COc1cc2ncnc(Nc3ccc(F)c(Cl)c3)c2cc1NC(=O)/C=C/CN1CCN(C(=O)COCCOCCSc2cccc3c2C(=O)N(C2CCC(=O)NC2=O)C3=O)CC1] |
| 24 | SIAIS262006 | (E)-N-(4-((3-chloro-4-fluorophenyl)amino)-7-methoxyquinazolin-6-yl)-4-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)but-2-enamide | 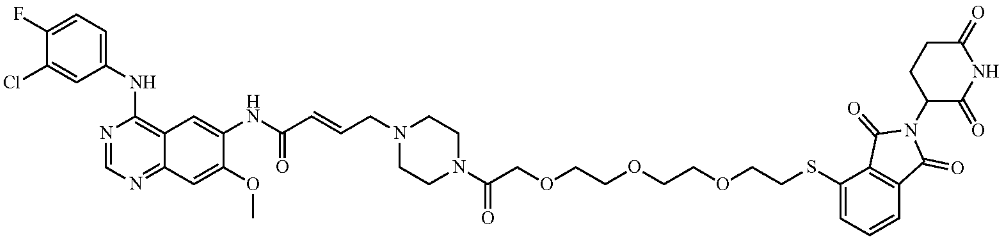 [SMILES: COc1cc2ncnc(Nc3ccc(F)c(Cl)c3)c2cc1NC(=O)/C=C/CN1CCN(C(=O)COCCOCCOCCSc2cccc3c2C(=O)N(C2CCC(=O)NC2=O)C3=O)CC1] |

TABLE 1-continued

| | Compound No. | The compounds' name | Structure of the compounds |
|---|---|---|---|
| 25 | SIAIS262007 | (E)-N-(4-((3-chloro-4-fluorophenyl)amino)-7-methoxyquinazolin-6-yl)-4-(4-(14-((2-(2,6-dioxopiperidin-3-yl)-1,3-dioxoisoindolin-4-yl)thio)-3,6,9,12-tetraoxatetradecanoyl)piperazin-1-yl)but-2-enamide | 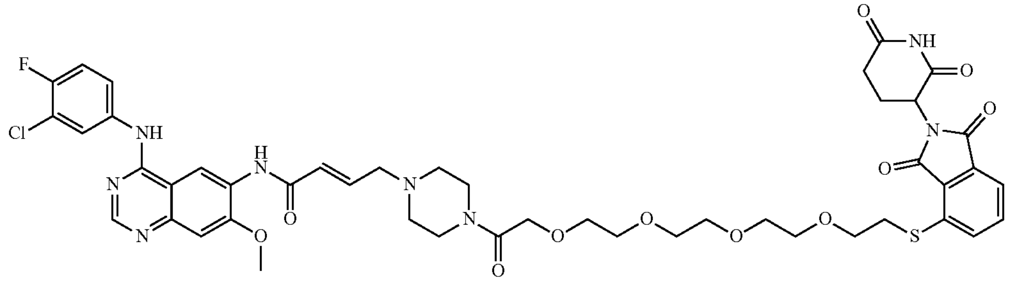 [SMILES: COc1cc2ncnc(Nc3ccc(F)c(Cl)c3)c2cc1NC(=O)/C=C/CN1CCN(C(=O)COCCOCCOCCOCCSc2cccc3c2C(=O)N(C2CCC(=O)NC2=O)C3=O)CC1] |
| 26 | SIAIS262008 | (E)-N-(4-((3-chloro-4-fluorophenyl)amino)-7-methoxyquinazolin-6-yl)-4-(4-(17-((2-(2,6-dioxopiperidin-3-yl)-1,3-dioxoisoindolin-4-yl)thio)-3,6,9,12,15-pentaoxaheptadecanoyl)piperazin-1-yl)but-2-enamide | 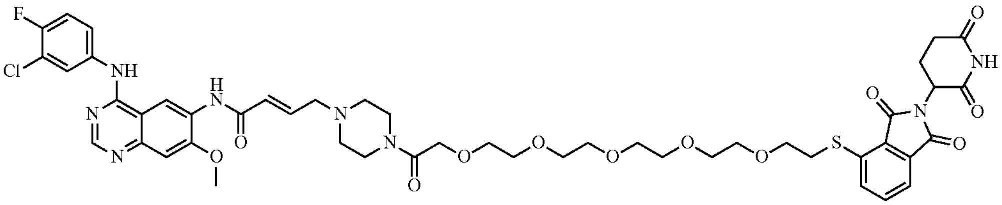 [SMILES: COc1cc2ncnc(Nc3ccc(F)c(Cl)c3)c2cc1NC(=O)/C=C/CN1CCN(C(=O)COCCOCCOCCOCCOCCSc2cccc3c2C(=O)N(C2CCC(=O)NC2=O)C3=O)CC1] |
| 27 | SIAIS219185 | (E)-N-(4-((3-chloro-4-fluorophenyl)amino)-7-methoxyquinazolin-6-yl)-4-(4-(2-((2-(2,6-dioxopiperidin-3-yl)-1-oxoisoindolin-4-yl)thio)acetyl)piperazin-1-yl)but-2-enamide | 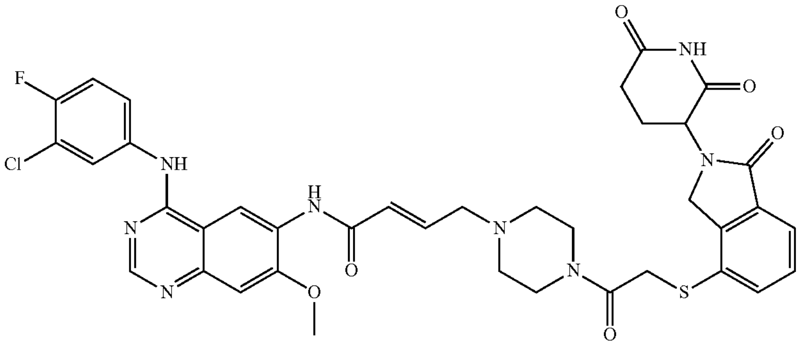 [SMILES: COc1cc2ncnc(Nc3ccc(F)c(Cl)c3)c2cc1NC(=O)/C=C/CN1CCN(C(=O)CSc2cccc3c2CN(C2CCC(=O)NC2=O)C3=O)CC1] |

TABLE 1-continued

| | Compound No. | The compounds' name | Structure of the compounds |
|---|---|---|---|
| 28 | SIAIS219186 | (E)-N-(4-((3-chloro-4-fluorophenyl)amino)-7-methoxyquinazolin-6-yl)-4-(4-(3-((2-(2,6-dioxopiperidin-3-yl)-1-oxoisoindolin-4-yl)thio)propanoyl)piperazin-1-yl)but-2-enamide | 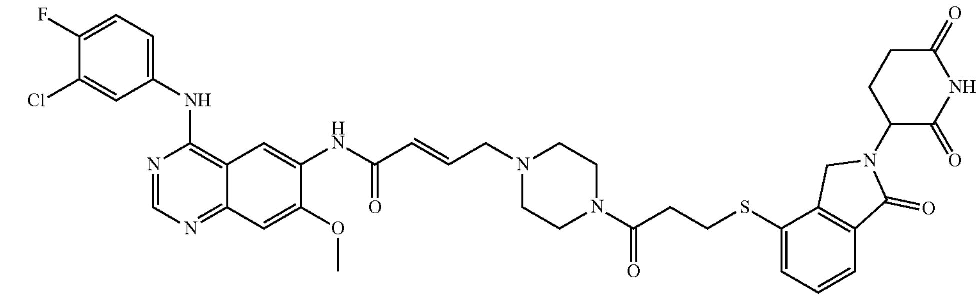 [SMILES: COc1cc2ncnc(Nc3ccc(F)c(Cl)c3)c2cc1NC(=O)/C=C/CN1CCN(C(=O)CCSc2cccc3c2CN(C2CCC(=O)NC2=O)C3=O)CC1] |
| 29 | SIAIS219187 | (E)-N-(4-((3-chloro-4-fluorophenyl)amino)-7-methoxyquinazolin-6-yl)-4-(4-(4-((2-(2,6-dioxopiperidin-3-yl)-1-oxoisoindolin-4-yl)thio)butanoyl)piperazin-1-yl)but-2-enamide | 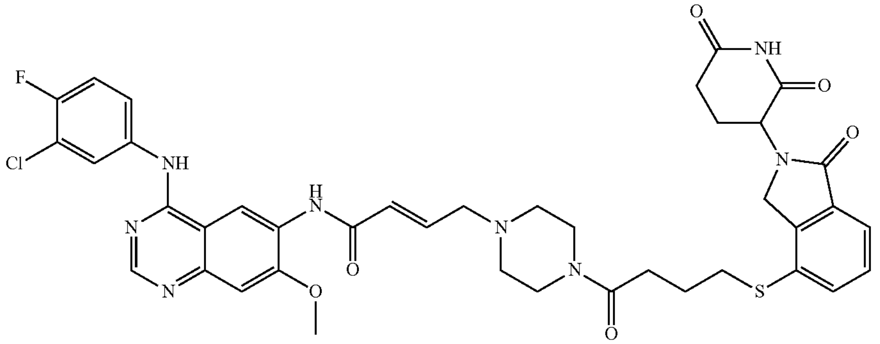 [SMILES: COc1cc2ncnc(Nc3ccc(F)c(Cl)c3)c2cc1NC(=O)/C=C/CN1CCN(C(=O)CCCSc2cccc3c2CN(C2CCC(=O)NC2=O)C3=O)CC1] |
| 30 | SIAIS219188 | (E)-N-(4-((3-chloro-4-fluorophenyl)amino)-7-methoxyquinazolin-6-yl)-4-(4-(5-((2-(2,6-dioxopiperidin-3-yl)-1-oxoisoindolin-4-yl)thio)pentanoyl)piperazin-1-yl)but-2-enamide | 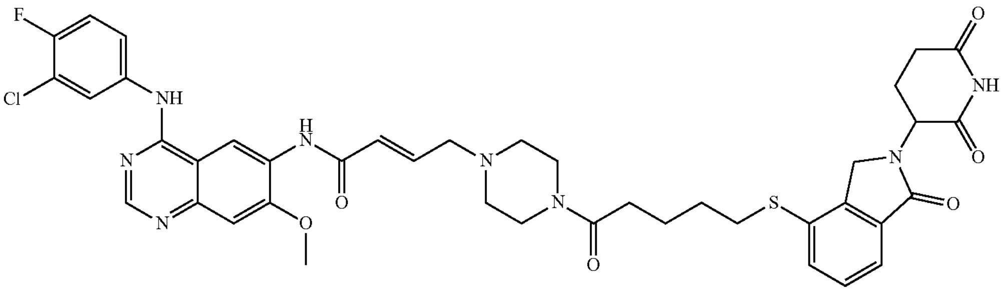 [SMILES: COc1cc2ncnc(Nc3ccc(F)c(Cl)c3)c2cc1NC(=O)/C=C/CN1CCN(C(=O)CCCCSc2cccc3c2CN(C2CCC(=O)NC2=O)C3=O)CC1] |

TABLE 1-continued

| Compound No. | | The compounds' name | Structure of the compounds |
|---|---|---|---|
| 31 | SIAIS219189 | (E)-N-(4-((3-chloro-4-fluorophenyl)amino)-7-methoxyquinazolin-6-yl)-4-(4-(6-((2-(2,6-dioxopiperidin-3-yl)-1-oxoisoindolin-4-yl)thio)hexanoyl)piperazin-1-yl)but-2-enamide | 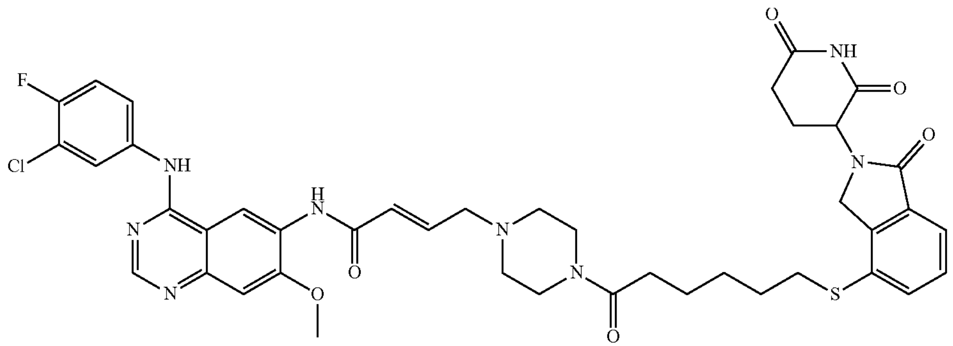 [SMILES: COc1cc2ncnc(Nc3ccc(F)c(Cl)c3)c2cc1NC(=O)/C=C/CN1CCN(C(=O)CCCCCSc2cccc3c2CN(C2CCC(=O)NC2=O)C3=O)CC1] |
| 32 | SIAIS219190 | (E)-N-(4-((3-chloro-4-fluorophenyl)amino)-7-methoxyquinazolin-6-yl)-4-(4-(7-((2-(2,6-dioxopiperidin-3-yl)-1-oxoisoindolin-4-yl)thio)heptanoyl)piperazin-1-yl)but-2-enamide | 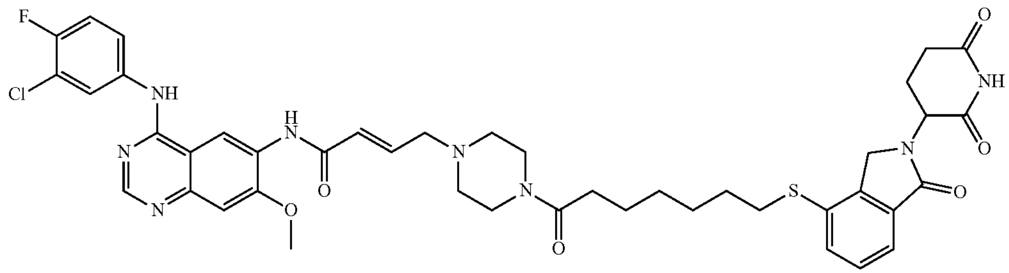 [SMILES: COc1cc2ncnc(Nc3ccc(F)c(Cl)c3)c2cc1NC(=O)/C=C/CN1CCN(C(=O)CCCCCCSc2cccc3c2CN(C2CCC(=O)NC2=O)C3=O)CC1] |
| 33 | SIAIS219193 | (E)-N-(4-((3-chloro-4-fluorophenyl)amino)-7-methoxyquinazolin-6-yl)-4-(4-(2-(2-((2-(2,6-dioxopiperidin-3-yl)-1-oxoisoindolin-4-yl)thio)ethoxy)acetyl)piperazin-1-yl)but-2-enamide | 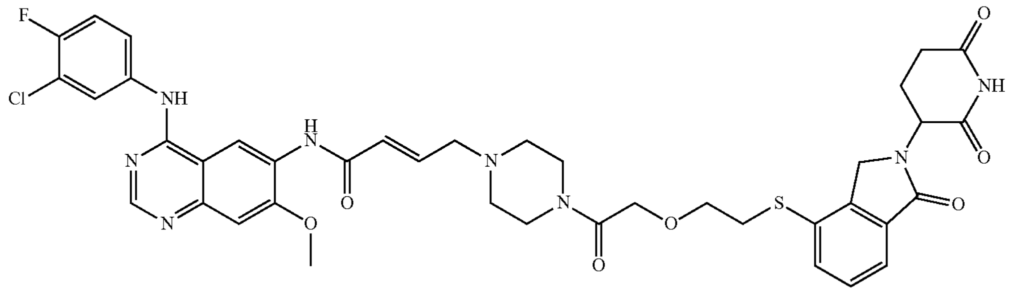 |

TABLE 1-continued

| | Compound No. | The compounds' name | Structure of the compounds |
|---|---|---|---|
| 34 | SIAIS262001 | (E)-N-(4-((3-chloro-4-fluorophenyl)amino)-7-methoxyquinazolin-6-yl)-4-(4-(2-(2-(2-((2-(2,6-dioxopiperidin-3-yl)-1-oxoisoindolin-4-yl)thio)ethoxy)ethoxy)acetyl)piperazin-1-yl)but-2-enamide | 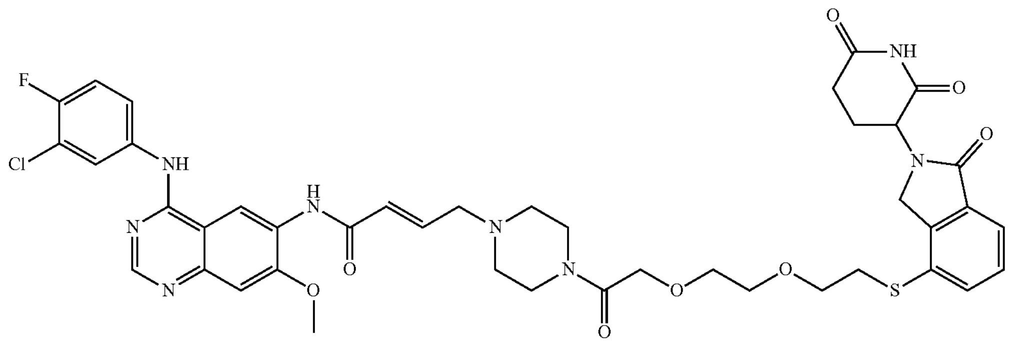 [SMILES: COc1cc2ncnc(Nc3ccc(F)c(Cl)c3)c2cc1NC(=O)/C=C/CN1CCN(C(=O)COCCOCCSc2cccc3c2CN(C2CCC(=O)NC2=O)C3=O)CC1] |
| 35 | SIAIS262002 | (E)-N-(4-((3-chloro-4-fluorophenyl)amino)-7-methoxyquinazolin-6-yl)-4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)but-2-enamide | 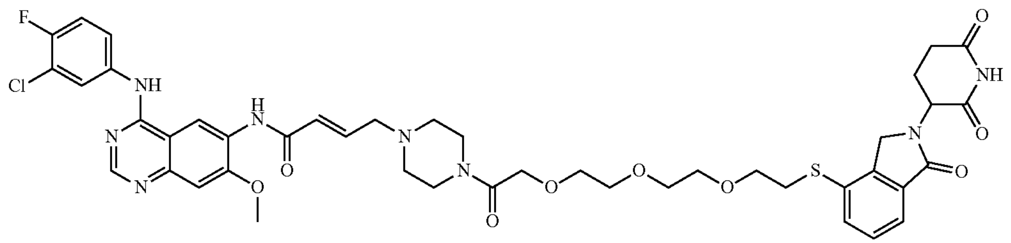 [SMILES: COc1cc2ncnc(Nc3ccc(F)c(Cl)c3)c2cc1NC(=O)/C=C/CN1CCN(C(=O)COCCOCCOCCSc2cccc3c2CN(C2CCC(=O)NC2=O)C3=O)CC1] |
| 36 | SIAIS262003 | (E)-N-(4-((3-chloro-4-fluorophenyl)amino)-7-methoxyquinazolin-6-yl)-4-(4-(14-((2-(2,6-dioxopiperidin-3-yl)-1-oxoisoindolin-4-yl)thio)-3,6,9,12-tetraoxatetradecan-1-oyl)piperazin-1-yl)but-2-enamide | 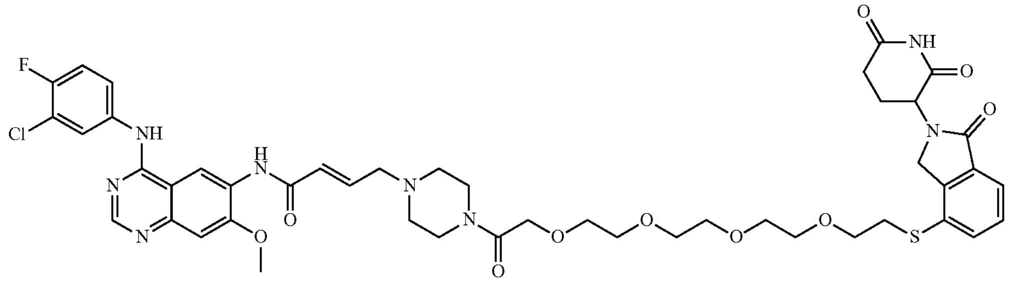 [SMILES: COc1cc2ncnc(Nc3ccc(F)c(Cl)c3)c2cc1NC(=O)/C=C/CN1CCN(C(=O)COCCOCCOCCOCCSc2cccc3c2CN(C2CCC(=O)NC2=O)C3=O)CC1] |

TABLE 1-continued

| | Compound No. | The compounds' name | Structure of the compounds |
|---|---|---|---|
| 37 | SIAIS262004 | (E)-N-(4-((3-chloro-4-fluorophenyl)amino)-7-methoxyquinazolin-6-yl)-4-(4-(17-((2-(2,6-dioxopiperidin-3-yl)-1-oxoisoindolin-4-yl)thio)-3,6,9,12,15-pentaoxaheptadecan-1-oyl)piperazin-1-yl)but-2-enamide | 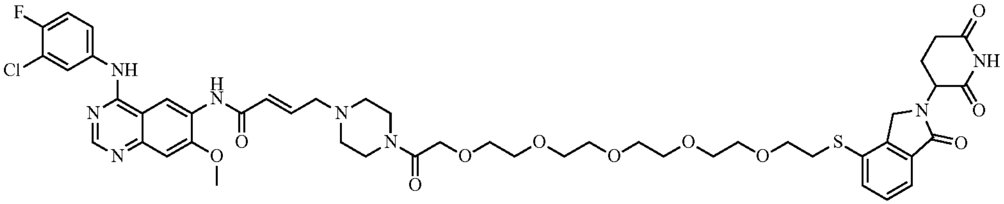 [SMILES: COc1cc2ncnc(Nc3ccc(F)c(Cl)c3)c2cc1NC(=O)/C=C/CN1CCN(C(=O)COCCOCCOCCOCCOCCSc2cccc3c2CN(C2CCC(=O)NC2=O)C3=O)CC1] |
| 38 | SIAIS249045 | (2S,4R)-1-((S)-2-(3-(2-(3-(4-((E)-4-((4-((3-chloro-4-fluorophenyl)amino)-7-methoxyquinazolin-6-yl)amino)-4-oxobut-2-en-1-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide | 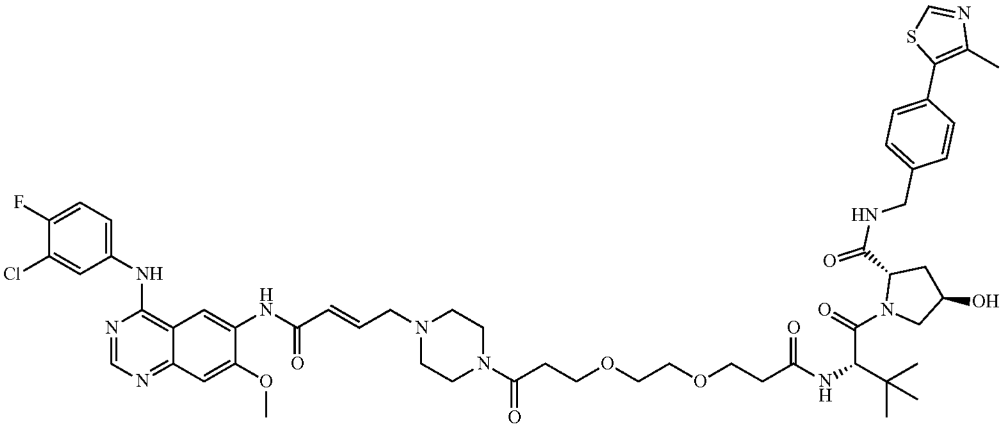 [SMILES: COc1cc2ncnc(Nc3ccc(F)c(Cl)c3)c2cc1NC(=O)/C=C/CN1CCN(C(=O)CCOCCOCCC(=O)N[C@H](C(=O)N2C[C@H](O)C[C@H]2C(=O)NCc2ccc(-c3scnc3C)cc2)C(C)(C)C)CC1] |

TABLE 1-continued

| Compound No. | | The compounds' name | Structure of the compounds |
|---|---|---|---|
| 39 | SIAIS249041 | (2S,4R)-1-((S)-2-(4-(4-((E)-4-((4-((3-chloro-4-fluorophenyl)amino)-7-methoxyquinazolin-6-yl)amino)-4-oxobut-2-en-1-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide | 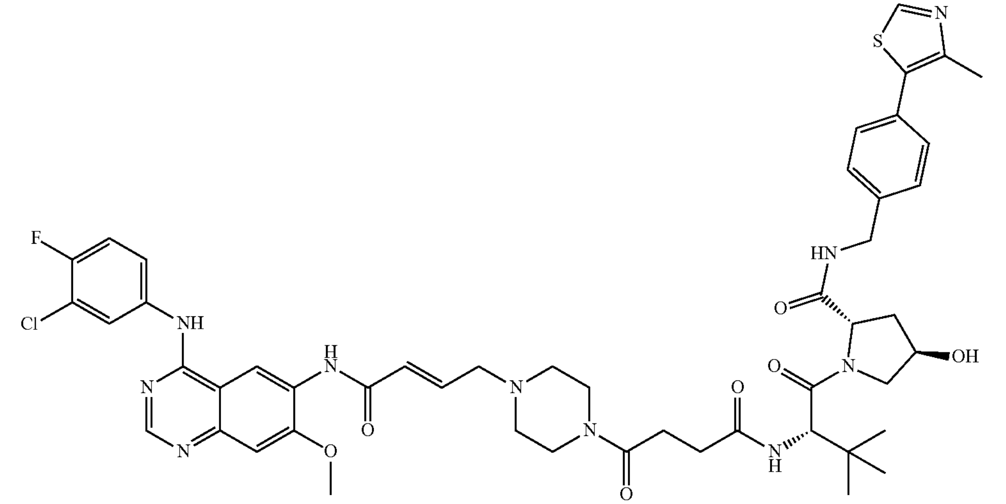 [SMILES: COc1cc2ncnc(Nc3ccc(F)c(Cl)c3)c2cc1NC(=O)/C=C/CN1CCN(C(=O)CCC(=O)N[C@H](C(=O)N2C[C@H](O)C[C@H]2C(=O)NCc2ccc(-c3scnc3C)cc2)C(C)(C)C)CC1] |
| 40 | SIAIS249042 | (2S,4R)-1-((S)-2-(6-(4-((E)-4-((4-((3-chloro-4-fluorophenyl)amino)-7-methoxyquinazolin-6-yl)amino)-4-oxobut-2-en-1-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide | 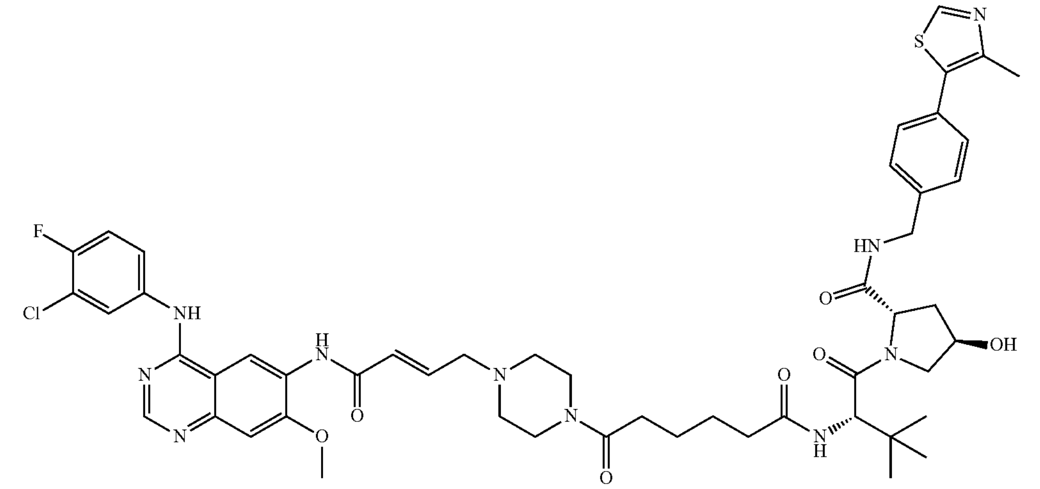 [SMILES: COc1cc2ncnc(Nc3ccc(F)c(Cl)c3)c2cc1NC(=O)/C=C/CN1CCN(C(=O)CCCCC(=O)N[C@H](C(=O)N2C[C@H](O)C[C@H]2C(=O)NCc2ccc(-c3scnc3C)cc2)C(C)(C)C)CC1] |

TABLE 1-continued

| Compound No. | The compounds' name | Structure of the compounds |
|---|---|---|
| 41 (SIAIS249043 | (2S,4R)-1-((S)-2-(8-(4-((E)-4-((4-((3-chloro-4-fluorophenyl)amino)-7-methoxyquinazolin-6-yl)amino)-4-oxobut-2-en-1-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide | 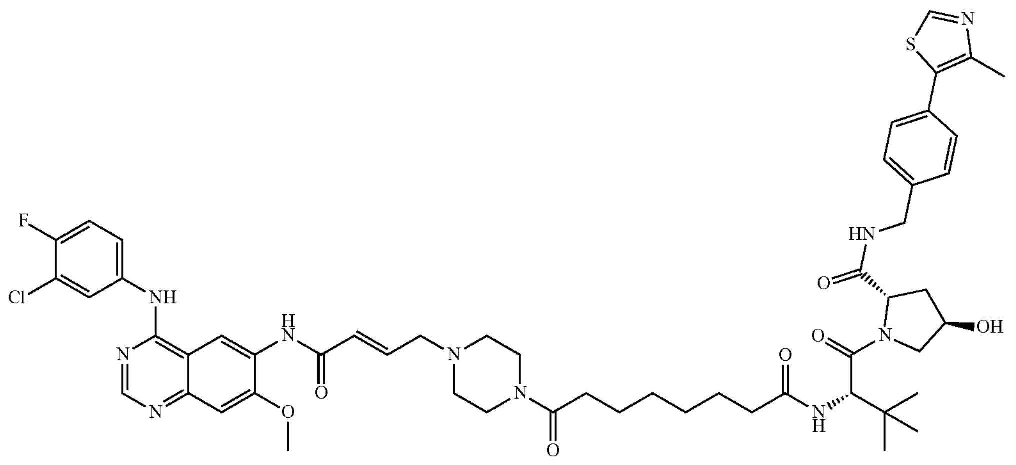 [SMILES: COc1cc2ncnc(Nc3ccc(F)c(Cl)c3)c2cc1NC(=O)/C=C/CN1CCN(C(=O)CCCCCCC(=O)N[C@H](C(=O)N2C[C@H](O)C[C@H]2C(=O)NCc2ccc(-c3scnc3C)cc2)C(C)(C)C)CC1] |
| 42 SIAIS262032 | (E)-N-(4-((3-chloro-4-fluorophenyl)amino)-7-methoxyquinazolin-6-yl)-4-(4-(4-(6-((2-(2,6-dioxopiperidin-3-yl)-1,3-dioxoisoindolin-4-yl)thio)hexanoyl)piperazin-1-yl)piperidin-1-yl)but-2-enamide | 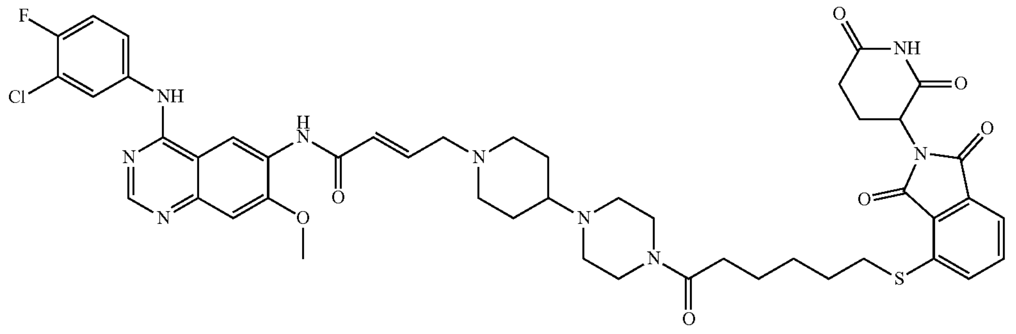 |

TABLE 1-continued

| Compound No. | | The compounds' name | Structure of the compounds |
|---|---|---|---|
| 43 | SIAI262033S | (E)-N-(4-((3-chloro-4-fluorophenyl)amino)-7-methoxyquinazolin-6-yl)-4-(4-(4-(7-((2-(2,6-dioxopiperidin-3-yl)-1,3-dioxoisoindolin-4-yl)thio)heptanoyl)piperazin-1-yl)piperidin-1-yl)but-2-enamide | 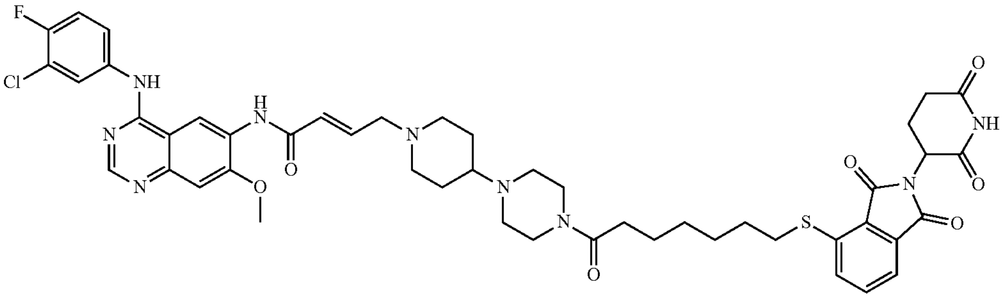 [SMILES: COc1cc2ncnc(Nc3ccc(F)c(Cl)c3)c2cc1NC(=O)/C=C/CN1CCC(N2CCN(C(=O)CCCCCCSc3cccc4c3C(=O)N(C3CCC(=O)NC3=O)C4=O)CC2)CC1] |
| 44 | SIAIS262034 | (E)-N-(4-((3-chloro-4-fluorophenyl)amino)-7-methoxyquinazolin-6-yl)-4-(4-(4-(2-((2-(2,6-dioxopiperidin-3-yl)-1-oxoisoindolin-4-yl)thio)acetyl)piperazin-1-yl)piperidin-1-yl)but-2-enamide | 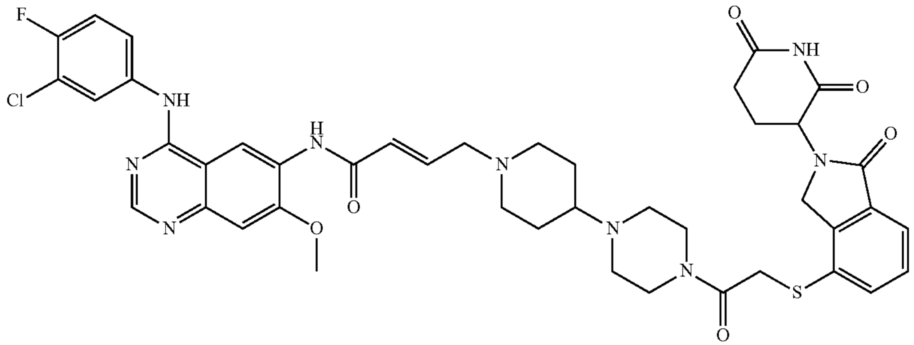 |
| 45 | SIAIS262035 | (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)thio)hexanoyl)piperazin-1-yl)piperidin-1-yl)but-2-enamide | 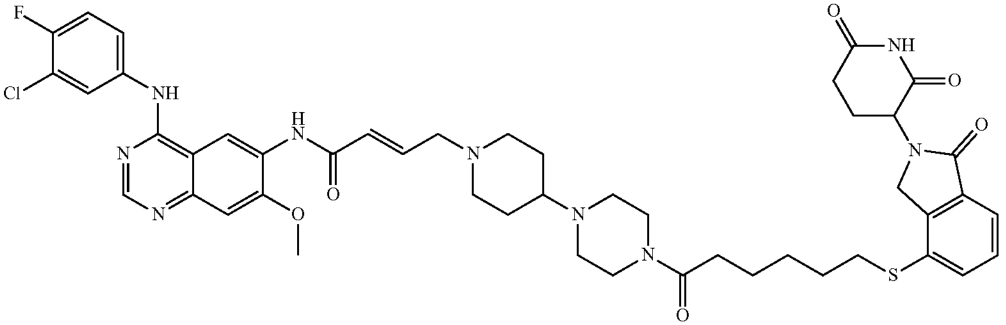 [SMILES: COc1cc2ncnc(Nc3ccc(F)c(Cl)c3)c2cc1NC(=O)/C=C/CN1CCC(N2CCN(C(=O)CCCCCSc3cccc4c3CN(C3CCC(=O)NC3=O)C4=O)CC2)CC1] |

TABLE 1-continued

| Compound No. | | The compounds' name | Structure of the compounds |
|---|---|---|---|
| 46 | SIAIS262036 | (E)-N-(4-((3-chloro-4-fluorophenyl)amino)-7-methoxyquinazolin-6-yl)-4-(4-(4-(2-((2-(2,6-dioxopiperidin-3-yl)-1,3-dioxoisoindolin-4-yl)amino)acetyl)piperazin-1-yl)piperidin-1-yl)but-2-enamide | 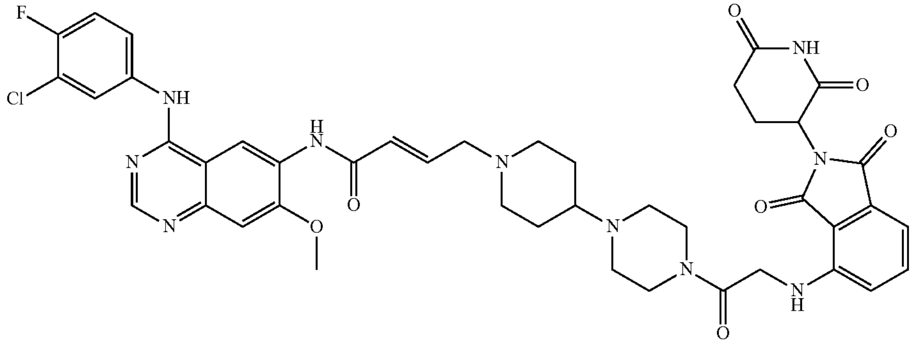 [SMILES: COc1cc2ncnc(Nc3ccc(F)c(Cl)c3)c2cc1NC(=O)/C=C/CN1CCC(N2CCN(C(=O)CNc3cccc4c3C(=O)N(C3CCC(=O)NC3=O)C4=O)CC2)CC1] |
| 47 | SIAIS262037 | (E)-N-(4-((3-chloro-4-fluorophenyl)amino)-7-methoxyquinazolin-6-yl)-4-(4-(4-(7-((2-(2,6-dioxopiperidin-3-yl)-1,3-dioxoisoindolin-4-yl)amino)heptanoyl)piperazin-1-yl)piperidin-1-yl)but-2-enamide | 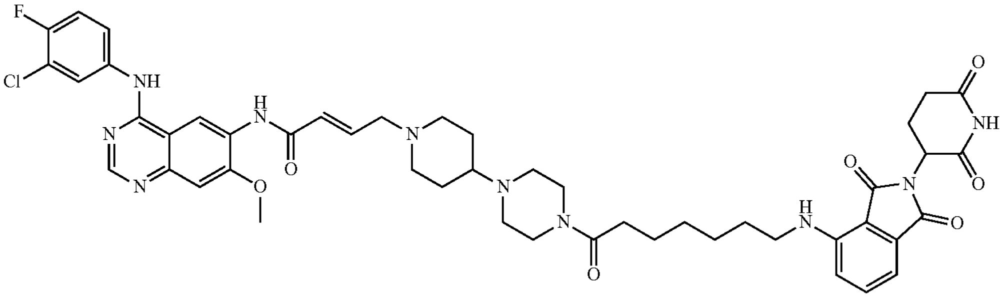 [SMILES: COc1cc2ncnc(Nc3ccc(F)c(Cl)c3)c2cc1NC(=O)/C=C/CN1CCC(N2CCN(C(=O)CCCCCCNc3cccc4c3C(=O)N(C3CCC(=O)NC3=O)C4=O)CC2)CC1] |
| 48 | SIAIS262052 | (E)-N-(4-((3-chloro-4-fluorophenyl)amino)-7-methoxyquinazolin-6-yl)-4-(4-(4-(3-(2-(2,6-dioxopiperidin-3-yl)-1-oxoisoindolin-4-yl)propanoyl)piperazin-1-yl)piperidin-1-yl)but-2-enamide | 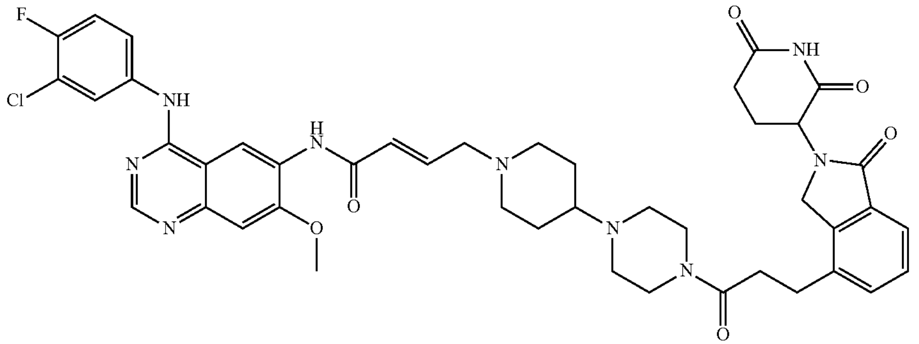 [SMILES: COc1cc2ncnc(Nc3ccc(F)c(Cl)c3)c2cc1NC(=O)/C=C/CN1CCC(N2CCN(C(=O)CCc3cccc4c3CN(C3CCC(=O)NC3=O)C4=O)CC2)CC1] |

TABLE 1-continued

| Compound No. | | The compounds' name | Structure of the compounds |
|---|---|---|---|
| 49 | SIAIS249029 | 4-((2-(3-(4-((4-((3,4-dichloro-2-fluorophenyl)amino)-7-methoxyquinazolin-6-yl)oxy)piperidin-1-yl)-3-oxopropoxy)ethyl)amino)-2-(2,6-dioxopiperidin-3-yl)isoindoline-1,3-dione | 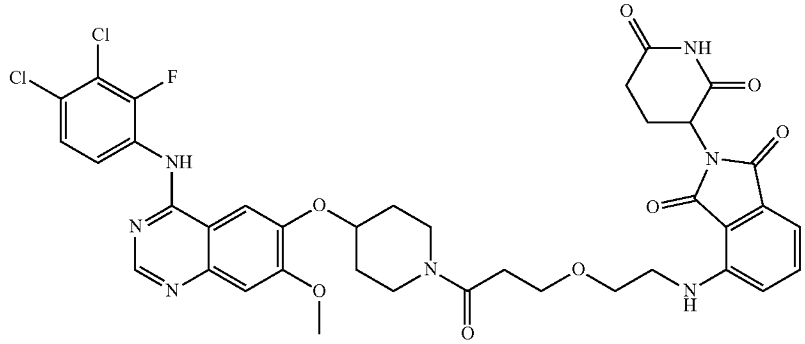 |
| 50 | SIAIS249030 | 4-((2-(2-(3-(4-((4-((3,4-dichloro-2-fluorophenyl)amino)-7-methoxyquinazolin-6-yl)oxy)piperidin-1-yl)-3-oxopropoxy)ethoxy)ethyl)amino)-2-(2,6-dioxopiperidin-3-yl)isoindoline-1,3-dione | 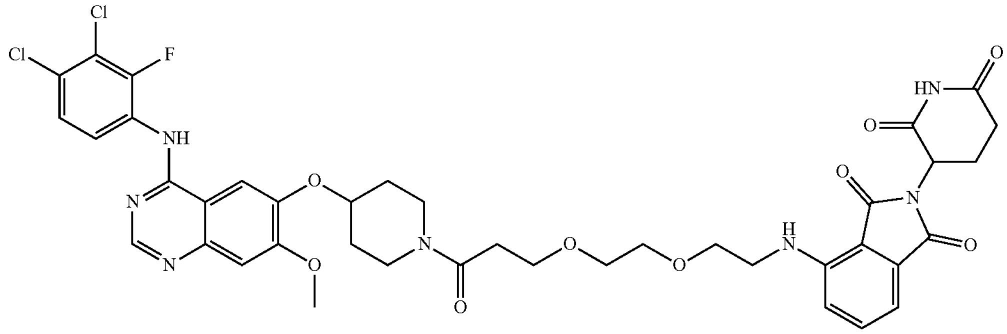 [SMILES: COc1cc2ncnc(Nc3ccc(Cl)c(Cl)c3F)c2cc1OC1CCN(C(=O)CCOCCOCCNc2cccc3c2C(=O)N(C2CCC(=O)NC2=O)C3=O)CC1] |
| 51 | SIAIS249031 | 4-((2-(2-(2-(3-(4-((4-((3,4-dichloro-2-fluorophenyl)amino)-7-methoxyquinazolin-6-yl)oxy)piperidin-1-yl)-3-oxopropoxy)ethoxy)ethoxy)ethyl)amino)-2-(2,6-dioxopiperidin-3-yl)isoindoline-1,3-dione | 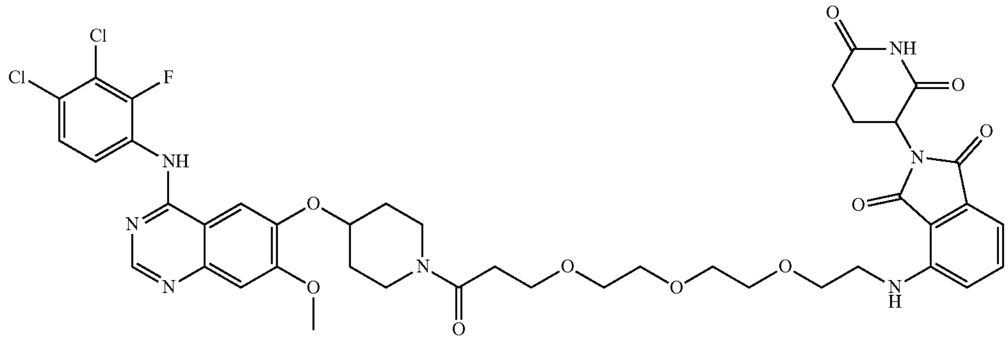 [SMILES: COc1cc2ncnc(Nc3ccc(Cl)c(Cl)c3F)c2cc1OC1CCN(C(=O)CCOCCOCCOCCNc2cccc3c2C(=O)N(C2CCC(=O)NC2=O)C3=O)CC1] |

TABLE 1-continued

| | Compound No. | The compounds' name | Structure of the compounds |
|---|---|---|---|
| 52 | SIAIS249032 | 4-((15-(4-((4-((3,4-dichloro-2-fluorophenyl)amino)-7-methoxyquinazolin-6-yl)oxy)piperidin-1-yl)-15-oxo-3,6,9,12-tetraoxapentadecyl)amino)-2-(2,6-dioxopiperidin-3-yl)isoindoline-1,3-dione | 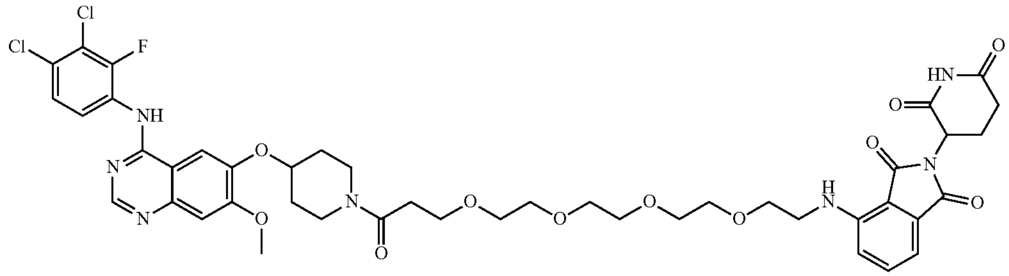 [SMILES: COc1cc2ncnc(Nc3ccc(Cl)c(Cl)c3F)c2cc1OC1CCN(C(=O)CCOCCOCCOCCOCCNc2cccc3c2C(=O)N(C2CCC(=O)NC2=O)C3=O)CC1] |
| 53 | SIAIS249033 | 4-((18-(4-((4-((3,4-dichloro-2-fluorophenyl)amino)-7-methoxyquinazolin-6-yl)oxy)piperidin-1-yl)-18-oxo-3,6,9,12,15-pentaoxaoctadecyl)amino)-2-(2,6-dioxopiperidin-3-yl)isoindoline-1,3-dione | 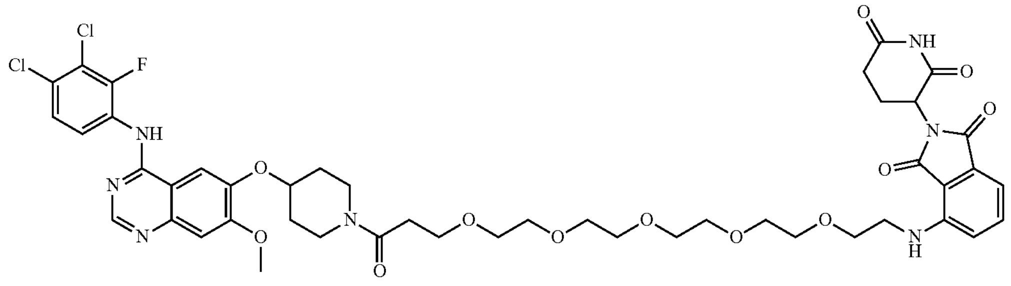 [SMILES: COc1cc2ncnc(Nc3ccc(Cl)c(Cl)c3F)c2cc1OC1CCN(C(=O)CCOCCOCCOCCOCCOCCNc2cccc3c2C(=O)N(C2CCC(=O)NC2=O)C3=O)CC1] |
| 54 | SIAIS219177 | 4-((2-(4-((4-((3,4-dichloro-2-fluorophenyl)amino)-7-methoxyquinazolin-6-yl)oxy)piperidin-1-yl)-2-oxoethyl)amino)-2-(2,6-dioxopiperidin-3-yl)isoindoline-1,3-dione | 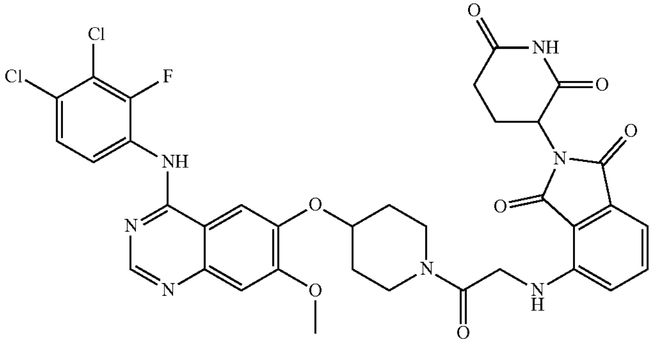 [SMILES: COc1cc2ncnc(Nc3ccc(Cl)c(Cl)c3F)c2cc1OC1CCN(C(=O)CNc2cccc3c2C(=O)N(C2CCC(=O)NC2=O)C3=O)CC1] |

TABLE 1-continued
| Compound No. | | The compounds' name | Structure of the compounds |
|---|---|---|---|
| 55 | SIAIS219179 | 4-((4-(4-((4-((3,4-dichloro-2-fluorophenyl)amino)-7-methoxyquinazolin-6-yl)oxy)piperidin-1-yl)-4-oxobutyl)amino)-2-(2,6-dioxopiperidin-3-yl)isoindoline-1,3-dione | 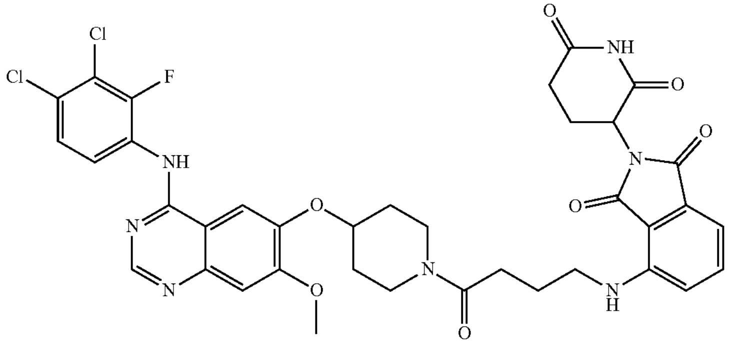 [SMILES: COc1cc2ncnc(Nc3ccc(Cl)c(Cl)c3F)c2cc1OC1CCN(C(=O)CCCNc2cccc3c2C(=O)N(C2CCC(=O)NC2=O)C3=O)CC1] |
| 56 | SIAIS219180 | 4-((5-(4-((4-((3,4-dichloro-2-fluorophenyl)amino)-7-methoxyquinazolin-6-yl)oxy)piperidin-1-yl)-5-oxopentyl)amino)-2-(2,6-dioxopiperidin-3-yl)isoindoline-1,3-dione | 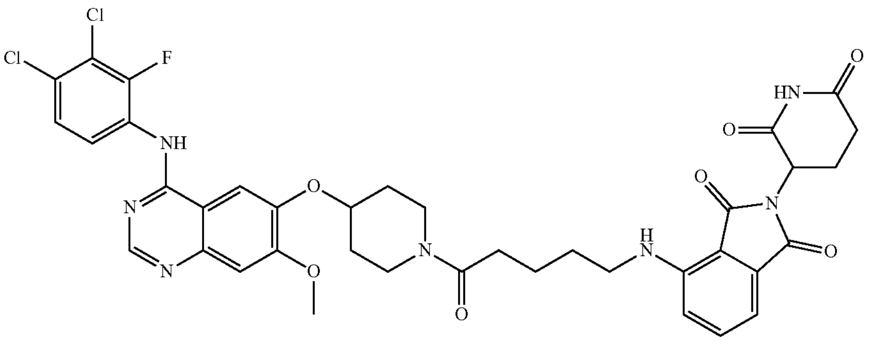 [SMILES: COc1cc2ncnc(Nc3ccc(Cl)c(Cl)c3F)c2cc1OC1CCN(C(=O)CCCCNc2cccc3c2C(=O)N(C2CCC(=O)NC2=O)C3=O)CC1] |

TABLE 1-continued
| | Compound No. | The compounds' name | Structure of the compounds |
|---|---|---|---|
| 57 | SIAIS219181 | 4-((6-(4-((4-((3,4-dichloro-2-fluorophenyl)amino)-7-methoxyquinazolin-6-yl)oxy)piperidin-1-yl)-6-oxohexyl)amino)-2-(2,6-dioxopiperidin-3-yl)isoindoline-1,3-dione | 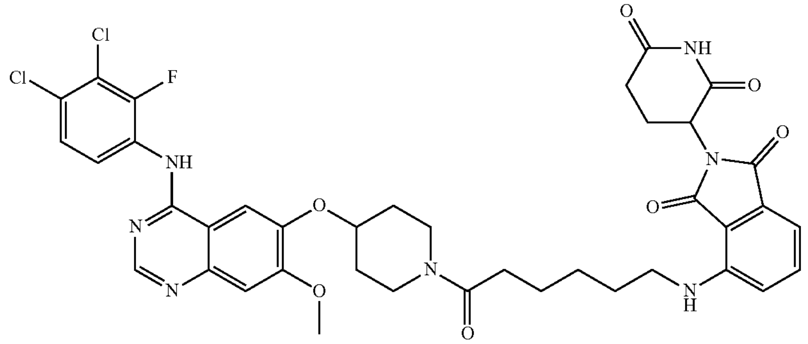 |
| 58 | SIAIS249014 | 4-((2-(4-((4-((3,4-dichloro-2-fluorophenyl)amino)-7-methoxyquinazolin-6-yl)oxy)piperidin-1-yl)-2-oxoethyl)thio)-2-(2,6-dioxopiperidin-3-yl)isoindoline-1,3-dione | 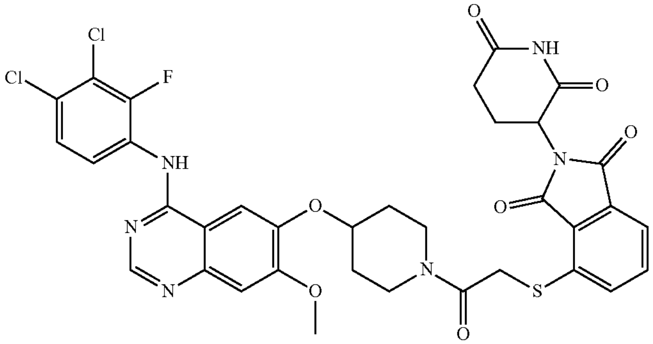 [SMILES: COc1cc2ncnc(Nc3ccc(Cl)c(Cl)c3F)c2cc1OC1CCN(C(=O)CSc2cccc3c2C(=O)N(C2CCC(=O)NC2=O)C3=O)CC1] |

TABLE 1-continued

| Compound No. | | The compounds' name | Structure of the compounds |
|---|---|---|---|
| 59 | SIAIS249015 | 4-((3-(4-((4-((3,4-dichloro-2-fluorophenyl)amino)-7-methoxyquinazolin-6-yl)oxy)piperidin-1-yl)-3-oxopropyl)thio)-2-(2,6-dioxopiperidin-3-yl)isoindoline-1,3-dione | 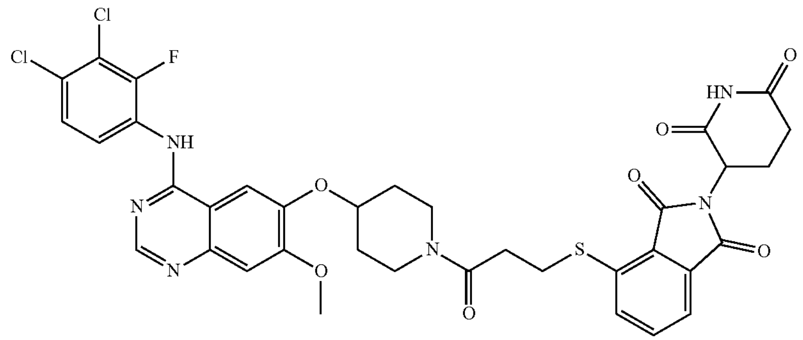 [SMILES: COc1cc2ncnc(Nc3ccc(Cl)c(Cl)c3F)c2cc1OC1CCN(C(=O)CCSc2cccc3c2C(=O)N(C2CCC(=O)NC2=O)C3=O)CC1] |
| 60 | SIAIS249016 | 4-((4-(4-((4-((3,4-dichloro-2-fluorophenyl)amino)-7-methoxyquinazolin-6-yl)oxy)piperidin-1-yl)-4-oxobutyl)thio)-2-(2,6-dioxopiperidin-3-yl)isoindoline-1,3-dione | 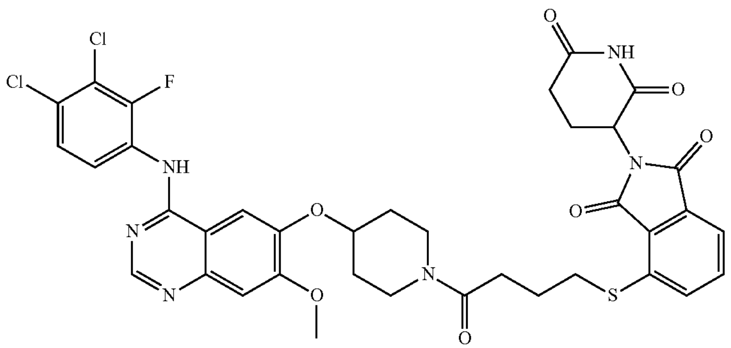 [SMILES: COc1cc2ncnc(Nc3ccc(Cl)c(Cl)c3F)c2cc1OC1CCN(C(=O)CCCSc2cccc3c2C(=O)N(C2CCC(=O)NC2=O)C3=O)CC1] |
| 61 | SIAIS249017 | 4-((5-(4-((4-((3,4-dichloro-2-fluorophenyl)amino)-7-methoxyquinazolin-6-yl)oxy)piperidin-1-yl)-5-oxopentyl)thio)-2-(2,6-dioxopiperidin-3-yl)isoindoline-1,3-dione | 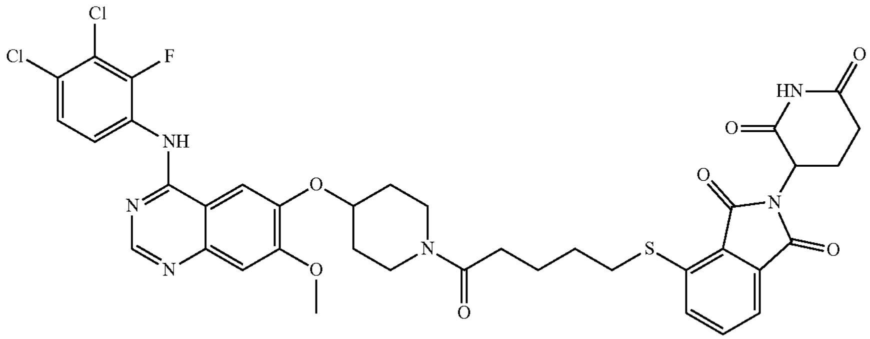 [SMILES: COc1cc2ncnc(Nc3ccc(Cl)c(Cl)c3F)c2cc1OC1CCN(C(=O)CCCCSc2cccc3c2C(=O)N(C2CCC(=O)NC2=O)C3=O)CC1] |

TABLE 1-continued
| Compound No. | | The compounds' name | Structure of the compounds |
|---|---|---|---|
| 62 | SIAIS249018 | 4-((6-(4-((4-((3,4-dichloro-2-fluorophenyl)amino)-7-methoxyquinazolin-6-yl)oxy)piperidin-1-yl)-6-oxohexyl)thio)-2-(2,6-dioxopiperidin-3-yl)isoindoline-1,3-dione | 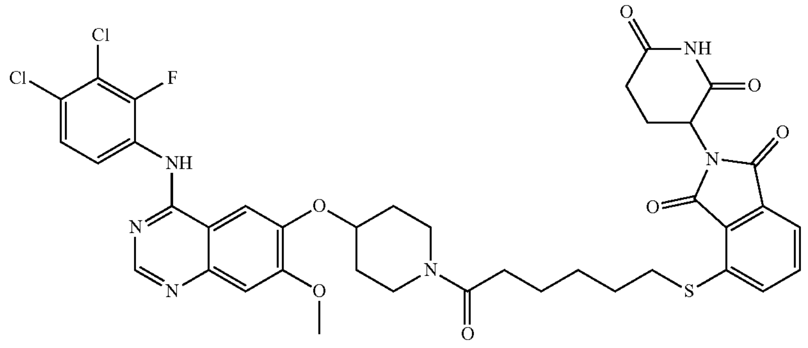 [SMILES: COc1cc2ncnc(Nc3ccc(Cl)c(Cl)c3F)c2cc1OC1CCN(C(=O)CCCCCSc2cccc3c2C(=O)N(C2CCC(=O)NC2=O)C3=O)CC1] |
| 63 | SIAIS249019 | 4-((7-(4-((4-((3,4-dichloro-2-fluorophenyl)amino)-7-methoxyquinazolin-6-yl)oxy)piperidin-1-yl)-7-oxoheptyl)thio)-2-(2,6-dioxopiperidin-3-yl)isoindoline-1,3-dione | 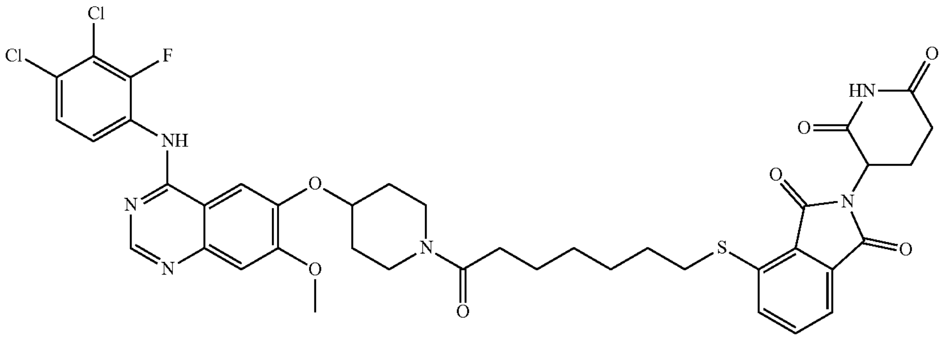 [SMILES: COc1cc2ncnc(Nc3ccc(Cl)c(Cl)c3F)c2cc1OC1CCN(C(=O)CCCCCCSc2cccc3c2C(=O)N(C2CCC(=O)NC2=O)C3=O)CC1] |

TABLE 1-continued
| | Compound No. | The compounds' name | Structure of the compounds |
|---|---|---|---|
| 64 | SIAIS219164 | 3-(4-((2-(4-((4-((3,4-dichloro-2-fluorophenyl)amino)-7-methoxyquinazolin-6-yl)oxy)piperidin-1-yl)-2-oxoethyl)thio)-1-oxoisoindolin-2-yl)piperidine-2,6-dione | 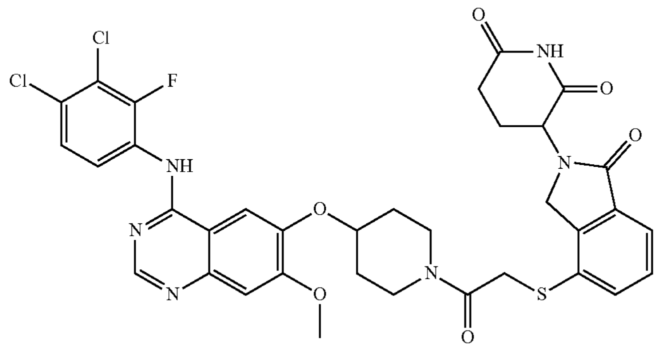 [SMILES: COc1cc2ncnc(Nc3ccc(Cl)c(Cl)c3F)c2cc1OC1CCN(C(=O)CSc2cccc3c2CN(C2CCC(=O)NC2=O)C3=O)CC1] |
| 65 | SIAIS219165 | 3-(4-((3-(4-((4-((3,4-dichloro-2-fluorophenyl)amino)-7-methoxyquinazolin-6-yl)oxy)piperidin-1-yl)-3-oxopropyl)thio)-1-oxoisoindolin-2-yl)piperidine-2,6-dione | 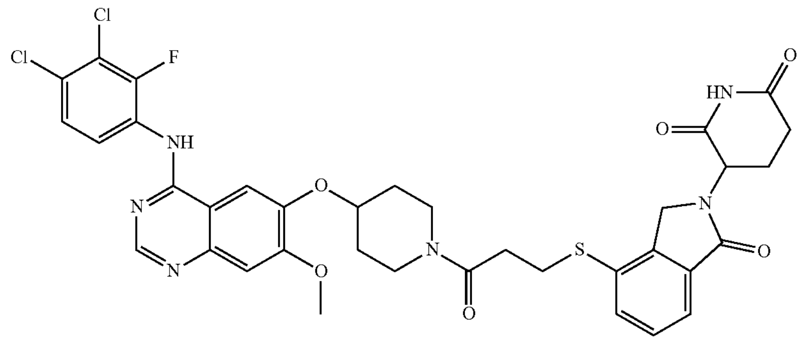 [SMILES: COc1cc2ncnc(Nc3ccc(Cl)c(Cl)c3F)c2cc1OC1CCN(C(=O)CCSc2cccc3c2CN(C2CCC(=O)NC2=O)C3=O)CC1] |

TABLE 1-continued
| Compound No. | The compounds' name | Structure of the compounds |
|---|---|---|
| 66 (SIAIS219166 | 3-(4-((4-(4-((4-((3,4-dichloro-2-fluorophenyl)amino)-7-methoxyquinazolin-6-yl)oxy)piperidin-1-yl)-4-oxobutyl)thio)-1-oxoisoindolin-2-yl)piperidine-2,6-dione | 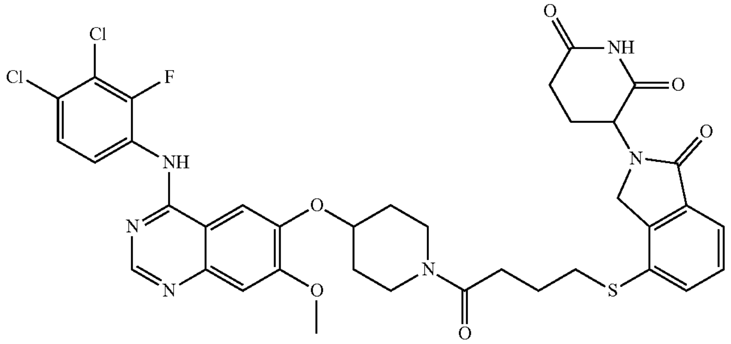 [SMILES: COc1cc2ncnc(Nc3ccc(Cl)c(Cl)c3F)c2cc1OC1CCN(C(=O)CCCSc2cccc3c2CN(C2CCC(=O)NC2=O)C3=O)CC1] |
| 67 SIAIS219167 | 3-(4-((5-(4-((4-((3,4-dichloro-2-fluorophenyl)amino)-7-methoxyquinazolin-6-yl)oxy)piperidin-1-yl)-5-oxopentyl)thio)-1-oxoisoindolin-2-yl)piperidine-2,6-dione | 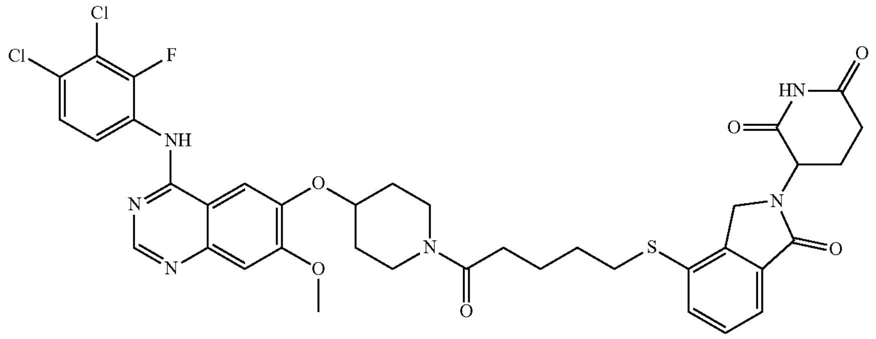 [SMILES: COc1cc2ncnc(Nc3ccc(Cl)c(Cl)c3F)c2cc1OC1CCN(C(=O)CCCCSc2cccc3c2CN(C2CCC(=O)NC2=O)C3=O)CC1] |

TABLE 1-continued
| | Compound No. | The compounds' name | Structure of the compounds |
|---|---|---|---|
| 68 | SIAIS219168 | 3-(4-((6-(4-((4-((3,4-dichloro-2-fluorophenyl)amino)-7-methoxyquinazolin-6-yl)oxy)piperidin-1-yl)-6-oxohexyl)thio)-1-oxoisoindolin-2-yl)piperidine-2,6-dione | 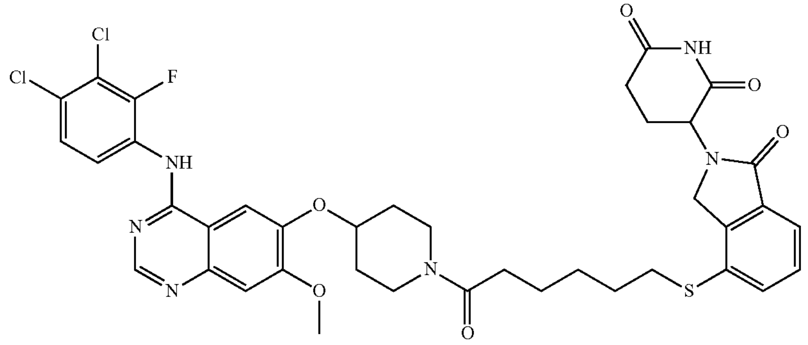 [SMILES: COc1cc2ncnc(Nc3ccc(Cl)c(Cl)c3F)c2cc1OC1CCN(C(=O)CCCCCSc2cccc3c2CN(C2CCC(=O)NC2=O)C3=O)CC1] |
| 69 | SIAIS219169 | 3-(4-((7-(4-((4-((3,4-dichloro-2-fluorophenyl)amino)-7-methoxyquinazolin-6-yl)oxy)piperidin-1-yl)-7-oxoheptyl)thio)-1-oxoisoindolin-2-yl)piperidine-2,6-dione | 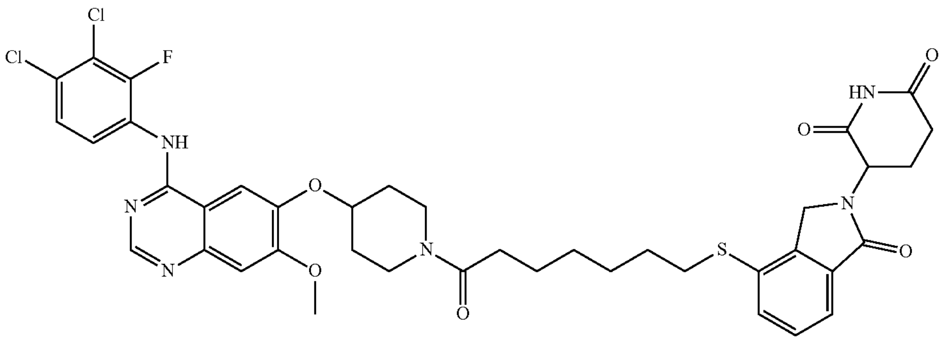 [SMILES: COc1cc2ncnc(Nc3ccc(Cl)c(Cl)c3F)c2cc1OC1CCN(C(=O)CCCCCCSc2cccc3c2CN(C2CCC(=O)NC2=O)C3=O)CC1] |

TABLE 1-continued

| Compound No. | | The compounds' name | Structure of the compounds |
|---|---|---|---|
| 70 | SIAIS249024 | (2S,4R)-1-((S)-2-(2-(2-(2-(4-((4-((3,4-dichloro-2-fluorophenyl)amino)-7-methoxyquinazolin-6-yl)oxy)piperidin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide | 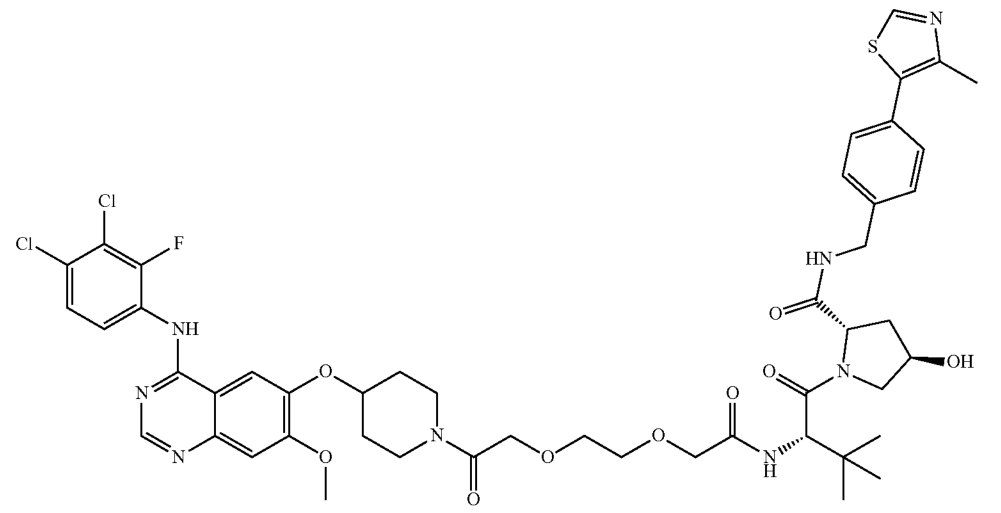 [SMILES: COc1cc2ncnc(Nc3ccc(Cl)c(Cl)c3F)c2cc1OC1CCN(C(=O)COCCOCC(=O)N[C@H](C(=O)N2C[C@H](O)C[C@H]2C(=O)NCc2ccc(-c3scnc3C)cc2)C(C)(C)C)CC1] |
| 71 | SIAIS249025 | (2S,4R)-1-((S)-2-(3-(2-(3-(4-((4-((3,4-dichloro-2-fluorophenyl)amino)-7-methoxyquinazolin-6-yl)oxy)piperidin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide | 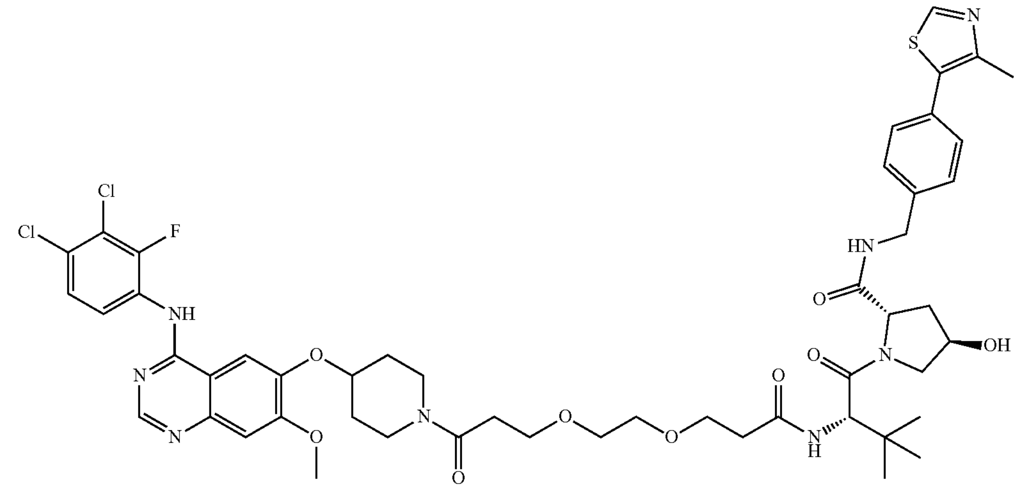 |

TABLE 1-continued

| Compound No. | | The compounds' name | Structure of the compounds |
|---|---|---|---|
| 72 | SIAIS249026 | (2S,4R)-1-((S)-2-(tert-butyl)-16-(4-((4-((3,4-dichloro-2-fluorophenyl)amino)-7-methoxyquinazolin-6-yl)oxy)piperidin-1-yl)-4,16-dioxo-7,10,13-trioxa-3-azahexadecan-1-oyl)-4-hydroxy-N-(4-(4-methylthiazol-5-yl)benzyl)pyrrolidine-2-carboxamide | 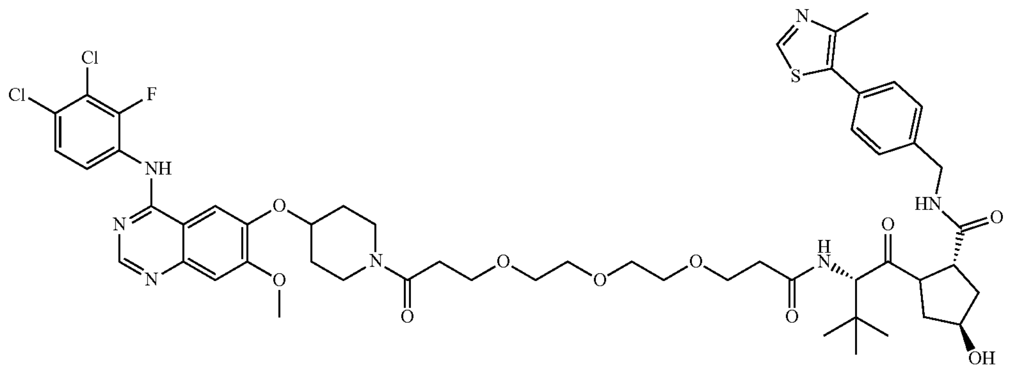 [SMILES: COc1cc2ncnc(Nc3ccc(Cl)c(Cl)c3F)c2cc1OC1CCN(C(=O)CCOCCOCCOCCC(=O)N[C@H](C(=O)C2C[C@H](O)C[C@H]2C(=O)NCc2ccc(-c3scnc3C)cc2)C(C)(C)C)CC1] |
| 73 | SIAIS249027 | (2S,4R)-1-((S)-2-(tert-butyl)-19-(4-((4-((3,4-dichloro-2-fluorophenyl)amino)-7-methoxyquinazolin-6-yl)oxy)piperidin-1-yl)-4,19-dioxo-7,10,13,16-tetraoxa-3-azanonadecan-1-oyl)-4-hydroxy-N-(4-(4-methylthiazol-5-yl)benzyl)pyrrolidine-2-carboxamide | 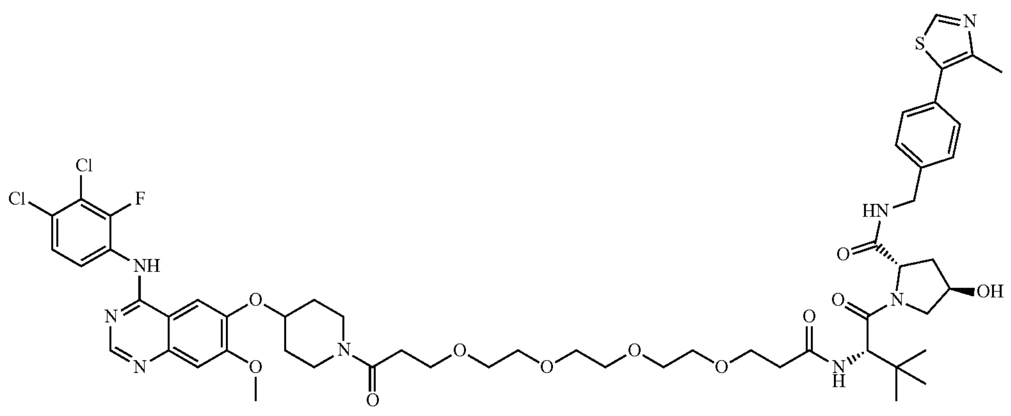 [SMILES: COc1cc2ncnc(Nc3ccc(Cl)c(Cl)c3F)c2cc1OC1CCN(C(=O)CCOCCOCCOCCOCCC(=O)N[C@H](C(=O)N2C[C@H](O)C[C@H]2C(=O)NCc2ccc(-c3scnc3C)cc2)C(C)(C)C)CC1] |

TABLE 1-continued

| Compound No. | | The compounds' name | Structure of the compounds |
|---|---|---|---|
| 74 | SIAIS249028 | (2S,4R)-1-((S)-2-(tert-butyl)-22-(4-((4-((3,4-dichloro-2-fluorophenyl)amino)-7-methoxyquinazolin-6-yl)oxy)piperidin-1-yl)-4,22-dioxo-7,10,13,16,19-pentaoxa-3-azadocosan-1-oyl)-4-hydroxy-N-(4-(4-methylthiazol-5-yl)benzyl)pyrrolidine-2-carboxamide | 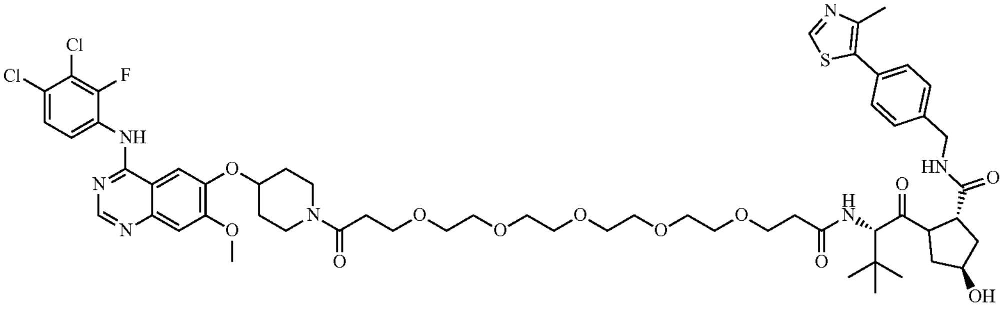 [SMILES: COc1cc2ncnc(Nc3ccc(Cl)c(Cl)c3F)c2cc1OC1CCN(C(=O)CCOCCOCCOCCOCCOCCC(=O)N[C@H](C(=O)C2C[C@H](O)C[C@H]2C(=O)NCc2ccc(-c3scnc3C)cc2)C(C)(C)C)CC1] |
| 75 | SIAIS249020 | (2S,4R)-1-((S)-2-(4-(4-((4-((3,4-dichloro-2-fluorophenyl)amino)-7-methoxyquinazolin-6-yl)oxy)piperidin-1-yl)-4-oxobutanamido)-3,3-dimethylbutanoyl)-4-hydroxy-N-(4-(4-methylthiazol-5-yl)benzyl)pyrrolidine-2-carboxamide | 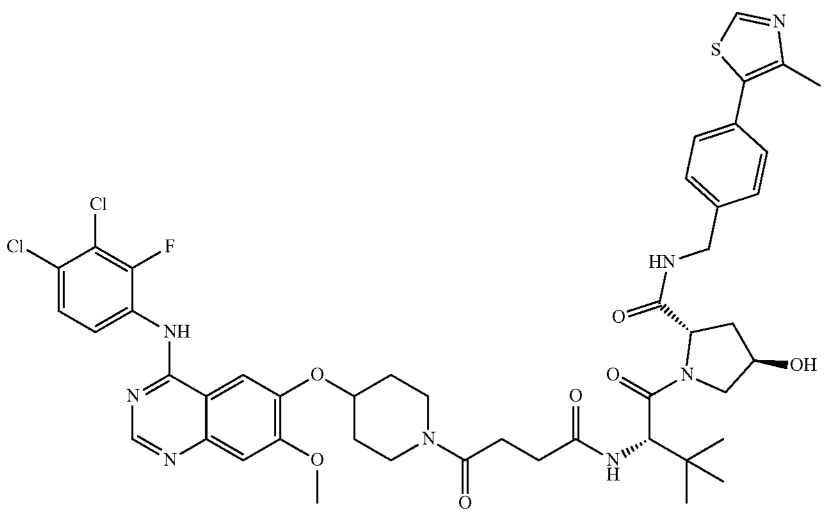 [SMILES: COc1cc2ncnc(Nc3ccc(Cl)c(Cl)c3F)c2cc1OC1CCN(C(=O)CCC(=O)N[C@H](C(=O)N2C[C@H](O)C[C@H]2C(=O)NCc2ccc(-c3scnc3C)cc2)C(C)(C)C)CC1] |

TABLE 1-continued

| Compound No. | | The compounds' name | Structure of the compounds |
|---|---|---|---|
| 76 | SIAIS249021 | (2S,4R)-1-((S)-2-(6-(4-((4-((3,4-dichloro-2-fluorophenyl)amino)-7-methoxyquinazolin-6-yl)oxypiperidin-1-yl)-6-oxohexanamido)-3,3-dimethylbutanoyl)-4-hydroxy-N-(4-(4-methylthiazol-5-yl)benzyl)pyrrolidine-2-carboxamide | 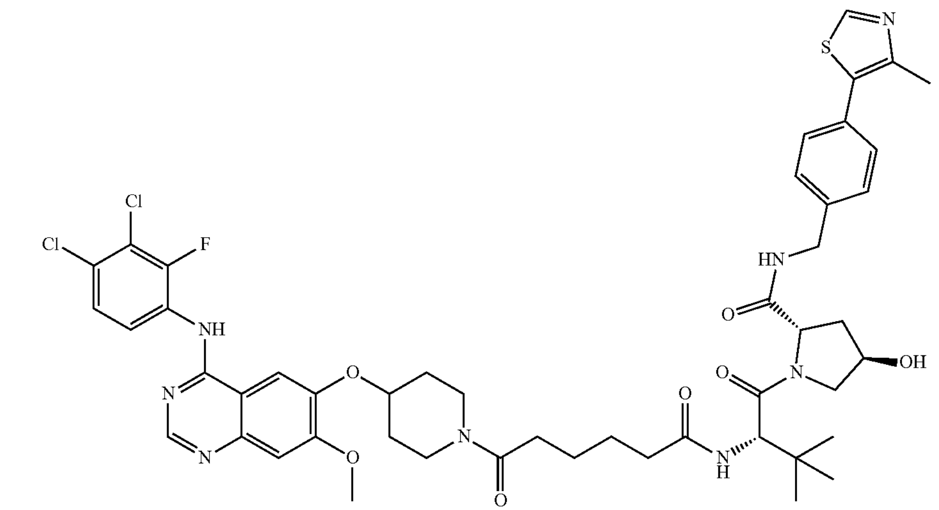 [SMILES: COc1cc2ncnc(Nc3ccc(Cl)c(Cl)c3F)c2cc1OC1CCN(C(=O)CCCCC(=O)N[C@H](C(=O)N2C[C@H](O)C[C@H]2C(=O)NCc2ccc(-c3scnc3C)cc2)C(C)(C)C)CC1] |
| 77 | SIAIS249022 | (2S,4R)-1-((S)-2-(8-(4-((4-((3,4-dichloro-2-fluorophenyl)amino)-7-methoxyquinazolin-6-yl)oxy)piperidin-1-yl)-8-oxooctanamido)-3,3-dimethylbutanoyl)-4-hydroxy-N-(4-(4-methylthiazol-5-yl)benzyl)pyrrolidine-2-carboxamide | 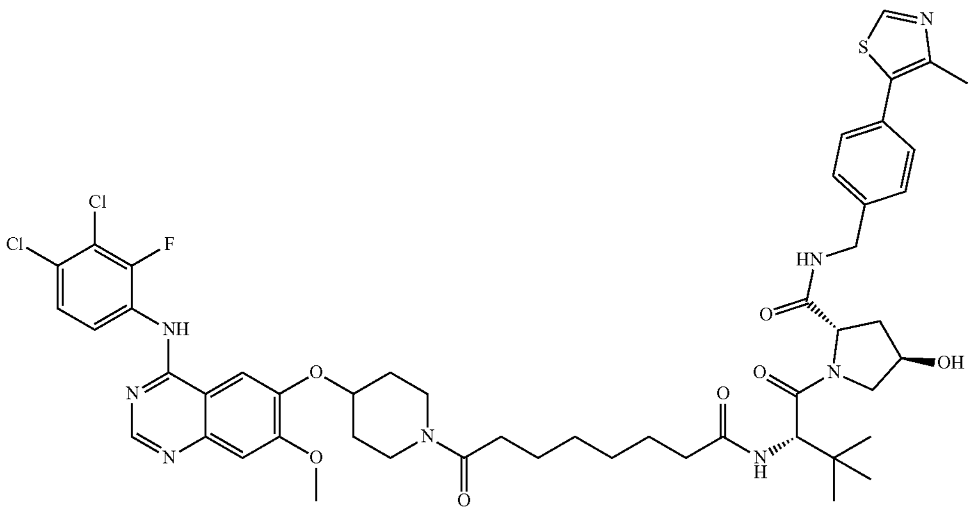 |

TABLE 1-continued

| Compound No. | | The compounds' name | Structure of the compounds |
|---|---|---|---|
| 78 | SIAIS249023 | (2S,4R)-1-((S)-2-(10-(4-((4-((3,4-dichloro-2-fluorophenyl)amino)-7-methoxyquinazolin-6-yl)oxy)piperidin-1-yl)-10-oxodecanamido)-3,3-dimethylbutanoyl)-4-hydroxy-N-(4-(4-methylthiazol-5-yl)benzyl)pyrrolidine-2-carboxamide | 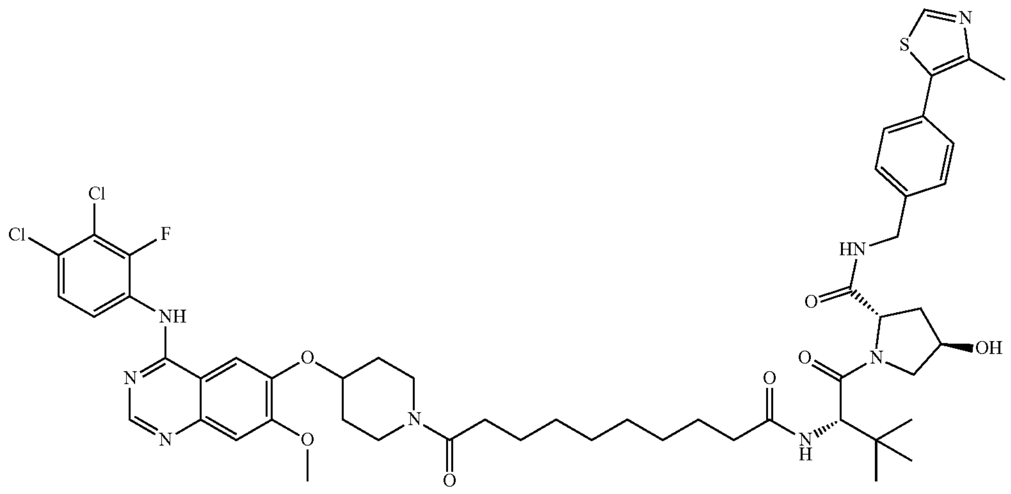 [SMILES: COc1cc2ncnc(Nc3ccc(Cl)c(Cl)c3F)c2cc1OC1CCN(C(=O)CCCCCCCCC(=O)N[C@H](C(=O)N2C[C@H](O)C[C@H]2C(=O)NCc2ccc(-c3scnc3C)cc2)C(C)(C)C)CC1] |
| 79 | SIAIS184164) | 4-((2-(4-(3-((4-((3-chloro-4-fluorophenyl)amino)-7-methoxyquinazolin-6-yl)oxy)propyl)piperazin-1-yl)-2-oxoethyl)thio)-2-(2,6-dioxopiperidin-3-yl)isoindoline-1,3-dione | 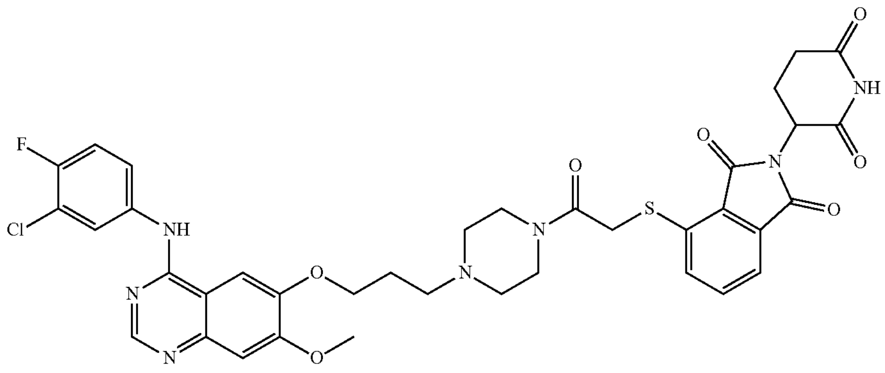 [SMILES: COc1cc2ncnc(Nc3ccc(F)c(Cl)c3)c2cc1OCCCN1CCN(C(=O)CSc2cccc3c2C(=O)N(C2CCC(=O)NC2=O)C3=O)CC1] |

TABLE 1-continued
| | Compound No. | The compounds' name | Structure of the compounds |
|---|---|---|---|
| 80 | SIAIS184165 | 4-((4-(4-(3-((4-((3-chloro-4-fluorophenyl)amino)-7-methoxyquinazolin-6-yl)oxy)propyl)piperazin-1-yl)-4-oxobutyl)thio)-2-(2,6-dioxopiperidin-3-yl)isoindoline-1,3-dione | 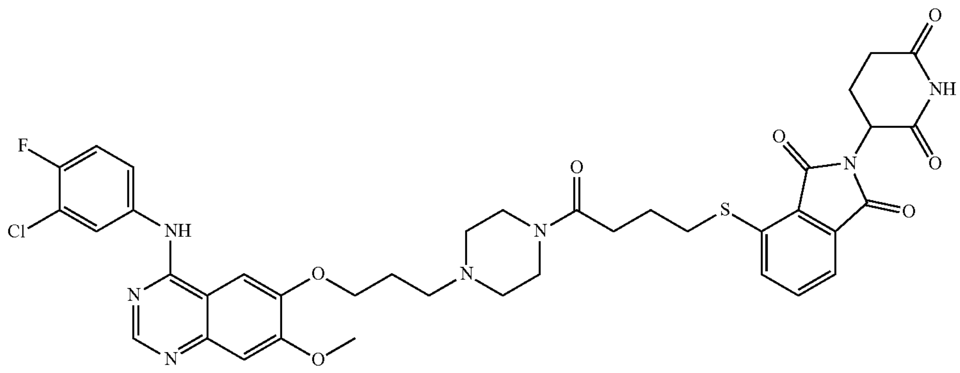 [SMILES: COc1cc2ncnc(Nc3ccc(F)c(Cl)c3)c2cc1OCCCN1CCN(C(=O)CCCSc2cccc3c2C(=O)N(C2CCC(=O)NC2=O)C3=O)CC1] |
| 81 | SIAIS184166 | 4-((6-(4-(3-((4-((3-chloro-4-fluorophenyl)amino)-7-methoxyquinazolin-6-yl)oxy)propyl)piperazin-1-yl)-6-oxohexyl)thio)-2-(2,6-dioxopiperidin-3-yl)isoindoline-1,3-dione | 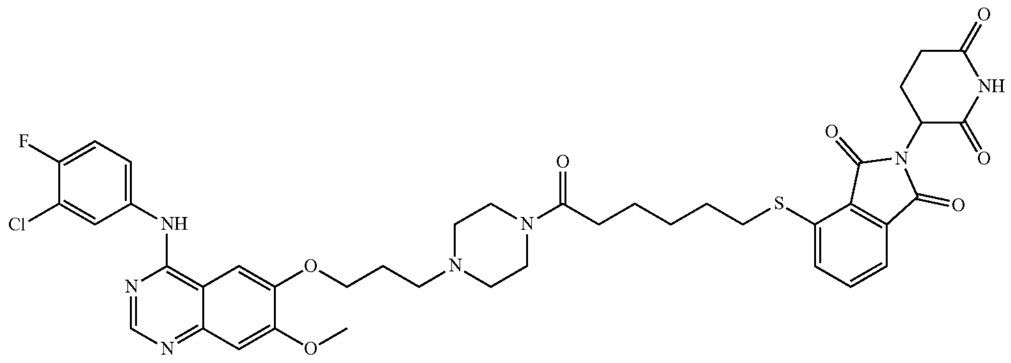 [SMILES: COc1cc2ncnc(Nc3ccc(F)c(Cl)c3)c2cc1OCCCN1CCN(C(=O)CCCCCSc2cccc3c2C(=O)N(C2CCC(=O)NC2=O)C3=O)CC1] |

TABLE 1-continued

| Compound No. | | The compounds' name | Structure of the compounds |
|---|---|---|---|
| 82 | SIAIS184168 | 4-((2-(2-(4-(3-((4-((3-chloro-4-fluorophenyl)amino)-7-methoxyquinazolin-6-yl)oxy)propyl)piperazin-1-yl)-2-oxoethoxy)ethyl)thio)-2-(2,6-dioxopiperidin-3-yl)isoindoline-1,3-dione | 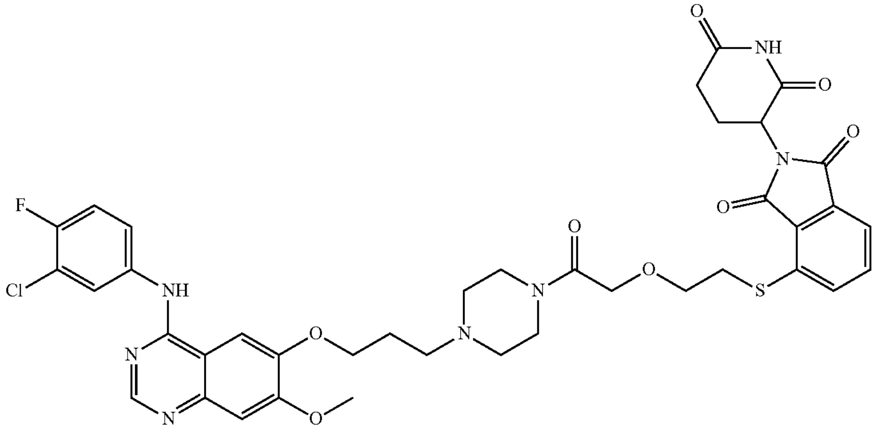 [SMILES: COc1cc2ncnc(Nc3ccc(F)c(Cl)c3)c2cc1OCCCN1CCN(C(=O)COCCSc2cccc3c2C(=O)N(C2CCC(=O)NC2=O)C3=O)CC1] |
| 83 | SIAIS184169 | 4-((2-(2-(2-(2-(4-(3-((4-((3-chloro-4-fluorophenyl)amino)-7-methoxyquinazolin-6-yl)oxy)propyl)piperazin-1-yl)-2-oxoethoxy)ethoxy)ethoxy)ethyl)thio)-2-(2,6-dioxopiperidin-3-yl)isoindoline-1,3-dione | 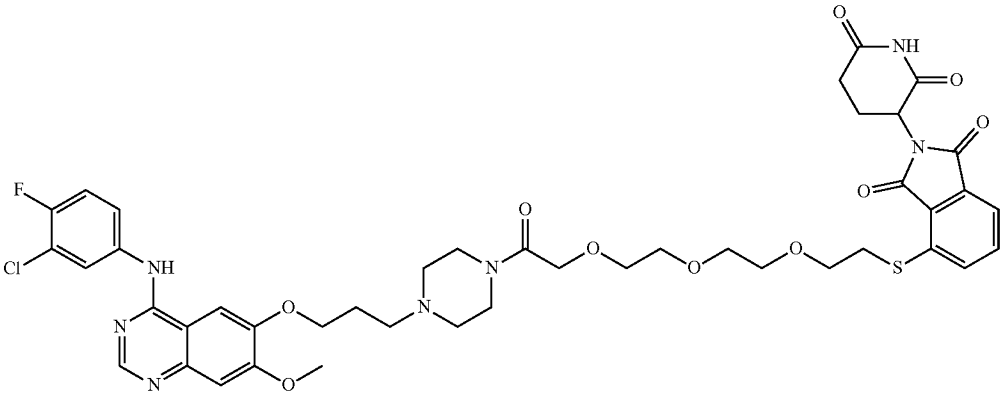 [SMILES: COc1cc2ncnc(Nc3ccc(F)c(Cl)c3)c2cc1OCCCN1CCN(C(=O)COCCOCCOCCSc2cccc3c2C(=O)N(C2CCC(=O)NC2=O)C3=O)CC1] |

TABLE 1-continued
| | Compound No. | The compounds' name | Structure of the compounds |
|---|---|---|---|
| 84 | SIAIS184170 | 4-((17-(4-(3-((4-((3-chloro-4-fluorophenyl)amino)-7-methoxyquinazolin-6-yl)oxy)propyl)piperazin-1-yl)-17-oxo-3,6,9,12,15-pentaoxaheptadecyl)thio)-2-(2,6-dioxopiperidin-3-yl)isoindoline-1,3-dione | 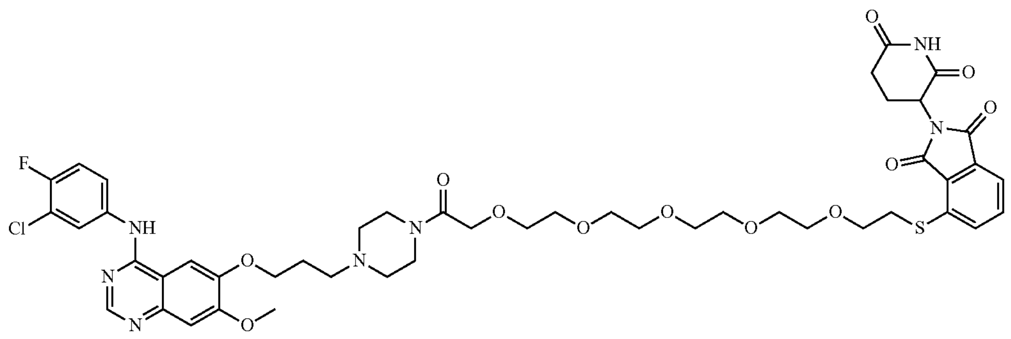 [SMILES: COc1cc2ncnc(Nc3ccc(F)c(Cl)c3)c2cc1OCCCN1CCN(C(=O)COCCOCCOCCOCCOCCSc2cccc3c2C(=O)N(C2CCC(=O)NC2=O)C3=O)CC1] |
| 85 | SIAIS184184 | 3-(4-((2-(4-(3-((4-((3-chloro-4-fluorophenyl)amino)-7-methoxyquinazolin-6-yl)oxy)propyl)piperazin-1-yl)-2-oxoethyl)thio)-1-oxoisoindolin-2-yl)piperidine-2,6-dione | 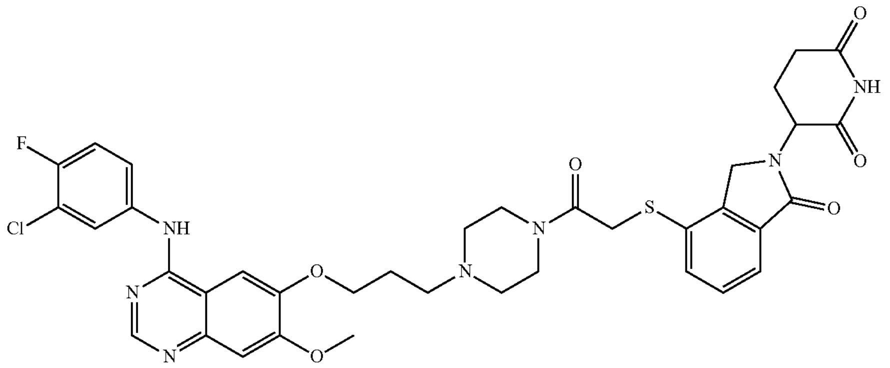 [SMILES: COc1cc2ncnc(Nc3ccc(F)c(Cl)c3)c2cc1OCCCN1CCN(C(=O)CSc2cccc3c2CN(C2CCC(=O)NC2=O)C3=O)CC1] |

TABLE 1-continued
| Compound No. | | The compounds' name | Structure of the compounds |
|---|---|---|---|
| 86 | SIAIS184185 | 3-(4-((4-(4-(3-((4-((3-chloro-4-fluorophenyl)amino)-7-methoxyquinazolin-6-yl)oxy)propyl)piperazin-1-yl)-4-oxobutyl)thio)-1-oxoisoindolin-2-yl)piperidine-2,6-dione | 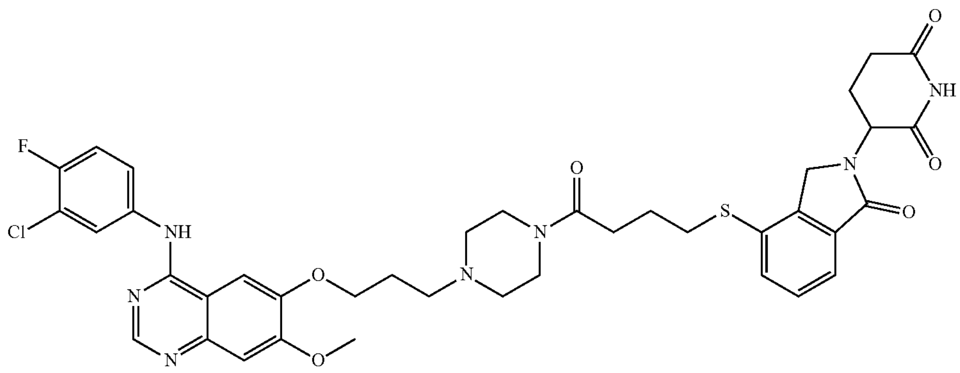 [SMILES: COc1cc2ncnc(Nc3ccc(F)c(Cl)c3)c2cc1OCCCN1CCN(C(=O)CCCSc2cccc3c2CN(C2CCC(=O)NC2=O)C3=O)CC1] |
| 87 | SIAIS184186 | 3-(4-((6-(4-(3-((4-((3-chloro-4-fluorophenyl)amino)-7-methoxyquinazolin-6-yl)oxy)propyl)piperazin-1-yl)-6-oxohexyl)thio)-1-oxoisoindolin-2-yl)piperidine-2,6-dione | 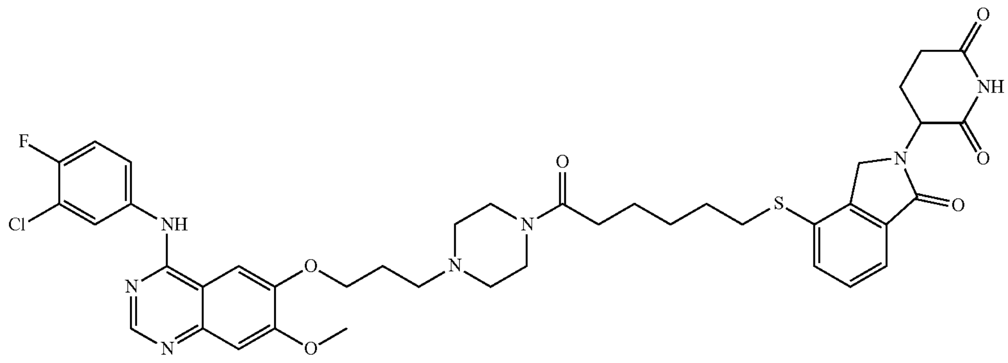 [SMILES: COc1cc2ncnc(Nc3ccc(F)c(Cl)c3)c2cc1OCCCN1CCN(C(=O)CCCCCSc2cccc3c2CN(C2CCC(=O)NC2=O)C3=O)CC1] |

TABLE 1-continued

| | Compound No. | The compounds' name | Structure of the compounds |
|---|---|---|---|
| 88 | SIAIS262085 | 3-(4-((2-(4-(1-(3-((4-((3-chloro-4-fluorophenyl)amino)-7-methoxyquinazolin-6-yl)oxy)propyl)piperidin-4-yl)piperazin-1-yl)-2-oxoethyl)thio)-1-oxoisoindolin-2-yl)piperidine-2,6-dione | 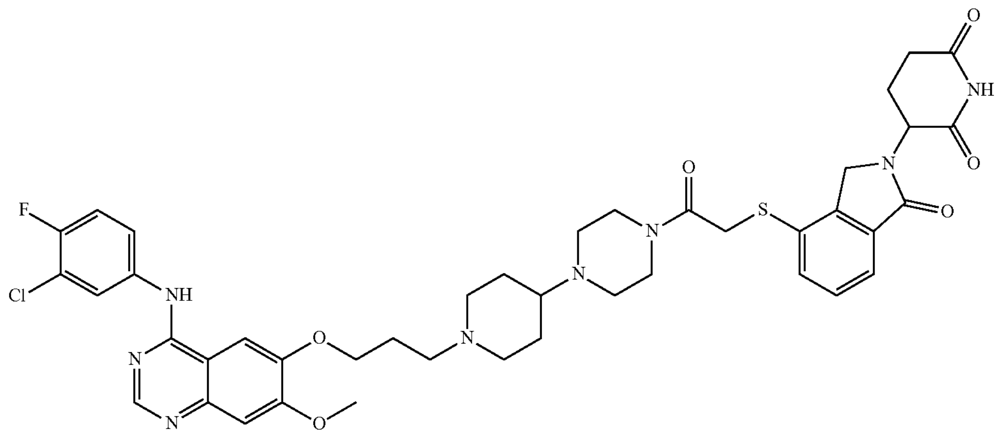 [SMILES: COc1cc2ncnc(Nc3ccc(F)c(Cl)c3)c2cc1OCCCN1CCC(N2CCN(C(=O)CSc3cccc4c3CN(C3CCC(=O)NC3=O)C4=O)CC2)CC1] |
| 89 | SIAIS262086 | 3-(4-((5-(4-(1-(3-((4-((3-chloro-4-fluorophenyl)amino)-7-methoxyquinazolin-6-yl)oxy)propyl)piperidin-4-yl)piperazin-1-yl)-5-oxopentyl)thio)-1-oxoisoindolin-2-yl)piperidine-2,6-dione | 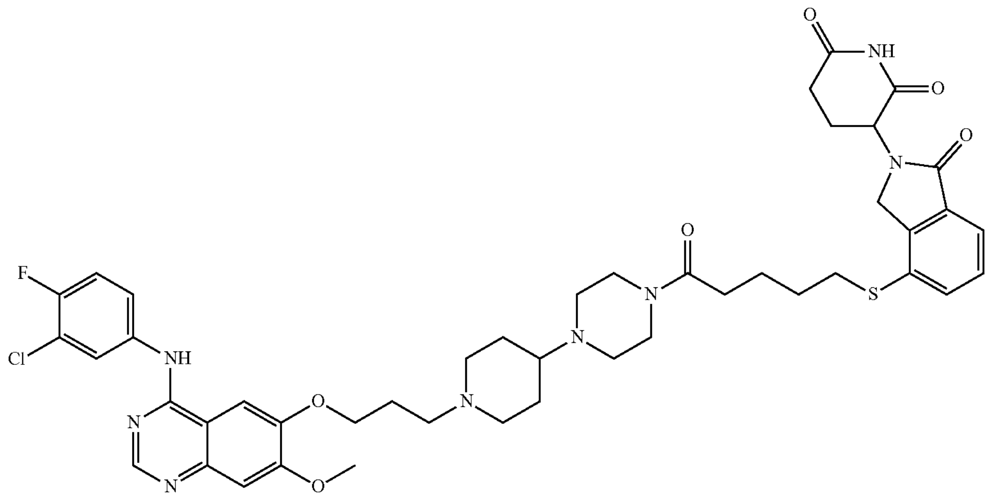 [SMILES: COc1cc2ncnc(Nc3ccc(F)c(Cl)c3)c2cc1OCCCN1CCC(N2CCN(C(=O)CCCCSc3cccc4c3CN(C3CCC(=O)NC3=O)C4=O)CC2)CC1] |

TABLE 1-continued
| Compound No. | | The compounds' name | Structure of the compounds |
|---|---|---|---|
| 90 | SIAIS262087 | 3-(4-((6-(4-(1-(3-((4-((3-chloro-4-fluorophenyl)amino)-7-methoxyquinazolin-6-yl)oxy)propyl)piperidin-4-yl)piperazin-1-yl)-6-oxohexyl)thio)-1-oxoisoindolin-2-yl)piperidine-2,6-dione | 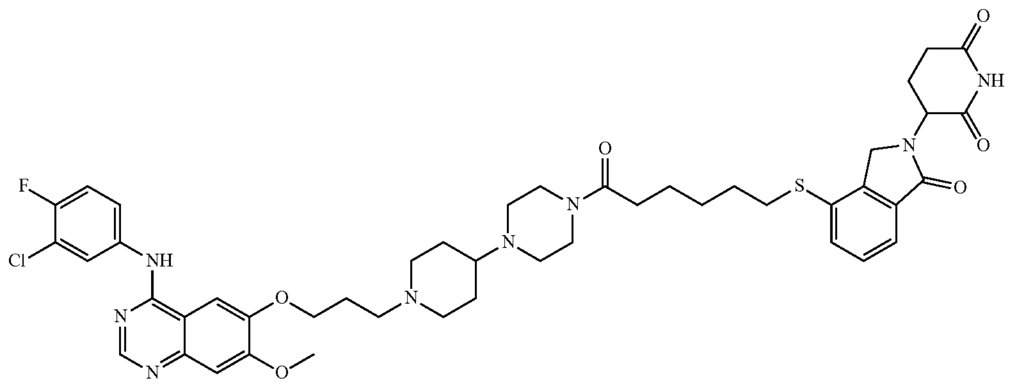 [SMILES: COc1cc2ncnc(Nc3ccc(F)c(Cl)c3)c2cc1OCCCN1CCC(N2CCN(C(=O)CCCCCSc3cccc4c3CN(C3CCC(=O)NC3=O)C4=O)CC2)CC1] |
| 91 | SIAIS184093 | N-(4-((3-chloro-4-fluorophenyl)amino)-7-(((S)-tetrahydrofuran-3-yl)oxy)quinazolin-6-yl)-2-((2-(2,6-dioxopiperidin-3-yl)-1,3-dioxoisoindolin-4-yl)thio)acetamide | 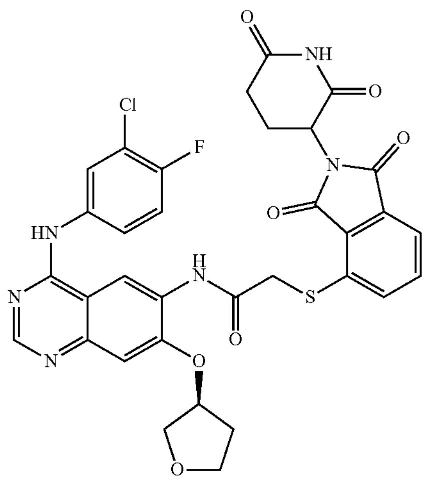 [SMILES: O=C1CCC(N2C(=O)c3cccc(SCC(=O)Nc4cc5c(Nc6ccc(F)c(Cl)c6)ncnc5cc4O[C@H]4CCOC4)c3C2=O)C(=O)N1] |

TABLE 1-continued
| | Compound No. | The compounds' name | Structure of the compounds |
|---|---|---|---|
| 92 | SIAIS184094 | N-(4-((3-chloro-4-fluorophenyl)amino)-7-(((S)-tetrahydrofuran-3-yl)oxy)quinazolin-6-yl)-4-((2-(2,6-dioxopiperidin-3-yl)-1,3-dioxoisoindolin-4-yl)thio)butanamide | 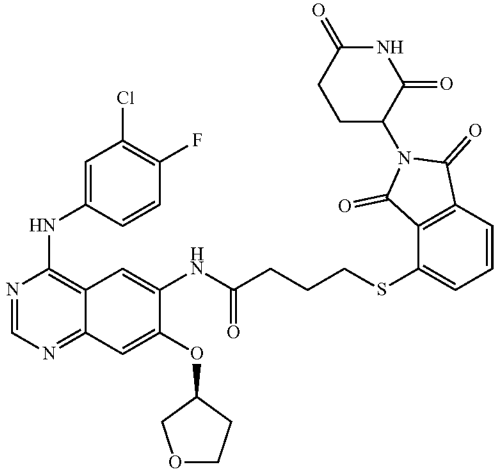 [SMILES: O=C1CCC(N2C(=O)c3cccc(SCCCC(=O)Nc4cc5c(Nc6ccc(F)c(Cl)c6)ncnc5cc4O[C@H]4CCOC4)c3C2=O)C(=O)N1] |
| 93 | SIAIS184095 | N-(4-((3-chloro-4-fluorophenyl)amino)-7-(((S)-tetrahydrofuran-3-yl)oxy)quinazolin-6-yl)-6-((2-(2,6-dioxopiperidin-3-yl)-1,3-dioxoisoindolin-4-yl)thio)hexanamide | 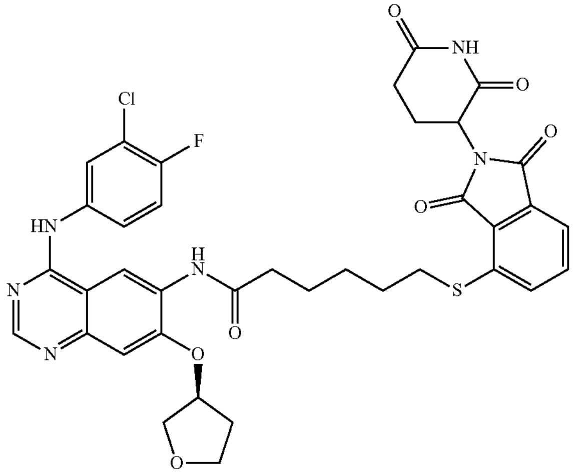 [SMILES: O=C1CCC(N2C(=O)c3cccc(SCCCCCC(=O)Nc4cc5c(Nc6ccc(F)c(Cl)c6)ncnc5cc4O[C@H]4CCOC4)c3C2=O)C(=O)N1] |

TABLE 1-continued
| | Compound No. | The compounds' name | Structure of the compounds |
|---|---|---|---|
| 94 | SIAIS184152 | N-(4-((3-chloro-4-fluorophenyl)amino)-7-(((S)-tetrahydrofuran-3-yl)oxy)quinazolin-6-yl)-2-(2-((2-(2,6-dioxopiperidin-3-yl)-1,3-dioxoisoindolin-4-yl)thio)ethoxy)acetamide | 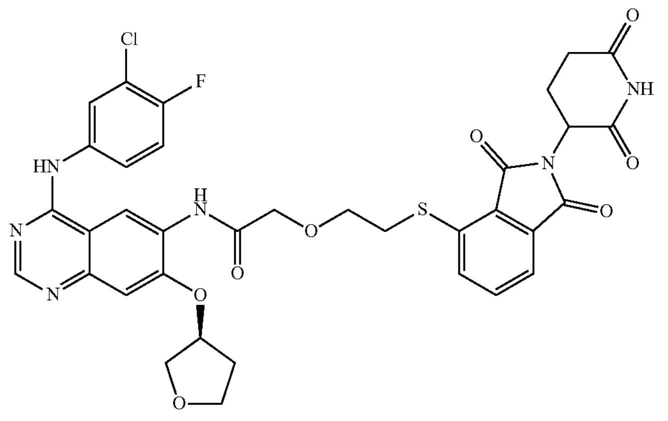 [SMILES: O=C1CCC(N2C(=O)c3cccc(SCCOCC(=O)Nc4cc5c(Nc6ccc(F)c(Cl)c6)ncnc5cc4O[C@H]4CCOC4)c3C2=O)C(=O)N1] |
| 95 | SIAIS184153 | N-(4-((3-chloro-4-fluorophenyl)amino)-7-(((S)-tetrahydrofuran-3-yl)oxy)quinazolin-6-yl)-2-(2-(2-((2-(2,6-dioxopiperidin-3-yl)-1,3-dioxoisoindolin-4-yl)thio)ethoxy)ethoxy)acetamide | 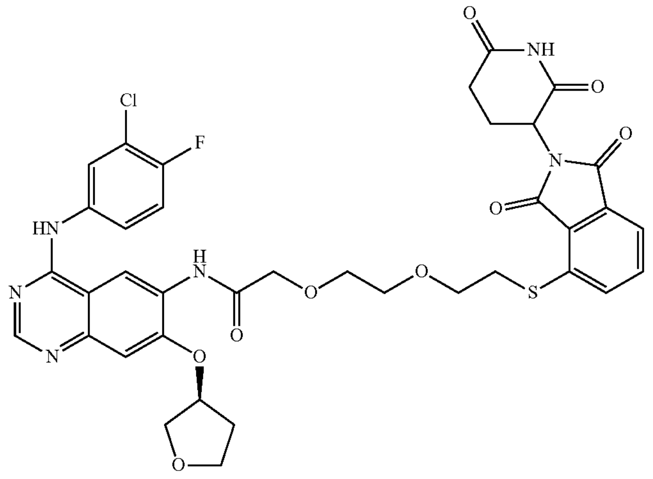 [SMILES: O=C1CCC(N2C(=O)c3cccc(SCCOCCOCC(=O)Nc4cc5c(Nc6ccc(F)c(Cl)c6)ncnc5cc4O[C@H]4CCOC4)c3C2=O)C(=O)N1] |

TABLE 1-continued

| | Compound No. | The compounds' name | Structure of the compounds |
|---|---|---|---|
| 96 | SIAIS184154 | N-(4-((3-chloro-4-fluorophenyl)amino)-7-(((S)-tetrahydrofuran-3-yl)oxy)quinazolin-6-yl)-2-(2-(2-(2-((2-(2,6-dioxopiperidin-3-yl)-1,3-dioxoisoindolin-4-yl)thio)ethoxy)ethoxy)ethoxy)acetamide | 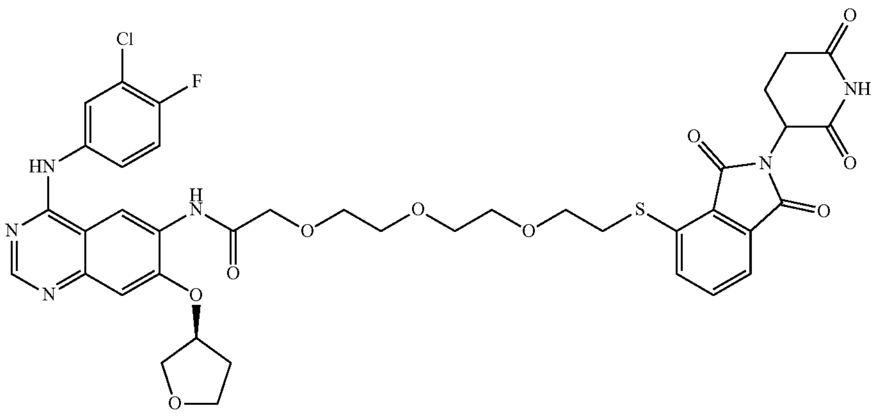 [SMILES: O=C1CCC(N2C(=O)c3cccc(SCCOCCOCCOCC(=O)Nc4cc5c(Nc6ccc(F)c(Cl)c6)ncnc5cc4O[C@H]4CCOC4)c3C2=O)C(=O)N1] |
| 97 | SIAIS184155 | N-(4-((3-chloro-4-fluorophenyl)amino)-7-(((S)-tetrahydrofuran-3-yl)oxy)quinazolin-6-yl)-14-((2-(2,6-dioxopiperidin-3-yl)-1,3-dioxoisoindolin-4-yl)thio)-3,6,9,12-tetraoxatetradecan-1-amide | 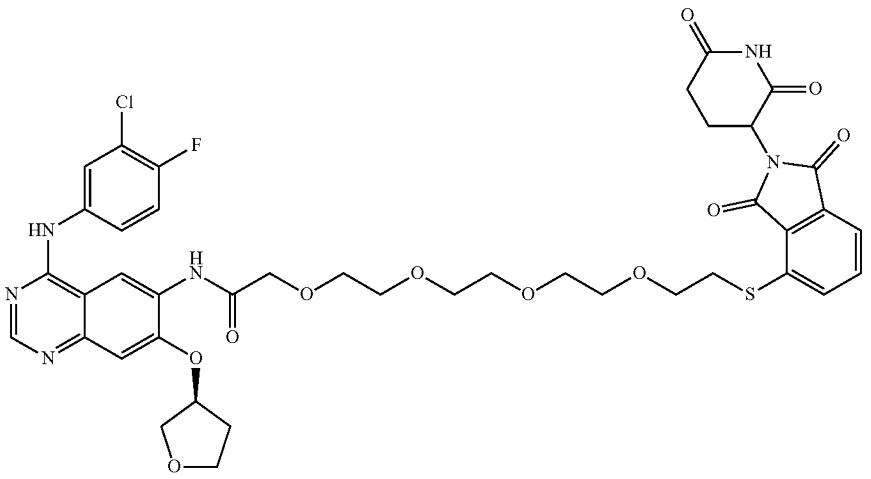 [SMILES: O=C1CCC(N2C(=O)c3cccc(SCCOCCOCCOCCOCC(=O)Nc4cc5c(Nc6ccc(F)c(Cl)c6)ncnc5cc4O[C@H]4CCOC4)c3C2=O)C(=O)N1] |

TABLE 1-continued
| | Compound No. | The compounds' name | Structure of the compounds |
|---|---|---|---|
| 98 | SIAIS184156 | N-(4-((3-chloro-4-fluorophenyl)amino)-7-(((S)-tetrahydrofuran-3-yl)oxy)quinazolin-6-yl)-17-(2-(2,6-dioxopiperidin-3-yl)-1,3-dioxoisoindolin-4-yl)thio)-3,6,9,12,15-pentaoxaheptadecan-1-amide | 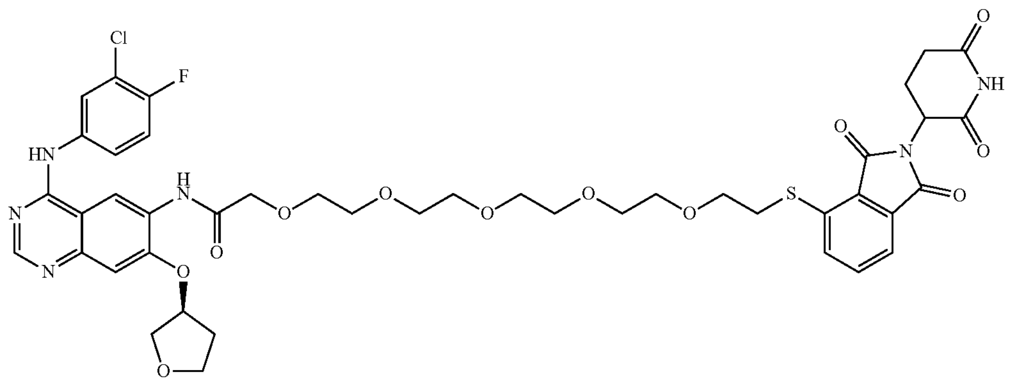 [SMILES: O=C1CCC(N2C(=O)c3cccc(SCCOCCOCCOCCOCCOCC(=O)Nc4cc5c(Nc6ccc(F)c(Cl)c6)ncnc5cc4O[C@H]4CCOC4)c3C2=O)C(=O)N1] |
| 99 | SIAIS1210085 | N-(4-((3-chloro-4-fluorophenyl)amino)-7-(((S)-tetrahydrofuran-3-yl)oxy)quinazolin-6-yl)-3-((2-(2,6-dioxopiperidin-3-yl)-1-oxoisoindolin-4-yl)thio)propanamide | 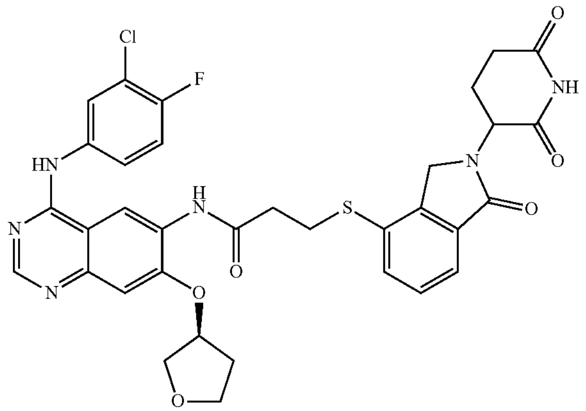 [SMILES: O=C1CCC(N2Cc3c(SCCC(=O)Nc4cc5c(Nc6ccc(F)c(Cl)c6)ncnc5cc4O[C@H]4CCOC4)cccc3C2=O)C(=O)N1] |

TABLE 1-continued
| Compound No. | | The compounds' name | Structure of the compounds |
|---|---|---|---|
| 100 | SIAIS1210087 | N-(4-((3-chloro-4-fluorophenyl)amino)-7-(((S)-tetrahydrofuran-3-yl)oxy)quinazolin-6-yl)-4-((2-(2,6-dioxopiperidin-3-yl)-1-oxoisoindolin-4-yl)thio)butanamide | 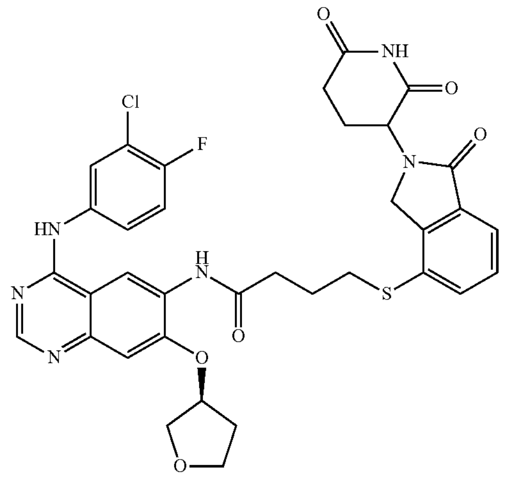 [SMILES: O=C1CCC(N2Cc3c(SCCCC(=O)Nc4cc5c(Nc6ccc(F)c(Cl)c6)ncnc5cc4O[C@H]4CCOC4)cccc3C2=O)C(=O)N1] |
| 101 | SIAIS1210089 | N-(4-((3-chloro-4-fluorophenyl)amino)-7-(((S)-tetrahydrofuran-3-yl)oxy)quinazolin-6-yl)-6-((2-(2,6-dioxopiperidin-3-yl)-1-oxoisoindolin-4-yl)thio)hexanamide | 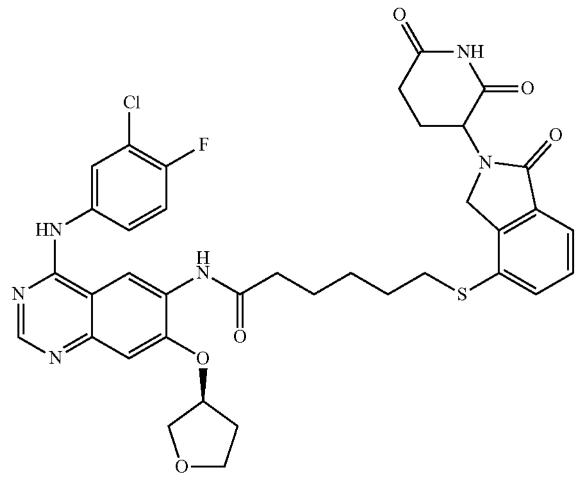 [SMILES: O=C1CCC(N2Cc3c(SCCCCCC(=O)Nc4cc5c(Nc6ccc(F)c(Cl)c6)ncnc5cc4O[C@H]4CCOC4)cccc3C2=O)C(=O)N1] |

TABLE 1-continued

| | Compound No. | The compounds' name | Structure of the compounds |
|---|---|---|---|
| 102 | SIAIS262050 | (E)-N-(4-((3-chloro-4-fluorophenyl)amino)-7-methoxyquinazolin-6-yl)-4-(4-(4-(5-(2-(2,6-dioxopiperidin-3-yl)-1-oxoisoindolin-4-yl)pent-4-yn-1-yl)piperazin-1-yl)piperidin-1-yl)but-2-enamide | 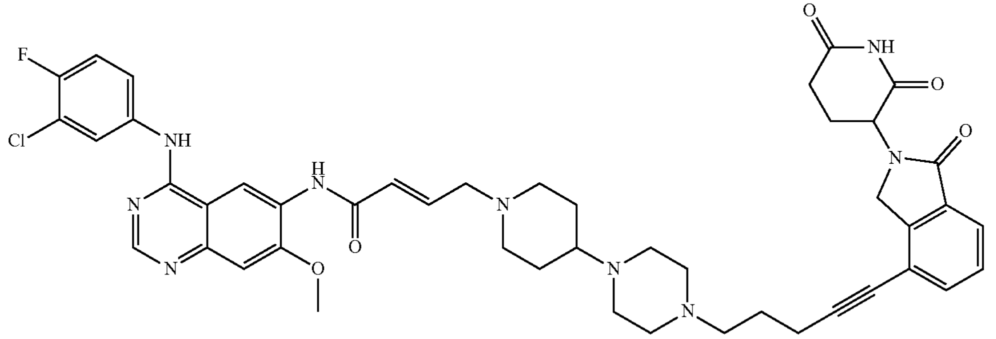 [SMILES: COc1cc2ncnc(Nc3ccc(F)c(Cl)c3)c2cc1NC(=O)/C=C/CN1CCC(N2CCN(CCCC#Cc3cccc4c3CN(C3CCC(=O)NC3=O)C4=O)CC2)CC1] |
| 103 | SIAIS262051 | (E)-N-(4-((3-chloro-4-fluorophenyl)amino)-7-methoxyquinazolin-6-yl)-4-(4-(4-(6-(2-(2,6-dioxopiperidin-3-yl)-1-oxoisoindolin-4-yl)hex-5-yn-1-yl)piperazin-1-yl)piperidin-1-yl)but-2-enamide | 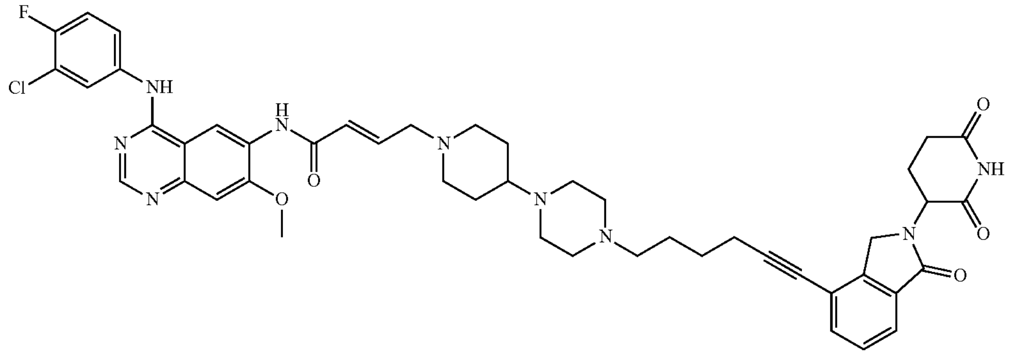 [SMILES: COc1cc2ncnc(Nc3ccc(F)c(Cl)c3)c2cc1NC(=O)/C=C/CN1CCC(N2CCN(CCCCC#Cc3cccc4c3CN(C3CCC(=O)NC3=O)C4=O)CC2)CC1] |

TABLE 1-continued
| | Compound No. | The compounds' name | Structure of the compounds |
|---|---|---|---|
| 104 | SIAIS262089 | 3-(4-(5-(4-(1-(3-((4-((3-chloro-4-fluorophenyl)amino)-7-methoxyquinazolin-6-yl)oxy)propyl)piperidin-4-yl)piperazin-1-yl)pent-1-yn-1-yl)-1-oxoisoindolin-2-yl)piperidine-2,6-dione | 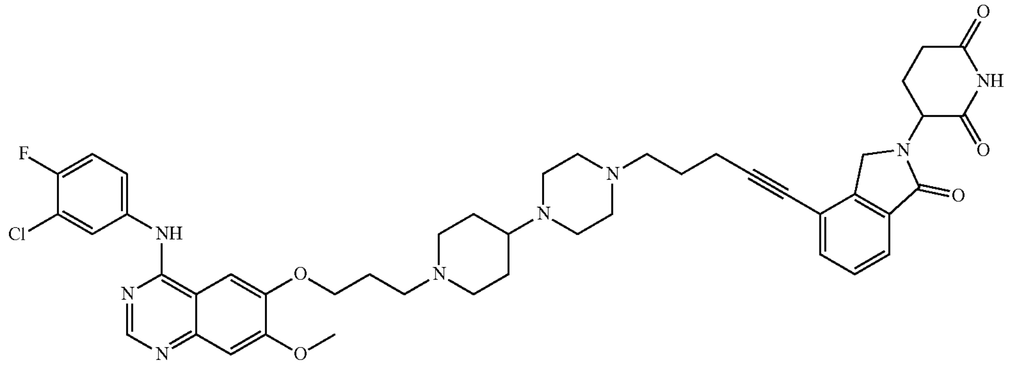 [SMILES: COc1cc2ncnc(Nc3ccc(F)c(Cl)c3)c2cc1OCCCN1CCC(N2CCN(CCCC#Cc3cccc4c3CN(C3CCC(=O)NC3=O)C4=O)CC2)CC1] |
| 105 | SIAIS262090 | 3-(4-(6-(4-(1-(3-((4-((3-chloro-4-fluorophenyl)amino)-7-methoxyquinazolin-6-yl)oxy)propyl)piperidin-4-yl)piperazin-1-yl)hex-1-yn-1-yl)-1-oxoisoindolin-2-yl)piperidine-2,6-dione | 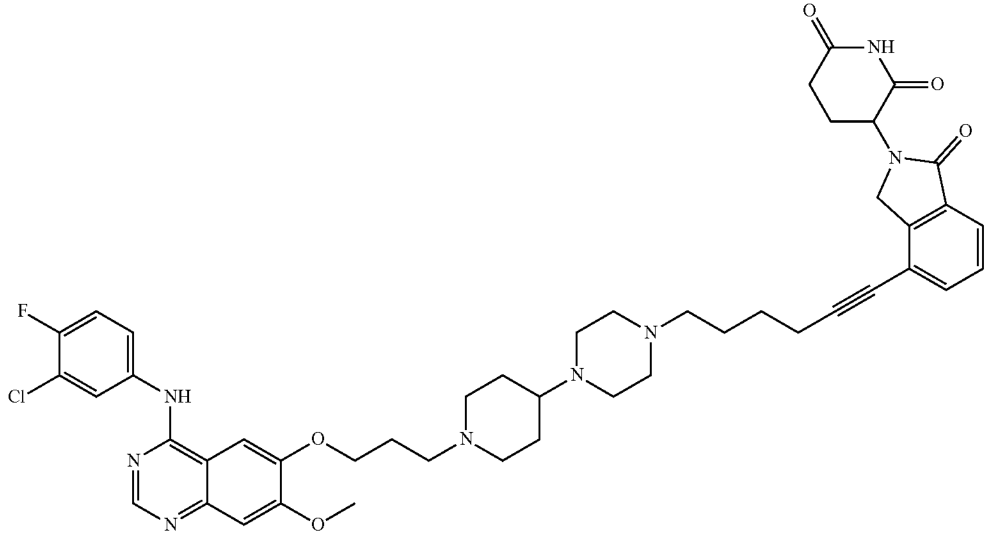 [SMILES: COc1cc2ncnc(Nc3ccc(F)c(Cl)c3)c2cc1OCCCN1CCC(N2CCN(CCCCC#Cc3cccc4c3CN(C3CCC(=O)NC3=O)C4=O)CC2)CC1] |

TABLE 1-continued

| Compound No. | | The compounds' name | Structure of the compounds |
|---|---|---|---|
| 106 | SIAIS262065 | (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)thio)hexyl)piperazin-1-yl)piperidin-1-yl)but-2-enamide | 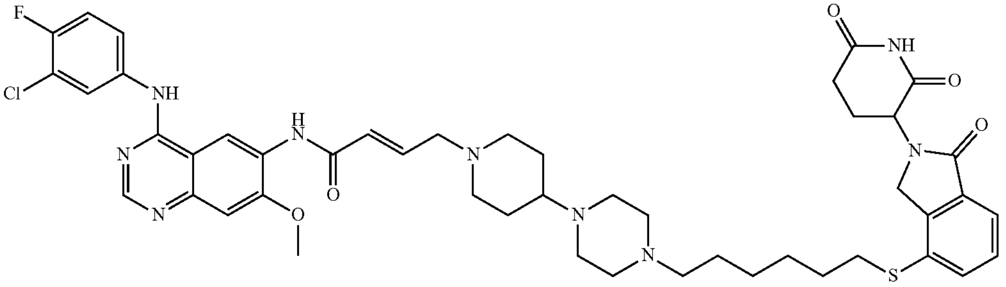 [SMILES: COc1cc2ncnc(Nc3ccc(F)c(Cl)c3)c2cc1NC(=O)/C=C/CN1CCC(N2CCN(CCCCCCSc3cccc4c3CN(C3CCC(=O)NC3=O)C4=O)CC2)CC1] |
| 107 | SIAIS262072 | (E)-N-(4-((3-chloro-4-fluorophenyl)amino)-7-methoxyquinazolin-6-yl)-4-(4-(4-(6-((2-(2,6-dioxopiperidin-3-yl)-1,3-dioxoisoindolin-4-yl)amino)hexyl)piperazin-1-yl)piperidin-1-yl)but-2-enamide | 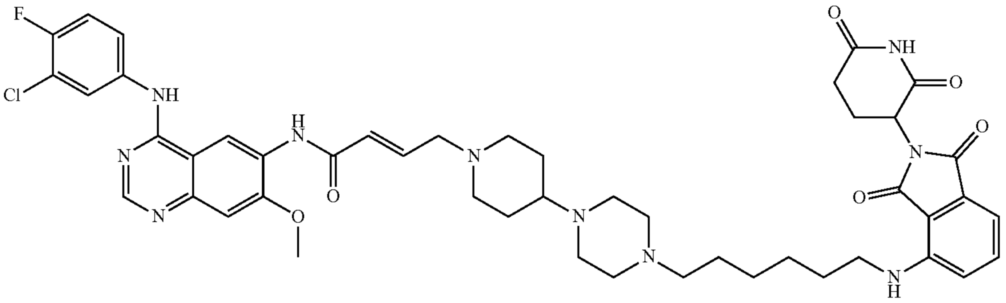 [SMILES: COc1cc2ncnc(Nc3ccc(F)c(Cl)c3)c2cc1NC(=O)/C=C/CN1CCC(N2CCN(CCCCCCNc3cccc4c3C(=O)N(C3CCC(=O)NC3=O)C4=O)CC2)CC1] |
| 108 | SIAIS262121 | N-(4-((3-chloro-4-fluorophenyl)amino)-7-(3-(4-(2-((2-(2,6-dioxopiperidin-3-yl)-1-oxoisoindolin-4-yl)thio)acetyl)piperazin-1-yl)propoxy)quinazolin-6-yl)acrylamide | 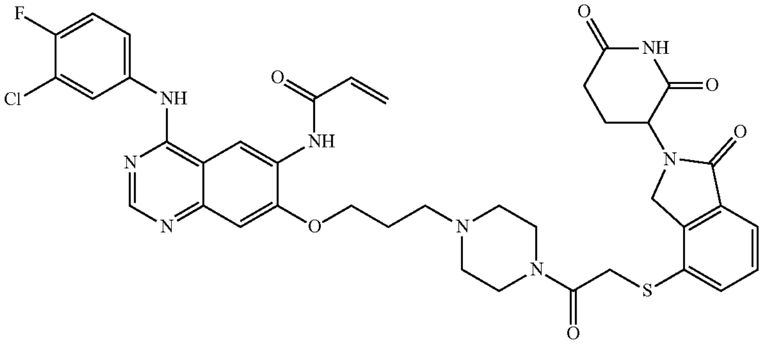 [SMILES: C=CC(=O)Nc1cc2c(Nc3ccc(F)c(Cl)c3)ncnc2cc1OCCCN1CCN(C(=O)CSc2cccc3c2CN(C2CCC(=O)NC2=O)C3=O)CC1] |

TABLE 1-continued
| Compound No. | | The compounds' name | Structure of the compounds |
|---|---|---|---|
| 109 | SIAIS262122 | N-(4-((3-chloro-4-fluorophenyl)amino)-7-(3-(4-(5-((2-(2,6-dioxopiperidin-3-yl)-1-oxoisoindolin-4-yl)thio)pentanoyl)piperazin-1-yl)propoxy)quinazolin-6-yl)acrylamide | 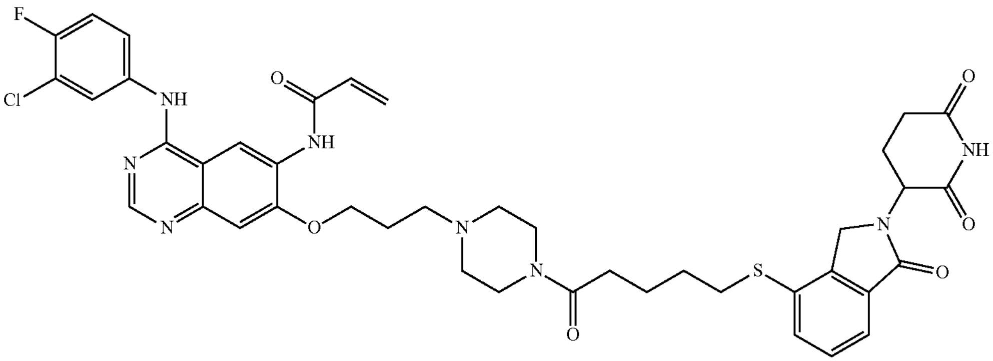 [SMILES: C=CC(=O)Nc1cc2c(Nc3ccc(F)c(Cl)c3)ncnc2cc1OCCCN1CCN(C(=O)CCCCSc2cccc3c2CN(C2CCC(=O)NC2=O)C3=O)CC1] |
| 110 | SIAIS262123 | N-(4-((3-chloro-4-fluorophenyl)amino)-7-(3-(4-(6-((2-(2,6-dioxopiperidin-3-yl)-1-oxoisoindolin-4-yl)thio)hexanoyl)piperazin-1-yl)propoxy)quinazolin-6-yl)acrylamide | 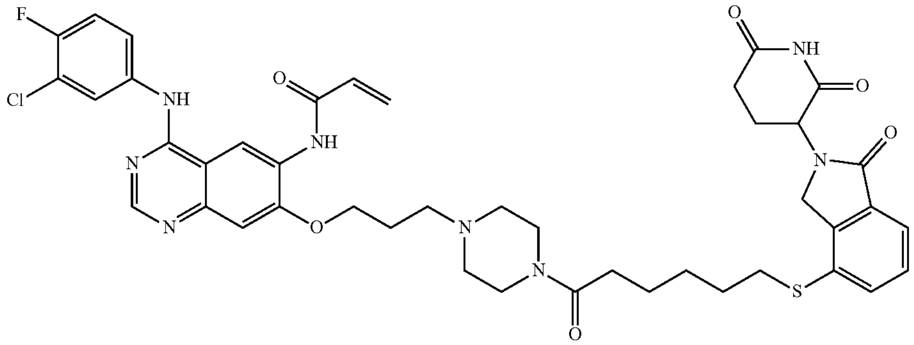 [SMILES: C=CC(=O)Nc1cc2c(Nc3ccc(F)c(Cl)c3)ncnc2cc1OCCCN1CCN(C(=O)CCCCCSc2cccc3c2CN(C2CCC(=O)NC2=O)C3=O)CC1] |

TABLE 1-continued
| | Compound No. | The compounds' name | Structure of the compounds |
|---|---|---|---|
| 111 | SIAIS262124 | N-(4-((3-chloro-4-fluorophenyl)amino)-7-(3-(4-(2-((2-(2,6-dioxopiperidin-3-yl)-1,3-dioxoisoindolin-4-yl)amino)acetyl)piperazin-1-yl)propoxy)quinazolin-6-yl)acrylamide | 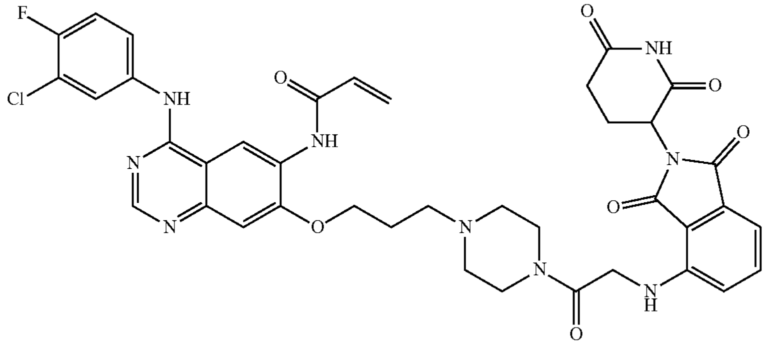 [SMILES: C=CC(=O)Nc1cc2c(Nc3ccc(F)c(Cl)c3)ncnc2cc1OCCCN1CCN(C(=O)CNc2cccc3c2C(=O)N(C2CCC(=O)NC2=O)C3=O)CC1] |
| 112 | SIAIS262125 | N-(4-((3-chloro-4-fluorophenyl)amino)-7-(3-(4-(6-((2-(2,6-dioxopiperidin-3-yl)-1,3-dioxoisoindolin-4-yl)amino)hexanoyl)piperazin-1-yl)propoxy)quinazolin-6-yl)acrylamide | 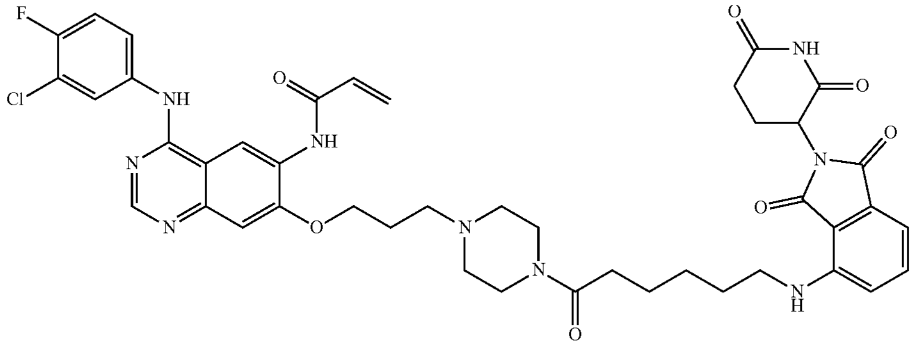 |

TABLE 1-continued

| | Compound No. | The compounds' name | Structure of the compounds |
|---|---|---|---|
| 113 | SIAIS262126 | N-(4-((3-chloro-4-fluorophenyl)amino)-7-(3-(4-(7-((2-(2,6-dioxopiperidin-3-yl)-1,3-dioxoisoindolin-4-yl)amino)heptanoyl)piperazin-1-yl)propoxy)quinazolin-6-yl)acrylamide | 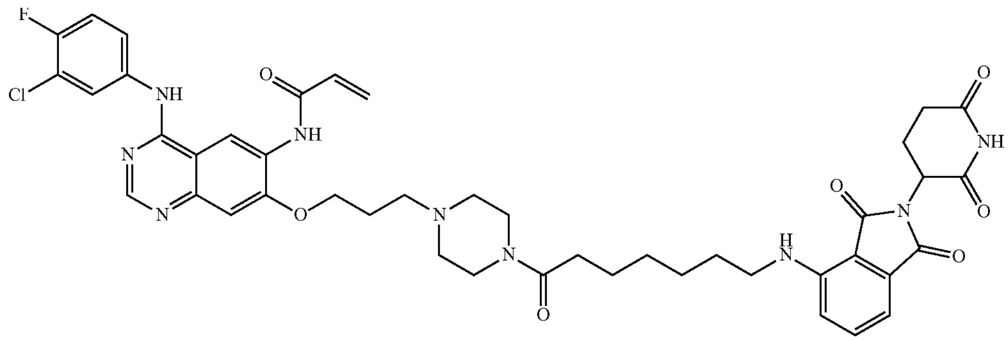 [SMILES: C=CC(=O)Nc1cc2c(Nc3ccc(F)c(Cl)c3)ncnc2cc1OCCCN1CCN(C(=O)CCCCCCNc2cccc3c2C(=O)N(C2CCC(=O)NC2=O)C3=O)CC1] |
| 114 | SIAIS262127 | N-(4-((3-chloro-4-fluorophenyl)amino)-7-(3-(4-(3-(2-(2-((2-(2,6-dioxopiperidin-3-yl)-1,3-dioxoisoindolin-4-yl)amino)ethoxy)ethoxy)propanoyl)piperazin-1-yl)propoxy)quinazolin-6-yl)acrylamide | 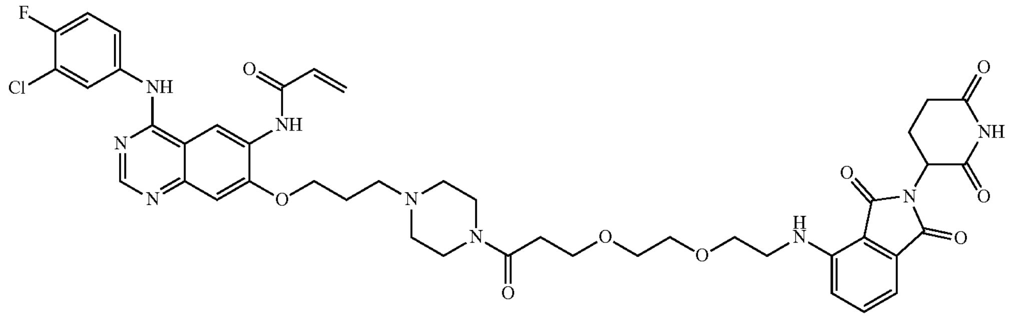 [SMILES: C=CC(=O)Nc1cc2c(Nc3ccc(F)c(Cl)c3)ncnc2cc1OCCCN1CCN(C(=O)CCOCCOCCNc2cccc3c2C(=O)N(C2CCC(=O)NC2=O)C3=O)CC1] |

TABLE 1-continued

| Compound No. | | The compounds' name | Structure of the compounds |
|---|---|---|---|
| 115 | SIAIS262128 | (2S,4R)-1-((S)-2-(5-(4-(3-((6-acrylamido-4-((3-chloro-4-fluorophenyl)amino)quinazolin-7-yl)oxy)propyl)piperazin-1-yl)-5-oxopentanamido)-3,3-dimethylbutanoyl)-4-hydroxy-N-(4-(4-methylthiazol-5-yl)benzyl)pyrrolidine-2-carboxamide | 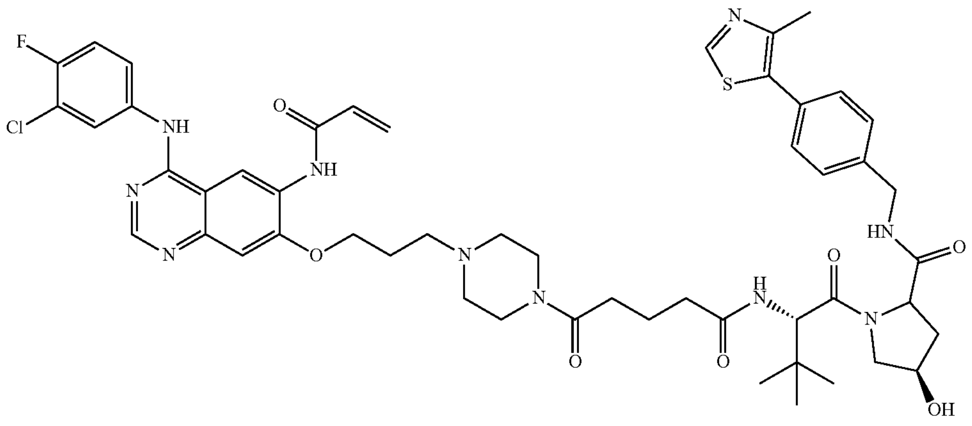 [SMILES: C=CC(=O)Nc1cc2c(Nc3ccc(F)c(Cl)c3)ncnc2cc1OCCCN1CCN(C(=O)CCCC(=O)N[C@H](C(=O)N2C[C@H](O)CC2C(=O)NCc2ccc(-c3scnc3C)cc2)C(C)(C)C)CC1] |
| 116 | SIAIS262131 | N-(4-((3-chloro-4-fluorophenyl)amino)-7-(3-(4-(6-(2-(2,6-dioxopiperidin-3-yl)-3-oxoisoindolin-1-yl)hex-5-yn-1-yl)piperazin-1-yl)propoxy)quinazolin-6-yl)acrylamide | 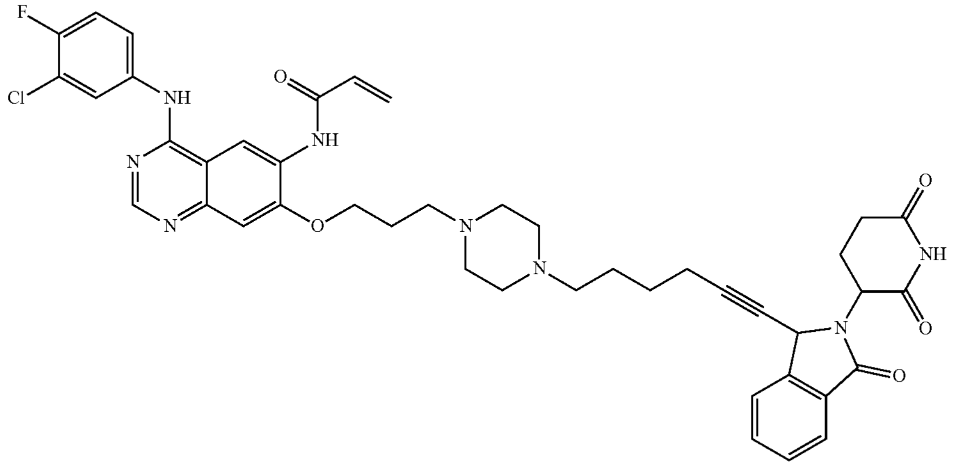 [SMILES: C=CC(=O)Nc1cc2c(Nc3ccc(F)c(Cl)c3)ncnc2cc1OCCCN1CCN(CCCCC#CC2c3ccccc3C(=O)N2C2CCC(=O)NC2=O)CC1] |

TABLE 1-continued
| | Compound No. | The compounds' name | Structure of the compounds |
|---|---|---|---|
| 117 | SIAIS262182 | N-(4-((3-chloro-4-fluorophenyl)amino)-7-(3-(4-(6-((2-(2,6-dioxopiperidin-3-yl)-1,3-dioxoisoindolin-4-yl)amino)hexyl)piperazin-1-yl)propoxy)quinazolin-6-yl)acrylamide | 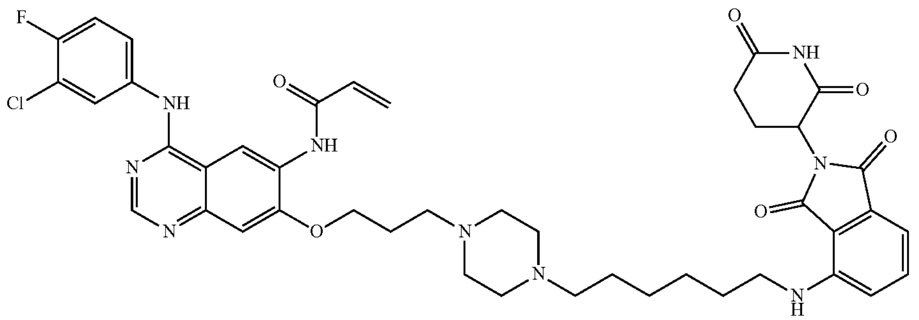 [SMILES: C=CC(=O)Nc1cc2c(Nc3ccc(F)c(Cl)c3)ncnc2cc1OCCCN1CCN(CCCCCCNc2cccc3c2C(=O)N(C2CCC(=O)NC2=O)C3=O)CC1] |
| 118 | SIAIS262174 | N-(4-((3-chloro-4-fluorophenyl)amino)-7-(3-(4-(4-(2-((2-(2,6-dioxopiperidin-3-yl)-1-oxoisoindolin-4-yl)thio)acetyl)piperazin-1-yl)piperidin-1-yl)propoxy)quinazolin-6-yl)acrylamide | 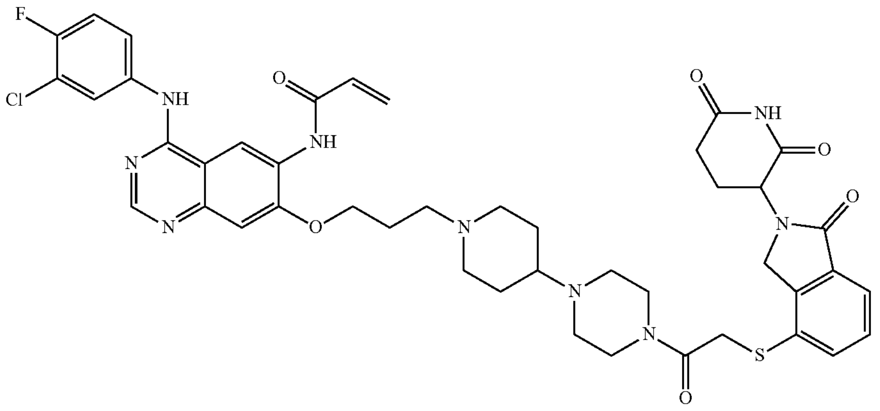 [SMILES: C=CC(=O)Nc1cc2c(Nc3ccc(F)c(Cl)c3)ncnc2cc1OCCCN1CCC(N2CCN(C(=O)CSc3cccc4c3CN(C3CCC(=O)NC3=O)C4=O)CC2)CC1] |

TABLE 1-continued

| Compound No. | | The compounds' name | Structure of the compounds |
|---|---|---|---|
| 119 | SIAIS262175 | N-(4-((3-chloro-4-fluorophenyl)amino)-7-(3-(4-(4-(5-((2-(2,6-dioxopiperidin-3-yl)-1-oxoisoindolin-4-yl)thio)pentanoyl)piperazin-1-yl)piperidin-1-yl)propoxy)quinazolin-6-yl)acrylamide | 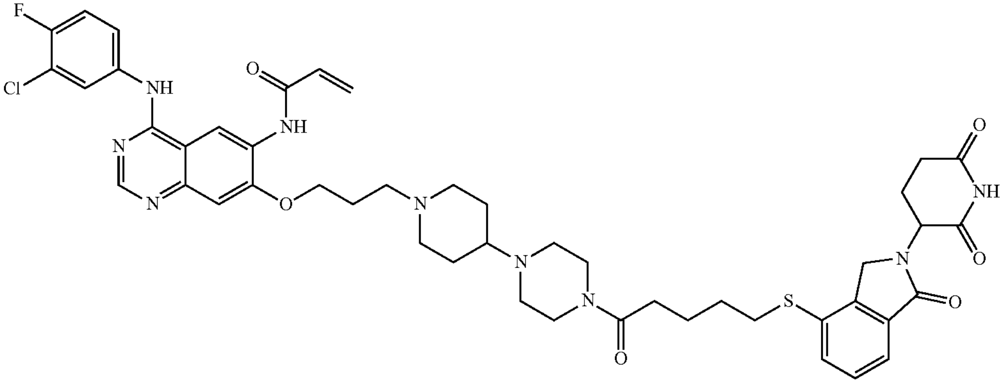 [SMILES: C=CC(=O)Nc1cc2c(Nc3ccc(F)c(Cl)c3)ncnc2cc1OCCCN1CCC(N2CCN(C(=O)CCCCSc3cccc4c3CN(C3CCC(=O)NC3=O)C4=O)CC2)CC1] |
| 120 | SIAIS262176 | N-(4-((3-chloro-4-fluorophenyl)amino)-7-(3-(4-(4-(6-((2-(2,6-dioxopiperidin-3-yl)-1-oxoisoindolin-4-yl)thio)hexanoyl)piperazin-1-yl)piperidin-1-yl)propoxy)quinazolin-6-yl)acrylamide | 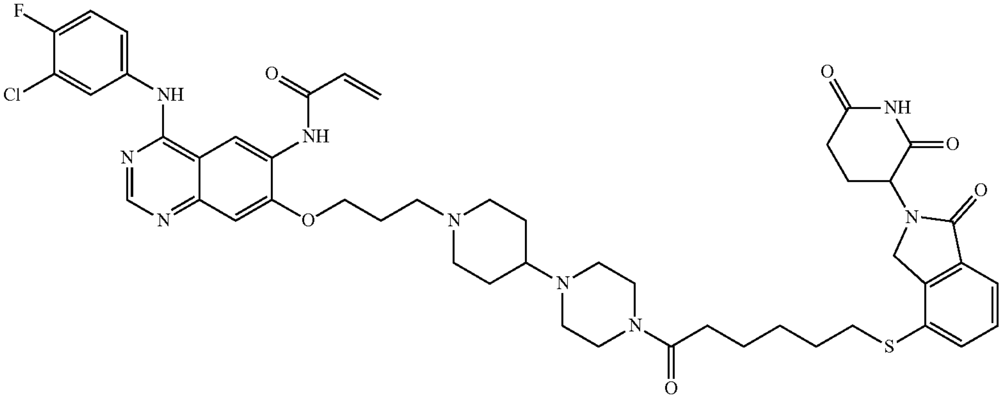 [SMILES: C=CC(=O)Nc1cc2c(Nc3ccc(F)c(Cl)c3)ncnc2cc1OCCCN1CCC(N2CCN(C(=O)CCCCCSc3cccc4c3CN(C3CCC(=O)NC3=O)C4=O)CC2)CC1] |

TABLE 1-continued

| Compound No. | | The compounds' name | Structure of the compounds |
|---|---|---|---|
| 121 | SIAIS262177 | N-(4-((3-chloro-4-fluorophenyl)amino)-7-(3-(4-(4-(2-((2-(2,6-dioxopiperidin-3-yl)-1,3-dioxoisoindolin-4-yl)amino)acetyl)piperazin-1-yl)piperidin-1-yl)propoxy)quinazolin-6-yl)acrylamide | 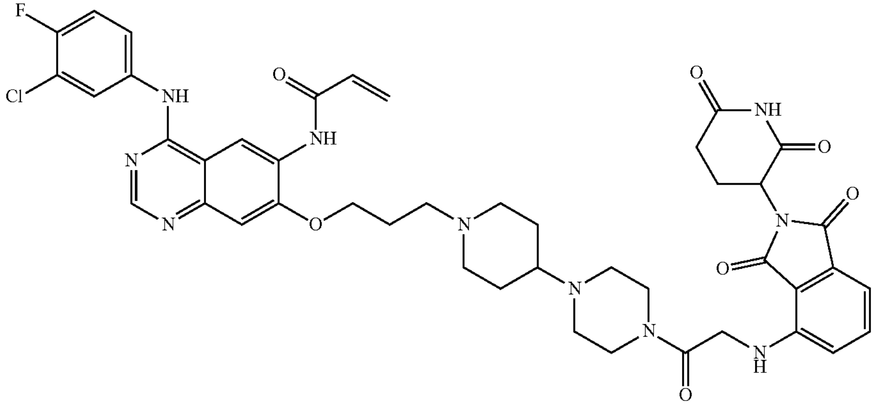 [SMILES: C=CC(=O)Nc1cc2c(Nc3ccc(F)c(Cl)c3)ncnc2cc1OCCCN1CCC(N2CCN(C(=O)CNc3cccc4c3C(=O)N(C3CCC(=O)NC3=O)C4=O)CC2)CC1] |
| 122 | SIAIS262178 | N-(4-((3-chloro-4-fluorophenyl)amino)-7-(3-(4-(4-(6-((2-(2,6-dioxopiperidin-3-yl)-1,3-dioxoisoindolin-4-yl)amino)hexanoyl)piperazin-1-yl)piperidin-1-yl)propoxy)quinazolin-6-yl)acrylamide | 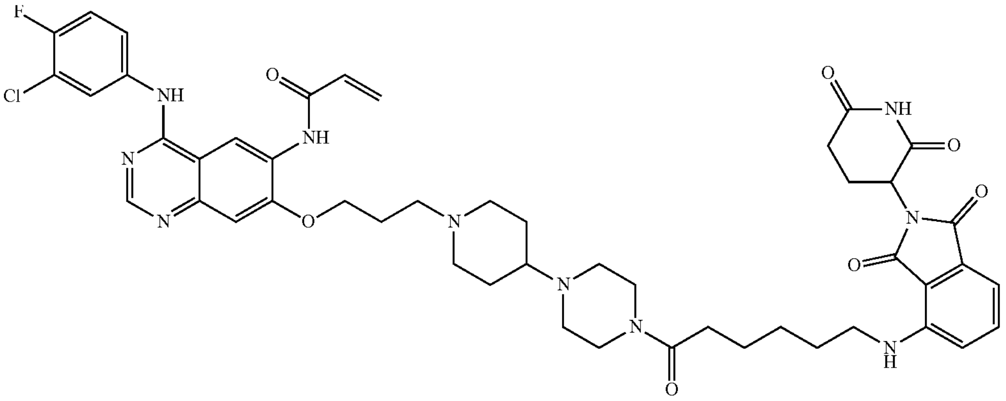 |

TABLE 1-continued

| Compound No. | | The compounds' name | Structure of the compounds |
|---|---|---|---|
| 123 | SIAIS262179 | N-(4-((3-chloro-4-fluorophenyl)amino)-7-(3-(4-(4-(7-((2-(2,6-dioxopiperidin-3-yl)-1,3-dioxoisoindolin-4-yl)amino)heptanoyl)piperazin-1-yl)piperidin-1-yl)propoxy)quinazolin-6-yl)acrylamide | 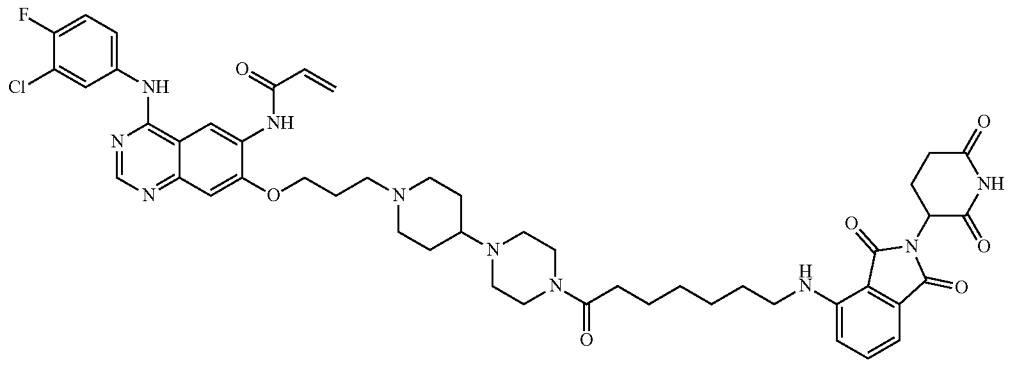 [SMILES: C=CC(=O)Nc1cc2c(Nc3ccc(F)c(Cl)c3)ncnc2cc1OCCCN1CCC(N2CCN(C(=O)CCCCCCNc3cccc4c3C(=O)N(C3CCC(=O)NC3=O)C4=O)CC2)CC1] |
| 124 | SIAIS262180 | N-(4-((3-chloro-4-fluorophenyl)amino)-7-(3-(4-(4-(6-((2-(2,6-dioxopiperidin-3-yl)-1-oxoisoindolin-4-yl)thio)hexyl)piperazin-1-yl)piperidin-1-yl)propoxy)quinazolin-6-yl)acrylamide | 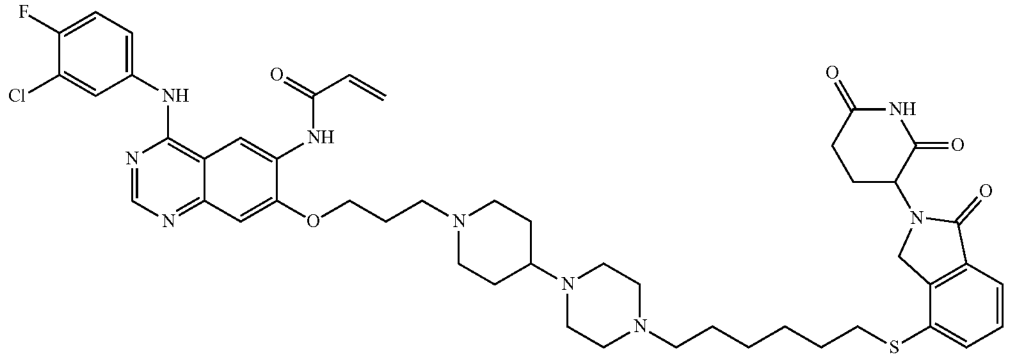 [SMILES: C=CC(=O)Nc1cc2c(Nc3ccc(F)c(Cl)c3)ncnc2cc1OCCCN1CCC(N2CCN(CCCCCCSc3cccc4c3CN(C3CCC(=O)NC3=O)C4=O)CC2)CC1] |

TABLE 1-continued

| Compound No. | | The compounds' name | Structure of the compounds |
|---|---|---|---|
| 125 | (SIAIS262183 | N-(4-((3-chloro-4-fluorophenyl)amino)-7-(3-(4-(4-(6-((2-(2,6-dioxopiperidin-3-yl)-1,3-dioxoisoindolin-4-yl)amino)hexyl)piperazin-1-yl)piperidin-1-yl)propoxy)quinazolin-6-yl)acrylamide | 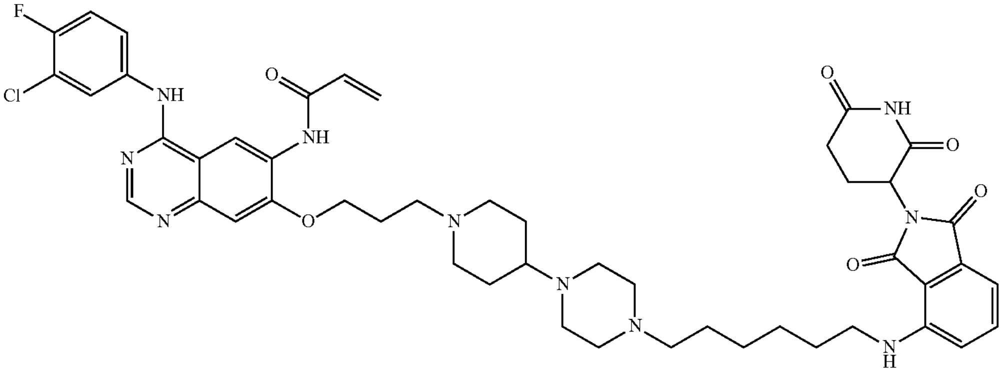 [SMILES: C=CC(=O)Nc1cc2c(Nc3ccc(F)c(Cl)c3)ncnc2cc1OCCCN1CCC(N2CCN(CCCCCCNc3cccc4c3C(=O)N(C3CCC(=O)NC3=O)C4=O)CC2)CC1] |
| 126 | (SIAIS293047 | 2-(4-((4-((3-chloro-4-fluorophenyl)amino)-7-methoxyquinazolin-6-yl)oxy)piperidin-1-yl)-N-(2-((2-(2,6-dioxopiperidin-3-yl)-1-oxoisoindolin-4-yl)thio)ethyl)acetamide | 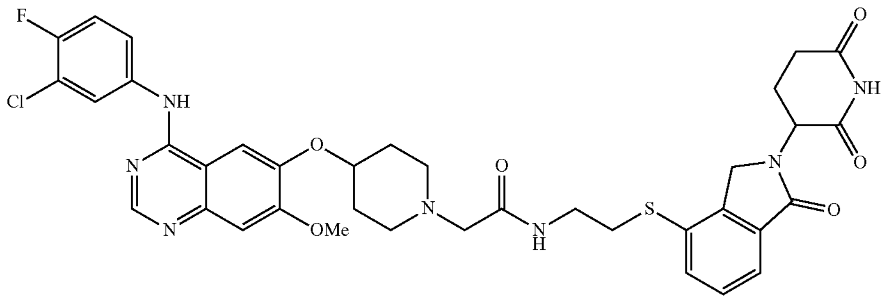 [SMILES: COc1cc2ncnc(Nc3ccc(F)c(Cl)c3)c2cc1OC1CCN(CC(=O)NCCSc2cccc3c2CN(C2CCC(=O)NC2=O)C3=O)CC1] |
| 127 | SIAIS293048 | 2-(4-((4-((3-chloro-4-fluorophenyl)amino)-7-methoxyquinazolin-6-yl)oxy)piperidin-1-yl)-N-(3-((2-(2,6-dioxopiperidin-3-yl)-1-oxoisoindolin-4-yl)thio)propyl)acetamide | 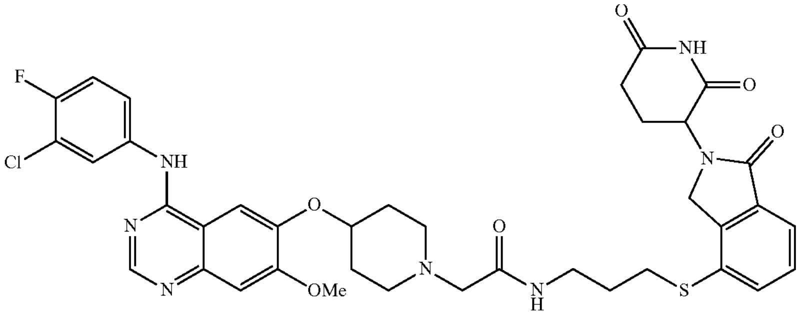 [SMILES: COc1cc2ncnc(Nc3ccc(F)c(Cl)c3)c2cc1OC1CCN(CC(=O)NCCCSc2cccc3c2CN(C2CCC(=O)NC2=O)C3=O)CC1] |

TABLE 1-continued

| | Compound No. | The compounds' name | Structure of the compounds |
|---|---|---|---|
| 128 | SIAIS293049 | 2-(4-((4-((3-chloro-4-fluorophenyl)amino)-7-methoxyquinazolin-6-yl)oxy)piperidin-1-yl)-N-(4-((2-(2,6-dioxopiperidin-3-yl)-1-oxoisoindolin-4-yl)thio)butyl)acetamide | 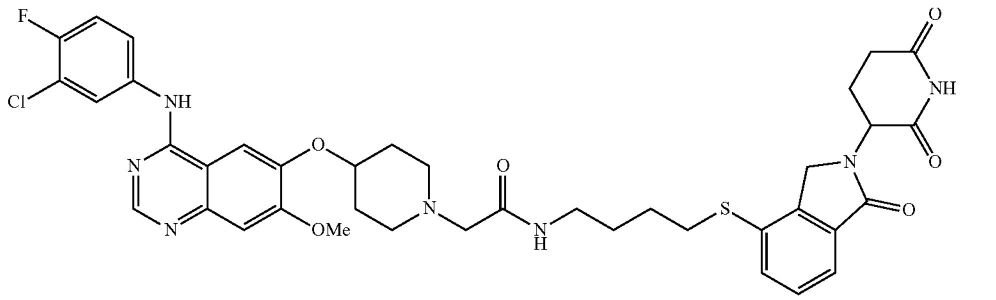 [SMILES: COc1cc2ncnc(Nc3ccc(F)c(Cl)c3)c2cc1OC1CCN(CC(=O)NCCCCSc2cccc3c2CN(C2CCC(=O)NC2=O)C3=O)CC1] |
| 129 | SIAIS293050 | 2-(4-((4-((3-chloro-4-fluorophenyl)amino)-7-methoxyquinazolin-6-yl)oxy)piperidin-1-yl)-N-(6-((2-(2,6-dioxopiperidin-3-yl)-1-oxoisoindolin-4-yl)thio)hexyl)acetamide | 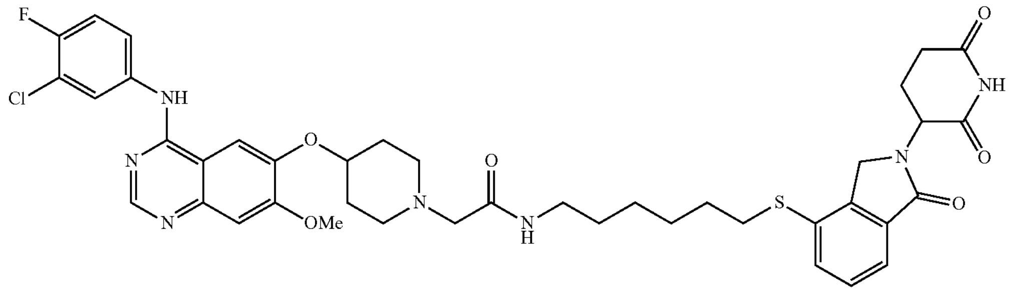 [SMILES: COc1cc2ncnc(Nc3ccc(F)c(Cl)c3)c2cc1OC1CCN(CC(=O)NCCCCCCSc2cccc3c2CN(C2CCC(=O)NC2=O)C3=O)CC1] |
| 130 | SIAIS293051 | 2-(4-((4-((3-chloro-4-fluorophenyl)amino)-7-methoxyquinazolin-6-yl)oxy)piperidin-1-yl)-N-(7-((2-(2,6-dioxopiperidin-3-yl)-1-oxoisoindolin-4-yl)thio)heptyl)acetamide | 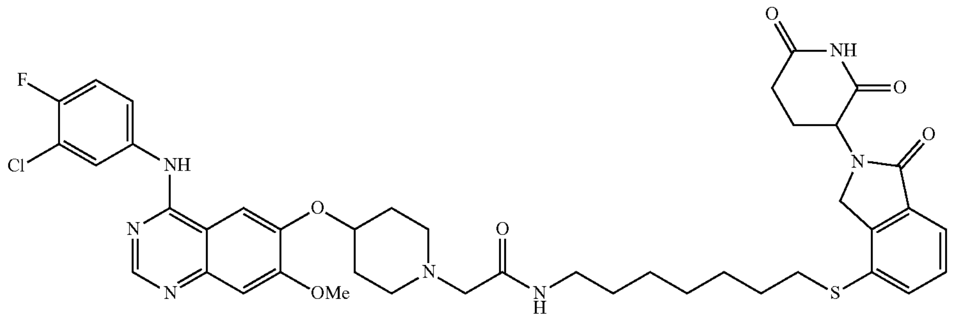 [SMILES: COc1cc2ncnc(Nc3ccc(F)c(Cl)c3)c2cc1OC1CCN(CC(=O)NCCCCCCCSc2cccc3c2CN(C2CCC(=O)NC2=O)C3=O)CC1] |

TABLE 1-continued

| | Com-pound No. | The compounds' name | Structure of the compounds |
|---|---|---|---|
| 131 | SIAIS293052 | 2-(4-((4-((3-chloro-4-fluorophenyl)amino)-7-methoxyquinazolin-6-yl)oxy)piperidin-1-yl)-N-(8-((2-(2,6-dioxopiperidin-3-yl)-1-oxoisoindolin-4-yl)thio)octyl)acetamide | 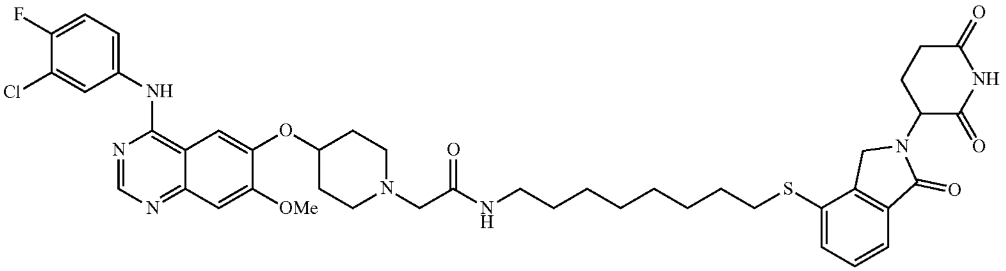 [SMILES: COc1cc2ncnc(Nc3ccc(F)c(Cl)c3)c2cc1OC1CCN(CC(=O)NCCCCCCCCSc2cccc3c2CN(C2CCC(=O)NC2=O)C3=O)CC1] |
| 132 | SIAIS293067 | 2-(4-((4-((3-chloro-2-fluorophenyl)amino)-7-methoxyquinazolin-6-yl)oxy)piperidin-1-yl)-N-(4-((2-(2,6-dioxopiperidin-3-yl)-1-oxoisoindolin-4-yl)thio)butyl)acetamide | 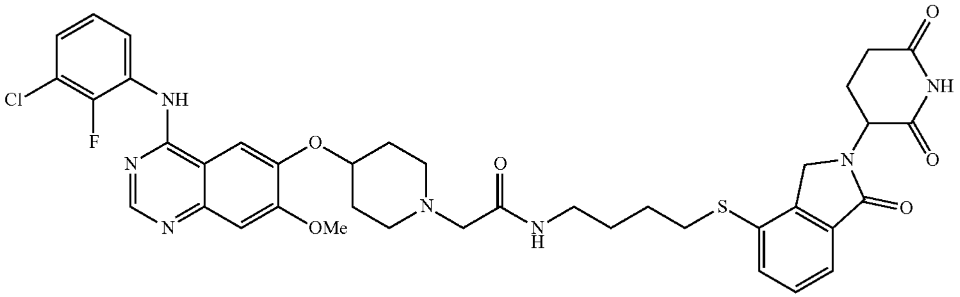 [SMILES: COc1cc2ncnc(Nc3cccc(Cl)c3F)c2cc1OC1CCN(CC(=O)NCCCCSc2cccc3c2CN(C2CCC(=O)NC2=O)C3=O)CC1] |
| 133 | SIAIS293068 | 2-(4-((4-((3-chloro-2-fluorophenyl)amino)-7-methoxyquinazolin-6-yl)oxy)piperidin-1-yl)-N-(6-((2-(2,6-dioxopiperidin-3-yl)-1-oxoisoindolin-4-yl)thio)hexyl)acetamide | 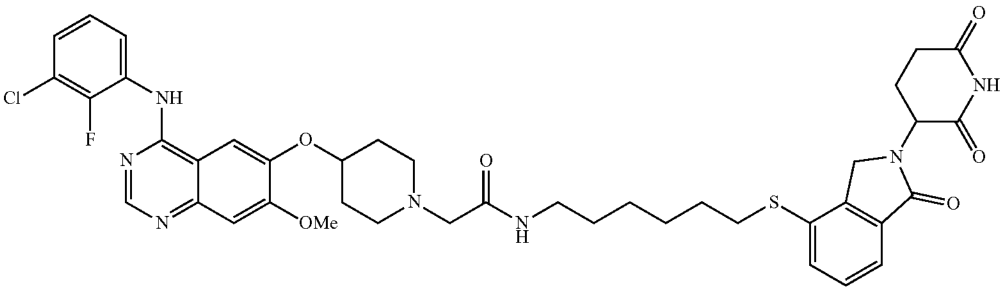 [SMILES: COc1cc2ncnc(Nc3cccc(Cl)c3F)c2cc1OC1CCN(CC(=O)NCCCCCCSc2cccc3c2CN(C2CCC(=O)NC2=O)C3=O)CC1] |

TABLE 1-continued
| | Compound No. | The compounds' name | Structure of the compounds |
|---|---|---|---|
| 134 | SIAIS293069 | 2-(4-((4-((3-chloro-2-fluorophenyl)amino)-7-methoxyquinazolin-6-yl)oxy)piperidin-1-yl)-N-(7-((2-(2,6-dioxopiperidin-3-yl)-1-oxoisoindolin-4-yl)thio)heptyl)acetamide | 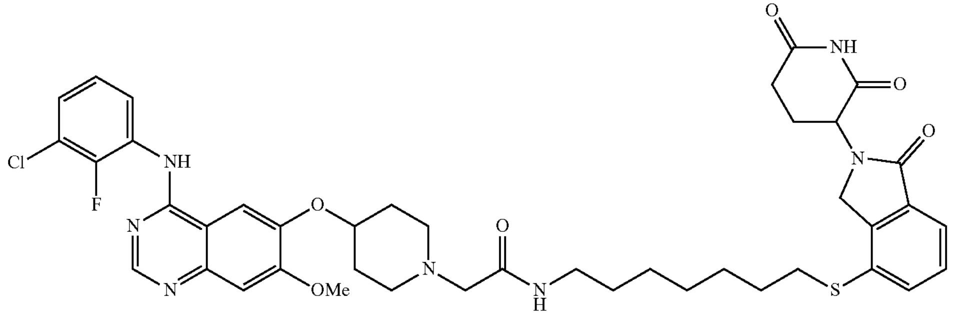 [SMILES: COc1cc2ncnc(Nc3cccc(Cl)c3F)c2cc1OC1CCN(CC(=O)NCCCCCCCSc2cccc3c2CN(C2CCC(=O)NC2=O)C3=O)CC1] |
| 135 | SIAIS293070 | 2-(4-((4-((3-chloro-2-fluorophenyl)amino)-7-methoxyquinazolin-6-yl)oxy)piperidin-1-yl)-N-(8-((2-(2,6-dioxopiperidin-3-yl)-1-oxoisoindolin-4-yl)thio)octyl)acetamide | 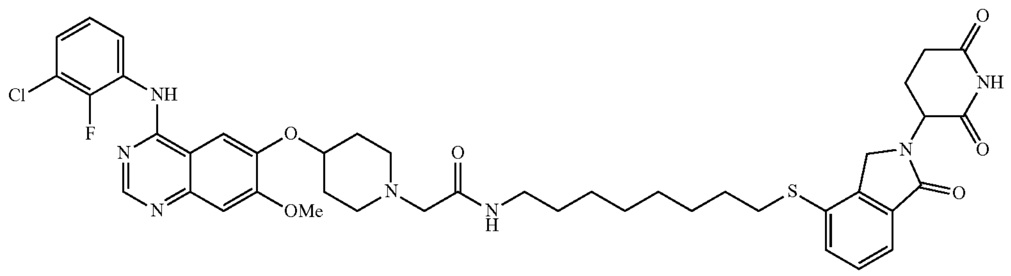 [SMILES: COc1cc2ncnc(Nc3cccc(Cl)c3F)c2cc1OC1CCN(CC(=O)NCCCCCCCCSc2cccc3c2CN(C2CCC(=O)NC2=O)C3=O)CC1] |

TABLE 1-continued

| | Compound No. | The compounds' name | Structure of the compounds |
|---|---|---|---|
| 136 | SIAIS337052 | N-(2-((2-(2-((2-(2,6-dioxopiperidin-3-yl)-1-oxoisoindolin-4-yl)thio)-N-methylacetamido)ethyl)(methyl)amino)-4-methoxy-5-((4-(1-methyl-1H-indol-3-yl)pyrimidin-2-yl)amino)phenyl)acrylamide | 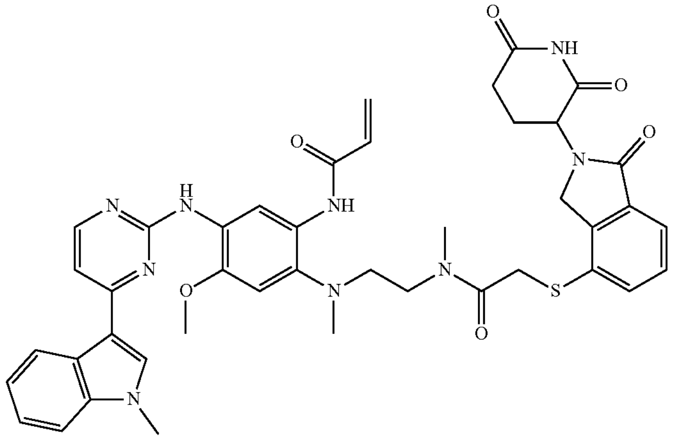 [SMILES: C=CC(=O)Nc1cc(Nc2nccc(-c3cn(C)c4ccccc34)n2)c(OC)cc1N(C)CCN(C)C(=O)CSc1cccc2c1CN(C1CCC(=O)NC1=O)C2=O] |
| 137 | SIAIS337053 | N-(2-((2-(3-((2-(2,6-dioxopiperidin-3-yl)-1-oxoisoindolin-4-yl)thio)-N-methylpropanamido)ethyl)(methyl)amino)-4-methoxy-5-((4-(1-methyl-1H-indol-3-yl)pyrimidin-2-yl)amino)phenyl)acrylamide | 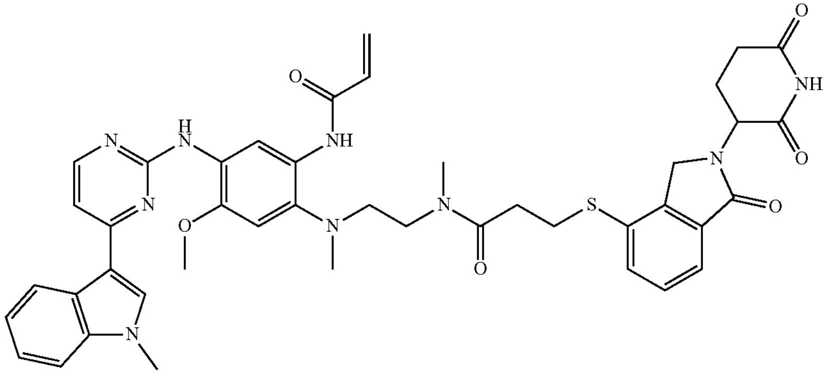 [SMILES: C=CC(=O)Nc1cc(Nc2nccc(-c3cn(C)c4ccccc34)n2)c(OC)cc1N(C)CCN(C)C(=O)CCSc1cccc2c1CN(C1CCC(=O)NC1=O)C2=O] |

TABLE 1-continued

| | Compound No. | The compounds' name | Structure of the compounds |
|---|---|---|---|
| 138 | SIAIS337054 | N-(2-((2-acrylamido-5-methoxy-4-((4-(1-methyl-1H-indol-3-yl)pyrimidin-2-yl)amino)phenyl)(methyl)amino)ethyl)-4-((2-(2,6-dioxopiperidin-3-yl)-1-oxoisoindolin-4-yl)thio)-N-methylbutanamide | 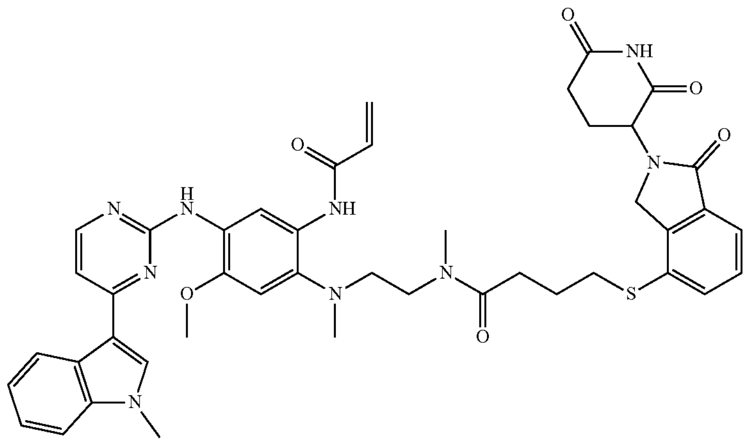 [SMILES: C=CC(=O)Nc1cc(Nc2nccc(-c3cn(C)c4ccccc34)n2)c(OC)cc1N(C)CCN(C)C(=O)CCCSc1cccc2c1CN(C1CCC(=O)NC1=O)C2=O] |
| 139 | SIAIS337055 | N-(2-((2-acrylamido-5-methoxy-4-((4-(1-methyl-1H-indol-3-yl)pyrimidin-2-yl)amino)phenyl)(methyl)amino)ethyl)-5-((2-(2,6-dioxopiperidin-3-yl)-1-oxoisoindolin-4-yl)thio)-N-methylpentanamide | 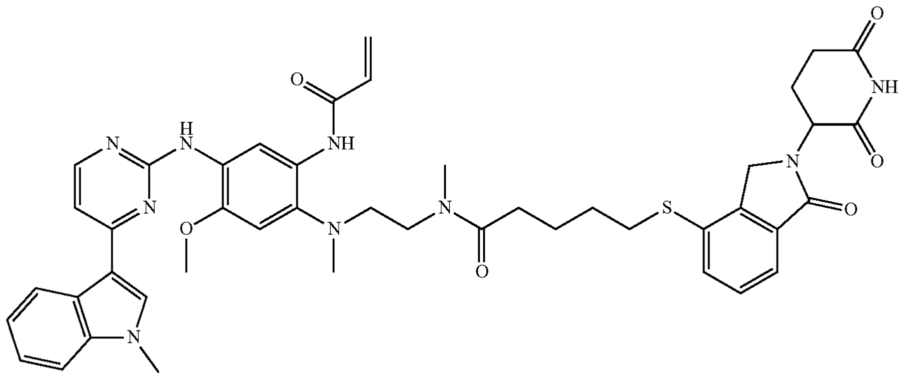 |

TABLE 1-continued

| | Compound No. | The compounds' name | Structure of the compounds |
|---|---|---|---|
| 140 | SIAIS337056 | N-(2-((2-acrylamido-5-methoxy-4-((4-(1-methyl-1H-indol-3-yl)pyrimidin-2-yl)amino)phenyl)(methyl)amino)ethyl)-6-((2-(2,6-dioxopiperidin-3-yl)-1-oxoisoindolin-4-yl)thio)-N-methylhexanamide | 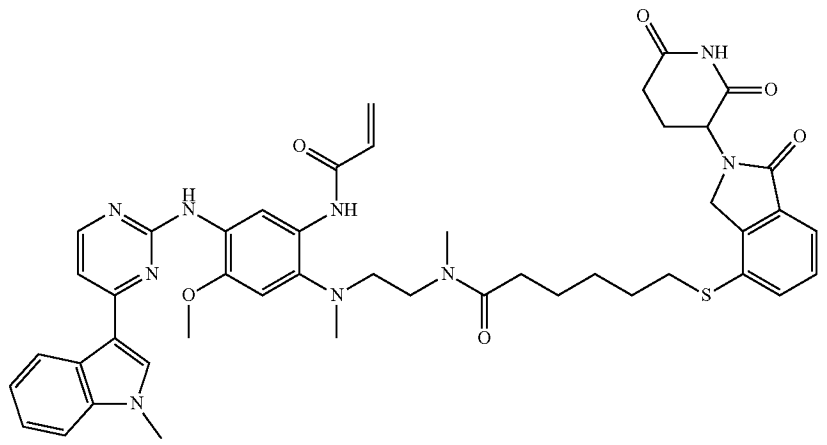 [SMILES: C=CC(=O)Nc1cc(Nc2nccc(-c3cn(C)c4ccccc34)n2)c(OC)cc1N(C)CCN(C)C(=O)CCCCCSc1cccc2c1CN(C1CCC(=O)NC1=O)C2=O] |
| 141 | SIAIS337057 | N-(2-((2-acrylamido-5-methoxy-4-((4-(1-methyl-1H-indol-3-yl)pyrimidin-2-yl)amino)phenyl)(methyl)amino)ethyl)-7-((2-(2,6-dioxopiperidin-3-yl)-1-oxoisoindolin-4-yl)thio)-N-methylheptanamide | 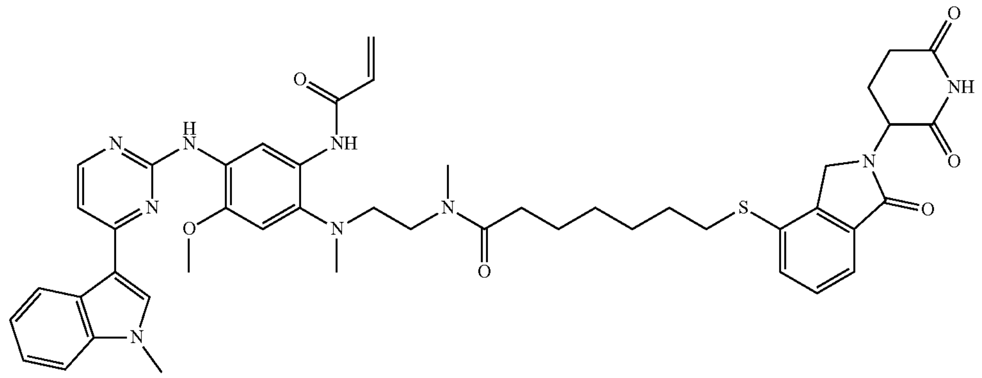 [SMILES: C=CC(=O)Nc1cc(Nc2nccc(-c3cn(C)c4ccccc34)n2)c(OC)cc1N(C)CCN(C)C(=O)CCCCCCSc1cccc2c1CN(C1CCC(=O)NC1=O)C2=O] |

TABLE 1-continued

| | Compound No. | The compounds' name | Structure of the compounds |
|---|---|---|---|
| 142 | SIAIS337059 | N-(2-((2-acrylamido-5-methoxy-4-((4-(1-methyl-1H-indol-3-yl)pyrimidin-2-yl)amino)phenyl)(methyl)amino)ethyl)-9-((2-(2,6-dioxopiperidin-3-yl)-1-oxoisoindolin-4-yl)thio)-N-methylnonanamide | 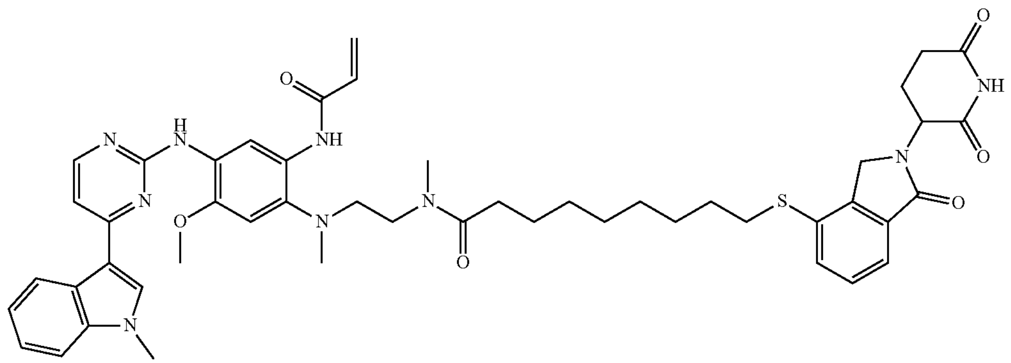 [SMILES: C=CC(=O)Nc1cc(Nc2nccc(-c3cn(C)c4ccccc34)n2)c(OC)cc1N(C)CCN(C)C(=O)CCCCCCCCSc1cccc2c1CN(C1CCC(=O)NC1=O)C2=O] |
| 143 | SIAIS337060 | N-(2-((2-acrylamido-5-methoxy-4-((4-(1-methyl-1H-indol-3-yl)pyrimidin-2-yl)amino)phenyl)(methyl)amino)ethyl)-10-((2-(2,6-dioxopiperidin-3-yl)-1-oxoisoindolin-4-yl)thio)-N-methyldecanamide | 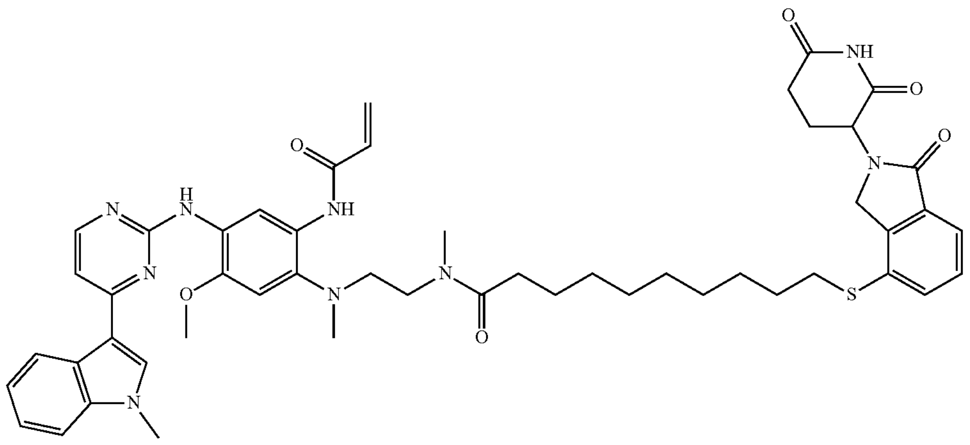 [SMILES: C=CC(=O)Nc1cc(Nc2nccc(-c3cn(C)c4ccccc34)n2)c(OC)cc1N(C)CCN(C)C(=O)CCCCCCCCCSc1cccc2c1CN(C1CCC(=O)NC1=O)C2=O] |

TABLE 1-continued

| | Compound No. | The compounds' name | Structure of the compounds |
|---|---|---|---|
| 144 | SIAIS337061 | N-(2-((2-acrylamido-5-methoxy-4-((4-(1-methyl-1H-indol-3-yl)pyrimidin-2-yl)amino)phenyl)(methyl)amino)ethyl)-11-((2-(2,6-dioxopiperidin-3-yl)-1-oxoisoindolin-4-yl)thio)-N-methylundecanamide | 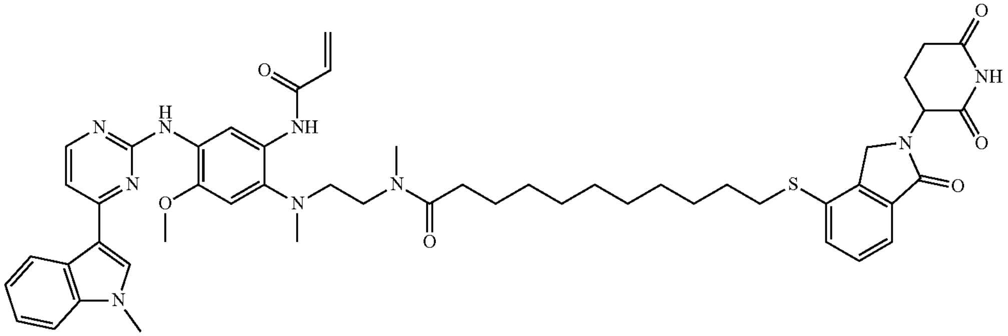 [SMILES: C=CC(=O)Nc1cc(Nc2nccc(-c3cn(C)c4ccccc34)n2)c(OC)cc1N(C)CCN(C)C(=O)CCCCCCCCCCSc1cccc2c1CN(C1CCC(=O)NC1=O)C2=O] |
| 145 | SIAIS337074 | N-(2-((2-(2-(2-((2-(2,6-dioxopiperidin-3-yl)-1-oxoisoindolin-4-yl)thio)ethoxy)-N-methylacetamido)ethyl)(methyl)amino)-4-methoxy-5-((4-(1-methyl-1H-indol-3-yl)pyrimidin-2-yl)amino)phenyl)acrylamide | 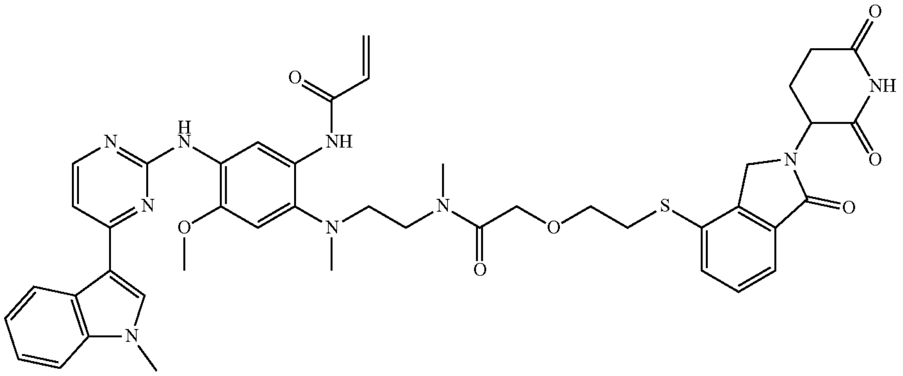 [SMILES: C=CC(=O)Nc1cc(Nc2nccc(-c3cn(C)c4ccccc34)n2)c(OC)cc1N(C)CCN(C)C(=O)COCCSc1cccc2c1CN(C1CCC(=O)NC1=O)C2=O] |

TABLE 1-continued

| Compound No. | | The compounds' name | Structure of the compounds |
|---|---|---|---|
| 146 | SIAIS337075 | N-(2-((2-(2-(2-(2-((2-(2,6-dioxopiperidin-3-yl)-1-oxoisoindolin-4-yl)thio)ethoxy)ethoxy)-N-methylacetamido)ethyl)(methyl)amino)-4-methoxy-5-((4-(1-methyl-1H-indol-3-yl)pyrimidin-2-yl)amino)phenyl)acrylamide | 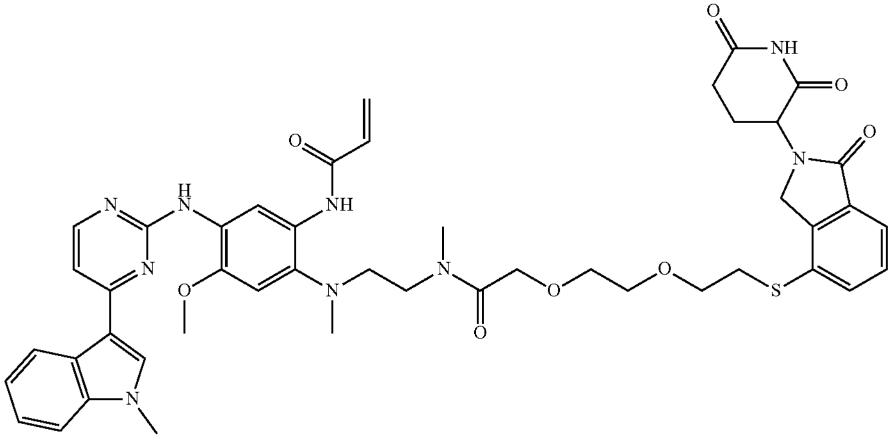 [SMILES: C=CC(=O)Nc1cc(Nc2nccc(-c3cn(C)c4ccccc34)n2)c(OC)cc1N(C)CCN(C)C(=O)COCCOCCSc1cccc2c1CN(C1CCC(=O)NC1=O)C2=O] |
| 147 | SIAIS337076 | N-(2-((14-((2-(2,6-dioxopiperidin-3-yl)-1-oxoisoindolin-4-yl)thio)-3-methyl-4-oxo-6,9,12-trioxa-3-azatetradecyl)(methyl)amino)-4-methoxy-5-((4-(1-methyl-1H-indol-3-yl)pyrimidin-2-yl)amino)phenyl)acrylamide | 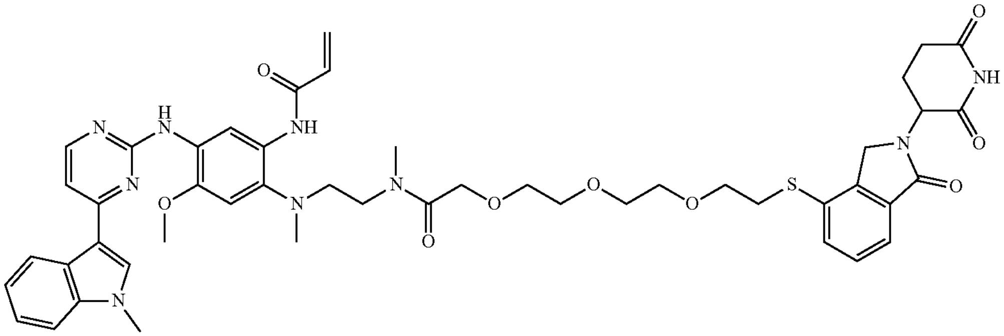 [SMILES: C=CC(=O)Nc1cc(Nc2nccc(-c3cn(C)c4ccccc34)n2)c(OC)cc1N(C)CCN(C)C(=O)COCCOCCOCCSc1cccc2c1CN(C1CCC(=O)NC1=O)C2=O] |

TABLE 1-continued

| | Compound No. | The compounds' name | Structure of the compounds |
|---|---|---|---|
| 148 | SIAIS337077 | N-(2-((2-acrylamido-5-methoxy-4-((4-(1-methyl-1H-indol-3-yl)pyrimidin-2-yl)amino)phenyl)(methyl)amino)ethyl)-14-((2-(2,6-dioxopiperidin-3-yl)-1-oxoisoindolin-4-yl)thio)-N-methyl-3,6,9,12-tetraoxatetradecanamide | 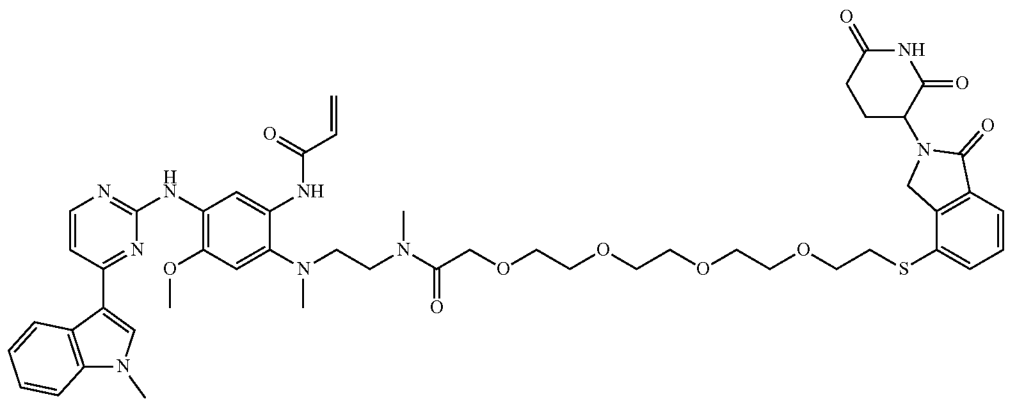 [SMILES: C=CC(=O)Nc1cc(Nc2nccc(-c3cn(C)c4ccccc34)n2)c(OC)cc1N(C)CCN(C)C(=O)COCCOCCOCCOCCSc1cccc2c1CN(C1CCC(=O)NC1=O)C2=O] |
| 149 | SIAIS337078 | N-(2-((2-acrylamido-5-methoxy-4-((4-(1-methyl-1H-indol-3-yl)pyrimidin-2-yl)amino)phenyl)(methyl)amino)ethyl)-17-((2-(2,6-dioxopiperidin-3-yl)-1-oxoisoindolin-4-yl)thio)-N-methyl-3,6,9,12,15-pentaoxaheptadecanamide | 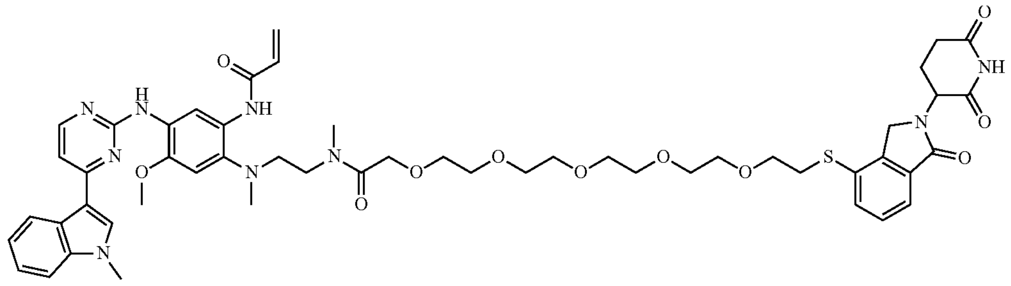 [SMILES: C=CC(=O)Nc1cc(Nc2nccc(-c3cn(C)c4ccccc34)n2)c(OC)cc1N(C)CCN(C)C(=O)COCCOCCOCCOCCOCCSc1cccc2c1CN(C1CCC(=O)NC1=O)C2=O] |

TABLE 1-continued

| | Compound No. | The compounds' name | Structure of the compounds |
|---|---|---|---|
| 150 | SIAIS337079 | N-(2-((2-((3-((2-(2,6-dioxopiperidin-3-yl)-1-oxoisoindolin-4-yl)thio)propyl)(methyl)amino)ethyl)(methyl)amino)-4-methoxy-5-((4-(1-methyl-1H-indol-3-yl)pyrimidin-2-yl)amino)phenyl)acrylamide | 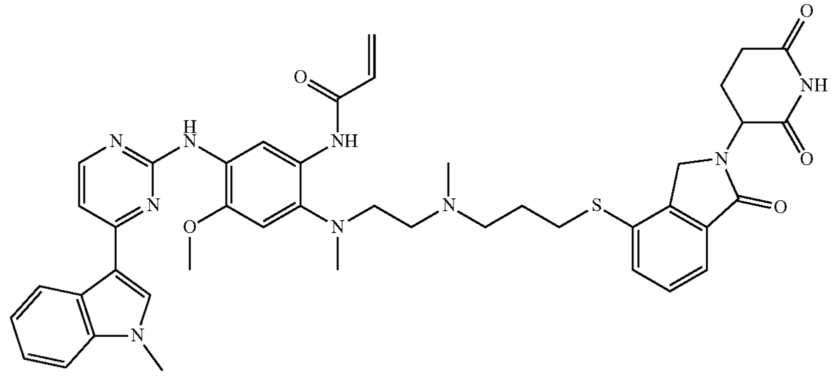 [SMILES: C=CC(=O)Nc1cc(Nc2nccc(-c3cn(C)c4ccccc34)n2)c(OC)cc1N(C)CCN(C)CCCSc1cccc2c1CN(C1CCC(=O)NC1=O)C2=O] |
| 151 | SIAIS337081 | N-(2-((2-((5-((2-(2,6-dioxopiperidin-3-yl)-1-oxoisoindolin-4-yl)thio)pentyl)(methyl)amino)ethyl)(methyl)amino)-4-methoxy-5-((4-(1-methyl-1H-indol-3-yl)pyrimidin-2-yl)amino)phenyl)acrylamide | 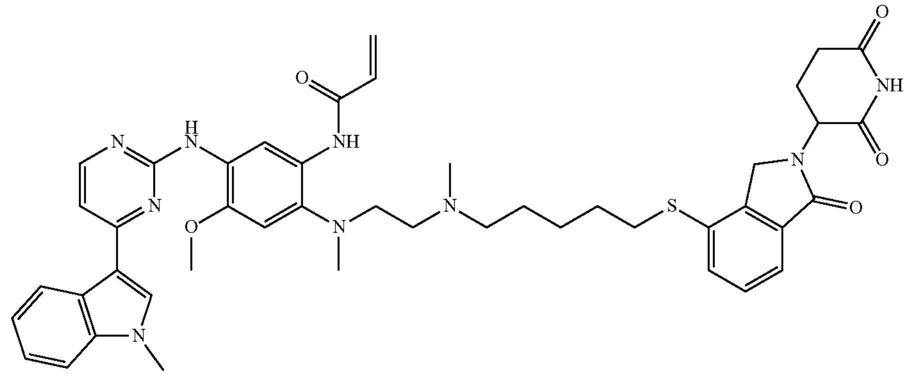 [SMILES: C=CC(=O)Nc1cc(Nc2nccc(-c3cn(C)c4ccccc34)n2)c(OC)cc1N(C)CCN(C)CCCCCSc1cccc2c1CN(C1CCC(=O)NC1=O)C2=O] |

TABLE 1-continued

| | Compound No. | The compounds' name | Structure of the compounds |
|---|---|---|---|
| 152 | SIAIS337082 | N-(2-((2-((6-((2-(2,6-dioxopiperidin-3-yl)-1-oxoisoindolin-4-yl)thio)hexyl)(methyl)amino)ethyl)(methyl)amino)-4-methoxy-5-((4-(1-methyl-1H-indol-3-yl)pyrimidin-2-yl)amino)phenyl)acrylamide | 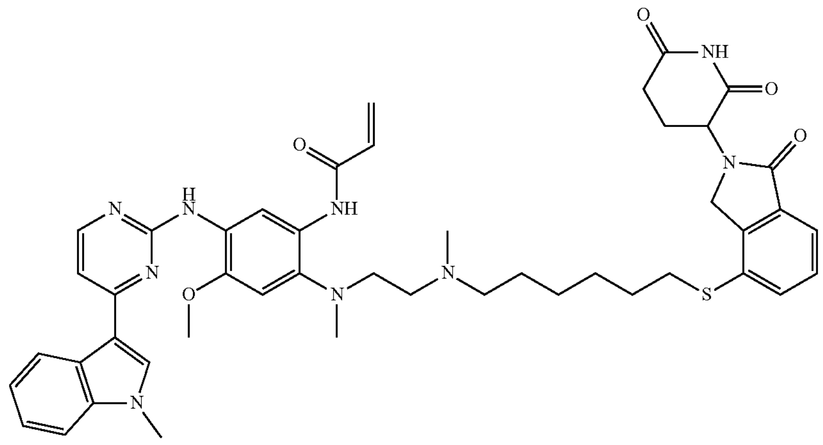 [SMILES: C=CC(=O)Nc1cc(Nc2nccc(-c3cn(C)c4ccccc34)n2)c(OC)cc1N(C)CCN(C)CCCCCCSc1cccc2c1CN(C1CCC(=O)NC1=O)C2=O] |
| 153 | SIAIS337083 | N-(2-((2-((7-((2-(2,6-dioxopiperidin-3-yl)-1-oxoisoindolin-4-yl)thio)heptyl)(methyl)amino)ethyl)(methyl)amino)-4-methoxy-5-((4-(1-methyl-1H-indol-3-yl)pyrimidin-2-yl)amino)phenyl)acrylamide | 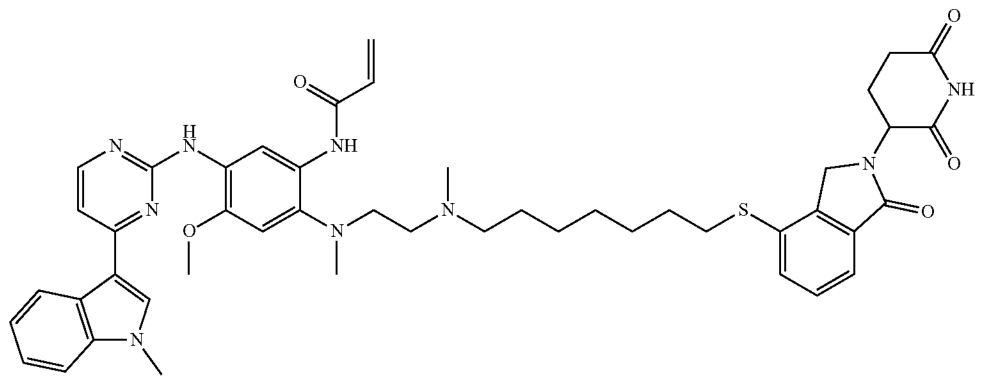 [SMILES: C=CC(=O)Nc1cc(Nc2nccc(-c3cn(C)c4ccccc34)n2)c(OC)cc1N(C)CCN(C)CCCCCCCSc1cccc2c1CN(C1CCC(=O)NC1=O)C2=O] |

TABLE 1-continued

| | Compound No. | The compounds' name | Structure of the compounds |
|---|---|---|---|
| 154 | SIAIS337084 | N-(2-((2-((8-((2-(2,6-dioxopiperidin-3-yl)-1-oxoisoindolin-4-yl)thio)octyl)(methyl)amino)ethyl)(methyl)amino)-4-methoxy-5-((4-(1-methyl-1H-indol-3-yl)pyrimidin-2-yl)amino)phenyl)acrylamide | 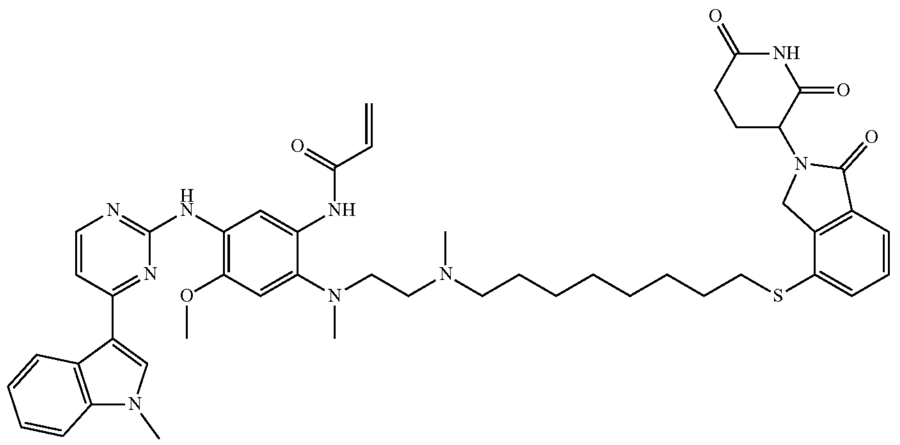 [SMILES: C=CC(=O)Nc1cc(Nc2nccc(-c3cn(C)c4ccccc34)n2)c(OC)cc1N(C)CCN(C)CCCCCCCCSc1cccc2c1CN(C1CCC(=O)NC1=O)C2=O] |
| 155 | SIAIS337085 | N-(2-((2-((9-((2-(2,6-dioxopiperidin-3-yl)-1-oxoisoindolin-4-yl)thio)nonyl)(methyl)amino)ethyl)(methyl)amino)-4-methoxy-5-((4-(1-methyl-1H-indol-3-yl)pyrimidin-2-yl)amino)phenyl)acrylamide | 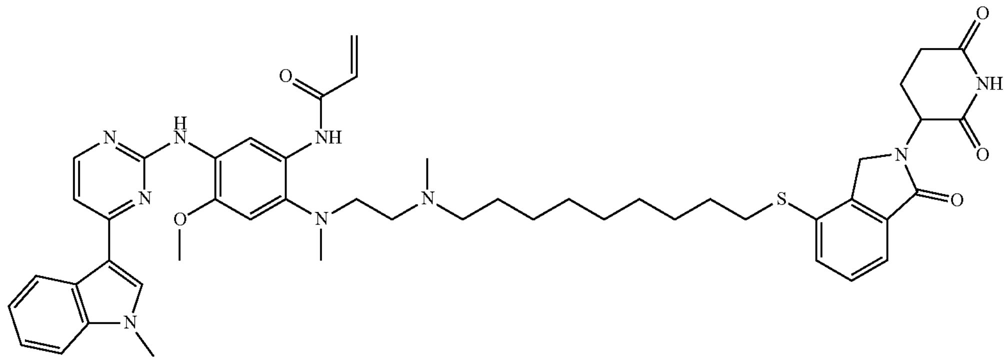 [SMILES: C=CC(=O)Nc1cc(Nc2nccc(-c3cn(C)c4ccccc34)n2)c(OC)cc1N(C)CCN(C)CCCCCCCCCSc1cccc2c1CN(C1CCC(=O)NC1=O)C2=O] |

TABLE 1-continued

| | Compound No. | The compounds' name | Structure of the compounds |
|---|---|---|---|
| 156 | SIAIS337086 | N-(2-((2-((10-((2-(2,6-dioxopiperidin-3-yl)-1-oxoisoindolin-4-yl)thio)decyl)(methyl)amino)ethyl)(methyl)amino)-4-methoxy-5-((4-(1-methyl-1H-indol-3-yl)pyrimidin-2-yl)amino)phenyl)acrylamide | 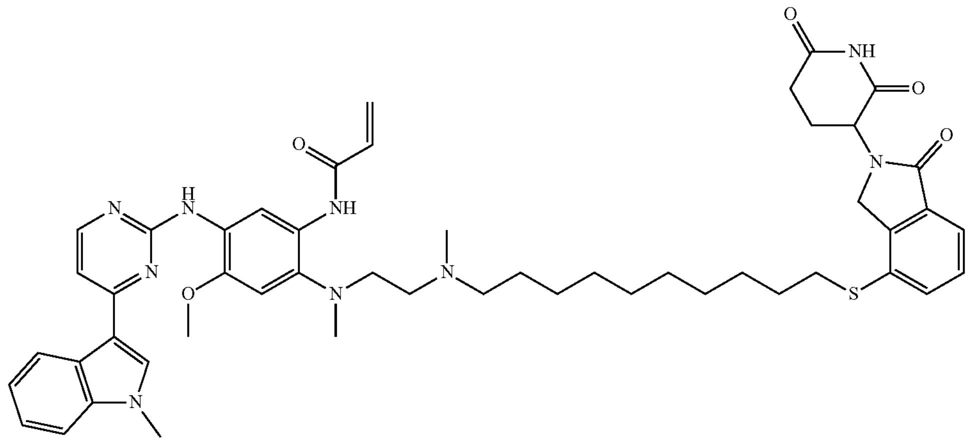 [SMILES: C=CC(=O)Nc1cc(Nc2nccc(-c3cn(C)c4ccccc34)n2)c(OC)cc1N(C)CCN(C)CCCCCCCCCCSc1cccc2c1CN(C1CCC(=O)NC1=O)C2=O] |
| 157 | SIAIS337087 | N-(2-((2-((11-((2-(2,6-dioxopiperidin-3-yl)-1-oxoisoindolin-4-yl)thio)undecyl)(methyl)amino)ethyl)(methyl)amino)-4-methoxy-5-((4-(1-methyl-1H-indol-3-yl)pyrimidin-2-yl)amino)phenyl)acrylamide | 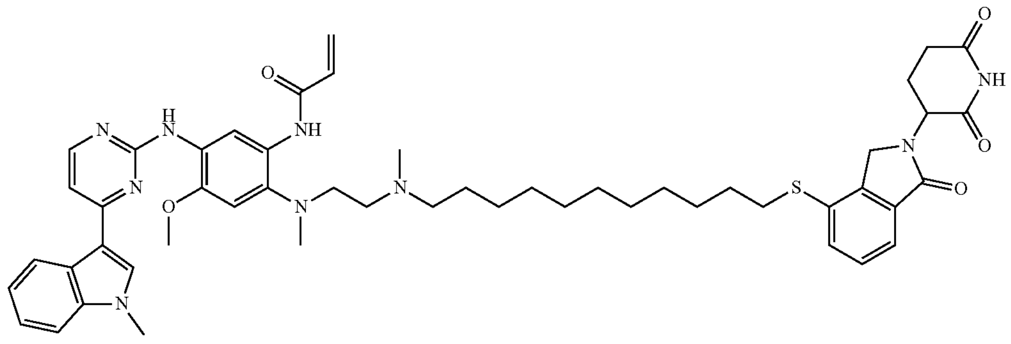 [SMILES: C=CC(=O)Nc1cc(Nc2nccc(-c3cn(C)c4ccccc34)n2)c(OC)cc1N(C)CCN(C)CCCCCCCCCCCSc1cccc2c1CN(C1CCC(=O)NC1=O)C2=O] |

TABLE 1-continued

| | Compound No. | The compounds' name | Structure of the compounds |
|---|---|---|---|
| 158 | SIAIS337088 | N-(2-((2-((4-(((2-(2,6-dioxopiperidin-3-yl)-1-oxoisoindolin-4-yl)thio)methyl)benzyl)(methyl)amino)ethyl)(methyl)amino)-4-methoxy-5-((4-(1-methyl-1H-indol-3-yl)pyrimidin-2-yl)amino)phenyl)acrylamide | 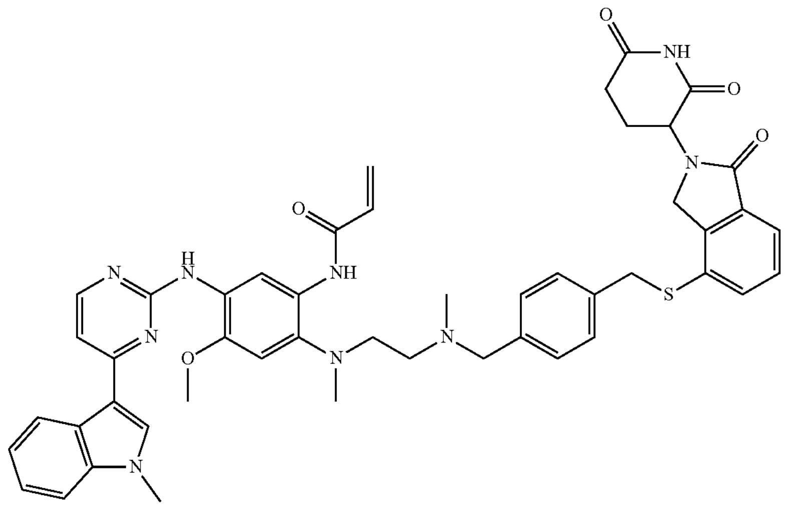 [SMILES: C=CC(=O)Nc1cc(Nc2nccc(-c3cn(C)c4ccccc34)n2)c(OC)cc1N(C)CCN(C)Cc1ccc(CSc2cccc3c2CN(C2CCC(=O)NC2=O)C3=O)cc1] |
| 159 | SIAIS337089 | N-(2-((2-((5-(2-(2,6-dioxopiperidin-3-yl)-1-oxoisoindolin-4-yl)pent-4-yn-1-yl)(methyl)amino)ethyl)(methyl)amino)-4-methoxy-5-((4-(1-methyl-1H-indol-3-yl)pyrimidin-2-yl)amino)phenyl)acrylamide | 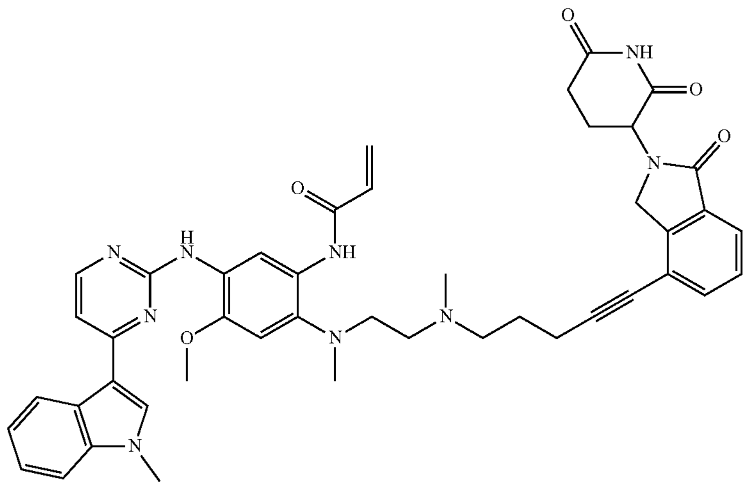 [SMILES: C=CC(=O)Nc1cc(Nc2nccc(-c3cn(C)c4ccccc34)n2)c(OC)cc1N(C)CCN(C)CCCC#Cc1cccc2c1CN(C1CCC(=O)NC1=O)C2=O] |

TABLE 1-continued

| | Compound No. | The compounds' name | Structure of the compounds |
|---|---|---|---|
| 160 | SIAIS337090 | N-(2-((2-((5-(2-(2,6-dioxopiperidin-3-yl)-1-oxoisoindolin-4-yl)pent-4-yn-1-yl)(methyl)amino)ethyl)(methyl)amino)-4-methoxy-5-((4-(1-methyl-1H-indol-3-yl)pyrimidin-2-yl)amino)phenyl)acrylamide | 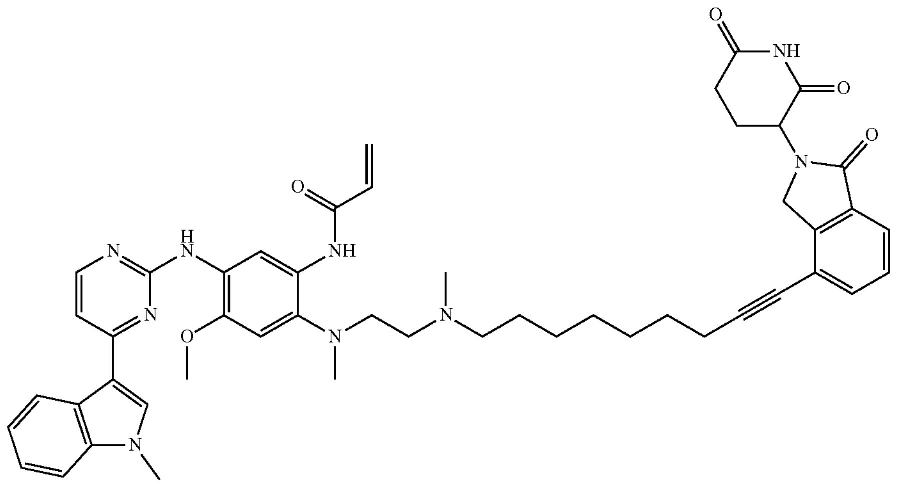 [SMILES: C=CC(=O)Nc1cc(Nc2nccc(-c3cn(C)c4ccccc34)n2)c(OC)cc1N(C)CCN(C)CCCCCCCC#Cc1cccc2c1CN(C1CCC(=O)NC1=O)C2=O] |
| 161 | SIAIS262116 | (E)-N-(4-((3-chloro-4-fluorophenyl)amino)-7-methoxyquinazolin-6-yl)-4-(4-((5-(2-(2,6-dioxopiperidin-3-yl)-1-oxoisoindolin-4-yl)pent-4-yn-1-yl)amino)piperidin-1-yl)but-2-enamide | 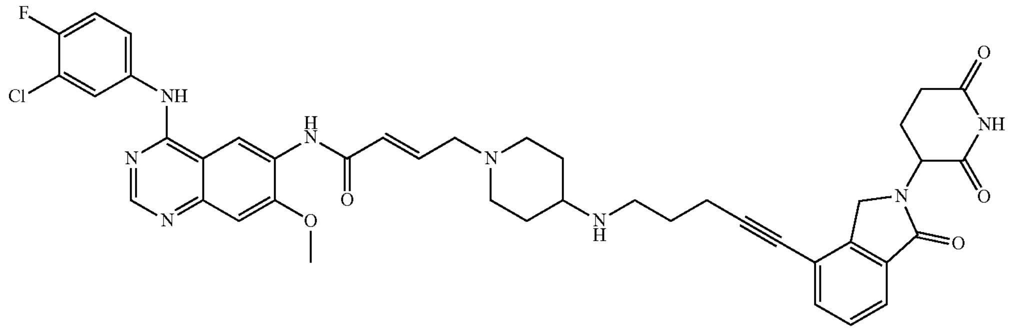 [SMILES: COc1cc2ncnc(Nc3ccc(F)c(Cl)c3)c2cc1NC(=O)/C=C/CN1CCC(NCCCC#Cc2cccc3c2CN(C2CCC(=O)NC2=O)C3=O)CC1] |

TABLE 1-continued
| Compound No. | | The compounds' name | Structure of the compounds |
|---|---|---|---|
| 162 | SIAIS262117 | (E)-N-(4-((3-chloro-4-fluorophenyl)amino)-7-methoxyquinazolin-6-yl)-4-(4-((6-(2-(2,6-dioxopiperidin-3-yl)-1-oxoisoindolin-4-yl)hex-5-yn-1-yl)amino)piperidin-1-yl)but-2-enamide | 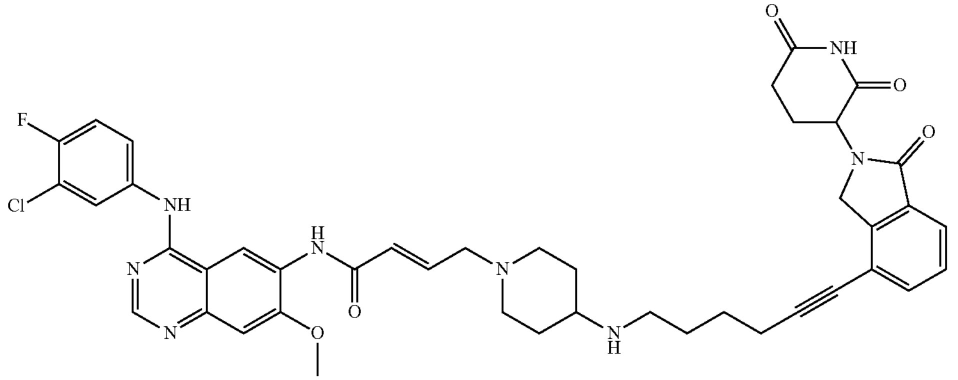 [SMILES: COc1cc2ncnc(Nc3ccc(F)c(Cl)c3)c2cc1NC(=O)/C=C/CN1CCC(NCCCCC#Cc2cccc3c2CN(C2CCC(=O)NC2=O)C3=O)CC1] |
| 163 | SIAIS262118 | (E)-N-(1-(4-((4-((3-chloro-4-fluorophenyl)amino)-7-methoxyquinazolin-6-yl)amino)-4-oxobut-2-en-1-yl)piperidin-4-yl)-11-((2-(2,6-dioxopiperidin-3-yl)-1-oxoisoindolin-4-yl)thio)undecanamide | 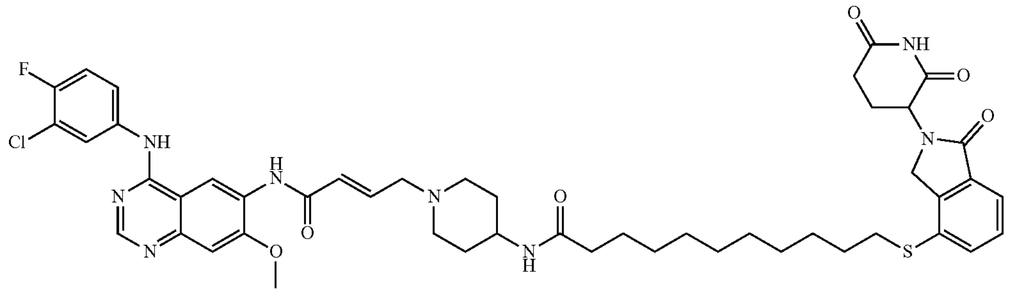 [SMILES: COc1cc2ncnc(Nc3ccc(F)c(Cl)c3)c2cc1NC(=O)/C=C/CN1CCC(NC(=O)CCCCCCCCCCSc2cccc3c2CN(C2CCC(=O)NC2=O)C3=O)CC1] |

TABLE 1-continued

| | Compound No. | The compounds' name | Structure of the compounds |
|---|---|---|---|
| 164 | SIAIS337021 | (E)-N-(4-((3-chloro-4-fluorophenyl)amino)-7-methoxyquinazolin-6-yl)-4-(4-(4-(4-(((2-(2,6-dioxopiperidin-3-yl)-1-oxoisoindolin-4-yl)thio)methyl)benzyl)piperazin-1-yl)piperidin-1-yl)but-2-enamide | 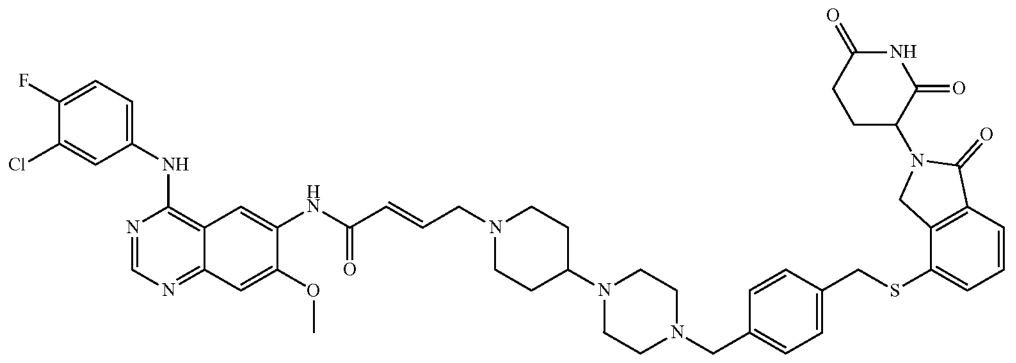 [SMILES: COc1cc2ncnc(Nc3ccc(F)c(Cl)c3)c2cc1NC(=O)/C=C/CN1CCC(N2CCN(Cc3ccc(CSc4cccc5c4CN(C4CCC(=O)NC4=O)C5=O)cc3)CC2)CC1] |
| 165 | SIAIS337024 | (E)-N-(4-((3-chloro-4-fluorophenyl)amino)-7-methoxyquinazolin-6-yl)-4-(4-(4-(4-(((2-(2,6-dioxopiperidin-3-yl)-1-oxoisoindolin-4-yl)amino)methyl)benzyl)piperazin-1-yl)piperidin-1-yl)but-2-enamide | 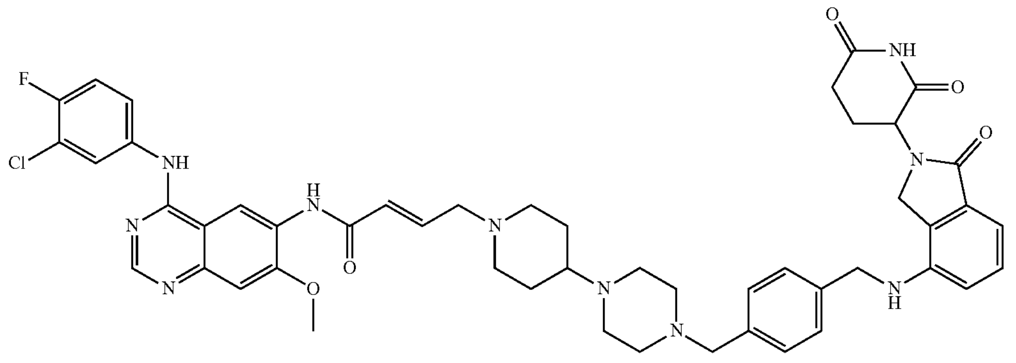 [SMILES: COc1cc2ncnc(Nc3ccc(F)c(Cl)c3)c2cc1NC(=O)/C=C/CN1CCC(N2CCN(Cc3ccc(CNc4cccc5c4CN(C4CCC(=O)NC4=O)C5=O)cc3)CC2)CC1] |

TABLE 1-continued

| | Compound No. | The compounds' name | Structure of the compounds |
|---|---|---|---|
| 166 | SIAIS337025 | (E)-N-(4-((3-chloro-4-fluorophenyl)amino)-7-methoxyquinazolin-6-yl)-4-(4-(4-(2-((2-(2,6-dioxopiperidin-3-yl)-1-oxoisoindolin-4-yl)oxy)acetyl)piperazin-1-yl)piperidin-1-yl)but-2-enamide | 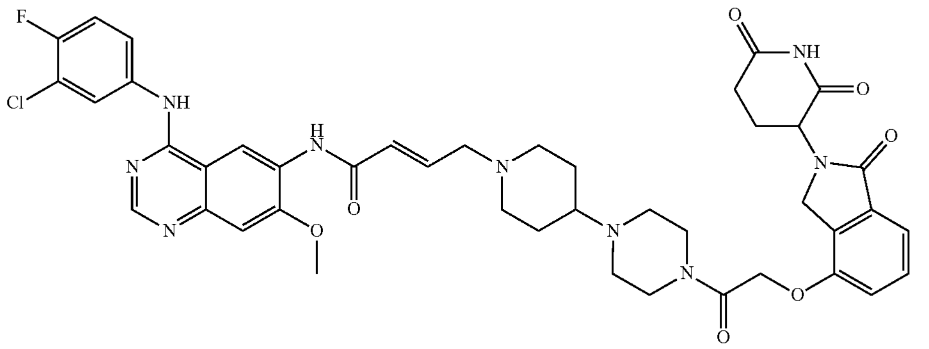 [SMILES: COc1cc2ncnc(Nc3ccc(F)c(Cl)c3)c2cc1NC(=O)/C=C/CN1CCC(N2CCN(C(=O)COc3cccc4c3CN(C3CCC(=O)NC3=O)C4=O)CC2)CC1] |
| 167 | SIAIS337026 | (E)-N-(4-((3-chloro-4-fluorophenyl)amino)-7-methoxyquinazolin-6-yl)-4-(4-(4-(5-((2-(2,6-dioxopiperidin-3-yl)-1-oxoisoindolin-4-yl)oxy)pentanoyl)piperazin-1-yl)piperidin-1-yl)but-2-enamide | 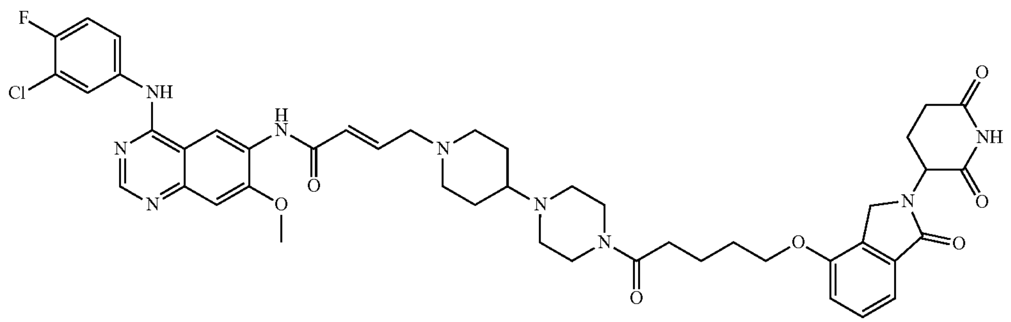 [SMILES: COc1cc2ncnc(Nc3ccc(F)c(Cl)c3)c2cc1NC(=O)/C=C/CN1CCC(N2CCN(C(=O)CCCCOc3cccc4c3CN(C3CCC(=O)NC3=O)C4=O)CC2)CC1] |
| 168 | SIAIS337027 | (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)oxy)hexanoyl)piperazin-1-yl)piperidin-1-yl)but-2-enamide | 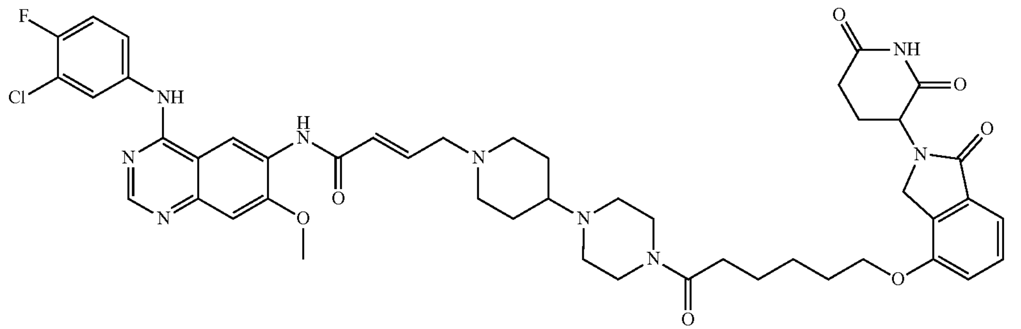 |

TABLE 1-continued

| | Compound No. | The compounds' name | Structure of the compounds |
|---|---|---|---|
| 169 | SIAIS337028 | (E)-N-(4-((3-chloro-4-fluorophenyl)amino)-7-methoxyquinazolin-6-yl)-4-(4-(4-(7-((2-(2,6-dioxopiperidin-3-yl)-1-oxoisoindolin-4-yl)oxy)heptanoyl)piperazin-1-yl)piperidin-1-yl)but-2-enamide | 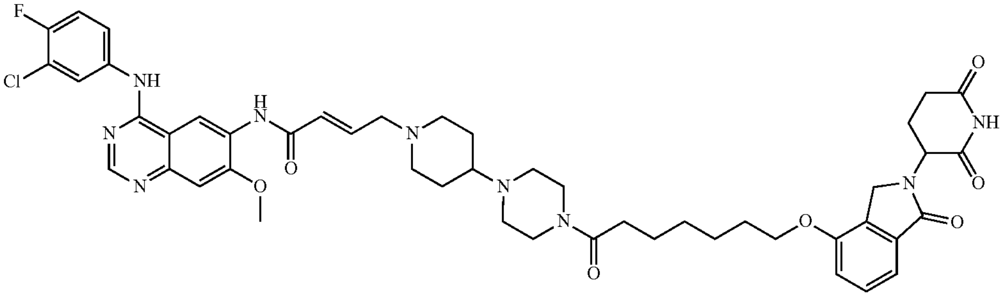 [SMILES: COc1cc2ncnc(Nc3ccc(F)c(Cl)c3)c2cc1NC(=O)/C=C/CN1CCC(N2CCN(C(=O)CCCCCCOc3cccc4c3CN(C3CCC(=O)NC3=O)C4=O)CC2)CC1] |
| 170 | SIAIS337029 | (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)oxy)hexyl)piperazin-1-yl)piperidin-1-yl)but-2-enamide | 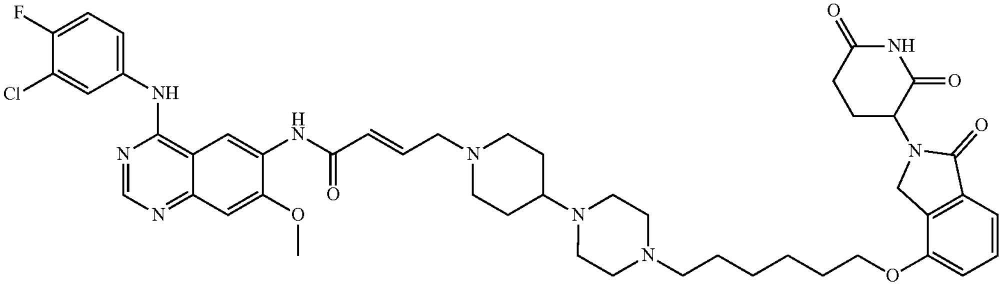 [SMILES: COc1cc2ncnc(Nc3ccc(F)c(Cl)c3)c2cc1NC(=O)/C=C/CN1CCC(N2CCN(CCCCCCOc3cccc4c3CN(C3CCC(=O)NC3=O)C4=O)CC2)CC1] |
| 171 | SIAIS337037 | (E)-N-(4-((3-chloro-4-fluorophenyl)amino)-7-methoxyquinazolin-6-yl)-4-(4-(4-(10-((2-(2,6-dioxopiperidin-3-yl)-1-oxoisoindolin-4-yl)thio)decanoyl)piperazin-1-yl)piperidin-1-yl)but-2-enamide | 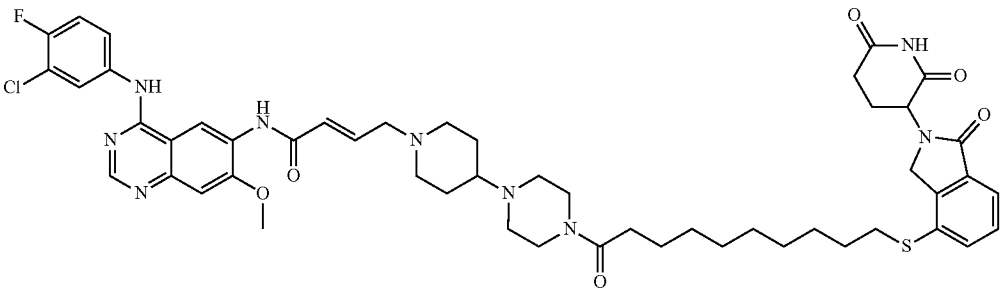 [SMILES: COc1cc2ncnc(Nc3ccc(F)c(Cl)c3)c2cc1NC(=O)/C=C/CN1CCC(N2CCN(C(=O)CCCCCCCCCSc3cccc4c3CN(C3CCC(=O)NC3=O)C4=O)CC2)CC1] |

TABLE 1-continued

| | Compound No. | The compounds' name | Structure of the compounds |
|---|---|---|---|
| 172 | SIAIS337038 | (E)-N-(4-((3-chloro-4-fluorophenyl)amino)-7-methoxyquinazolin-6-yl)-4-(4-(4-(11-((2-(2,6-dioxopiperidin-3-yl)-1-oxoisoindolin-4-yl)thio)undecanoyl)piperazin-1-yl)piperidin-1-yl)but-2-enamide | 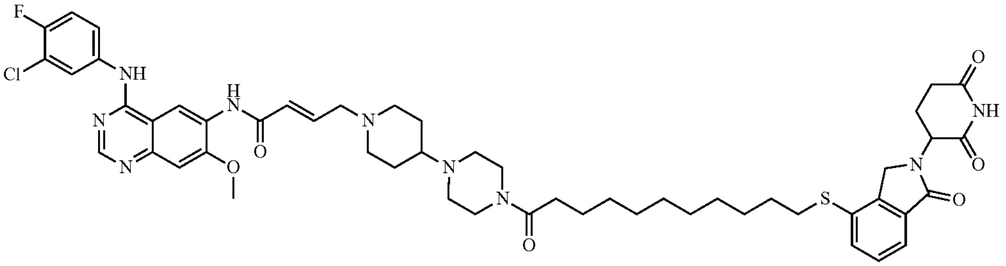 [SMILES: COc1cc2ncnc(Nc3ccc(F)c(Cl)c3)c2cc1NC(=O)/C=C/CN1CCC(N2CCN(C(=O)CCCCCCCCCCSc3cccc4c3CN(C3CCC(=O)NC3=O)C4=O)CC2)CC1] |
| 173 | SIAIS337039 | (E)-N-(4-((3-chloro-4-fluorophenyl)amino)-7-methoxyquinazolin-6-yl)-4-(4-(4-(10-((2-(2,6-dioxopiperidin-3-yl)-1-oxoisoindolin-4-yl)thio)decyl)piperazin-1-yl)piperidin-1-yl)but-2-enamide | 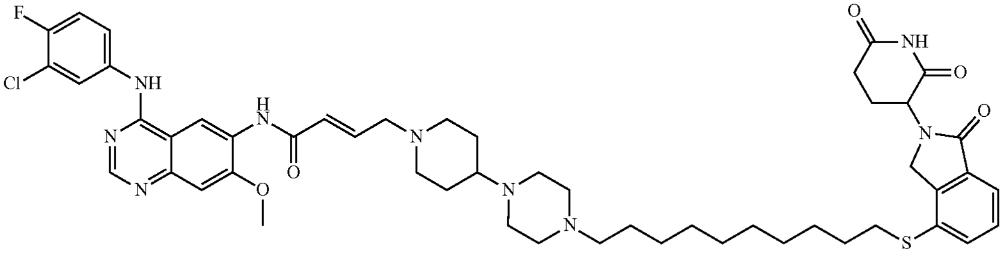 [SMILES: COc1cc2ncnc(Nc3ccc(F)c(Cl)c3)c2cc1NC(=O)/C=C/CN1CCC(N2CCN(CCCCCCCCCCSc3cccc4c3CN(C3CCC(=O)NC3=O)C4=O)CC2)CC1] |
| 174 | SIAIS337040 | (E)-N-(4-((3-chloro-4-fluorophenyl)amino)-7-methoxyquinazolin-6-yl)-4-(4-(4-(11-((2-(2,6-dioxopiperidin-3-yl)-1-oxoisoindolin-4-yl)thio)undecyl)piperazin-1-yl)piperidin-1-yl)but-2-enamide | 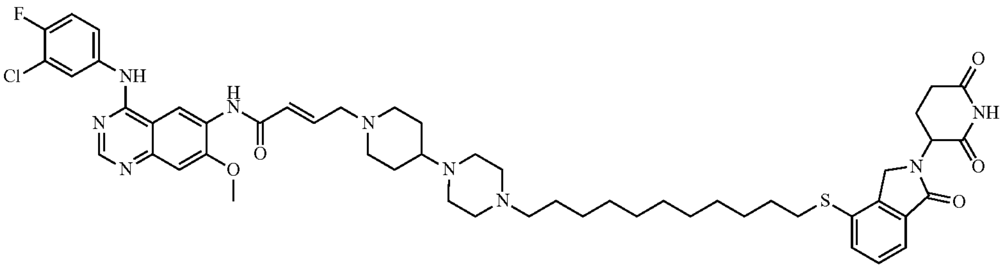 [SMILES: COc1cc2ncnc(Nc3ccc(F)c(Cl)c3)c2cc1NC(=O)/C=C/CN1CCC(N2CCN(CCCCCCCCCCCSc3cccc4c3CN(C3CCC(=O)NC3=O)C4=O)CC2)CC1] |

TABLE 1-continued

| Compound No. | | The compounds' name | Structure of the compounds |
|---|---|---|---|
| 175 | SIAIS262130 | (2S,4R)-1-((S)-19-(4-(3-((6-acrylamido-4-((3-chloro-4-fluorophenyl)amino)quinazolin-7-yl)oxy)propyl)piperazin-1-yl)-2-(tert-butyl)-4,19-dioxo-7,10,13,16-tetraoxa-3-azanonadecanoyl)-4-hydroxy-N-(4-(4-methylthiazol-5-yl)benzyl)pyrrolidine-2-carboxamide | 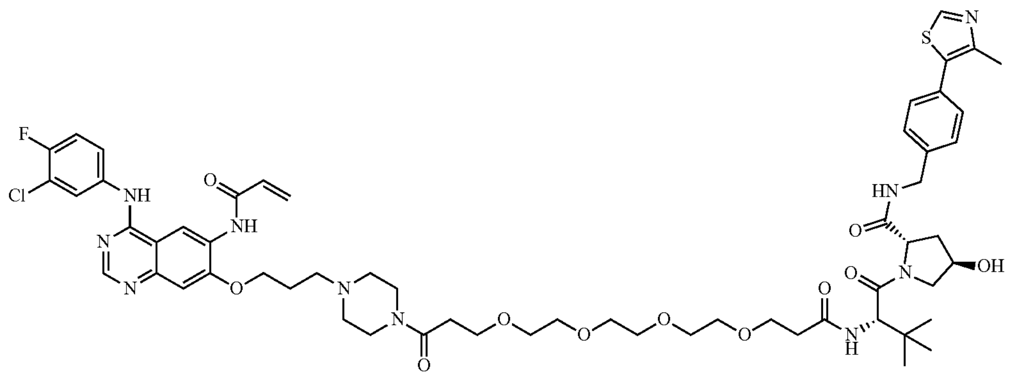 [SMILES: C=CC(=O)Nc1cc2c(Nc3ccc(F)c(Cl)c3)ncnc2cc1OCCCN1CCN(C(=O)CCOCCOCCOCCOCCC(=O)N[C@H](C(=O)N2C[C@H](O)C[C@H]2C(=O)NCc2ccc(-c3scnc3C)cc2)C(C)(C)C)CC1] |
| 176 | SIAIS249099 | 4-(4-(3-((6-acrylamido-4-((3-chloro-4-fluorophenyl)amino)quinazolin-7-yl)oxy)propyl)piperazin-1-yl)-N-(2-(2-((2-(2,6-dioxopiperidin-3-yl)-1,3-dioxoisoindolin-4-yl)amino)ethoxy)ethyl)-4-oxobutanamide | 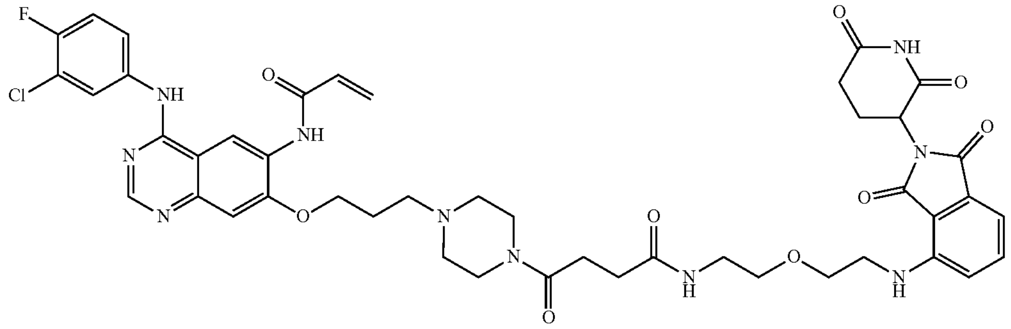 [SMILES: C=CC(=O)Nc1cc2c(Nc3ccc(F)c(Cl)c3)ncnc2cc1OCCCN1CCN(C(=O)CCC(=O)NCCOCCNc2cccc3c2C(=O)N(C2CCC(=O)NC2=O)C3=O)CC1] |

TABLE 1-continued

| Compound No. | | The compounds' name | Structure of the compounds |
|---|---|---|---|
| 177 | SIAIS249100 | 4-(4-(3((6-acrylamido-4-((3-chloro-4-fluorophenyl)amino)quinazolin-7-yl)oxy)propyl)piperazin-1-yl)-N-(2-((2-(2,6-dioxopiperidin-3-yl)-1,3-dioxoisoindolin-4-yl)amino)ethyl)-4-oxobutanamide | 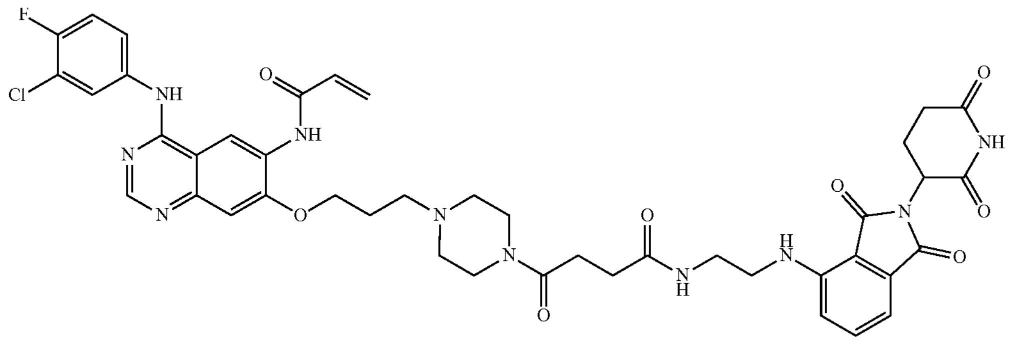 [SMILES: C=CC(=O)Nc1cc2c(Nc3ccc(F)c(Cl)c3)ncnc2cc1OCCCN1CCN(C(=O)CCC(=O)NCCNc2cccc3c2C(=O)N(C2CCC(=O)NC2=O)C3=O)CC1] |
| 178 | SIAIS249101 | (2S,4R)-1-((S)-2-(3-(4-(3-(4-(3-((6-acrylamido-4-((3-chloro-4-fluorophenyl)amino)quinazolin-7-yl)oxy)propyl)piperazin-1-yl)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide | 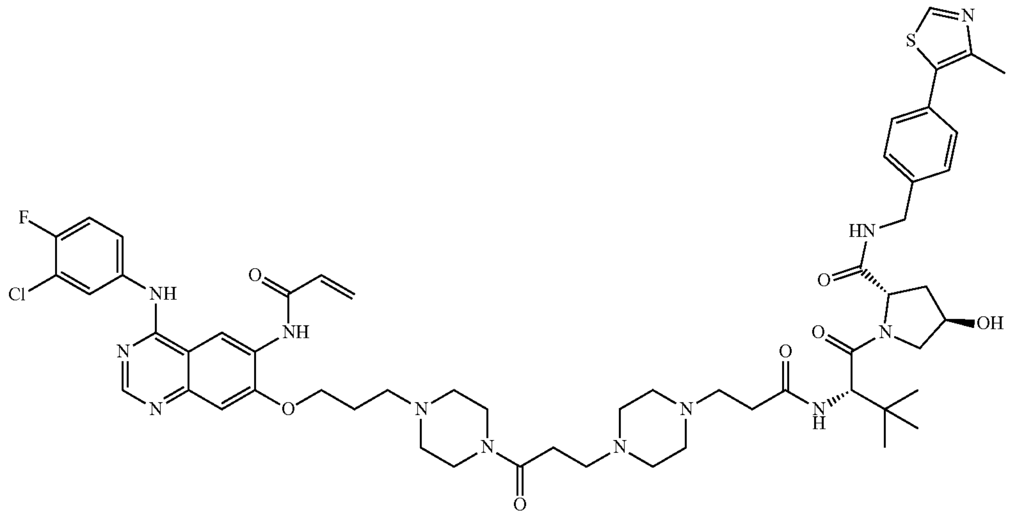 [SMILES: C=CC(=O)Nc1cc2c(Nc3ccc(F)c(Cl)c3)ncnc2cc1OCCCN1CCN(C(=O)CCN2CCN(CCC(=O)N[C@H](C(=O)N3C[C@H](O)C[C@H]3C(=O)NCc3ccc(-c4scnc4C)cc3)C(C)(C)C)CC2)CC1] |

TABLE 1-continued

| | Compound No. | The compounds' name | Structure of the compounds |
|---|---|---|---|
| 179 | SIAIS249102 | (2S,4R)-1-((S)-2-(3-(4-(3-(4-(3-((6-acrylamido-4-((3-chloro-4-fluorophenyl)amino)quinazolin-7-yl)oxy)propyl)piperazin-1-yl)-3-oxopropyl)phenyl)propanamido)-3,3-dimethylbutanoyl)-4-hydroxy-N-(4-(4-methylthiazol-5-yl)benzyl)pyrrolidine-2-carboxamide | 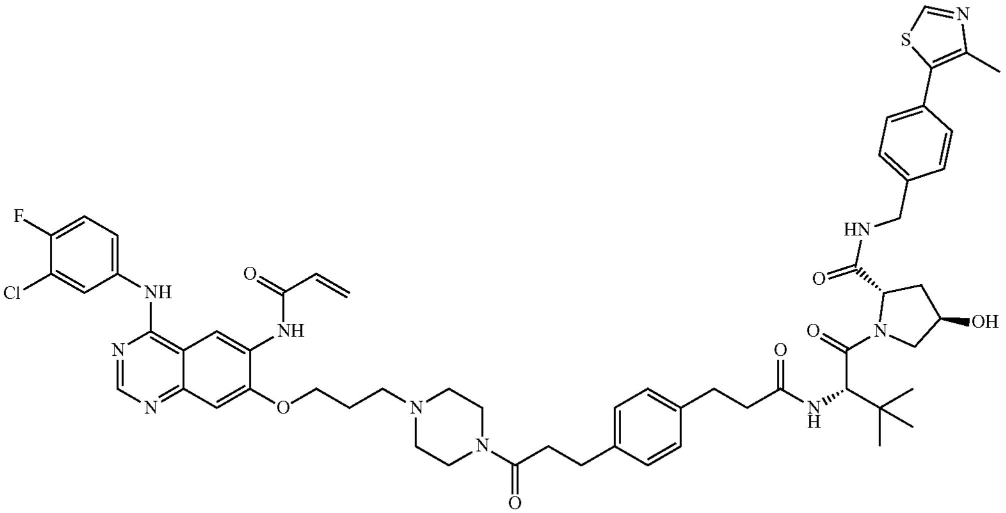 [SMILES: C=CC(=O)Nc1cc2c(Nc3ccc(F)c(Cl)c3)ncnc2cc1OCCCN1CCN(C(=O)CCc2ccc(CCC(=O)N[C@H](C(=O)N3C[C@H](O)C[C@H]3C(=O)NCc3ccc(-c4scnc4C)cc3)C(C)(C)C)cc2)CC1] |
| 180 | SIAIS249103 | (E)-N-(4-((3-chloro-4-fluorophenyl)amino)-7-methoxyquinazolin-6-yl)-4-(4-(4-(4-((2-(2-((2-(2,6-dioxopiperidin-3-yl)-1,3-dioxoisoindolin-4-yl)amino)ethoxy)ethyl)amino)-4-oxobutanoyl)piperazin-1-yl)piperidin-1-yl)but-2-enamide | 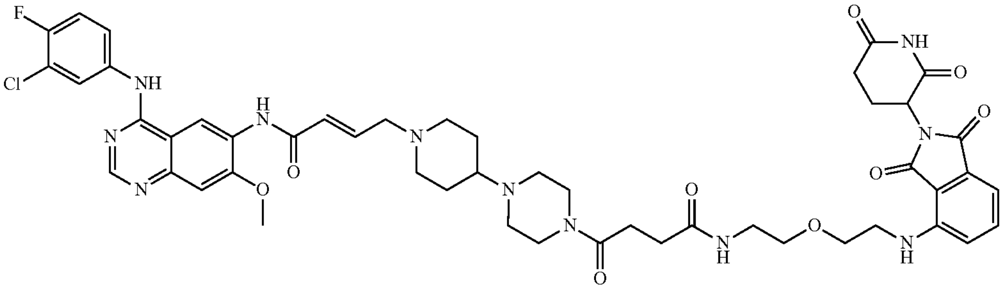 [SMILES: COc1cc2ncnc(Nc3ccc(F)c(Cl)c3)c2cc1NC(=O)/C=C/CN1CCC(N2CCN(C(=O)CCC(=O)NCCOCCNc3cccc4c3C(=O)N(C3CCC(=O)NC3=O)C4=O)CC2)CC1] |

TABLE 1-continued

| Compound No. | | The compounds' name | Structure of the compounds |
|---|---|---|---|
| 181 | SIAIS249104 | (E)-N-(4-((3-chloro-4-fluorophenyl)amino)-7-methoxyquinazolin-6-yl)-4-(4-(4-(4-((2-((2-(2,6-dioxopiperidin-3-yl)-1,3-dioxoisoindolin-4-yl)amino)ethyl)amino)-4-oxobutanoyl)piperazin-1-yl)piperidin-1-yl)but-2-enamide | 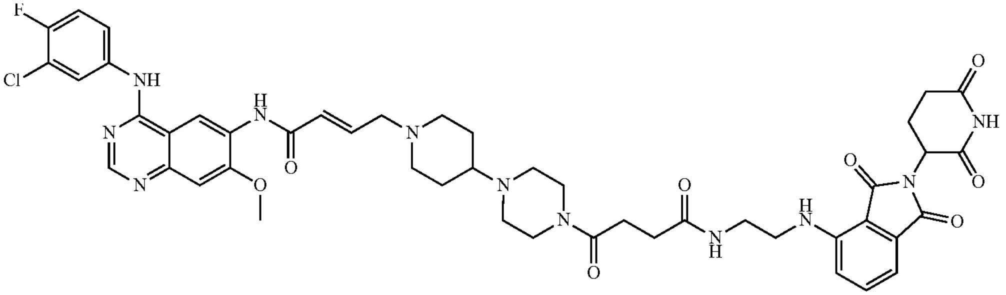 [SMILES: COc1cc2ncnc(Nc3ccc(F)c(Cl)c3)c2cc1NC(=O)/C=C/CN1CCC(N2CCN(C(=O)CCC(=O)NCCNc3cccc4c3C(=O)N(C3CCC(=O)NC3=O)C4=O)CC2)CC1] |
| 182 | SIAIS249105 | (2S,4R)-1-((S)-2-(3-(4-(3-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide | 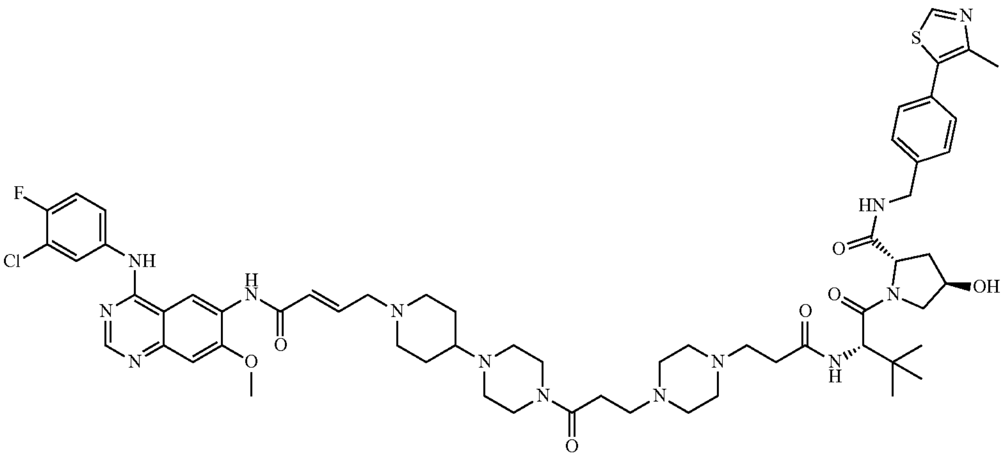 [SMILES: COc1cc2ncnc(Nc3ccc(F)c(Cl)c3)c2cc1NC(=O)/C=C/CN1CCC(N2CCN(C(=O)CCN3CCN(CCC(=O)N[C@H](C(=O)N4C[C@H](O)C[C@H]4C(=O)NCc4ccc(-c5scnc5C)cc4)C(C)(C)C)CC3)CC2)CC1] |

TABLE 1-continued
| Compound No. | | The compounds' name | Structure of the compounds |
|---|---|---|---|
| 183 | SIAIS249106 | (2S,4R)-1-((S)-2-(3-(4-(3-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-3-oxopropyl)phenyl)propamido)-3,3-dimethylbutanoyl)-4-hydroxy-N-(4-(4-methylthiazol-5-yl)benzyl)pyrrolidine-2-carboxamide | 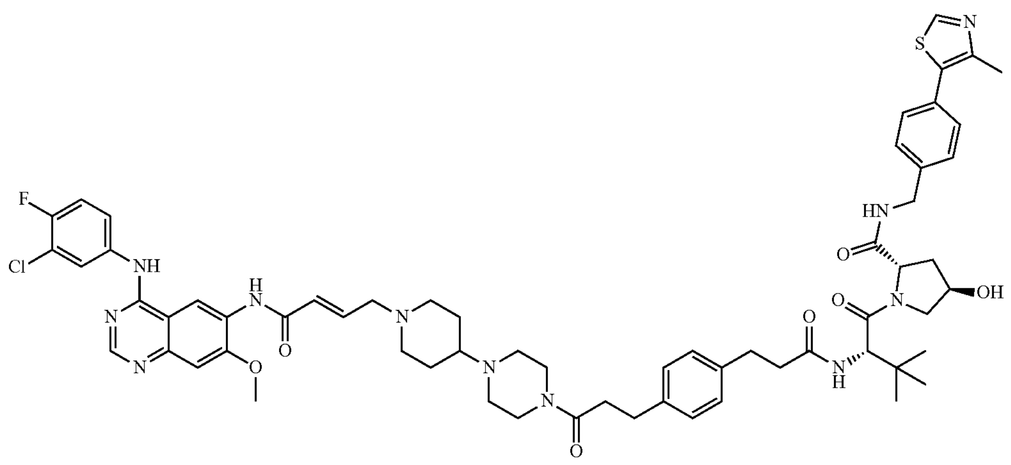 [SMILES: COc1cc2ncnc(Nc3ccc(F)c(Cl)c3)c2cc1NC(=O)/C=C/CN1CCC(N2CCN(C(=O)CCc3ccc(CCC(=O)N[C@H](C(=O)N4C[C@H](O)C[C@H]4C(=O)NCc4ccc(-c5scnc5C)cc4)C(C)(C)C)cc3)CC2)CC1] |

TABLE 2

| Compound No. | The compounds' names | Structure of the compounds |
|---|---|---|
| | (2S,4R)-1-((S)-2-(10-(4-((E)-4-((4-((3-chloro-4-fluorophenyl)amino)-7-methoxyquinazolin-6-yl)amino)-4-oxobut-2-en-1-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide | 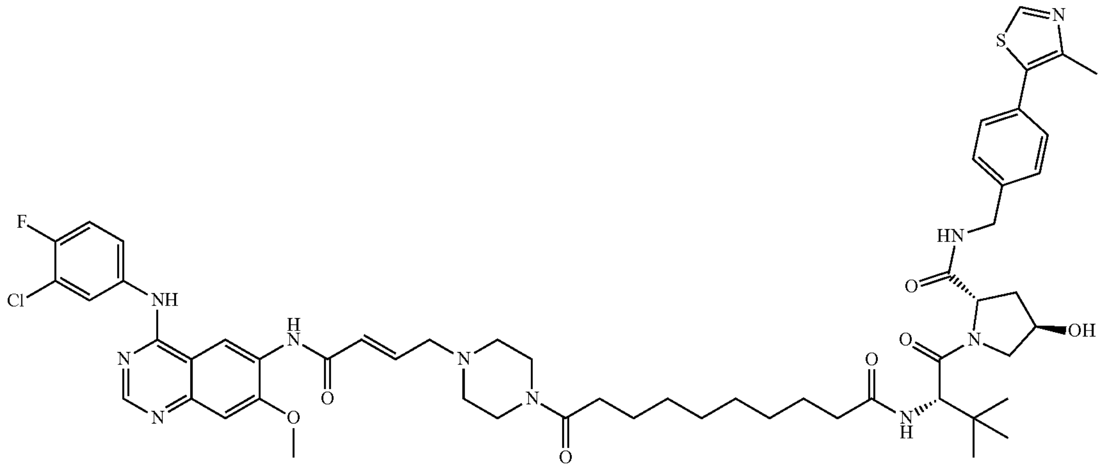 [SMILES: COc1cc2ncnc(Nc3ccc(F)c(Cl)c3)c2cc1NC(=O)/C=C/CN1CCN(C(=O)CCCCCCCCC(=O)N[C@H](C(=O)N2C[C@H](O)C[C@H]2C(=O)NCc2ccc(-c3scnc3C)cc2)C(C)(C)C)CC1] |
| | (E)-N-(4-((3-chloro-4-fluorophenyl)amino)-7-methoxyquinazolin-6-yl)-4-(4-(3-(2-((2-(2,6-dioxopiperidin-3-yl)-1,3-dioxoisoindolin-4-yl)amino)ethoxy)propanamido)piperidin-1-yl)but-2-enamide | 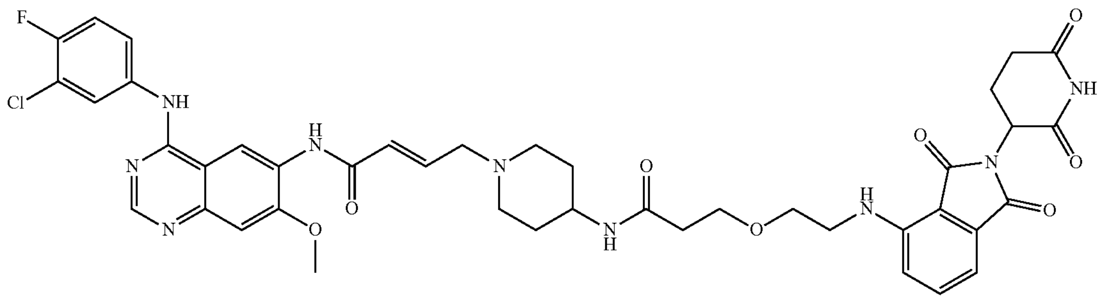 [SMILES: COc1cc2ncnc(Nc3ccc(F)c(Cl)c3)c2cc1NC(=O)/C=C/CN1CCC(NC(=O)CCOCCNc2cccc3c2C(=O)N(C2CCC(=O)NC2=O)C3=O)CC1] |

TABLE 2-continued

| Compound No. | The compounds' names | Structure of the compounds |
| --- | --- | --- |
| SIAIS249086 | (E)-N-(4-((3-chloro-4-fluorophenyl)amino)-7-methoxyquinazolin-6-yl)-4-(4-(3-(2-(2-((2-(2,6-dioxopiperidin-3-yl)-1,3-dioxoisoindolin-4-yl)amino)ethoxy)ethoxy)propanamido)piperidin-1-yl)but-2-enamide | 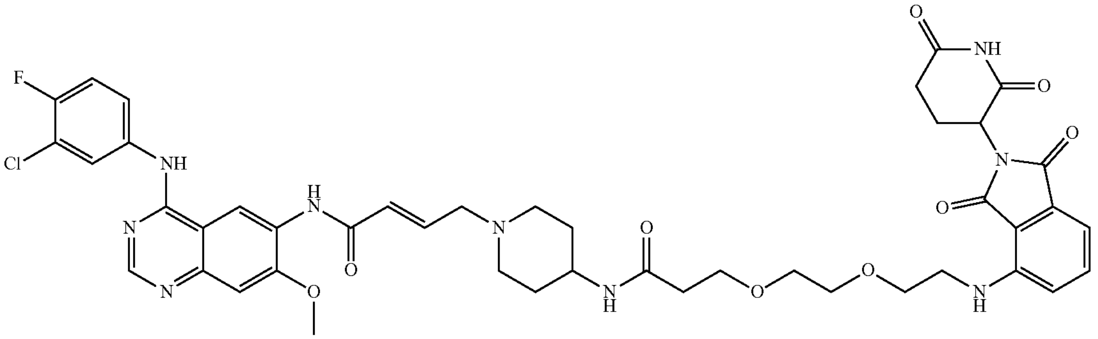 [SMILES: COc1cc2ncnc(Nc3ccc(F)c(Cl)c3)c2cc1NC(=O)/C=C/CN1CCC(NC(=O)CCOCCOCCNc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(3-(2-(2-(2-((2-(2,6-dioxopiperidin-3-yl)-1,3-dioxoisoindolin-4-yl)amino)ethoxy)ethoxy)ethoxy)propanamido)piperidin-1-yl)but-2-enamide | 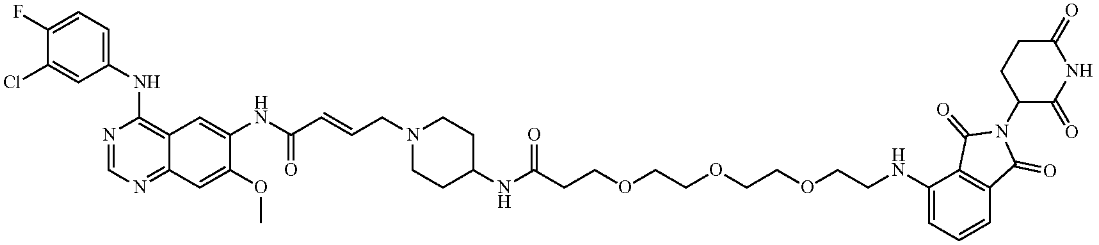 [SMILES: COc1cc2ncnc(Nc3ccc(F)c(Cl)c3)c2cc1NC(=O)/C=C/CN1CCC(NC(=O)CCOCCOCCOCCNc2cccc3c2C(=O)N(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-1-((2-(2,6-dioxopiperidin-3-yl)-1,3-dioxoisoindolin-4-yl)amino)-3,6,9,12-tetraoxapentadecan-15-amide | 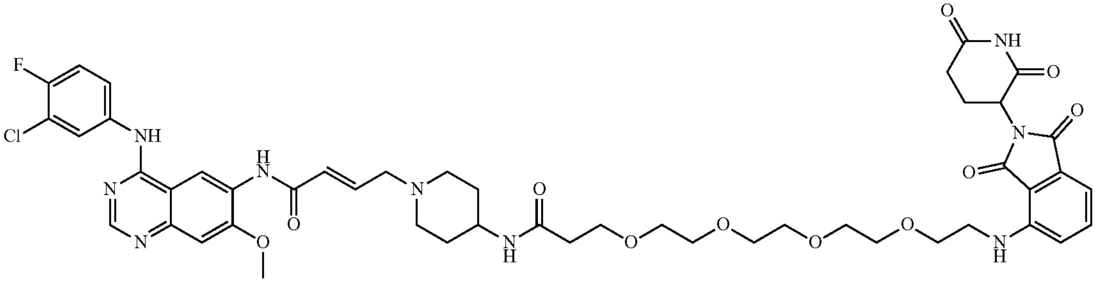 [SMILES: COc1cc2ncnc(Nc3ccc(F)c(Cl)c3)c2cc1NC(=O)/C=C/CN1CCC(NC(=O)CCOCCOCCOCCOCCNc2cccc3c2C(=O)N(C2CCC(=O)NC2=O)C3=O)CC1] |

TABLE 2-continued

| Compound No. | The compounds' names | Structure of the compounds |
|---|---|---|
| | (E)-N-(1-(4-((4-((3-chloro-4-fluorophenyl)amino)-7-methoxyquinazolin-6-yl)amino)-4-oxobut-2-en-1-yl)piperidin-4-yl)-1-((2-(2,6-dioxopiperidin-3-yl)-1,3-dioxoisoindolin-4-yl)amino)-3,6,9,12,15-pentaoxaoctadecan-18-amide | 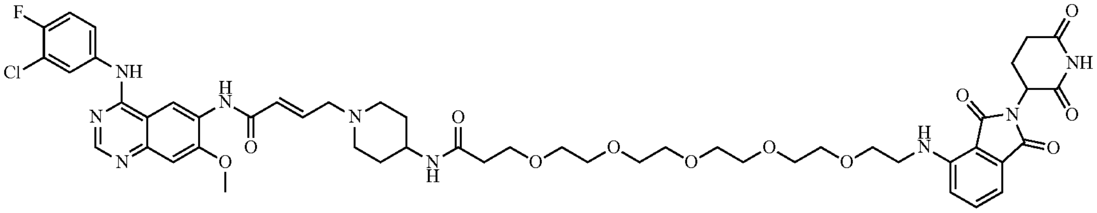 [SMILES: COc1cc2ncnc(Nc3ccc(F)c(Cl)c3)c2cc1NC(=O)/C=C/CN1CCC(NC(=O)CCOCCOCCOCCOCCOCCNc2cccc3c2C(=O)N(C2CCC(=O)NC2=O)C3=O)CC1] |
| SIAIS249081 | (E)-N-(4-((3-chloro-4-fluorophenyl)amino)-7-methoxyquinazolin-6-yl)-4-(4-(2-((2-(2,6-dioxopiperidin-3-yl)-1,3-dioxoisoindolin-4-yl)amino)acetamido)piperidin-1-yl)but-2-enamide | 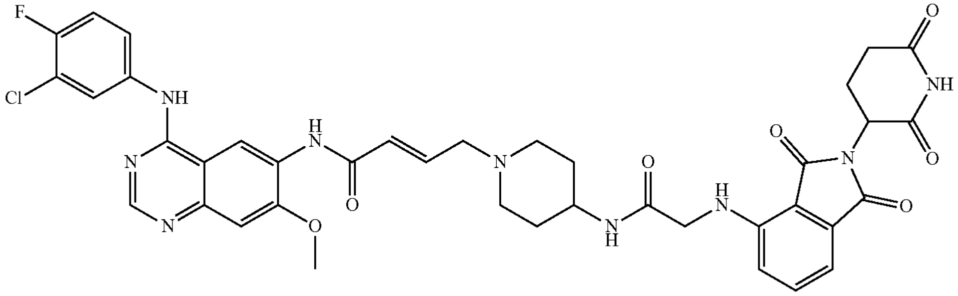 [SMILES: COc1cc2ncnc(Nc3ccc(F)c(Cl)c3)c2cc1NC(=O)/C=C/CN1CCC(NC(=O)CNc2cccc3c2C(=O)N(C2CCC(=O)NC2=O)C3=O)CC1] |
| SIAIS249082 | (E)-N-(4-((3-chloro-4-fluorophenyl)amino)-7-methoxyquinazolin-6-yl)-4-(4-(3-((2-(2,6-dioxopiperidin-3-yl)-1,3-dioxoisoindolin-4-yl)amino)propanamido)piperidin-1-yl)but-2-enamide | 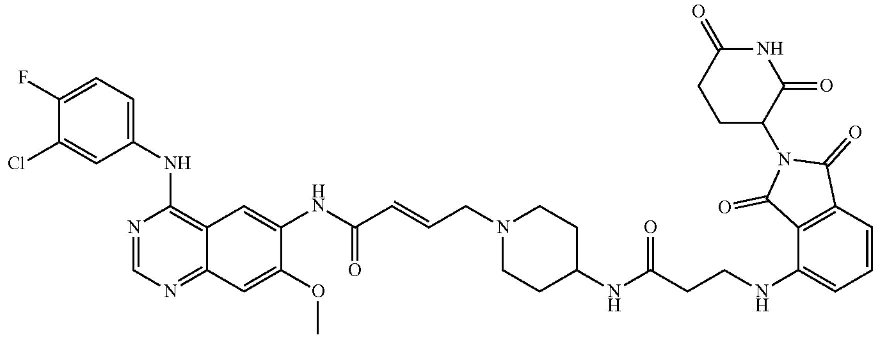 [SMILES: COc1cc2ncnc(Nc3ccc(F)c(Cl)c3)c2cc1NC(=O)/C=C/CN1CCC(NC(=O)CCNc2cccc3c2C(=O)N(C2CCC(=O)NC2=O)C3=O)CC1] |

TABLE 2-continued

| Compound No. | The compounds' names | Structure of the compounds |
| --- | --- | --- |
| SIAIS249083 | (E)-N-(4-((3-chloro-4-fluorophenyl)amino)-7-methoxyquinazolin-6-yl)-4-(4-(4-((2-(2,6-dioxopiperidin-3-yl)-1,3-dioxoisoindolin-4-yl)amino)butanamido)piperidin-1-yl)but-2-enamide | 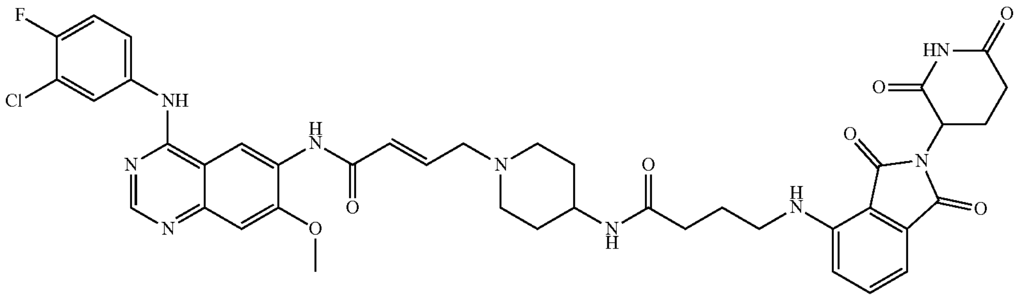 [SMILES: COc1cc2ncnc(Nc3ccc(F)c(Cl)c3)c2cc1NC(=O)/C=C/CN1CCC(NC(=O)CCCNc2cccc3c2C(=O)N(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-5-((2-(2,6-dioxopiperidin-3-yl)-1,3-dioxoisoindolin-4-yl)amino)pentanamide | 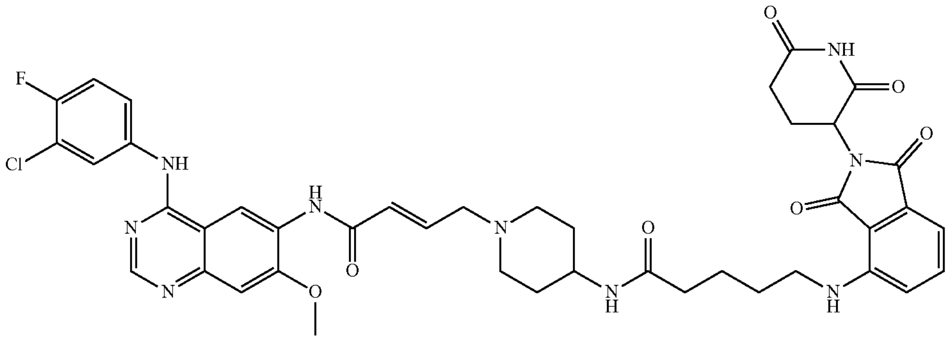 [SMILES: COc1cc2ncnc(Nc3ccc(F)c(Cl)c3)c2cc1NC(=O)/C=C/CN1CCC(NC(=O)CCCCNc2cccc3c2C(=O)N(C2CCC(=O)NC2=O)C3=O)CC1] |
| SIAIS249084 | (E)-N-(1-(4-((4-((3-chloro-4-fluorophenyl)amino)-7-methoxyquinazolin-6-yl)amino)-4-oxobut-2-en-1-yl)piperidin-4-yl)-6-((2-(2,6-dioxopiperidin-3-yl)-1,3-dioxoisoindolin-4-yl)amino)hexanamide | 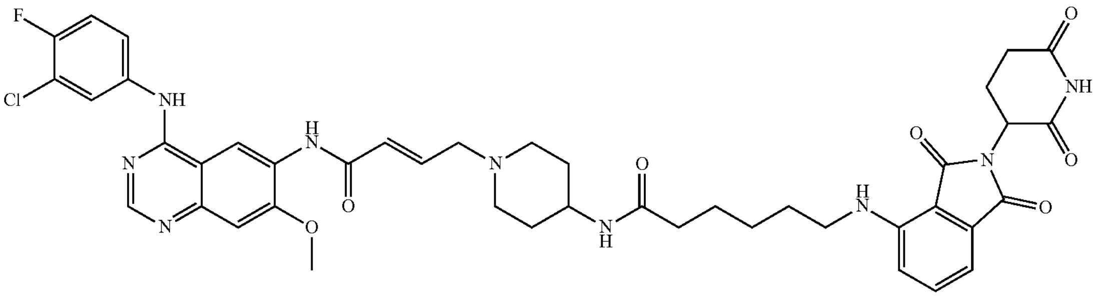 |

TABLE 2-continued

| Compound No. | The compounds' names | Structure of the compounds |
| --- | --- | --- |
| SIAIS249085 | (E)-N-(1-(4-((4-((3-chloro-4-fluorophenyl)amino)-7-methoxyquinazolin-6-yl)amino)-4-oxobut-2-en-1-yl)piperidin-4-yl)-7-((2-(2,6-dioxopiperidin-3-yl)-1,3-dioxoisoindolin-4-yl)amino)heptanamide | 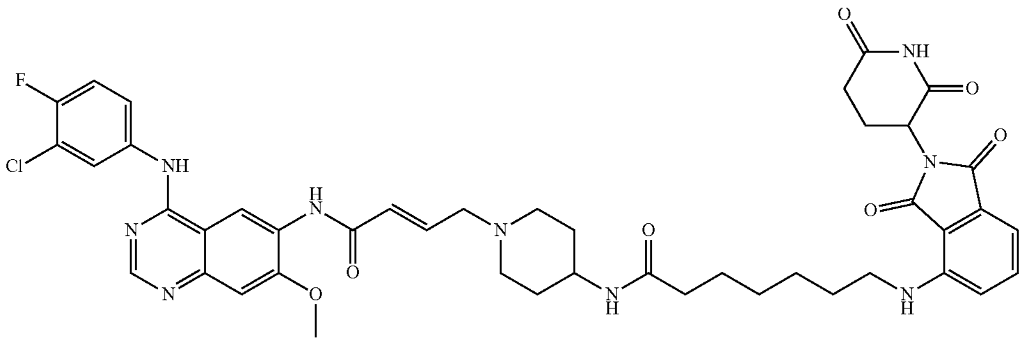 [SMILES: COc1cc2ncnc(Nc3ccc(F)c(Cl)c3)c2cc1NC(=O)/C=C/CN1CCC(NC(=O)CCCCCCNc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(2-(2-((2-(2,6-dioxopiperidin-3-yl)-1-oxoisoindolin-4-yl)amino)ethoxy)acetamido)piperidin-1-yl)but-2-enamide | 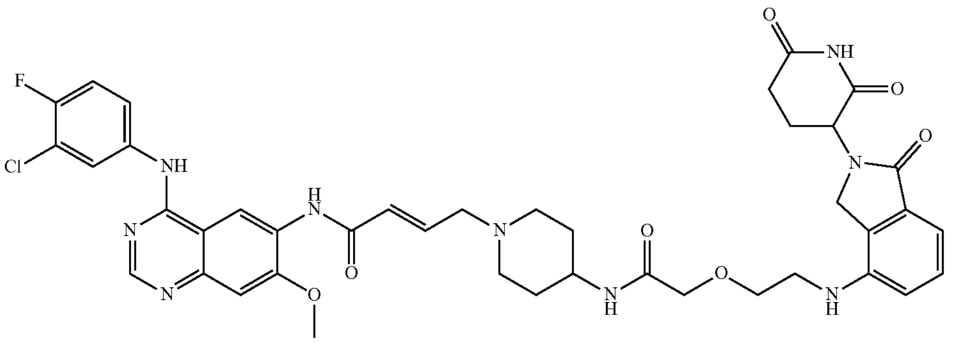 |
| | (E)-N-(4-((3-chloro-4-fluorophenyl)amino)-7-methoxyquinazolin-6-yl)-4-(4-(2-(2-(2-((2-(2,6-dioxopiperidin-3-yl)-1-oxoisoindolin-4-yl)amino)ethoxy)ethoxy)acetamido)piperidin-1-yl)but-2-enamide | 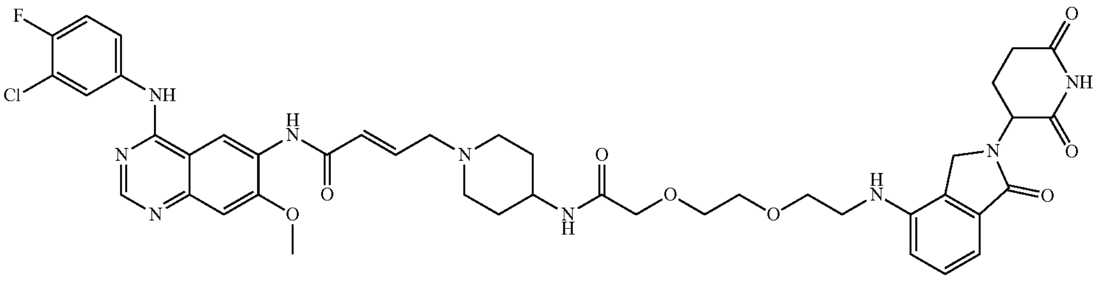 [SMILES: COc1cc2ncnc(Nc3ccc(F)c(Cl)c3)c2cc1NC(=O)/C=C/CN1CCC(NC(=O)COCCOCCNc2cccc3c2CN(C2CCC(=O)NC2=O)C3=O)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(2-(2-(2-(2-((2-(2,6-dioxopiperidin-3-yl)-1-oxoisoindolin-4-yl)amino)ethoxy)ethoxy)ethoxy)acetamido)piperidin-1-yl)but-2-enamide | 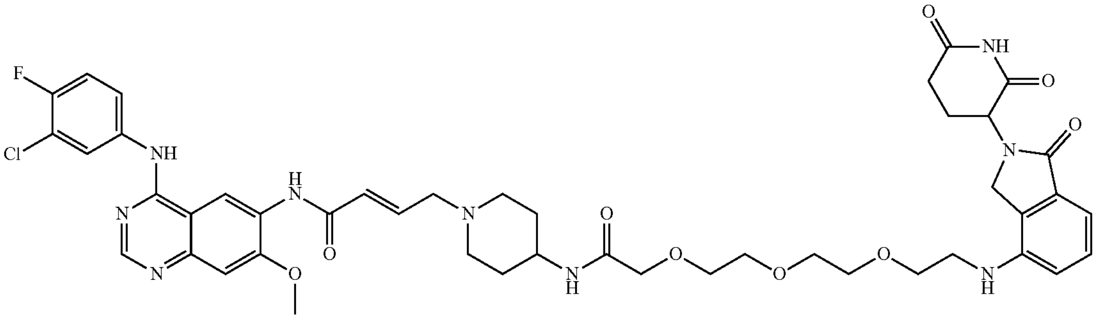 [SMILES: COc1cc2ncnc(Nc3ccc(F)c(Cl)c3)c2cc1NC(=O)/C=C/CN1CCC(NC(=O)COCCOCCOCCNc2cccc3c2CN(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-14-((2-(2,6-dioxopiperidin-3-yl)-1-oxoisoindolin-4-yl)amino)-3,6,9,12-tetraoxatetradecanamide | 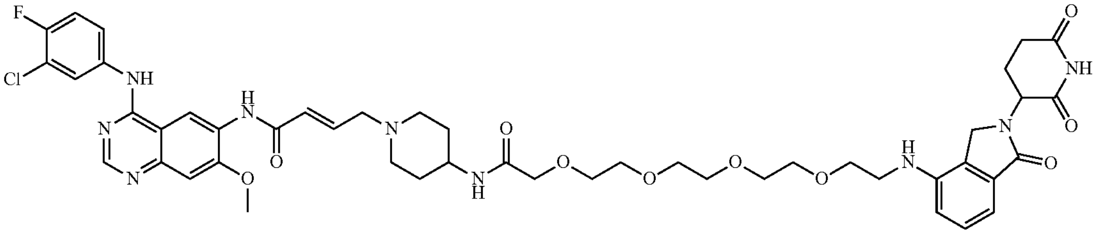 [SMILES: COc1cc2ncnc(Nc3ccc(F)c(Cl)c3)c2cc1NC(=O)/C=C/CN1CCC(NC(=O)COCCOCCOCCOCCNc2cccc3c2CN(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-17-((2-(2,6-dioxopiperidin-3-yl)-1-oxoisoindolin-4-yl)amino)-3,6,9,12,15-pentaoxaheptadecanamide | 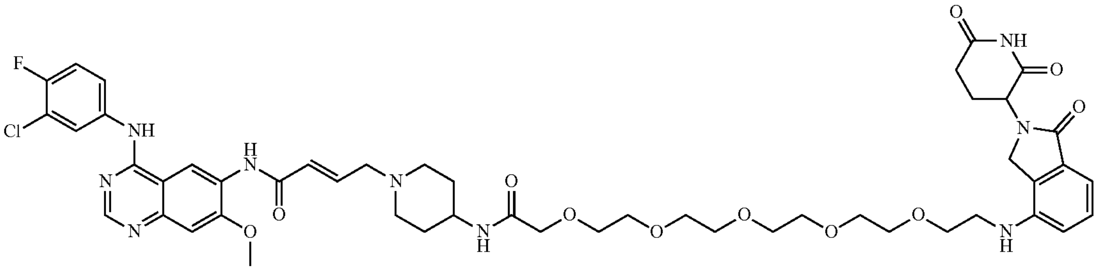 [SMILES: COc1cc2ncnc(Nc3ccc(F)c(Cl)c3)c2cc1NC(=O)/C=C/CN1CCC(NC(=O)COCCOCCOCCOCCOCCNc2cccc3c2CN(C2CCC(=O)NC2=O)C3=O)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(2-((2-(2,6-dioxopiperidin-3-yl)-1-oxoisoindolin-4-yl)amino)acetamido)piperidin-1-yl)but-2-enamide | 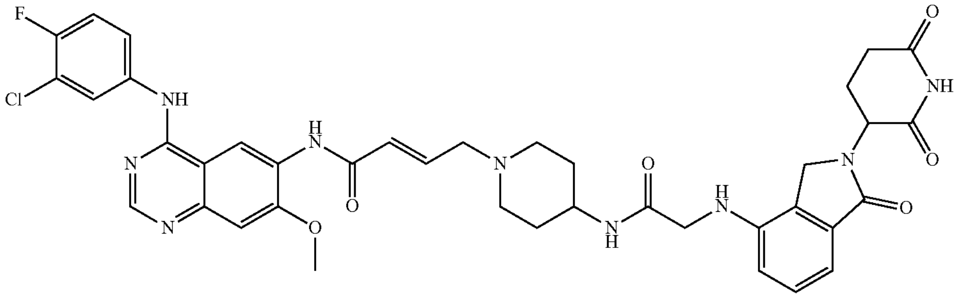 [SMILES: COc1cc2ncnc(Nc3ccc(F)c(Cl)c3)c2cc1NC(=O)/C=C/CN1CCC(NC(=O)CNc2cccc3c2CN(C2CCC(=O)NC2=O)C3=O)CC1] |
| | (E)-N-(4-((3-chloro-4-fluorophenyl)amino)-7-methoxyquinazolin-6-yl)-4-(4-(3-((2-(2,6-dioxopiperidin-3-yl)-1-oxoisoindolin-4-yl)amino)propanamido)piperidin-1-yl)but-2-enamide | 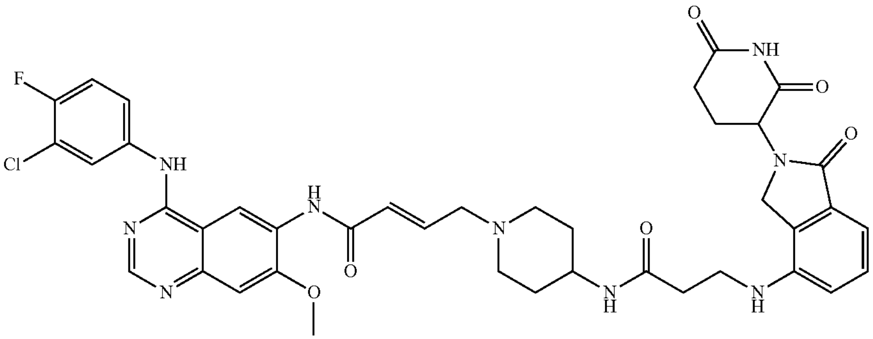 [SMILES: COc1cc2ncnc(Nc3ccc(F)c(Cl)c3)c2cc1NC(=O)/C=C/CN1CCC(NC(=O)CCNc2cccc3c2CN(C2CCC(=O)NC2=O)C3=O)CC1] |
| | (E)-N-(4-((3-chloro-4-fluorophenyl)amino)-7-methoxyquinazolin-6-yl)-4-(4-(4-((2-(2,6-dioxopiperidin-3-yl)-1-oxoisoindolin-4-yl)amino)butanamido)piperidin-1-yl)but-2-enamide | 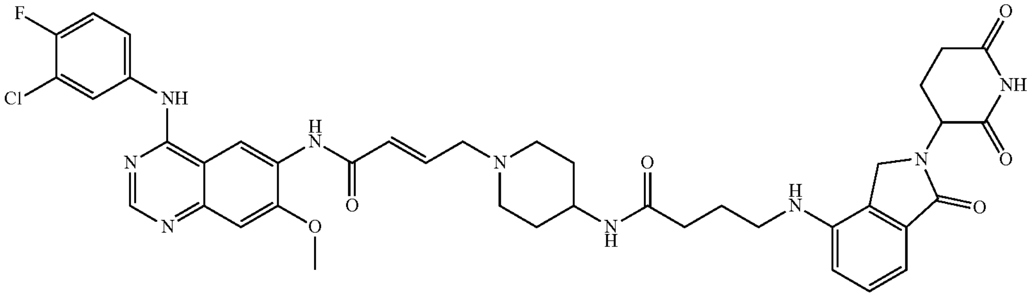 [SMILES: COc1cc2ncnc(Nc3ccc(F)c(Cl)c3)c2cc1NC(=O)/C=C/CN1CCC(NC(=O)CCCNc2cccc3c2CN(C2CCC(=O)NC2=O)C3=O)CC1] |

TABLE 2-continued

| Compound No. | The compounds' names | Structure of the compounds |
| --- | --- | --- |
| | (E)-N-(1-(4-((4-((3-chloro-4-fluorophenyl)amino)-7-methoxyquinazolin-6-yl)amino)-4-oxobut-2-en-1-yl)piperidin-4-yl)-5-((2-(2,6-dioxopiperidin-3-yl)-1-oxoisoindolin-4-yl)amino)pentanamide | 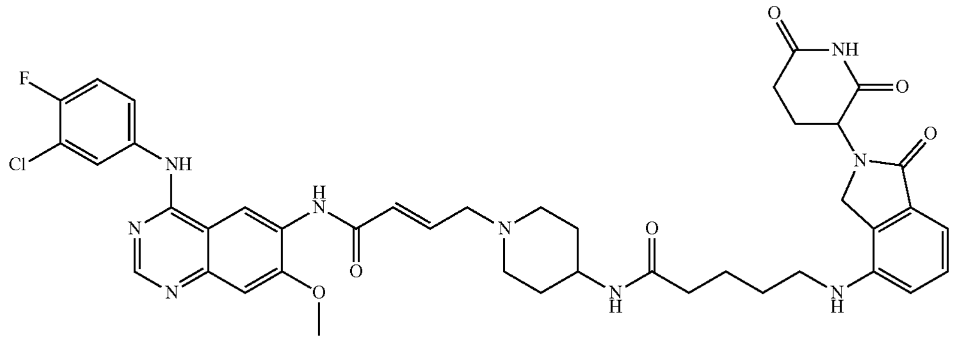 [SMILES: COc1cc2ncnc(Nc3ccc(F)c(Cl)c3)c2cc1NC(=O)/C=C/CN1CCC(NC(=O)CCCCNc2cccc3c2CN(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-6-((2-(2,6-dioxopiperidin-3-yl)-1-oxoisoindolin-4-yl)amino)hexanamide | 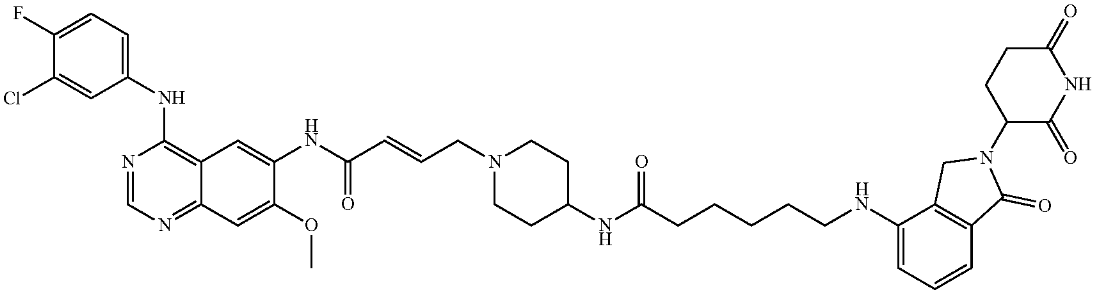 [SMILES: COc1cc2ncnc(Nc3ccc(F)c(Cl)c3)c2cc1NC(=O)/C=C/CN1CCC(NC(=O)CCCCCNc2cccc3c2CN(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-7-((2-(2,6-dioxopiperidin-3-yl)-1-oxoisoindolin-4-yl)amino)heptanamide | 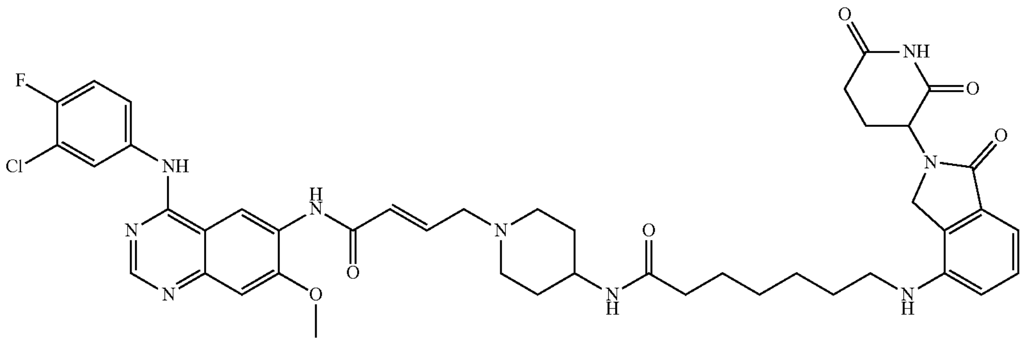 [SMILES: COc1cc2ncnc(Nc3ccc(F)c(Cl)c3)c2cc1NC(=O)/C=C/CN1CCC(NC(=O)CCCCCCNc2cccc3c2CN(C2CCC(=O)NC2=O)C3=O)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(2-(2-((2-(2,6-dioxopiperidin-3-yl)-1,3-dioxoisoindolin-4-yl)thio)ethoxy)acetamido)piperidin-1-yl)but-2-enamide | 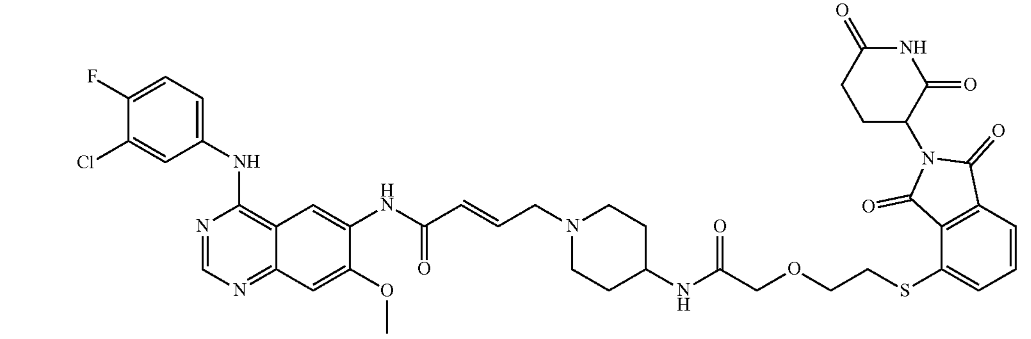 |
| | (E)-N-(4-((3-chloro-4-fluorophenyl)amino)-7-methoxyquinazolin-6-yl)-4-(4-(2-(2-(2-((2-(2,6-dioxopiperidin-3-yl)-1,3-dioxoisoindolin-4-yl)thio)ethoxy)ethoxy)acetamido)piperidin-1-yl)but-2-enamide | 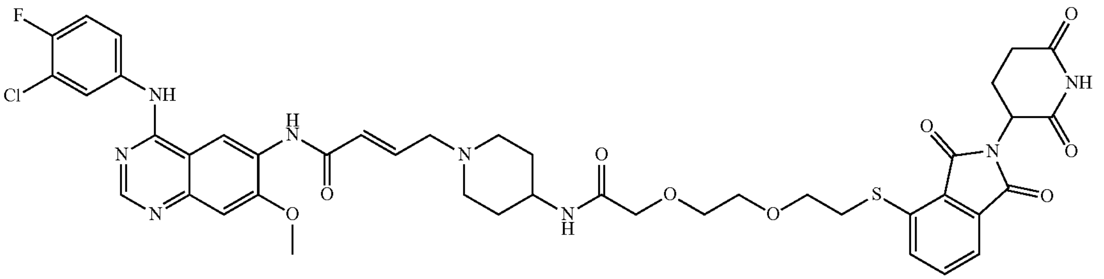 [SMILES: COc1cc2ncnc(Nc3ccc(F)c(Cl)c3)c2cc1NC(=O)/C=C/CN1CCC(NC(=O)COCCOCCSc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(2-(2-(2-(2-((2-(2,6-dioxopiperidin-3-yl)-1,3-dioxoisoindolin-4-yl)thio)ethoxy)ethoxy)ethoxy)acetamido)piperidin-1-yl)but-2-enamide | 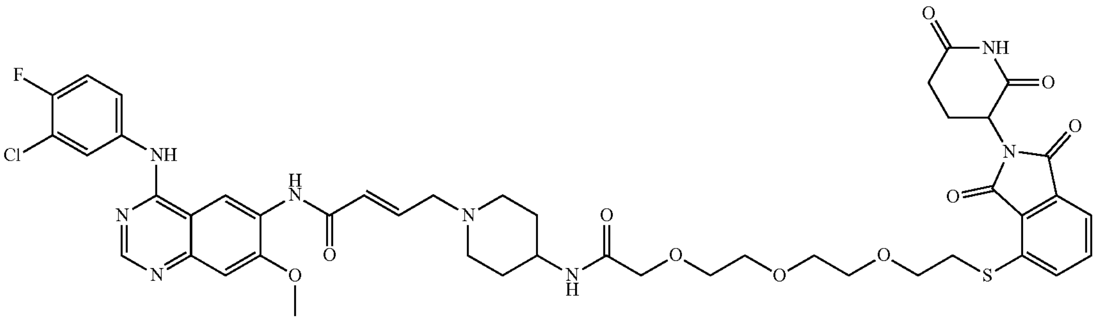 [SMILES: COc1cc2ncnc(Nc3ccc(F)c(Cl)c3)c2cc1NC(=O)/C=C/CN1CCC(NC(=O)COCCOCCOCCSc2cccc3c2C(=O)N(C2CCC(=O)NC2=O)C3=O)CC1] |

TABLE 2-continued

| Compound No. | The compounds' names | Structure of the compounds |
| --- | --- | --- |
| | (E)-N-(1-(4-((4-((3-chloro-4-fluorophenyl)amino)-7-methoxyquinazolin-6-yl)amino)-4-oxobut-2-en-1-yl)piperidin-4-yl)-14-((2-(2,6-dioxopiperidin-3-yl)-1,3-dioxoisoindolin-4-yl)thio)-3,6,9,12-tetraoxatetradecanamide | 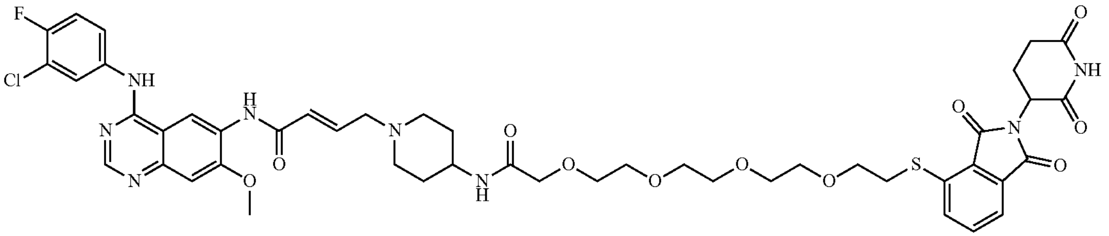 [SMILES: COc1cc2ncnc(Nc3ccc(F)c(Cl)c3)c2cc1NC(=O)/C=C/CN1CCC(NC(=O)COCCOCCOCCOCCSc2cccc3c2C(=O)N(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-17-((2-(2,6-dioxopiperidin-3-yl)-1,3-dioxoisoindolin-4-yl)thio)-3,6,9,12,15-pentaoxaheptadecanamide | 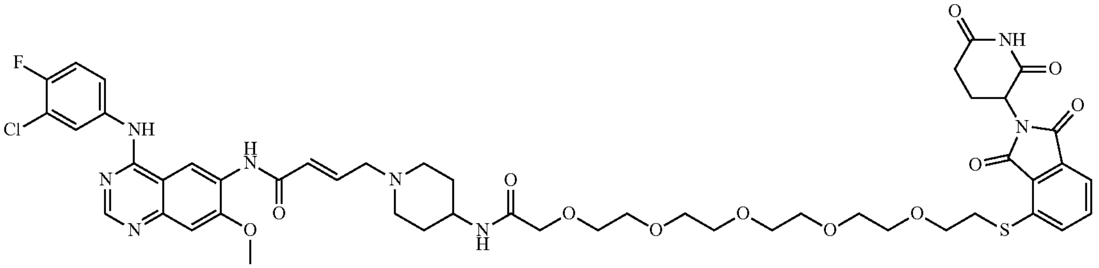 [SMILES: COc1cc2ncnc(Nc3ccc(F)c(Cl)c3)c2cc1NC(=O)/C=C/CN1CCC(NC(=O)COCCOCCOCCOCCOCCSc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(2-((2-(2,6-dioxopiperidin-3-yl)-1,3-dioxoisoindolin-4-yl)thio)acetamido)piperidin-1-yl)but-2-enamide | 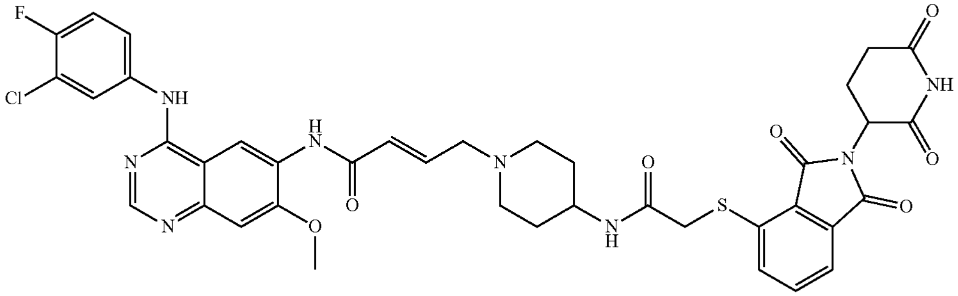 [SMILES: COc1cc2ncnc(Nc3ccc(F)c(Cl)c3)c2cc1NC(=O)/C=C/CN1CCC(NC(=O)CSc2cccc3c2C(=O)N(C2CCC(=O)NC2=O)C3=O)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(3-((2-(2,6-dioxopiperidin-3-yl)-1,3-dioxoisoindolin-4-yl)thio)propanamido)piperidin-1-yl)but-2-enamide | 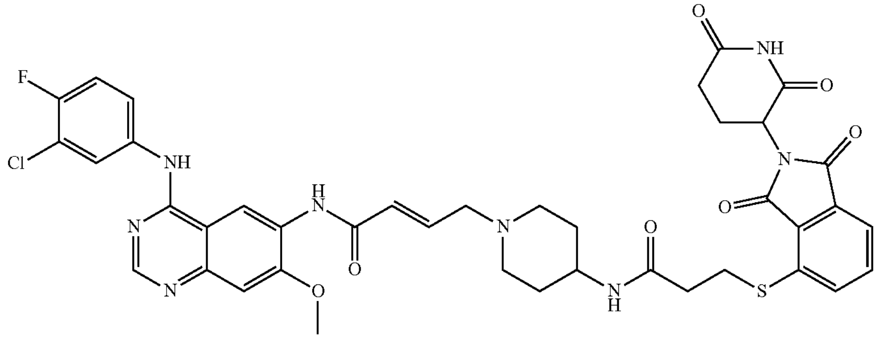 [SMILES: COc1cc2ncnc(Nc3ccc(F)c(Cl)c3)c2cc1NC(=O)/C=C/CN1CCC(NC(=O)CCSc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(4-((2-(2,6-dioxopiperidin-3-yl)-1,3-dioxoisoindolin-4-yl)thio)butanamido)piperidin-1-yl)but-2-enamide | 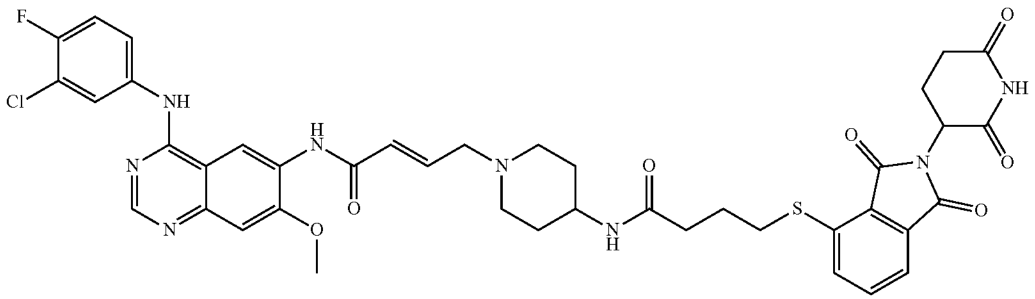 [SMILES: COc1cc2ncnc(Nc3ccc(F)c(Cl)c3)c2cc1NC(=O)/C=C/CN1CCC(NC(=O)CCCSc2cccc3c2C(=O)N(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-5-((2-(2,6-dioxopiperidin-3-yl)-1,3-dioxoisoindolin-4-yl)thio)pentanamide | 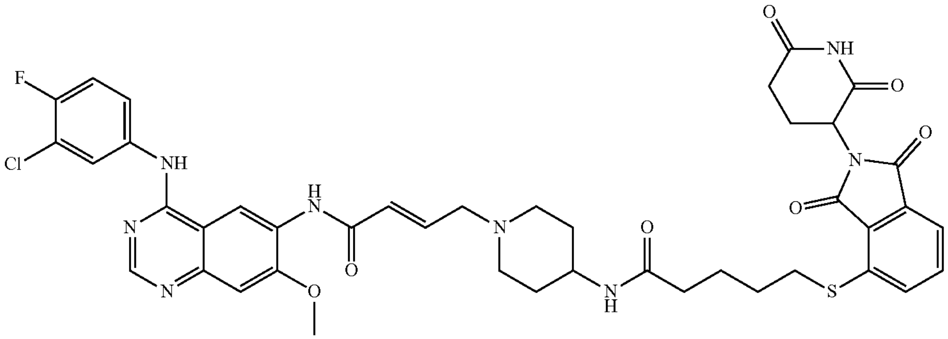 [SMILES: COc1cc2ncnc(Nc3ccc(F)c(Cl)c3)c2cc1NC(=O)/C=C/CN1CCC(NC(=O)CCCCSc2cccc3c2C(=O)N(C2CCC(=O)NC2=O)C3=O)CC1] |

TABLE 2-continued

| Compound No. | The compounds' names | Structure of the compounds |
|---|---|---|
| | (E)-N-(1-(4-((4-((3-chloro-4-fluorophenyl)amino)-7-methoxyquinazolin-6-yl)amino)-4-oxobut-2-en-1-yl)piperidin-4-yl)-6-((2-(2,6-dioxopiperidin-3-yl)-1,3-dioxoisoindolin-4-yl)thio)hexanamide | 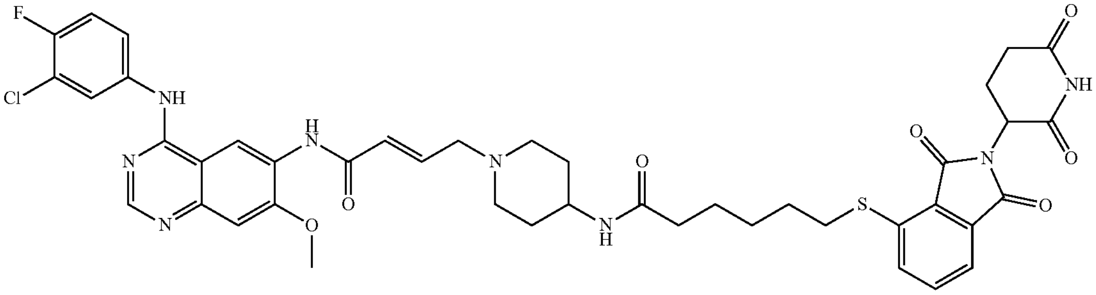 [SMILES: COc1cc2ncnc(Nc3ccc(F)c(Cl)c3)c2cc1NC(=O)/C=C/CN1CCC(NC(=O)CCCCCSc2cccc3c2C(=O)N(C2CCC(=O)NC2=O)C3=O)CC1] |
| | (E)-N-(1-(4-((4-((3-chloro-4-fluorophenyl)amino)-7-methoxyquinazolin-6-yl)amino)-4-oxobut-2-en-1-yl)piperidin-4-yl)-7-((2-(2,6-dioxopiperidin-3-yl)-1,3-dioxoisoindolin-4-yl)thio)heptanamide | 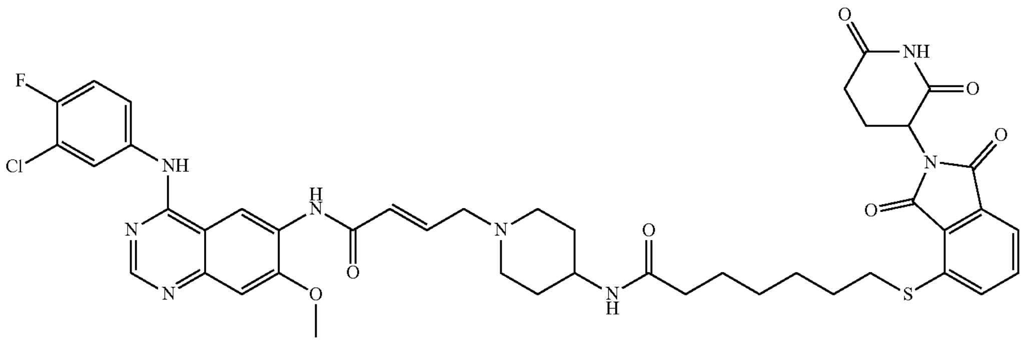 [SMILES: COc1cc2ncnc(Nc3ccc(F)c(Cl)c3)c2cc1NC(=O)/C=C/CN1CCC(NC(=O)CCCCCCSc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(2-(2-((2-(2,6-dioxopiperidin-3-yl)-1-oxoisoindolin-4-yl)thio)ethoxy)acetamido)piperidin-1-yl)but-2-enamide | 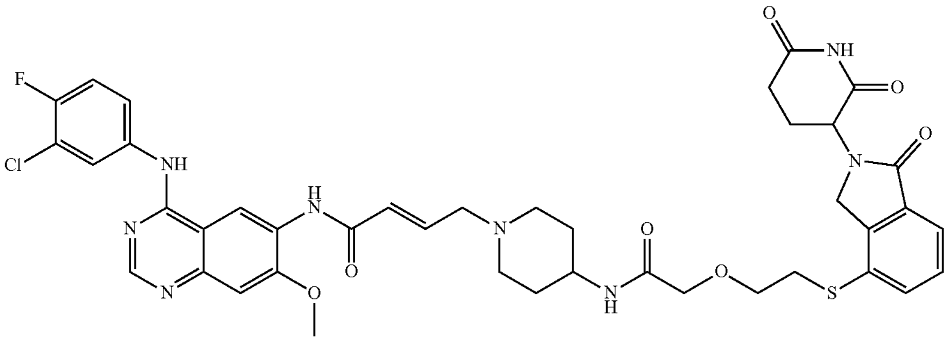 [SMILES: COc1cc2ncnc(Nc3ccc(F)c(Cl)c3)c2cc1NC(=O)/C=C/CN1CCC(NC(=O)COCCSc2cccc3c2CN(C2CCC(=O)NC2=O)C3=O)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(2-(2-(2-((2-(2,6-dioxopiperidin-3-yl)-1-oxoisoindolin-4-yl)thio)ethoxy)ethoxy)acetamido)piperidin-1-yl)but-2-enamide | 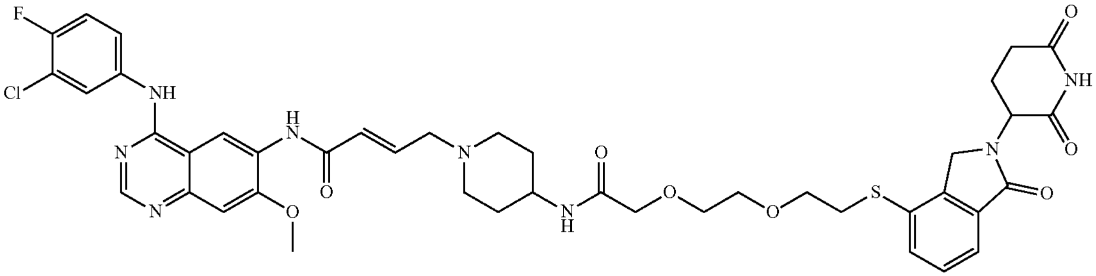 [SMILES: COc1cc2ncnc(Nc3ccc(F)c(Cl)c3)c2cc1NC(=O)/C=C/CN1CCC(NC(=O)COCCOCCSc2cccc3c2CN(C2CCC(=O)NC2=O)C3=O)CC1] |
| | (E)-N-(4-((3-chloro-4-fluorophenyl)amino)-7-methoxyquinazolin-6-yl)-4-(4-(2-(2-(2-(2-((2-(2,6-dioxopiperidin-3-yl)-1-oxoisoindolin-4-yl)thio)ethoxy)ethoxy)ethoxy)acetamido)piperidin-1-yl)but-2-enamide | 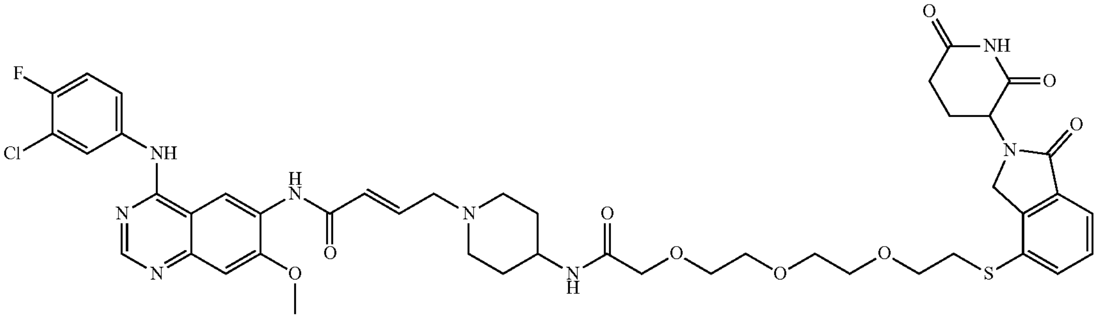 |
| | (E)-N-(1-(4-((4-((3-chloro-4-fluorophenyl)amino)-7-methoxyquinazolin-6-yl)amino)-4-oxobut-2-en-1-yl)piperidin-4-yl)-14-((2-(2,6-dioxopiperidin-3-yl)-1-oxoisoindolin-4-yl)thio)-3,6,9,12-tetraoxatetradecanamide | 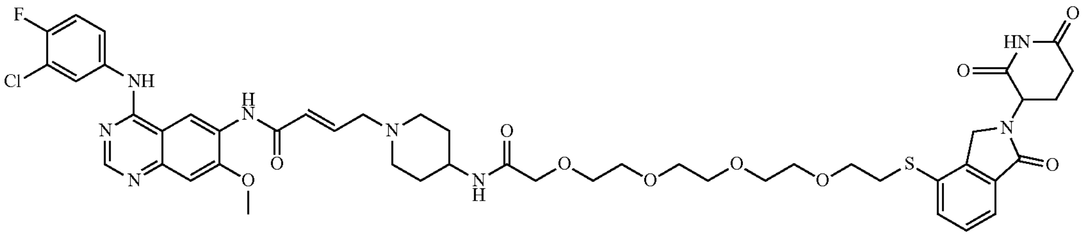 [SMILES: COc1cc2ncnc(Nc3ccc(F)c(Cl)c3)c2cc1NC(=O)/C=C/CN1CCC(NC(=O)COCCOCCOCCOCCSc2cccc3c2CN(C2CCC(=O)NC2=O)C3=O)CC1] |

TABLE 2-continued

| Compound No. | The compounds' names | Structure of the compounds |
| --- | --- | --- |
| | (E)-N-(1-(4-((4-((3-chloro-4-fluorophenyl)amino)-7-methoxyquinazolin-6-yl)amino)-4-oxobut-2-en-1-yl)piperidin-4-yl)-17-((2-(2,6-dioxopiperidin-3-yl)-1-oxoisoindolin-4-yl)thio)-3,6,9,12,15-pentaoxaheptadecanamide | 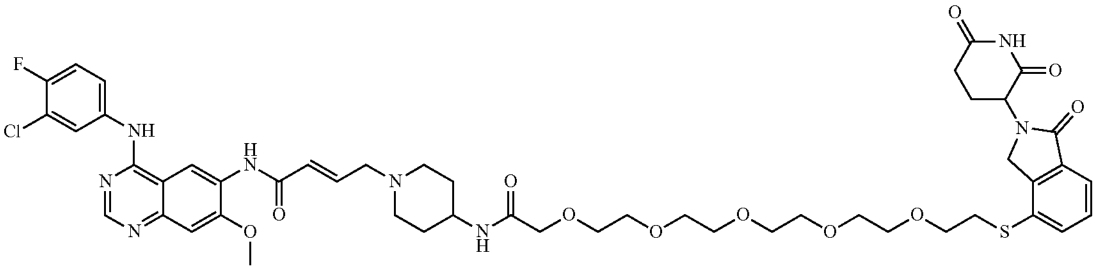 [SMILES: COc1cc2ncnc(Nc3ccc(F)c(Cl)c3)c2cc1NC(=O)/C=C/CN1CCC(NC(=O)COCCOCCOCCOCCOCCSc2cccc3c2CN(C2CCC(=O)NC2=O)C3=O)CC1] |
| SIAIS262110 | (E)-N-(4-((3-chloro-4-fluorophenyl)amino)-7-methoxyquinazolin-6-yl)-4-(4-(2-((2-(2,6-dioxopiperidin-3-yl)-1-oxoisoindolin-4-yl)thio)acetamido)piperidin-1-yl)but-2-enamide | 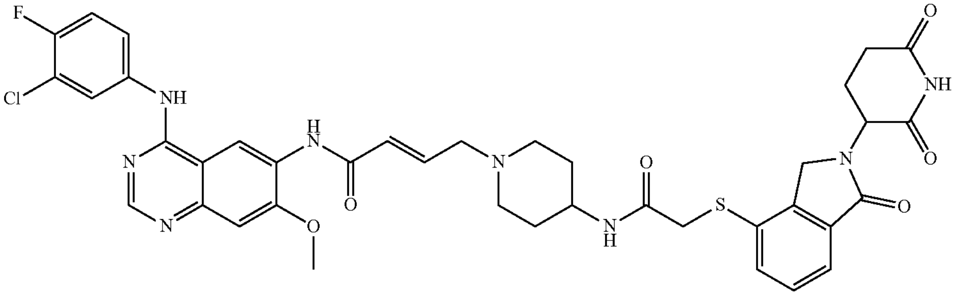 [SMILES: COc1cc2ncnc(Nc3ccc(F)c(Cl)c3)c2cc1NC(=O)/C=C/CN1CCC(NC(=O)CSc2cccc3c2CN(C2CCC(=O)NC2=O)C3=O)CC1] |
| | (E)-N-(4-((3-chloro-4-fluorophenyl)amino)-7-methoxyquinazolin-6-yl)-4-(4-(3-((2-(2,6-dioxopiperidin-3-yl)-1-oxoisoindolin-4-yl)thio)propanamido)piperidin-1-yl)but-2-enamide | 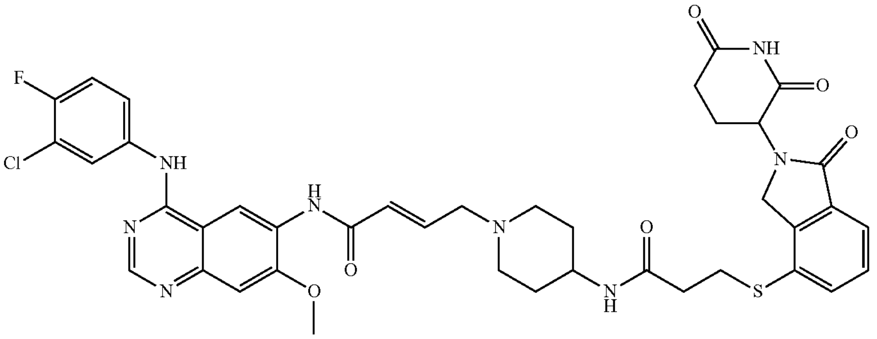 [SMILES: COc1cc2ncnc(Nc3ccc(F)c(Cl)c3)c2cc1NC(=O)/C=C/CN1CCC(NC(=O)CCSc2cccc3c2CN(C2CCC(=O)NC2=O)C3=O)CC1] |

TABLE 2-continued

| Compound No. | The compounds' names | Structure of the compounds |
| --- | --- | --- |
| SIAIS262112 | (E)-N-(4-((3-chloro-4-fluorophenyl)amino)-7-methoxyquinazolin-6-yl)-4-(4-(4-((2-(2,6-dioxopiperidin-3-yl)-1-oxoisoindolin-4-yl)thio)butanamido)piperidin-1-yl)but-2-enamide | 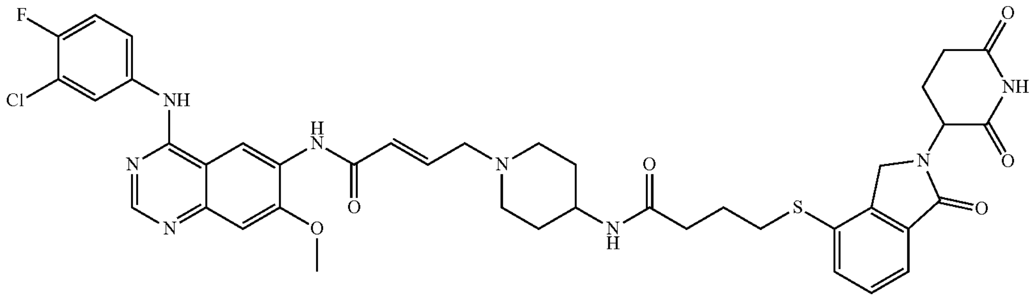 [SMILES: COc1cc2ncnc(Nc3ccc(F)c(Cl)c3)c2cc1NC(=O)/C=C/CN1CCC(NC(=O)CCCSc2cccc3c2CN(C2CCC(=O)NC2=O)C3=O)CC1] |
| SIAIS262113 | (E)-N-(1-(4-((4-((3-chloro-4-fluorophenyl)amino)-7-methoxyquinazolin-6-yl)amino)-4-oxobut-2-en-1-yl)piperidin-4-yl)-5-((2-(2,6-dioxopiperidin-3-yl)-1-oxoisoindolin-4-yl)thio)pentanamide | 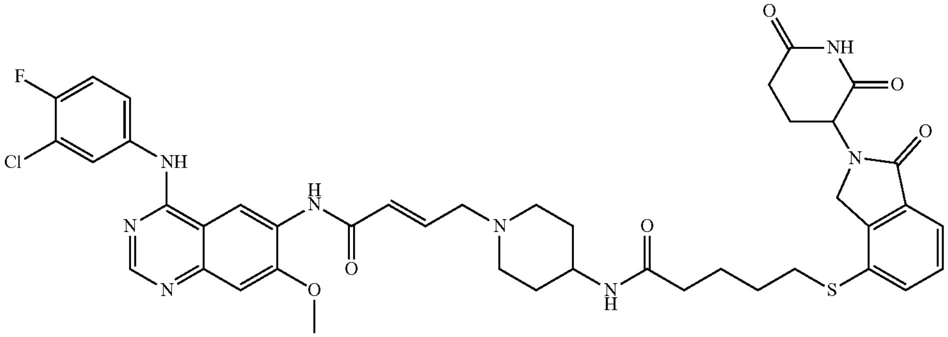 [SMILES: COc1cc2ncnc(Nc3ccc(F)c(Cl)c3)c2cc1NC(=O)/C=C/CN1CCC(NC(=O)CCCCSc2cccc3c2CN(C2CCC(=O)NC2=O)C3=O)CC1] |
| SIAIS262114 | (E)-N-(1-(4-((4-((3-chloro-4-fluorophenyl)amino)-7-methoxyquinazolin-6-yl)amino)-4-oxobut-2-en-1-yl)piperidin-4-yl)-6-((2-(2,6-dioxopiperidin-3-yl)-1-oxoisoindolin-4-yl)thio)hexanamide | 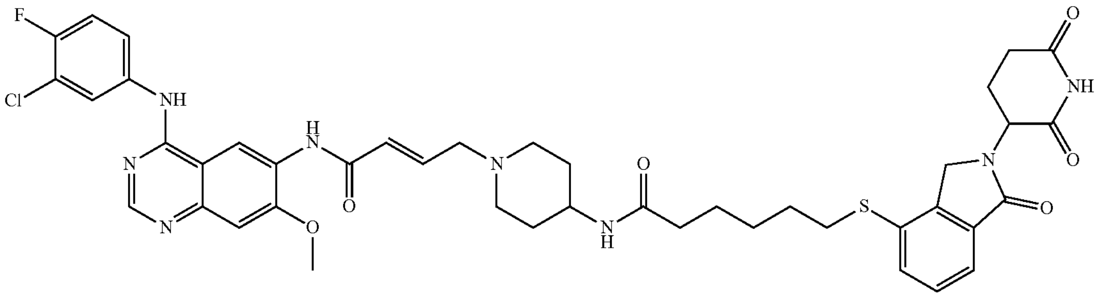 [SMILES: COc1cc2ncnc(Nc3ccc(F)c(Cl)c3)c2cc1NC(=O)/C=C/CN1CCC(NC(=O)CCCCCSc2cccc3c2CN(C2CCC(=O)NC2=O)C3=O)CC1] |

TABLE 2-continued

| Compound No. | The compounds' names | Structure of the compounds |
|---|---|---|
| SIAIS262115 | (E)-N-(1-(4-((4-((3-chloro-4-fluorophenyl)amino)-7-methoxyquinazolin-6-yl)amino)-4-oxobut-2-en-1-yl)piperidin-4-yl)-7-((2-(2,6-dioxopiperidin-3-yl)-1-oxoisoindolin-4-yl)thio)heptanamide | 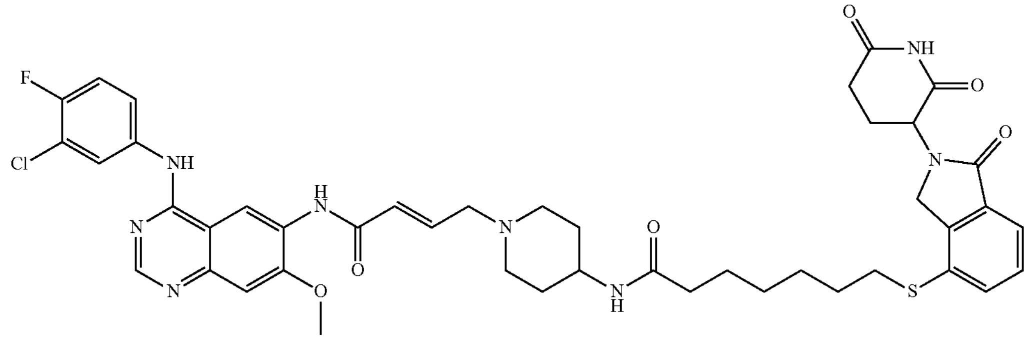 [SMILES: COc1cc2ncnc(Nc3ccc(F)c(Cl)c3)c2cc1NC(=O)/C=C/CN1CCC(NC(=O)CCCCCCSc2cccc3c2CN(C2CCC(=O)NC2=O)C3=O)CC1] |
| | (2S,4R)-1-((S)-2-(2-(2-(2-((1-((E)-4-((4-((3-chloro-4-fluorophenyl)amino)-7-methoxyquinazolin-6-yl)amino)-4-oxobut-2-en-1-yl)piperidin-4-yl)amino)-2-oxoethoxy)ethoxy)acetamido)-3,3-dimethylbutanoyl)-4-hydroxy-N-(4-(4-methylthiazol-5-yl)benzyl)pyrrolidine-2-carboxamide | 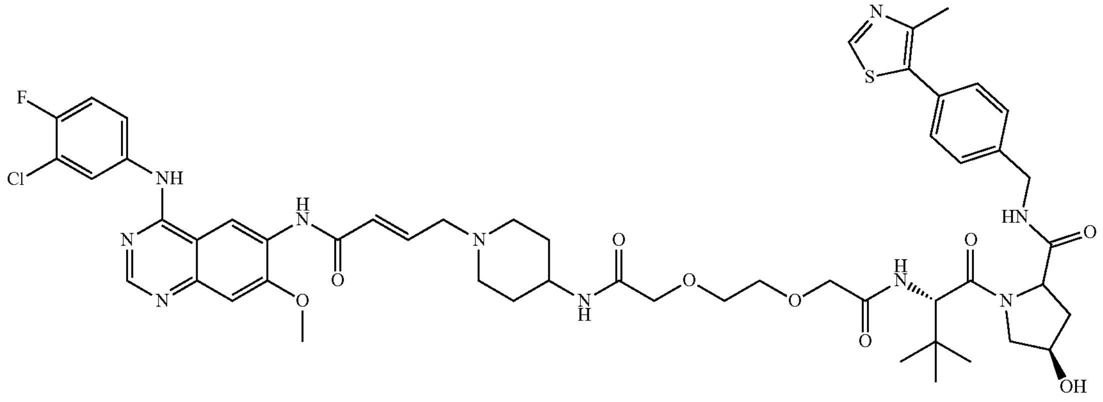 [SMILES: COc1cc2ncnc(Nc3ccc(F)c(Cl)c3)c2cc1NC(=O)/C=C/CN1CCC(NC(=O)COCCOCC(=O)N[C@H](C(=O)N2C[C@H](O)CC2C(=O)NCc2ccc(-c3scnc3C)cc2)C(C)(C)C)CC1] |

TABLE 2-continued

| Compound No. | The compounds' names | Structure of the compounds |
|---|---|---|
| | N1-(1-((E)-4-((4-((3-chloro-4-fluorophenyl)amino)-7-methoxyquinazolin-6-yl)amino)-4-oxobut-2-en-1-yl)piperidin-4-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide | 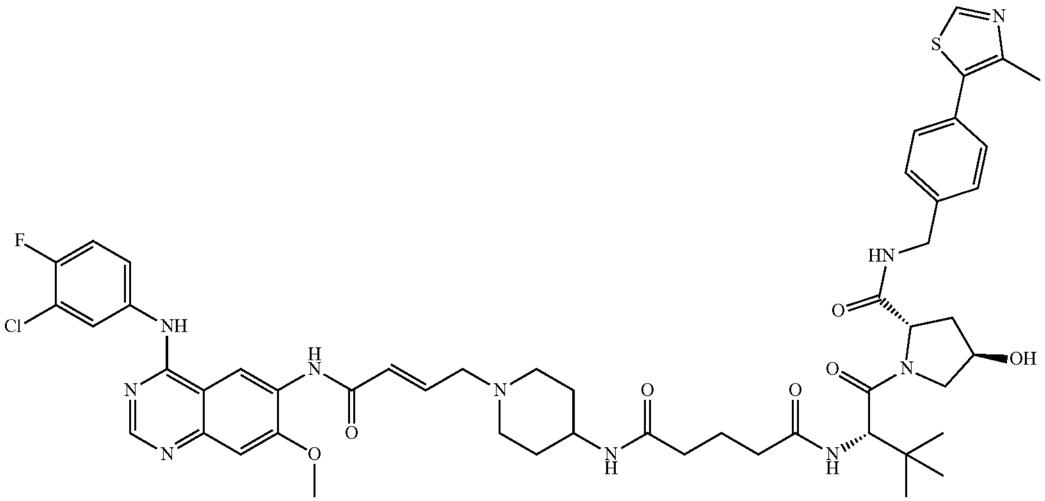 [SMILES: COc1cc2ncnc(Nc3ccc(F)c(Cl)c3)c2cc1NC(=O)/C=C/CN1CCC(NC(=O)CCCC(=O)N[C@H](C(=O)N2C[C@H](O)C[C@H]2C(=O)NCc2ccc(-c3scnc3C)cc2)C(C)(C)C)CC1] |
| | N1-(1-((E)-4-((4-((3-chloro-4-fluorophenyl)amino)-7-methoxyquinazolin-6-yl)amino)-4-oxobut-2-en-1-yl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide | 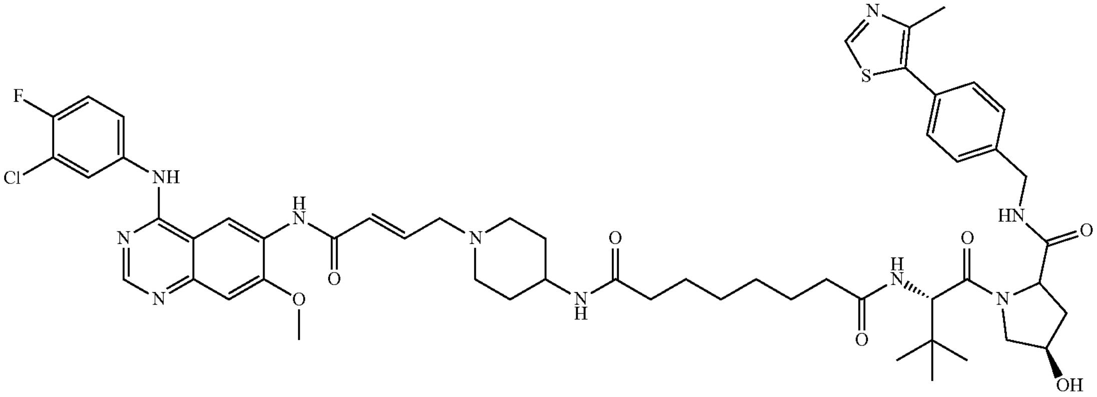 [SMILES: COc1cc2ncnc(Nc3ccc(F)c(Cl)c3)c2cc1NC(=O)/C=C/CN1CCC(NC(=O)CCCCCCC(=O)N[C@H](C(=O)N2C[C@H](O)CC2C(=O)NCc2ccc(-c3scnc3C)cc2)C(C)(C)C)CC1] |

TABLE 2-continued

| Compound No. | The compounds' names | Structure of the compounds |
|---|---|---|
| | N1-(1-((E)-4-((4-((3-chloro-4-fluorophenyl)amino)-7-methoxyquinazolin-6-yl)amino)-4-oxobut-2-en-1-yl)piperidin-4-yl)-N11-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide | 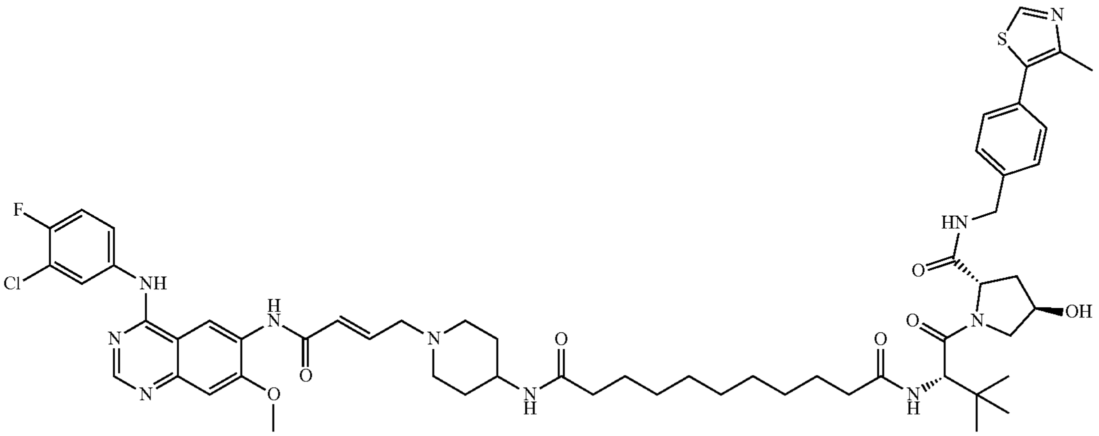 [SMILES: COc1cc2ncnc(Nc3ccc(F)c(Cl)c3)c2cc1NC(=O)/C=C/CN1CCC(NC(=O)CCCCCCCCCC(=O)N[C@H](C(=O)N2C[C@H](O)C[C@H]2C(=O)NCc2ccc(-c3scnc3C)cc2)C(C)(C)C)CC1] |
| | (E)-N-(4-((3-chloro-4-fluorophenyl)amino)-7-methoxyquinazolin-6-yl)-4-(4-((5-(2-(2,6-dioxopiperidin-3-yl)-1,3-dioxoisoindolin-4-yl)pent-4-yn-1-yl)amino)piperidin-1-yl)but-2-enamide | 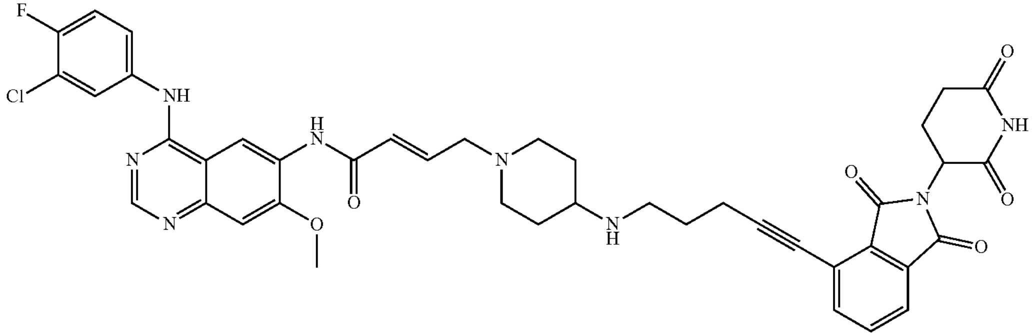 [SMILES: COc1cc2ncnc(Nc3ccc(F)c(Cl)c3)c2cc1NC(=O)/C=C/CN1CCC(NCCCC#Cc2cccc3c2C(=O)N(C2CCC(=O)NC2=O)C3=O)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(3-(2-((2-(2,6-dioxopiperidin-3-yl)-1,3-dioxoisoindolin-4-yl)amino)ethoxy)propanoyl)piperazin-1-yl)piperidin-1-yl)but-2-enamide | 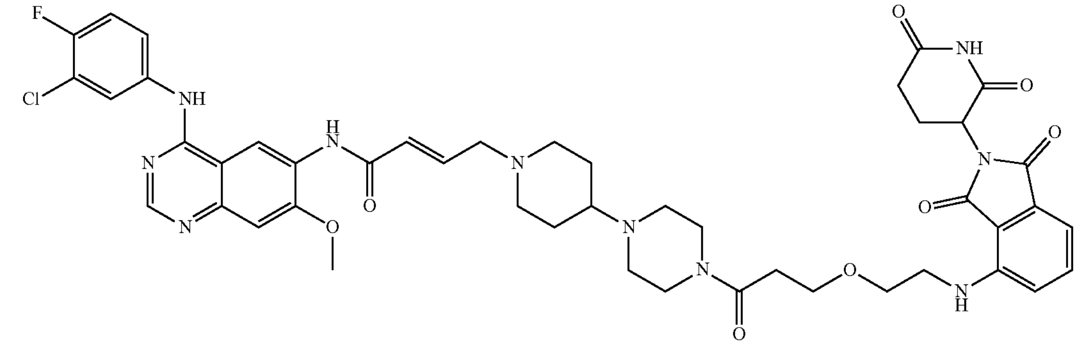 [SMILES: COc1cc2ncnc(Nc3ccc(F)c(Cl)c3)c2cc1NC(=O)/C=C/CN1CCC(N2CCN(C(=O)CCOCCNc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(3-(2-(2-((2-(2,6-dioxopiperidin-3-yl)-1,3-dioxoisoindolin-4-yl)amino)ethoxy)ethoxy)propnoyl)piperazin-1-yl)piperidin-1-yl)but-2-enamide | 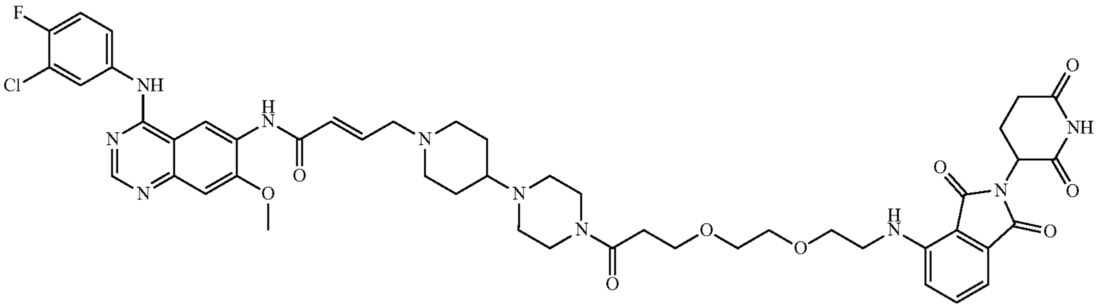 [SMILES: COc1cc2ncnc(Nc3ccc(F)c(Cl)c3)c2cc1NC(=O)/C=C/CN1CCC(N2CCN(C(=O)CCOCCOCCNc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)piperidin-1-yl)but-2-enamide | 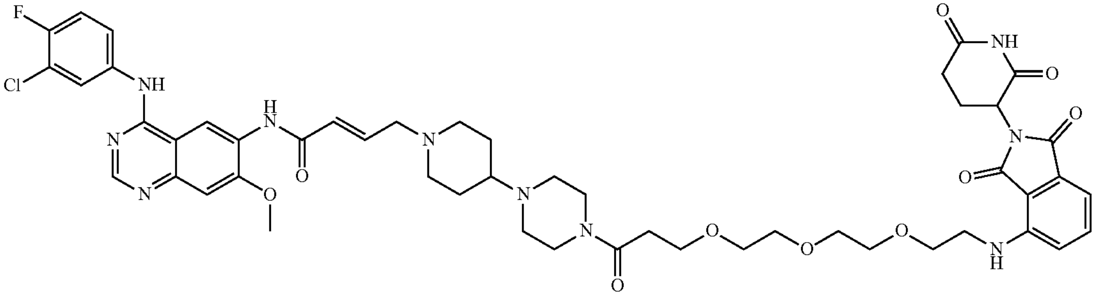 [SMILES: COc1cc2ncnc(Nc3ccc(F)c(Cl)c3)c2cc1NC(=O)/C=C/CN1CCC(N2CCN(C(=O)CCOCCOCCOCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)piperidin-1-yl)but-2-enamide | 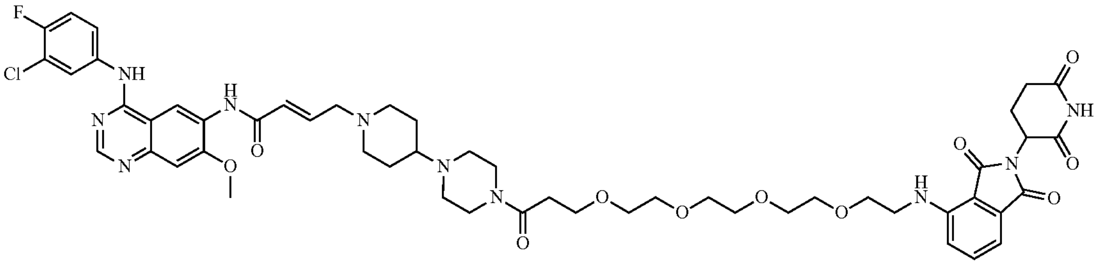 [SMILES: COc1cc2ncnc(Nc3ccc(F)c(Cl)c3)c2cc1NC(=O)/C=C/CN1CCC(N2CCN(C(=O)CCOCCOCCOCCOCCNc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)piperidin-1-yl)but-2-enamide | 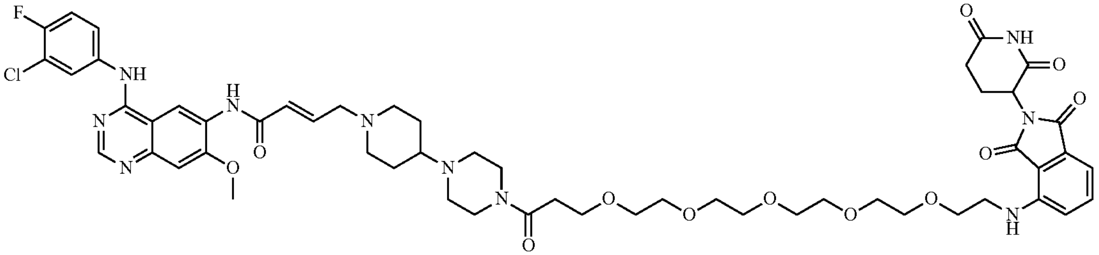 [SMILES: COc1cc2ncnc(Nc3ccc(F)c(Cl)c3)c2cc1NC(=O)/C=C/CN1CCC(N2CCN(C(=O)CCOCCOCCOCCOCCOCCNc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(3-((2-(2,6-dioxopiperidin-3-yl)-1,3-dioxoisoindolin-4-yl)amino)propanoyl)piperazin-1-yl)piperidin-1-yl)but-2-enamide | 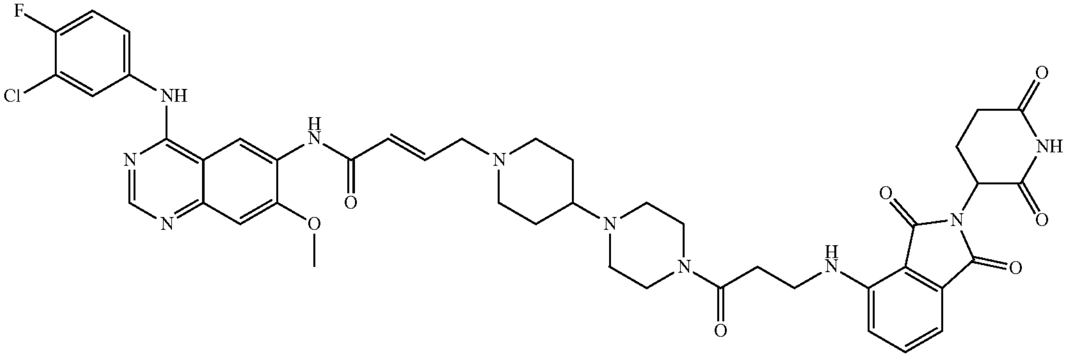 [SMILES: COc1cc2ncnc(Nc3ccc(F)c(Cl)c3)c2cc1NC(=O)/C=C/CN1CCC(N2CCN(C(=O)CCNc3cccc4c3C(=O)N(C3CCC(=O)NC3=O)C4=O)CC2)CC1] |

TABLE 2-continued

| Compound No. | The compounds' names | Structure of the compounds |
| --- | --- | --- |
| | (E)-N-(4-((3-chloro-4-fluorophenyl)amino)-7-methoxyquinazolin-6-yl)-4-(4-(4-(4-((2-(2,6-dioxopiperidin-3-yl)-1,3-dioxoisoindolin-4-yl)amino)butanoyl)piperazin-1-yl)piperidin-1-yl)but-2-enamide | 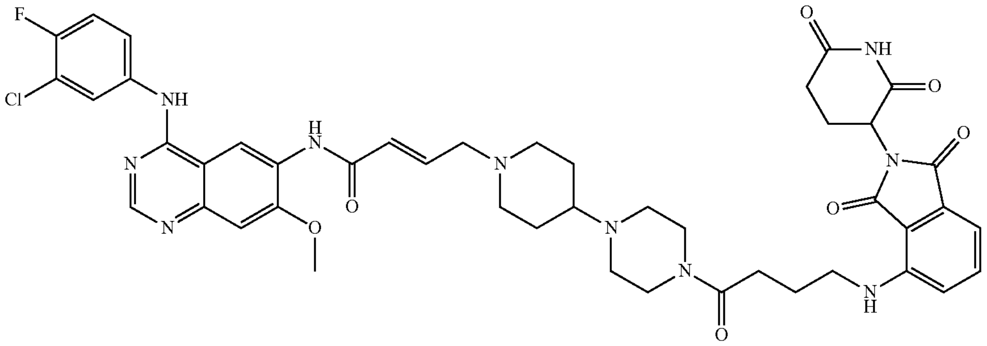 [SMILES: COc1cc2ncnc(Nc3ccc(F)c(Cl)c3)c2cc1NC(=O)/C=C/CN1CCC(N2CCN(C(=O)CCCNc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(5-((2-(2,6-dioxopiperidin-3-yl)-1,3-dioxoisoindolin-4-yl)amino)pentanoyl)piperazin-1-yl)piperidin-1-yl)but-2-enamide | 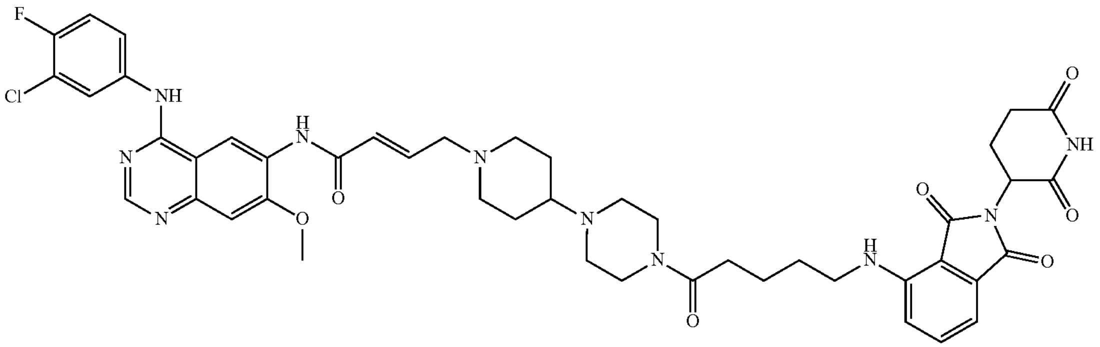 |

TABLE 2-continued

| Compound No. | The compounds' names | Structure of the compounds |
| --- | --- | --- |
| | (E)-N-(4-((3-chloro-4-fluorophenyl)amino)-7-methoxyquinazolin-6-yl)-4-(4-(4-(6-((2-(2,6-dioxopiperidin-3-yl)-1,3-dioxoisoindolin-4-yl)amino)hexanoyl)piperazin-1-yl)piperidin-1-yl)but-2-enamide | 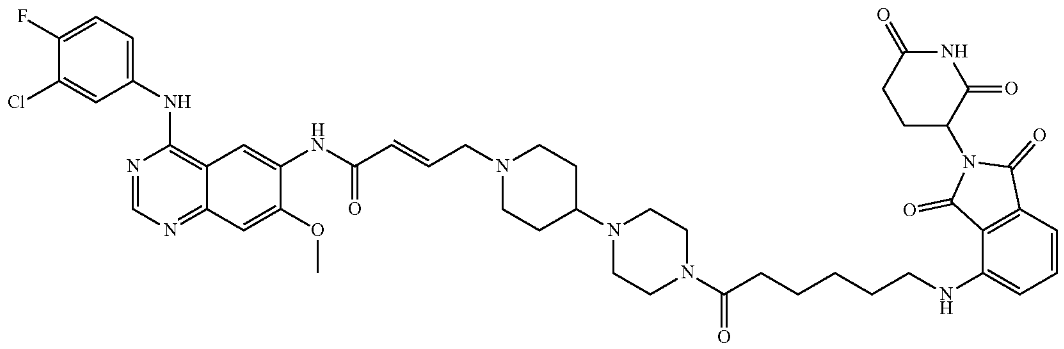 |
| | (E)-N-(4-((3-chloro-4-fluorophenyl)amino)-7-methoxyquinazolin-6-yl)-4-(4-(4-(3-((2-(2,6-dioxopiperidin-3-yl)-1,3-dioxoisoindolin-4-yl)amino)propyl)piperazin-1-yl)piperidin-1-yl)but-2-enamide | 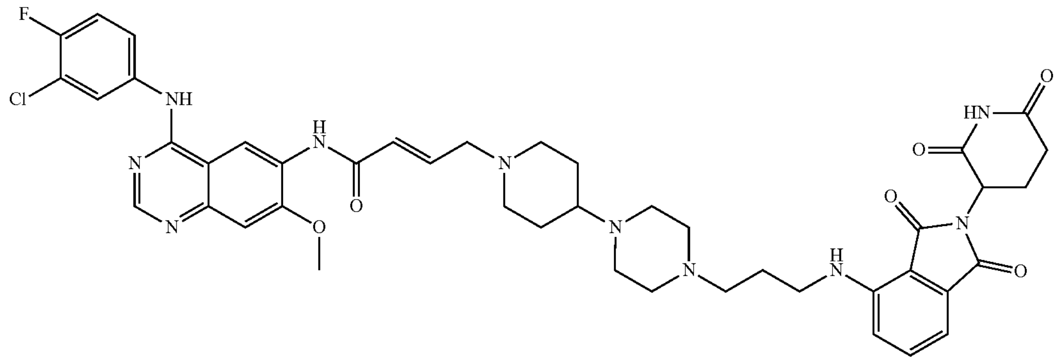 [SMILES: COc1cc2ncnc(Nc3ccc(F)c(Cl)c3)c2cc1NC(=O)/C=C/CN1CCC(N2CCN(CCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| SIAIS262071 | (E)-N-(4-((3-chloro-4-fluorophenyl)amino)-7-methoxyquinazolin-6-yl)-4-(4-(4-(5-((2-(2,6-dioxopiperidin-3-yl)-1,3-dioxoisoindolin-4-yl)amino)pentyl)piperazin-1-yl)piperidin-1-yl)but-2-enamide | 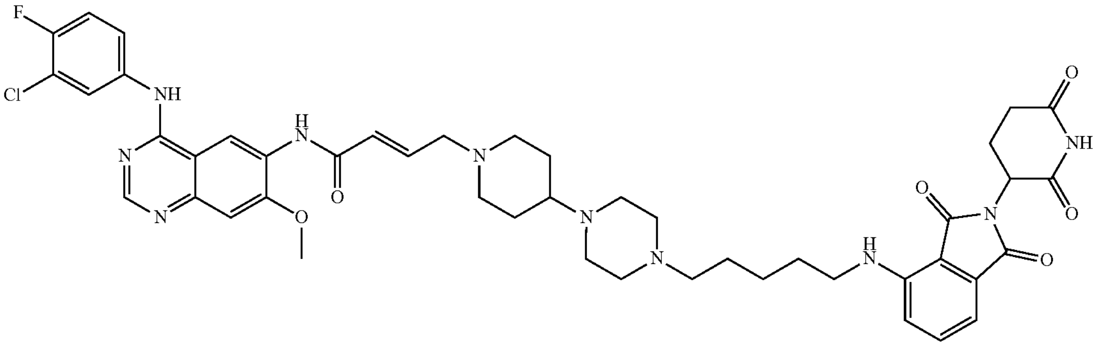 [SMILES: COc1cc2ncnc(Nc3ccc(F)c(Cl)c3)c2cc1NC(=O)/C=C/CN1CCC(N2CCN(CCCCCNc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(2-(2-((2-(2,6-dioxopiperidin-3-yl)-1-oxoisoindolin-4-yl)amino)ethoxy)acetyl)piperazin-1-yl)piperidin-1-yl)but-2-enamide | 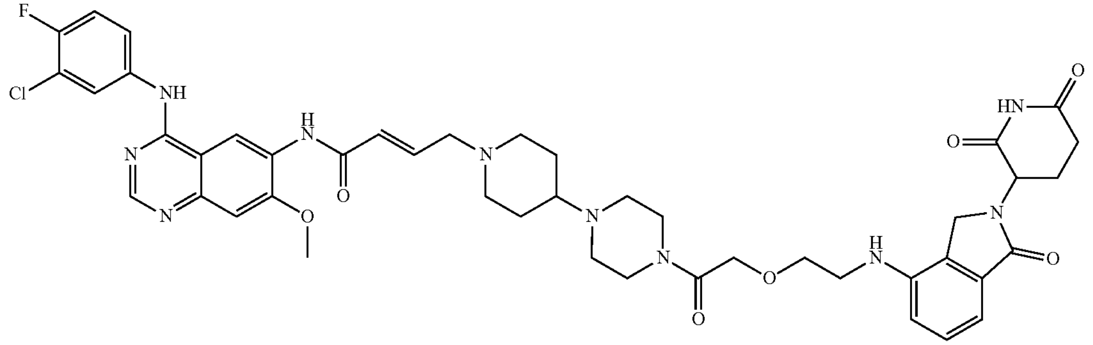 [SMILES: COc1cc2ncnc(Nc3ccc(F)c(Cl)c3)c2cc1NC(=O)/C=C/CN1CCC(N2CCN(C(=O)COCCNc3cccc4c3CN(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(2-(2-(2-((2-(2,6-dioxopiperidin-3-yl)-1-oxoisoindolin-4-yl)amino)ethoxy)ethoxy)acetyl)piperazin-1-yl)piperidin-1-yl)but-2-enamide | 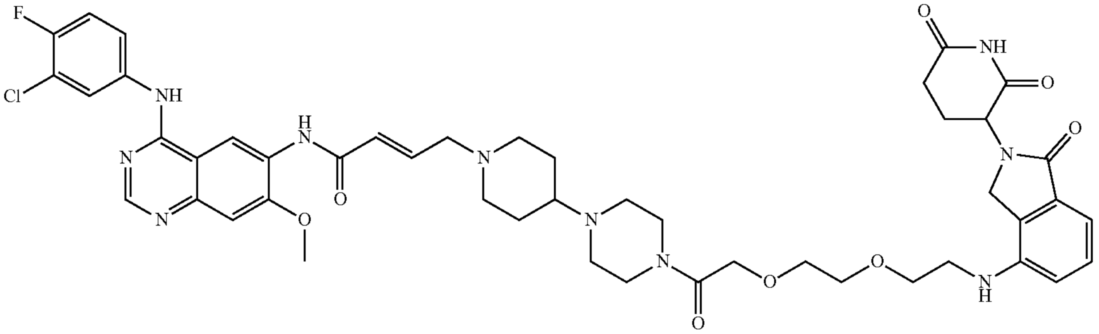 [SMILES: COc1cc2ncnc(Nc3ccc(F)c(Cl)c3)c2cc1NC(=O)/C=C/CN1CCC(N2CCN(C(=O)COCCOCCNc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(2-(2-(2-(2-((2-(2,6-dioxopiperidin-3-yl)-1-oxoisoindolin-4-yl)amino)ethoxy)ethoxy)ethoxy)acetyl)piperazin-1-yl)piperidin-1-yl)but-2-enamide | 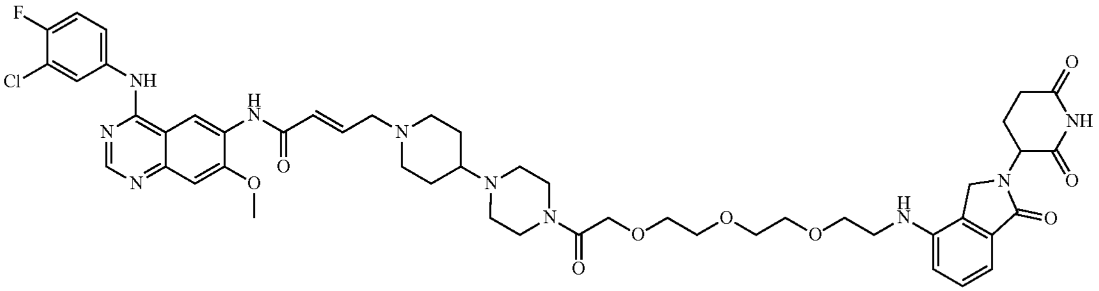 [SMILES: COc1cc2ncnc(Nc3ccc(F)c(Cl)c3)c2cc1NC(=O)/C=C/CN1CCC(N2CCN(C(=O)COCCOCCOCCNc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(14-((2-(2,6-dioxopiperidin-3-yl)-1-oxoisoindolin-4-yl)amino)-3,6,9,12-tetraoxatetradecan-1-o yl)piperazin-1-yl)piperidin-1-yl)but-2-enamide | 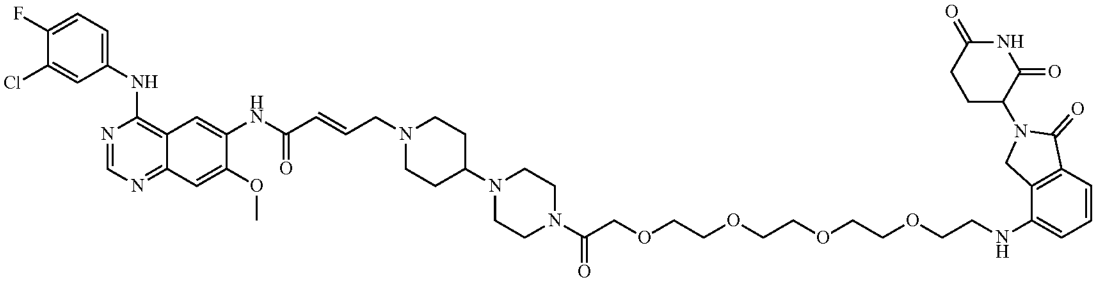 |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(17-((2-(2,6-dioxopiperidin-3-yl)-1-oxoisoindolin-4-yl)amino)-3,6,9,12,15-pentaoxaheptadecan-1-oyl)piperazin-1-yl)piperidin-1-yl)but-2-enamide | 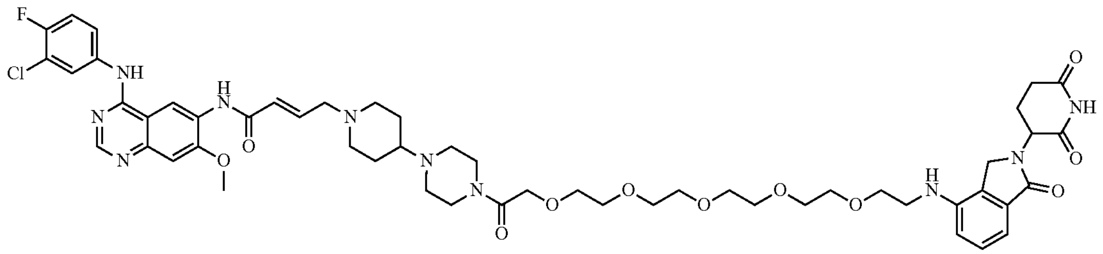 [SMILES: COc1cc2ncnc(Nc3ccc(F)c(Cl)c3)c2cc1NC(=O)/C=C/CN1CCC(N2CCN(C(=O)COCCOCCOCCOCCOCCNc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(2-((2-(2,6-dioxopiperidin-3-yl)-1-oxoisoindolin-4-yl)amino)acetyl)piperazin-1-yl)piperidin-1-yl)but-2-enamide | 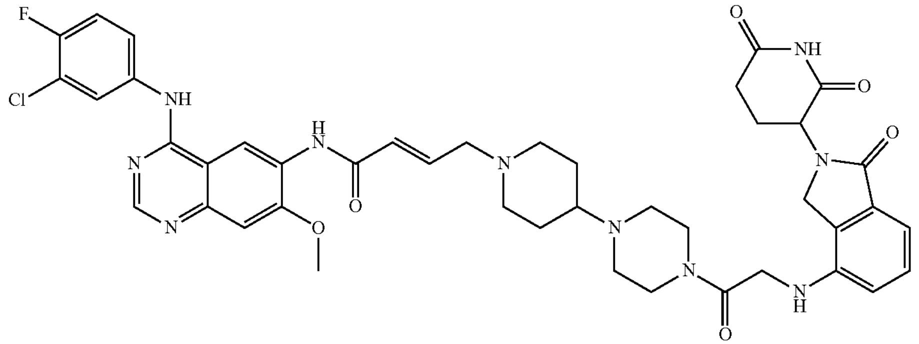 [SMILES: COc1cc2ncnc(Nc3ccc(F)c(Cl)c3)c2cc1NC(=O)/C=C/CN1CCC(N2CCN(C(=O)CNc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(3-((2-(2,6-dioxopiperidin-3-yl)-1-oxoisoindolin-4-yl)amino)propanoyl)piperazin-1-yl)piperidin-1-yl)but-2-enamide | 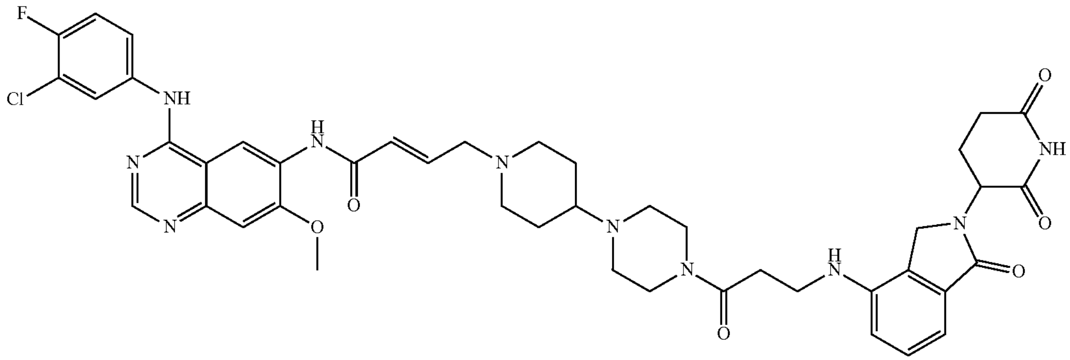 [SMILES: COc1cc2ncnc(Nc3ccc(F)c(Cl)c3)c2cc1NC(=O)/C=C/CN1CCC(N2CCN(C(=O)CCNc3cccc4c3CN(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(4-((2-(2,6-dioxopiperidin-3-yl)-1-oxoisoindolin-4-yl)amino)butanoyl)piperazin-1-yl)piperidin-1-yl)but-2-enamide | 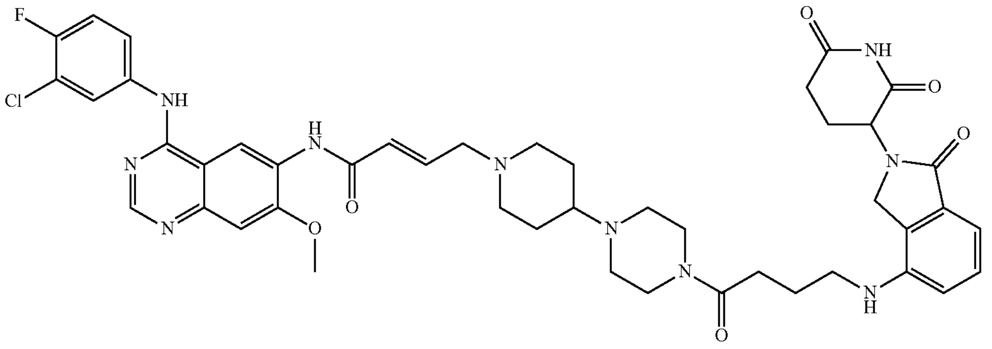 |
| | (E)-N-(4-((3-chloro-4-fluorophenyl)amino)-7-methoxyquinazolin-6-yl)-4-(4-(4-(5-((2-(2,6-dioxopiperidin-3-yl)-1-oxoisoindolin-4-yl)amino)pentanoyl)piperazin-1-yl)piperidin-1-yl)but-2-enamide | 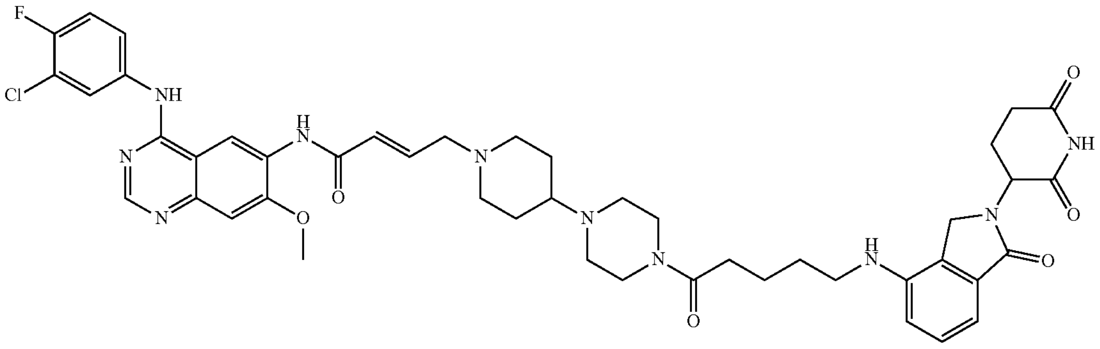 [SMILES: COc1cc2ncnc(Nc3ccc(F)c(Cl)c3)c2cc1NC(=O)/C=C/CN1CCC(N2CCN(C(=O)CCCCNc3cccc4c3CN(C3CCC(=O)NC3=O)C4=O)CC2)CC1] |

TABLE 2-continued

| Compound No. | The compounds' names | Structure of the compounds |
|---|---|---|
| SIAIS337035 | (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)amino)hexanoyl)piperazin-1-yl)piperidin-1-yl)but-2-enamide | 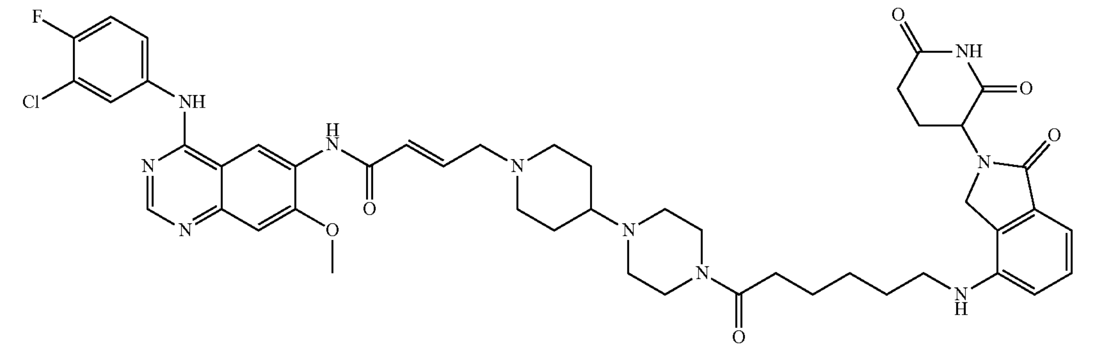 [SMILES: COc1cc2ncnc(Nc3ccc(F)c(Cl)c3)c2cc1NC(=O)/C=C/CN1CCC(N2CCN(C(=O)CCCCCNc3cccc4c3CN(C3CCC(=O)NC3=O)C4=O)CC2)CC1] |
| SIAIS337036 | (E)-N-(4-((3-chloro-4-fluorophenyl)amino)-7-methoxyquinazolin-6-yl)-4-(4-(4-(7-((2-(2,6-dioxopiperidin-3-yl)-1-oxoisoindolin-4-yl)amino)heptanoyl)piperazin-1-yl)piperidin-1-yl)but-2-enamide | 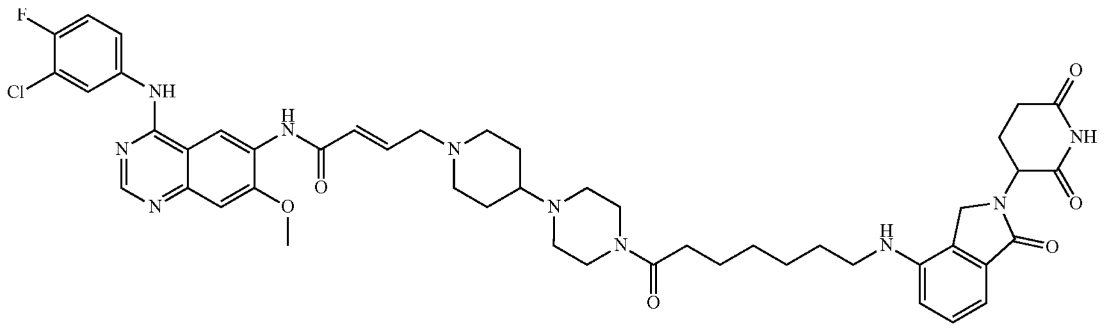 [SMILES: COc1cc2ncnc(Nc3ccc(F)c(Cl)c3)c2cc1NC(=O)/C=C/CN1CCC(N2CCN(C(=O)CCCCCCNc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(2-((2-(2,6-dioxopiperidin-3-yl)-1,3-dioxoisoindolin-4-yl)thio)acetyl)piperazin-1-yl)piperidin-1-yl)but-2-enamide | 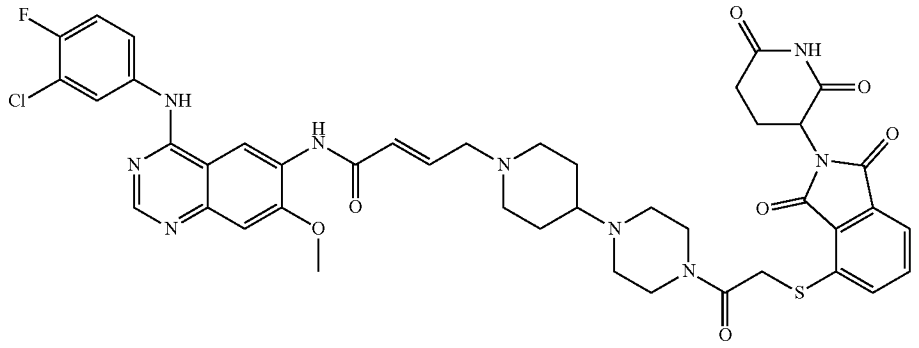 |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(3-((2-(2,6-dioxopiperidin-3-yl)-1,3-dioxoisoindolin-4-yl)thio)propanoyl)piperazin-1-yl)piperidin-1-yl)but-2-enamide | 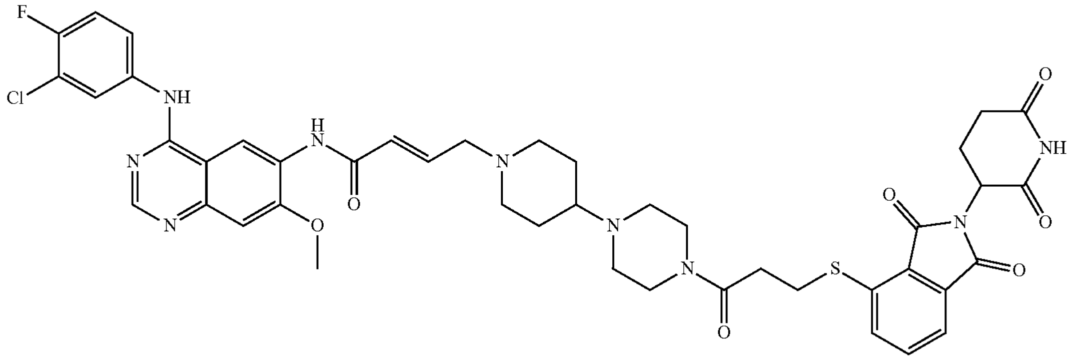 [SMILES: COc1cc2ncnc(Nc3ccc(F)c(Cl)c3)c2cc1NC(=O)/C=C/CN1CCC(N2CCN(C(=O)CCSc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(4-((2-(2,6-dioxopiperidin-3-yl)-1,3-dioxoisoindolin-4-yl)thio)butanoyl)piperazin-1-yl)piperidin-1-yl)but-2-enamide | 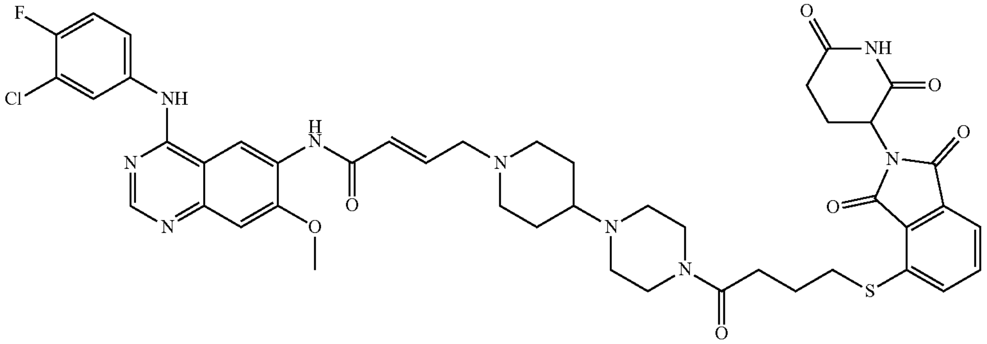 [SMILES: COc1cc2ncnc(Nc3ccc(F)c(Cl)c3)c2cc1NC(=O)/C=C/CN1CCC(N2CCN(C(=O)CCCSc3cccc4c3C(=O)N(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(5-((2-(2,6-dioxopiperidin-3-yl)-1,3-dioxoisoindolin-4-yl)thio)pentanoyl)piperazin-1-yl)piperidin-1-yl)but-2-enamide | 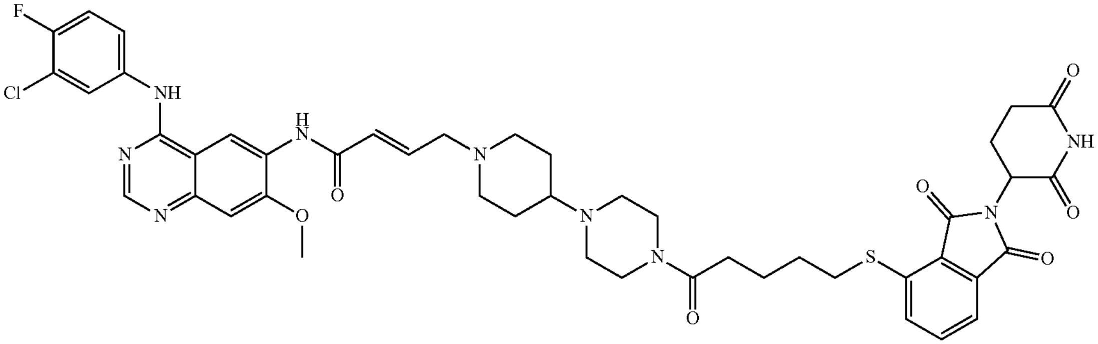 [SMILES: COc1cc2ncnc(Nc3ccc(F)c(Cl)c3)c2cc1NC(=O)/C=C/CN1CCC(N2CCN(C(=O)CCCCSc3cccc4c3C(=O)N(C3CCC(=O)NC3=O)C4=O)CC2)CC1] |
| SIAIS262064 | (E)-N-(4-((3-chloro-4-fluorophenyl)amino)-7-methoxyquinazolin-6-yl)-4-(4-(4-(5-((2-(2,6-dioxopiperidin-3-yl)-1-oxoisoindolin-4-yl)thio)pentyl)piperazin-1-yl)piperidin-1-yl)but-2-enamide | 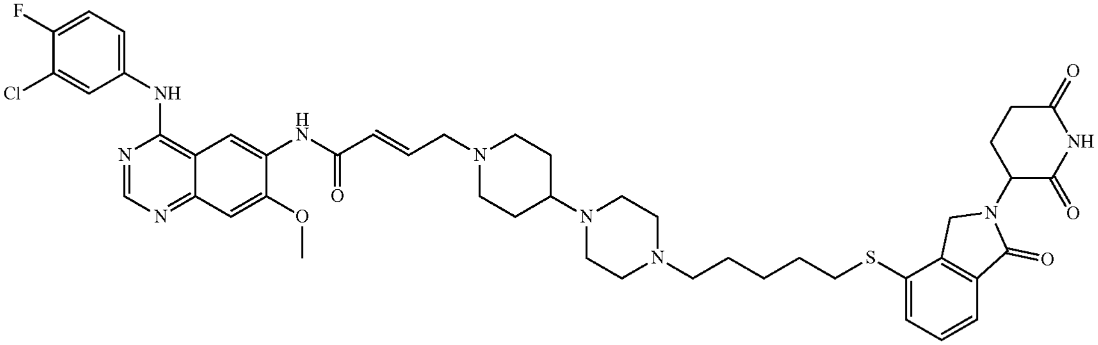 [SMILES: COc1cc2ncnc(Nc3ccc(F)c(Cl)c3)c2cc1NC(=O)/C=C/CN1CCC(N2CCN(CCCCCSc3cccc4c3CN(C3CCC(=O)NC3=O)C4=O)CC2)CC1] |

TABLE 2-continued

| Compound No. | The compounds' names | Structure of the compounds |
| --- | --- | --- |
| | (E)-N-(4-((3-chloro-4-fluorophenyl)amino)-7-methoxyquinazolin-6-yl)-4-(4-(4-(2-(2-((2-(2,6-dioxopiperidin-3-yl)-1,3-dioxoisoindolin-4-yl)thio)ethoxy)acetyl)piperazin-1-yl)piperidin-1-yl)but-2-enamide | 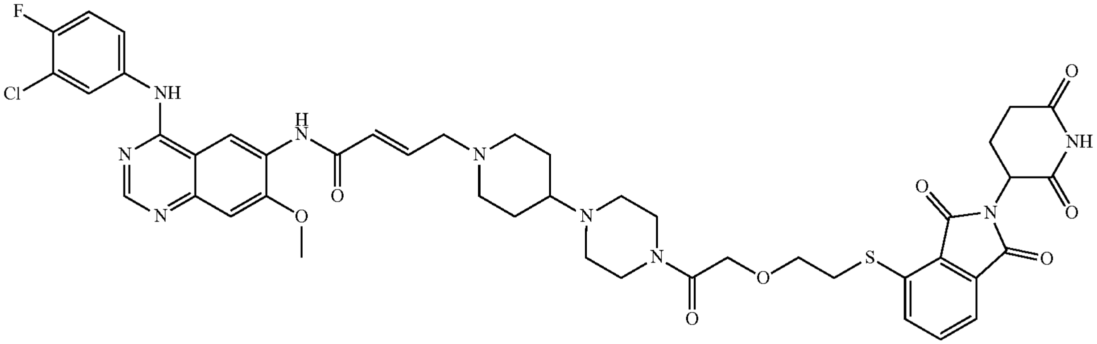 |
| | (E)-N-(4-((3-chloro-4-fluorophenyl)amino)-7-methoxyquinazolin-6-yl)-4-(4-(4-(2-(2-(2-((2-(2,6-dioxopiperidin-3-yl)-1,3-dioxoisoindolin-4-yl)thio)ethoxy)ethoxy)acetyl)piperazin-1-yl)piperidin-1-yl)but-2-enamide | 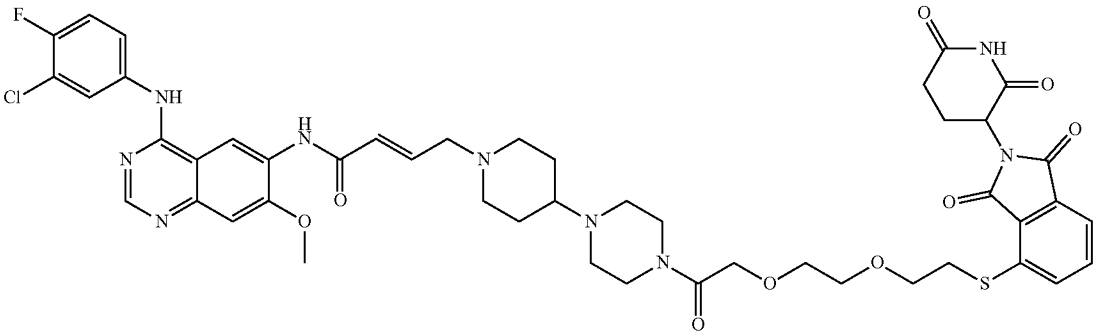 [SMILES: COc1cc2ncnc(Nc3ccc(F)c(Cl)c3)c2cc1NC(=O)/C=C/CN1CCC(N2CCN(C(=O)COCCOCCSc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)piperidin-1-yl)but-2-enamide | 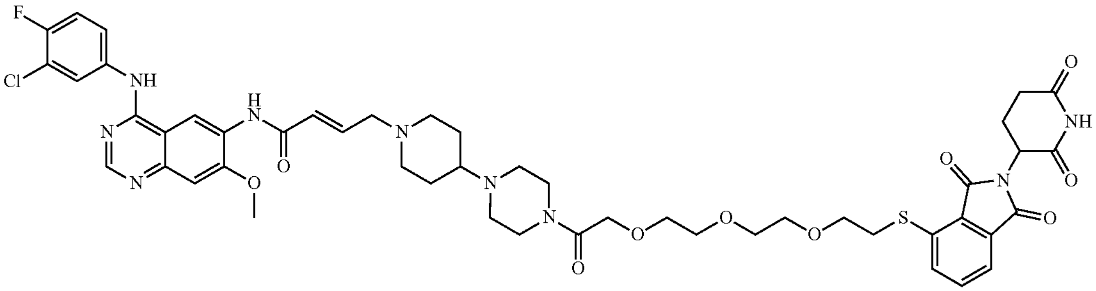 [SMILES: COc1cc2ncnc(Nc3ccc(F)c(Cl)c3)c2cc1NC(=O)/C=C/CN1CCC(N2CCN(C(=O)COCCOCCOCCSc3cccc4c3C(=O)N(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(14-((2-(2,6-dioxopiperidin-3-yl)-1,3-dioxoisoindolin-4-yl)thio)-3,6,9,12-tetraoxatetradecan-1-oyl)piperazin-1-yl)piperidin-1-yl)but-2-enamide | 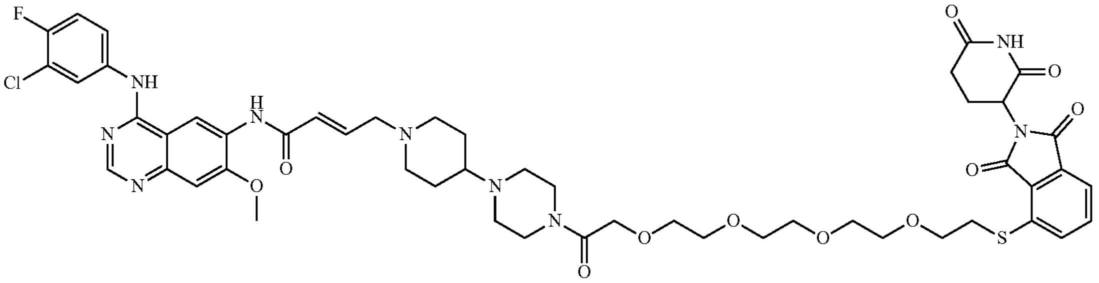 [SMILES: COc1cc2ncnc(Nc3ccc(F)c(Cl)c3)c2cc1NC(=O)/C=C/CN1CCC(N2CCN(C(=O)COCCOCCOCCOCCSc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(17-((2-(2,6-dioxopiperidin-3-yl)-1,3-dioxoisoindolin-4-yl)thio)-3,6,9,12,15-pentaoxaheptadecan-1-oyl)piperazin-1-yl)piperidin-1-yl)but-2-enamide | 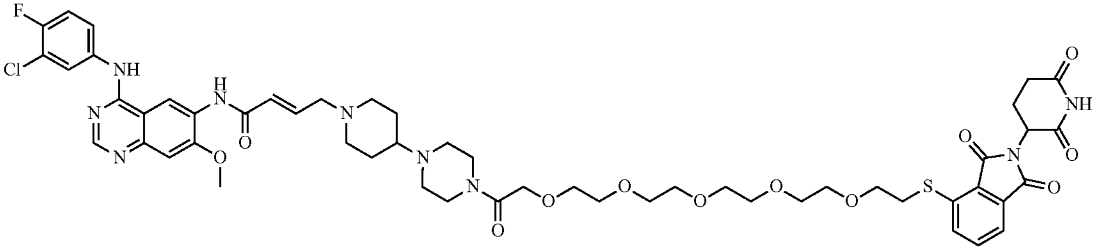 [SMILES: COc1cc2ncnc(Nc3ccc(F)c(Cl)c3)c2cc1NC(=O)/C=C/CN1CCC(N2CCN(C(=O)COCCOCCOCCOCCOCCSc3cccc4c3C(=O)N(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(3-((2-(2,6-dioxopiperidin-3-yl)-1-oxoisoindolin-4-yl)thio)propanoyl)piperazin-1-yl)piperidin-1-yl)but-2-enamide | 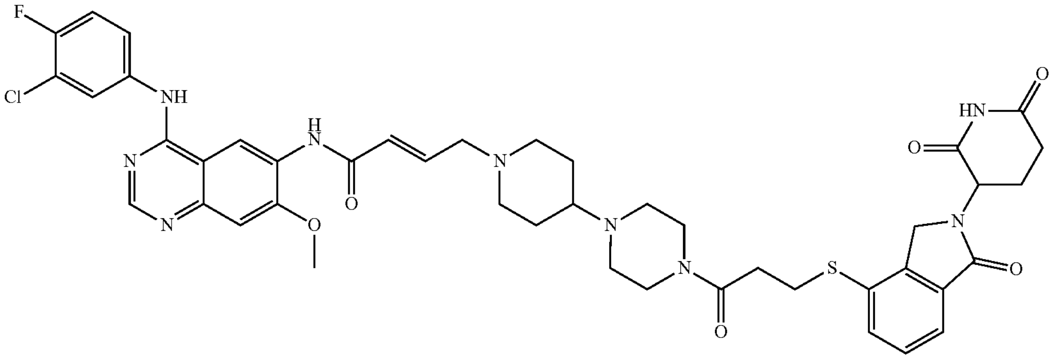 [SMILES: COc1cc2ncnc(Nc3ccc(F)c(Cl)c3)c2cc1NC(=O)/C=C/CN1CCC(N2CCN(C(=O)CCSc3cccc4c3CN(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(4-((2-(2,6-dioxopiperidin-3-yl)-1-oxoisoindolin-4-yl)thio)butanoyl)piperazin-1-yl)piperidin-1-yl)but-2-enamide | 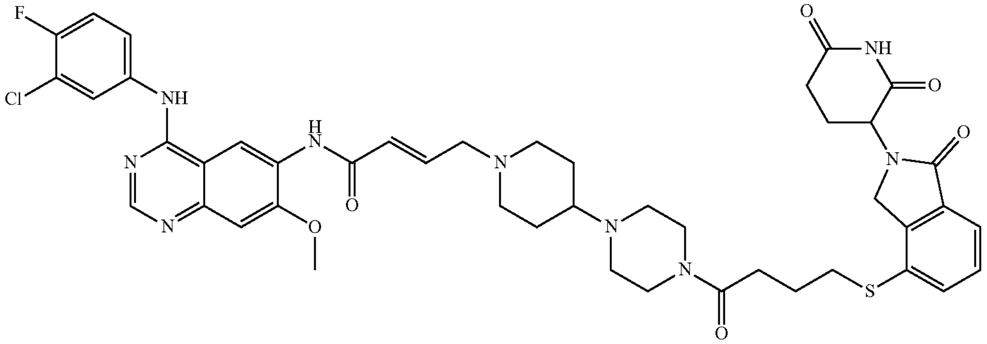 [SMILES: COc1cc2ncnc(Nc3ccc(F)c(Cl)c3)c2cc1NC(=O)/C=C/CN1CCC(N2CCN(C(=O)CCCSc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(5-((2-(2,6-dioxopiperidin-3-yl)-1-oxoisoindolin-4-yl)thio)pentanoyl)piperazin-1-yl)piperidin-1-yl)but-2-enamide | 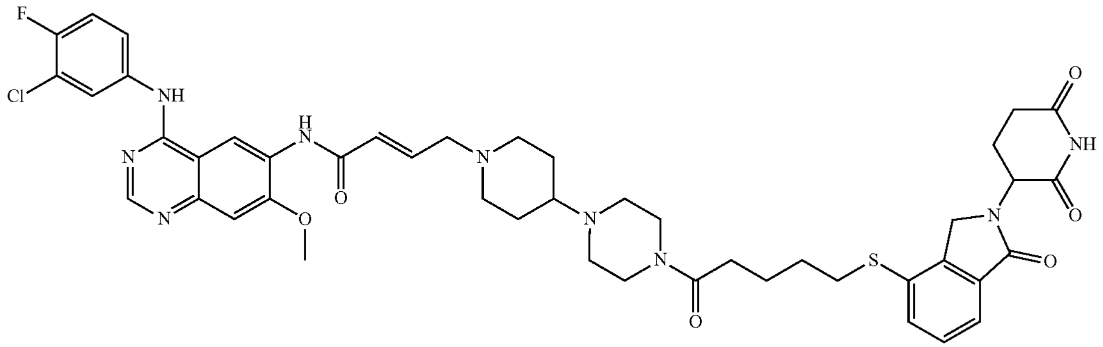 [SMILES: COc1cc2ncnc(Nc3ccc(F)c(Cl)c3)c2cc1NC(=O)/C=C/CN1CCC(N2CCN(C(=O)CCCCSc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(7-((2-(2,6-dioxopiperidin-3-yl)-1-oxoisoindolin-4-yl)thio)heptanoyl)piperazin-1-yl)piperidin-1-yl)but-2-enamide | 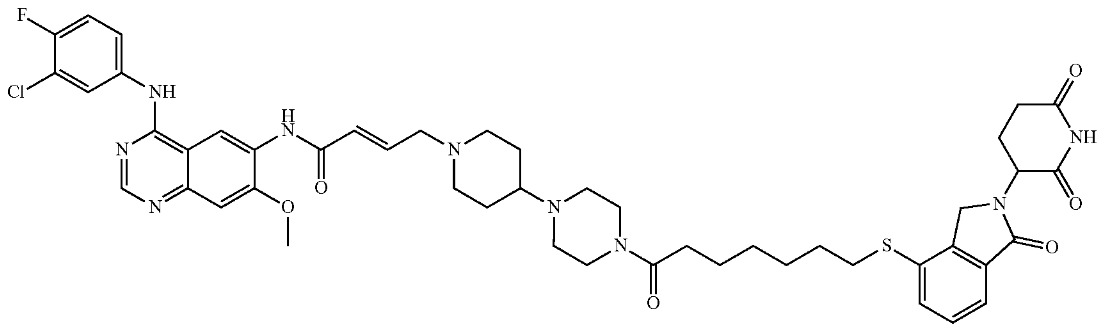 [SMILES: COc1cc2ncnc(Nc3ccc(F)c(Cl)c3)c2cc1NC(=O)/C=C/CN1CCC(N2CCN(C(=O)CCCCCCSc3cccc4c3CN(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(2-(2-((2-(2,6-dioxopiperidin-3-yl)-1-oxoisoindolin-4-yl)thio)ethoxy)acetyl)piperazin-1-yl)piperidin-1-yl)but-2-enamide | 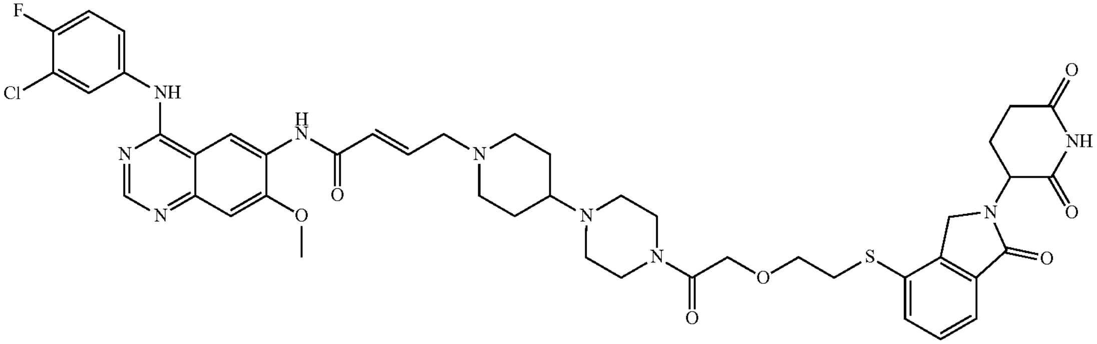 |
| | (E)-N-(4-((3-chloro-4-fluorophenyl)amino)-7-methoxyquinazolin-6-yl)-4-(4-(4-(2-(2-(2-((2-(2,6-dioxopiperidin-3-yl)-1-oxoisoindolin-4-yl)thio)ethoxy)ethoxy)acetyl)piperazin-1-yl)piperidin-1-yl)but-2-enamide | 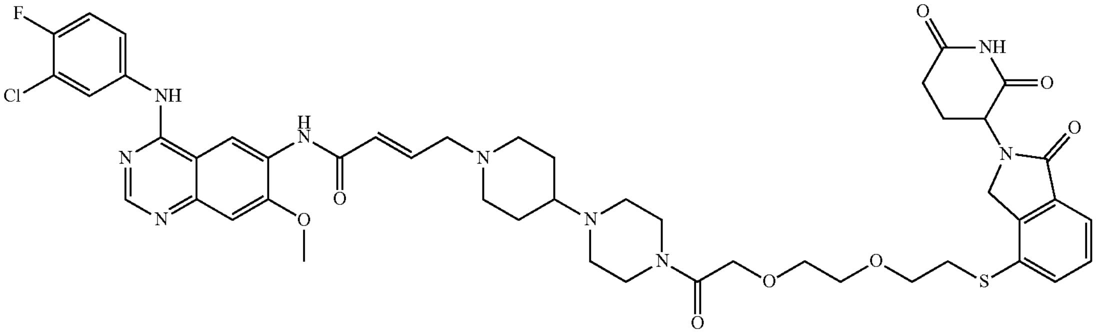 [SMILES: COc1cc2ncnc(Nc3ccc(F)c(Cl)c3)c2cc1NC(=O)/C=C/CN1CCC(N2CCN(C(=O)COCCOCCSc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)piperidin-1-yl)but-2-enamide | 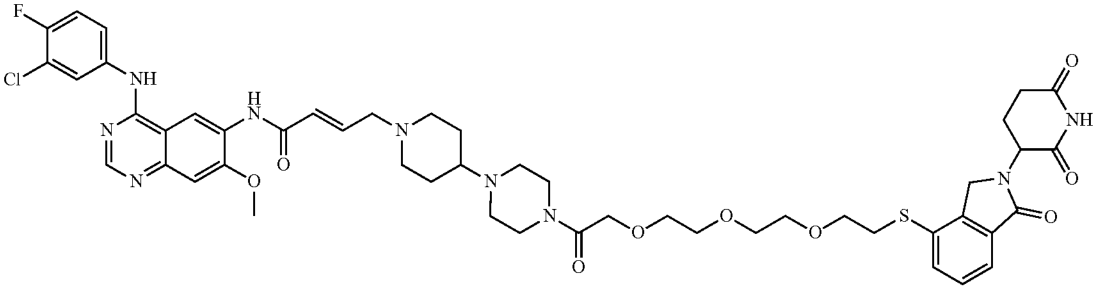 [SMILES: COc1cc2ncnc(Nc3ccc(F)c(Cl)c3)c2cc1NC(=O)/C=C/CN1CCC(N2CCN(C(=O)COCCOCCOCCSc3cccc4c3CN(C3CCC(=O)NC3=O)C4=O)CC2)CC1] |

TABLE 2-continued

| Compound No. | The compounds' names | Structure of the compounds |
|---|---|---|
| | (E)-N-(4-((3-chloro-4-fluorophenyl)amino)-7-methoxyquinazolin-6-yl)-4-(4-(4-(14-((2-(2,6-dioxopiperidin-3-yl)-1-oxoisoindolin-4-yl)thio)-3,6,9,12-tetraoxatetradecan-1-oyl)piperazin-1-yl)piperidin-1-yl)but-2-enamide | 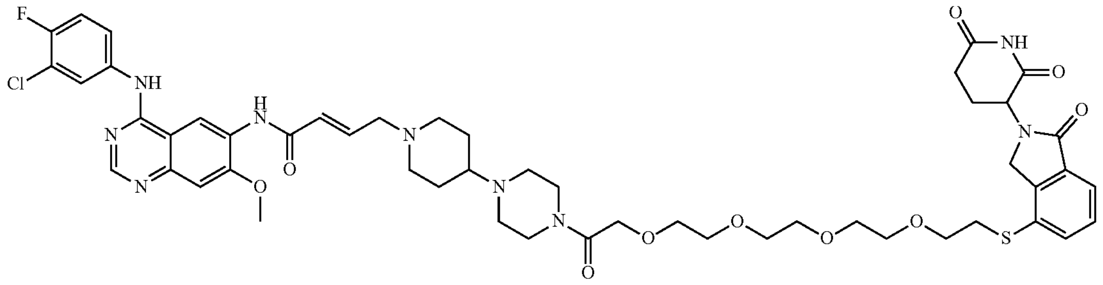 [SMILES: COc1cc2ncnc(Nc3ccc(F)c(Cl)c3)c2cc1NC(=O)/C=C/CN1CCC(N2CCN(C(=O)COCCOCCOCCOCCSc3cccc4c3CN(C3CCC(=O)NC3=O)C4=O)CC2)CC1] |
| | (E)-N-(4-((3-chloro-4-fluorophenyl)amino)-7-methoxyquinazolin-6-yl)-4-(4-(4-(17-((2-(2,6-dioxopiperidin-3-yl)-1-oxoisoindolin-4-yl)thio)-3,6,9,12,15-pentaoxaheptadecan-1-o yl)piperazin-1-yl)piperidin-1-yl)but-2-enamide | 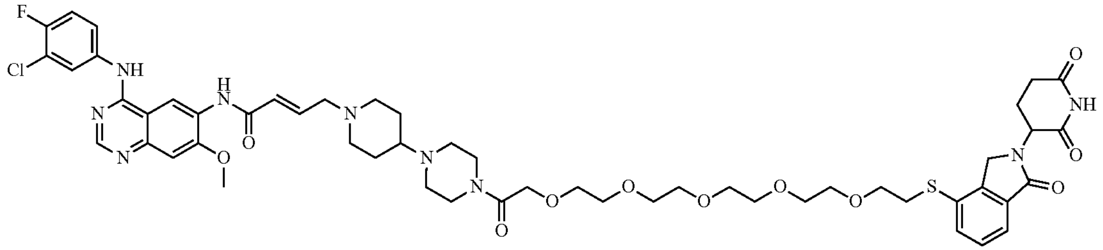 [SMILES: COc1cc2ncnc(Nc3ccc(F)c(Cl)c3)c2cc1NC(=O)/C=C/CN1CCC(N2CCN(C(=O)COCCOCCOCCOCCOCCSc3cccc4c3CN(C3CCC(=O)NC3=O)C4=O)CC2)CC1] |
| | (2S,4R)-1-((S)-2-(2-(2-(2-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide | 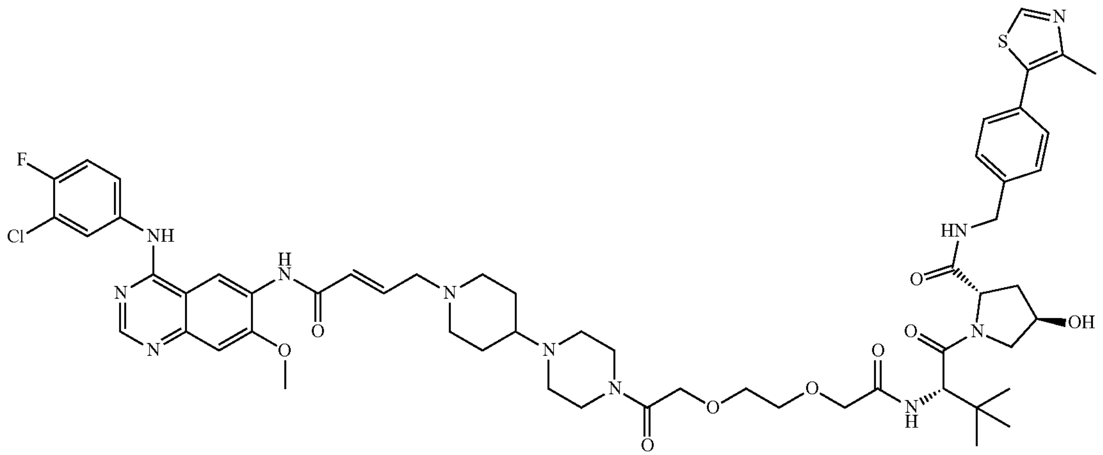 |

TABLE 2-continued

| Compound No. | The compounds' names | Structure of the compounds |
|---|---|---|
| | (2S,4R)-1-((S)-2-(tert-butyl)-19-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-4,19-dioxo-7,10,13,16-tetraoxa-3-azanonadecan-1-oyl)-4-hydroxy-N-(4-(4-methylthiazol-5-yl)benzyl)pyrrolidine-2-carboxamide | 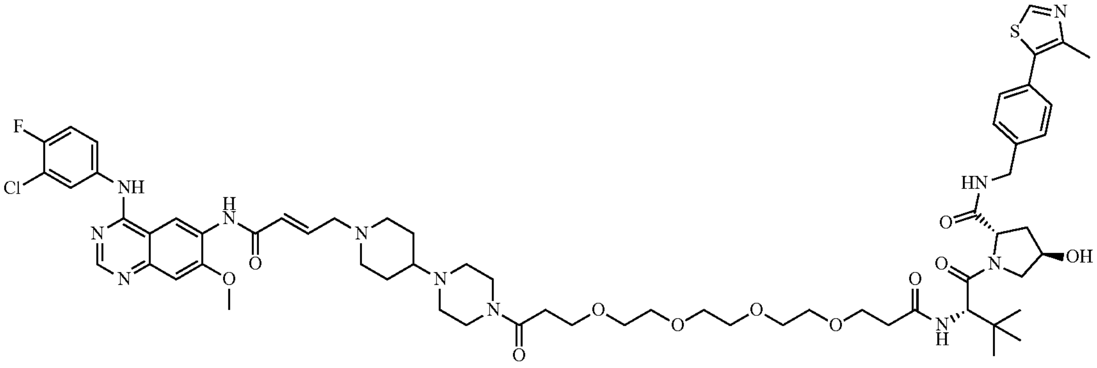 [SMILES: COc1cc2ncnc(Nc3ccc(F)c(Cl)c3)c2cc1NC(=O)/C=C/CN1CCC(N2CCN(C(=O)CCOCCOCCOCCOCCC(=O)N[C@H](C(=O)N3C[C@H](O)C[C@H]3C(=O)NCc3ccc(-c4scnc4C)cc3)C(C)(C)C)CC2)CC1] |
| | (2S,4R)-1-((S)-2-(4-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide | 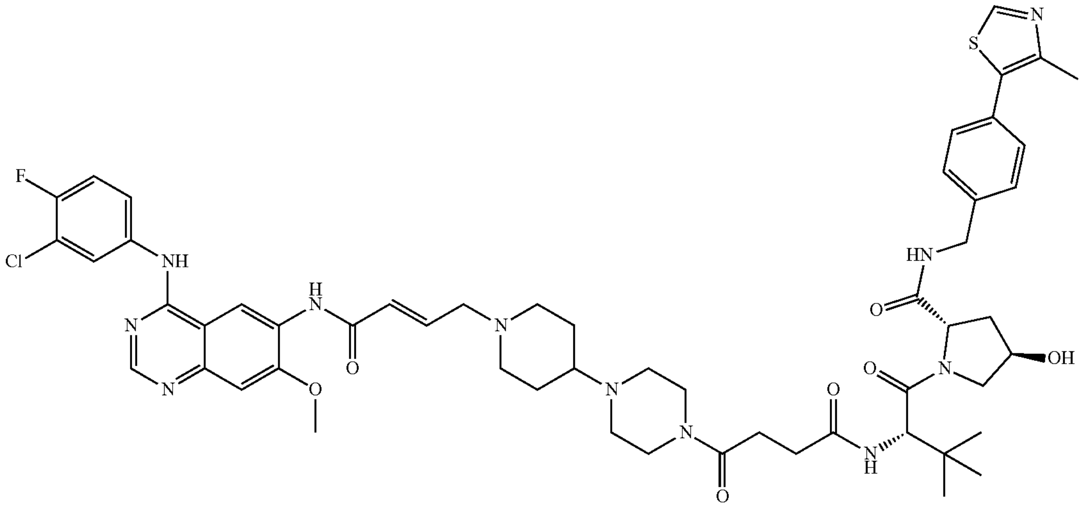 [SMILES: COc1cc2ncnc(Nc3ccc(F)c(Cl)c3)c2cc1NC(=O)/C=C/CN1CCC(N2CCN(C(=O)CCC(=O)N[C@H](C(=O)N3C[C@H](O)C[C@H]3C(=O)NCc3ccc(-c4scnc4C)cc3)C(C)(C)C)CC2)CC1] |

TABLE 2-continued

| Compound No. | The compounds' names | Structure of the compounds |
|---|---|---|
| | (2S,4R)-1-((S)-2-(6-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide | 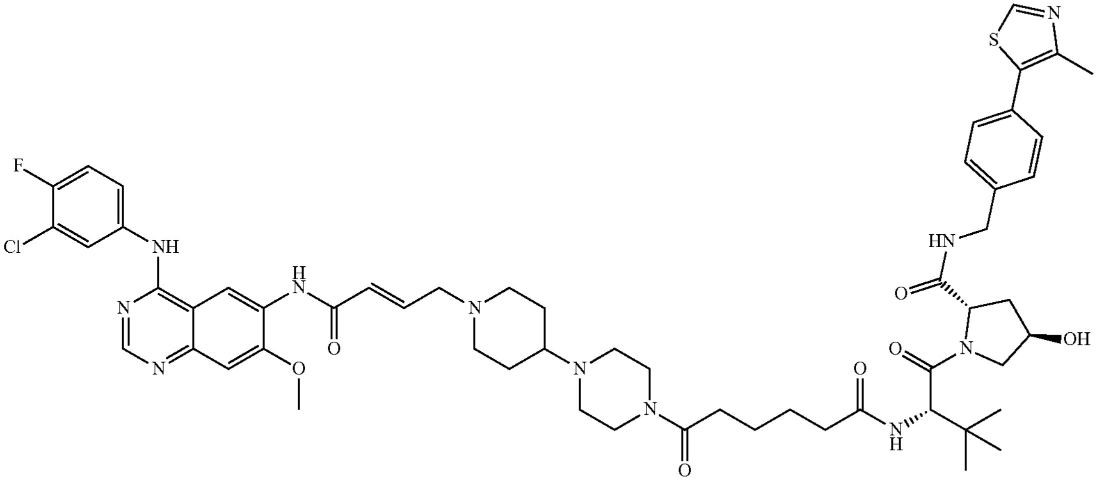 [SMILES: COc1cc2ncnc(Nc3ccc(F)c(Cl)c3)c2cc1NC(=O)/C=C/CN1CCC(N2CCN(C(=O)CCCCC(=O)N[C@H](C(=O)N3C[C@H](O)C[C@H]3C(=O)NCc3ccc(-c4scnc4C)cc3)C(C)(C)C)CC2)CC1] |
| | (2S,4R)-1-((S)-2-(8-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide | 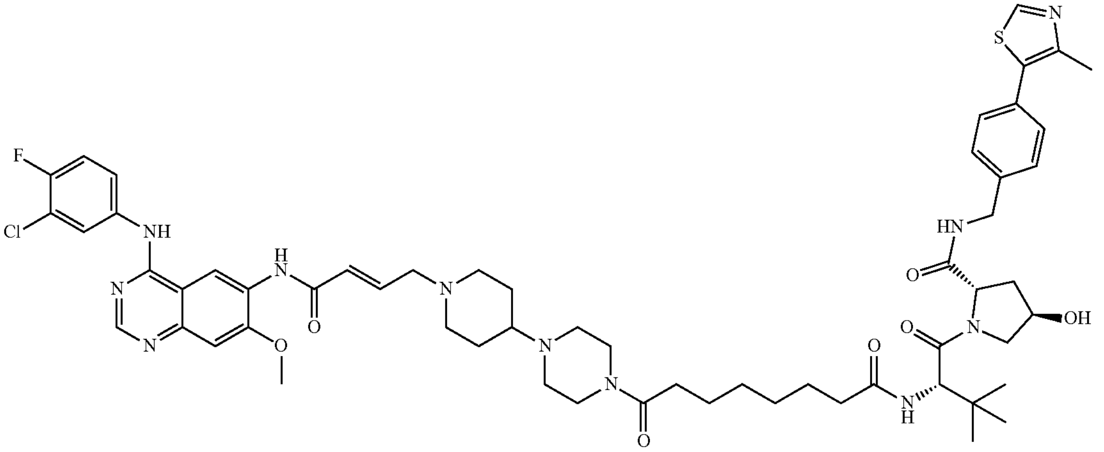 [SMILES: COc1cc2ncnc(Nc3ccc(F)c(Cl)c3)c2cc1NC(=O)/C=C/CN1CCC(N2CCN(C(=O)CCCCCCC(=O)N[C@H](C(=O)N3C[C@H](O)C[C@H]3C(=O)NCc3ccc(-c4scnc4C)cc3)C(C)(C)C)CC2)CC1] |

TABLE 2-continued

| Compound No. | The compounds' names | Structure of the compounds |
|---|---|---|
| | (2S,4R)-1-((S)-2-(10-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide | 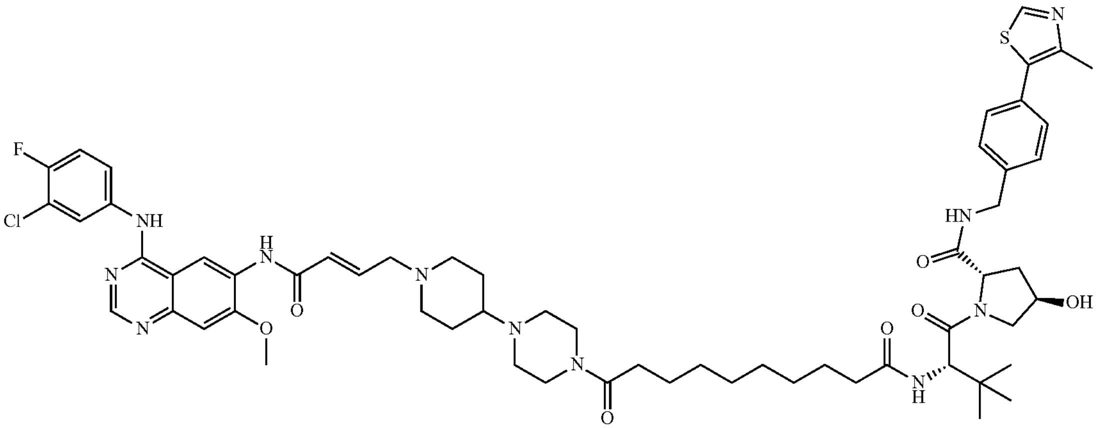 [SMILES: COc1cc2ncnc(Nc3ccc(F)c(Cl)c3)c2cc1NC(=O)/C=C/CN1CCC(N2CCN(C(=O)CCCCCCCCC(=O)N[C@H](C(=O)N3C[C@H](O)C[C@H]3C(=O)NCc3ccc(-c4scnc4C)cc3)C(C)(C)C)CC2)CC1] |
| | N-(4-((3-chloro-4-fluorophenyl)amino)-7-(3-(4-(3-((2-(2,6-dioxopiperidin-3-yl)-1,3-dioxoisoindolin-4-yl)amino)propanoyl)piperazin-1-yl)propoxy)quinazolin-6-yl)acrylamide | 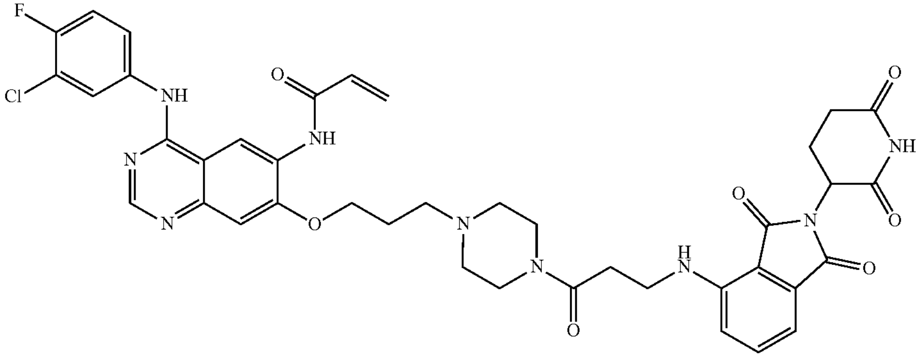 [SMILES: C=CC(=O)Nc1cc2c(Nc3ccc(F)c(Cl)c3)ncnc2cc1OCCCN1CCN(C(=O)CCNc2cccc3c2C(=O)N(C2CCC(=O)NC2=O)C3=O)CC1] |

TABLE 2-continued

| Compound No. | The compounds' names | Structure of the compounds |
|---|---|---|
| | N-(4-((3-chloro-4-fluorophenyl)amino)-7-(3-(4-(4-((2-(2,6-dioxopiperidin-3-yl)-1,3-dioxoisoindolin-4-yl)amino)butanoyl)piperazin-1-yl)propoxy)quinazolin-6-yl)acrylamide | 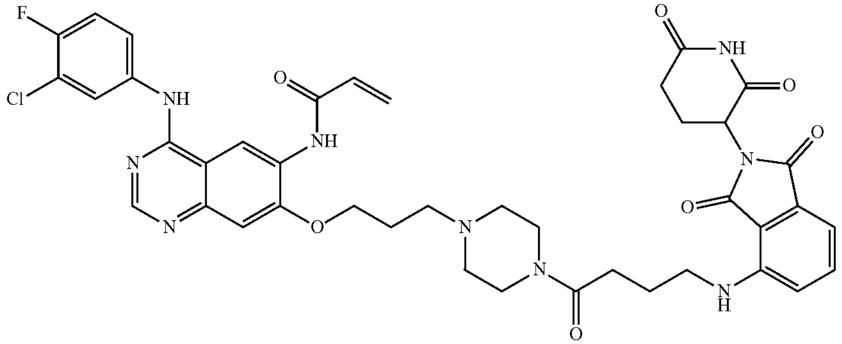 [SMILES: C=CC(=O)Nc1cc2c(Nc3ccc(F)c(Cl)c3)ncnc2cc1OCCCN1CCN(C(=O)CCCNc2cccc3c2C(=O)N(C2CCC(=O)NC2=O)C3=O)CC1] |
| | N-(4-((3-chloro-4-fluorophenyl)amino)-7-(3-(4-(5-((2-(2,6-dioxopiperidin-3-yl)-1,3-dioxoisoindolin-4-yl)amino)pentanoyl)piperazin-1-yl)propoxy)quinazolin-6-yl)acrylamide | 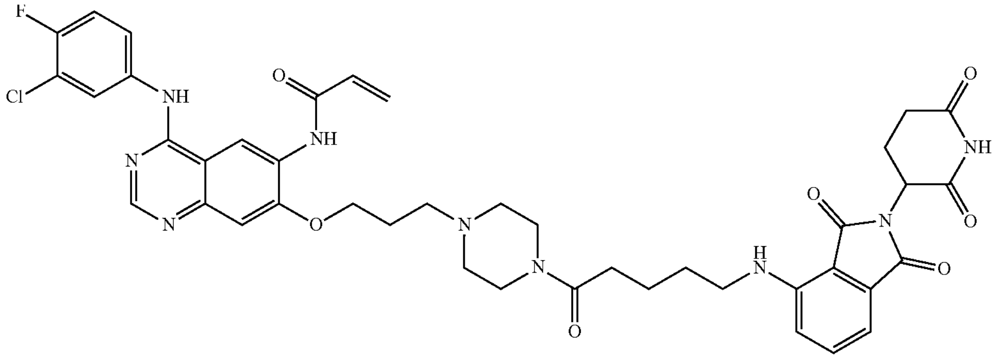 |
| | N-(4-((3-chloro-4-fluorophenyl)amino)-7-(3-(4-(2-((2-(2,6-dioxopiperidin-3-yl)-1,3-dioxoisoindolin-4-yl)amino)ethyl)piperazin-1-yl)propoxy)quinazolin-6-yl)acrylamide | 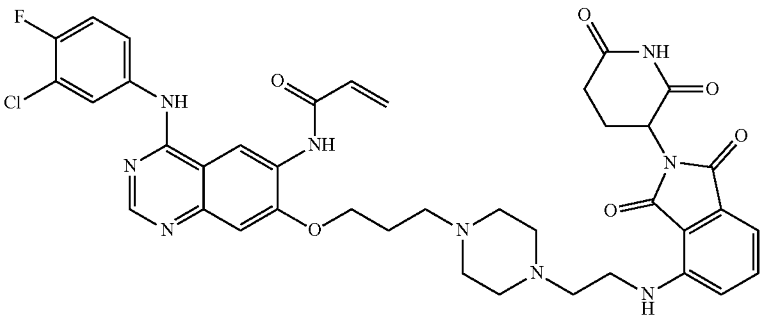 [SMILES: C=CC(=O)Nc1cc2c(Nc3ccc(F)c(Cl)c3)ncnc2cc1OCCCN1CCN(CCNc2cccc3c2C(=O)N(C2CCC(=O)NC2=O)C3=O)CC1] |

TABLE 2-continued
| Compound No. | The compounds' names | Structure of the compounds |
|---|---|---|
| | N-(4-((3-chloro-4-fluorophenyl)amino)-7-(3-(4-(3-((2-(2,6-dioxopiperidin-3-yl)-1,3-dioxoisoindolin-4-yl)amino)propyl)piperazin-1-yl)propoxy)quinazolin-6-yl)acrylamide | 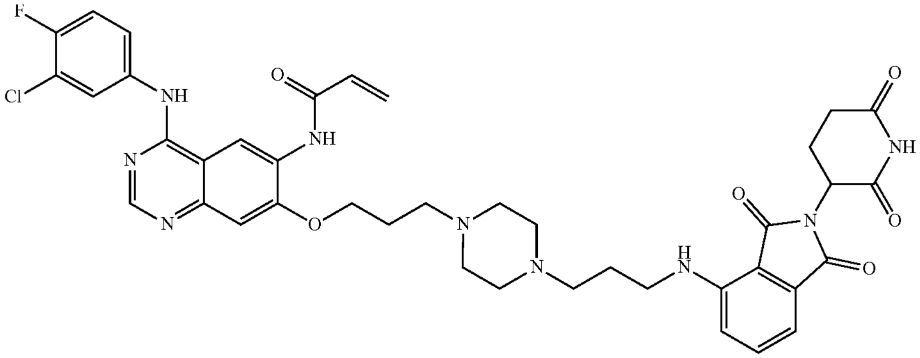 [SMILES: C=CC(=O)Nc1cc2c(Nc3ccc(F)c(Cl)c3)ncnc2cc1OCCCN1CCN(CCCNc2cccc3c2C(=O)N(C2CCC(=O)NC2=O)C3=O)CC1] |
| | N-(4-((3-chloro-4-fluorophenyl)amino)-7-(3-(4-(4-((2-(2,6-dioxopiperidin-3-yl)-1,3-dioxoisoindolin-4-yl)amino)butyl)piperazin-1-yl)propoxy)quinazolin-6-yl)acrylamide | 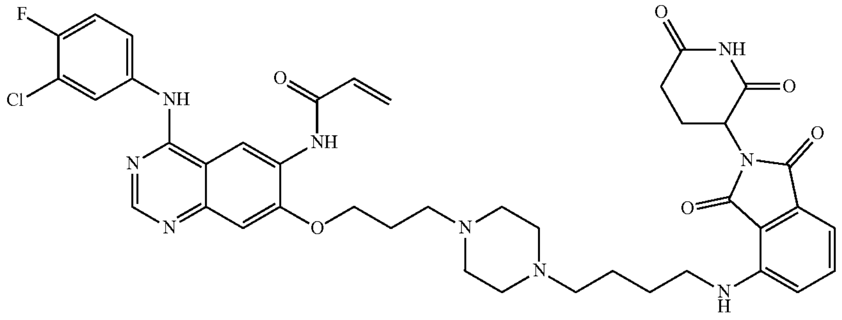 [SMILES: C=CC(=O)Nc1cc2c(Nc3ccc(F)c(Cl)c3)ncnc2cc1OCCCN1CCN(CCCCNc2cccc3c2C(=O)N(C2CCC(=O)NC2=O)C3=O)CC1] |

TABLE 2-continued
| Compound No. | The compounds' names | Structure of the compounds |
| --- | --- | --- |
| | N-(4-((3-chloro-4-fluorophenyl)amino)-7-(3-(4-(5-((2-(2,6-dioxopiperidin-3-yl)-1,3-dioxoisoindolin-4-yl)amino)pentyl)piperazin-1-yl)propoxy)quinazolin-6-yl)acrylamide | 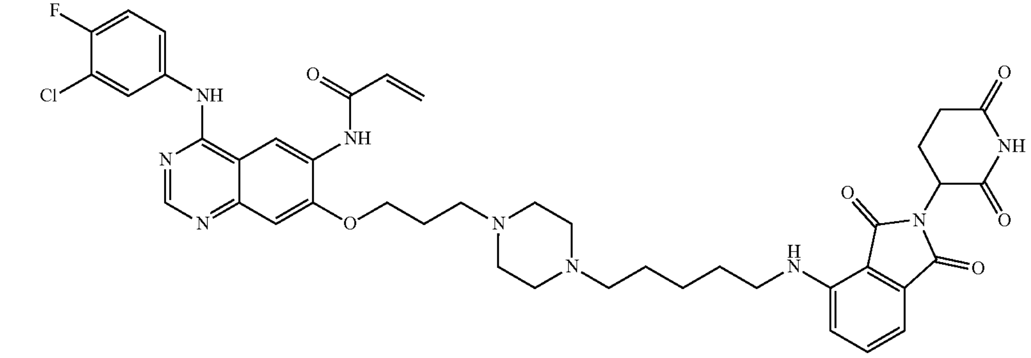 [SMILES: C=CC(=O)Nc1cc2c(Nc3ccc(F)c(Cl)c3)ncnc2cc1OCCCN1CCN(CCCCCNc2cccc3c2C(=O)N(C2CCC(=O)NC2=O)C3=O)CC1] |
| | N-(4-((3-chloro-4-fluorophenyl)amino)-7-(3-(4-(7-((2-(2,6-dioxopiperidin-3-yl)-1,3-dioxoisoindolin-4-yl)amino)heptyl)piperazin-1-yl)propoxy)quinazolin-6-yl)acrylamide | 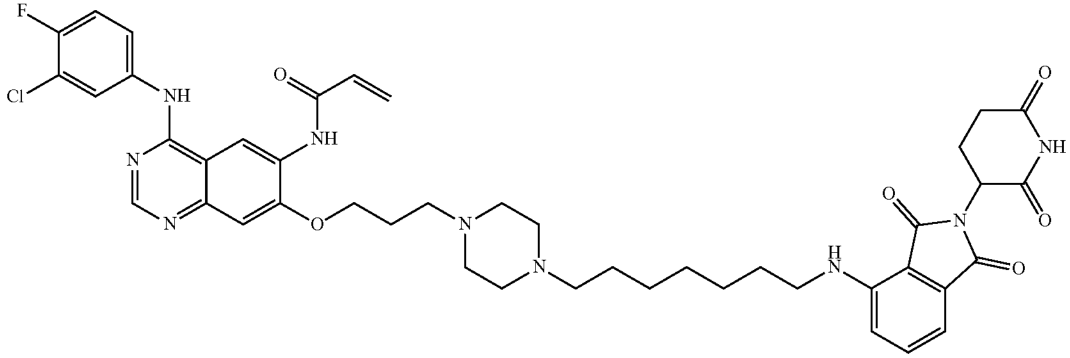 [SMILES: C=CC(=O)Nc1cc2c(Nc3ccc(F)c(Cl)c3)ncnc2cc1OCCCN1CCN(CCCCCCCNc2cccc3c2C(=O)N(C2CCC(=O)NC2=O)C3=O)CC1] |

TABLE 2-continued

| Compound No. | The compounds' names | Structure of the compounds |
| --- | --- | --- |
| | N-(4-((3-chloro-4-fluorophenyl)amino)-7-(3-(4-(3-(2-((2-(2,6-dioxopiperidin-3-yl)-1,3-dioxoisoindolin-4-yl)amino)ethoxy)propanoyl)piperazin-1-yl)propoxy)quinazolin-6-yl)acrylamide | 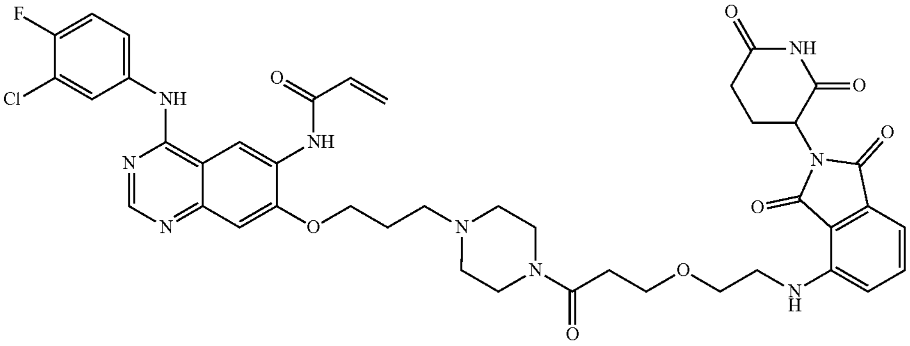 [SMILES: C=CC(=O)Nc1cc2c(Nc3ccc(F)c(Cl)c3)ncnc2cc1OCCCN1CCN(C(=O)CCOCCNc2cccc3c2C(=O)N(C2CCC(=O)NC2=O)C3=O)CC1] |
| | N-(4-((3-chloro-4-fluorophenyl)amino)-7-(3-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)propoxy)quinazolin-6-yl)acrylamide | 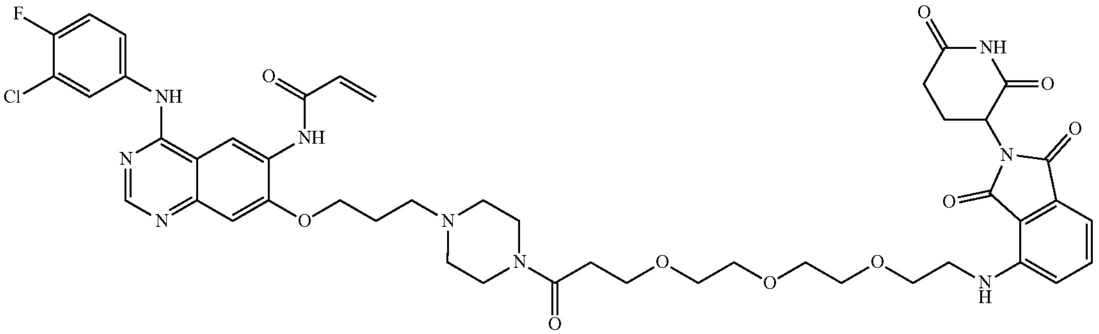 [SMILES: C=CC(=O)Nc1cc2c(Nc3ccc(F)c(Cl)c3)ncnc2cc1OCCCN1CCN(C(=O)CCOCCOCCOCCNc2cccc3c2C(=O)N(C2CCC(=O)NC2=O)C3=O)CC1] |
| | N-(4-((3-chloro-4-fluorophenyl)amino)-7-(3-(4-(1-((2-(2,6-dioxopiperidin-3-yl)-1,3-dioxoisoindolin-4-yl)amino)-3,6,9,12-tetraoxapentadecan-15-oyl)piperazin-1-yl)propoxy)quinazolin-6-yl)acrylamide | 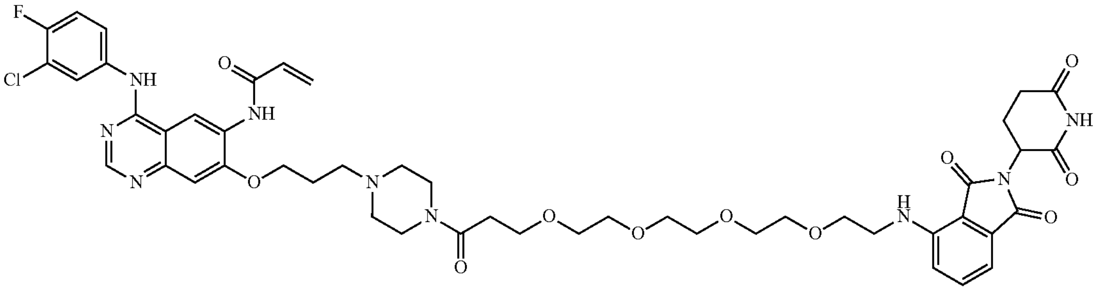 [SMILES: C=CC(=O)Nc1cc2c(Nc3ccc(F)c(Cl)c3)ncnc2cc1OCCCN1CCN(C(=O)CCOCCOCCOCCOCCNc2cccc3c2C(=O)N(C2CCC(=O)NC2=O)C3=O)CC1] |

TABLE 2-continued

| Compound No. | The compounds' names | Structure of the compounds |
|---|---|---|
| | N-(4-((3-chloro-4-fluorophenyl)amino)-7-(3-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)propoxy)quinazolin-6-yl)acrylamide | 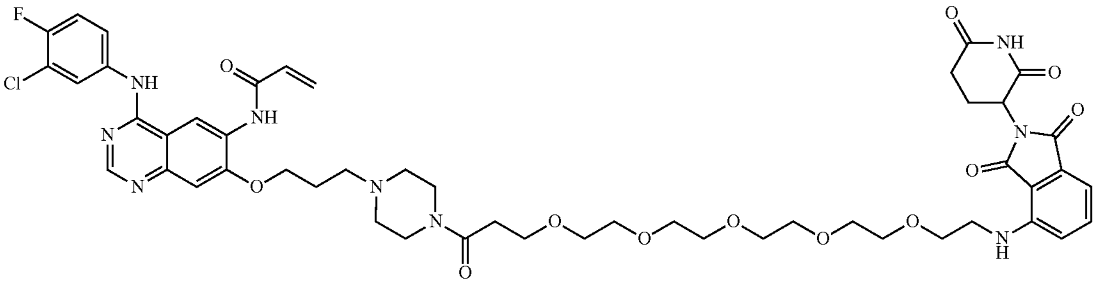 [SMILES: C=CC(=O)Nc1cc2c(Nc3ccc(F)c(Cl)c3)ncnc2cc1OCCCN1CCN(C(=O)CCOCCOCCOCCOCCOCCNc2cccc3c2C(=O)N(C2CCC(=O)NC2=O)C3=O)CC1] |
| | N-(4-((3-chloro-4-fluorophenyl)amino)-7-(3-(4-(2-((2-(2,6-dioxopiperidin-3-yl)-1-oxoisoindolin-4-yl)amino)ethyl)piperazin-1-yl)propoxy)quinazolin-6-yl)acrylamide | 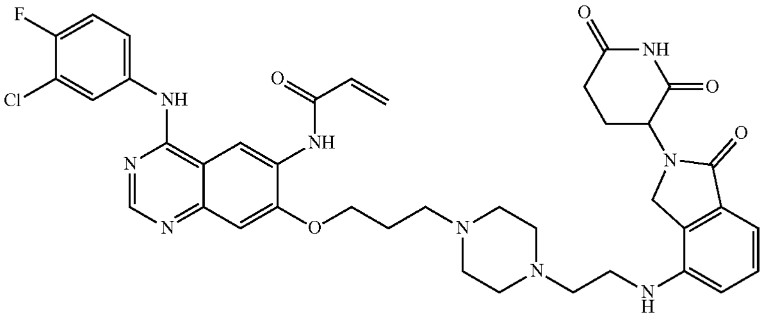 [SMILES: C=CC(=O)Nc1cc2c(Nc3ccc(F)c(Cl)c3)ncnc2cc1OCCCN1CCN(CCNc2cccc3c2CN(C2CCC(=O)NC2=O)C3=O)CC1] |
| | N-(4-((3-chloro-4-fluorophenyl)amino)-7-(3-(4-(3-((2-(2,6-dioxopiperidin-3-yl)-1-oxoisoindolin-4-yl)amino)propyl)piperazin-1-yl)propoxy)quinazolin-6-yl)acrylamide | 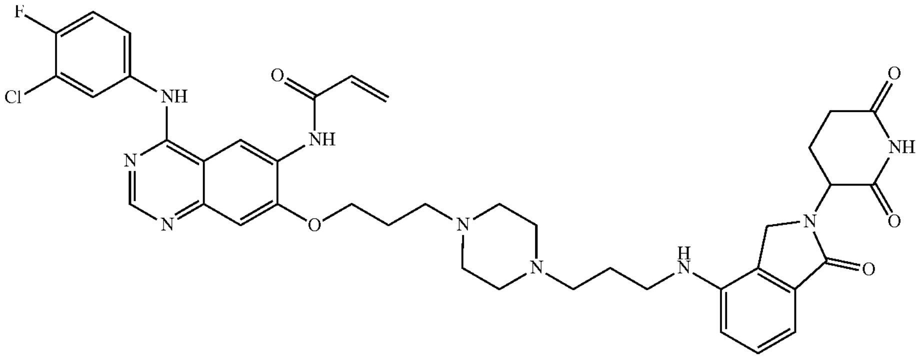 [SMILES: C=CC(=O)Nc1cc2c(Nc3ccc(F)c(Cl)c3)ncnc2cc1OCCCN1CCN(CCCNc2cccc3c2CN(C2CCC(=O)NC2=O)C3=O)CC1] |

TABLE 2-continued

| Compound No. | The compounds' names | Structure of the compounds |
|---|---|---|
| | N-(4-((3-chloro-4-fluorophenyl)amino)-7-(3-(4-(4-((2-(2,6-dioxopiperidin-3-yl)-1-oxoisoindolin-4-yl)amino)butyl)piperazin-1-yl)propoxy)quinazolin-6-yl)acrylamide | 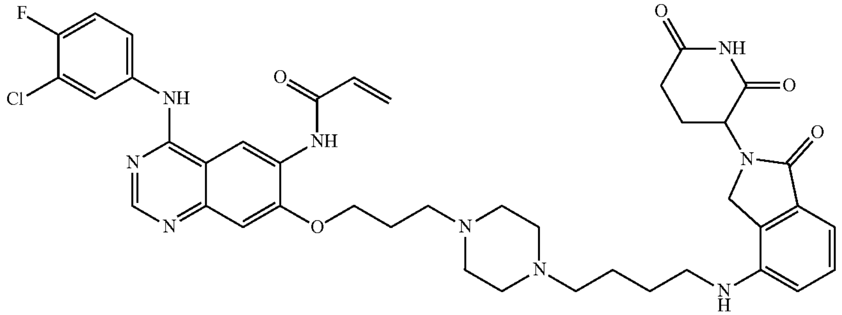 [SMILES: C=CC(=O)Nc1cc2c(Nc3ccc(F)c(Cl)c3)ncnc2cc1OCCCN1CCN(CCCCNc2cccc3c2CN(C2CCC(=O)NC2=O)C3=O)CC1] |
| | N-(4-((3-chloro-4-fluorophenyl)amino)-7-(3-(4-(5-((2-(2,6-dioxopiperidin-3-yl)-1-oxoisoindolin-4-yl)amino)pentyl)piperazin-1-yl)propoxy)quinazolin-6-yl)acrylamide | 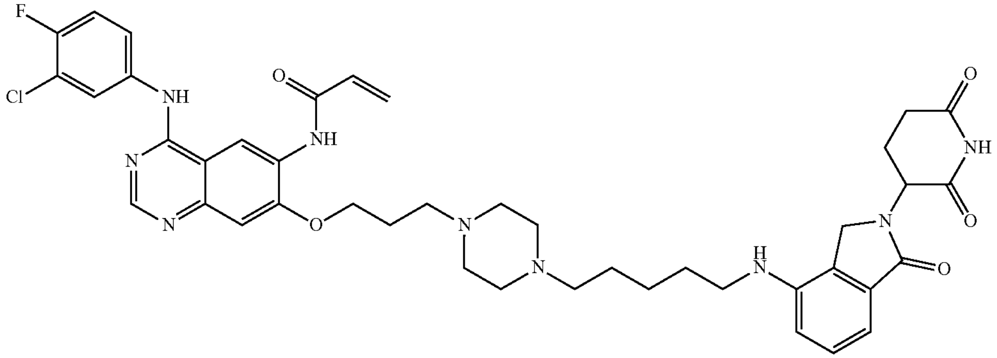 [SMILES: C=CC(=O)Nc1cc2c(Nc3ccc(F)c(Cl)c3)ncnc2cc1OCCCN1CCN(CCCCCNc2cccc3c2CN(C2CCC(=O)NC2=O)C3=O)CC1] |
| | N-(4-((3-chloro-4-fluorophenyl)amino)-7-(3-(4-(6-((2-(2,6-dioxopiperidin-3-yl)-1-oxoisoindolin-4-yl)amino)hexyl)piperazin-1-yl)propoxy)quinazolin-6-yl)acrylamide | 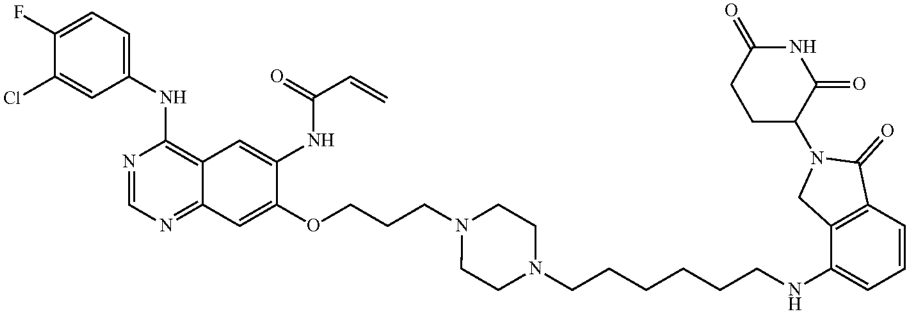 [SMILES: C=CC(=O)Nc1cc2c(Nc3ccc(F)c(Cl)c3)ncnc2cc1OCCCN1CCN(CCCCCCNc2cccc3c2CN(C2CCC(=O)NC2=O)C3=O)CC1] |

TABLE 2-continued
| Compound No. | The compounds' names | Structure of the compounds |
|---|---|---|
| | N-(4-((3-chloro-4-fluorophenyl)amino)-7-(3-(4-(7-((2-(2,6-dioxopiperidin-3-yl)-1-oxoisoindolin-4-yl)amino)heptyl)piperazin-1-yl)propoxy)quinazolin-6-yl)acrylamide | 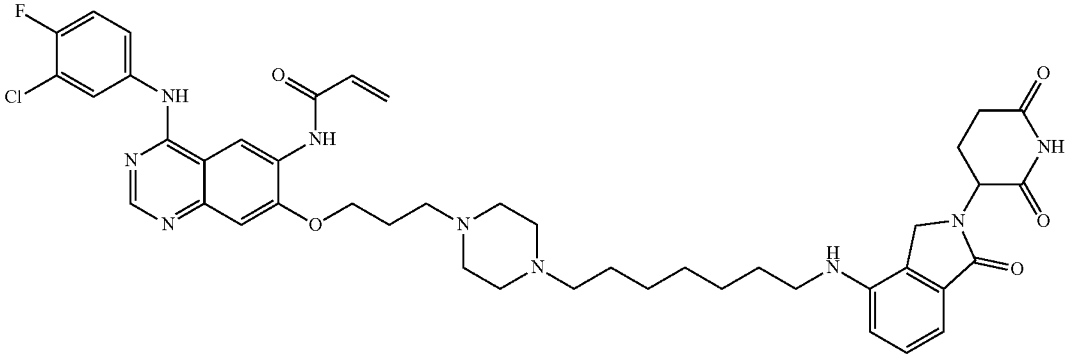 [SMILES: C=CC(=O)Nc1cc2c(Nc3ccc(F)c(Cl)c3)ncnc2cc1OCCCN1CCN(CCCCCCCNc2cccc3c2CN(C2CCC(=O)NC2=O)C3=O)CC1] |
| | N-(4-((3-chloro-4-fluorophenyl)amino)-7-(3-(4-(2-((2-(2,6-dioxopiperidin-3-yl)-1,3-dioxoisoindolin-4-yl)thio)acetyl)piperazin-1-yl)propoxy)quinazolin-6-yl)acrylamide | 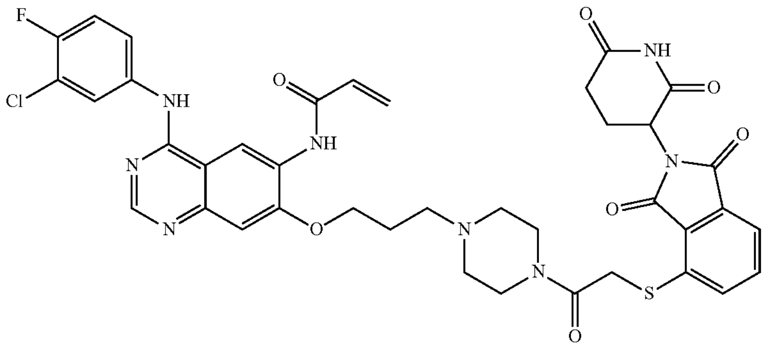 [SMILES: C=CC(=O)Nc1cc2c(Nc3ccc(F)c(Cl)c3)ncnc2cc1OCCCN1CCN(C(=O)CSc2cccc3c2C(=O)N(C2CCC(=O)NC2=O)C3=O)CC1] |

TABLE 2-continued
| Compound No. | The compounds' names | Structure of the compounds |
|---|---|---|
| | N-(4-((3-chloro-4-fluorophenyl)amino)-7-(3-(4-(3-((2-(2,6-dioxopiperidin-3-yl)-1,3-dioxoisoindolin-4-yl)thio)propanoyl)piperazin-1-yl)propoxy)quinazolin-6-yl)acrylamide | 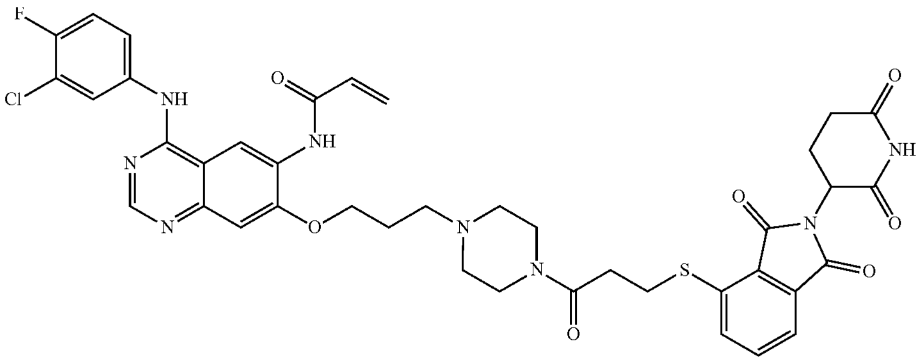 [SMILES: C=CC(=O)Nc1cc2c(Nc3ccc(F)c(Cl)c3)ncnc2cc1OCCCN1CCN(C(=O)CCSc2cccc3c2C(=O)N(C2CCC(=O)NC2=O)C3=O)CC1] |
| | N-(4-((3-chloro-4-fluorophenyl)amino)-7-(3-(4-(4-((2-(2,6-dioxopiperidin-3-yl)-1,3-dioxoisoindolin-4-yl)thio)butanoyl)piperazin-1-yl)propoxy)quinazolin-6-yl)acrylamide | 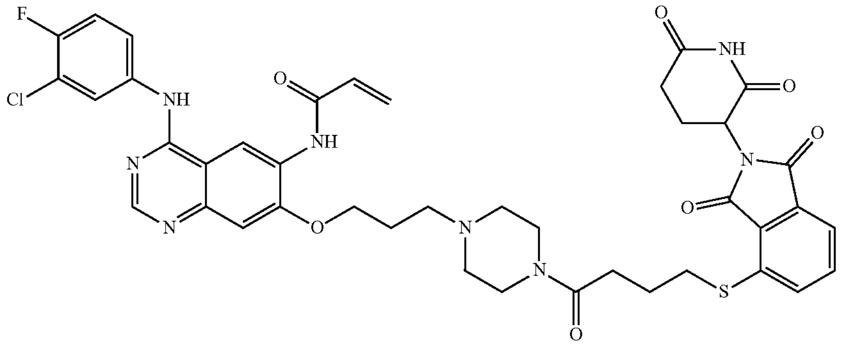 |

TABLE 2-continued
| Compound No. | The compounds' names | Structure of the compounds |
|---|---|---|
| | N-(4-((3-chloro-4-fluorophenyl)amino)-7-(3-(4-(5-((2-(2,6-dioxopiperidin-3-yl)-1,3-dioxoisoindolin-4-yl)thio)pentanoyl)piperazin-1-yl)propoxy)quinazolin-6-yl)acrylamide | 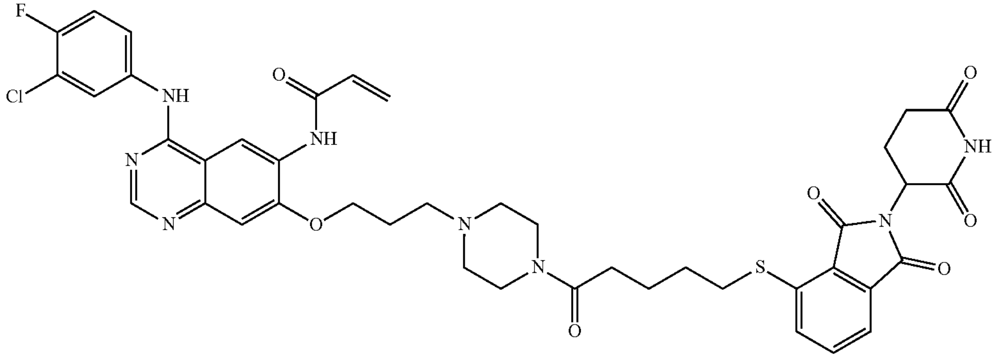 [SMILES: C=CC(=O)Nc1cc2c(Nc3ccc(F)c(Cl)c3)ncnc2cc1OCCCN1CCN(C(=O)CCCCSc2cccc3c2C(=O)N(C2CCC(=O)NC2=O)C3=O)CC1] |
| | N-(4-((3-chloro-4-fluorophenyl)amino)-7-(3-(4-(6-((2-(2,6-dioxopiperidin-3-yl)-1,3-dioxoisoindolin-4-yl)thio)hexanoyl)piperazin-1-yl)propoxy)quinazolin-6-yl)acrylamide | 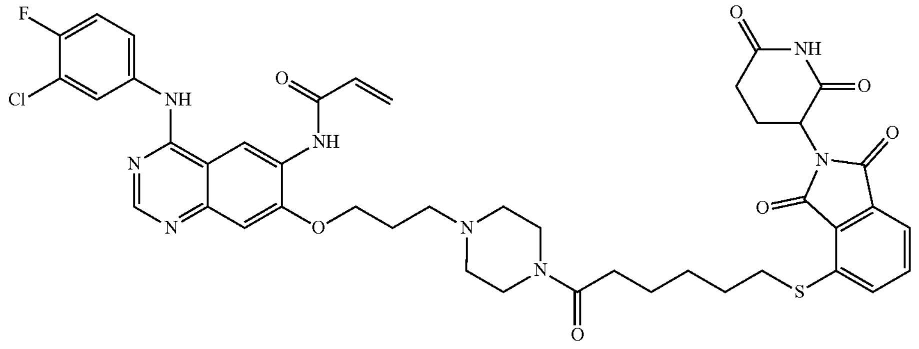 [SMILES: C=CC(=O)Nc1cc2c(Nc3ccc(F)c(Cl)c3)ncnc2cc1OCCCN1CCN(C(=O)CCCCCSc2cccc3c2C(=O)N(C2CCC(=O)NC2=O)C3=O)CC1] |

TABLE 2-continued
| Compound No. | The compounds' names | Structure of the compounds |
| --- | --- | --- |
| | N-(4-((3-chloro-4-fluorophenyl)amino)-7-(3-(4-(7-((2-(2,6-dioxopiperidin-3-yl)-1,3-dioxoisoindolin-4-yl)thio)heptanoyl)piperazin-1-yl)propoxy)quinazolin-6-yl)acrylamide | 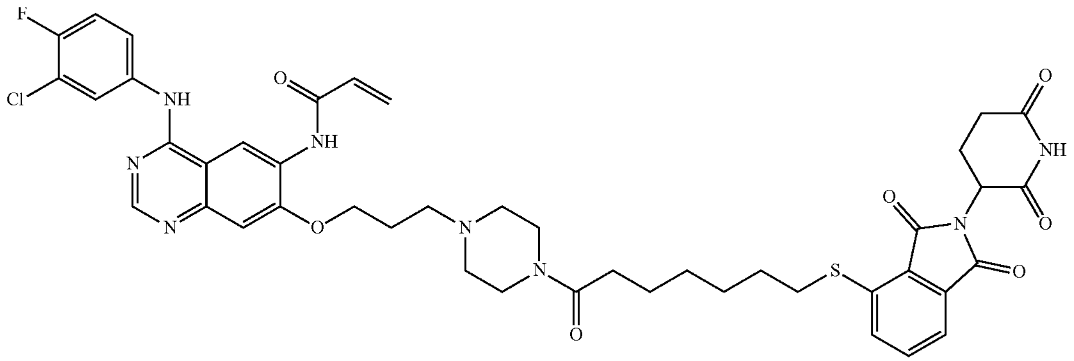 [SMILES: C=CC(=O)Nc1cc2c(Nc3ccc(F)c(Cl)c3)ncnc2cc1OCCCN1CCN(C(=O)CCCCCCSc2cccc3c2C(=O)N(C2CCC(=O)NC2=O)C3=O)CC1] |
| | N-(4-((3-chloro-4-fluorophenyl)amino)-7-(3-(4-(2-(2-((2-(2,6-dioxopiperidin-3-yl)-1-oxoisoindolin-4-yl)thio)ethoxy)acetyl)piperazin-1-yl)propoxy)quinazolin-6-yl)acrylamide | 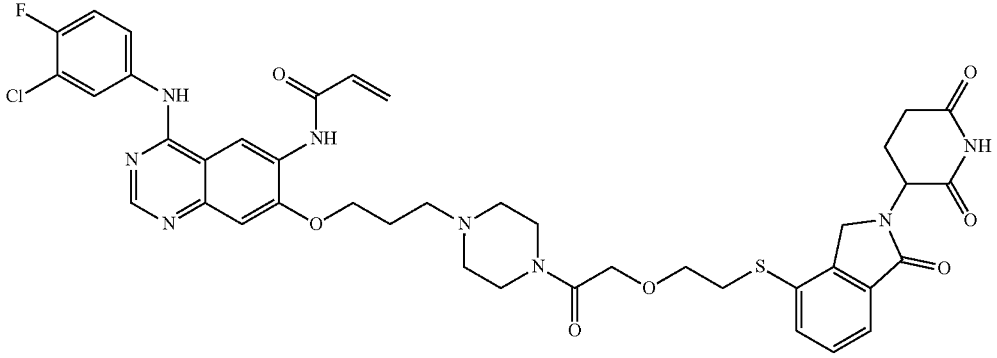 |

TABLE 2-continued

| Compound No. | The compounds' names | Structure of the compounds |
| --- | --- | --- |
| | N-(4-((3-chloro-4-fluorophenyl)amino)-7-(3-(4-(2-(2-(2-((2-(2,6-dioxopiperidin-3-yl)-1-oxoisoindolin-4-yl)thio)ethoxy)ethoxy)acetyl)piperazin-1-yl)propoxy)quinazolin-6-yl)acrylamide | 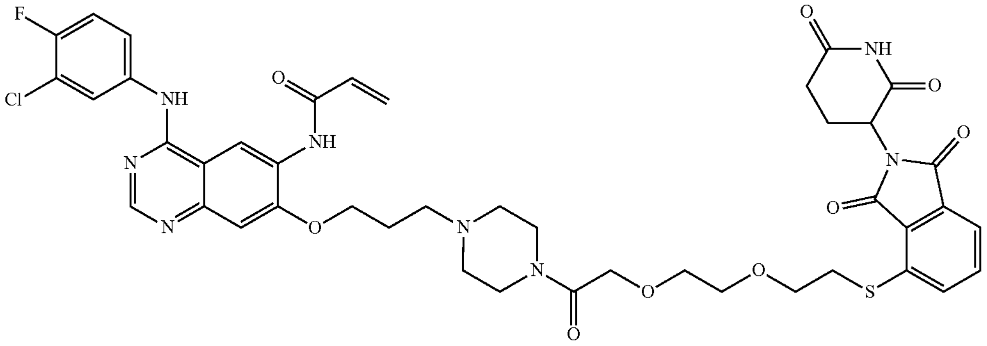 [SMILES: C=CC(=O)Nc1cc2c(Nc3ccc(F)c(Cl)c3)ncnc2cc1OCCCN1CCN(C(=O)COCCOCCSc2cccc3c2C(=O)N(C2CCC(=O)NC2=O)C3=O)CC1] |
| | (E)-N-(4-((3-chloro-4-fluorophenyl)amino)-7-methoxyquinazolin-6-yl)-4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)but-2-enamide | 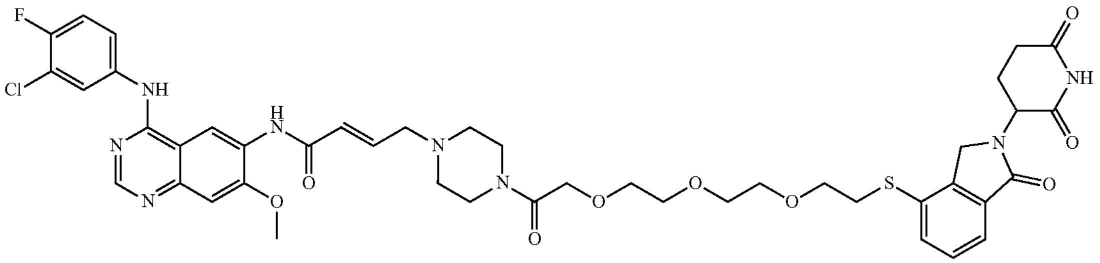 [SMILES: COc1cc2ncnc(Nc3ccc(F)c(Cl)c3)c2cc1NC(=O)/C=C/CN1CCN(C(=O)COCCOCCOCCSc2cccc3c2CN(C2CCC(=O)NC2=O)C3=O)CC1] |
| | (E)-N-(4-((3-chloro-4-fluorophenyl)amino)-7-methoxyquinazolin-6-yl)-4-(4-(14-((2-(2,6-dioxopiperidin-3-yl)-1-oxoisoindolin-4-yl)thio)-3,6,9,12-tetraoxatetradecan-1-oyl)piperazin-1-yl)but-2-enamide | 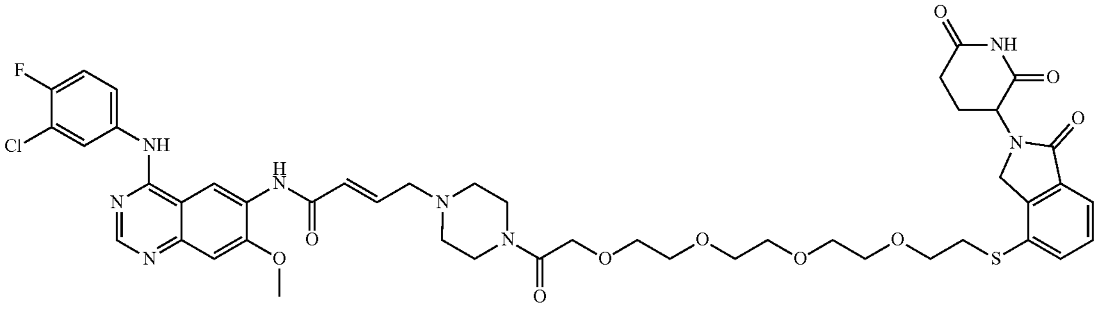 [SMILES: COc1cc2ncnc(Nc3ccc(F)c(Cl)c3)c2cc1NC(=O)/C=C/CN1CCN(C(=O)COCCOCCOCCOCCSc2cccc3c2CN(C2CCC(=O)NC2=O)C3=O)CC1] |

TABLE 2-continued

| Compound No. | The compounds' names | Structure of the compounds |
|---|---|---|
| | N-(4-((3-chloro-4-fluorophenyl)amino)-7-(3-(4-(17-((2-(2,6-dioxopiperidin-3-yl)-1-oxoisoindolin-4-yl)thio)-3,6,9,12,15-pentaoxaheptadecan-1-oyl)piperazin-1-yl)propoxy)quinazolin-6-yl)acrylamide | 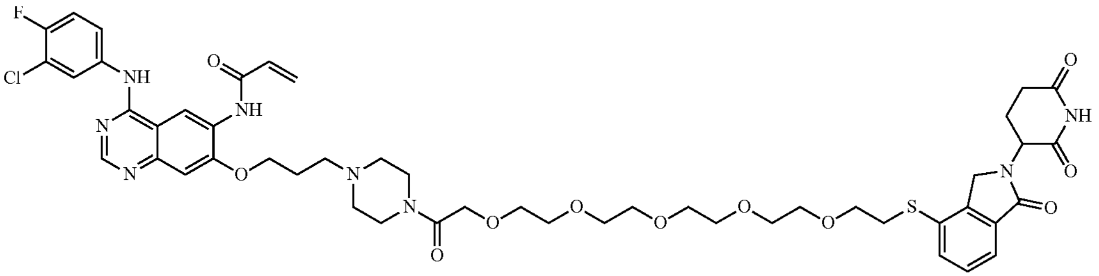 [SMILES: C=CC(=O)Nc1cc2c(Nc3ccc(F)c(Cl)c3)ncnc2cc1OCCCN1CCN(C(=O)COCCOCCOCCOCCOCCSc2cccc3c2CN(C2CCC(=O)NC2=O)C3=O)CC1] |
| | N-(4-((3-chloro-4-fluorophenyl)amino)-7-(3-(4-(3-((2-(2,6-dioxopiperidin-3-yl)-1-oxoisoindolin-4-yl)thio)propanoyl)piperazin-1-yl)propoxy)quinazolin-6-yl)acrylamide | 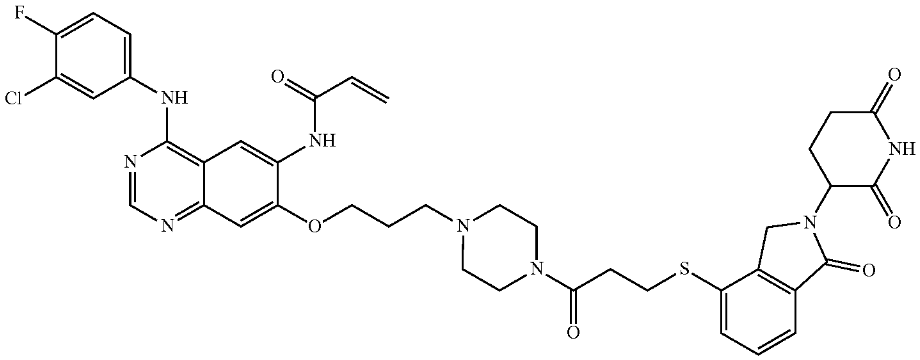 [SMILES: C=CC(=O)Nc1cc2c(Nc3ccc(F)c(Cl)c3)ncnc2cc1OCCCN1CCN(C(=O)CCSc2cccc3c2CN(C2CCC(=O)NC2=O)C3=O)CC1] |
| | N-(4-((3-chloro-4-fluorophenyl)amino)-7-(3-(4-(4-((2-(2,6-dioxopiperidin-3-yl)-1-oxoisoindolin-4-yl)thio)butanoyl)piperazin-1-yl)propoxy)quinazolin-6-yl)acrylamide | 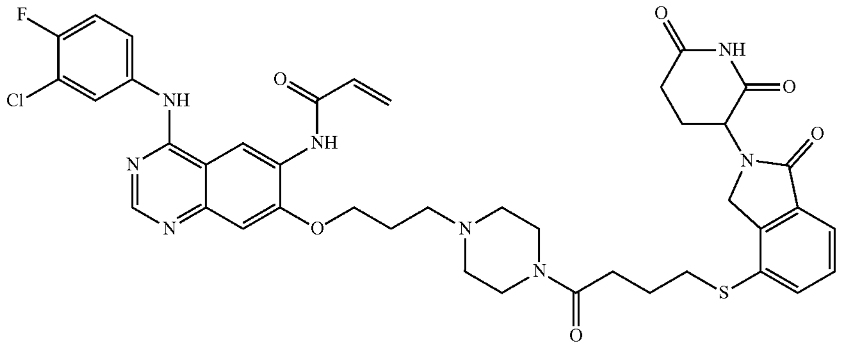 [SMILES: C=CC(=O)Nc1cc2c(Nc3ccc(F)c(Cl)c3)ncnc2cc1OCCCN1CCN(C(=O)CCCSc2cccc3c2CN(C2CCC(=O)NC2=O)C3=O)CC1] |

TABLE 2-continued

| Compound No. | The compounds' names | Structure of the compounds |
| --- | --- | --- |
| | N-(4-((3-chloro-4-fluorophenyl)amino)-7-(3-(4-(7-((2-(2,6-dioxopiperidin-3-yl)-1-oxoisoindolin-4-yl)thio)heptanoyl)piperazin-1-yl)propoxy)quinazolin-6-yl)acrylamide | 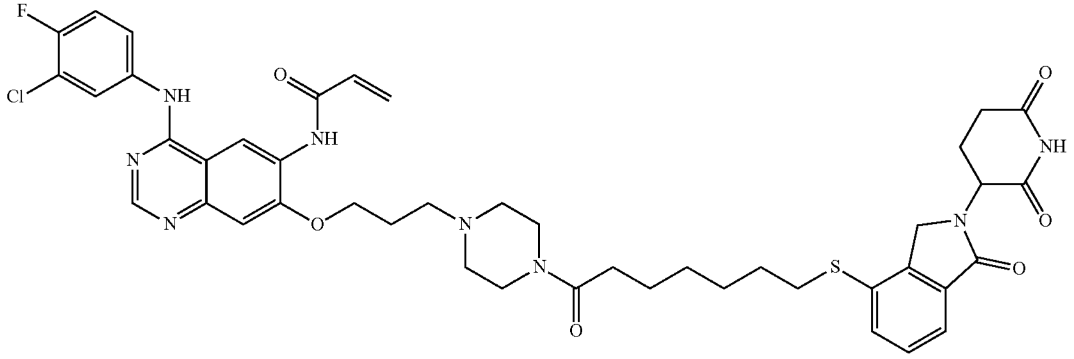 [SMILES: C=CC(=O)Nc1cc2c(Nc3ccc(F)c(Cl)c3)ncnc2cc1OCCCN1CCN(C(=O)CCCCCCSc2cccc3c2CN(C2CCC(=O)NC2=O)C3=O)CC1] |
| | N-(4-((3-chloro-4-fluorophenyl)amino)-7-(3-(4-(2-((2-(2,6-dioxopiperidin-3-yl)-1-oxoisoindolin-4-yl)thio)ethyl)piperazin-1-yl)propoxy)quinazolin-6-yl)acrylamide | 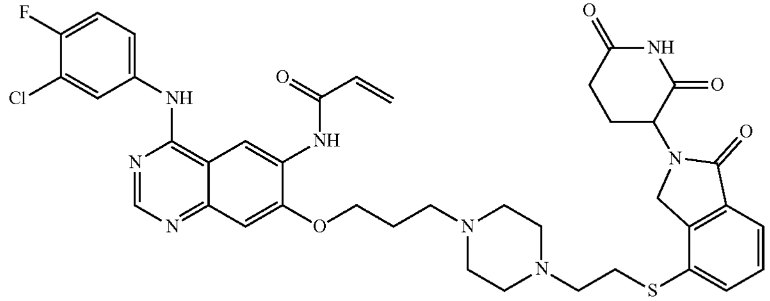 [SMILES: C=CC(=O)Nc1cc2c(Nc3ccc(F)c(Cl)c3)ncnc2cc1OCCCN1CCN(CCSc2cccc3c2CN(C2CCC(=O)NC2=O)C3=O)CC1] |
| | N-(4-((3-chloro-4-fluorophenyl)amino)-7-(3-(4-(3-((2-(2,6-dioxopiperidin-3-yl)-1-oxoisoindolin-4-yl)thio)propyl)piperazin-1-yl)propoxy)quinazolin-6-yl)acrylamide | 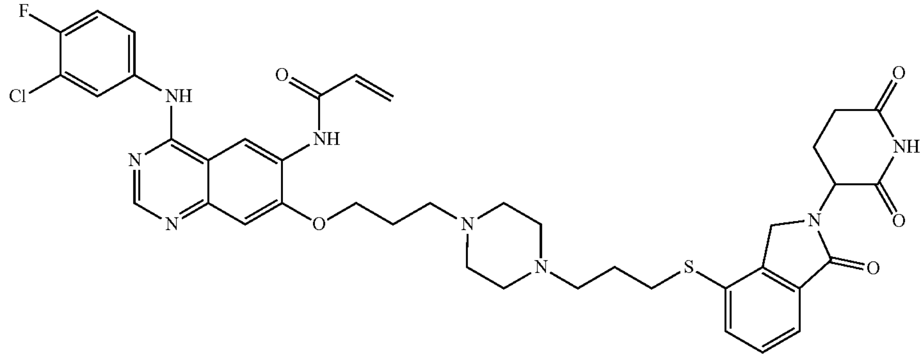 [SMILES: C=CC(=O)Nc1cc2c(Nc3ccc(F)c(Cl)c3)ncnc2cc1OCCCN1CCN(CCCSc2cccc3c2CN(C2CCC(=O)NC2=O)C3=O)CC1] |

TABLE 2-continued

| Compound No. | The compounds' names | Structure of the compounds |
|---|---|---|
| | N-(4-((3-chloro-4-fluorophenyl)amino)-7-(3-(4-(4-((2-(2,6-dioxopiperidin-3-yl)-1-oxoisoindolin-4-yl)thio)butyl)piperazin-1-yl)propoxy)quinazolin-6-yl)acrylamide | 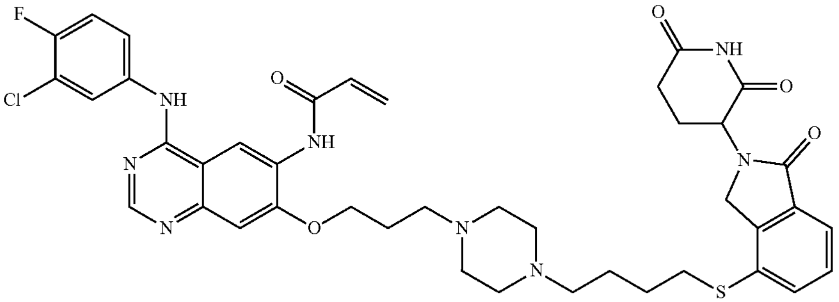 [SMILES: C=CC(=O)Nc1cc2c(Nc3ccc(F)c(Cl)c3)ncnc2cc1OCCCN1CCN(CCCCSc2cccc3c2CN(C2CCC(=O)NC2=O)C3=O)CC1] |
| | N-(4-((3-chloro-4-fluorophenyl)amino)-7-(3-(4-(5-((2-(2,6-dioxopiperidin-3-yl)-1-oxoisoindolin-4-yl)thio)pentyl)piperazin-1-yl)propoxy)quinazolin-6-yl)acrylamide | 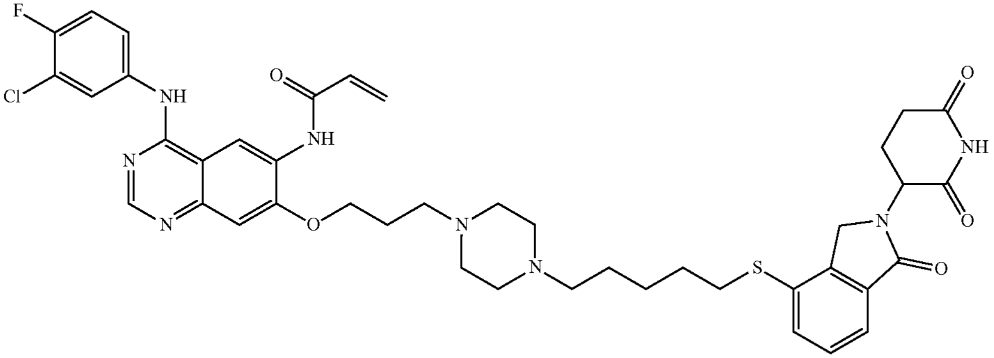 [SMILES: C=CC(=O)Nc1cc2c(Nc3ccc(F)c(Cl)c3)ncnc2cc1OCCCN1CCN(CCCCCSc2cccc3c2CN(C2CCC(=O)NC2=O)C3=O)CC1] |
| | N-(4-((3-chloro-4-fluorophenyl)amino)-7-(3-(4-(6-((2-(2,6-dioxopiperidin-3-yl)-1-oxoisoindolin-4-yl)thio)hexyl)piperazin-1-yl)propoxy)quinazolin-6-yl)acrylamide | 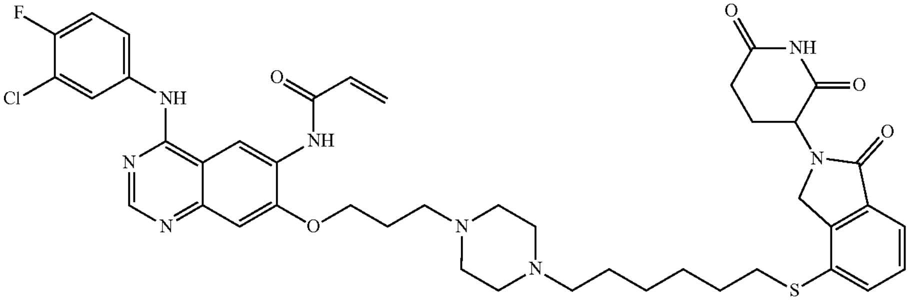 [SMILES: C=CC(=O)Nc1cc2c(Nc3ccc(F)c(Cl)c3)ncnc2cc1OCCCN1CCN(CCCCCCSc2cccc3c2CN(C2CCC(=O)NC2=O)C3=O)CC1] |

TABLE 2-continued

| Compound No. | The compounds' names | Structure of the compounds |
|---|---|---|
| | N-(4-((3-chloro-4-fluorophenyl)amino)-7-(3-(4-(7-((2-(2,6-dioxopiperidin-3-yl)-1-oxoisoindolin-4-yl)thio)heptyl)piperazin-1-yl)propoxy)quinazolin-6-yl)acrylamide | 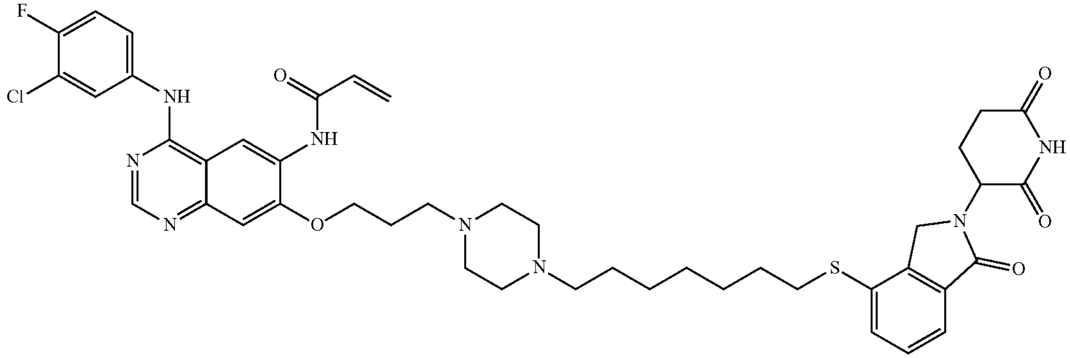 [SMILES: C=CC(=O)Nc1cc2c(Nc3ccc(F)c(Cl)c3)ncnc2cc1OCCCN1CCN(CCCCCCCSc2cccc3c2CN(C2CCC(=O)NC2=O)C3=O)CC1] |
| | N-(4-((3-chloro-4-fluorophenyl)amino)-7-(3-(4-(8-((2-(2,6-dioxopiperidin-3-yl)-1-oxoisoindolin-4-yl)thio)octyl)piperazin-1-yl)propoxy)quinazolin-6-yl)acrylamide | 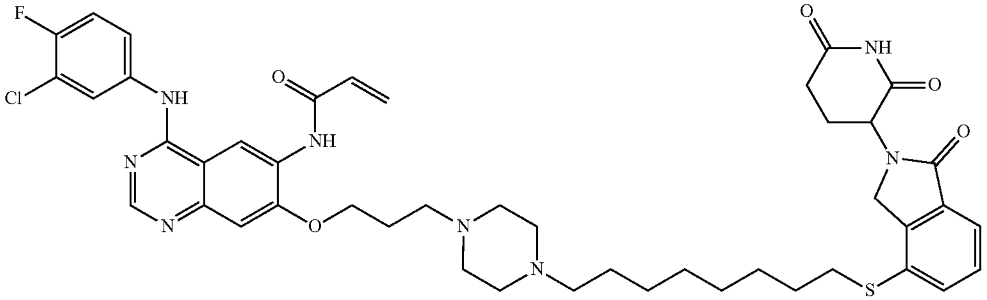 [SMILES: C=CC(=O)Nc1cc2c(Nc3ccc(F)c(Cl)c3)ncnc2cc1OCCCN1CCN(CCCCCCCCSc2cccc3c2CN(C2CCC(=O)NC2=O)C3=O)CC1] |
| | N-(4-((3-chloro-4-fluorophenyl)amino)-7-(3-(4-(5-(2-(2,6-dioxopiperidin-3-yl)-1-oxoisoindolin-4-yl)pent-4-yn-1-yl)piperazin-1-yl)propoxy)quinazolin-6-yl)acrylamide | 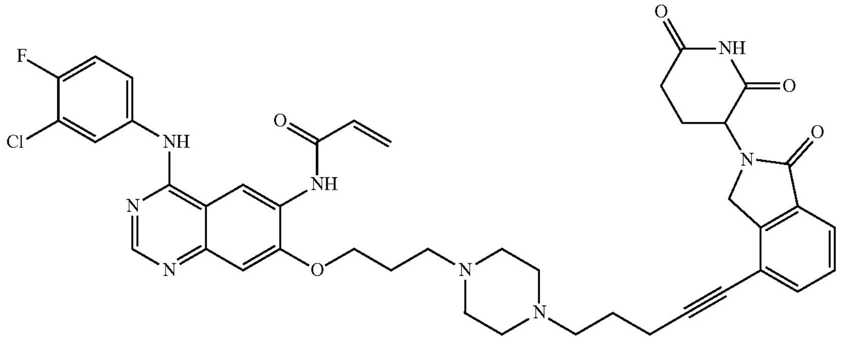 [SMILES: C=CC(=O)Nc1cc2c(Nc3ccc(F)c(Cl)c3)ncnc2cc1OCCCN1CCN(CCCC#Cc2cccc3c2CN(C2CCC(=O)NC2=O)C3=O)CC1] |

TABLE 2-continued
| Compound No. | The compounds' names | Structure of the compounds |
| --- | --- | --- |
| | N-(4-((3-chloro-4-fluorophenyl)amino)-7-(3-(4-(7-(2-(2,6-dioxopiperidin-3-yl)-1-oxoisoindolin-4-yl)hept-6-yn-1-yl)piperazin-1-yl)propoxy)quinazolin-6-yl)acrylamide | 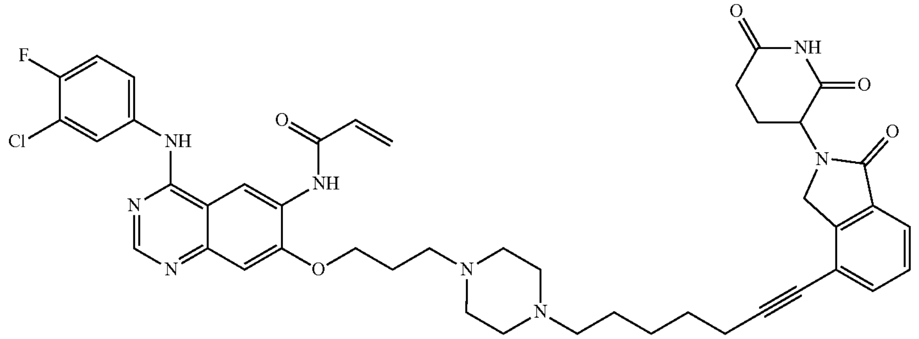 [SMILES: C=CC(=O)Nc1cc2c(Nc3ccc(F)c(Cl)c3)ncnc2cc1OCCCN1CCN(CCCCCC#Cc2cccc3c2CN(C2CCC(=O)NC2=O)C3=O)CC1] |
| | N-(4-((3-chloro-4-fluorophenyl)amino)-7-(3-(4-(8-(2-(2,6-dioxopiperidin-3-yl)-3-oxoisoindolin-1-yl)oct-7-yn-1-yl)piperazin-1-yl)propoxy)quinazolin-6-yl)acrylamide | 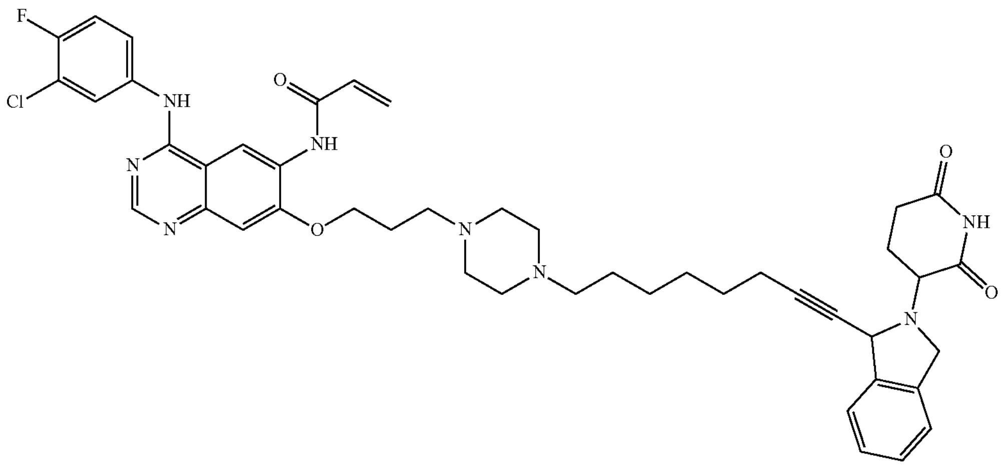 [SMILES: C=CC(=O)Nc1cc2c(Nc3ccc(F)c(Cl)c3)ncnc2cc1OCCCN1CCN(CCCCCCC#CC2c3ccccc3CN2C2CCC(=O)NC2=O)CC1] |

TABLE 2-continued

| Compound No. | The compounds' names | Structure of the compounds |
| --- | --- | --- |
| | N-(4-((3-chloro-4-fluorophenyl)amino)-7-(3-(4-(9-(2-(2,6-dioxopiperidin-3-yl)-1-oxoisoindolin-4-yl)non-8-yn-1-yl)piperazin-1-yl)propoxy)quinazolin-6-yl)acrylamide | 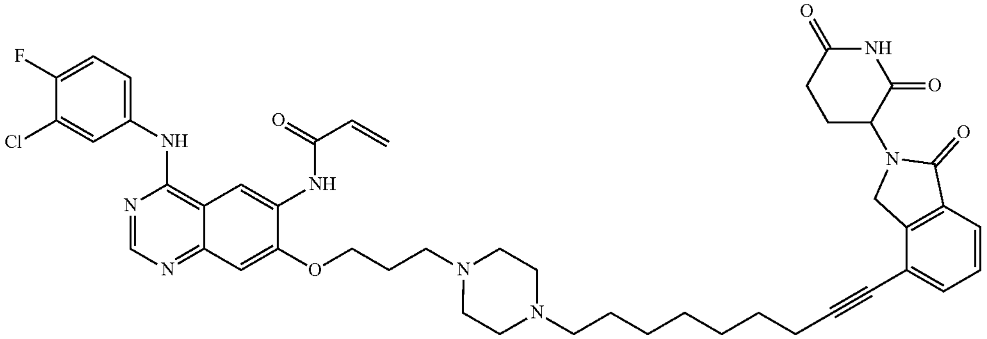 [SMILES: C=CC(=O)Nc1cc2c(Nc3ccc(F)c(Cl)c3)ncnc2cc1OCCCN1CCN(CCCCCCCC#Cc2cccc3c2CN(C2CCC(=O)NC2=O)C3=O)CC1] |
| | (2S,4R)-1-((S)-2-(8-(4-(3-((6-acrylamido-4-((3-chloro-4-fluorophenyl)amino)quinazolin-7-yl)oxy)propyl)piperazin-1-yl)-8-oxooctanamido)-3,3-dimethylbutanoyl)-4-hydroxy-N-(4-(4-methylthiazol-5-yl)benzyl)pyrrolidine-2-carboxamide | 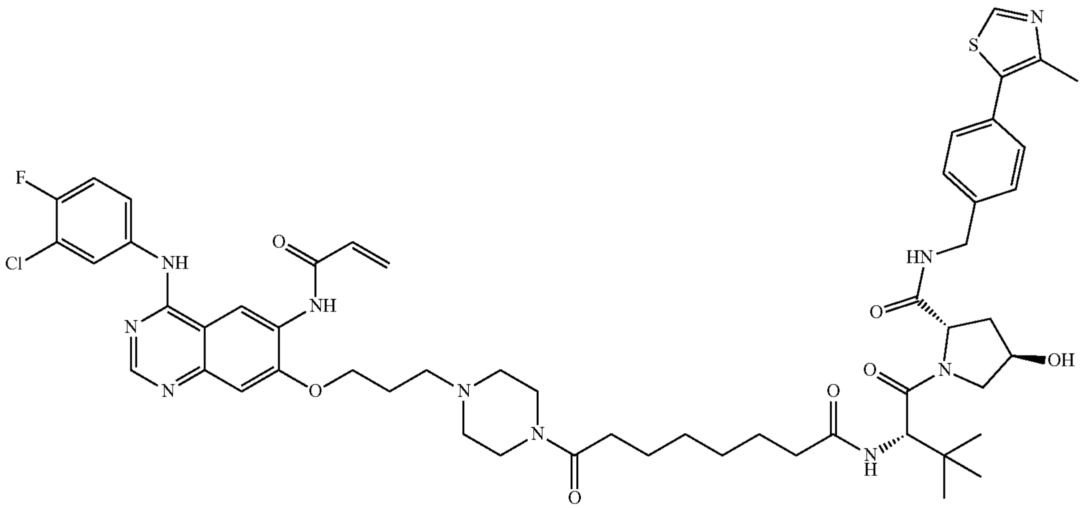 [SMILES: C=CC(=O)Nc1cc2c(Nc3ccc(F)c(Cl)c3)ncnc2cc1OCCCN1CCN(C(=O)CCCCCCC(=O)N[C@H](C(=O)N2C[C@H](O)C[C@H]2C(=O)NCc2ccc(-c3scnc3C)cc2)C(C)(C)C)CC1] |

TABLE 2-continued

| Compound No. | The compounds' names | Structure of the compounds |
|---|---|---|
| | (2S,4R)-1-((S)-2-(11-(4-(3-((6-acrylamido-4-((3-chloro-4-fluorophenyl)amino)quinazolin-7-yl)oxy)propyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide | 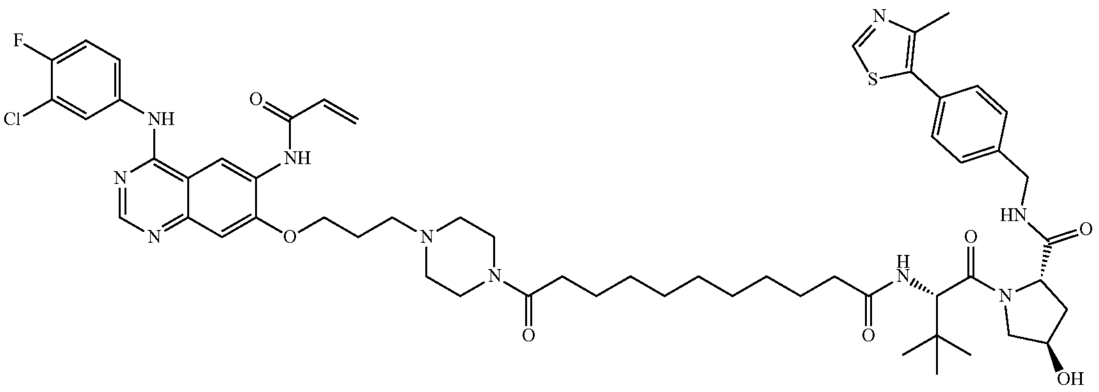 [SMILES: C=CC(=O)Nc1cc2c(Nc3ccc(F)c(Cl)c3)ncnc2cc1OCCCN1CCN(C(=O)CCCCCCCCCC(=O)N[C@H](C(=O)N2C[C@H](O)C[C@H]2C(=O)NCc2ccc(-c3scnc3C)cc2)C(C)(C)C)CC1] |
| | N-(4-((3-chloro-4-fluorophenyl)amino)-7-(3-(4-(4-(3-(2-((2-(2,6-dioxopiperidin-3-yl)-1,3-dioxoisoindolin-4-yl)amino)ethoxy)propanoyl)piperazin-1-yl)piperidin-1-yl)propoxy)quinazolin-6-yl)acrylamide | 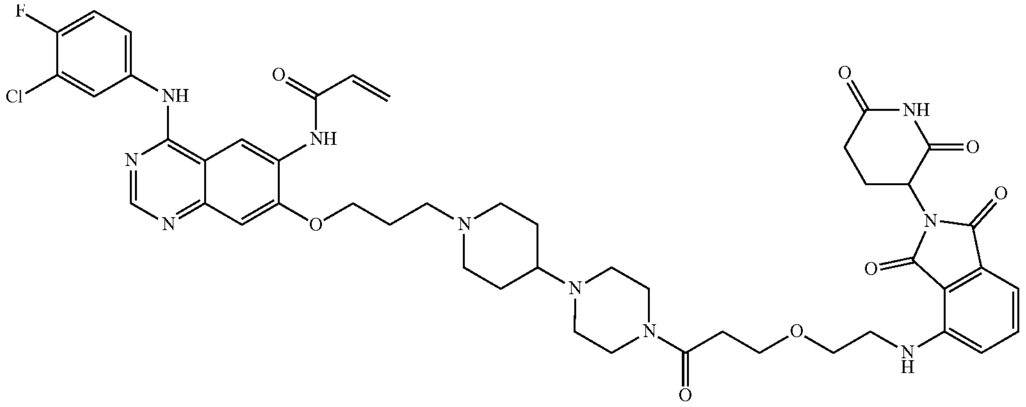 [SMILES: C=CC(=O)Nc1cc2c(Nc3ccc(F)c(Cl)c3)ncnc2cc1OCCCN1CCC(N2CCN(C(=O)CCOCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(3-(2-(2-((2-(2,6-dioxopiperidin-3-yl)-1,3-dioxoisoindolin-4-yl)amino)ethoxy)ethoxy)propanoyl)piperazin-1-yl)piperidin-1-yl)propoxy)quinazolin-6-yl)acrylamide | 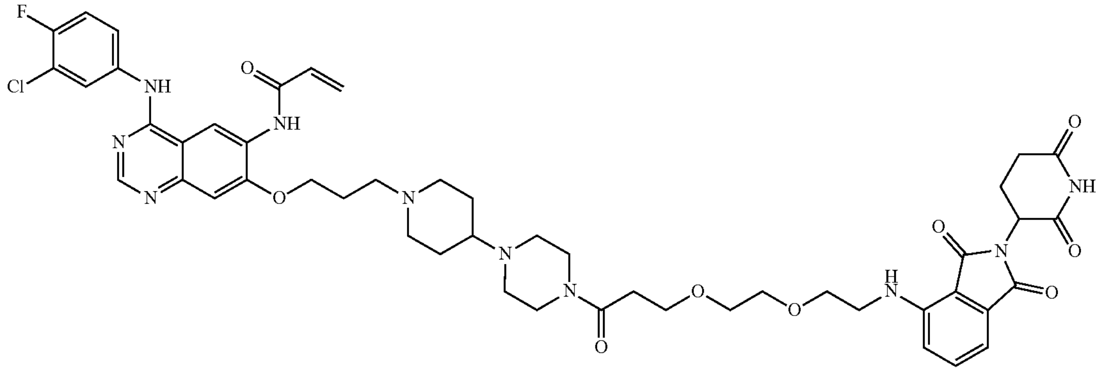 [SMILES: C=CC(=O)Nc1cc2c(Nc3ccc(F)c(Cl)c3)ncnc2cc1OCCCN1CCC(N2CCN(C(=O)CCOCCOCCNc3cccc4c3C(=O)N(C3CCC(=O)NC3=O)C4=O)CC2)CC1] |
| | N-(4-((3-chloro-4-fluorophenyl)amino)-7-(3-(4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)piperidin-1-yl)propoxy)quinazolin-6-yl)acrylamide | 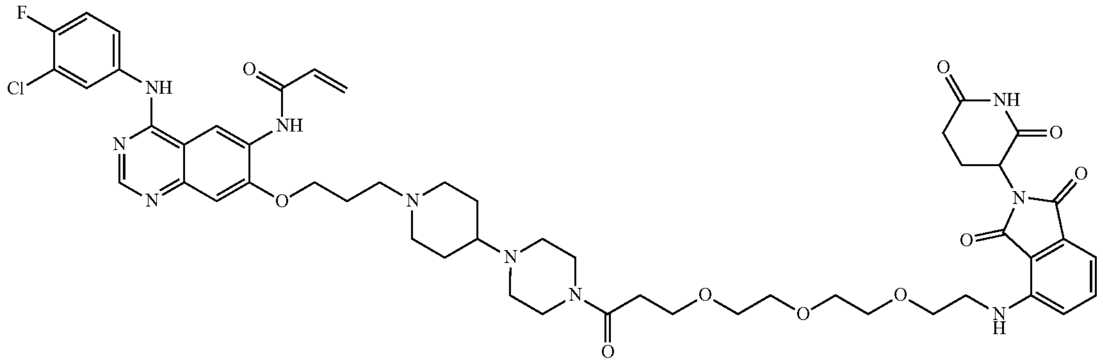 [SMILES: C=CC(=O)Nc1cc2c(Nc3ccc(F)c(Cl)c3)ncnc2cc1OCCCN1CCC(N2CCN(C(=O)CCOCCOCCOCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)piperidin-1-yl)propoxy)quinazolin-6-yl)acrylamide | 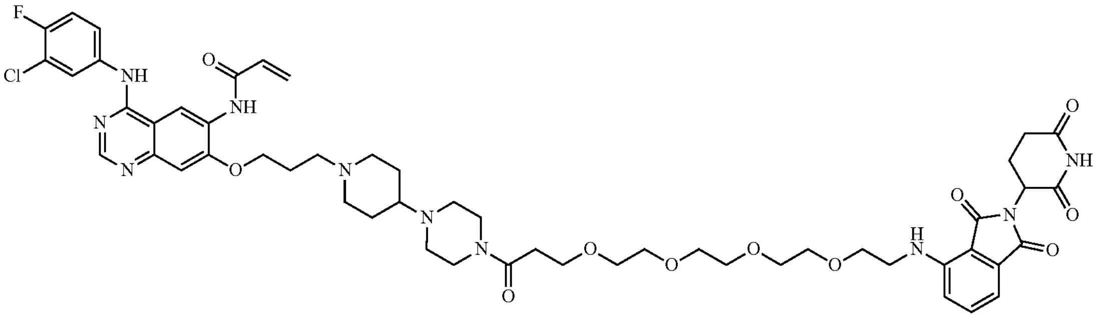 [SMILES: C=CC(=O)Nc1cc2c(Nc3ccc(F)c(Cl)c3)ncnc2cc1OCCCN1CCC(N2CCN(C(=O)CCOCCOCCOCCOCCNc3cccc4c3C(=O)N(C3CCC(=O)NC3=O)C4=O)CC2)CC1] |
| | N-(4-((3-chloro-4-fluorophenyl)amino)-7-(3-(4-(4-(1-((2-(2,6-dioxopiperidin-3-yl)-1,3-dioxoisoindolin-4-yl)amino)-3,6,9,12,15-pentaoxaoctadecan-1 8-o yl)piperazin-1-yl) piperidin-1-yl)propoxy)quinazolin-6-yl)acrylamide | 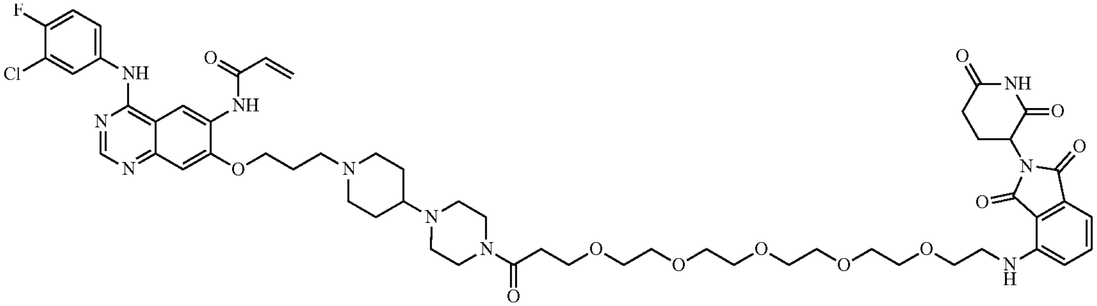 [SMILES: C=CC(=O)Nc1cc2c(Nc3ccc(F)c(Cl)c3)ncnc2cc1OCCCN1CCC(N2CCN(C(=O)CCOCCOCCOCCOCCOCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(3-((2-(2,6-dioxopiperidin-3-yl)-1,3-dioxoisoindolin-4-yl)amino)propanoyl)piperazin-1-yl)piperidin-1-yl)propoxy)quinazolin-6-yl)acrylamide | 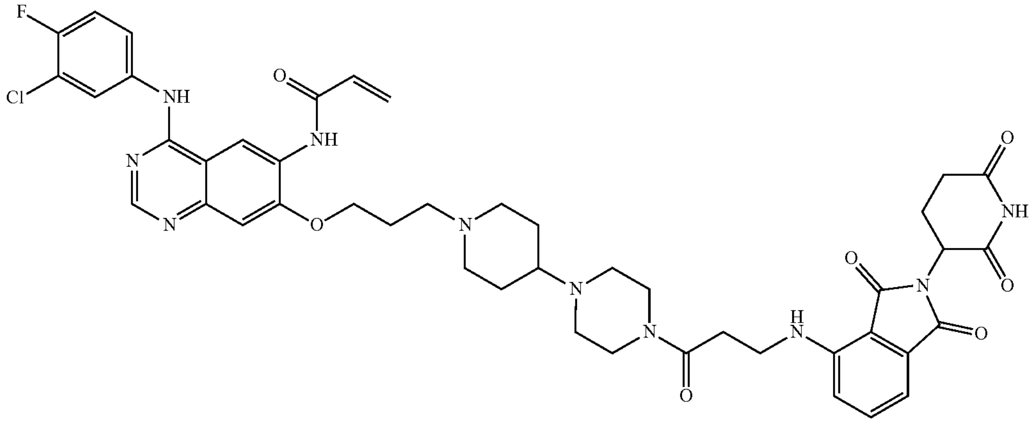 [SMILES: C=CC(=O)Nc1cc2c(Nc3ccc(F)c(Cl)c3)ncnc2cc1OCCCN1CCC(N2CCN(C(=O)CCNc3cccc4c3C(=O)N(C3CCC(=O)NC3=O)C4=O)CC2)CC1] |
| | N-(4-((3-chloro-4-fluorophenyl)amino)-7-(3-(4-(4-(4-((2-(2,6-dioxopiperidin-3-yl)-1,3-dioxoisoindolin-4-yl)amino)butanoyl)piperazin-1-yl)piperidin-1-yl)propoxy)quinazolin-6-yl)acrylamide | 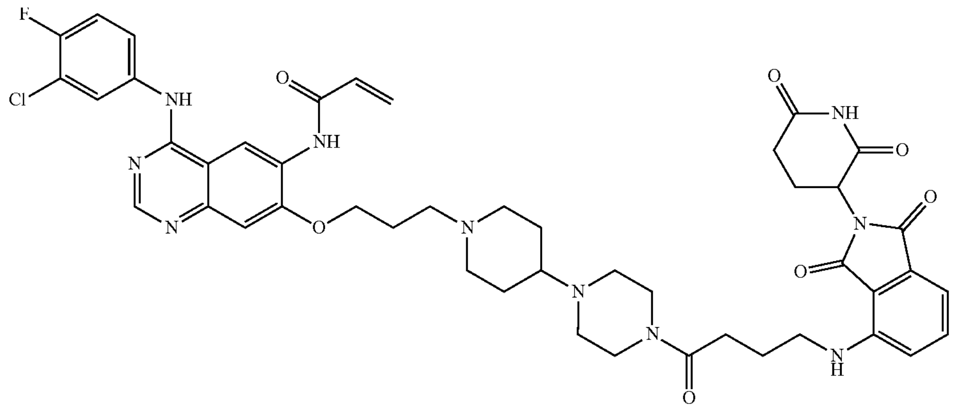 [SMILES: C=CC(=O)Nc1cc2c(Nc3ccc(F)c(Cl)c3)ncnc2cc1OCCCN1CCC(N2CCN(C(=O)CCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(5-((2-(2,6-dioxopiperidin-3-yl)-1,3-dioxoisoindolin-4-yl)amino)pentanoyl)piperazin-1-yl)piperidin-1-yl)propoxy)quinazolin-6-yl)acrylamide | 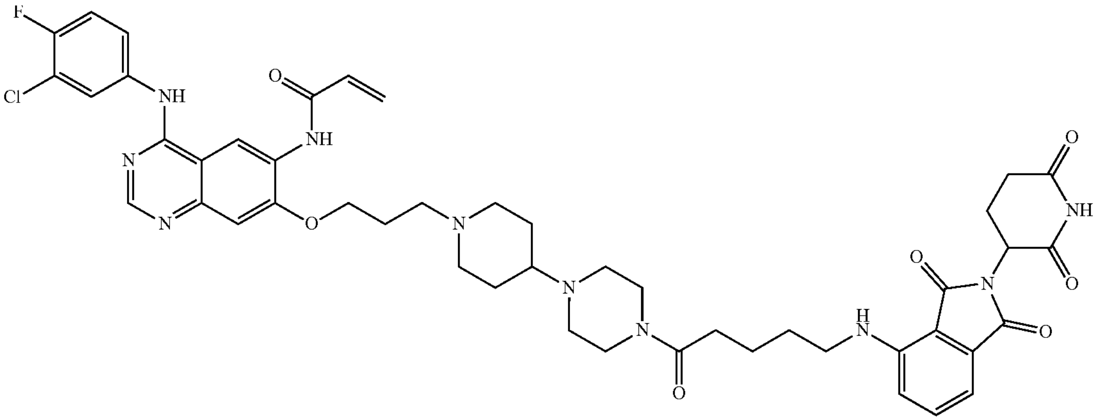 [SMILES: C=CC(=O)Nc1cc2c(Nc3ccc(F)c(Cl)c3)ncnc2cc1OCCCN1CCC(N2CCN(C(=O)CCCCNc3cccc4c3C(=O)N(C3CCC(=O)NC3=O)C4=O)CC2)CC1] |
| | N-(4-((3-chloro-4-fluorophenyl)amino)-7-(3-(4-(4-(5-((2-(2,6-dioxopiperidin-3-yl)-1,3-dioxoisoindolin-4-yl)amino)pentyl)piperazin-1-yl)piperidin-1-yl)propoxy)quinazolin-6-yl)acrylamide | 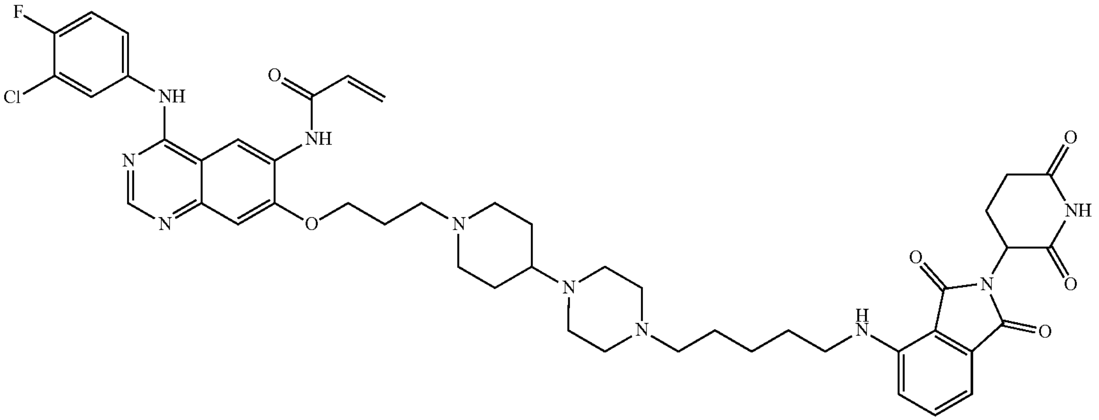 [SMILES: C=CC(=O)Nc1cc2c(Nc3ccc(F)c(Cl)c3)ncnc2cc1OCCCN1CCC(N2CCN(CCCCCNc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-(2-((2-(2,6-dioxopiperidin-3-yl)-1-oxoisoindolin-4-yl)amino)ethoxy)acetyl)piperazin-1-yl)piperidin-1-yl)propoxy)quinazolin-6-yl)acrylamide | 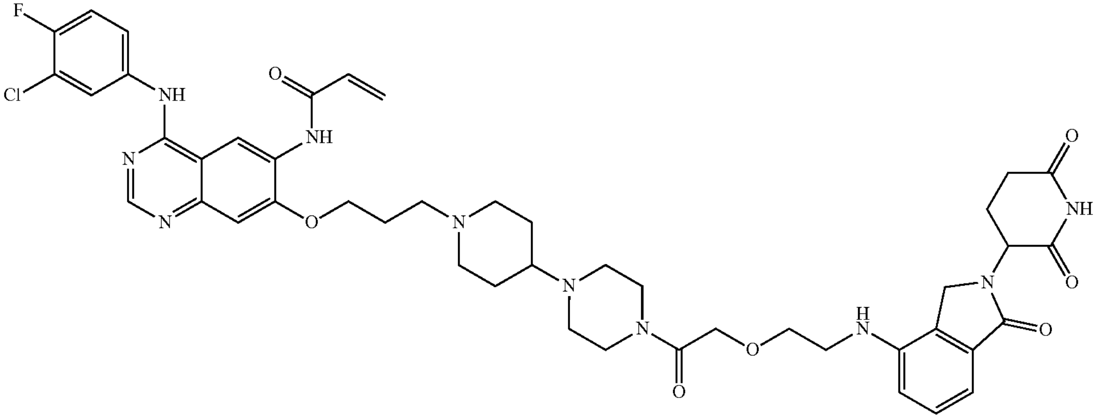 [SMILES: C=CC(=O)Nc1cc2c(Nc3ccc(F)c(Cl)c3)ncnc2cc1OCCCN1CCC(N2CCN(C(=O)COCCNc3cccc4c3CN(C3CCC(=O)NC3=O)C4=O)CC2)CC1] |
| | N-(4-((3-chloro-4-fluorophenyl)amino)-7-(3-(4-(4-(2-(2-(2-((2-(2,6-dioxopiperidin-3-yl)-1-oxoisoindolin-4-yl)amino)ethoxy)ethoxy)acetyl)piperazin-1-yl)piperidin-1-yl)propoxy)quinazolin-6-yl)acrylamide | 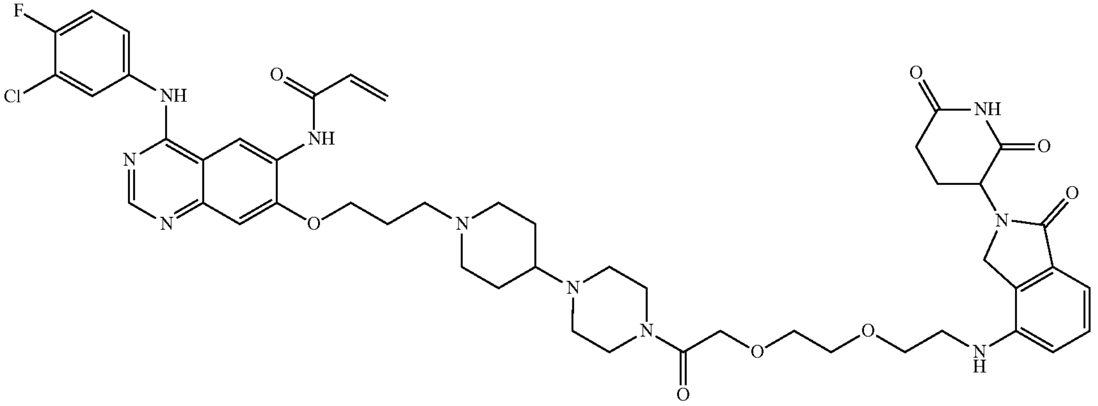 [SMILES: C=CC(=O)Nc1cc2c(Nc3ccc(F)c(Cl)c3)ncnc2cc1OCCCN1CCC(N2CCN(C(=O)COCCOCCNc3cccc4c3CN(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-(2-(2-(2-((2-(2,6-dioxopiperidin-3-yl)-1-oxoisoindolin-4-yl)amino)ethoxy)ethoxy)ethoxy)acetyl)piperazin-1-yl)piperidin-1-yl)propoxy)quinazolin-6-yl)acrylamide | 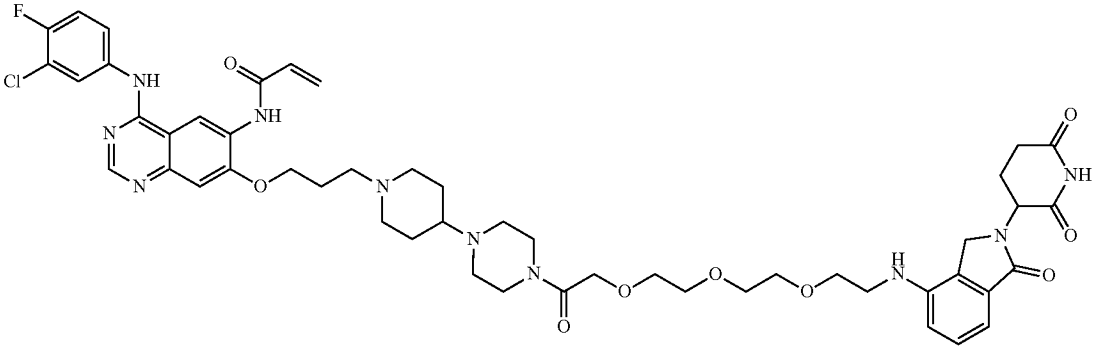 [SMILES: C=CC(=O)Nc1cc2c(Nc3ccc(F)c(Cl)c3)ncnc2cc1OCCCN1CCC(N2CCN(C(=O)COCCOCCOCCNc3cccc4c3CN(C3CCC(=O)NC3=O)C4=O)CC2)CC1] |
| | N-(4-((3-chloro-4-fluorophenyl)amino)-7-(3-(4-(4-(14-((2-(2,6-dioxopiperidin-3-yl)-1-oxoisoindolin-4-yl)amino)-3,6,9,12-tetraoxatetradecan-1-oyl)piperazin-1-yl)piperidin-1-yl)propoxy)quinazolin-6-yl)acrylamide | 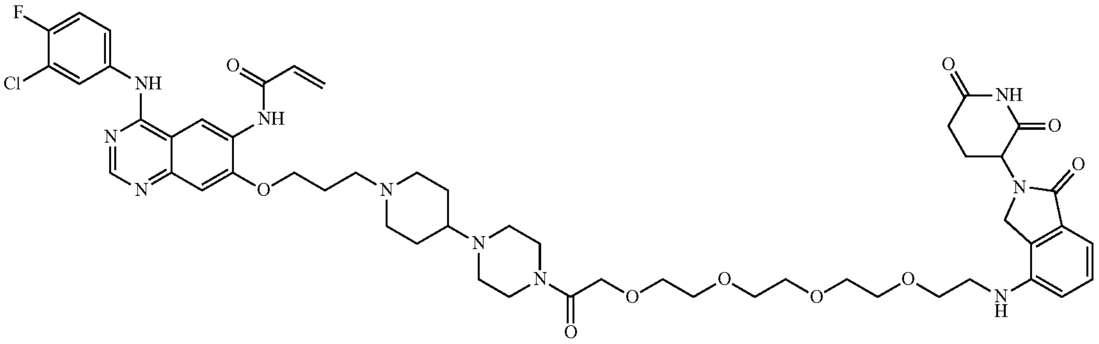 [SMILES: C=CC(=O)Nc1cc2c(Nc3ccc(F)c(Cl)c3)ncnc2cc1OCCCN1CCC(N2CCN(C(=O)COCCOCCOCCOCCNc3cccc4c3CN(C3CCC(=O)NC3=O)C4=O)CC2)CC1] |
| | N-(4-((3-chloro-4-fluorophenyl)amino)-7-(3-(4-(4-(17-((2-(2,6-dioxopiperidin-3-yl)-1-oxoisoindolin-4-yl)amino)-3,6,9,12,15-pentaoxaheptadecan-1-oyl)piperazin-1-yl)piperidin-1-yl)propoxy)quinazolin-6-yl)acrylamide | 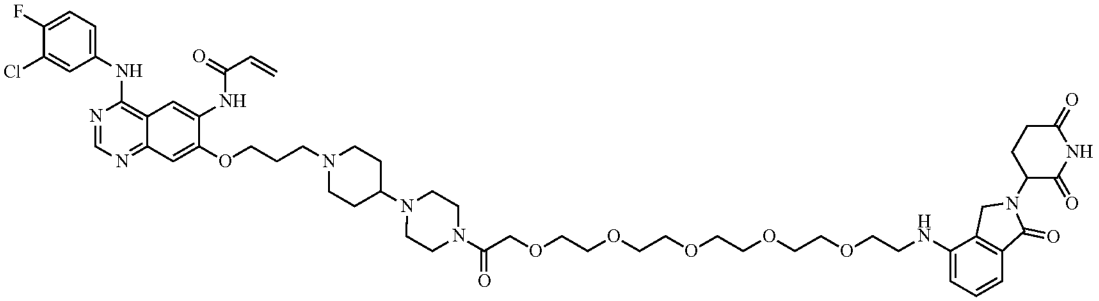 [SMILES: C=CC(=O)Nc1cc2c(Nc3ccc(F)c(Cl)c3)ncnc2cc1OCCCN1CCC(N2CCN(C(=O)COCCOCCOCCOCCOCCNc3cccc4c3CN(C3CCC(=O)NC3=O)C4=O)CC2)CC1] |

TABLE 2-continued

| Compound No. | The compounds' names | Structure of the compounds |
| --- | --- | --- |
| | N-(4-((3-chloro-4-fluorophenyl)amino)-7-(3-(4-(4-(2-((2-(2,6-dioxopiperidin-3-yl)-1-oxoisoindolin-4-yl)amino)acetyl)piperazin-1-yl)piperidin-1-yl)propoxy)quinazolin-6-yl)acrylamide | 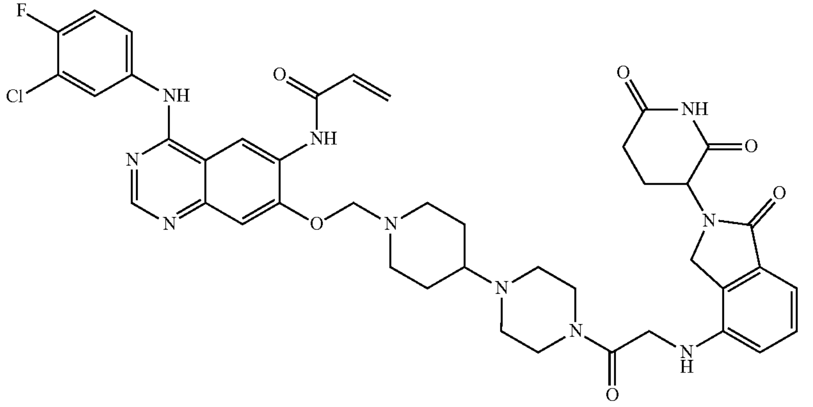 [SMILES: C=CC(=O)Nc1cc2c(Nc3ccc(F)c(Cl)c3)ncnc2cc1OCN1CCC(N2CCN(C(=O)CNc3cccc4c3CN(C3CCC(=O)NC3=O)C4=O)CC2)CC1] |
| | N-(4-((3-chloro-4-fluorophenyl)amino)-7-(3-(4-(4-(3-((2-(2,6-dioxopiperidin-3-yl)-1-oxoisoindolin-4-yl)amino)propanoyl)piperazin-1-yl)piperidin-1-yl)propoxy)quinazolin-6-yl)acrylamide | 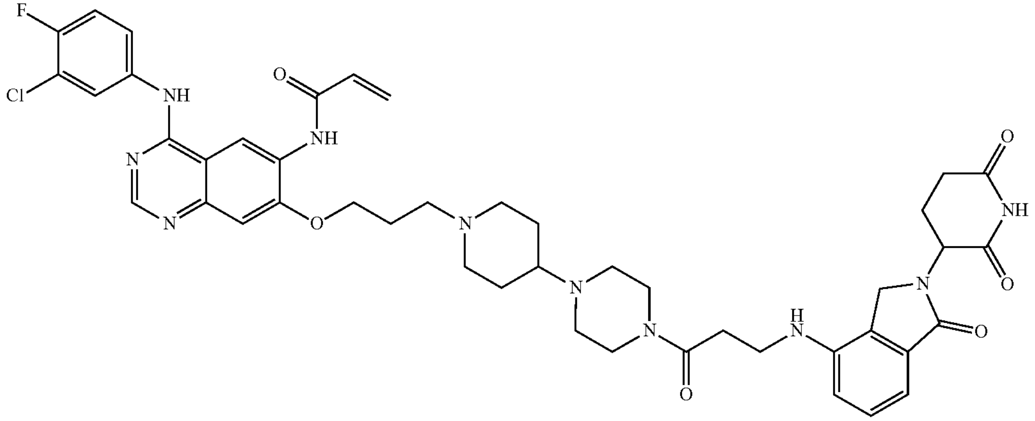 [SMILES: C=CC(=O)Nc1cc2c(Nc3ccc(F)c(Cl)c3)ncnc2cc1OCCCN1CCC(N2CCN(C(=O)CCNc3cccc4c3CN(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(4-((2-(2,6-dioxopiperidin-3-yl)-1-oxoisoindolin-4-yl)amino)butanoyl)piperazin-1-yl)piperidin-1-yl)propoxy)quinazolin-6-yl)acrylamide | 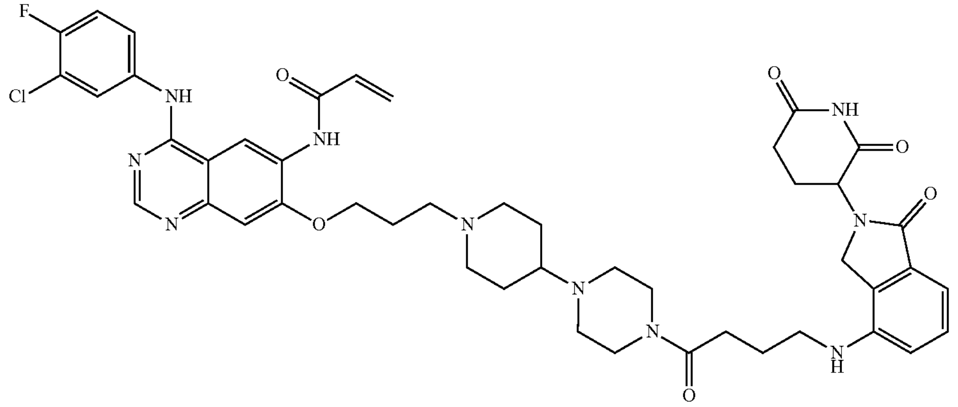 [SMILES: C=CC(=O)Nc1cc2c(Nc3ccc(F)c(Cl)c3)ncnc2cc1OCCCN1CCC(N2CCN(C(=O)CCCNc3cccc4c3CN(C3CCC(=O)NC3=O)C4=O)CC2)CC1] |
| | N-(4-((3-chloro-4-fluorophenyl)amino)-7-(3-(4-(4-(5-((2-(2,6-dioxopiperidin-3-yl)-1-oxoisoindolin-4-yl)amino)pentanoyl)piperazin-1-yl)piperidin-1-yl)propoxy)quinazolin-6-yl)acrylamide | 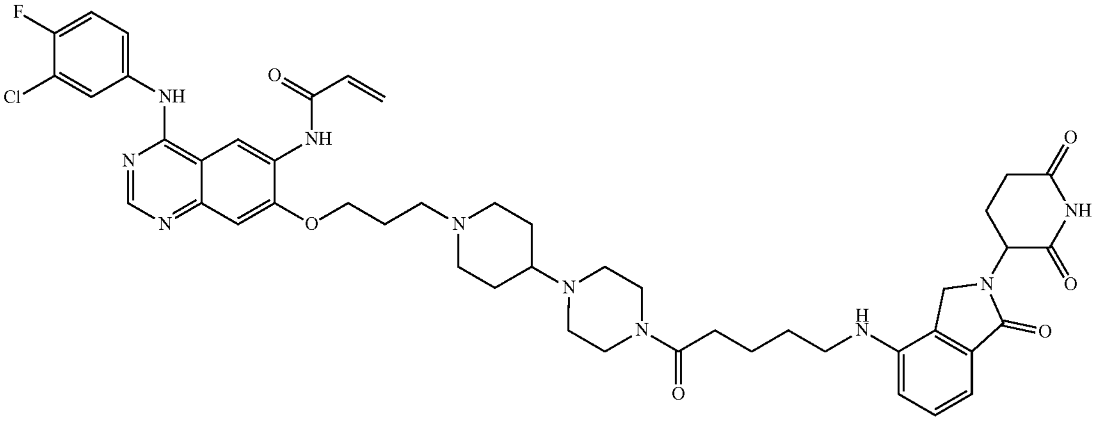 |

TABLE 2-continued

| Compound No. | The compounds' names | Structure of the compounds |
|---|---|---|
| | N-(4-((3-chloro-4-fluorophenyl)amino)-7-(3-(4-(4-(6-((2-(2,6-dioxopiperidin-3-yl)-1-oxoisoindolin-4-yl)amino)hexanoyl)piperazin-1-yl)piperidin-1-yl)propoxy)quinazolin-6-yl)acrylamide | 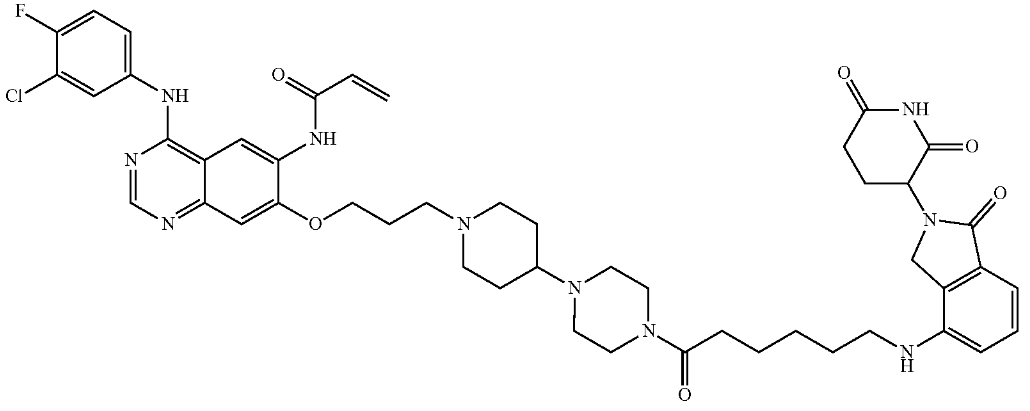 [SMILES: C=CC(=O)Nc1cc2c(Nc3ccc(F)c(Cl)c3)ncnc2cc1OCCCN1CCC(N2CCN(C(=O)CCCCCNc3cccc4c3CN(C3CCC(=O)NC3=O)C4=O)CC2)CC1] |
| | N-(4-((3-chloro-4-fluorophenyl)amino)-7-(3-(4-(4-(7-((2-(2,6-dioxopiperidin-3-yl)-1-oxoisoindolin-4-yl)amino)heptanoyl)piperazin-1-yl)piperidin-1-yl)propoxy)quinazolin-6-yl)acrylamide | 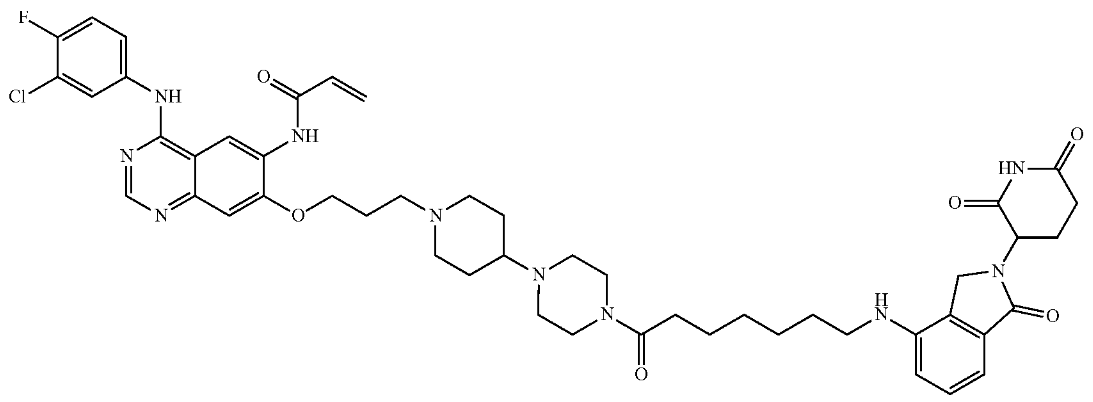 [SMILES: C=CC(=O)Nc1cc2c(Nc3ccc(F)c(Cl)c3)ncnc2cc1OCCCN1CCC(N2CCN(C(=O)CCCCCCNc3cccc4c3CN(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-((2-(2,6-dioxopiperidin-3-yl)-1,3-dioxoisoindolin-4-yl)thio)acetyl)piperazin-1-yl)piperidin-1-yl)propoxy)quinazolin-6-yl)acrylamide | 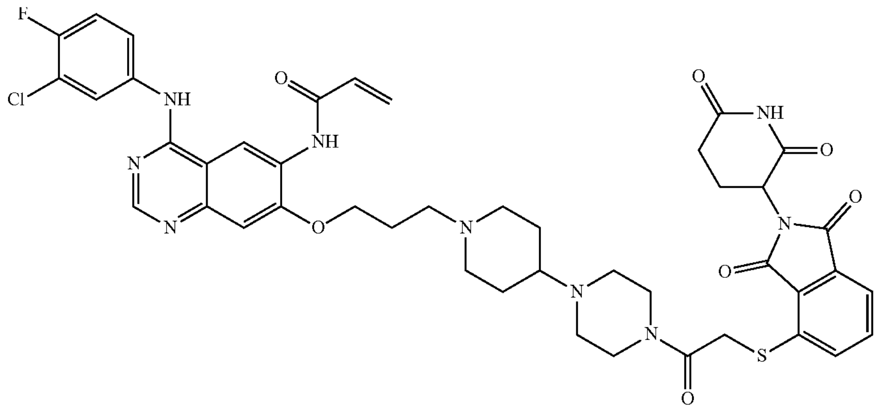 |
| | N-(4-((3-chloro-4-fluorophenyl)amino)-7-(3-(4-(4-(3-((2-(2,6-dioxopiperidin-3-yl)-1,3-dioxoisoindolin-4-yl)thio)propanoyl)piperazin-1-yl)piperidin-1-yl)propoxy)quinazolin-6-yl)acrylamide | 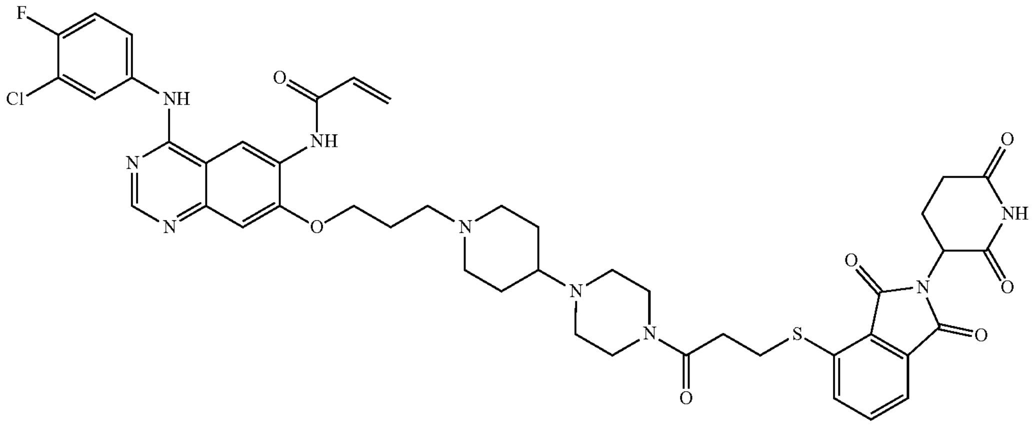 [SMILES: C=CC(=O)Nc1cc2c(Nc3ccc(F)c(Cl)c3)ncnc2cc1OCCCN1CCC(N2CCN(C(=O)CCSc3cccc4c3C(=O)N(C3CCC(=O)NC3=O)C4=O)CC2)CC1] |

TABLE 2-continued

| Compound No. | The compounds' names | Structure of the compounds |
| --- | --- | --- |
| | N-(4-((3-chloro-4-fluorophenyl)amino)-7-(3-(4-(4-(4-((2-(2,6-dioxopiperidin-3-yl)-1,3-dioxoisoindolin-4-yl)thio)butanoyl)piperazin-1-yl)piperidin-1-yl)propoxy)quinazolin-6-yl)acrylamide | 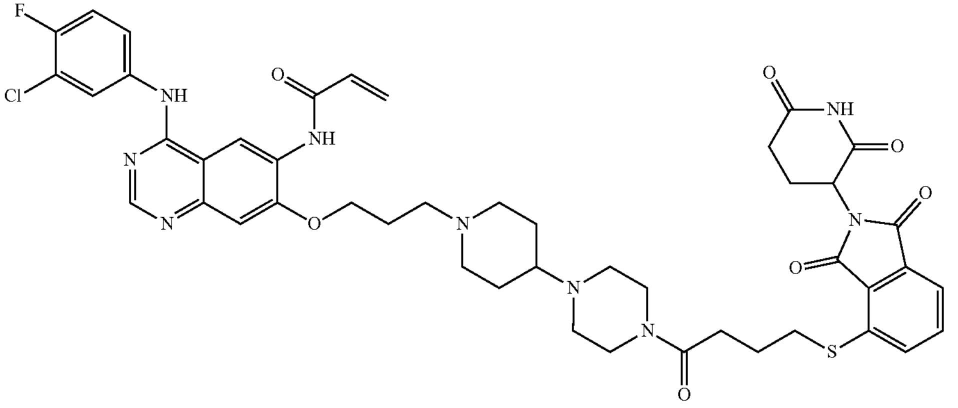 [SMILES: C=CC(=O)Nc1cc2c(Nc3ccc(F)c(Cl)c3)ncnc2cc1OCCCN1CCC(N2CCN(C(=O)CCCSc3cccc4c3C(=O)N(C3CCC(=O)NC3=O)C4=O)CC2)CC1] |
| | N-(4-((3-chloro-4-fluorophenyl)amino)-7-(3-(4-(4-(5-((2-(2,6-dioxopiperidin-3-yl)-1,3-dioxoisoindolin-4-yl)thio)pentanoyl)piperazin-1-yl)piperidin-1-yl)propoxy)quinazolin-6-yl)acrylamide | 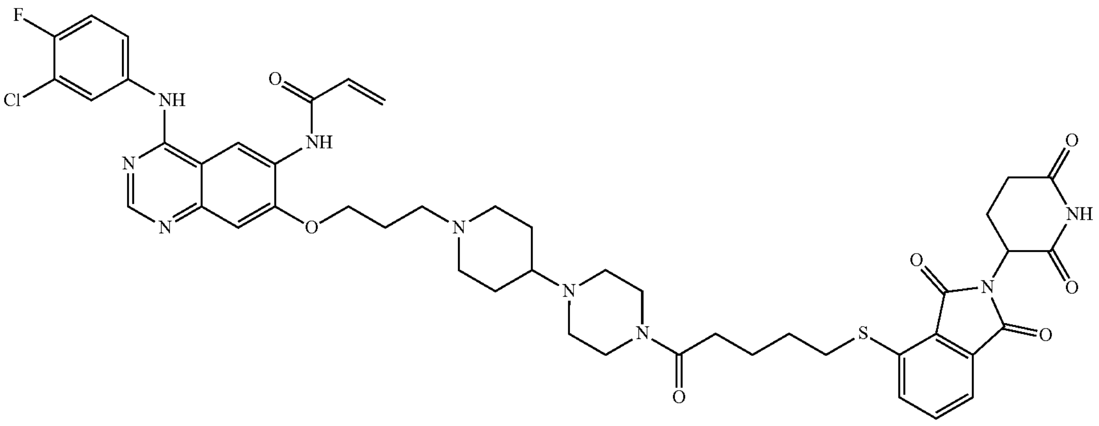 [SMILES: C=CC(=O)Nc1cc2c(Nc3ccc(F)c(Cl)c3)ncnc2cc1OCCCN1CCC(N2CCN(C(=O)CCCCSc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(6-((2-(2,6-dioxopiperidin-3-yl)-1,3-dioxoisoindolin-4-yl)thio)hexanoyl)piperazin-1-yl)piperidin-1-yl)propoxy)quinazolin-6-yl)acrylamide | 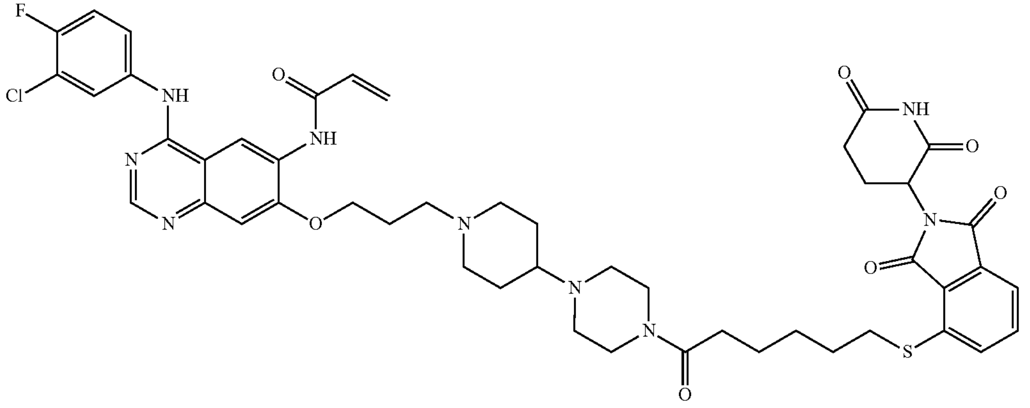 [SMILES: C=CC(=O)Nc1cc2c(Nc3ccc(F)c(Cl)c3)ncnc2cc1OCCCN1CCC(N2CCN(C(=O)CCCCCSc3cccc4c3C(=O)N(C3CCC(=O)NC3=O)C4=O)CC2)CC1] |
| | N-(4-((3-chloro-4-fluorophenyl)amino)-7-(3-(4-(4-(7-((2-(2,6-dioxopiperidin-3-yl)-1,3-dioxoisoindolin-4-yl)thio)heptanoyl)piperazin-1-yl)piperidin-1-yl)propoxy)quinazolin-6-yl)acrylamide | 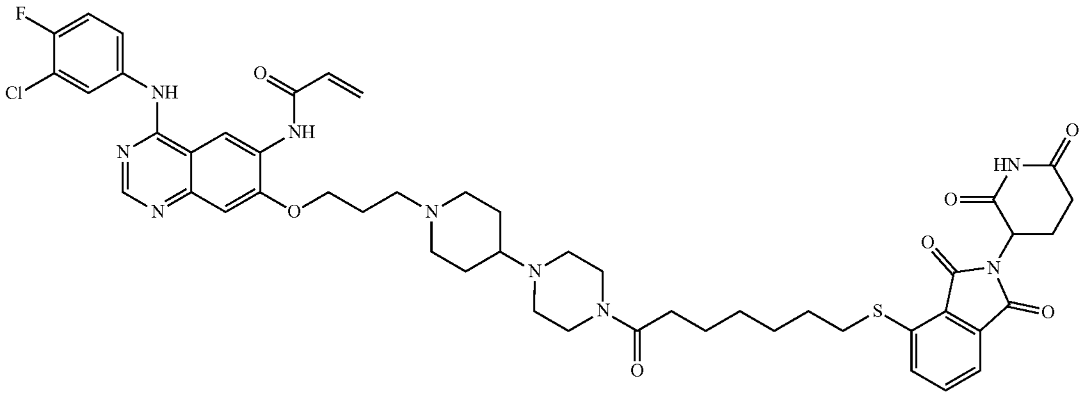 [SMILES: C=CC(=O)Nc1cc2c(Nc3ccc(F)c(Cl)c3)ncnc2cc1OCCCN1CCC(N2CCN(C(=O)CCCCCCSc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-(2-((2-(2,6-dioxopiperidin-3-yl)-1,3-dioxoisoindolin-4-yl)thio)ethoxy)acetyl)piperazin-1-yl)piperidin-1-yl)propoxy)quinazolin-6-yl)acrylamide | 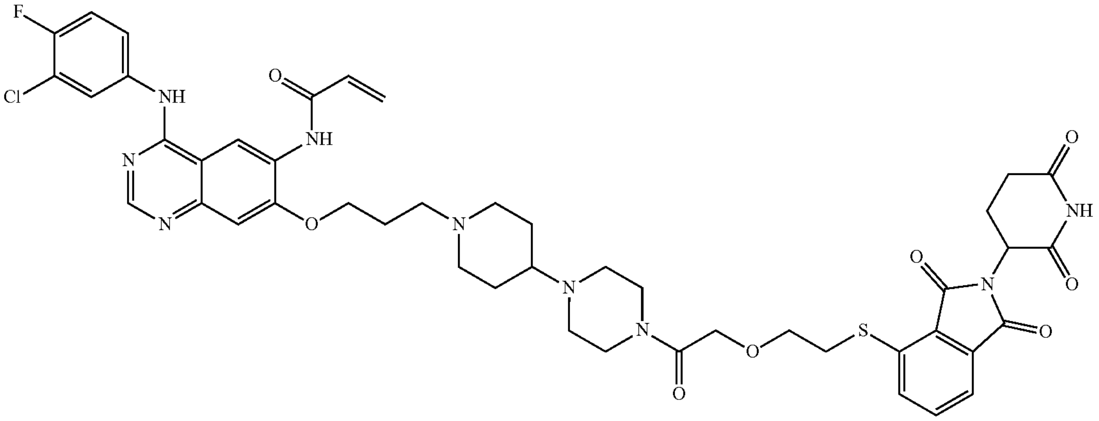 |
| | N-(4-((3-chloro-4-fluorophenyl)amino)-7-(3-(4-(4-(2-(2-(2-((2-(2,6-dioxopiperidin-3-yl)-1,3-dioxoisoindolin-4-yl)thio)ethoxy)ethoxy)acetyl)piperazin-1-yl)piperidin-1-yl)propoxy)quinazolin-6-yl)acrylamide | 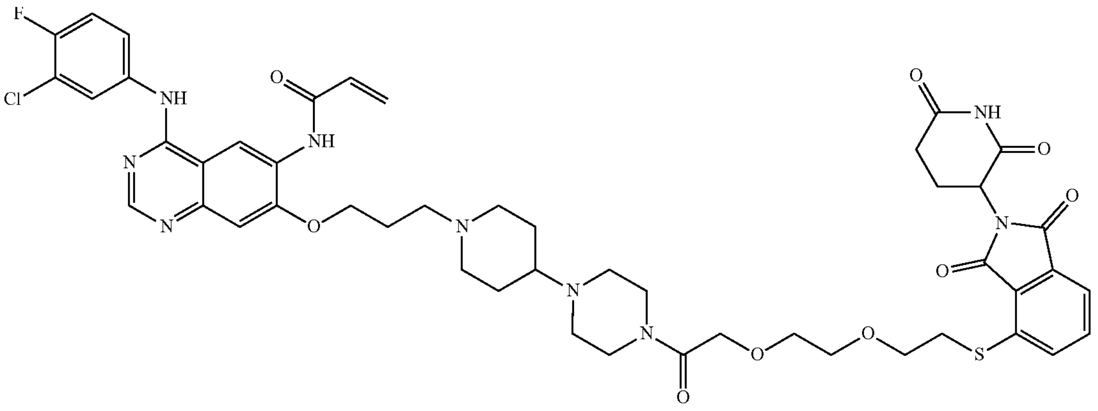 [SMILES: C=CC(=O)Nc1cc2c(Nc3ccc(F)c(Cl)c3)ncnc2cc1OCCCN1CCC(N2CCN(C(=O)COCCOCCSc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)piperidin-1-yl)propoxy)quinazolin-6-yl)acrylamide | 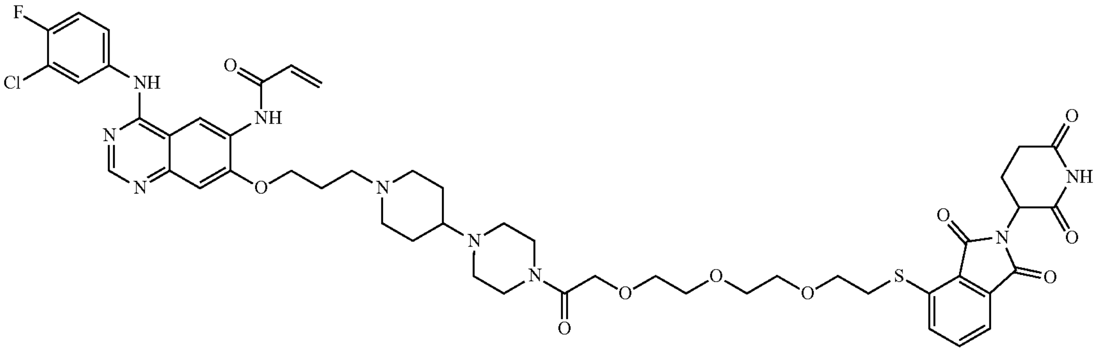 [SMILES: C=CC(=O)Nc1cc2c(Nc3ccc(F)c(Cl)c3)ncnc2cc1OCCCN1CCC(N2CCN(C(=O)COCCOCCOCCSc3cccc4c3C(=O)N(C3CCC(=O)NC3=O)C4=O)CC2)CC1] |
| | N-(4-((3-chloro-4-fluorophenyl)amino)-7-(3-(4-(4-(14-((2-(2,6-dioxopiperidin-3-yl)-1,3-dioxoisoindolin-4-yl)thio)-3,6,9,12-tetraoxatetradecan-1-oyl)piperazin-1-yl)piperidin-1-yl)propoxy)quinazolin-6-yl)acrylamide | 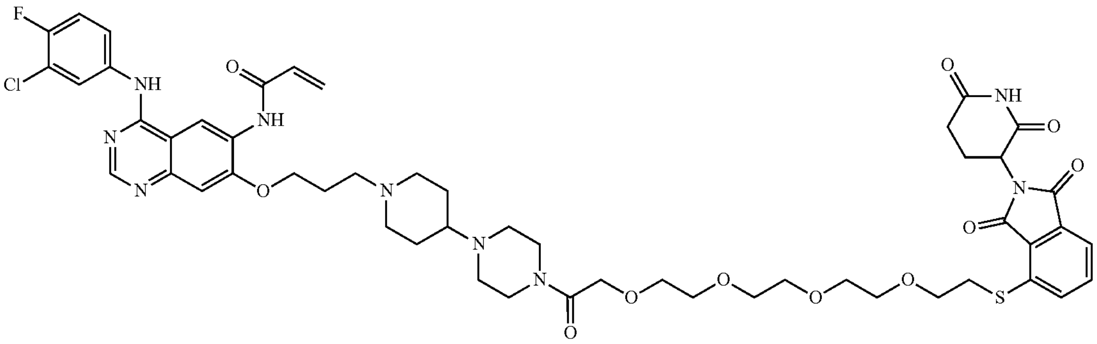 [SMILES: C=CC(=O)Nc1cc2c(Nc3ccc(F)c(Cl)c3)ncnc2cc1OCCCN1CCC(N2CCN(C(=O)COCCOCCOCCOCCSc3cccc4c3C(=O)N(C3CCC(=O)NC3=O)C4=O)CC2)CC1] |
| | N-(4-((3-chloro-4-fluorophenyl)amino)-7-(3-(4-(4-(17-((2-(2,6-dioxopiperidin-3-yl)-1,3-dioxoisoindolin-4-yl)thio)-3,6,9,12,15-pentaoxaheptadecan-1-oyl)piperazin-1-yl)piperidin-1-yl)propoxy)quinazolin-6-yl)acrylamide | 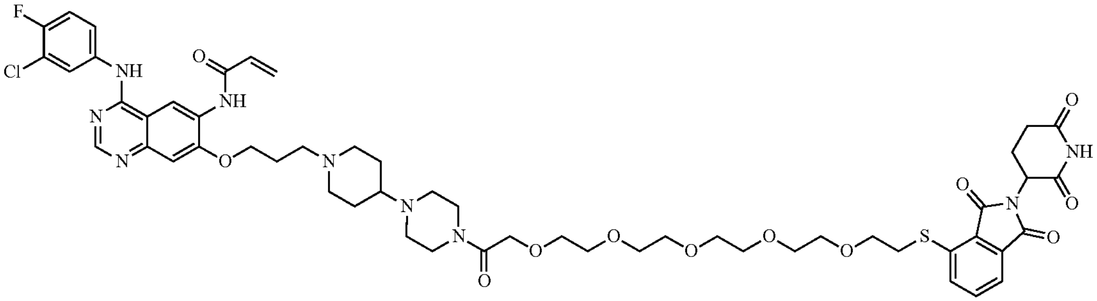 [SMILES: C=CC(=O)Nc1cc2c(Nc3ccc(F)c(Cl)c3)ncnc2cc1OCCCN1CCC(N2CCN(C(=O)COCCOCCOCCOCCOCCSc3cccc4c3C(=O)N(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(3-((2-(2,6-dioxopiperidin-3-yl)-1-oxoisoindolin-4-yl)thio)propanoyl)piperazin-1-yl)piperidin-1-yl)propoxy)quinazolin-6-yl)acrylamide | 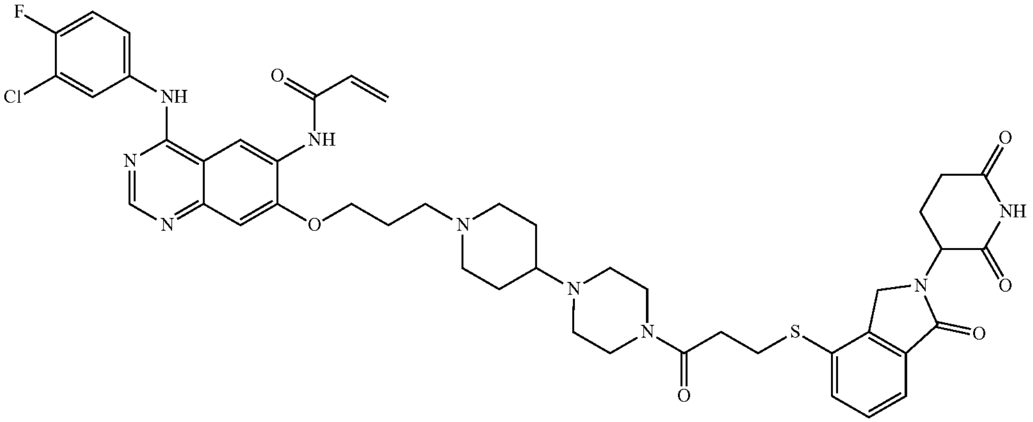 [SMILES: C=CC(=O)Nc1cc2c(Nc3ccc(F)c(Cl)c3)ncnc2cc1OCCCN1CCC(N2CCN(C(=O)CCSc3cccc4c3CN(C3CCC(=O)NC3=O)C4=O)CC2)CC1] |
| | N-(4-((3-chloro-4-fluorophenyl)amino)-7-(3-(4-(4-(4-((2-(2,6-dioxopiperidin-3-yl)-1-oxoisoindolin-4-yl)thio)butanoyl)piperazin-1-yl)piperidin-1-yl)propoxy)quinazolin-6-yl)acrylamide | 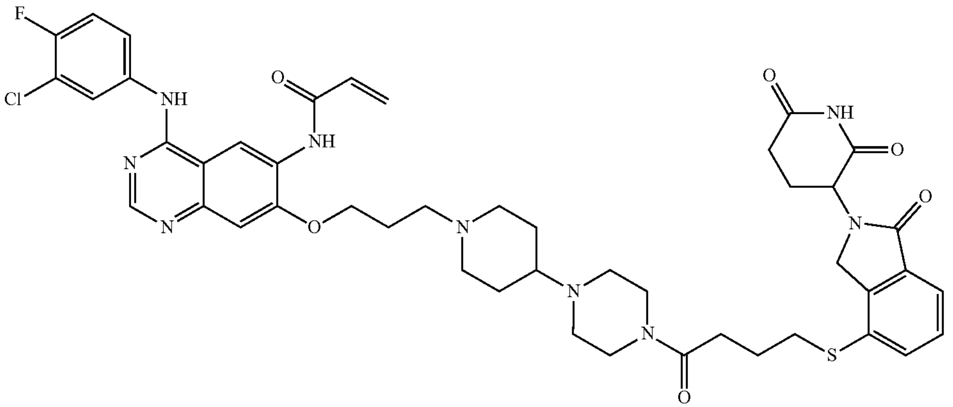 [SMILES: C=CC(=O)Nc1cc2c(Nc3ccc(F)c(Cl)c3)ncnc2cc1OCCCN1CCC(N2CCN(C(=O)CCCSc3cccc4c3CN(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(5-((2-(2,6-dioxopiperidin-3-yl)-1-oxoisoindolin-4-yl)thio)pentyl)piperazin-1-yl)piperidin-1-yl)propoxy)quinazolin-6-yl)acrylamide | 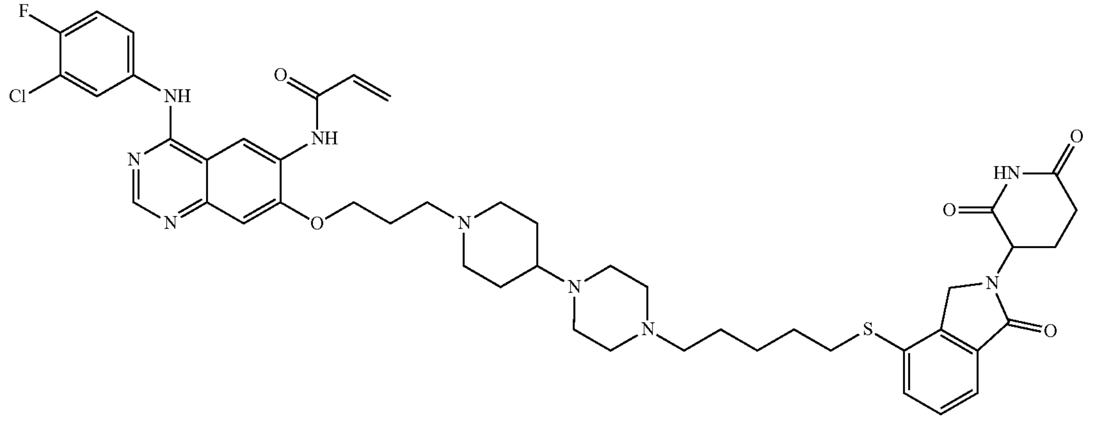 [SMILES: C=CC(=O)Nc1cc2c(Nc3ccc(F)c(Cl)c3)ncnc2cc1OCCCN1CCC(N2CCN(CCCCCSc3cccc4c3CN(C3CCC(=O)NC3=O)C4=O)CC2)CC1] |
| | N-(4-((3-chloro-4-fluorophenyl)amino)-7-(3-(4-(4-(7-((2-(2,6-dioxopiperidin-3-yl)-1-oxoisoindolin-4-yl)thio)heptanoyl)piperazin-1-yl)piperidin-1-yl)propoxy)quinazolin-6-yl)acrylamide | 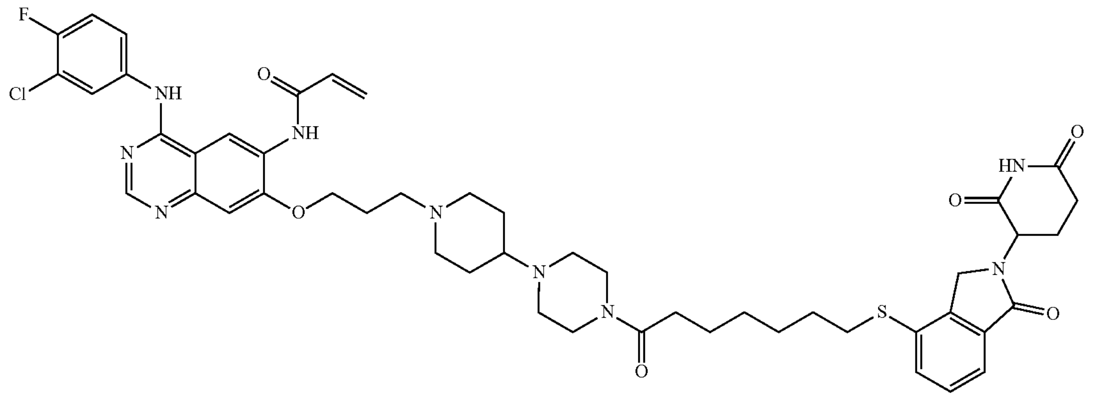 [SMILES: C=CC(=O)Nc1cc2c(Nc3ccc(F)c(Cl)c3)ncnc2cc1OCCCN1CCC(N2CCN(C(=O)CCCCCCSc3cccc4c3CN(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-(2-((2-(2,6-dioxopiperidin-3-yl)-1-oxoisoindolin-4-yl)thio)ethoxy)acetyl)piperazin-1-yl)piperidin-1-yl)propoxy)quinazolin-6-yl)acrylamide | 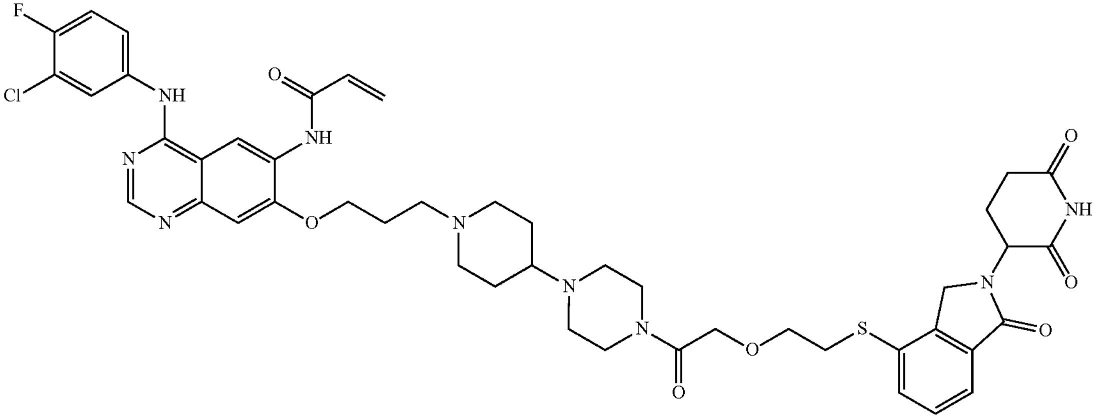 [SMILES: C=CC(=O)Nc1cc2c(Nc3ccc(F)c(Cl)c3)ncnc2cc1OCCCN1CCC(N2CCN(C(=O)COCCSc3cccc4c3CN(C3CCC(=O)NC3=O)C4=O)CC2)CC1] |
| | N-(4-((3-chloro-4-fluorophenyl)amino)-7-(3-(4-(4-(2-(2-(2-((2-(2,6-dioxopiperidin-3-yl)-1-oxoisoindolin-4-yl)thio)ethoxy)ethoxy)acetyl)piperazin-1-yl)piperidin-1-yl)propoxy)quinazolin-6-yl)acrylamide | 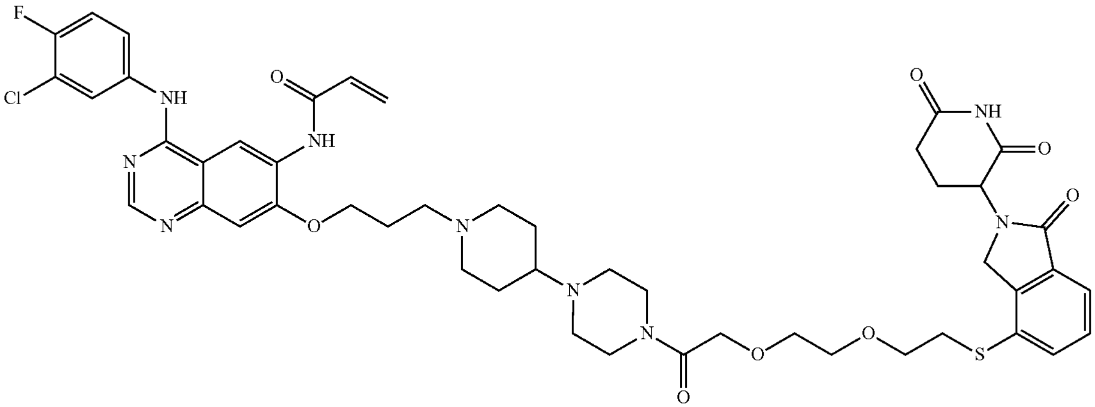 [SMILES: C=CC(=O)Nc1cc2c(Nc3ccc(F)c(Cl)c3)ncnc2cc1OCCCN1CCC(N2CCN(C(=O)COCCOCCSc3cccc4c3CN(C3CCC(=O)NC3=O)C4=O)CC2)CC1] |

TABLE 2-continued

| Compound No. | The compounds' names | Structure of the compounds |
|---|---|---|
| | N-(4-((3-chloro-4-fluorophenyl)amino)-7-(3-(4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)piperidin-1-yl)propoxy)quinazolin-6-yl)acrylamide | 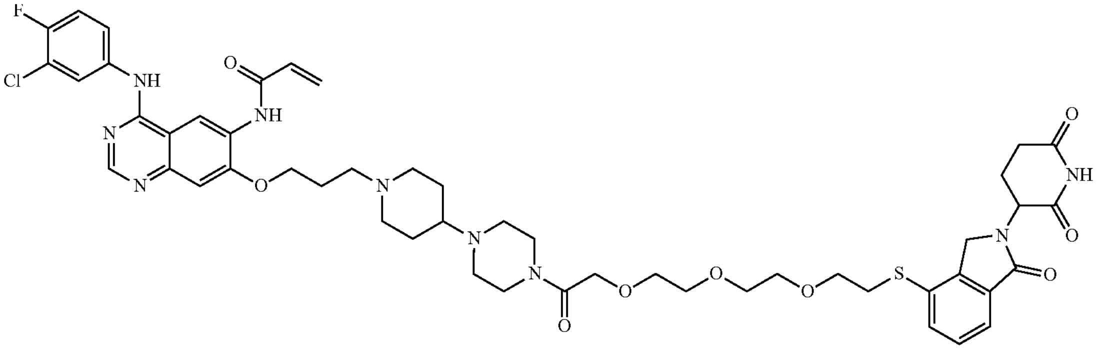 [SMILES: C=CC(=O)Nc1cc2c(Nc3ccc(F)c(Cl)c3)ncnc2cc1OCCCN1CCC(N2CCN(C(=O)COCCOCCOCCSc3cccc4c3CN(C3CCC(=O)NC3=O)C4=O)CC2)CC1] |
| | N-(4-((3-chloro-4-fluorophenyl)amino)-7-(3-(4-(4-(14-((2-(2,6-dioxopiperidin-3-yl)-1-oxoisoindolin-4-yl)thio)-3,6,9,12-tetraoxatetradecan-1-oyl)piperazin-1-yl)piperidin-1-yl)propoxy)quinazolin-6-yl)acrylamide | 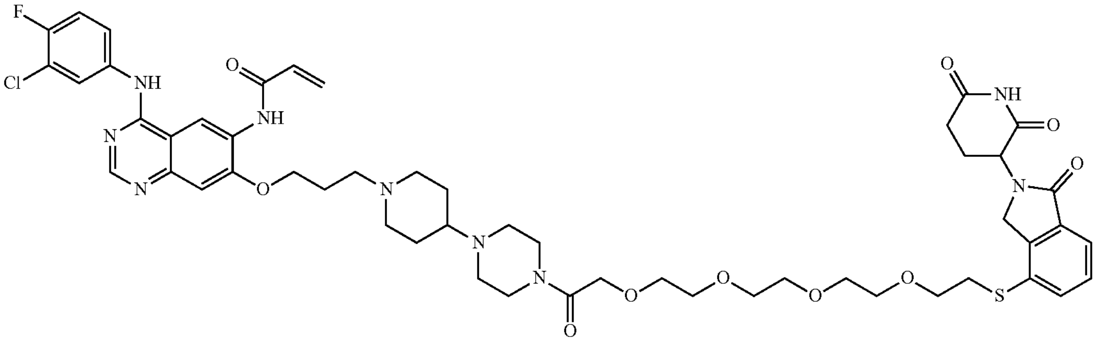 [SMILES: C=CC(=O)Nc1cc2c(Nc3ccc(F)c(Cl)c3)ncnc2cc1OCCCN1CCC(N2CCN(C(=O)COCCOCCOCCOCCSc3cccc4c3CN(C3CCC(=O)NC3=O)C4=O)CC2)CC1] |
| | N-(4-((3-chloro-4-fluorophenyl)amino)-7-(3-(4-(4-(17-((2-(2,6-dioxopiperidin-3-yl)-1-isoindolin-4-yl)thio)-3,6,9,12,15-pentaoxaheptadecan-1-oyl)piperazin-1-yl)piperidin-1-yl)propoxy)quinazolin-6-yl)acrylamide | 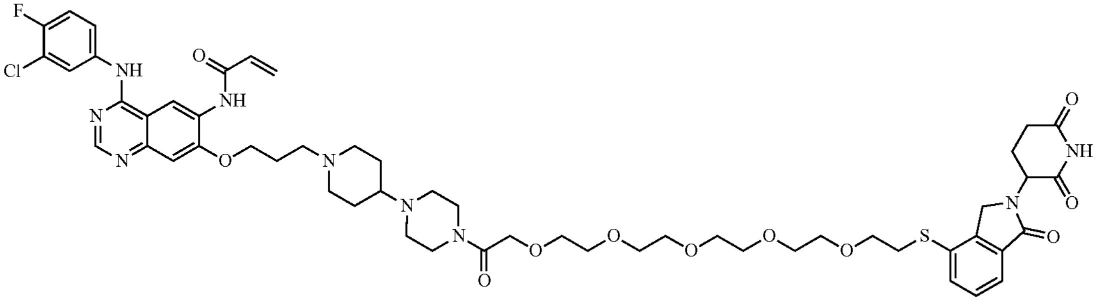 [SMILES: C=CC(=O)Nc1cc2c(Nc3ccc(F)c(Cl)c3)ncnc2cc1OCCCN1CCC(N2CCN(C(=O)COCCOCCOCCOCCOCCSc3cccc4c3CN(C3CCC(=O)NC3=O)C4=O)CC2)CC1] |

TABLE 2-continued

| Compound No. | The compounds' names | Structure of the compounds |
|---|---|---|
| | (2S,4R)-1-((S)-2-(3-(2-(3-(4-(1-(3-((6-acrylamido-4-((3-chloro-4-fluorophenyl)amino)quinazolin-7-yl)oxy)propyl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide | 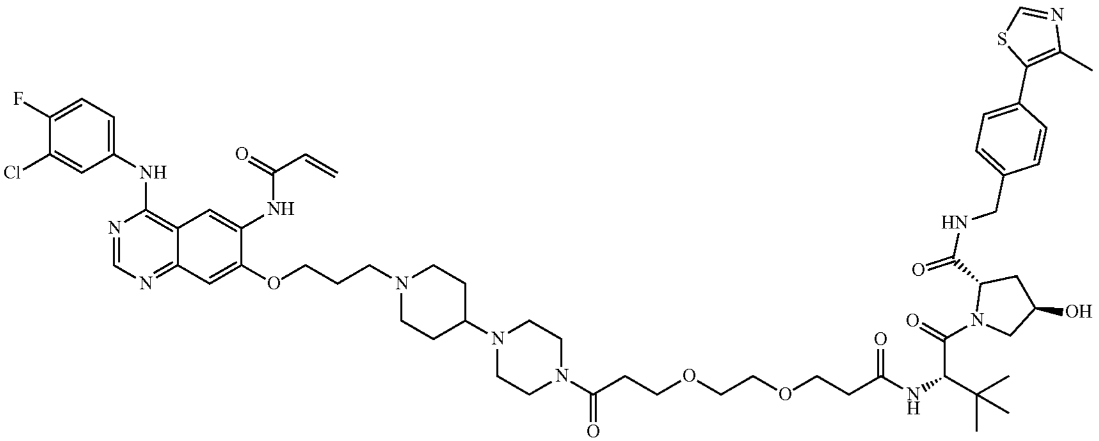 [SMILES: C=CC(=O)Nc1cc2c(Nc3ccc(F)c(Cl)c3)ncnc2cc1OCCCN1CCC(N2CCN(C(=O)CCOCCOCCC(=O)N[C@H](C(=O)N3C[C@H](O)C[C@H]3C(=O)NCc3ccc(-c4scnc4C)cc3)C(C)(C)C)CC2)CC1] |
| | (2S,4R)-1-((S)-19-(4-(1-(3-((6-acrylamido-4-((3-chloro-4-fluorophenyl)amino)quinazolin-7-yl)oxy)propyl)piperidin-4-yl)piperazin-1-yl)-2-(tert-butyl)-4,19-dioxo-7,10,13,16-tetraoxa-3-azanonadecan-1-oyl)-4-hydroxy-N-(4-(4-methylthiazol-5-yl)benzyl)pyrrolidine-2-carboxamide | 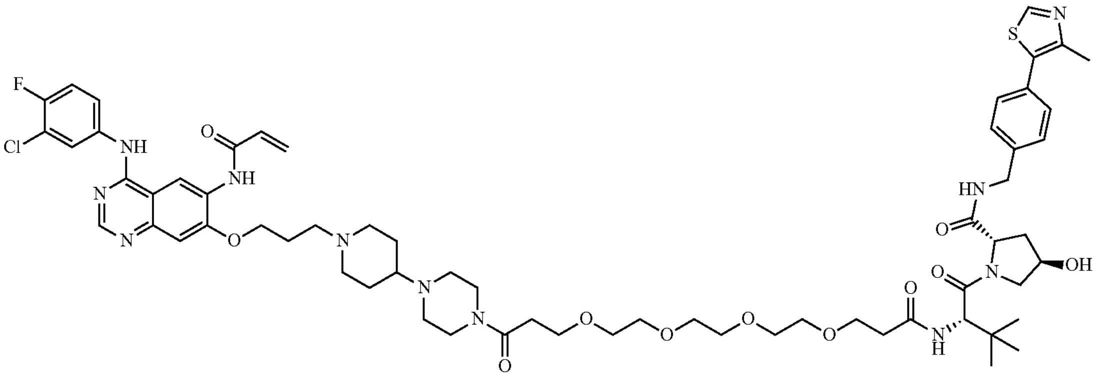 [SMILES: C=CC(=O)Nc1cc2c(Nc3ccc(F)c(Cl)c3)ncnc2cc1OCCCN1CCC(N2CCN(C(=O)CCOCCOCCOCCOCCC(=O)N[C@H](C(=O)N3C[C@H](O)C[C@H]3C(=O)NCc3ccc(-c4scnc4C)cc3)C(C)(C)C)CC2)CC1] |

TABLE 2-continued

| Compound No. | The compounds' names | Structure of the compounds |
| --- | --- | --- |
| 343 | (2S,4R)-1-((S)-2-(4-(4-(1-(3-((6-acrylamido-4-((3-chloro-4-fluorophenyl)amino)quinazolin-7-yl)oxy)propyl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide | 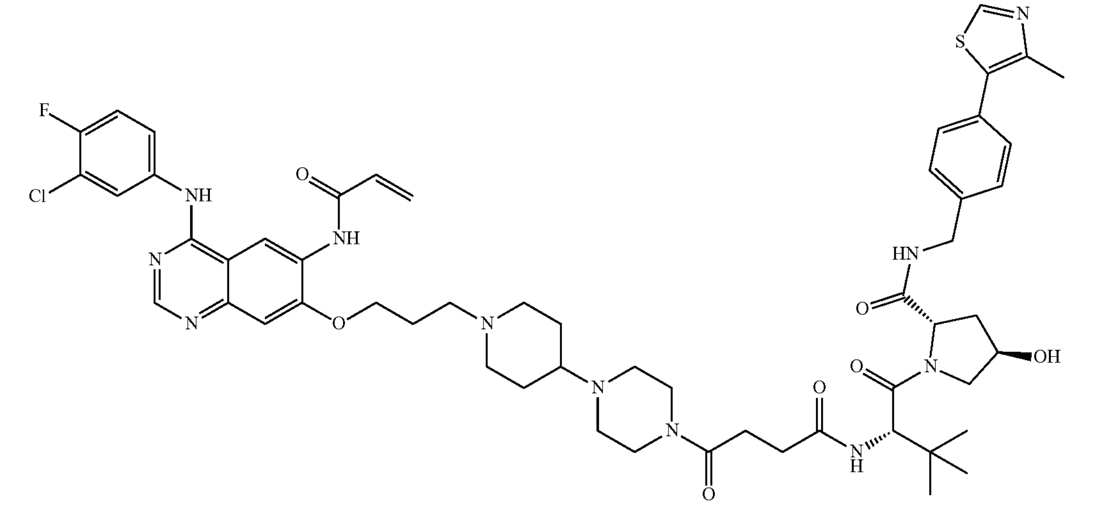 [SMILES: C=CC(=O)Nc1cc2c(Nc3ccc(F)c(Cl)c3)ncnc2cc1OCCCN1CCC(N2CCN(C(=O)CCC(=O)N[C@H](C(=O)N3C[C@H](O)C[C@H]3C(=O)NCc3ccc(-c4scnc4C)cc3)C(C)(C)C)CC2)CC1] |
| 344 | (2S,4R)-1-((S)-2-(6-(4-(1-(3-((6-acrylamido-4-((3-chloro-4-fluorophenyl)amino)quinazolin-7-yl)oxy)propyl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide | 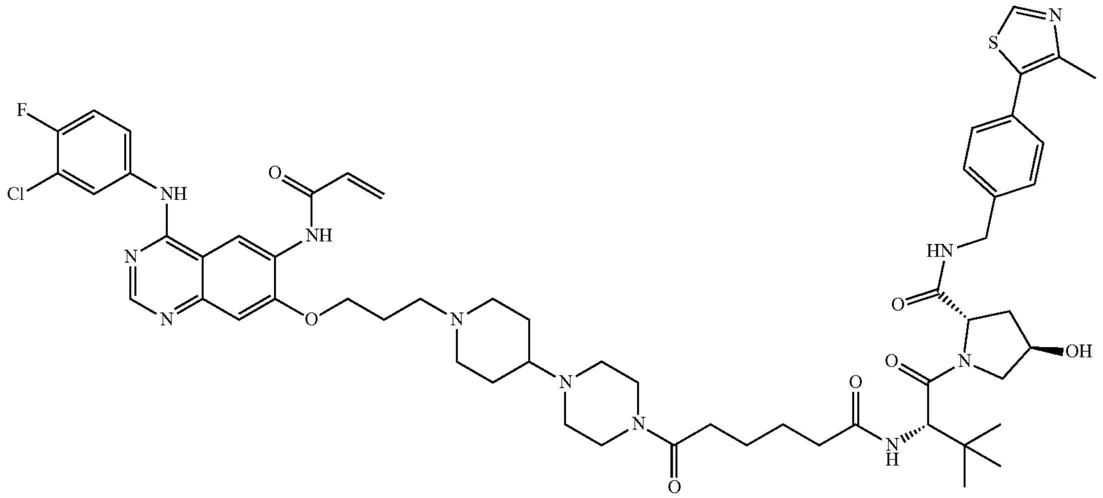 [SMILES: C=CC(=O)Nc1cc2c(Nc3ccc(F)c(Cl)c3)ncnc2cc1OCCCN1CCC(N2CCN(C(=O)CCCCC(=O)N[C@H](C(=O)N3C[C@H](O)C[C@H]3C(=O)NCc3ccc(-c4scnc4C)cc3)C(C)(C)C)CC2)CC1] |

TABLE 2-continued

| Com-pound No. | The compounds' names | Structure of the compounds |
|---|---|---|
| | (2S,4R)-1-((S)-2-(8-(4-(1-(3-((6-acrylamido-4-((3-chloro-4-fluorophenyl)amino)quinazolin-7-yl)oxy)propyl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide | 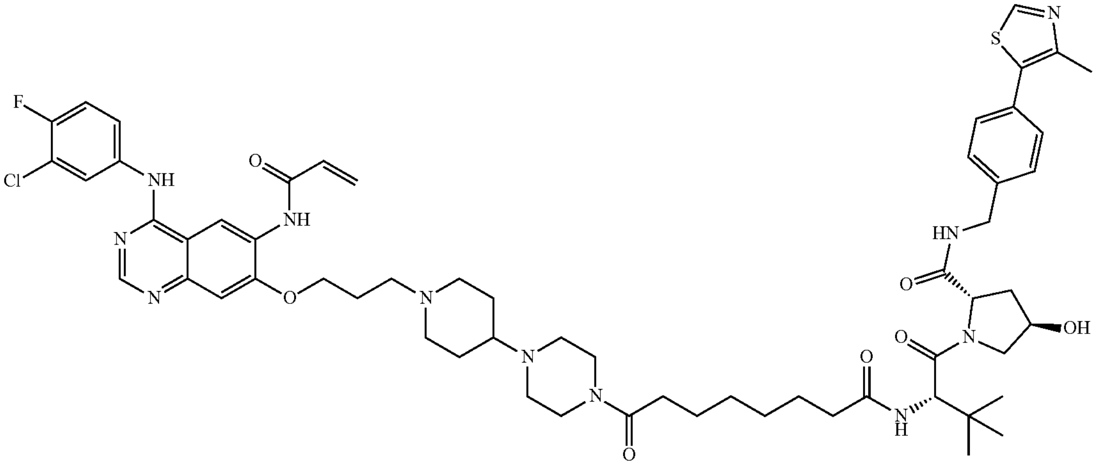 [SMILES: C=CC(=O)Nc1cc2c(Nc3ccc(F)c(Cl)c3)ncnc2cc1OCCCN1CCC(N2CCN(C(=O)CCCCCCC(=O)N[C@H](C(=O)N3C[C@H](O)C[C@H]3C(=O)NCc3ccc(-c4scnc4C)cc3)C(C)(C)C)CC2)CC1] |
| | (2S,4R)-1-((S)-2-(10-(4-(1-(3-((6-acrylamido-4-((3-chloro-4-fluorophenyl)amino)quinazolin-7-yl)oxy)propyl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide | 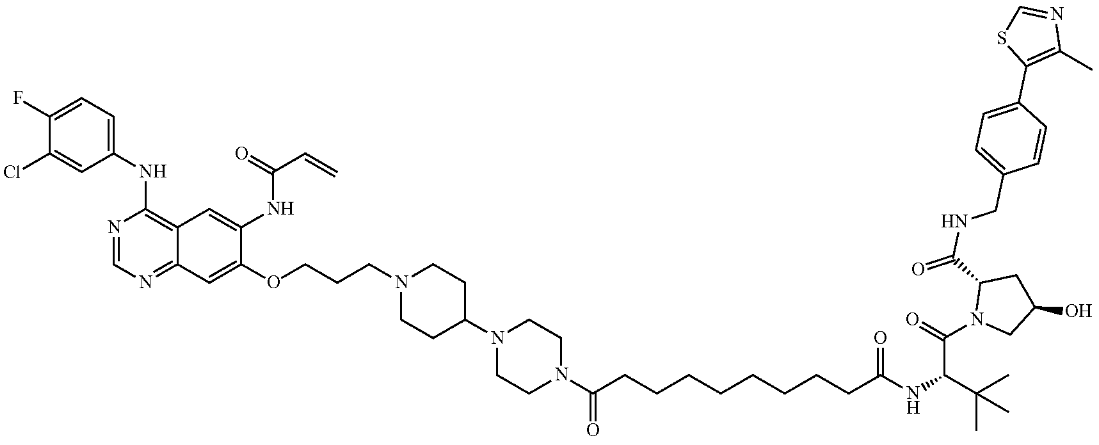 [SMILES: C=CC(=O)Nc1cc2c(Nc3ccc(F)c(Cl)c3)ncnc2cc1OCCCN1CCC(N2CCN(C(=O)CCCCCCCCC(=O)N[C@H](C(=O)N3C[C@H](O)C[C@H]3C(=O)NCc3ccc(-c4scnc4C)cc3)C(C)(C)C)CC2)CC1] |

TABLE 2-continued
| Compound No. | The compounds' names | Structure of the compounds |
|---|---|---|
| | 2-(6-(4-(4-(4-((2-(2,6-dioxopiperidin-3-yl)-1-oxoisoindolin-4-yl)thio)butyl)piperazin-1-yl)piperidin-1-yl)-1-oxoisoindolin-2-yl)-2-phenyl-N-(thiazol-2-yl)acetamide | 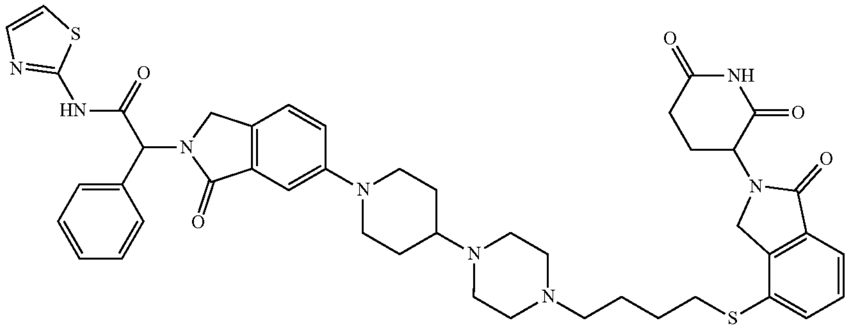 [SMILES: O=C1CCC(N2Cc3c(SCCCCN4CCN(C5CCN(c6ccc7c(c6)C(=O)N(C(C(=O)Nc6nccs6)c6ccccc6)C7)CC5)CC4)cccc3C2=O)C(=O)N1] |
| | 2-(6-(4-(4-(6-((2-(2,6-dioxopiperidin-3-yl)-1-oxoisoindolin-4-yl)thio)hexyl)piperazin-1-yl)piperidin-1-yl)-1-oxoisoindolin-2-yl)-2-phenyl-N-(thiazol-2-yl)acetamide | 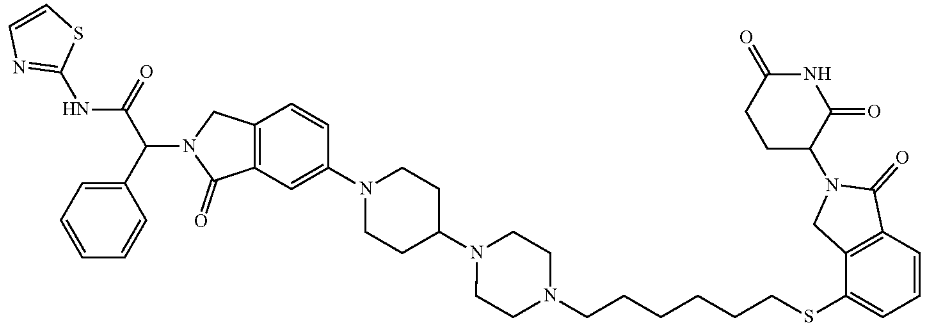 [SMILES: O=C1CCC(N2Cc3c(SCCCCCCN4CCN(C5CCN(c6ccc7c(c6)C(=O)N(C(C(=O)Nc6nccs6)c6ccccc6)C7)CC5)CC4)cccc3C2=O)C(=O)N1] |

TABLE 2-continued
| Compound No. | The compounds' names | Structure of the compounds |
|---|---|---|
| | 2-(6-(4-(4-(7-((2-(2,6-dioxopiperidin-3-yl)-1-oxoisoindolin-4-yl)thio)heptyl)piperazin-1-yl)piperidin-1-yl)-1-oxoisoindolin-2-yl)-2-phenyl-N-(thiazol-2-yl)acetamide | 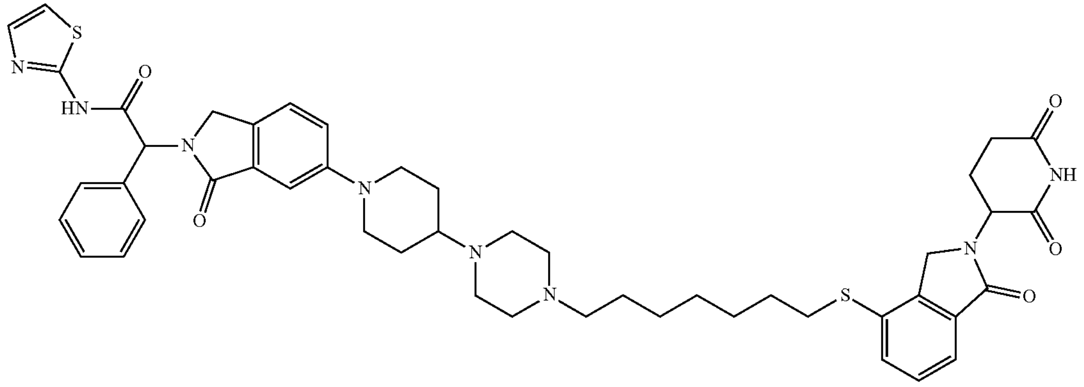 [SMILES: O=C1CCC(N2Cc3c(SCCCCCCCN4CCN(C5CCN(c6ccc7c(c6)C(=O)N(C(C(=O)Nc6nccs6)c6ccccc6)C7)CC5)CC4)cccc3C2=O)C(=O)N1] |
| | 2-(6-(4-(4-(8-((2-(2,6-dioxopiperidin-3-yl)-1-oxoisoindolin-4-yl)thio)octyl)piperazin-1-yl)piperidin-1-yl)-1-oxoisoindolin-2-yl)-2-phenyl-N-(thiazol-2-yl)acetamide | 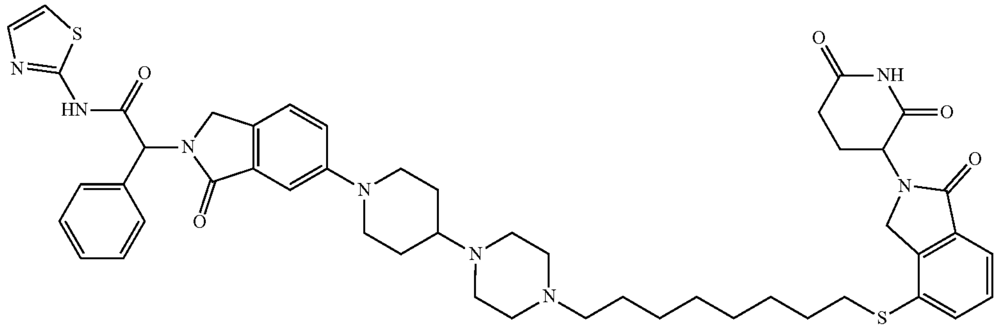 [SMILES: O=C1CCC(N2Cc3c(SCCCCCCCCN4CCN(C5CCN(c6ccc7c(c6)C(=O)N(C(C(=O)Nc6nccs6)c6ccccc6)C7)CC5)CC4)cccc3C2=O)C(=O)N1] |

TABLE 2-continued
| Compound No. | The compounds' names | Structure of the compounds |
|---|---|---|
| | 2-(6-(4-(4-(11-((2-(2,6-dioxopiperidin-3-yl)-1-oxoisoindolin-4-yl)thio)undecyl)piperazin-1-yl)piperidin-1-yl)-1-oxoisoindolin-2-yl)-2-phenyl-N-(thiazol-2-yl)acetamide | 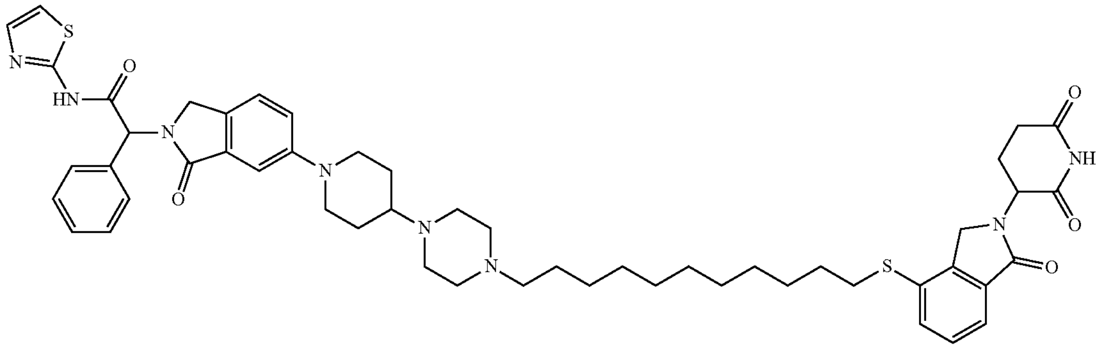 [SMILES: O=C1CCC(N2Cc3c(SCCCCCCCCCCCN4CCN(C5CCN(c6ccc7c(c6)C(=O)N(C(C(=O)Nc6nccs6)c6ccccc6)C7)CC5)CC4)cccc3C2=O)C(=O)N1] |
| | 2-(6-(4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)piperidin-1-yl)-1-oxoisoindolin-2-yl)-2-phenyl-N-(thiazol-2-yl)acetamide | 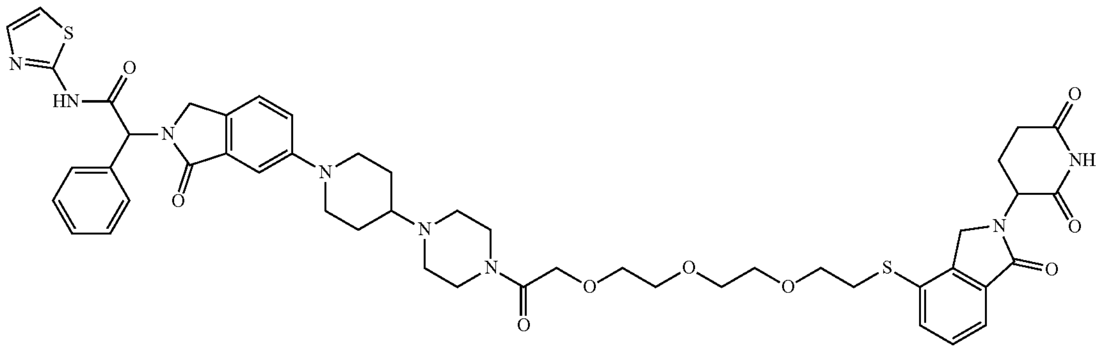 [SMILES: O=C1CCC(N2Cc3c(SCCOCCOCCOCC(=O)N4CCN(C5CCN(c6ccc7c(c6)C(=O)N(C(C(=O)Nc6nccs6)c6ccccc6)C7)CC5)CC4)cccc3C2=O)C(=O)N1] |

TABLE 2-continued
| Compound No. | The compounds' names | Structure of the compounds |
|---|---|---|
| | 2-(6-(4-(4-(14-((2-(2,6-dioxopiperidin-3-yl)-1-oxoisoindolin-4-yl)thio)-3,6,9,12-tetraoxatetradecan-1-oyl)piperazin-1-yl)piperidin-1-yl)-1-oxoisoindolin-2-yl)-2-phenyl-N-(thiazol-2-yl)acetamide | 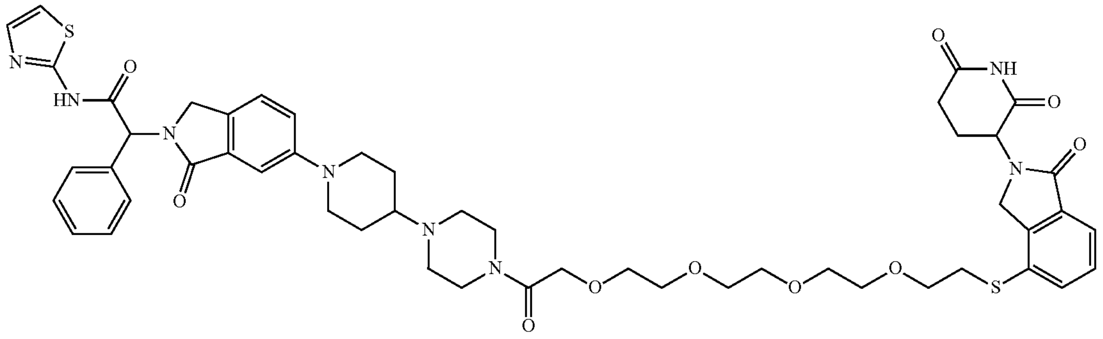 [SMILES: O=C1CCC(N2Cc3c(SCCOCCOCCOCCOCC(=O)N4CCN(C5CCN(c6ccc7c(c6)C(=O)N(C(C(=O)Nc6nccs6)c6ccccc6)C7)CC5)CC4)cccc3C2=O)C(=O)N1] |
| | 2-(6-(4-(4-(2-((2-(2,6-dioxopiperidin-3-yl)-1,3-dioxoisoindolin-4-yl)amino)acetyl)piperazin-1-yl)piperidin-1-yl)-1-oxoisoindolin-2-yl)-2-phenyl-N-(thiazol-2-yl)acetamide | 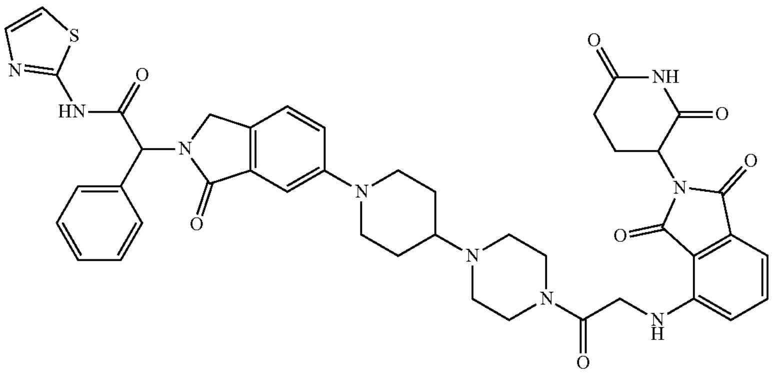 [SMILES: O=C1CCC(N2C(=O)c3cccc(NCC(=O)N4CCN(C5CCN(c6ccc7c(c6)C(=O)N(C(C(=O)Nc6nccs6)c6ccccc6)C7)CC5)CC4)c3C2=O)C(=O)N1] |

TABLE 2-continued
| Compound No. | The compounds' names | Structure of the compounds |
|---|---|---|
| | 2-(6-(4-(4-(5-((2-(2,6-dioxopiperidin-3-yl)-1,3-dioxoisoindolin-4-yl)amino)pentyl)piperazin-1-yl)piperidin-1-yl)-1-oxoisoindolin-2-yl)-2-phenyl-N-(thiazol-2-yl)acetamide | 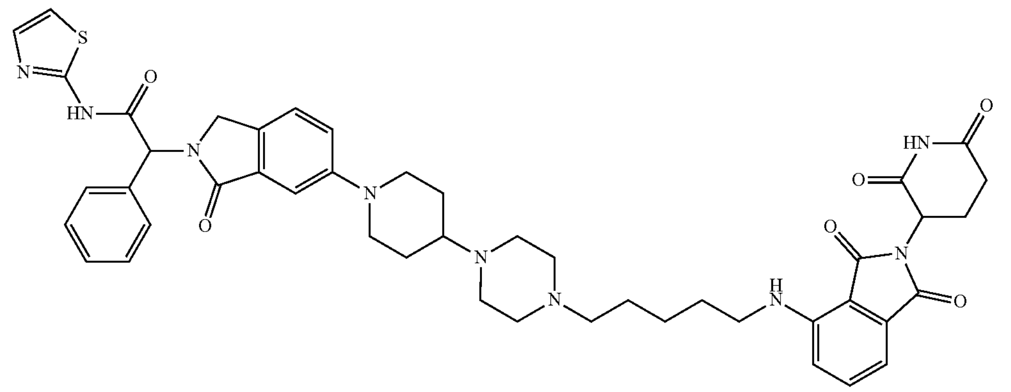 [SMILES: O=C1CCC(N2C(=O)c3cccc(NCCCCCN4CCN(C5CCN(c6ccc7c(c6)C(=O)N(C(C(=O)Nc6nccs6)c6ccccc6)C7)CC5)CC4)c3C2=O)C(=O)N1] |
| | 2-(6-(4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)piperidin-1-yl)-1-oxoisoindolin-2-yl)-2-phenyl-N-(thiazol-2-yl)acetamide | 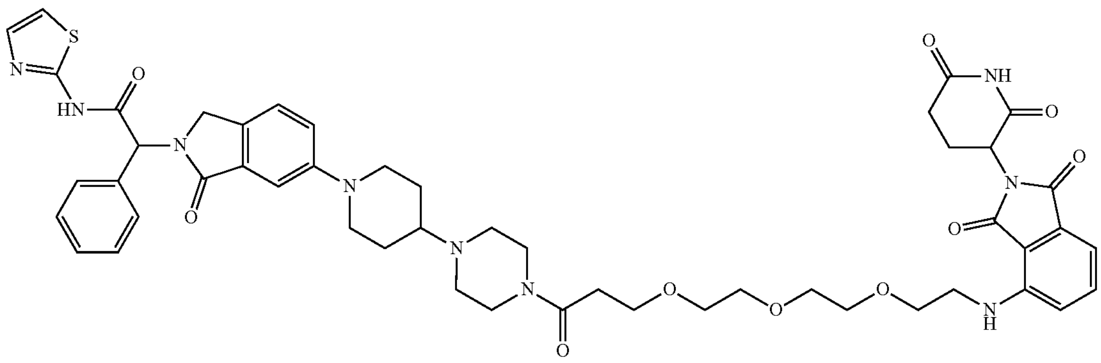 [SMILES: O=C1CCC(N2C(=O)c3cccc(NCCOCCOCCOCCC(=O)N4CCN(C5CCN(c6ccc7c(c6)C(=O)N(C(C(=O)Nc6nccs6)c6ccccc6)C7)CC5)CC4)c3C2=O)C(=O)N1] |

TABLE 2-continued
| Compound No. | The compounds' names | Structure of the compounds |
|---|---|---|
| | 2-(6-(4-(4-(5-(2-(2,6-dioxopiperidin-3-yl)-1-oxoisoindolin-4-yl)pent-4-yn-1-yl)piperazin-1-yl)piperidin-1-yl)-1-oxoisoindolin-2-yl)-2-phenyl-N-(thiazol-2-yl)acetamide | 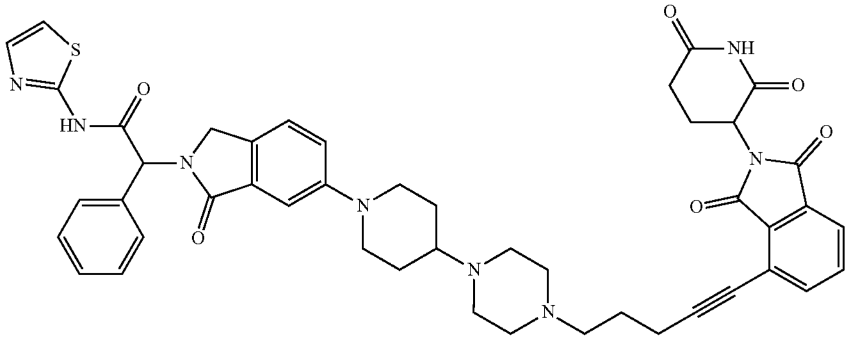 [SMILES: O=C1CCC(N2C(=O)c3cccc(C#CCCCN4CCN(C5CCN(c6ccc7c(c6)C(=O)N(C(C(=O)Nc6nccs6)c6ccccc6)C7)CC5)CC4)c3C2=O)C(=O)N1] |
| | 2-(6-(4-(4-(6-(2-(2,6-dioxopiperidin-3-yl)-1-oxoisoindolin-4-yl)hex-5-yn-1-yl)piperazin-1-yl)piperidin-1-yl)-1-oxoisoindolin-2-yl)-2-phenyl-N-(thiazol-2-yl)acetamide | 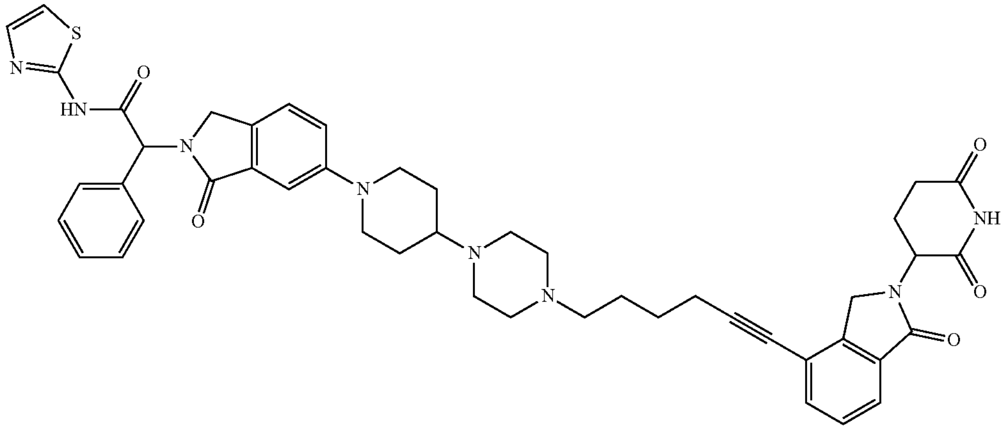 [SMILES: O=C1CCC(N2Cc3c(C#CCCCCN4CCN(C5CCN(c6ccc7c(c6)C(=O)N(C(C(=O)Nc6nccs6)c6ccccc6)C7)CC5)CC4)cccc3C2=O)C(=O)N1] |

TABLE 2-continued
| Compound No. | The compounds' names | Structure of the compounds |
|---|---|---|
| | 2-(6-(4-(4-(9-(2-(2,6-dioxopiperidin-3-yl)-1-oxoisoindolin-4-yl)non-8-yn-1-yl)piperazin-1-yl)piperidin-1-yl)-1-oxoisoindolin-2-yl)-2-phenyl-N-(thiazol-2-yl)acetamide | 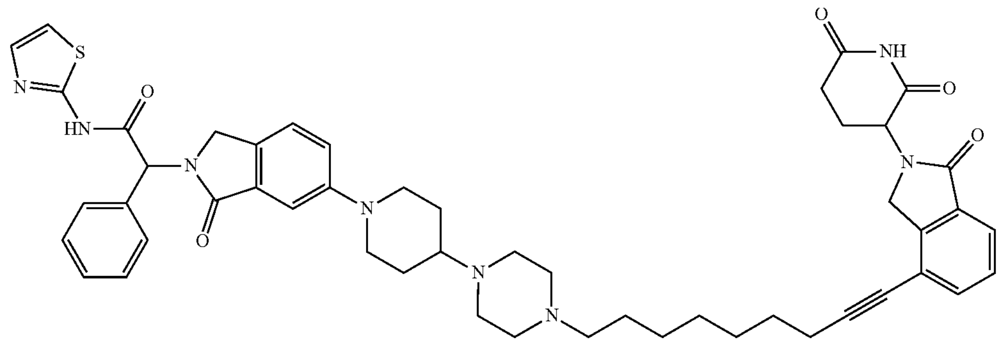 [SMILES: O=C1CCC(N2Cc3c(C#CCCCCCCCN4CCN(C5CCN(c6ccc7c(c6)C(=O)N(C(C(=O)Nc6nccs6)c6ccccc6)C7)CC5)CC4)cccc3C2=O)C(=O)N1] |
| | 2-(6-(4-(4-(3-(2-((2-(2,6-dioxopiperidin-3-yl)-1,3-dioxoisoindolin-4-yl)amino)ethoxy)propanoyl)piperazin-1-yl)piperidin-1-yl)-1-oxoisoindolin-2-yl)-2-(5-fluoro-2-hydroxyphenyl)-N-(thiazol-2-yl)acetamide | 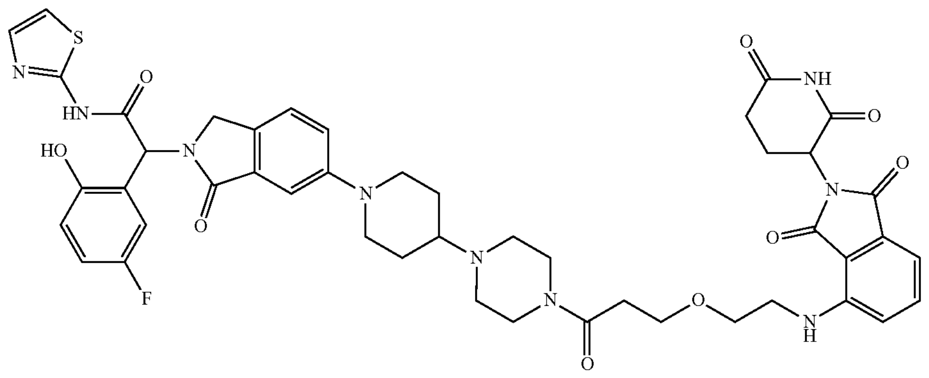 [SMILES: O=C1CCC(N2C(=O)c3cccc(NCCOCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(3-(2-(2-((2-(2,6-dioxopiperidin-3-yl)-1,3-dioxoisoindolin-4-yl)amino)ethoxy)ethoxy)propanoyl)piperazin-1-yl)piperidin-1-yl)-1-oxoisoindolin-2-yl)-2-(5-fluoro-2-hydroxyphenyl)-N-(thiazol-2-yl)acetamide | 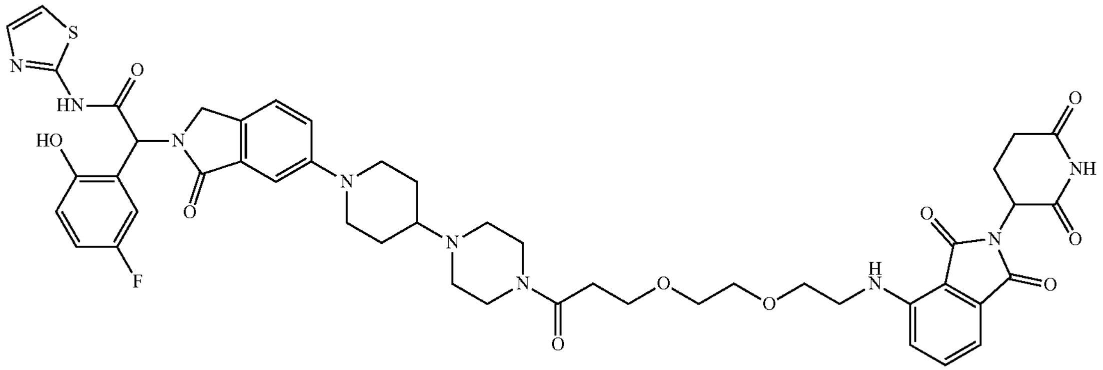 [SMILES: O=C1CCC(N2C(=O)c3cccc(NCCOCCOCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)piperidin-1-yl)-1-oxoisoindolin-2-yl)-2-(5-fluoro-2-hydroxyphenyl)-N-(thiazol-2-yl)acetamide | 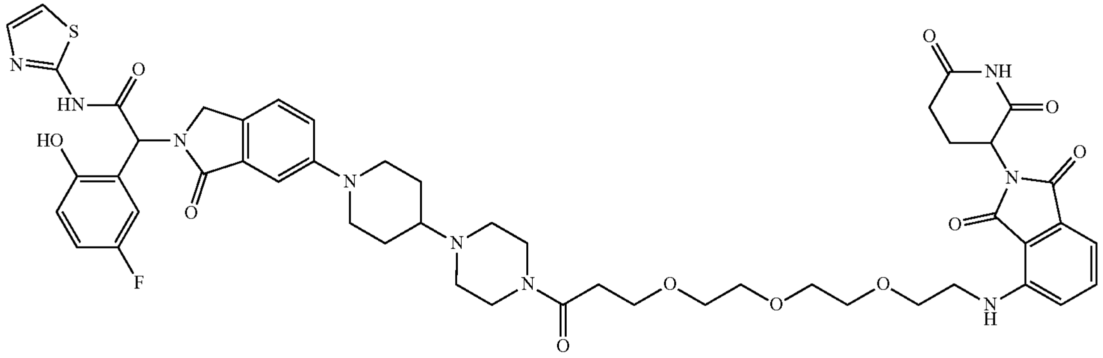 [SMILES: O=C1CCC(N2C(=O)c3cccc(NCCOCCOCCOCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
| --- | --- | --- |
| | 2-(6-(4-(4-(1-((2-(2,6-dioxopiperidin-3-yl)-1,3-dioxoisoindolin-4-yl)amino)-3,6,9,12-tetraoxapentadecan-15-o yl)piperazin-1-yl)piperidin-1-yl)-1-oxoisoindolin-2-yl)-2-(5-fluoro-2-hydroxyphenyl)-N-(thiazol-2-yl)acetamide | 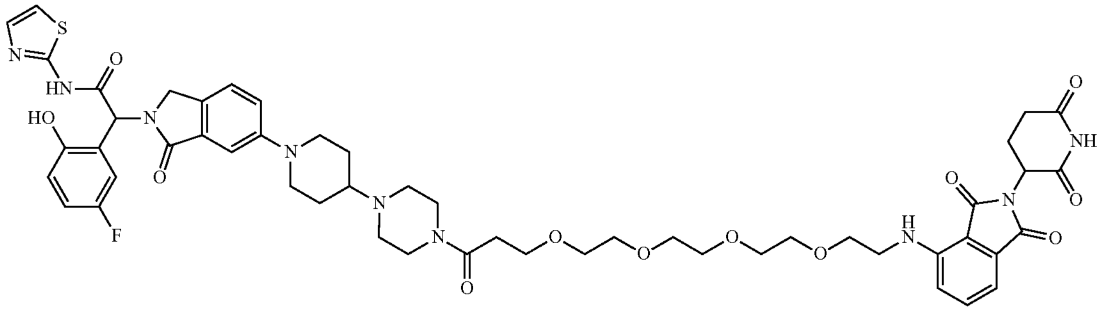 [SMILES: O=C1CCC(N2C(=O)c3cccc(NCCOCCOCCOCCOCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)piperidin-1-yl)-1-oxoisoindolin-2-yl)-2-(5-fluoro-2-hydroxyphenyl)-N-(thiazol-2-yl)acetamide | 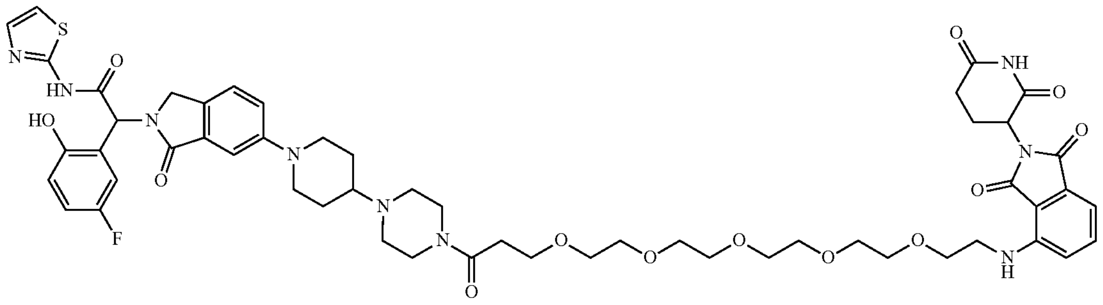 [SMILES: O=C1CCC(N2C(=O)c3cccc(NCCOCCOCCOCCOCCOCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(2-((2-(2,6-dioxopiperidin-3-yl)-1,3-dioxoisoindolin-4-yl)amino)acetyl)piperazin-1-yl)piperidin-1-yl)-1-oxoisoindolin-2-yl)-2-(5-fluoro-2-hydroxyphenyl)-N-(thiazol-2-yl)acetamide | 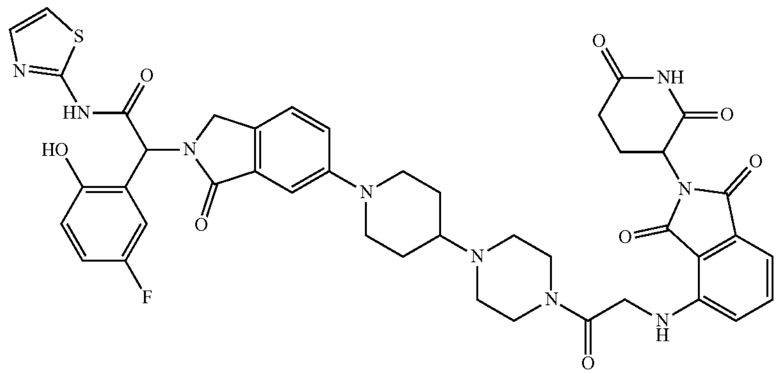 |

TABLE 2-continued

| Compound No. | The compounds' names | Structure of the compounds |
|---|---|---|
| | 2-(6-(4-(4-(3-((2-(2,6-dioxopiperidin-3-yl)-1,3-dioxoisoindolin-4-yl)amino)propanoyl)piperazin-1-yl)piperidin-1-yl)-1-oxoisoindolin-2-yl)-2-(5-fluoro-2-hydroxyphenyl)-N-(thiazol-2-yl)acetamide | 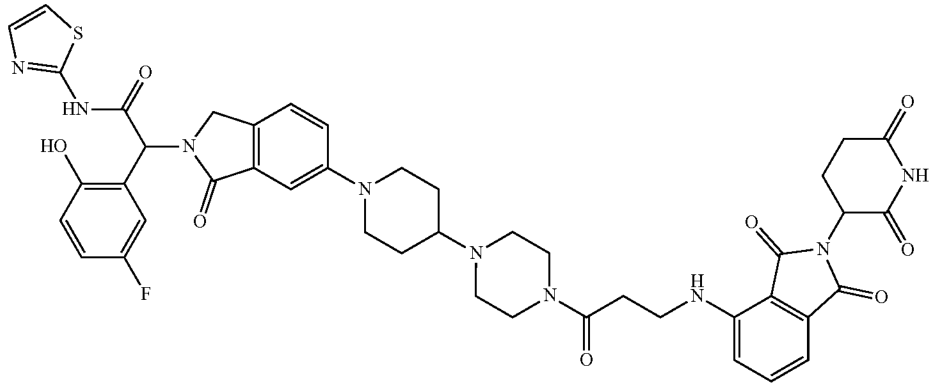 [SMILES: O=C1CCC(N2C(=O)c3cccc(NCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(4-((2-(2,6-dioxopiperidin-3-yl)-1,3-dioxoisoindolin-4-yl)amino)butanoyl)piperazin-1-yl)piperidin-1-yl)-1-oxoisoindolin-2-yl)-2-(5-fluoro-2-hydroxyphenyl)-N-(thiazol-2-yl)acetamide | 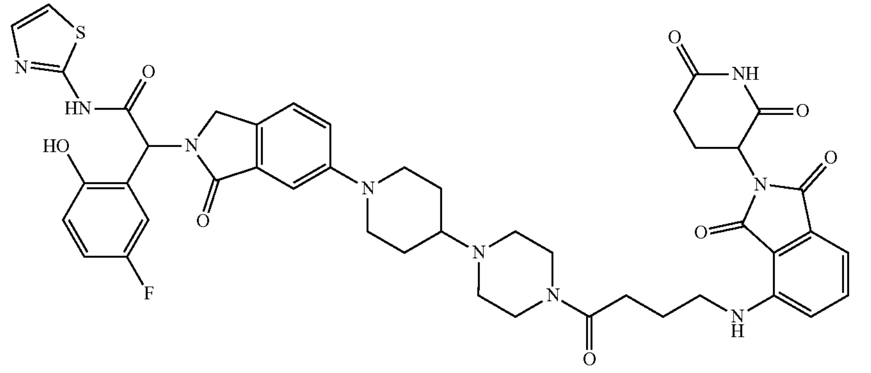 [SMILES: O=C1CCC(N2C(=O)c3cccc(NCCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(5-((2-(2,6-dioxopiperidin-3-yl)-1,3-dioxoisoindolin-4-yl)amino)pentanoyl)piperazin-1-yl)piperidin-1-yl)-1-oxoisoindolin-2-yl)-2-(5-fluoro-2-hydroxyphenyl)-N-(thiazol-2-yl)acetamide | 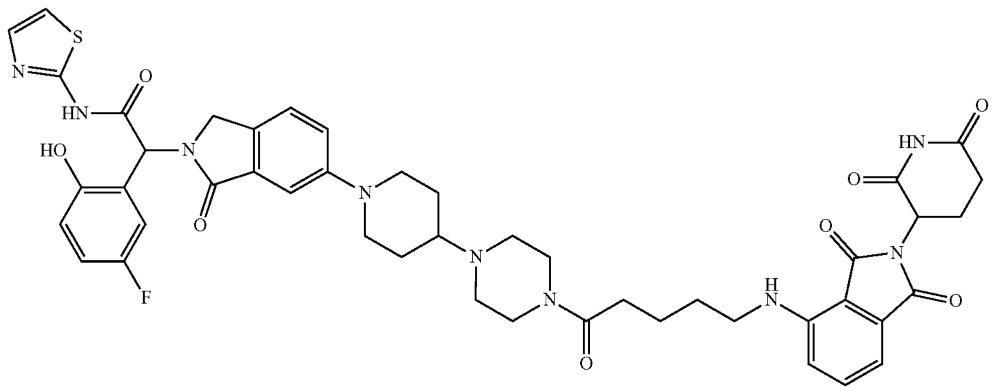 [SMILES: O=C1CCC(N2C(=O)c3cccc(NCCCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(6-((2-(2,6-dioxopiperidin-3-yl)-1,3-dioxoisoindolin-4-yl)amino)hexanoyl)piperazin-1-yl)piperidin-1-yl)-1-oxoisoindolin-2-yl)-2-(5-fluoro-2-hydroxyphenyl)-N-(thiazol-2-yl)acetamide | 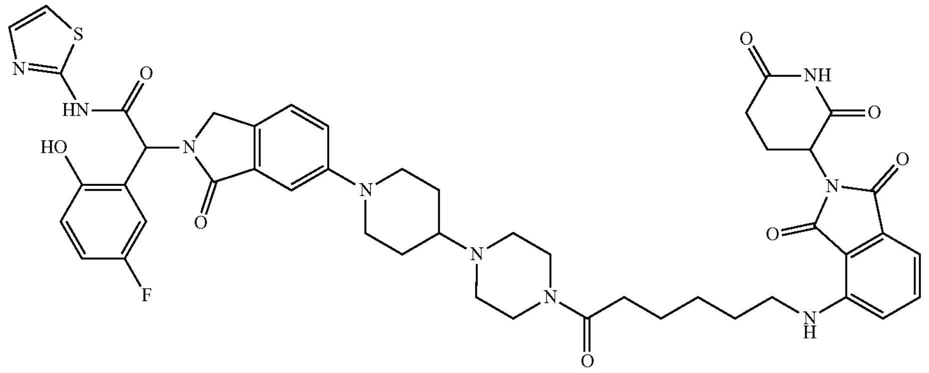 |

TABLE 2-continued

| Compound No. | The compounds' names | Structure of the compounds |
|---|---|---|
| | 2-(6-(4-(4-(7-((2-(2,6-dioxopiperidin-3-yl)-1,3-dioxoisoindolin-4-yl)amino)heptanoyl)piperazin-1-yl)piperidin-1-yl)-1-oxoisoindolin-2-yl)-2-(5-fluoro-2-hydroxyphenyl)-N-(thiazol-2-yl)acetamide | 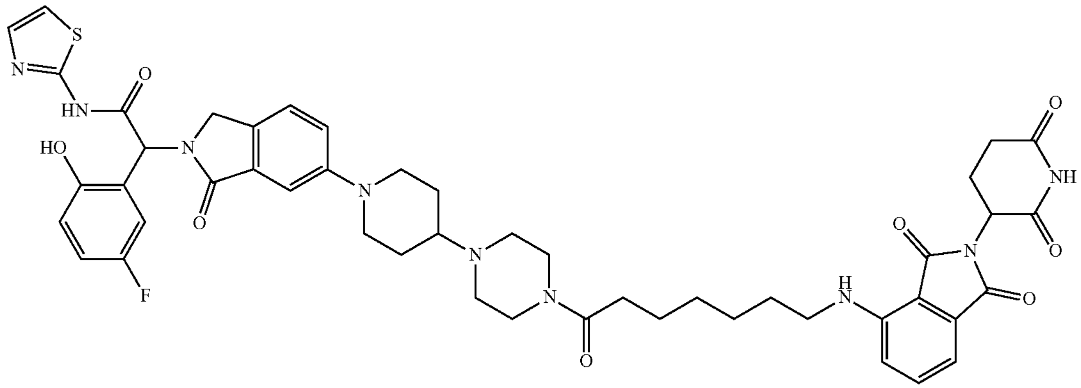 [SMILES: O=C1CCC(N2C(=O)c3cccc(NCCCCCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(2-((2-(2,6-dioxopiperidin-3-yl)-1,3-dioxoisoindolin-4-yl)amino)ethyl)piperazin-1-yl)piperidin-1-yl)-1-oxoisoindolin-2-yl)-2-(5-fluoro-2-hydroxyphenyl)-N-(thiazol-2-yl)acetamide | 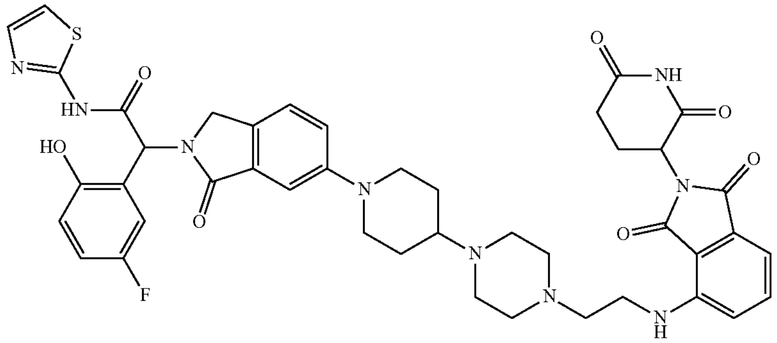 [SMILES: O=C1CCC(N2C(=O)c3cccc(NCCN4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
| --- | --- | --- |
| | 2-(6-(4-(4-(3-((2-(2,6-dioxopiperidin-3-yl)-1,3-dioxoisoindolin-4-yl)amino)propyl)piperazin-1-yl)piperidin-1-yl)-1-oxoisoindolin-2-yl)-2-(5-fluoro-2-hydroxyphenyl)-N-(thiazol-2-yl)acetamide | 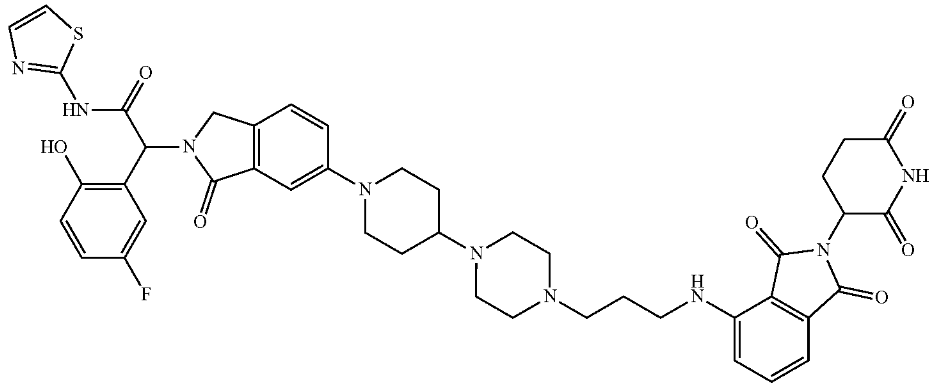 [SMILES: O=C1CCC(N2C(=O)c3cccc(NCCCN4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(4-((2-(2,6-dioxopiperidin-3-yl)-1,3-dioxoisoindolin-4-yl)amino)butyl)piperazin-1-yl)piperidin-1-yl)-1-oxoisoindolin-2-yl)-2-(5-fluoro-2-hydroxyphenyl)-N-(thiazol-2-yl)acetamide | 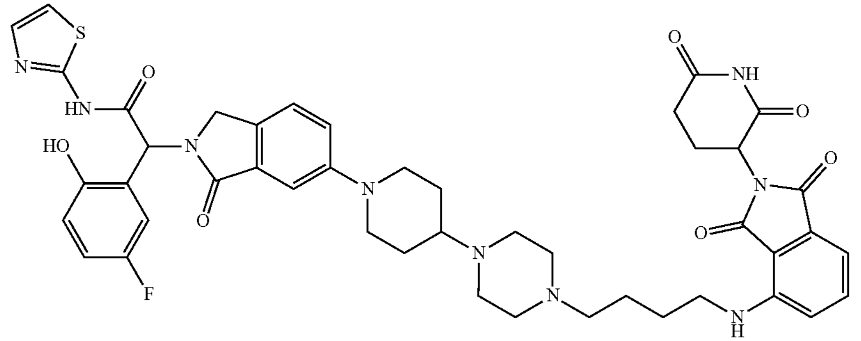 [SMILES: O=C1CCC(N2C(=O)c3cccc(NCCCCN4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(5-((2-(2,6-dioxopiperidin-3-yl)-1,3-dioxoisoindolin-4-yl)amino)pentyl)piperazin-1-yl)piperidin-1-yl)-1-oxoisoindolin-2-yl)-2-(5-fluoro-2-hydroxyphenyl)-N-(thiazol-2-yl)acetamide | 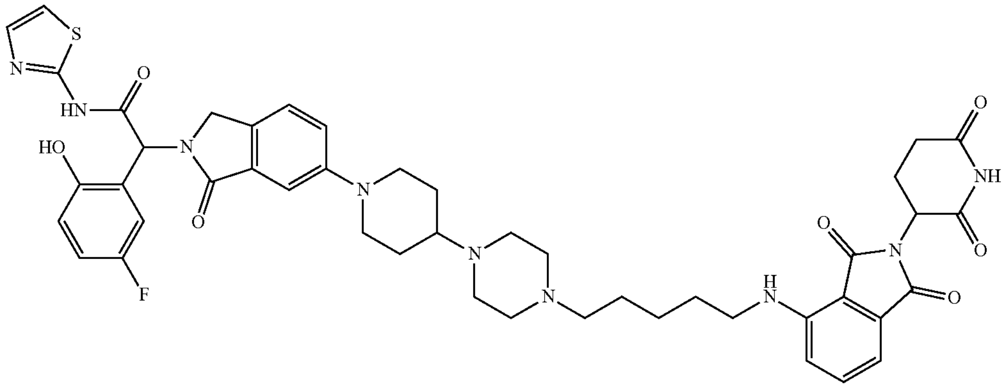 [SMILES: O=C1CCC(N2C(=O)c3cccc(NCCCCCN4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(6-((2-(2,6-dioxopiperidin-3-yl)-1,3-dioxoisoindolin-4-yl)amino)hexyl)piperazin-1-yl)piperidin-1-yl)-1-oxoisoindolin-2-yl)-2-(5-fluoro-2-hydroxyphenyl)-N-(thiazol-2-yl)acetamide | 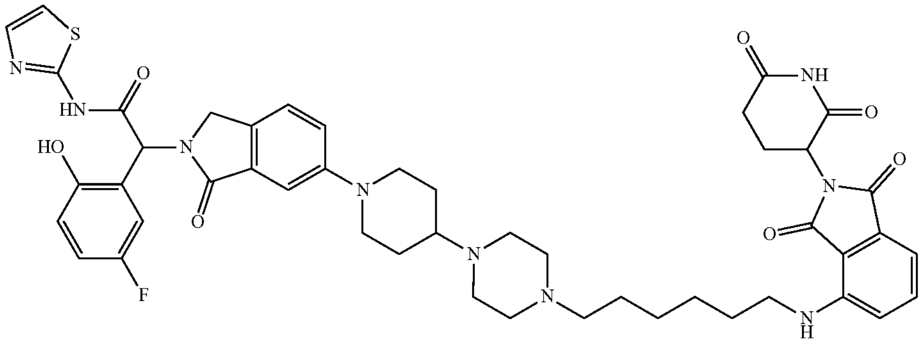 [SMILES: O=C1CCC(N2C(=O)c3cccc(NCCCCCCN4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
| --- | --- | --- |
| | 2-(6-(4-(4-(7-((2-(2,6-dioxopiperidin-3-yl)-1,3-dioxoisoindolin-4-yl)amino)heptyl)piperazin-1-yl)piperidin-1-yl)-1-oxoisoindolin-2-yl)-2-(5-fluoro-2-hydroxyphenyl)-N-(thiazol-2-yl)acetamide | 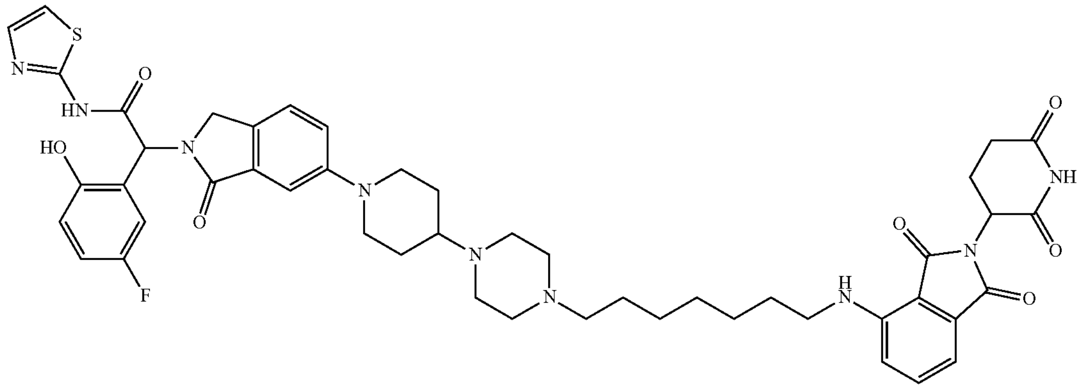 [SMILES: O=C1CCC(N2C(=O)c3cccc(NCCCCCCCN4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(2-((2-(2,6-dioxopiperidin-3-yl)-1-oxoisoindolin-4-yl)amino)acetyl)piperazin-1-yl)piperidin-1-yl)-1-oxoisoindolin-2-yl)-2-(5-fluoro-2-hydroxyphenyl)-N-(thiazol-2-yl)acetamide | 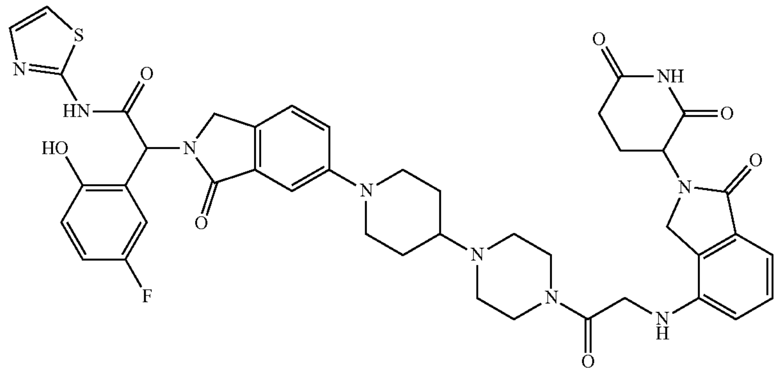 [SMILES: O=C1CCC(N2Cc3c(NCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(3-((2-(2,6-dioxopiperidin-3-yl)-1-oxoisoindolin-4-yl)amino)propanoyl)piperazin-1-yl)piperidin-1-yl)-1-oxoisoindolin-2-yl)-2-(5-fluoro-2-hydroxyphenyl)-N-(thiazol-2-yl)acetamide | 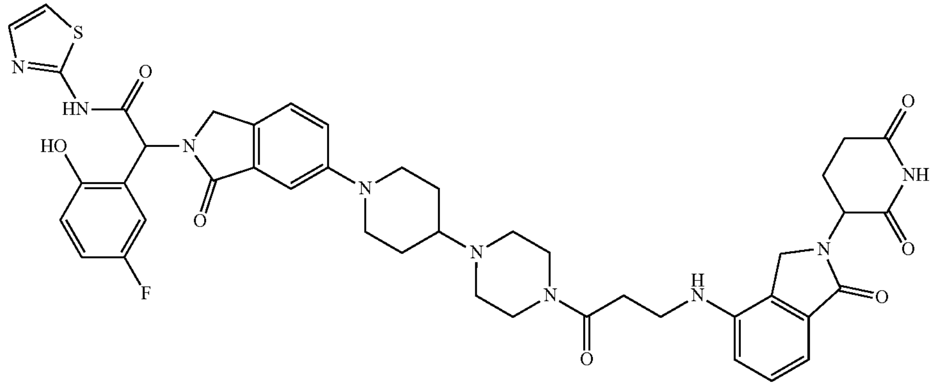 [SMILES: O=C1CCC(N2Cc3c(NCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(4-((2-(2,6-dioxopiperidin-3-yl)-1-oxoisoindolin-4-yl)amino)butanoyl)piperazin-1-yl)piperidin-1-yl)-1-oxoisoindolin-2-yl)-2-(5-fluoro-2-hydroxyphenyl)-N-(thiazol-2-yl)acetamide | 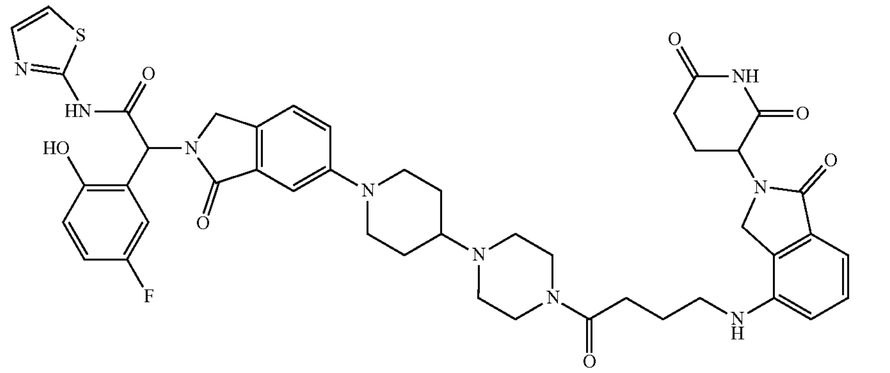 [SMILES: O=C1CCC(N2Cc3c(NCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(5-((2-(2,6-dioxopiperidin-3-yl)-1-oxoisoindolin-4-yl)amino)pentanoyl)piperazin-1-yl)piperidin-1-yl)-1-oxoisoindolin-2-yl)-2-(5-fluoro-2-hydroxyphenyl)-N-(thiazol-2-yl)acetamide | 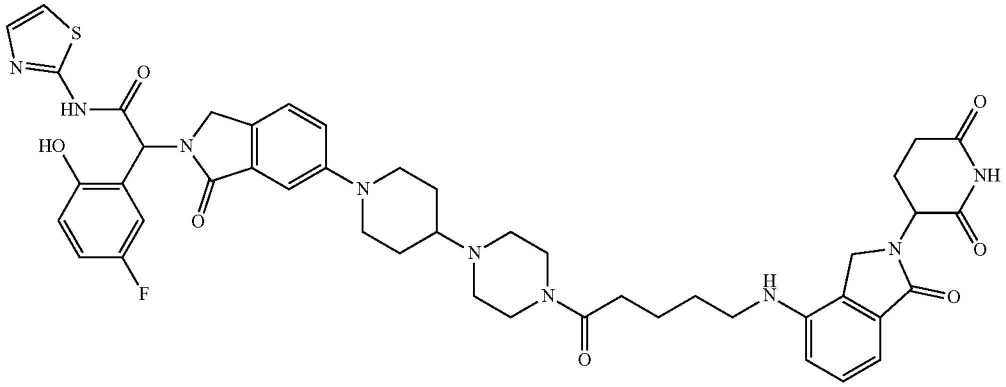 [SMILES: O=C1CCC(N2Cc3c(NCCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(6-((2-(2,6-dioxopiperidin-3-yl)-1-oxoisoindolin-4-yl)amino)hexanoyl)piperazin-1-yl)piperidin-1-yl)-1-oxoisoindolin-2-yl)-2-(5-fluoro-2-hydroxyphenyl)-N-(thiazol-2-yl)acetamide | 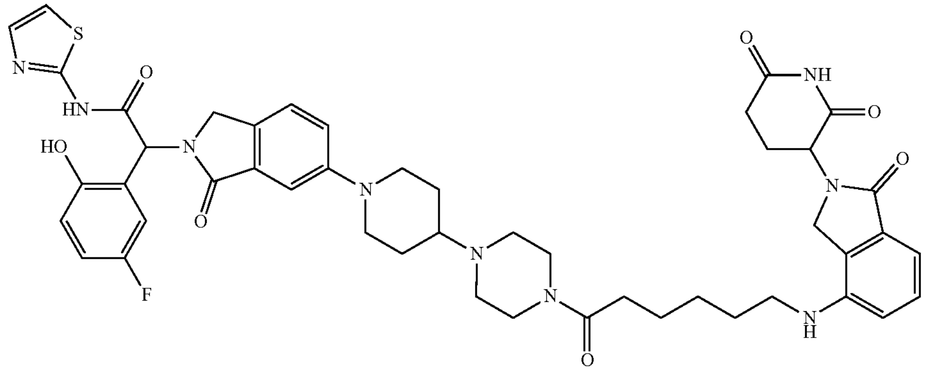 [SMILES: O=C1CCC(N2Cc3c(NCCCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
| --- | --- | --- |
| | 2-(6-(4-(4-(7-((2-(2,6-dioxopiperidin-3-yl)-1-oxoisoindolin-4-yl)amino)heptanoyl)piperazin-1-yl)piperidin-1-yl)-1-oxoisoindolin-2-yl)-2-(5-fluoro-2-hydroxyphenyl)-N-(thiazol-2-yl)acetamide | 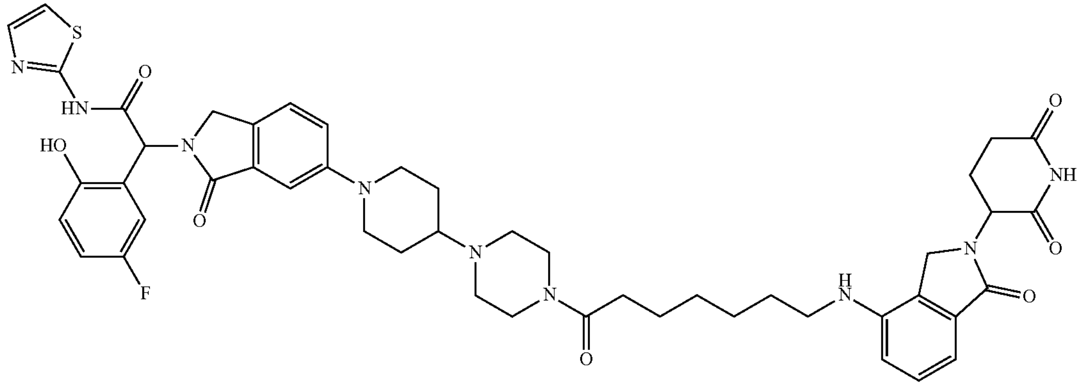 [SMILES: O=C1CCC(N2Cc3c(NCCCCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(2-((2-(2,6-dioxopiperidin-3-yl)-1,3-dioxoisoindolin-4-yl)thio)acetyl)piperazin-1-yl)piperidin-1-yl)-1-oxoisoindolin-2-yl)-2-(5-fluoro-2-hydroxyphenyl)-N-(thiazol-2-yl)acetamide | 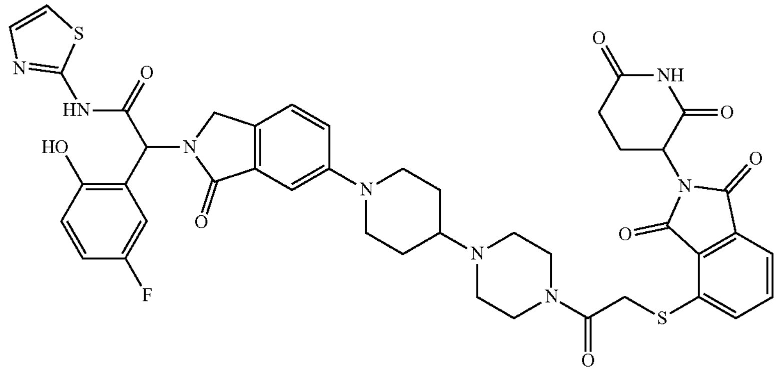 [SMILES: O=C1CCC(N2C(=O)c3cccc(SCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(3-((2-(2,6-dioxopiperidin-3-yl)-1,3-dioxoisoindolin-4-yl)thio)propanoyl)piperazin-1-yl)piperidin-1-yl)-1-oxoisoindolin-2-yl)-2-(5-fluoro-2-hydroxyphenyl)-N-(thiazol-2-yl)acetamide | 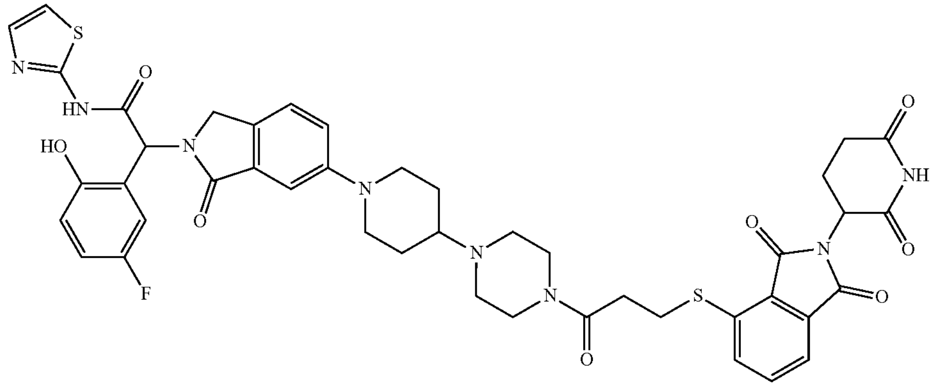 [SMILES: O=C1CCC(N2C(=O)c3cccc(SCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(4-((2-(2,6-dioxopiperidin-3-yl)-1,3-dioxoisoindolin-4-yl)thio)butanoyl)piperazin-1-yl)piperidin-1-yl)-1-oxoisoindolin-2-yl)-2-(5-fluoro-2-hydroxyphenyl)-N-(thiazol-2-yl)acetamide | 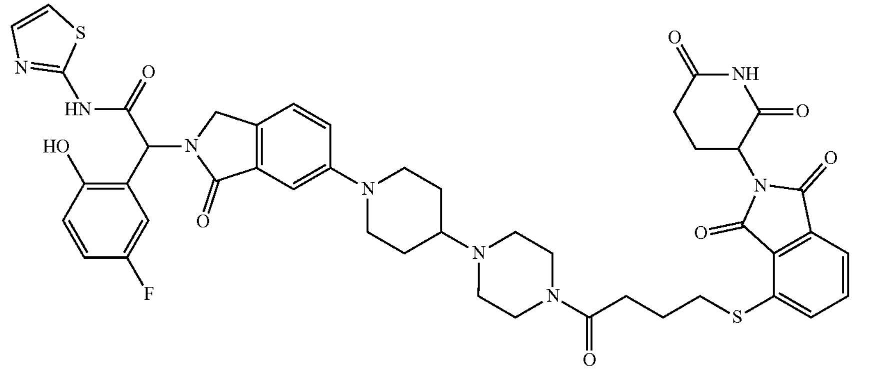 [SMILES: O=C1CCC(N2C(=O)c3cccc(SCCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(5-((2-(2,6-dioxopiperidin-3-yl)-1,3-dioxoisoindolin-4-yl)thio)pentanoyl)piperazin-1-yl)piperidin-1-yl)-1-oxoisoindolin-2-yl)-2-(5-fluoro-2-hydroxyphenyl)-N-(thiazol-2-yl)acetamide | 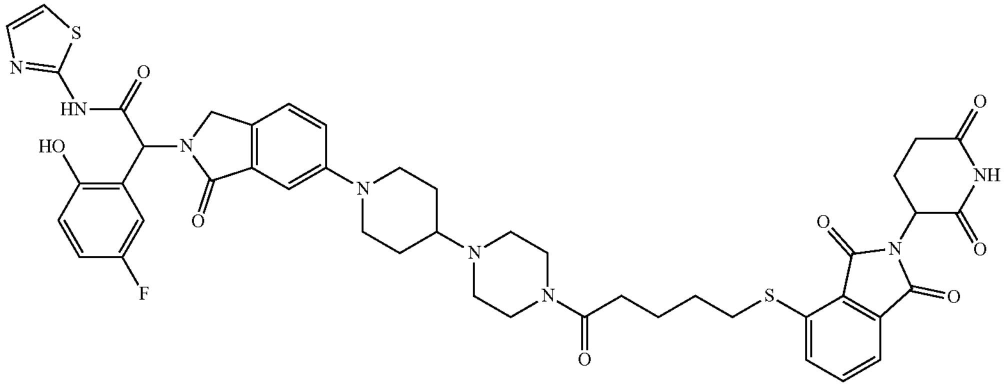 |
| | 2-(6-(4-(4-(6-((2-(2,6-dioxopiperidin-3-yl)-1,3-dioxoisoindolin-4-yl)thio)hexanoyl)piperazin-1-yl)piperidin-1-yl)-1-oxoisoindolin-2-yl)-2-(5-fluoro-2-hydroxyphenyl)-N-(thiazol-2-yl)acetamide | 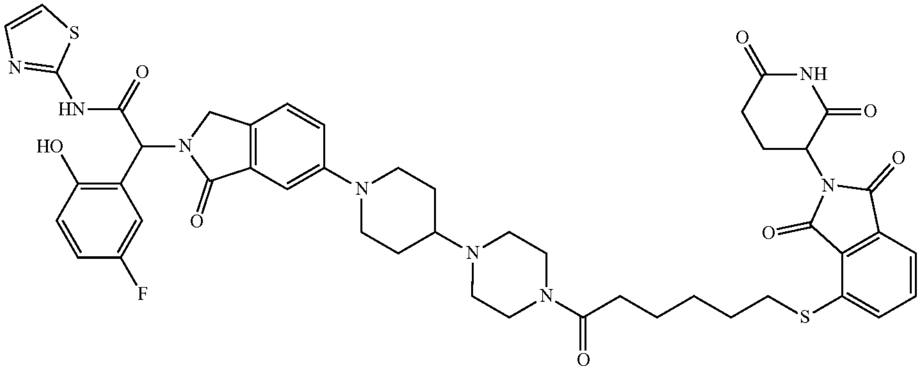 [SMILES: O=C1CCC(N2C(=O)c3cccc(SCCCCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(7-((2-(2,6-dioxopiperidin-3-yl)-1,3-dioxoisoindolin-4-yl)thio)heptanoyl)piperazin-1-yl)piperidin-1-yl)-1-oxoisoindolin-2-yl)-2-(5-fluoro-2-hydroxyphenyl)-N-(thiazol-2-yl)acetamide | 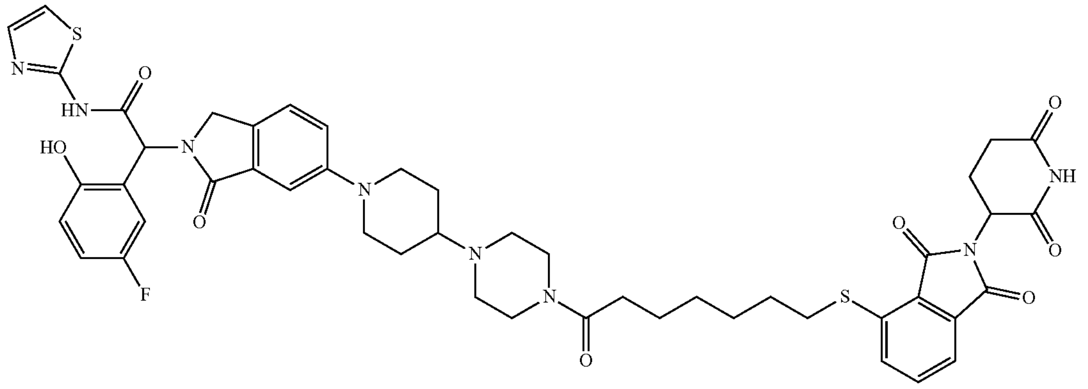 [SMILES: O=C1CCC(N2C(=O)c3cccc(SCCCCCCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(2-(2-((2-(2,6-dioxopiperidin-3-yl)-1,3-dioxoisoindolin-4-yl)thio)ethoxy)acetyl)piperazin-1-yl)piperidin-1-yl)-1-oxoisoindolin-2-yl)-2-(5-fluoro-2-hydroxyphenyl)-N-(thiazol-2-yl)acetamide | 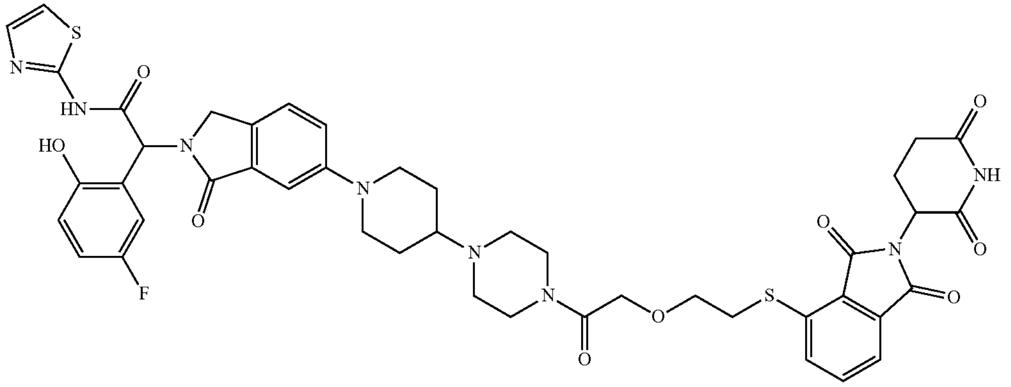 [SMILES: O=C1CCC(N2C(=O)c3cccc(SCCOCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(2-(2-(2-((2-(2,6-dioxopiperidin-3-yl)-1,3-dioxoisoindolin-4-yl)thio)ethoxy)ethoxy)acetyl)piperazin-1-yl)piperidin-1-yl)-1-oxoisoindolin-2-yl)-2-(5-fluoro-2-hydroxyphenyl)-N-(thiazol-2-yl)acetamide | 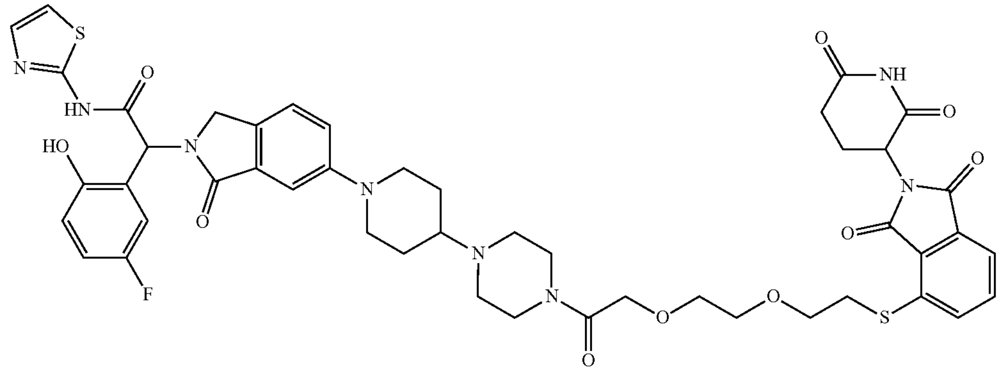 [SMILES: O=C1CCC(N2C(=O)c3cccc(SCCOCCOCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)piperidin-1-yl)-1-oxoisoindolin-2-yl)-2-(5-fluoro-2-hydroxyphenyl)-N-(thiazol-2-yl)acetamide | 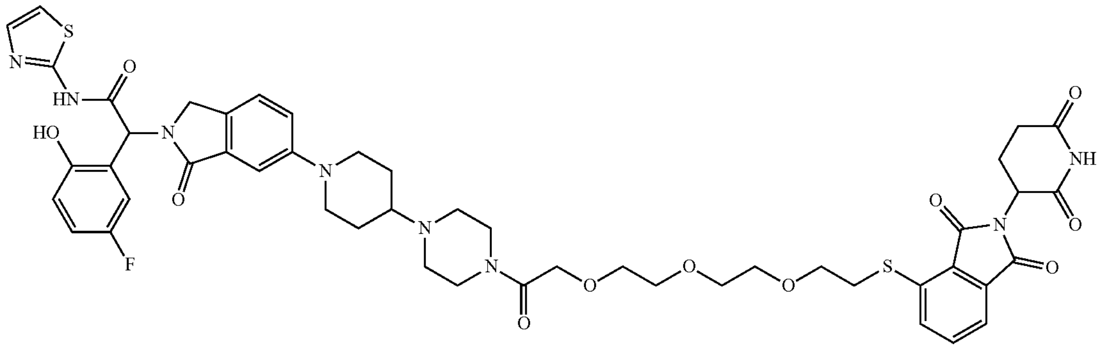 [SMILES: O=C1CCC(N2C(=O)c3cccc(SCCOCCOCCOCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |

TABLE 2-continued

| Compound No. | The compounds' names | Structure of the compounds |
|---|---|---|
| | 2-(6-(4-(4-(14-((2-(2,6-dioxopiperidin-3-yl)-1,3-dioxoisoindolin-4-yl)thio)-3,6,9,12-tetraoxatetradecan-1-oyl)piperazin-1-yl)piperidin-1-yl)-1-oxoisoindolin-2-yl)-2-(5-fluoro-2-hydroxyphenyl)-N-(thiazol-2-yl)acetamide | 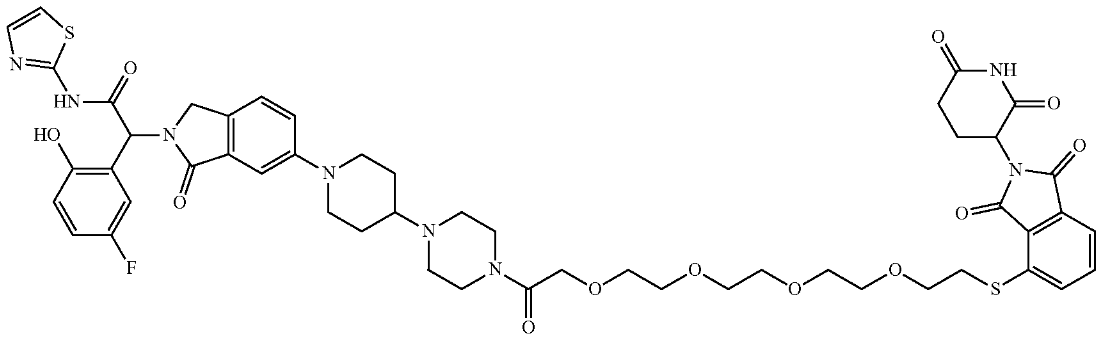 [SMILES: O=C1CCC(N2C(=O)c3cccc(SCCOCCOCCOCCOCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(17-((2-(2,6-dioxopiperidin-3-yl)-1,3-dioxoisoindolin-4-yl)thio)-3,6,9,12,15-pentaoxaheptadecan-1-oyl)piperazin-1-yl)piperidin-1-yl)-1-oxoisoindolin-2-yl)-2-(5-fluoro-2-hydroxyphenyl)-N-(thiazol-2-yl)acetamide | 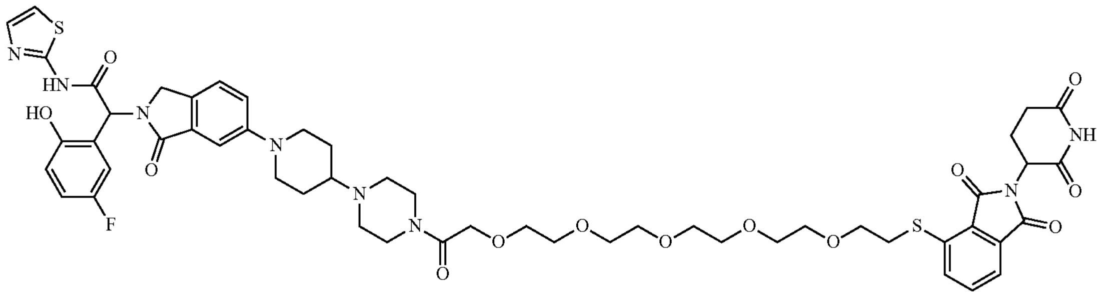 [SMILES: O=C1CCC(N2C(=O)c3cccc(SCCOCCOCCOCCOCCOCC(=O)N4CCN(C5CCN(c6ccc7c(c6)C(=O)N(C(C(=O)Nc6nccs6)c6cc(F)ccc6O)C7)CC5)CC4)c3C2=O)C(=O)N1] |
| | 2-(6-(4-(4-(2-((2-(2,6-dioxopiperidin-3-yl)-1-oxoisoindolin-4-yl)thio)acetyl)piperazin-1-yl)piperidin-1-yl)-1-oxoisoindolin-2-yl)-2-(5-fluoro-2-hydroxyphenyl)-N-(thiazol-2-yl)acetamide | 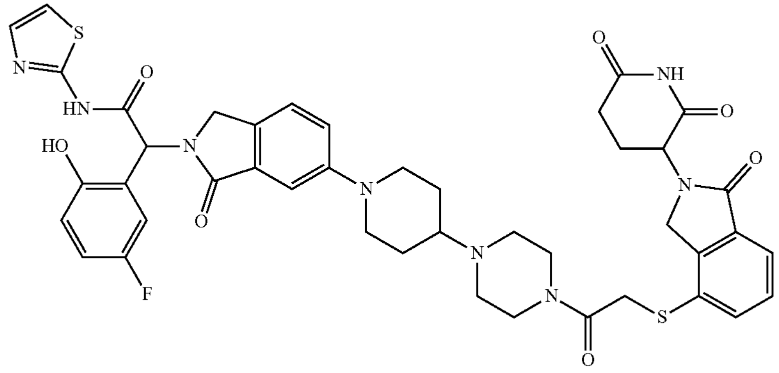 [SMILES: O=C1CCC(N2Cc3c(SCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(3-((2-(2,6-dioxopiperidin-3-yl)-1-oxoisoindolin-4-yl)thio)propanoyl)piperazin-1-yl)piperidin-1-yl)-1-oxoisoindolin-2-yl)-2-(5-fluoro-2-hydroxyphenyl)-N-(thiazol-2-yl)acetamide | 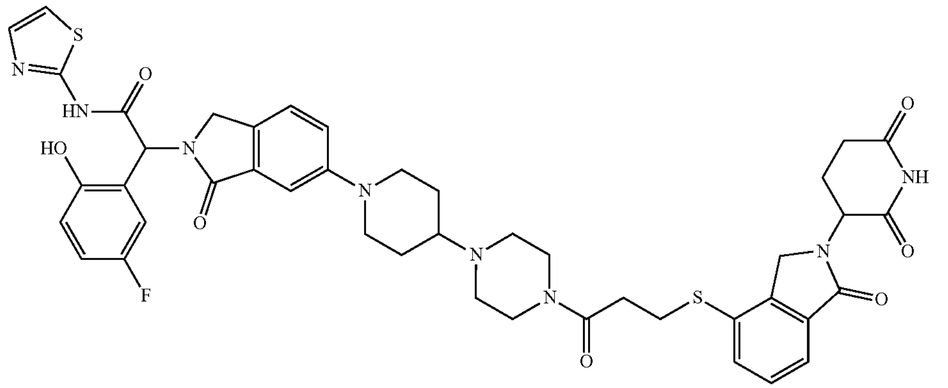 [SMILES: O=C1CCC(N2Cc3c(SCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(4-((2-(2,6-dioxopiperidin-3-yl)-1-oxoisoindolin-4-yl)thio)butanoyl)piperazin-1-yl)piperidin-1-yl)-1-oxoisoindolin-2-yl)-2-(5-fluoro-2-hydroxyphenyl)-N-(thiazol-2-yl)acetamide | 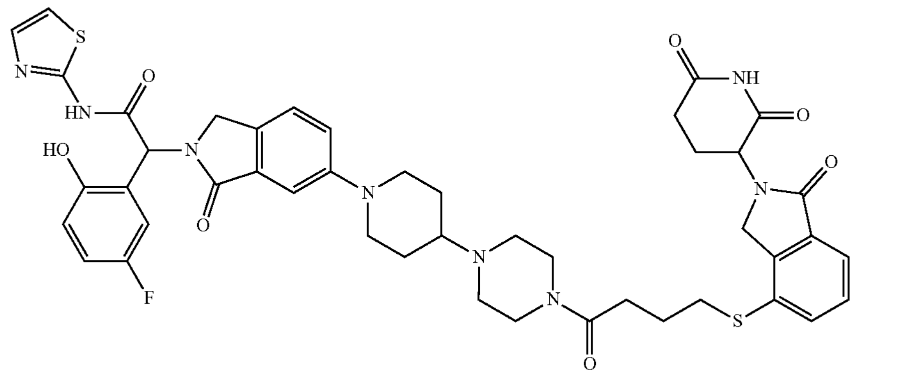 [SMILES: O=C1CCC(N2Cc3c(SCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(5-((2-(2,6-dioxopiperidin-3-yl)-1-oxoisoindolin-4-yl)thio)pentanoyl)piperazin-1-yl)piperidin-1-yl)-1-oxoisoindolin-2-yl)-2-(5-fluoro-2-hydroxyphenyl)-N-(thiazol-2-yl)acetamide | 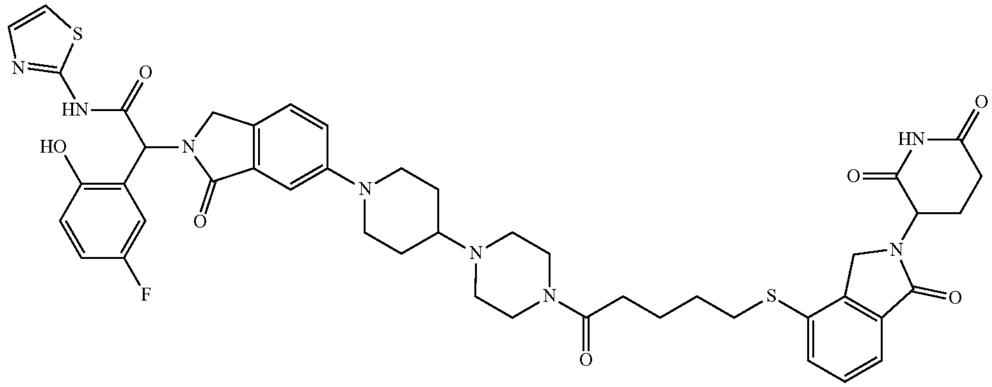 [SMILES: O=C1CCC(N2Cc3c(SCCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(6-((2-(2,6-dioxopiperidin-3-yl)-1-oxoisoindolin-4-yl)thio)hexanoyl)piperazin-1-yl)piperidin-1-yl)-1-oxoisoindolin-2-yl)-2-(5-fluoro-2-hydroxyphenyl)-N-(thiazol-2-yl)acetamide | 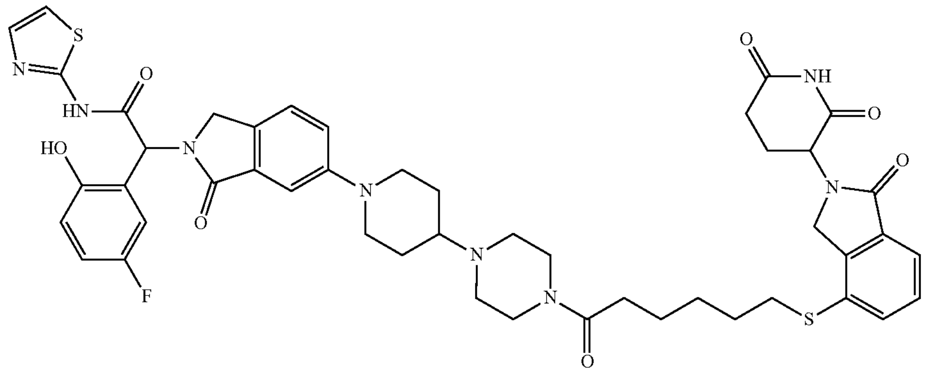 [SMILES: O=C1CCC(N2Cc3c(SCCCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued
| Compound No. | The compounds' names | Structure of the compounds |
|---|---|---|
| | 2-(6-(4-(4-(7-((2-(2,6-dioxopiperidin-3-yl)-1-oxoisoindolin-4-yl)thio)heptanoyl)piperazin-1-yl)piperidin-1-yl)-1-oxoisoindolin-2-yl)-2-(5-fluoro-2-hydroxyphenyl)-N-(thiazol-2-yl)acetamide | 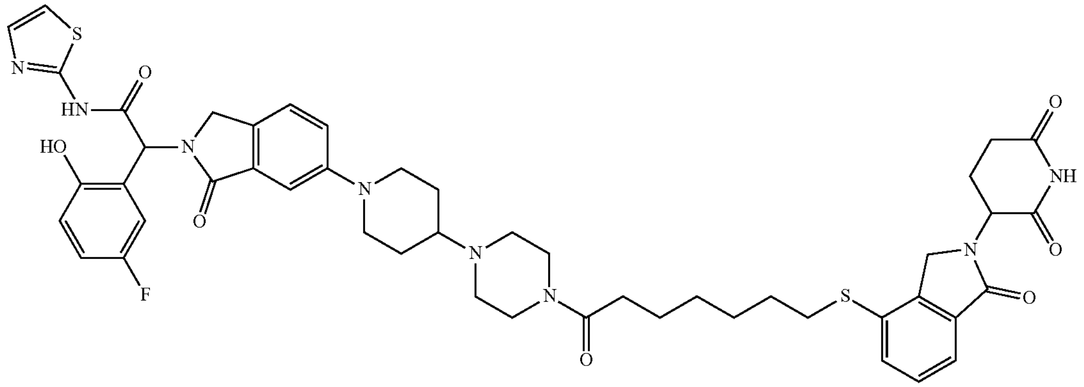 [SMILES: O=C1CCC(N2Cc3c(SCCCCCCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(2-((2-(2,6-dioxopiperidin-3-yl)-1-oxoisoindolin-4-yl)thio)ethyl)piperazin-1-yl)piperidin-1-yl)-1-oxoisoindolin-2-yl)-2-(5-fluoro-2-hydroxyphenyl)-N-(thiazol-2-yl)acetamide | 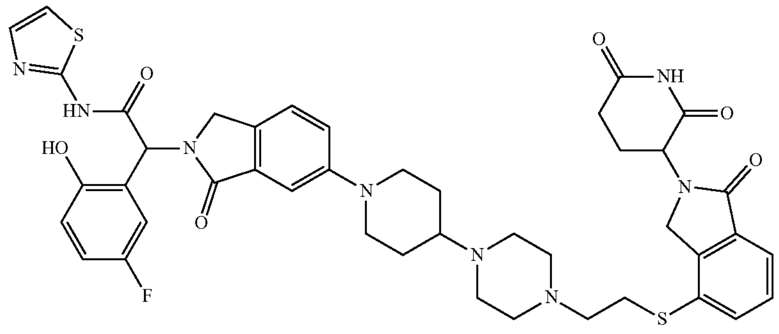 [SMILES: O=C1CCC(N2Cc3c(SCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued
| Compound No. | The compounds' names | Structure of the compounds |
|---|---|---|
| | 2-(6-(4-(4-(3-((2-(2,6-dioxopiperidin-3-yl)-1-oxoisoindolin-4-yl)thio)propyl)piperazin-1-yl)piperidin-1-yl)-1-oxoisoindolin-2-yl)-2-(5-fluoro-2-hydroxyphenyl)-N-(thiazol-2-yl)acetamide | 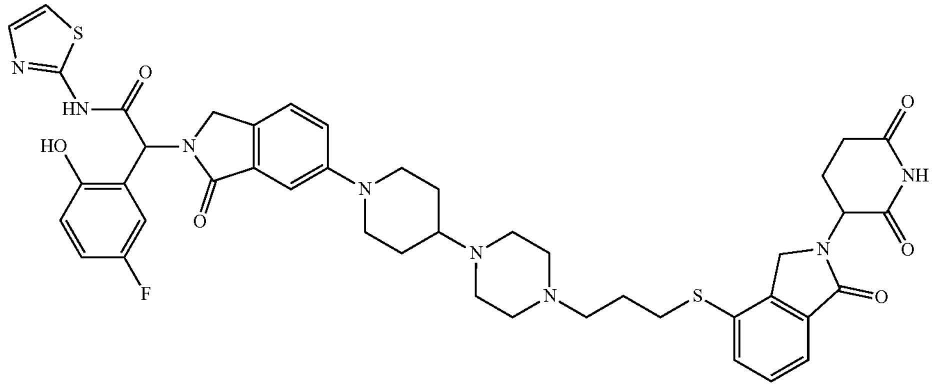 [SMILES: O=C1CCC(N2Cc3c(SCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(4-((2-(2,6-dioxopiperidin-3-yl)-1-oxoisoindolin-4-yl)thio)butyl)piperazin-1-yl)piperidin-1-yl)-1-oxoisoindolin-2-yl)-2-(5-fluoro-2-hydroxyphenyl)-N-(thiazol-2-yl)acetamide | 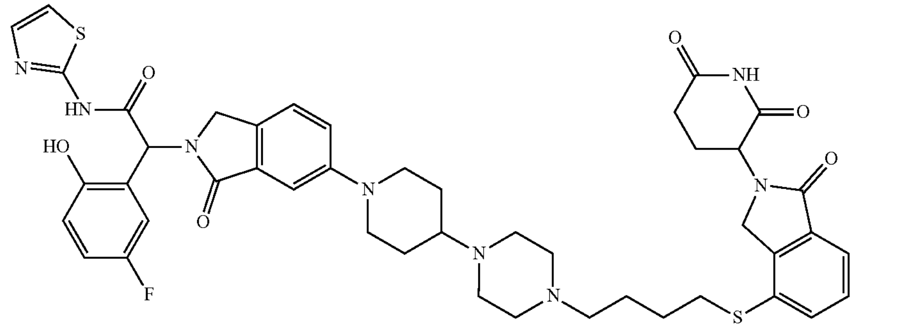 [SMILES: O=C1CCC(N2Cc3c(SCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued
| Compound No. | The compounds' names | Structure of the compounds |
|---|---|---|
| | 2-(6-(4-(4-(5-((2-(2,6-dioxopiperidin-3-yl)-1-oxoisoindolin-4-yl)thio)pentyl)piperazin-1-yl)piperidin-1-yl)-1-oxoisoindolin-2-yl)-2-(5-fluoro-2-hydroxyphenyl)-N-(thiazol-2-yl)acetamide | 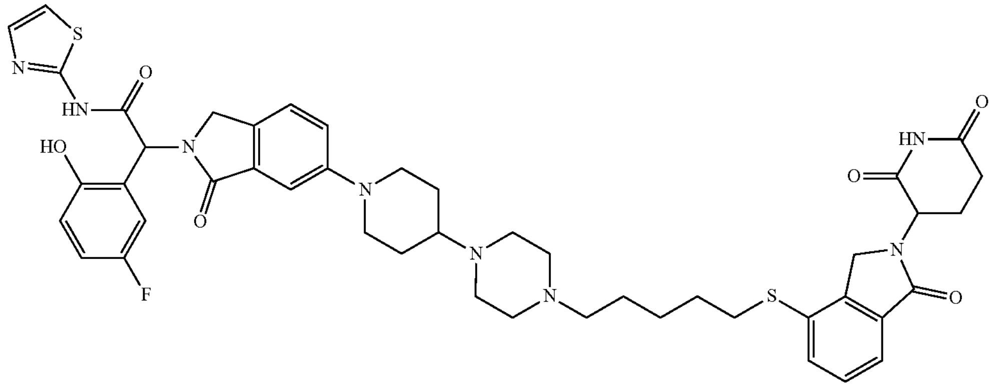 [SMILES: O=C1CCC(N2Cc3c(SCCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(6-((2-(2,6-dioxopiperidin-3-yl)-1-oxoisoindolin-4-yl)thio)hexyl)piperazin-1-yl)piperidin-1-yl)-1-oxoisoindolin-2-yl)-2-(5-fluoro-2-hydroxyphenyl)-N-(thiazol-2-yl)acetamide | 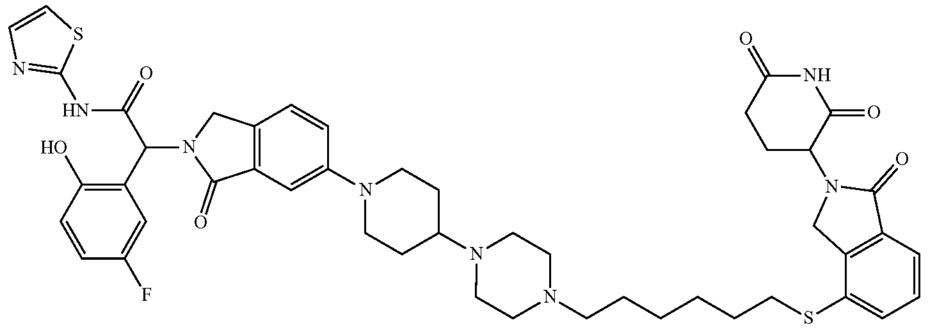 [SMILES: O=C1CCC(N2Cc3c(SCCCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued
| Compound No. | The compounds' names | Structure of the compounds |
|---|---|---|
| | 2-(6-(4-(4-(7-((2-(2,6-dioxopiperidin-3-yl)-1-oxoisoindolin-4-yl)thio)heptyl)piperazin-1-yl)piperidin-1-yl)-1-oxoisoindolin-2-yl)-2-(5-fluoro-2-hydroxyphenyl)-N-(thiazol-2-yl)acetamide | 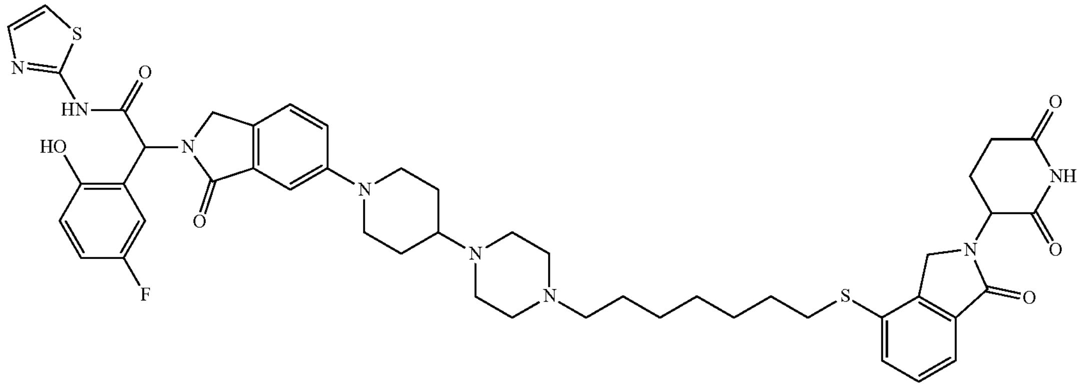 [SMILES: O=C1CCC(N2Cc3c(SCCCCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(8-((2-(2,6-dioxopiperidin-3-yl)-1-oxoisoindolin-4-yl)thio)octyl)piperazin-1-yl)piperidin-1-yl)-1-oxoisoindolin-2-yl)-2-(5-fluoro-2-hydroxyphenyl)-N-(thiazol-2-yl)acetamide | 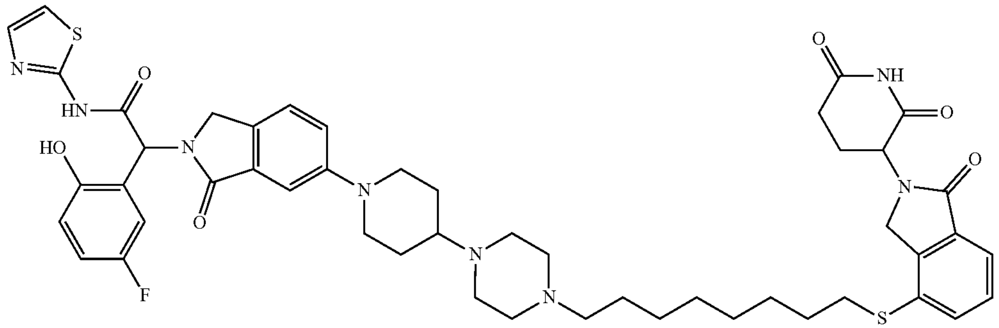 [SMILES: O=C1CCC(N2Cc3c(SCCCCCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(2-(2-((2-(2,6-dioxopiperidin-3-yl)-1-oxoisoindolin-4-yl)thio)ethoxy)acetyl)piperazin-1-yl)piperidin-1-yl)-1-oxoisoindolin-2-yl)-2-(5-fluoro-2-hydroxyphenyl)-N-(thiazol-2-yl)acetamide | 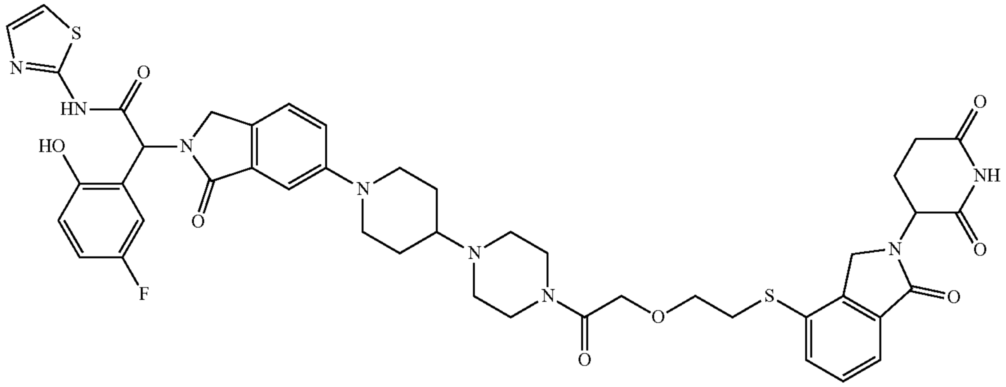 [SMILES: O=C1CCC(N2Cc3c(SCCOCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(2-(2-(2-((2-(2,6-dioxopiperidin-3-yl)-1-oxoisoindolin-4-yl)thio)ethoxy)ethoxy)acetyl)piperazin-1-yl)piperidin-1-yl)-1-oxoisoindolin-2-yl)-2-(5-fluoro-2-hydroxyphenyl)-N-(thiazol-2-yl)acetamide | 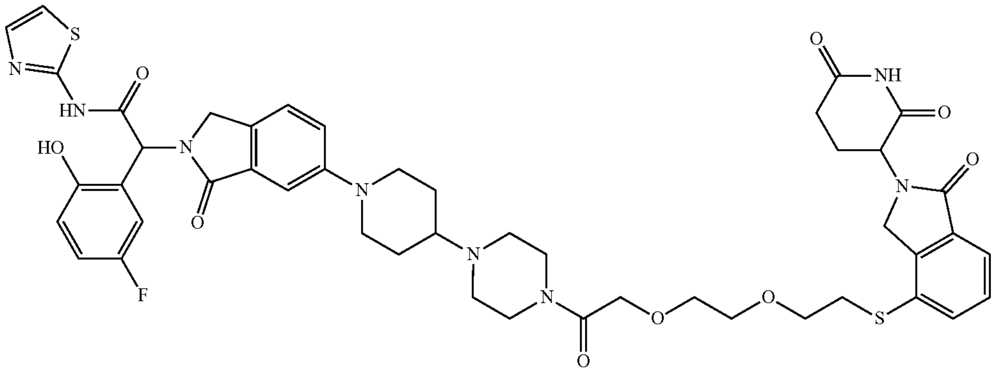 [SMILES: O=C1CCC(N2Cc3c(SCCOCCOCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(2-(2-(2-(2-((2-(2,6-dioxopiperidin-3-yl)-i-oxoisoindolin-4-yl)thio)ethoxy)ethoxy)ethoxy)acetyl)piperazin-1-yl)piperidin-1-yl)-1-oxoisoindolin-2-yl)-2-(5-fluoro-2-hydroxyphenyl)-N-(thiazol-2-yl)acetamide | 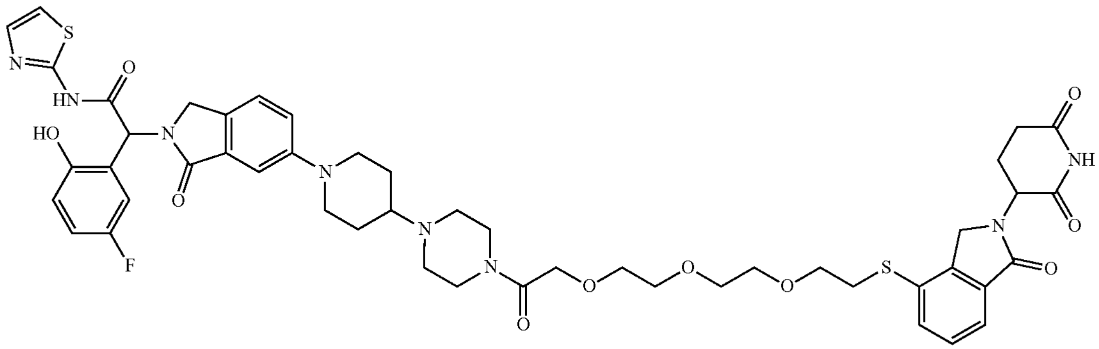 [SMILES: O=C1CCC(N2Cc3c(SCCOCCOCCOCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(14-((2-(2,6-dioxopiperidin-3-yl)-1-oxoisoindolin-4-yl)thio)-3,6,9,12-tetraoxatetradecan-1-oyl)piperazin-1-yl)piperidin-1-yl)-1-oxoisoindolin-2-yl)-2-(5-fluoro-2-hydroxyphenyl)-N-(thiazol-2-yl)acetamide | 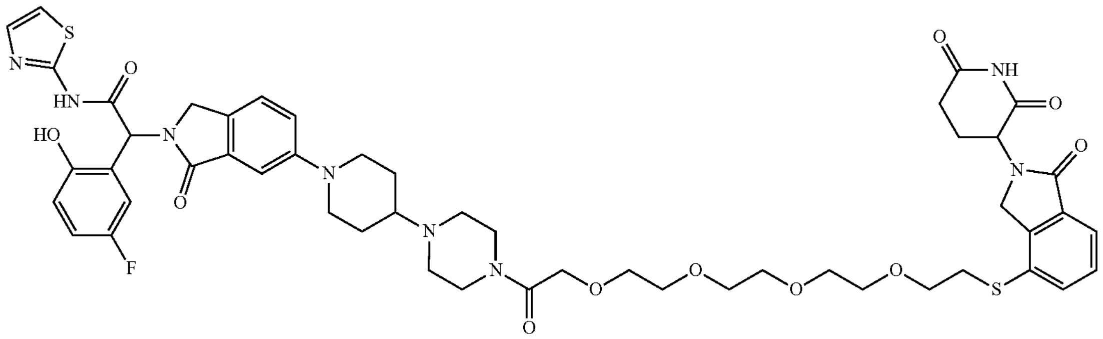 [SMILES: O=C1CCC(N2Cc3c(SCCOCCOCCOCCOCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(17-((2-(2,6-dioxopiperidin-3-yl)-1-oxoisoindolin-4-yl)thio)-3,6,9,12,15-pentaoxaheptadecan-1-oyl)piperazin-1-yl)piperidin-1-yl)-1-oxoisoindolin-2-yl)-2-(5-fluoro-2-hydroxyphenyl)-N-(thiazol-2-yl)acetamide | 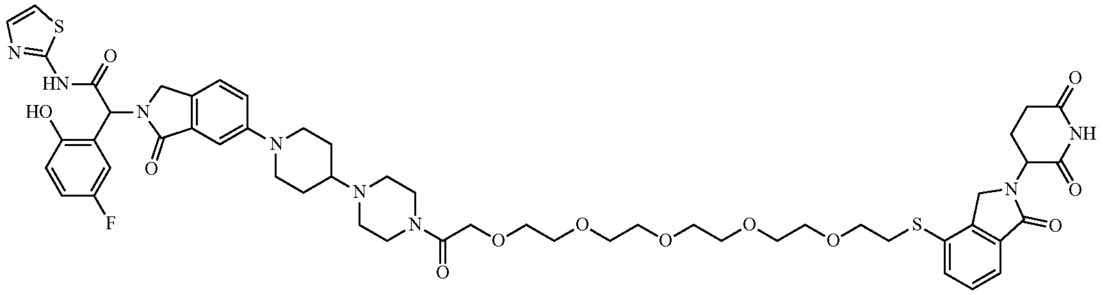 [SMILES: O=C1CCC(N2Cc3c(SCCOCCOCCOCCOCCOCC(=O)N4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued
| Compound No. | The compounds' names | Structure of the compounds |
|---|---|---|
| | 2-(6-(4-(4-(5-(2-(2,6-dioxopiperidin-3-yl)-1-oxoisoindolin-4-yl)pent-4-yn-1-yl)piperazin-1-yl)piperidin-1-yl)-1-oxoisoindolin-2-yl)-2-(5-fluoro-2-hydroxyphenyl)-N-(thiazol-2-yl)acetamide | 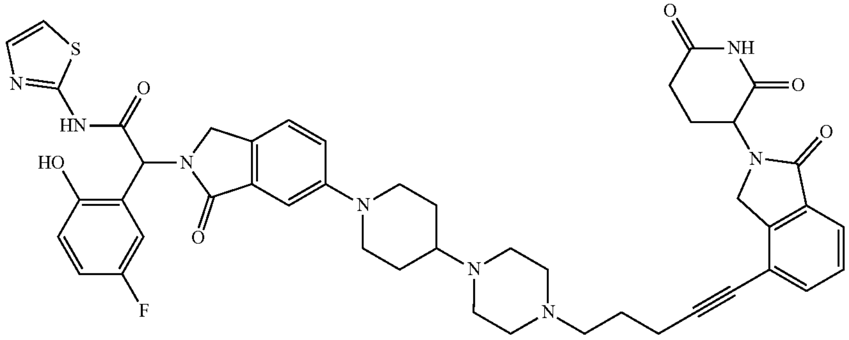 [SMILES: O=C1CCC(N2Cc3c(C#CCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | 2-(6-(4-(4-(6-(2-(2,6-dioxopiperidin-3-yl)-1-oxoisoindolin-4-yl)hex-5-yn-1-yl)piperazin-1-yl)piperidin-1-yl)-1-oxoisoindolin-2-yl)-2-(5-fluoro-2-hydroxyphenyl)-N-(thiazol-2-yl)acetam | 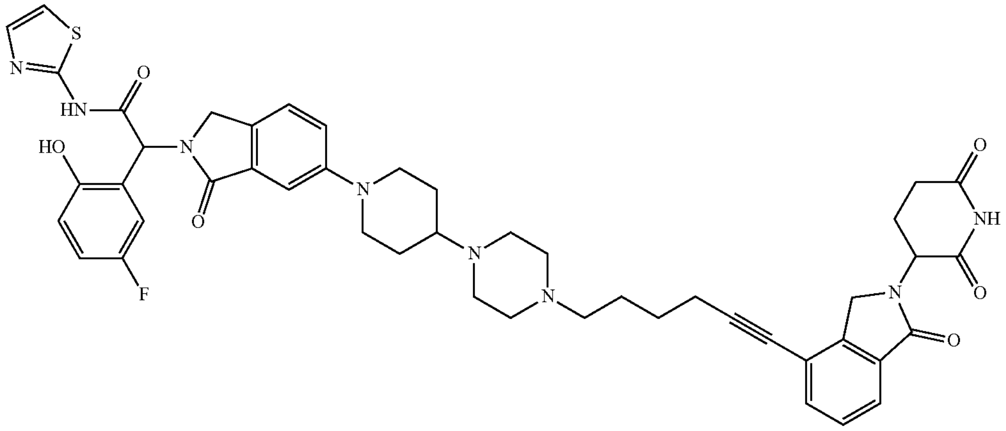 [SMILES: O=C1CCC(N2Cc3c(C#CCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |

TABLE 2-continued

| Compound No. | The compounds' names | Structure of the compounds |
|---|---|---|
| | 2-(6-(4-(4-(9-(2-(2,6-dioxopiperidin-3-yl)-1-oxoisoindolin-4-yl)non-8-yn-1-yl)piperazin-1-yl)piperidin-1-yl)-1-oxoisoindolin-2-yl)-2-(5-fluoro-2-hydroxyphenyl)-N-(thiazol-2-yl)acetamide | 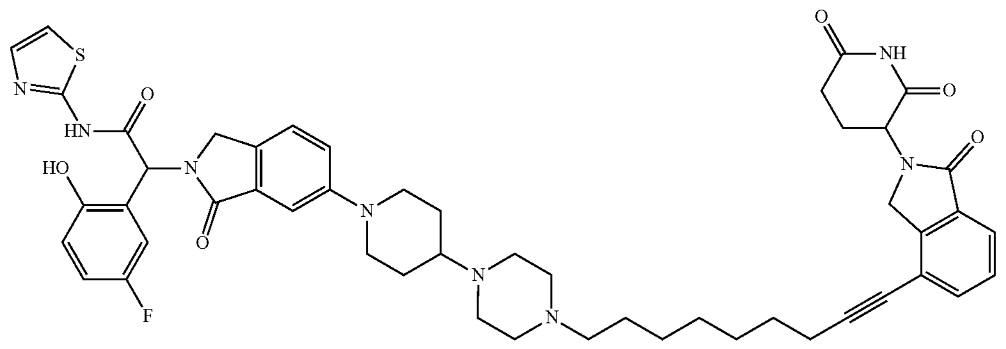 [SMILES: O=C1CCC(N2Cc3c(C#CCCCCCCCN4CCN(C5CCN(c6ccc7c(c6)C(=O)N(C(C(=O)Nc6nccs6)c6cc(F)ccc6O)C7)CC5)CC4)cccc3C2=O)C(=O)N1] |
| | (2S,4R)-1-((2S)-2-(3-(2-(3-(4-(1-(2-(1-(5-fluoro-2-hydroxyphenyl)-2-oxo-2-(thiazol-2-ylamino)ethyl)-3-oxoisoindolin-5-yl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide | 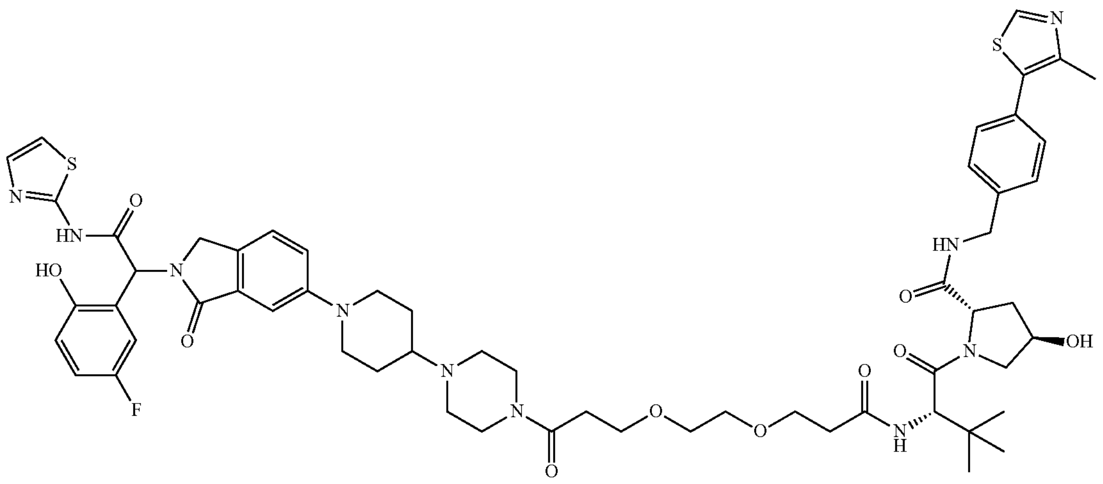 [SMILES: Cc1ncsc1-c1ccc(CNC(=O)[C@@H]2C[C@@H](O)CN2C(=O)[C@@H](NC(=O)CCOCCOCCC(=O)N2CCN(C3CCN(c4ccc5c(c4)C(=O)N(C(C(=O)Nc4nccs4)c4cc(F)ccc4O)C5)CC3)CC2)C(C)(C)C)cc1] |

TABLE 2-continued

| Compound No. | The compounds' names | Structure of the compounds |
|---|---|---|
| | (2S,4R)-1-((2S)-2-(tert-butyl)-19-(4-(1-(2-(1-(5-fluoro-2-hydroxyphenyl)-2-oxo-2-(thiazol-2-ylamino)ethyl)-3-oxoisoindolin-5-yl)piperidin-4-yl)piperazin-1-yl)-4,19-dioxo-7,10,13,16-tetraoxa-3-azanonadecan-1-oyl)-4-hydroxy-N-(4-(4-methylthiazol-5-yl)benzyl)pyrrolidine-2-carboxamide | 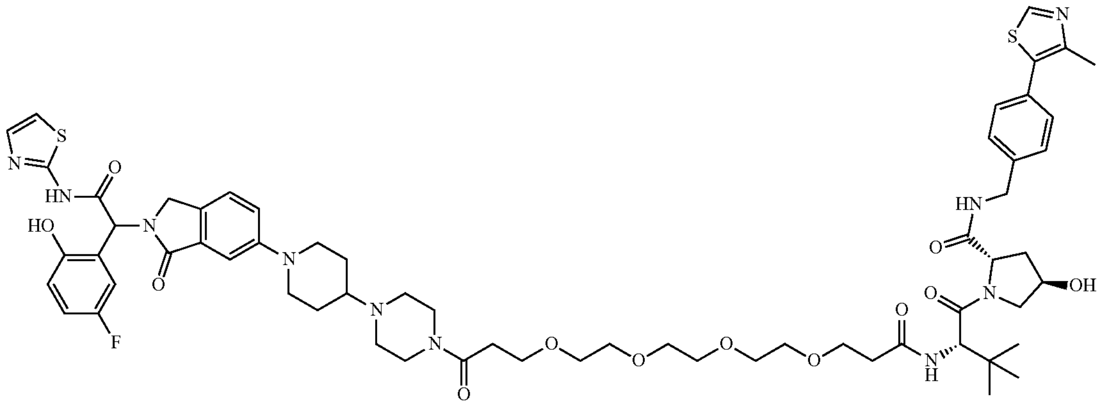 [SMILES: Cc1ncsc1-c1ccc(CNC(=O)[C@@H]2C[C@@H](O)CN2C(=O)[C@@H](NC(=O)CCOCCOCCOCCOCCC(=O)N2CCN(C3CCN(c4ccc5c(c4)C(=O)N(C(C(=O)Nc4nccs4)c4cc(F)ccc4O)C5)CC3)CC2)C(C)(C)C)cc1] |
| | (2S,4R)-1-((2S)-2-(4-(4-(1-(2-(1-(5-fluoro-2-hydroxyphenyl)-2-oxo-2-(thiazol-2-ylamino)ethyl)-3-oxoisoindolin-5-yl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide | 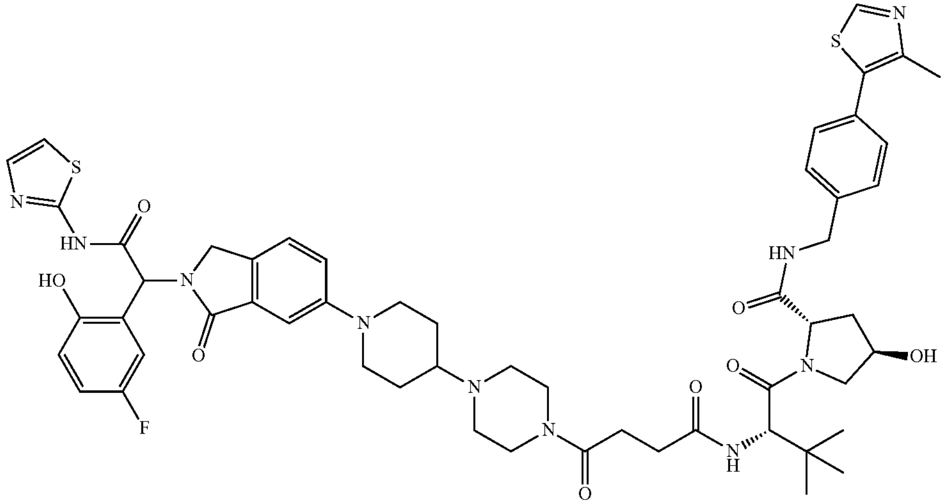 [SMILES: Cc1ncsc1-c1ccc(CNC(=O)[C@@H]2C[C@@H](O)CN2C(=O)[C@@H](NC(=O)CCC(=O)N2CCN(C3CCN(c4ccc5c(c4)C(=O)N(C(C(=O)Nc4nccs4)c4cc(F)ccc4O)C5)CC3)CC2)C(C)(C)C)cc1] |

TABLE 2-continued

| Compound No. | The compounds' names | Structure of the compounds |
|---|---|---|
| | (2S,4R)-1-((2S)-2-(6-(4-(1-(2-(1-(5-fluoro-2-hydroxyphenyl)-2-oxo-2-(thiazol-2-ylamino)ethyl)-3-oxoisoindolin-5-yl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide | 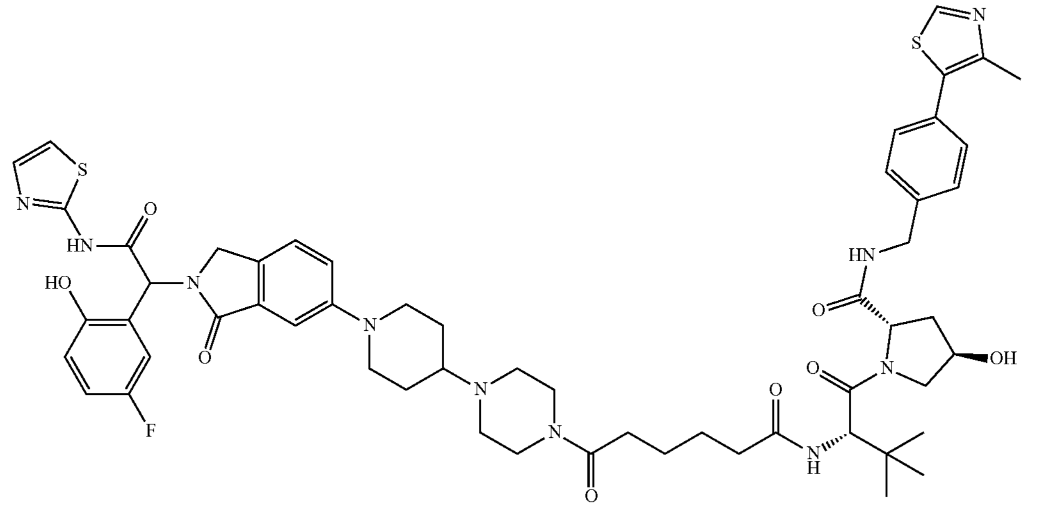 [SMILES: Cc1ncsc1-c1ccc(CNC(=O)[C@@H]2C[C@@H](O)CN2C(=O)[C@@H](NC(=O)CCCCC(=O)N2CCN(C3CCN(c4ccc5c(c4)C(=O)N(C(C(=O)Nc4nccs4)c4cc(F)ccc4O)C5)CC3)CC2)C(C)(C)C)cc1] |
| | (2S,4R)-1-((2S)-2-(8-(4-(1-(2-(1-(5-fluoro-2-hydroxyphenyl)-2-oxo-2-(thiazol-2-ylamino)ethyl)-3-oxoisoindolin-5-yl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide | 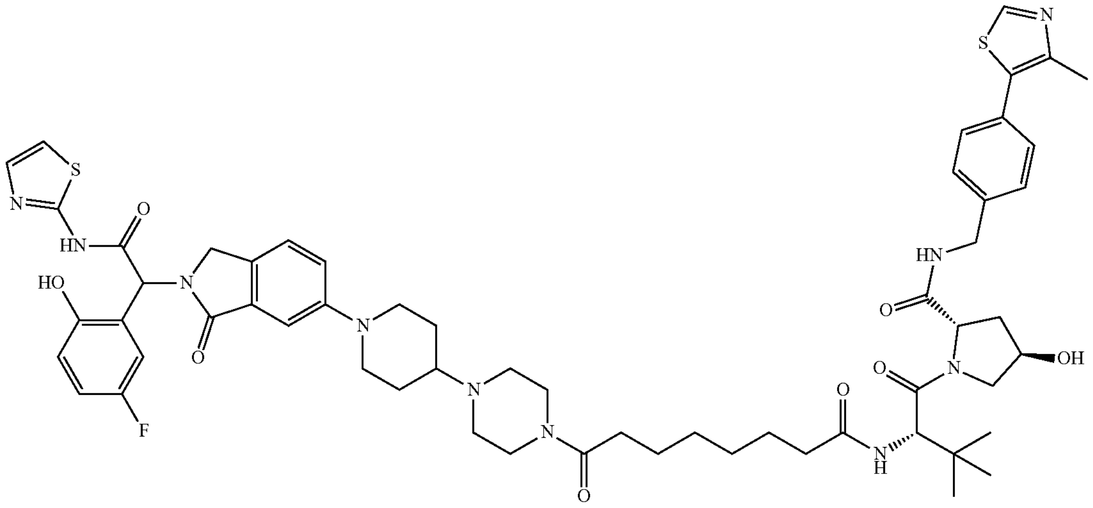 [SMILES: Cc1ncsc1-c1ccc(CNC(=O)[C@@H]2C[C@@H](O)CN2C(=O)[C@@H](NC(=O)CCCCCCC(=O)N2CCN(C3CCN(c4ccc5c(c4)C(=O)N(C(C(=O)Nc4nccs4)c4cc(F)ccc4O)C5)CC3)CC2)C(C)(C)C)cc1] |

TABLE 2-continued

| Compound No. | The compounds' names | Structure of the compounds |
|---|---|---|
| | (2S,4R)-1-((2S)-2-(10-(4-0-(2-0-(5-fluoro-2-hydroxyphenyl)-2-oxo-2-(thiazol-2-ylamino)ethyl)-3-oxoisoindolin-5-yl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide | 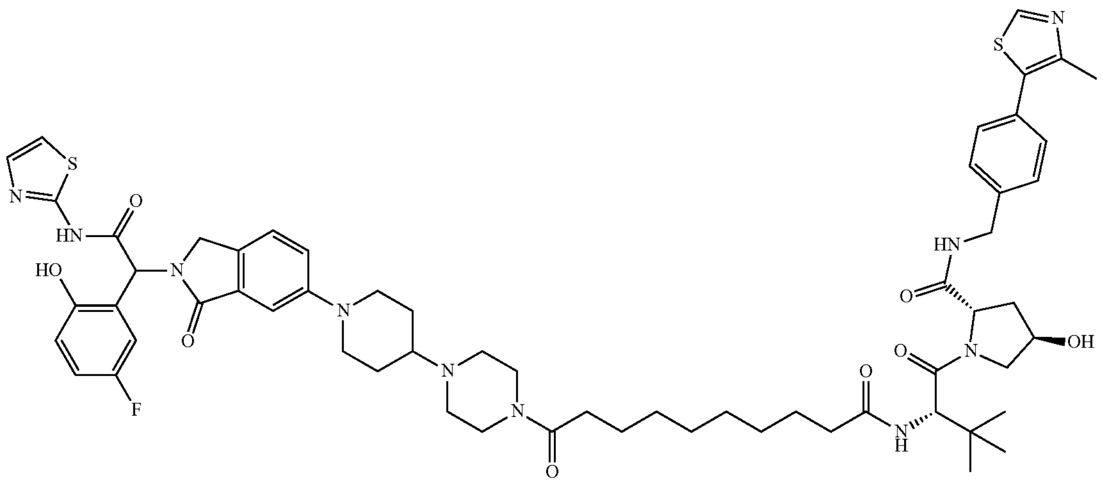 [SMILES: Cc1ncsc1-c1ccc(CNC(=O)[C@@H]2C[C@@H](O)CN2C(=O)[C@@H](NC(=O)CCCCCCCCC(=O)N2CCN(C3CCN(c4ccc5c(c4)C(=O)N(C(C(=O)Nc4nccs4)c4cc(F)ccc4O)C5)CC3)CC2)C(C)(C)C)cc1] |
| | N-(2-(2-(2-((2-(2,6-dioxopiperidin-3-yl)-1-oxoisoindolin-4-yl)thio)-N-methylacetamido)ethoxy)-4-methoxy-5-((4-(1-methyl-1H-indol-3-yl)pyrimidin-2-yl)amino)phenyl)acrylamide | 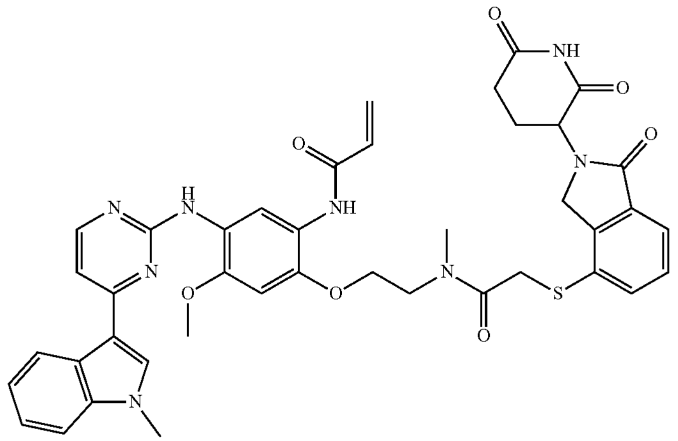 [SMILES: C=CC(=O)Nc1cc(Nc2nccc(-c3cn(C)c4ccccc34)n2)c(OC)cc1OCCN(C)C(=O)CSc1cccc2c1CN(C1CCC(=O)NC1=O)C2=O] |

TABLE 2-continued
| Compound No. | The compounds' names | Structure of the compounds |
|---|---|---|
| | N-(2-(2-(4-(2-((2-(2,6-dioxopiperidin-3-yl)-1-oxoisoindolin-4-yl)thio)acetyl)piperazin-1-yl)ethoxy)-4-methoxy-5-((4-(1-methyl-1H-indol-3-yl)pyrimidin-2-yl)amino)phenyl)acrylamide | 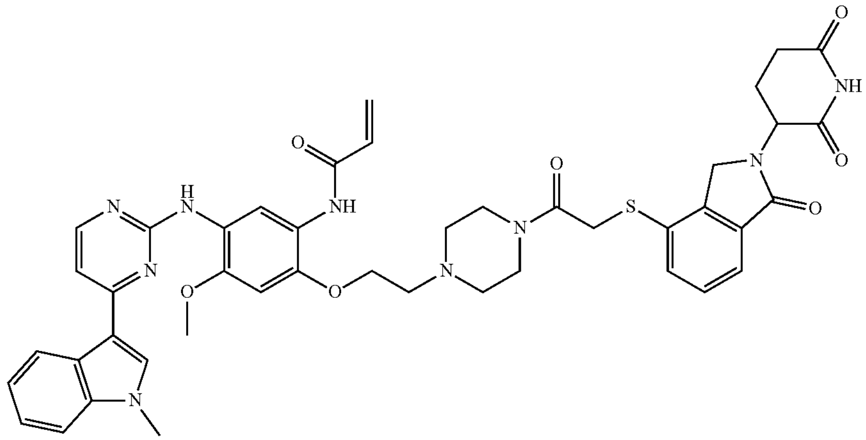 [SMILES: C=CC(=O)Nc1cc(Nc2nccc(-c3cn(C)c4ccccc34)n2)c(OC)cc1OCCN1CCN(C(=O)CSc2cccc3c2CN(C2CCC(=O)NC2=O)C3=O)CC1] |
| | N-(2-(2-(4-(2-((2-(2,6-dioxopiperidin-3-yl)-1-oxoisoindolin-4-yl)thio)acetamido)piperidin-1-yl)ethoxy)-4-methoxy-5-((4-(1-methyl-1H-indol-3-yl)pyrimidin-2-yl)amino)phenyl)acrylamide | 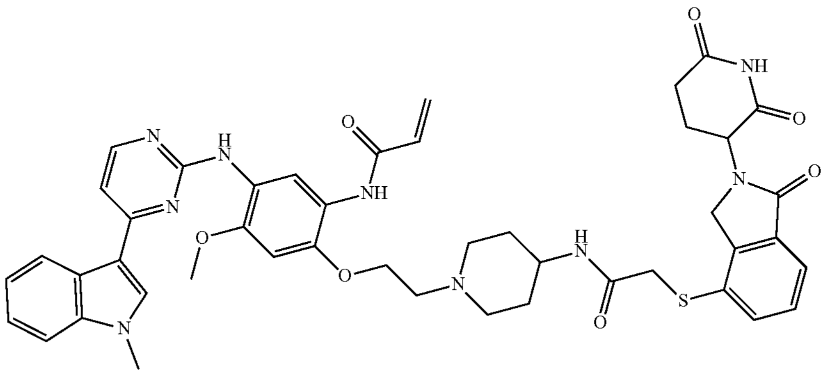 [SMILES: C=CC(=O)Nc1cc(Nc2nccc(-c3cn(C)c4ccccc34)n2)c(OC)cc1OCCN1CCC(NC(=O)CSc2cccc3c2CN(C2CCC(=O)NC2=O)C3=O)CC1] |

TABLE 2-continued

| Compound No. | The compounds' names | Structure of the compounds |
|---|---|---|
| | N-(2-(2-(4-(4-(2-((2-(2,6-dioxopiperidin-3-yl)-1-oxoisoindolin-4-yl)thio)acetyl)piperazin-1-yl)piperidin-1-yl)ethoxy)-4-methoxy-5-((4-(1-methyl-1H-indol-3-yl)pyrimidin-2-yl)amino)phenyl)acrylamide | 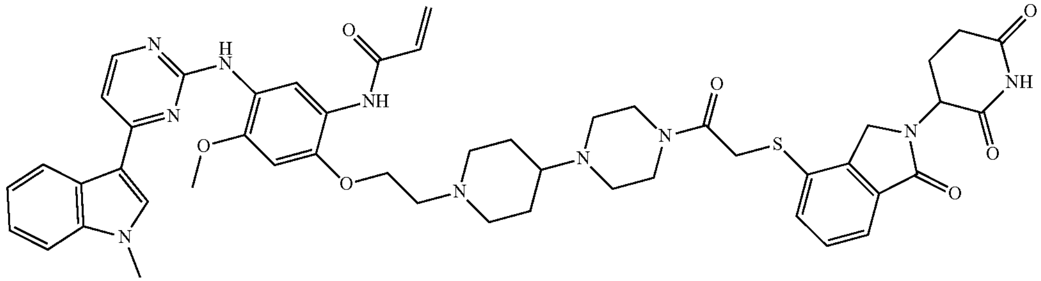 [SMILES: C=CC(=O)Nc1cc(Nc2nccc(-c3cn(C)c4ccccc34)n2)c(OC)cc1OCCN1CCC(N2CCN(C(=O)CSc3cccc4c3CN(C3CCC(=O)NC3=O)C4=O)CC2)CC1] |
| | (E)-N-(2-(2-(dimethylamino)ethoxy)-4-methoxy-5-((4-(1-methyl-1H-indol-3-yl)pyrimidin-2-yl)amino)phenyl)-4-(4-(2-((2-(2,6-dioxopiperidin-3-yl)-1-oxoisoindolin-4-yl)thio)acetyl)piperazin-1-yl)but-2-enamide | 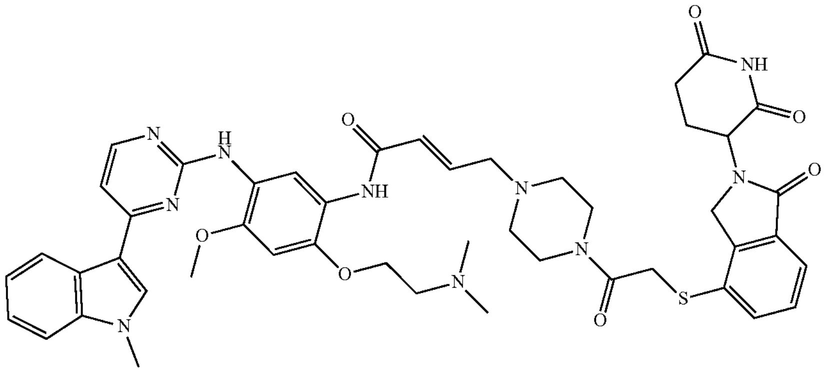 [SMILES: COc1cc(OCCN(C)C)c(NC(=O)/C=C/CN2CCN(C(=O)CSc3cccc4c3CN(C3CCC(=O)NC3=O)C4=O)CC2)cc1Nc1nccc(-c2cn(C)c3ccccc23)n1] |

TABLE 2-continued

| Compound No. | The compounds' names | Structure of the compounds |
|---|---|---|
| | (E)-N-(2-(2-(dimethylamino)ethoxy)-4-methoxy-5-((4-(1-methyl-1H-indol-3-yl)pyrimidin-2-yl)amino)phenyl)-4-(4-(2-((2-(2,6-dioxopiperidin-3-yl)-1-oxoisoindolin-4-yl)thio)acetamido)piperidin-1-yl)but-2-enamide | 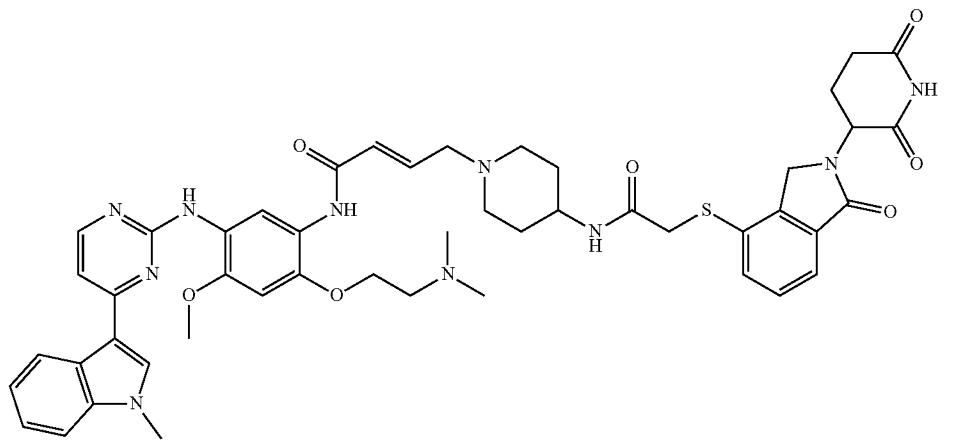 [SMILES: COc1cc(OCCN(C)C)c(NC(=O)/C=C/CN2CCC(NC(=O)CSc3cccc4c3CN(C3CCC(=O)NC3=O)C4=O)CC2)cc1Nc1nccc(-c2cn(C)c3ccccc23)n1] |
| | (E)-N-(2-(2-(dimethylamino)ethoxy)-4-methoxy-5-((4-(1-methyl-1H-indol-3-yl)pyrimidin-2-yl)amino)phenyl)-4-(4-(4-(2-((2-2,6-dioxopiperidin-3-yl)-1-oxoisoindolin-4-yl)thio)acetyl)piperazin-1-yl)piperidin-1-yl)but-2-enamide | 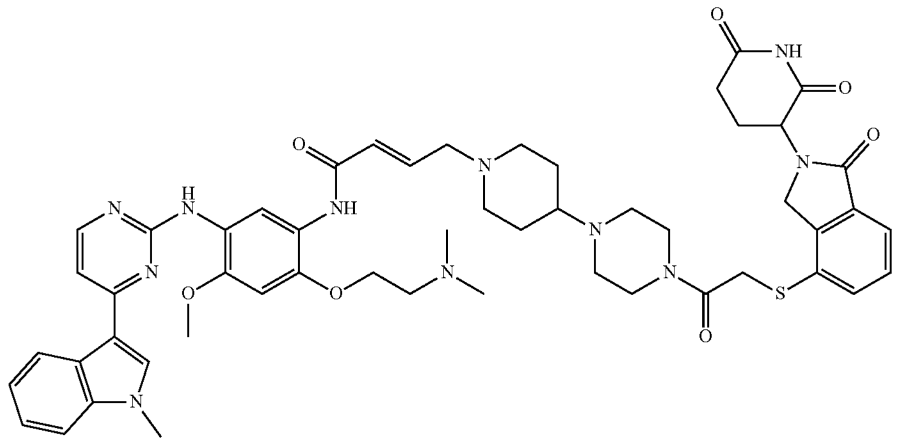 [SMILES: COc1cc(OCCN(C)C)c(NC(=O)/C=C/CN2CCC(N3CCN(C(=O)CSc4cccc5c4CN(C4CCC(=O)NC4=O)C5=O)CC3)CC2)cc1Nc1nccc(-c2cn(C)c3ccccc23)n1] |

In a second aspect of the present invention, there is provided the use of the bifunctional compounds provided in the first aspect of the present invention in the preparation of a medicament. As mentioned above, the bifunctional compounds of the present invention include the EGFR TKIs moiety and the ULM moiety, which are covalently linked to LIN, respectively. The EGFR TKIs moiety is usually used as a protein target binding moiety (PTM, protein target moiety), which (epidermal growth factor receptor (EGFR) tyrosine kinase inhibitors) can act on the intracellular protein tyrosine kinase domain of EGFR, and the ULM moiety can compel the target protein ubiquitinated, thereby inducing the degradation of the target protein by activating the intracellular proteasome system. The ubiquitination degradation pathway can degrade most of the ubiquitinated proteins in the cells. For example, it can degrade 80% to 90% or higher of the ubiquitinated proteins in the cells. If this system can be activated to specifically clean up the carcinogen protein, which restores the cellular protein homeostasis, it is likely to alleviate or treat cancers. The PROTAD technology takes advantage of this, and uses the specially designed dual-specific degraders to tag the target proteins as "to be ubiquitined" to achieve targeted degradation. Therefore, the bifunctional compounds exhibit a good inhibitory effect on EGFR, and are good EGFR inhibitors, which can be used to regulate epidermal growth factor receptor (EGFR) and/or its mutants, and suitable for the treatment of receptor tyrosine kinase (RTK)-related diseases, or diseases related to EGFR overexpression or high EGFR activity, wherein the diseases can be specifically selected from tumors, myeloid tumors, or solid tumors, cancers, leukemia, lymphoma, colorectal cancer, brain cancer, bone cancer, epithelial cell-derived tumors (epithelial cancer), basal cell carcinoma, adenocarcinoma, gastrointestinal cancer, lip cancer, oral cancer, esophageal cancer, small intestine cancer, gastric cancer, colon cancer, liver cancer, bladder cancer, pancreatic cancer, ovarian cancer, cervical cancer, lung cancer, breast cancer, skin cancer, squamous cell and/or basal cell carcinoma, prostate cancer, glioma, glioblastoma, renal cell carcinoma and other cancers known to affect systemic epithelial cells, chronic granulocytic leukemia (CML), acute myeloid leukemia (AML), and acute promyelocytic leukemia (APL).

In a third aspect of the present invention, there is provided a pharmaceutical composition comprising the bifunctional compounds provided in the first aspect of the present invention or a pharmaceutically acceptable salt, an isomer, a prodrug, a polymorph, or a solvate thereof, and at least one pharmaceutically acceptable carrier.

In the present invention, the composition may include one or more pharmaceutically acceptable carriers, which generally refer to carriers for administration of therapeutic agents, which themselves do not induce the production of antibodies detrimental to the individual receiving the composition, and do not cause excessive toxicity after administration. These carriers are well known to those skilled in the art, e.g., those described in Remington's Pharmaceutical Sciences (Mack Pub. Co., N. J. 1991). Specifically, the carrier may include, but is not limited to, a combination of one or more of saline, buffer, glucose, water, glycerol, ethanol, adjuvant, etc.

The pharmaceutical composition of the present invention can comprise the bifunctional compound as a sole active ingredient, or a combination of the bifunctional compound with an additional active ingredient to form a combined formulation. The additional active ingredient may be various drugs that can be used to treat tumors, myeloma or solid tumors, and cancers. The amount of the active ingredient in the composition is usually a safe and effective amount, which should be adjustable for those skilled in the art. For example, the dosages of the bifunctional compound and the active ingredient of the pharmaceutical composition usually depend on the weight of the patient, the type of administration, and the condition and severity of the diseases. For example, the dosage of the bifunctional compound as an active ingredient can usually be 1 to 1000 mg/kg/day, 20 to 200 mg/kg/day, 1 to 3 mg/kg/day, 3 to 5 mg/kg/day, 5 to 10 mg/kg/day, 10 to 20 mg/kg/day, 20 to 30 mg/kg/day, 30 to 40 mg/kg/day, 40 to 60 mg/kg/day, 60 to 80 mg/kg/day, 80 to 100 mg/kg/day, 100 to 150 mg/kg/day, 150 to 200 mg/kg/day, 200 to 300 mg/kg/day, 300 to 500 mg/kg/day, or 500 to 1000 mg/kg/day.

The bifunctional compounds of the present invention can be adapted to any route of administration, which can be oral or parenteral administration, e.g., pulmonary administration, nasal administration, rectal administration and/or intravenous injection, and more specifically intradermal, subcutaneous, intramuscular, intraarticular, intraperitoneal, lung, buccal, sublingual, nasal, transdermal, vaginal, oral or parenteral administration. Those skilled in the art can select a suitable formulation form according to the route of administration, e.g., formulations suitable for oral administration which may include, but are not limited to, pills, tablets, masticatory, capsules, granules, drops or syrups; e.g., formulations suitable for parenteral administration which may include, but are not limited to, solutions, suspensions, reconstitutable dry formulations or sprays; e.g., formulations suitable for rectal administration which may include, but are not limited to, suppositories.

In a fourth aspect of the present invention, there is provided a treatment method comprising: administering to an individual a therapeutically effective amount of the bifunctional compounds provided in the first aspect of the present invention or the pharmaceutical composition provided in the third aspect of the present invention.

In the present invention, "individuals" generally include humans and non-human primates, such as mammals, dogs, cats, horses, sheep, pigs, cattle, etc., which can benefit from treatment with the formulations, kits or combined formulations.

In the present invention, "therapeutically effective amount" generally refers to an amount that can achieve the effect of treating the diseases listed above after a proper administration period.

The bifunctional compound of the present invention is a bifunctional compound based on an epidermal growth factor receptor tyrosine kinase inhibitor, which can not only promote the degradation of EGFR protein, but also inhibit the activity of EGFR kinase and have a significant inhibitory effect on the proliferation of EGFR mutation-positive cells.

In the following description, numerous specific embodiments are set forth in order to provide a thorough understanding of the present invention, and those skilled in the art can easily understand other advantages and effects of the present invention from the content disclosed in this specification. The present invention can also be implemented or applied through other different specific embodiments, and various details in this specification can also be modified or changed based on different viewpoints and applications without departing from the spirit of the present invention.

It should be noted that the process equipments or devices not specifically noted in the following embodiments are all conventional equipments or devices in the art.

In addition, unless otherwise specified, it should be understood that one or more method steps mentioned in the present invention do not exclude that there may be additional method steps before and after the combined steps, or additional method steps inserted between these explicitly mentioned steps. Unless otherwise specified, it should also be understood that the combined connection relationship between one or more equipments/devices mentioned in the present invention does not exclude that additional equipments/devices may also exist before and after the combined equipments/devices, or additional equipments/devices may also be inserted between the two explicitly mentioned equipments/devices. Moreover, unless otherwise specified, the number of each method step is only a convenient tool for identifying each method step, not to limit the sequence of each method step or to limit the scope of the present invention, and the changes or adjustments of the relative relationship of the number of each method step fall within the scope of the present invention without substantial change in the technical content.

The following abbreviations are used throughout the description and examples:

Boc t-butyloxy carbonyl
Con. concentration
DCM dichloromethane
DMF N,N-dimethylformamide
DMSO dimethyl sulfoxide
DIPEA N, N-diisopropylethylamine
EDCI 1-(3-dimethylaminopropyl)-3-ethylcarbodiimide
ESI electrospray ionization
equiv equivalent
EtOH ethanol
HOAT 1-hydroxy-7-azabenzotriazole
HPLC high performance liquid chromatography
HRMS high resolution mass spectrometry
LC-MS liquid chromatography-mass spectrometry
LRMS low resolution mass spectrometry
LC liquid chromatography
Me methyl
MeCN acetonitrile
MeOH methanol
MS mass spectrum
MW microwave
NMM N-methylmorpholine
NMP N-methylpyrrolidone
$^1$H NMR Proton nuclear magnetic resonance
rt room temperature
TFA trifluoroacetic acid
TLC thin layer chromatography
TMS trimethylsilyl
Xantphos; or X-phos 4,5-Bisdiphenylphosphine-9,9-dimethylxanthene In the present disclosure, the $^1$H NMR spectra were recorded on a Bruker-500 MHz nuclear magnetic resonance instrument, by using, as a solvent and an internal standard, $CD_3OD$ containing 0.1% TMS ($^1$H NMR in $CD_3OD$; δ=3.31 ppm); or using, as a solvent and an internal standard, $CDCl_3$ containing 0.1% TMS ($^1$H NMR in $CDCl_3$; δ=7.26 ppm); or using, as a solvent and an internal standard, DMSO-$d_6$ containing 0.03% TMS ($^1$H NMR in DMSO-$d_6$; δ=2.50 ppm). LRMS spectrum was recorded on an AB Triple 4600 mass spectrometer, HPLC preparation was measured on a SHIMADZU LC-20AP type instrument, and HPLC purity was measured on a SHIMADZU LC-30AP or Waters 1525 type instrument. Unless otherwise specified, all reactions were performed in the air atmosphere. The reactions were tracked by TLC or LC-MS.

Solvents and reagents are processed as follows:

The solvents used in the reactions such as DCM, DMF, anhydrous EtOH, and anhydrous MeOH were purchased from Chinese Sinopharm Group; Preparative grade $CH_3CN$ and deionized water were used in HPLC preparation.

Unless otherwise specified, dacomitinib, alectinib derivative A, crizotinib, ceritinib, brigatinib, TAE684 (NVP-TAE684), ASP3026, GSK1838705A, AZD3463, Entrectinib (RXDX-101), Ensartinib (X-396)), various carbon chain linking unit linkers of different lengths (i.e., compounds used to form the group represented by LIN), and other reagents and medicines were commercially available and used directly without special instructions.

General Synthesis Methods Used in the Examples are Summarized as Follows:

General Synthesis Method of Dacomitinib Derivatives A and B (EGFR Inhibitors):

Scheme 1

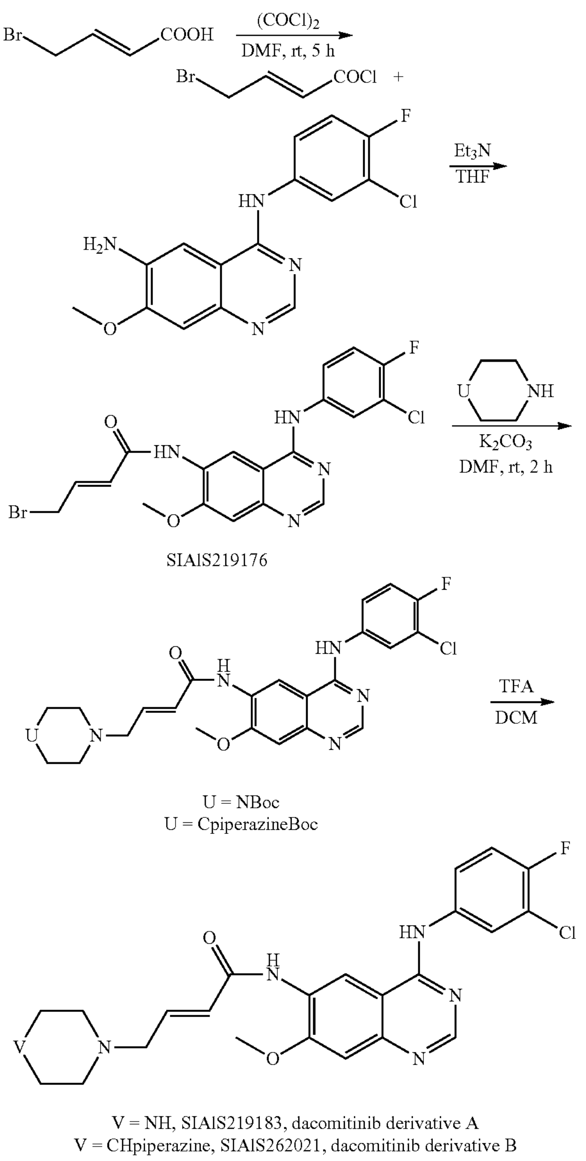

SIAIS219176

U = NBoc
U = CpiperazineBoc

V = NH, SIAIS219183, dacomitinib derivative A
V = CHpiperazine, SIAIS262021, dacomitinib derivative B The groups U and V are as shown in Scheme 1.

General Synthesis Method of Poziotinib Derivatives (EGFR Inhibitors):
Scheme 2
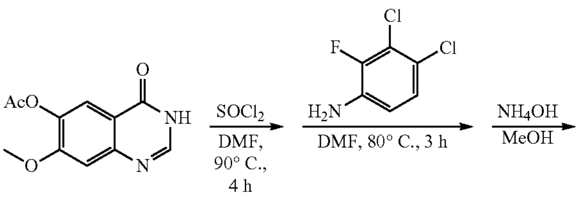
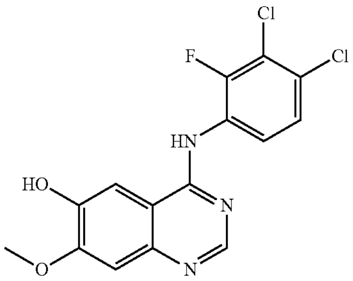
SIAIS219148
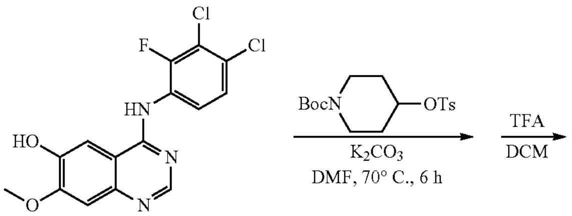
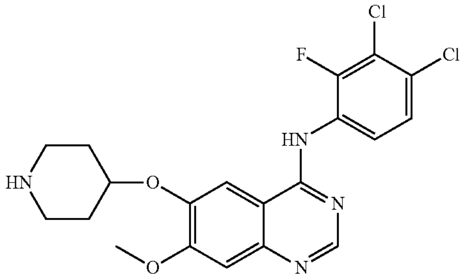
SIAIS219149B
General Synthesis Method of Gefitinib Derivatives (EGFR Inhibitors):
Scheme 3
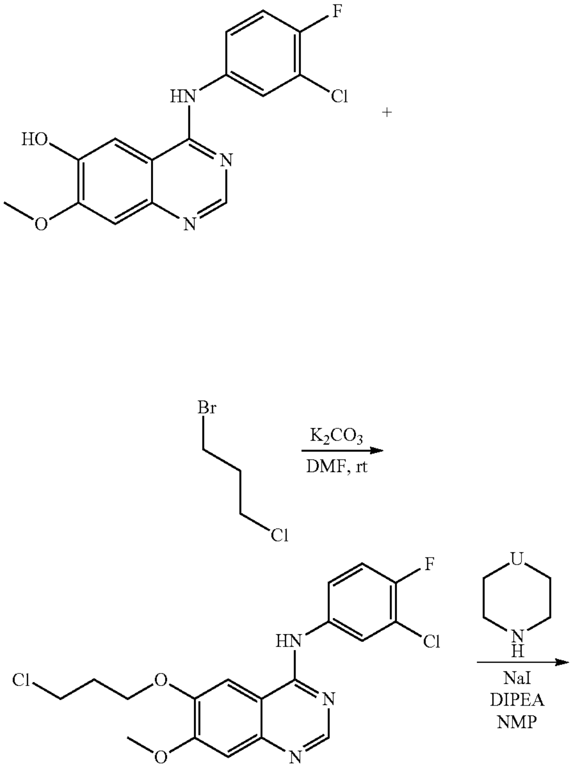
SIAIS184151
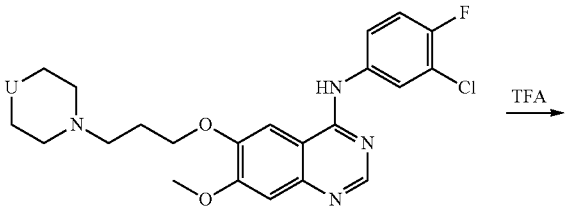
U = NBoc
U = CpiperazineBoc
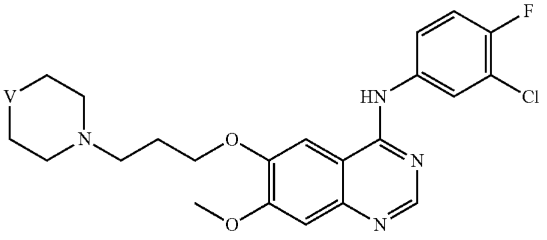
V = NH, SIAIS184161, Gefitinib derivative A
V = CHpiperazine, SIAI262080, Gefitinib derivative B General Synthesis Method of Canertinib Derivatives (EGFR Inhibitors):

Scheme 4

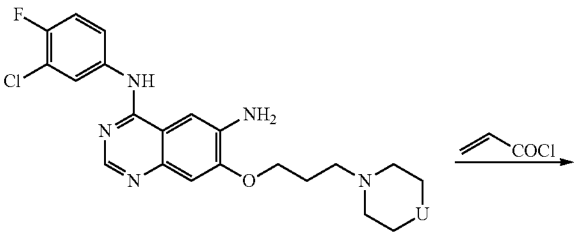

U = NBoc
U = CpiperazineBoc

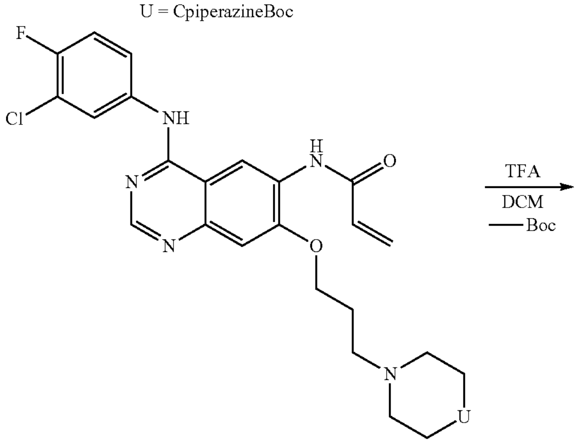

-continued

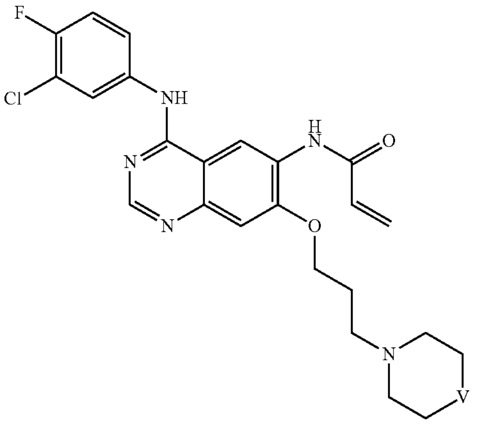

V = NH, SIAIS, Canetinib derivative A
V = CHpiperazine, SIAIS262080, Canetinib derivative B General Synthesis Method of Sapitinib Derivative and Gefitinib Derivative D (EGFR Inhibitors):

Scheme 5

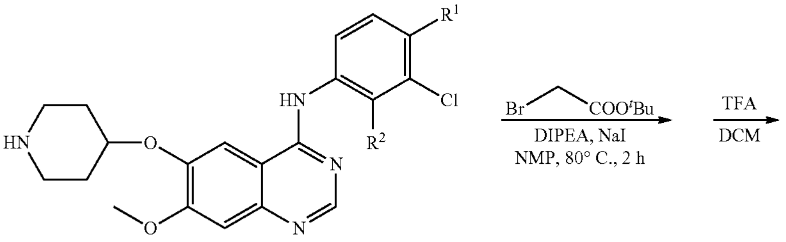

$R^1$ or $R^2$ = F or H

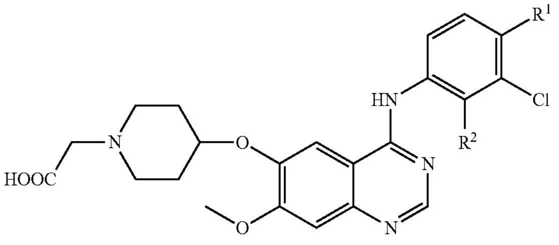

$R^1$ = F, $R^1$ = H, SIAIS184161. Gefitinib derivative C
$R^1$ = H, $R^2$ = F, SIAIS184161, Sapitinib derivative A General Synthesis Method of Intermediates LM (Thio-Pomalidomide with Alkylene Chain-Carboxylic Acid Group Linker):

Scheme 6

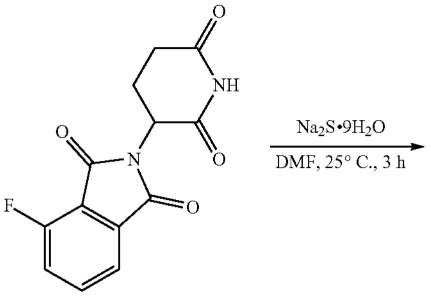

pomalidomide

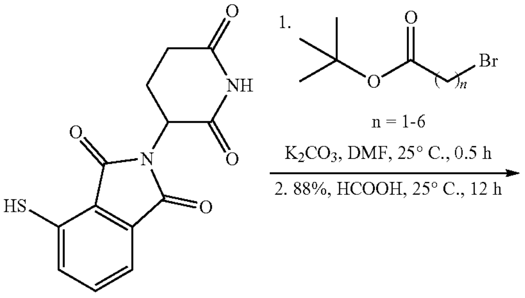

SIAIS151014

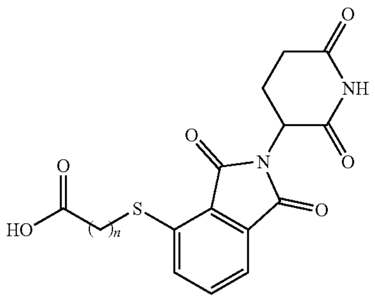

wherein n=an integer of 1-10, as shown in Scheme 6.

General Synthesis Method of Intermediates LM (Thio-Pomalidomide with PEG Chain-Carboxylic Acid Group Linker):

Scheme 7

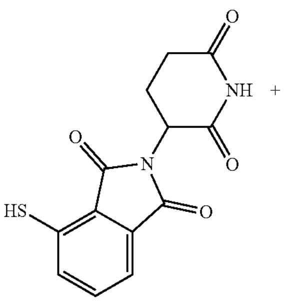

-continued

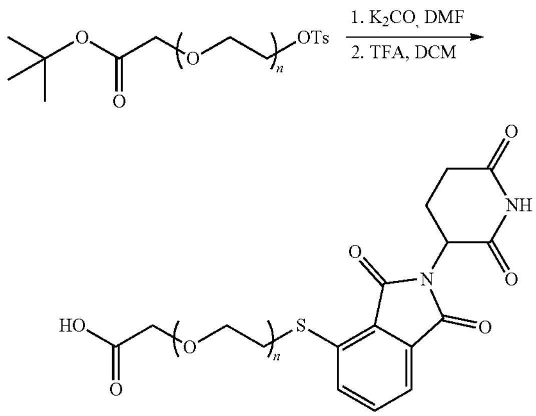

wherein n=an integer of 1-5, as shown in Scheme 7.

General Synthesis Method of Intermediates LM (Thio-Lenalidomide with Alkylene Chain-Carboxylic Acid Group Linker):

Scheme 8

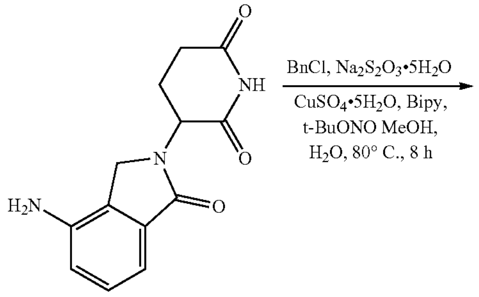

lenalidomide

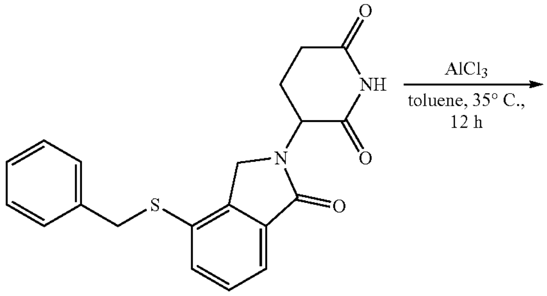

SIAIS171088

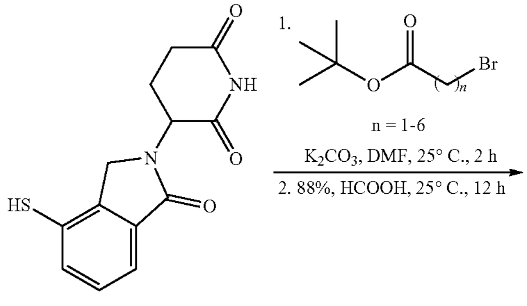

SIAIS171095

-continued

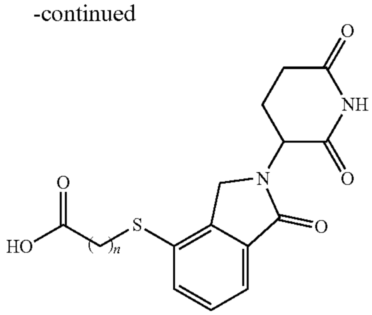

wherein n=an integer of 1-10, as shown in Scheme 8.

General Synthesis Method of Intermediates LM (Thio-Lenalidomide with PEG Chain-Carboxylic Acid Group Linker):

Scheme 9

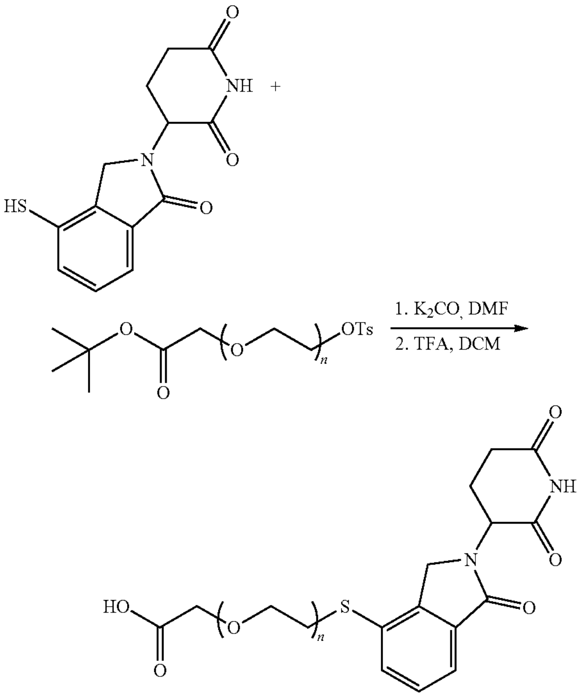

wherein n=an integer of 1-5, as shown in scheme 9.

General Synthesis Method of Intermediates LM (Lenalidomide with Alkylene Chain-Alkynyl Linker):

Scheme 10

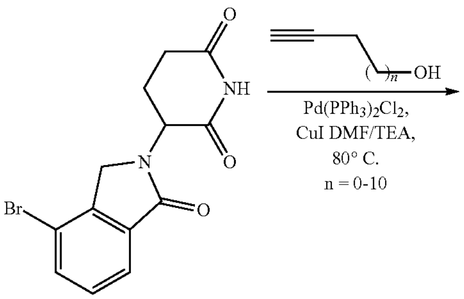

-continued

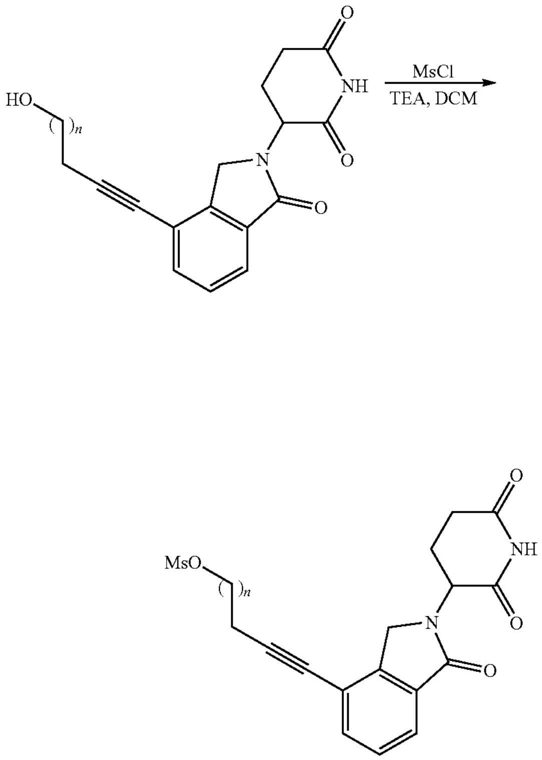

wherein n=an integer of 1-10, as shown in scheme 10.

General Synthesis Method of Intermediates LM (Thio-Lenalidomide with Alkylene Chain-Amino Linker):

Scheme 11

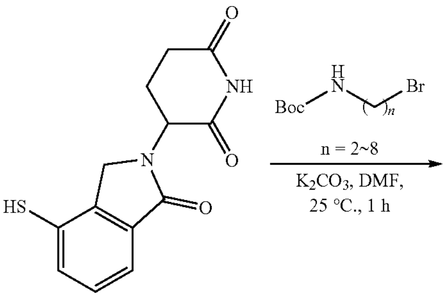

SIAIS171095

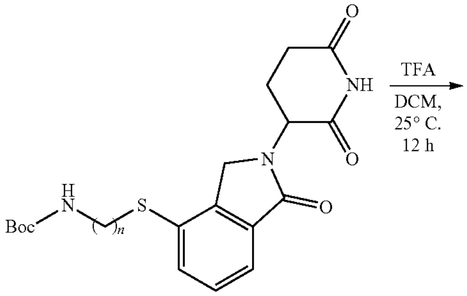

-continued
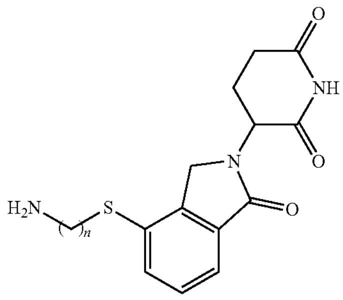
wherein n=an integer of 1-10, as shown in scheme 11.
General Synthesis Method of Intermediates LM (Thio-Lenalidomide with Alkylene Chain-Bromine Linker):
Scheme 12
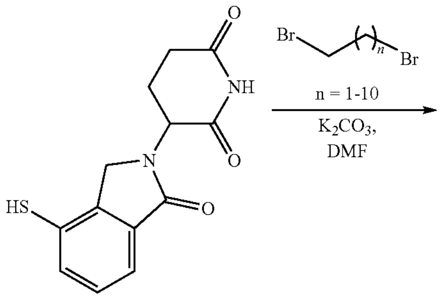
SIAIS171095
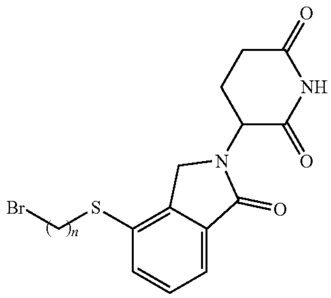
wherein n=an integer of 1-10, as shown in Scheme 12.
General Synthesis Method of Intermediates LM (Pomalidomide with Alkylene Chain-Iodine Linker):
Scheme 13
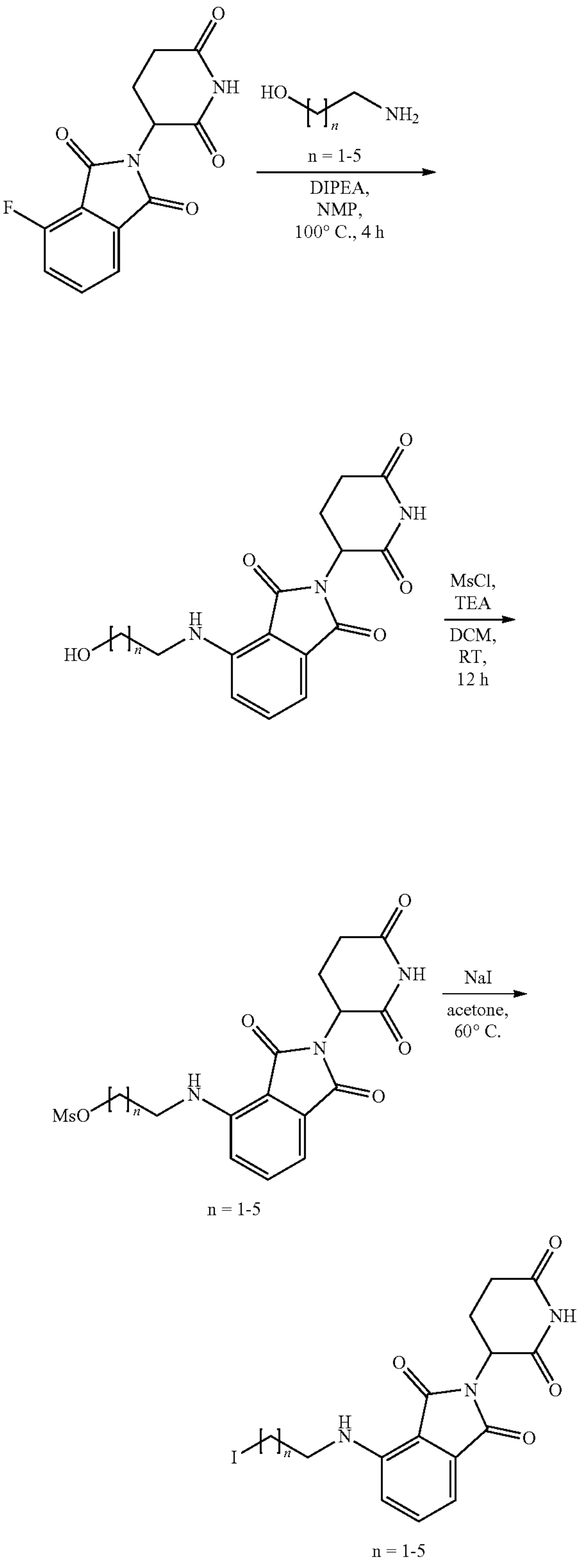

General Synthesis Method of the Compounds of the Present Invention:
Scheme 14
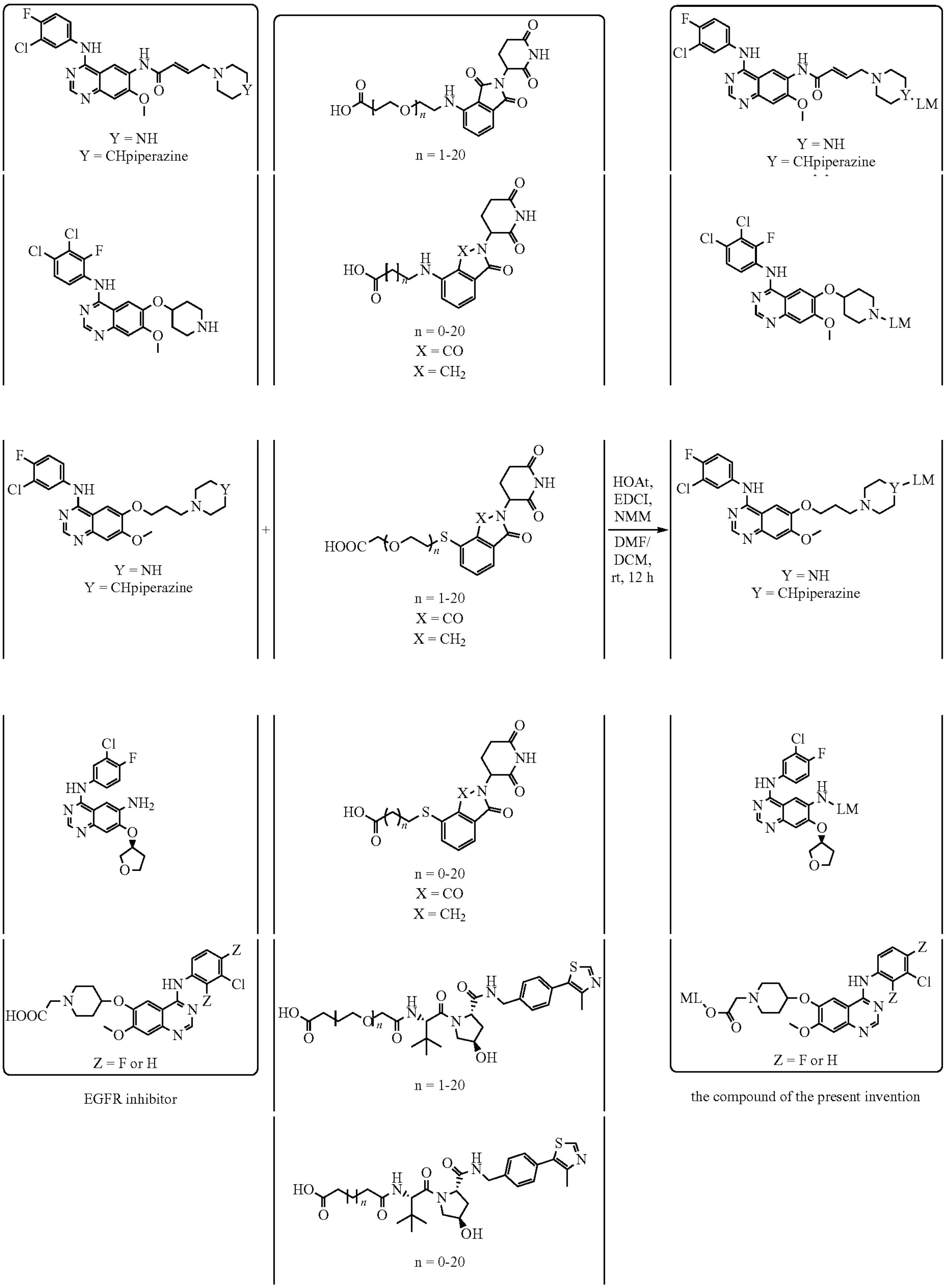

-continued
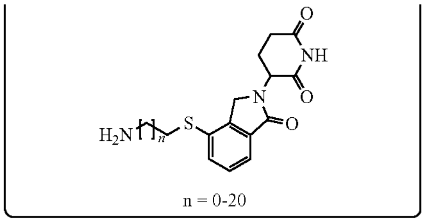
LM
Special Synthesis Method of the Compounds of the Present Invention (Alkylation Reaction):
Scheme 15
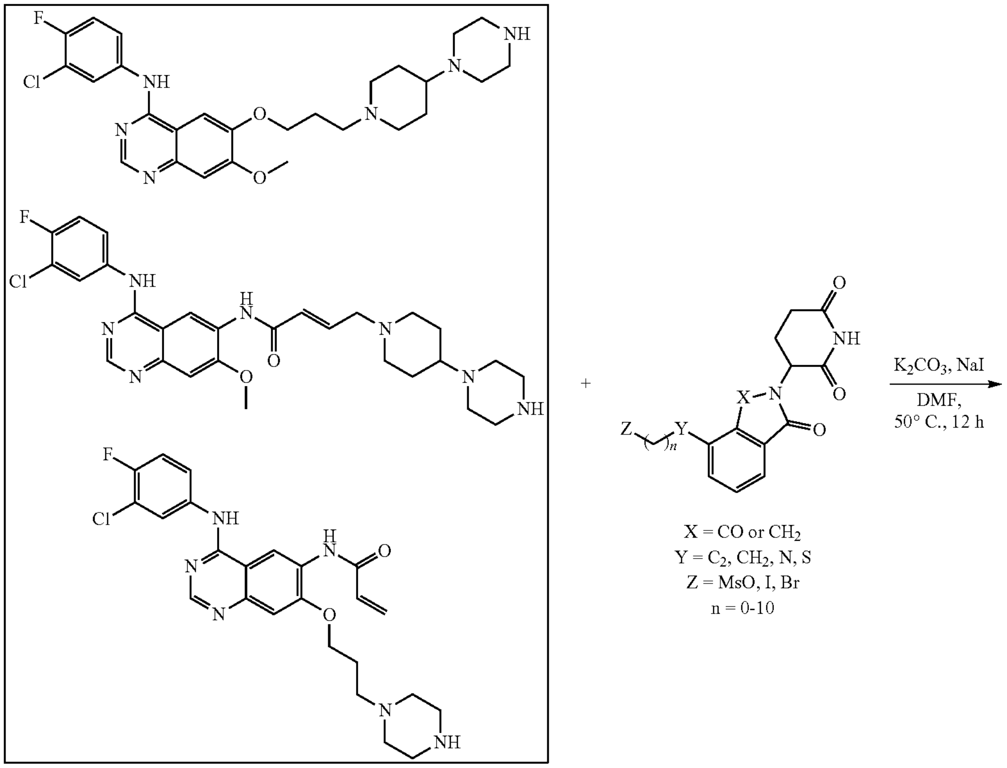

-continued

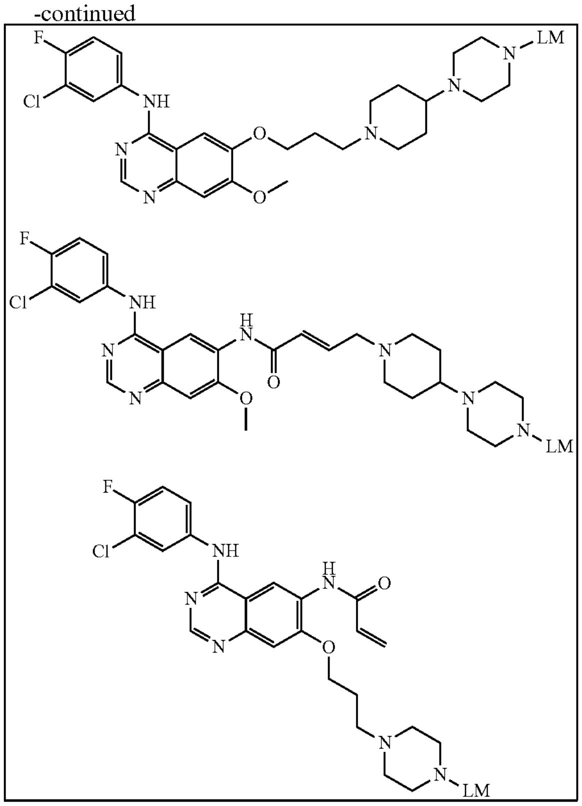

Intermediate Example 1

Preparation of Dacomitinib Derivative A (SIAIS219183):

Dacomitinib Derivative A (SIAIS219183) was prepared according to Scheme 1.

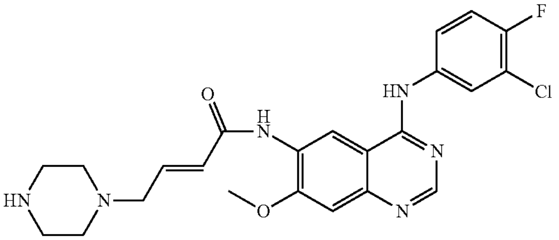 [SMILES: COc1cc2ncnc(Nc3ccc(F)c(Cl)c3)c2cc1NC(=O)/C=C/CN1CCNCC1]

Preparation of (E)-4-bromo-N-(4-((3-chloro-4-fluorophenyl)amino)-7-methoxyquinazolin-6-yl)but-2-enamide (SIAIS219176)

4-bromo-crotonic acid (825 mg, 5 mmol) was dissolved in 4 mL of oxalyl chloride under an argon atmosphere. Then to the mixture was added a drop of DMF to initiate the reaction. The mixture was stirred at room temperature for 2 h, and rotary evaporated under low-temperature to remove the excess oxalyl chloride. A 100 mL clean egg-shaped flask was sequentially charged with N-(3-chloro-4-fluorophenyl)-7-methoxy-6-aminoquinazolin-4-amine (636 mg, 2 mmol), 4 mL THF, and triethylamine (417 mg, 3 mmol) with stirring at room temperature, followed by addition of a solution of the acyl chloride prepared in-situ in 4 mL THF. The reaction mixture was reacted at room temperature for 1 h. After the reaction was complete, the reaction was quenched with water. The mixture was extracted with ethyl acetate. The organic phase was washed with water and saturated brine, dried over anhydrous sodium sulfate, and rotary evaporated to obtain the crude product. The crude product was subjected to C18 reverse phase column chromatography (eluent: MeOH/water) for purification to give the target product SIAIS219176 as a yellow solid (754 mg, yield 81%). $^1H$ NMR (500 MHz, MeOD) δ 9.25 (s, 1H), 8.77 (s, 1H), 7.94 (dd, J=6.6, 2.6 Hz, 1H), 7.69-7.64 (m, 1H), 7.38 (t, J=8.9 Hz, 1H), 7.34 (s, 1H), 7.07-7.01 (m, 1H), 6.69 (d, J=15.3 Hz, 1H), 4.18 (s, 3H), 3.53-3.48 (m, 2H). HRMS (ESI) m/z: calcd for $C_{19}H_{16}BrClFN_4O_2^+$ [M+H]$^+$, 465.0124; found, 465.0121.

Preparation of (E)-N-(4-((3-chloro-4-fluorophenyl)amino)-7-methoxyquinazolin-6-yl)-4-(piperazin-1-yl)but-2-enamide (SIAIS219183)

An egg-shaped flask was sequentially charged with SIAIS219176 (200 mg, 0.43 mmol), 4 mL DMF, N-tert-butoxycarbonylpiperazine (160.2 mg, 0.86 mmol), and potassium carbonate (356.6 mg, 1.29 mmol) at room temperature, followed by evacuation and refilling with argon gas and reacting at 40° C. for 2 h. After the reaction was complete as monitored by TLC, the mixture was subject to a reversed phase C18 column chromatography (eluent: MeOH/water) for purification to give a yellow solid which was used directly in the next step. To a solution of the obtained yellow solid dissolved in DCM (6 mL) was added 2 mL $CF_3COOH$. The mixture was stirred at room temperature for 2 h. After the reaction was complete as monitored by LC-MS, the mixture was rotary evaporated to remove most of the $CF_3COOH$, and the pH was adjusted to alkaline with saturated sodium bicarbonate solution. The resulting mixture was extracted with dichloromethane. The organic phase was dried over anhydrous sodium sulfate, and rotary evaporated to obtain the crude product. The crude product was subjected to C18 reverse phase column chromatography (eluent: MeOH/water) for purification to give the target product SIAIS219183 as a yellow solid (178 mg, total yield of two steps 88%). $^1H$ NMR (500 MHz, MeOD) δ 9.24 (s, 1H), 8.75 (s, 1H), 7.93 (dd, J=6.6, 2.6 Hz, 1H), 7.66 (ddd, J=8.9, 4.1, 2.7 Hz, 1H), 7.37 (t, J=8.9 Hz, 1H), 7.33 (s, 1H), 7.03 (dt, J=15.3, 6.2 Hz, 1H), 6.68 (d, J=15.3 Hz, 1H), 4.17 (s, 3H), 3.51-3.48 (m, 2H), 3.36-3.33 (m, 4H), 2.93 (s, 4H). HRMS (ESI) m/z: calcd for $C_{23}H_{25}ClFN_6O_2^+$ $[M+H]^+$, 471.1706; found, 471.1706.

Intermediate Example 2

Preparation of Dacomitinib Derivative B:

Referring to Scheme 1, Dacomitinib derivative B was prepared by using a method similar to that of dacomitinib derivative A in Intermediate Example 1. The synthetic and structural characterization data of the intermediate are as follows:

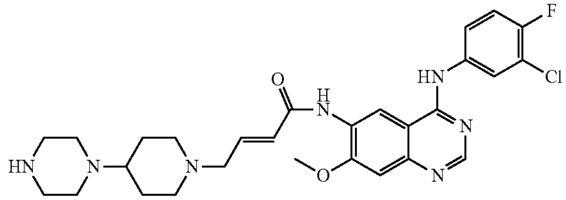 [SMILES: COc1cc2ncnc(Nc3ccc(F)c(Cl)c3)c2cc1NC(=O)/C=C/CN1CCC(N2CCNCC2)CC1]

(E)-N-(4-((3-chloro-4-fluorophenyl)amino)-7-methoxyquinazolin-6-yl)-4-(4-(piperazin-1-yl)piperidin-1-yl)but-2-enamide (SIAIS262021). (yellow solid, 166.3 mg, total yield of two steps 79%) $^1H$ NMR (500 MHz, MeOD) δ 9.26 (s, 1H), 8.75 (s, 1H), 7.93 (dd, J=6.6, 2.6 Hz, 1H), 7.67-7.63 (m, 1H), 7.40-7.34 (m, 2H), 7.05-7.01 (m, 1H), 6.84 (d, J=15.2 Hz, 1H), 4.17 (s, 3H), 4.03 (d, J=7.0 Hz, 2H), 3.66 (s, 1H), 3.29-3.26 (m, 4H), 3.22-3.09 (m, 2H), 3.01-2.80 (m, 6H), 2.16 (s, 2H), 2.01-1.85 (m, 2H). HRMS (ESI) m/z: calcd for $C_{28}H_{34}ClFN_7O_2^+$ $[M+H]^+$, 554.2441; found, 554.2433.

Intermediate Example 3

Preparation of Poziotinib Derivative A (SIAIS219149B):

Poziotinib derivative A (SIAIS219149B) was prepared according to Scheme 2.

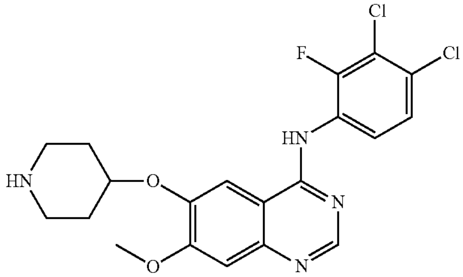 [SMILES: COc1cc2ncnc(Nc3ccc(Cl)c(Cl)c3F)c2cc1OC1CCNCC1]

Preparation of 4-((3,4-dichloro-2-fluorophenyl) amino)-7-methoxyquinazolin-6-ol (SIAIS219148)

6-acetoxy-7-methoxy-3,4-dihydroquinazolin-4(3H)-one (468.4 mg, 2 mmol) was dissolved in 4 mL of sulfoxide chloride under an argon atmosphere. Then to the mixture was added a drop of DMF to initiate the reaction. The mixture was stirred at 90° C. for 4 h, and rotary evaporated under low-temperature to remove the excess sulfoxide chloride, and the obtained residue was used directly in the next step. A 100 mL clean egg-shaped flask was sequentially charged with the product obtained from the previous step (2 mmol), 10 mL DMF, and 3,4-dichloro-2-fluoroaniline (432 mg, 2.4 mmol) with stirring at 80° C. for 1 h. After the reaction was complete, the reaction was quenched with ice water, and the mixture was filtered to obtain the intermediate which was used directly in the next step. A 100 mL clean egg-shaped flask was sequentially charged with the intermediate obtained from the previous step (2 mmol), 10 mL methanol, and 2 mL aqueous ammonia solution with stirring under reflux at 70° C. for 2 h. The reaction mixture was cooled, filtered, and wased with a small amount of cold methanol to give the target product SIAIS219148 as a yellow solid (310 mg, total yield of three steps 44%). $^1H$ NMR (500 MHz, MeOD) δ 8.38 (s, 1H), 7.78 (s, 1H), 7.61 (t, J=8.2 Hz, 1H), 7.40 (dd, J=8.8, 1.9 Hz, 1H), 7.21 (s, 1H). HRMS (ESI) m/z: calcd for $C_{15}H_{11}Cl_2FN_3O_2^+$ $[M+H]^+$, 354.0207; found, 354.0202.

Preparation of N-(3,4-dichloro-2-fluorophenyl)-7-methoxy-6-(piperidin-4-yloxy)quinazolin-4-amine (SIAIS219149B)

An egg-shaped flask was sequentially charged with SIAIS219148 (177.1 mg, 0.5 mmol), 4 ml DMF, tert-butyl 4-(tosyloxy)piperidine-1-carboxylate (213.3 mg, 0.6 mmol), and potassium carbonate (207.3 mg, 1.5 mmol) at room temperature, followed by evacuation and refilling with argon gas and reacting at 70° C. for 5 h. After the reaction was complete as monitored by TLC, the mixture was subject to a reversed phase C18 column chromatography (eluent: MeOH/water) for purification to give a yellow solid which was used directly in the next step. To a solution of the obtained yellow solid dissolved in DCM (6 mL) was added 2 mL $CF_3COOH$. The mixture was stirred at room temperature for 2 h. After the reaction was complete as monitored by LC-MS, the mixture was rotary evaporated to remove most of the $CF_3COOH$, and the pH was adjusted to alkaline with saturated sodium bicarbonate solution. The resulting mixture was extracted with dichloromethane. The organic phase was dried over anhydrous sodium sulfate, and rotary evaporated to obtain the crude product. The crude product was subjected to C18 reverse phase column chromatography (eluent: MeOH/water) for purification to give the target product SIAIS219149B as a yellow solid (196.8 mg, total yield of two steps 90%). $^1H$ NMR (500 MHz, MeOD) δ 8.37 (s, 1H), 7.79 (s, 1H), 7.59 (t, J=8.2 Hz, 1H), 7.42 (dd, J=8.8, 1.9 Hz, 1H), 7.20 (s, 1H), 4.85-4.80 (m, 1H), 4.00 (s, 3H), 3.98-3.89 (m, 2H), 3.71-3.59 (m, 2H), 2.08 (dd, J=8.4, 3.7 Hz, 2H), 1.90 (dd, J=10.1, 6.6 Hz, 2H). HRMS (ESI) m/z: calcd for $C_{20}H_{20}Cl_2FN_4O_2^+$ $[M+H]^+$, 437.0942; found, 437.0942.

Intermediate Example 4

Preparation of Gefitinib Derivative A (SIAIS219161):

Gefitinib derivative A (SIAIS219161) was prepared according to Scheme 3.

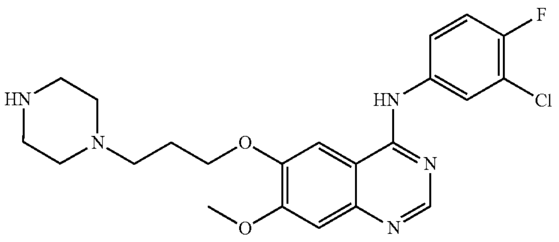 [SMILES: COc1cc2ncnc(Nc3ccc(F)c(Cl)c3)c2cc1OCCCN1CCNCC1]

Preparation of N-(3-chloro-4-fluorophenyl)-6-(3-chloropropoxy)-7-methoxyquinazolin-4-amine (SIAIS184151)

4-((3-chloro-4-fluorophenyl)amino)-7-methoxyquinazolin-6-ol (639.4 mg, 2 mmol), 5 mL DMF, 1-bromo-3-chloropropane (630 mg, 4 mmol), and potassium carbonate (829.3 mg, 6 mmol) were reacted at room temperature under an argon atmosphere for 12 h. After the reaction was complete, the mixture was subjected to C18 reverse phase column chromatography (eluent: MeOH/water) for separation to give the target product SIAIS184151 as a yellow solid (350 mg, yield 44%). $^{1}H$ NMR (500 MHz, MeOD) δ 8.44 (s, 1H), 8.00 (dd, J=6.7, 2.6 Hz, 1H), 7.75 (s, 1H), 7.67 (ddd, J=8.8, 4.0, 2.7 Hz, 1H), 7.25 (t, J=9.0 Hz, 1H), 7.17 (s, 1H), 4.33 (t, J=5.9 Hz, 2H), 4.00 (s, 3H), 3.84 (t, J=6.3 Hz, 2H), 2.34 (p, J=6.1 Hz, 2H). HRMS (ESI) m/z: calcd for $C_{18}H_{17}Cl_2FN_3O_2^+$ $[M+H]^+$, 396.0676; found, 396.0676.

Preparation of N-(3-chloro-4-fluorophenyl)-7-methoxy-6-(3-(piperazin-1-yl)propoxy)quinazolin-4-amine (SIAIS184161)

An egg-shaped flask was sequentially charged with SIAIS184151 (350 mg, 0.883 mmol), 4 mL NMP, N-tert-butoxycarbonylpiperazine (328.9 mg, 1.766 mmol), DIPEA (456.5 mg, 3.532 mmol), and NaI (264.7 mg, 1.766 mmol) at room temperature, followed by evacuation and refilling with argon gas and reacting at 90° C. for 2 h. After the reaction was complete as monitored by TLC, the mixture was subject to a reversed phase C18 column chromatography (eluent: MeOH/water) for separation to give a yellow solid which was used directly in the next step. To a solution of the obtained yellow solid dissolved in DCM (6 mL) was added 2 mL $CF_3COOH$. The mixture was stirred at room temperature for 2 h. After the reaction was complete as monitored by LC-MS, the mixture was rotary evaporated to remove most of the $CF_3COOH$, and the pH was adjusted to alkaline with saturated sodium bicarbonate solution. The resulting mixture was extracted with dichloromethane, dried over anhydrous sodium sulfate, and rotary evaporated to obtain the crude product. The crude product was subjected to C18 reverse phase column chromatography (eluent: MeOH/water) for separation to give the target product SIAIS184161 as a yellow solid (320 mg, total yield of two steps 81%). $^{1}H$ NMR (500 MHz, MeOD) δ 8.74 (s, 1H), 7.98 (s, 1H), 7.94 (dd, J=6.6, 2.6 Hz, 1H), 7.69-7.63 (m, 1H), 7.37 (t, J=8.9 Hz, 1H), 7.27 (s, 1H), 4.37 (t, J=5.6 Hz, 2H), 4.09 (s, 3H), 3.57-3.52 (m, 4H), 3.48-3.40 (m, 4H), 3.32 (d, J=4.4 Hz, 2H), 2.41-2.32 (m, 2H). HRMS (ESI) m/z: calcd for $C_{22}H_{26}ClFN_5O_2^+$ $[M+H]^+$, 446.1754; found, 446.1754.

Intermediate Example 5

Preparation of Gefitinib Derivative B:

Referring to Scheme 3, Gefitinib derivative B was prepared by using a method similar to that of Gefitinib derivative A in Intermediate Example 4. The synthetic and structural characterization data of the intermediate are as follows:

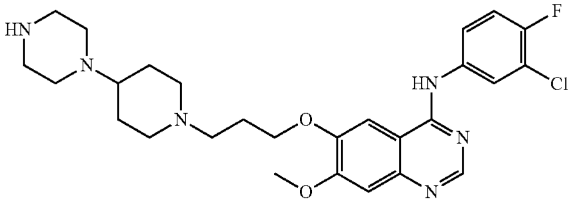 [SMILES: COc1cc2ncnc(Nc3ccc(F)c(Cl)c3)c2cc1OCCCN1CCC(N2CCNCC2)CC1]

N-(3-chloro-4-fluorophenyl)-7-methoxy-6-(3-(4-(piperazin-1-yl)piperidin-1-yl)propoxy)quinazolin-4-amine (SIAIS262080). (yellow solid, 401 mg, total yield of two steps 76%) $^{1}H$ NMR (500 MHz, MeOD) δ 8.75 (s, 1H), 7.99 (s, 1H), 7.94 (dd, J=6.6, 2.6 Hz, 1H), 7.71-7.62 (m, 1H), 7.38 (t, J=8.9 Hz, 1H), 7.29 (s, 1H), 4.38 (t, J=5.6 Hz, 2H), 4.08 (s, 3H), 3.58-3.52 (m, 8H), 3.49-3.40 (m, 9H), 3.34 (d, J=4.4 Hz, 2H), 2.41-2.31 (m, 2H). HRMS (ESI) m/z: calcd for $C_{27}H_{35}ClFN_6O_2^+$ $[M+H]^+$, 529.2489, found, 529.2489.

Intermediate Example 6

Preparation of Canertinib Derivative A (SIAIS293064):

Canertinib derivative A (SIAIS293064) was prepared according to Scheme 4.

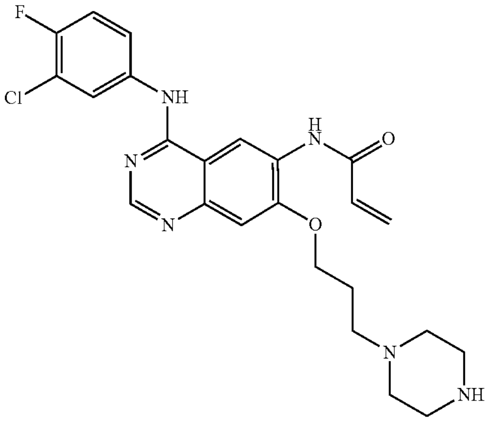 [SMILES: C=CC(=O)Nc1cc2c(Nc3ccc(F)c(Cl)c3)ncnc2cc1OCCCN1CCNCC1]

Preparation of N-(4-((3-chloro-4-fluorophenyl)amino)-7-(3-(piperazin-1-yl)propoxy)quinazolin-6-yl)acrylamide (SIAIS293064)

To a solution of tert-butyl 4-(3-((6-amino-4-((3-chloro-4-fluorophenyl)amino)quinazolin-7-yl)oxy)propyl)piperazine-1-carboxylate (531 mg, 1 mmol) in 5 mL of THF was added acryloyl chloride (362 mg, 4 mmol) in 0° C. ice-water bath under an argon atmosphere. The mixture was then warmed up to room temperature and reacted for 1 h. After the reaction was complete, the reaction was quenched with water. The mixture was extracted with dichloromethane. The organic phase was dried over anhydrous sodium sulfate, and rotary evaporated to obtain the intermediate which was then subjected to silica gel column chromatography (eluent (v/v): dichloromethane/methanol=20:1 to 10:1) for purification to give a yellow solid which was used directly in the next step. To a solution of the obtained yellow solid dissolved in DCM (6 mL) was added 2 mL $CF_3COOH$. The mixture was stirred at room temperature for 2 h. After the reaction was complete as monitored by LC-MS, the mixture was rotary evaporated to remove most of the $CF_3COOH$, and the pH was adjusted to alkaline with saturated sodium bicarbonate solution. The resulting mixture was extracted with dichloromethane. The organic phase was dried over anhydrous sodium sulfate, and rotary evaporated to obtain the crude product. The crude product was subjected to C18 reverse phase column chromatography (eluent: MeOH/water) for separation to give the target product SIAIS293064 as a yellow solid (341 mg, total yield of two steps 70%). $^1$H NMR (500 MHz, MeOD) δ 9.20 (s, 1H), 8.76 (s, 1H), 7.95-7.91 (m, 1H), 7.66 (ddd, J=8.9, 4.2, 2.6 Hz, 1H), 7.37 (d, J=5.5 Hz, 1H), 6.89 (dd, J=16.9, 10.3 Hz, 1H), 6.52 (dd, J=16.9, 1.5 Hz, 1H), 5.90 (dd, J=10.3, 1.6 Hz, 1H), 4.51 (t, J=5.8 Hz, 2H), 3.72 (dd, J=21.9, 11.5 Hz, 6H), 3.61-3.56 (m, 2H), 2.54 (td, J=11.7, 5.8 Hz, 2H). HRMS (ESI) m/z: calcd for $C_{24}H_{27}ClFN_6O_2^+$ $[M+H]^+$, 485.1863; found, 485.1861.

Intermediate Example 7

Preparation of Canertinib Derivative B:

Referring to Scheme 4, Canertinib Derivative B was prepared by using a method similar to that of Canertinib Derivative A in Intermediate Example 6. The synthetic and structural characterization data of the intermediate are as follows:

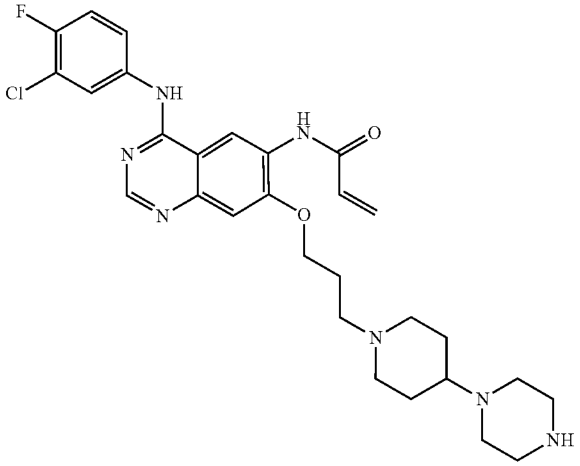 [SMILES: C=CC(=O)Nc1cc2c(Nc3ccc(F)c(Cl)c3)ncnc2cc1OCCCN1CCC(N2CCNCC2)CC1]

N-(4-((3-chloro-4-fluorophenyl)amino)-7-(3-(4-(piperazin-1-yl)piperidin-1-yl)propoxy)quinazolin-6-yl)acrylamide (SIAIS249183). (yellow solid, 200 mg, total yield of two steps 62%) $^1$H NMR (500 MHz, MeOD) δ 9.22 (s, 1H), 8.78 (s, 1H), 7.96-7.91 (m, 1H), 7.67-7.62 (m, 1H), 7.38 (d, J=5.5 Hz, 1H), 6.89-6.83 (m, 1H), 6.55-6.51 (m, 1H), 5.91 (dd, J=10.3, 1.6 Hz, 1H), 4.52 (t, J=5.8 Hz, 2H), 3.79-3.68 (m, 10H), 3.64-3.56 (m, 3H), 2.54-2.43 (m, 6H). HRMS (ESI) m/z: calcd for $C_{29}H_{36}ClFN_7O_2^+$ $[M+H]^+$, 568.2598, found, 568.2591.

Intermediate Example 8

Preparation of Gefitinib Derivative C (SIAIS293033):

Gefitinib derivative C(SIAIS293033) was prepared according to Scheme 5.

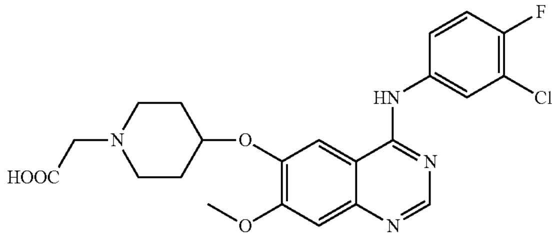 [SMILES: COc1cc2ncnc(Nc3ccc(F)c(Cl)c3)c2cc1OC1CCN(CC(=O)O)CC1]

Preparation of 2-(4-((4-((3-chloro-4-fluorophenyl)amino)-7-methoxyquinazolin-6-yl)oxy)piperidin-1-yl)acetic acid (SIAIS293033)

To a solution of N-(3-chloro-4-fluorophenyl)-7-methoxy-6-(piperidin-4-yloxy)quinazolin-4-amine (400 mg, 0.8 mmol) in 5 mL NMP were sequentially added 3-(tert-butoxy)-3-oxopropanoic acid (234 mg, 1.2 mmol), NaI (240 mg, 1.6 mmol), and DIPEA (310 mg, 2.4 mmol) under air atmosphere. The mixture was reacted at 80° C. for 2 h. After the reaction was complete, the reaction was quenched with water. The mixture was extracted with dichloromethane. The organic phase was dried over anhydrous sodium sulfate, and rotary evaporated to obtain the intermediate which was then subjected to silica gel column chromatography (eluent (v/v): dichloromethane/methanol=20:1 to 10:1) for purification to give a yellow solid which was used directly in the next step. To a solution of the obtained yellow solid dissolved in DCM (6 mL) was added 2 mL $CF_3COOH$. The mixture was reacted at room temperature for 2 h. After the reaction was complete as monitored by LC-MS, the mixture was rotary evaporated to remove most of the $CF_3COOH$, and the pH was adjusted to alkaline with saturated sodium bicarbonate solution. The resulting mixture was extracted with dichloromethane. The organic phase was dried over anhydrous sodium sulfate, and rotary evaporated to obtain the crude product. The crude product was subjected to C18 reverse phase column chromatography (eluent: MeOH/water) for purification to give the target product SIAIS293033 as a yellow solid (320 mg, total yield of two steps 87%). $^1$H NMR (500 MHz, MeOD) δ 8.74 (s, 1H), 8.11 (s, 1H), 7.93 (d, J=4.5 Hz, 1H), 7.66 (d, J=8.8 Hz, 1H), 7.37 (t, J=8.9 Hz, 1H), 7.30 (s, 1H), 4.95 (s, 2H), 4.12 (s, 1H), 4.10 (s, 3H), 3.57 (d, J=15.2 Hz, 4H), 2.34 (s, 4H). HRMS (ESI) m/z: calcd for $C_{22}H_{23}ClFN_4O_4^+$ $[M+H]^+$, 461.1386, found, 461.1385.

Intermediate Example 9

Preparation of Sapitinib Derivative A:

Referring to Scheme 5, Sapitinib Derivative A was prepared by using a method similar to that of Gefitinib derivative C in Intermediate Example 8. The synthetic and structural characterization data of the intermediate are as follows:

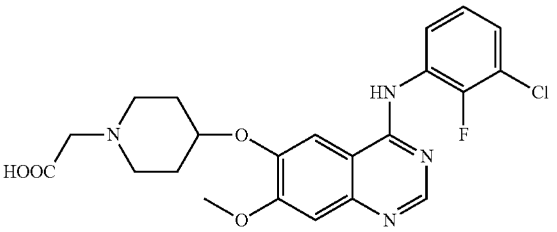 [SMILES: COc1cc2ncnc(Nc3cccc(Cl)c3F)c2cc1OC1CCN(CC(=O)O)CC1]

2-(4-((4-((3-chloro-2-fluorophenyl)amino)-7-methoxy-quinazolin-6-yl)oxy)piperidin-1-yl)acetic acid (SIAIS293061). (yellow solid, 335 mg, total yield of two steps 61%) $^1H$ NMR (500 MHz, MeOD) δ 8.67 (s, 1H), 8.21 (s, 1H), 7.62 (d, J=7.6 Hz, 2H), 7.53-7.48 (m, 3H), 7.33-7.27 (m, 2H), 4.94 (s, 2H), 4.14 (s, 1H), 4.11 (s, 3H), 3.58 (d, J=15.2 Hz, 4H), 2.34 (s, 4H). HRMS (ESI) m/z: calcd for $C_{22}H_{23}ClFN_4O_4^+$ [M+H]$^+$, 461.1386, found, 461.1381.

The synthetic methods and structural characterization data of the intermediates SIAIS151001, SIAIS151004, SIAIS151005, SIAIS151006, SIAIS151007, SIAIS151025, SIAIS151026, SIAIS151019, SIAIS151020, SIAIS151027, SIAIS151086, SIAIS1204057, SIAIS1204085, SIAIS1210133, SIAIS1204061, SIAIS1210133, SIAIS1204061, SIAIS120, SIA151074, SIAIS0101061, SIAIS120, SIAIS151008 SIAIS074012, SIAIS074013, SIAIS074014, SIAIS074015, SIAIS074016, SIAIS074019, SIAIS074020, and SIAIS172147 that act as linkers, can be seen in China Appl. Pub. No. CN109912655 A.

The synthetic methods and structural characterization data of the intermediates SIAIS1220099, SIAIS299138, SIAIS299135, SIAIS213132, SIAIS213135, SIAIS1216135, SIAIS1216137, SIAIS1220059, SIAIS1220013, SIAIS1220015, and SIAIS1220141 that act as linkers, can be seen in China Pat. No. 201910279248.9.

The synthetic methods and structural characterization data of the intermediates SIAIS164118 and SIAIS164119 that act as linkers, can be seen in PCT publication WO 2019170150 (A1).

The synthetic methods and structural characterization data of the intermediates SIAIS1213061 and SIAIS1213011 that act as linkers, can be seen in PCT publication WO2020103878 (A1).

Intermediate Example 10

Preparation of 2-(2-((2-(2,6-dioxopiperidin-3-yl)-1,3-dioxoisoindolin-4-yl)thio)ethoxy)acetic acid (SIAIS1204137)

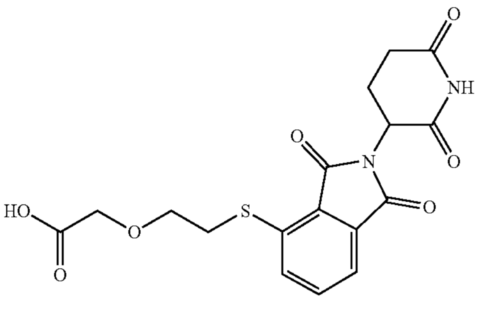 [SMILES: O=C(O)COCCSc1cccc2c1C(=O)N(C1CCC(=O)NC1=O)C2=O]

According to Scheme 7, a 50 mL egg-shaped flask was sequentially charged with the intermediate compound SIAIS151014 (0.724 mmol, 1 equiv), anhydrous N,N-dimethylformamide (10 mL) and anhydrous potassium carbonate (1.448 mmol, 2 equiv), followed by slow addition of the corresponding p-toluenesulfonate-substituted substrate (0.869 mmol, 1.2 equiv) as a linker with stirring at room temperature. After the completion of addition, the mixture was stirred at room temperature for 0.5 h. After the starting materials were consumed, the reaction mixture was filtered to remove the insoluble substance, and the filtrate was then directly subjected to a reverse phase C18 column chromatography (eluent (v/v): acetonitrile/water=10%-100%) for separation, and the collected fractions were concentrated under reduced pressure to remove the solvents, to give the corresponding tert-butyl ester intermediate compound. The corresponding tert-butyl ester intermediate compound, dichloromethane (1 mL) and trifluoroacetic acid (3 mL) were sequentially added to a 25 mL egg-shaped flask, and stirred at room temperature for 1 h, and then concentrated under reduced pressure to remove the solvents. The resulting residue was treated by addition of water and lyophilized to afford the corresponding target compound SIAIS1204137 (light yellow solid, 185 mg, yield 69%). $^1H$ NMR (500 MHz, DMSO) δ 11.12 (s, 1H), 7.83-7.73 (m, 2H), 7.64 (d, J=6.6 Hz, 1H), 5.12 (dd, J=12.8, 5.4 Hz, 1H), 4.08 (s, 2H), 3.77 (t, J=6.4 Hz, 2H), 3.14-3.07 (m, 2H), 2.94-2.82 (m, 1H), 2.66-2.55 (m, 2H), 2.09-2.01 (m, 1H). HRMS (ESI) m/z: calcd for $C_{17}H_{17}N_2O_7S^+$ [M+H]$^+$, 393.0751; found, 393.0763.

Intermediate Example 11

Preparation of 2-(2-(2-((2-(2,6-dioxopiperidin-3-yl)-1,3-dioxoisoindolin-4-yl)thio)ethoxy)ethoxy) acetic acid (SIAIS1204139)

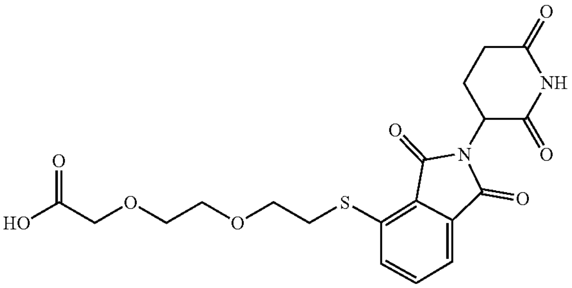 [SMILES: O=C(O)COCCOCCSc1cccc2c1C(=O)N(C1CCC(=O)NC1=O)C2=O]

The compound SIAIS1204139 was prepared according to the method of intermediate example 10, except that the p-toluenesulfonate-substituted substrate was tert-butyl 2-(2-(2-(tosyloxy)ethoxy)ethoxy)acetate. The target compound SIAIS1204139 was obtained as a light yellow solid (190 mg, yield 63%). $^1H$ NMR (500 MHz, DMSO) δ 11.12 (s, 1H), 7.83-7.76 (m, 2H), 7.63 (dd, J=6.4, 1.3 Hz, 1H), 5.12 (dd, J=12.9, 5.4 Hz, 1H), 4.02 (s, 2H), 3.72 (t, J=6.3 Hz, 2H), 3.59 (s, 4H), 3.39-3.30 (m, 2H), 3.13-3.06 (m, 1H), 2.64-2.52 (m, 2H), 2.09-2.02 (m, 1H). HRMS (ESI) m/z: calcd for $C_{19}H_{21}BN_2O_8S^+$ [M+H]$^+$, 437.1013; found, 437.1032.

Intermediate Example 12

Preparation of 2-(2-(2-(2-((2-(2,6-dioxopiperidin-3-yl)-1,3-dioxoisoindolin-4-yl)thio)ethoxy) ethoxy) ethoxy)acetic acid (SIAIS1204141)

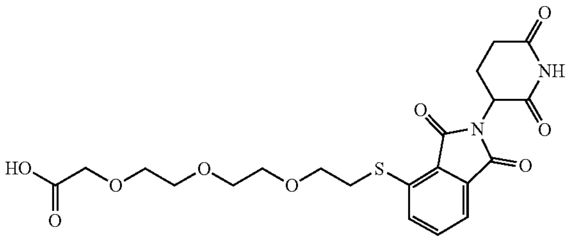 [SMILES: O=C(O)COCCOCCOCCSc1cccc2c1C(=O)N(C1CCC(=O)NC1=O)C2=O]

The compound SIAIS1204141 was prepared according to the method of intermediate example 10, except that the p-toluenesulfonate-substituted substrate was tert-butyl 2-(2-(2-(2-(tosyloxy)ethoxy)ethoxy)ethoxy)acetate. The target compound SIAIS1204141 was obtained as a light yellow solid (246 mg, yield 74%). $^1$H NMR (500 MHz, DMSO) δ 11.12 (s, 1H), 7.85-7.73 (m, 2H), 7.63 (dd, J=6.1, 1.9 Hz, 1H), 5.12 (dd, J=12.9, 5.4 Hz, 1H), 4.02 (s, 2H), 3.71 (t, J=6.3 Hz, 2H), 3.62-3.48 (m, 8H), 3.35 (t, J=6.3 Hz, 2H), 2.94-2.84 (m, 1H), 2.63-2.52 (m, 2H), 2.11-1.99 (m, 1H). HRMS (ESI) m/z: calcd for $C_{21}H_{25}N_2O_9S^+$ $[M+H]^+$, 481.1275; found, 481.1273.

Intermediate Example 13

Preparation of 14-((2-(2,6-dioxopiperidin-3-yl)-1,3-dioxoisoindolin-4-yl)thio)-3,6,9,12-tetraoxatetradecanoic acid (SIAIS1204147)

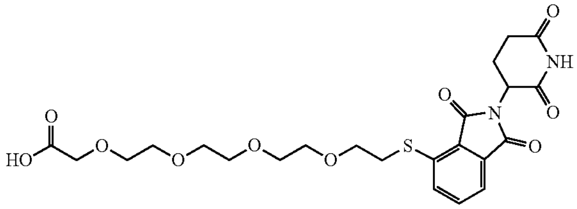 [SMILES: O=C(O)COCCOCCOCCOCCSc1cccc2c1C(=O)N(C1CCC(=O)NC1=O)C2=O]

The compound SIAIS1204147 was prepared according to the method of intermediate example 10, except that the p-toluenesulfonate-substituted substrate was tert-butyl 14-(tosyloxy)-3,6,9,12-tetraoxatetradecanoate. The target compound SIAIS1204147 was obtained as a light yellow solid (228 mg, yield 63%). $^1$H NMR (500 MHz, DMSO) δ 11.12 (s, 1H), 7.83-7.73 (m, 2H), 7.63 (dd, J=6.2, 1.7 Hz, 1H), 5.12 (dd, J=12.9, 5.4 Hz, 1H), 4.01 (s, 2H), 3.71 (t, J=6.3 Hz, 2H), 3.59-3.54 (m, 4H), 3.54-3.49 (m, 8H), 3.35 (t, J=6.3 Hz, 2H), 2.94-2.84 (m, 1H), 2.64-2.56 (m, 1H), 2.55-2.51 (m, 1H), 2.08-2.02 (m, 1H). HRMS (ESI) m/z: calcd for $C_{23}H_{29}N_2O_{10}S^+$ $[M+H]^+$, 525.1537; found, 525.1536.

Intermediate Example 14

Preparation of 17-((2-(2,6-dioxopiperidin-3-yl)-1,3-dioxoisoindolin-4-yl)thio)-3,6,9,12,15-pentaoxaheptadecanoic acid (SIAIS1204149)

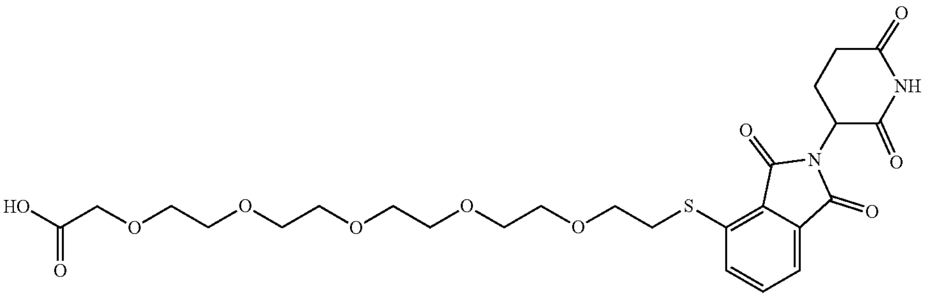 [SMILES: O=C(O)COCCOCCOCCOCCOCCSc1cccc2c1C(=O)N(C1CCC(=O)NC1=O)C2=O]

The compound SIAIS1204149 was prepared according to the method of intermediate example 10, except that the p-toluenesulfonate-substituted substrate was tert-butyl 17-(tosyloxy)-3,6,9,12,15-pentaoxaheptadecanoate. The target compound SIAIS1204149 was obtained as a light yellow solid (259 mg, yield 66%). $^1$H NMR (500 MHz, DMSO) δ 11.12 (s, 1H), 7.83-7.74 (m, 2H), 7.63 (dd, J=6.2, 1.8 Hz, 1H), 5.12 (dd, J=12.9, 5.4 Hz, 1H), 4.01 (s, 2H), 3.71 (t, J=6.3 Hz, 2H), 3.60-3.55 (m, 4H), 3.55-3.47 (m, 12H), 3.35 (t, J=6.3 Hz, 2H), 2.93-2.84 (m, 1H), 2.64-2.56 (m, 1H), 2.55-2.51 (m, 1H), 2.08-2.02 (m, 1H). HRMS (ESI) m/z: calcd for $C_{25}H_{33}N_2O_{11}S^+$ [M+H]$^+$, 569.1800; found, 569.1814.

Intermediate Example 15

Preparation of 2-((2-(2,6-dioxopiperidin-3-yl)-1,3-dioxoisoindolin-4-yl)thio)acetic acid (SIAIS151045)

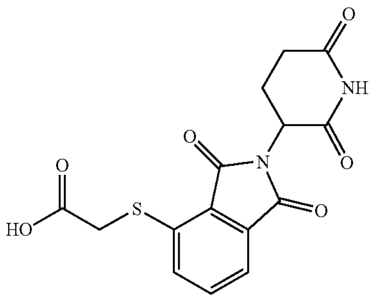 [SMILES: O=C(O)CSc1cccc2c1C(=O)N(C1CCC(=O)NC1=O)C2=O]

The compound SIAIS151045 was prepared according to the method of Scheme 6, except that the brominated substrate as the linker was tert-butyl 2-bromoacetate. The target compound SIAIS151045 was obtained as a light yellow solid (0.69 g, yield 80%). $^1$H NMR (500 MHz, DMSO) δ 13.06 (s, 1H), 11.15 (s, 1H), 7.80 (dd, J=8.1, 7.3 Hz, 1H), 7.66 (t, J=7.9 Hz, 2H), 5.13 (dd, J=12.9, 5.4 Hz, 1H), 4.09 (s, 2H), 2.92-2.85 (m, 1H), 2.66-2.51 (m, 2H), 2.08-2.03 (m, 1H). HRMS (ESI) m/z: calcd for $C_{15}H_{13}N_2O_6S^+$ [M+H]$^+$, 349.0489; found, 349.0297.

Intermediate Example 16

Preparation of 3-((2-(2,6-dioxopiperidin-3-yl)-1,3-dioxoisoindolin-4-yl)thio)propanoic acid (SIAIS151138B)

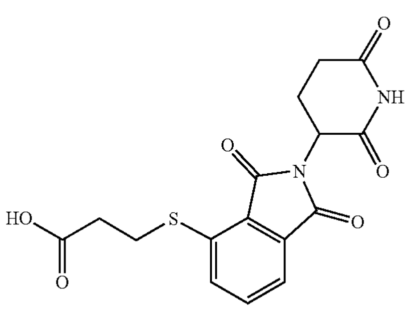 [SMILES: O=C(O)CCSc1cccc2c1C(=O)N(C1CCC(=O)NC1=O)C2=O]

The compound SIAIS151138B was prepared according to the method of intermediate example 15, except that the brominated substrate as the linker was tert-butyl 3-bromopropionate. The target compound SIAIS151138B was obtained as a light yellow solid (0.64 g, yield 74%). $^1$H NMR (500 MHz, DMSO) δ 11.12 (s, 1H), 7.81-7.76 (m, 2H), 7.64 (d, J=6.7 Hz, 1H), 5.11 (dd, J=12.9, 5.4 Hz, 1H), 3.32 (t, J=7.0 Hz, 2H), 2.92-2.84 (m, 1H), 2.66 (t, J=7.0 Hz, 2H), 2.62-2.51 (m, 2H), 2.07-2.00 (m, 1H). HRMS (ESI) m/z: calcd for $C_{16}H_{15}N_2O_6S^+$ [M+H]$^+$, 363.0645; found, 363.0802.

Intermediate Example 17

Preparation of 4-((2-(2,6-dioxopiperidin-3-yl)-1,3-dioxoisoindolin-4-yl)thio)butanoic acid (SIAIS151139B)

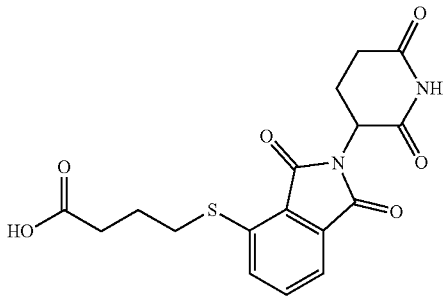 [SMILES: O=C(O)CCCSc1cccc2c1C(=O)N(C1CCC(=O)NC1=O)C2=O]

The compound SIAIS151139B was prepared according to the method of intermediate example 15, except that the brominated substrate as the linker was tert-butyl 4-bromobutyrate. The target compound SIAIS151139B was obtained as a light yellow solid (0.71 g, yield 82%). $^1$H NMR (500 MHz, DMSO) δ 12.24 (s, 1H), 11.12 (s, 1H), 7.86-7.74 (m, 2H), 7.63 (d, J=6.2 Hz, 1H), 5.11 (dd, J=12.9, 5.4 Hz, 1H), 3.15 (t, J=7.2 Hz, 2H), 2.92-2.84 (m, 1H), 2.64-2.51 (m, 2H), 2.42 (t, J=7.2 Hz, 2H), 2.09-2.02 (m, 1H), 1.93-1.83 (m, 2H). HRMS (ESI) m/z: calcd for $C_{17}H_{17}N_2O_6S^+$ [M+H]$^+$, 377.0802; found, 377.0962.

Intermediate Example 18

Preparation of 5-((2-(2,6-dioxopiperidin-3-yl)-1,3-dioxoisoindolin-4-yl)thio)pentanoic acid (SIAIS151140B)

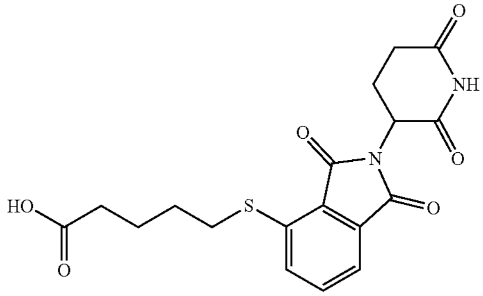 [SMILES: O=C(O)CCCCSc1cccc2c1C(=O)N(C1CCC(=O)NC1=O)C2=O]

The compound SIAIS151140B was prepared according to the method of intermediate example 15, except that the brominated substrate as the linker was tert-butyl 5-bromopentanoate. The target compound SIAIS151140B was obtained as a light yellow solid (0.9 g, yield 74%). $^1H$ NMR (500 MHz, DMSO) δ 11.12 (s, 1H), 7.83-7.71 (m, 2H), 7.62 (d, J=6.9 Hz, 1H), 5.11 (dd, J=12.9, 5.4 Hz, 1H), 3.13 (t, J=6.6 Hz, 2H), 2.92-2.85 (m, 1H), 2.64-2.52 (m, 2H), 2.28 (t, J=6.6 Hz, 2H), 2.08-2.02 (m, 1H), 1.72-1.65 (m, 4H). HRMS (ESI) m/z: calcd for $C_{18}H_{19}N_2O_6S^+$ $[M+H]^+$, 391.0958; found, 391.1109.

Intermediate Example 19

Preparation of 6-((2-(2,6-dioxopiperidin-3-yl)-1,3-dioxoisoindolin-4-yl)thio)hexanoic acid (SIAIS151141B)

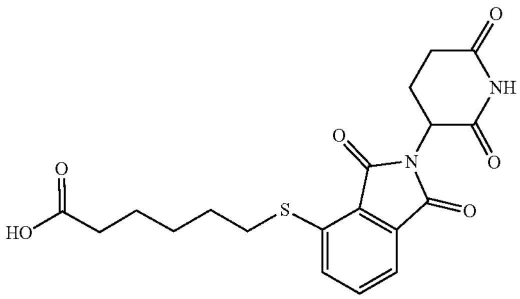 [SMILES: O=C(O)CCCCCSc1cccc2c1C(=O)N(C1CCC(=O)NC1=O)C2=O]

The compound SIAIS151141B was prepared according to the method of intermediate example 15, except that the brominated substrate as the linker was tert-butyl 6-bromohexanoate. The target compound SIAIS151141B was obtained as a light yellow solid (0.71 g, yield 74%). $^1H$ NMR (500 MHz, DMSO) δ 12.01 (s, 1H), 11.12 (s, 1H), 7.82-7.70 (m, 2H), 7.62 (d, J=7.1 Hz, 1H), 5.11 (dd, J=12.9, 5.4 Hz, 1H), 3.12 (t, J=7.2 Hz, 2H), 2.92-2.85 (m, 1H), 2.62-2.48 (m, 2H), 2.22 (t, J=7.2 Hz, 2H), 2.08-2.03 (m, 1H), 1.71-1.63 (m, 2H), 1.59-1.51 (m, 2H), 1.49-1.40 (m, 2H). HRMS (ESI) m/z: calcd for $C_{19}H_{21}N_2O_6S^+$ $[M+H]^+$, 405.1115; found, 405.1268.

Intermediate Example 20

Preparation of 7-((2-(2,6-dioxopiperidin-3-yl)-1,3-dioxoisoindolin-4-yl)thio)heptanoic acid (SIAIS151142B)

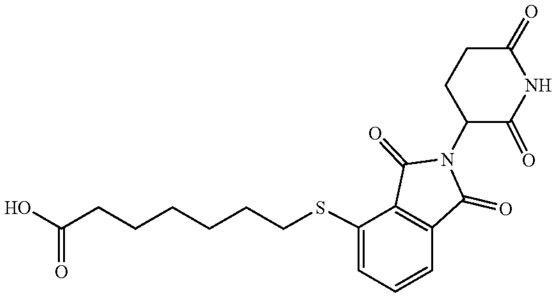 [SMILES: O=C(O)CCCCCCSc1cccc2c1C(=O)N(C1CCC(=O)NC1=O)C2=O]

The compound SIAIS151142B was prepared according to the method of intermediate example 15, except that the brominated substrate as the linker was tert-butyl 7-bromoheptanoate. The target compound SIAIS151142B was obtained as a light yellow solid (0.7 g, yield 80%). $^1H$ NMR (500 MHz, DMSO) δ 11.12 (s, 1H), 7.80-7.71 (m, 2H), 7.62 (d, J=6.9 Hz, 1H), 5.11 (dd, J=12.9, 5.4 Hz, 1H), 3.12 (t, J=7.3 Hz, 2H), 2.92-2.85 (m, 1H), 2.62-2.52 (m, 2H), 2.20 (t, J=7.3 Hz, 2H), 2.07-2.00 (m, 1H), 1.69-1.62 (m, 2H), 1.53-1.47 (m, 2H), 1.46-1.41 (m, 2H), 1.36-1.27 (m, 2H). HRMS (ESI) m/z: calcd for $C_{20}H_{23}N_2O_6S^+$ $[M+H]^+$, 419.1271; found, 419.1432.

Intermediate Example 21

Preparation of 2-(2-((2-(2,6-dioxopiperidin-3-yl)-1-oxoisoindolin-4-yl)thio)ethoxy)acetic acid (SIAIS1213129)

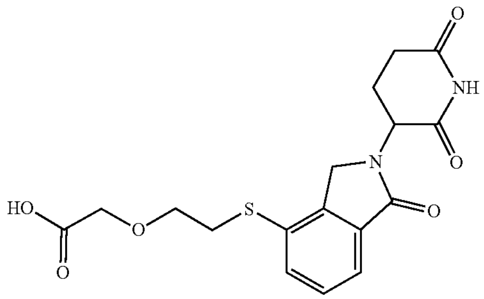 [SMILES: O=C(O)COCCSc1cccc2c1CN(C1CCC(=O)NC1=O)C2=O]

According to Scheme 9, a 50 mL egg-shaped flask was sequentially charged with the intermediate compound SIAIS171095 (0.724 mmol, 1 equiv), anhydrous N,N-dimethylformamide (10 mL) and anhydrous potassium carbonate (1.448 mmol, 2 equiv), followed by slow addition of the corresponding p-toluenesulfonate-substituted substrate (0.869 mmol, 1.2 equiv) as a linker with stirring at room temperature. After the completion of addition, the mixture was stirred at room temperature for 0.5 h. After the starting materials were consumed, the reaction mixture was filtered to remove the insoluble substance, and the filtrate was then directly subjected to a reverse phase C18 column chromatography (eluent (v/v): acetonitrile/water=10%-100%) for separation, and the collected fractions were concentrated under reduced pressure to remove the solvents, to give the corresponding tert-butyl ester intermediate compound. The corresponding tert-butyl ester intermediate compound, dichloromethane (1 mL) and trifluoroacetic acid (3 mL) were sequentially added to a 25 mL egg-shaped flask, and stirred at room temperature for 1 h, and then concentrated under reduced pressure to remove the solvents. The resulting residue was treated by addition of water and lyophilized to afford the corresponding target compound SIAIS1213129 (light yellow solid, 148 mg, yield 54%). $^1H$ NMR (500 MHz, $CDCl_3$) δ 8.90 (s, 1H), 7.81 (d, J=7.5 Hz, 1H), 7.68 (d, J=7.7 Hz, 1H), 7.54 (t, J=7.7 Hz, 1H), 5.33 (dd, J=13.4, 5.1 Hz, 1H), 4.60 (d, J=17.2 Hz, 1H), 4.47 (d, J=17.2 Hz, 1H), 4.11 (s, 2H), 3.78-3.73 (m, 1H), 3.72-3.66 (m, 1H), 3.22 (t, J=6.2 Hz, 2H), 2.98-2.93 (m, 1H), 2.90-2.82 (m, 1H), 2.53-2.43 (m, 1H), 2.32-2.25 (m, 1H). HRMS (ESI) m/z: calcd for $C_{17}H_{19}N_2O_6S^+$ $[M+H]^+$, 379.0958; found, 379.0963.

Intermediate Example 22

Preparation of 2-(2-(2-((2-(2,6-dioxopiperidin-3-yl)-1-oxoisoindolin-4-yl)thio)ethoxy)ethoxy)acetic acid (SIAIS1213131)

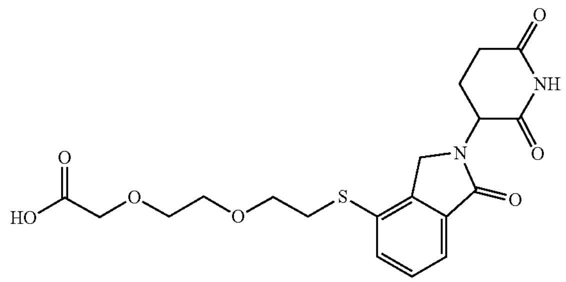 [SMILES: O=C(O)COCCOCCSc1cccc2c1CN(C1CCC(=O)NC1=O)C2=O]

The compound SIAIS1213131 was prepared according to the method of intermediate example 21, except that the p-toluenesulfonate-substituted substrate was tert-butyl 2-(2-(2-(tosyloxy)ethoxy)ethoxy)acetate. The target compound SIAIS1213131 was obtained as a light yellow solid (158 mg, yield 52%). $^1$H NMR (500 MHz, $CDCl_3$) δ 8.77 (s, 1H), 7.68 (d, J=7.5 Hz, 1H), 7.53 (d, J=7.7 Hz, 1H), 7.42 (t, J=7.7 Hz, 1H), 5.21 (dd, J=13.4, 5.1 Hz, 1H), 4.41 (d, J=17.1 Hz, 1H), 4.32 (d, J=17.1 Hz, 1H), 4.06 (s, 2H), 3.65-3.59 (m, 4H), 3.54 (t, J=4.1 Hz, 2H), 3.11 (t, J=6.1 Hz, 2H), 2.88-2.83 (m, 1H), 2.81-2.76 (m, 1H), 2.42-2.34 (m, 1H), 2.20-2.14 (m, 1H). HRMS (ESI) m/z: calcd for $C_{19}H_{23}BN_2O_7S^+$ [M+H]$^+$, 423.1200; found, 423.1205.

Intermediate Example 23

Preparation of 2-(2-(2-(2-((2-(2,6-dioxopiperidin-3-yl)-1-oxoisoindolin-4-yl)thio)ethoxy)ethoxy)ethoxy)acetic acid (SIAIS1213133)

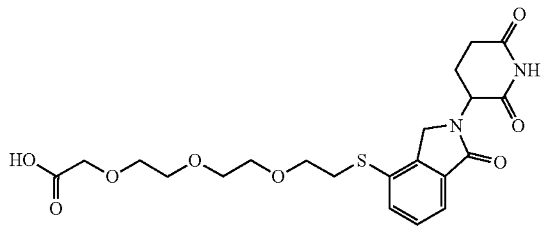 [SMILES: O=C(O)COCCOCCOCCSc1cccc2c1CN(C1CCC(=O)NC1=O)C2=O]

The compound SIAIS1213133 was prepared according to the method of intermediate example 21, except that the p-toluenesulfonate-substituted substrate was tert-butyl 2-(2-(2-(2-(tosyloxy)ethoxy)ethoxy)ethoxy)acetate. The target compound SIAIS1213133 was obtained as a light yellow oil (149 mg, yield 44%). $^1$H NMR (500 MHz, $CDCl_3$) δ 8.91 (s, 1H), 7.75 (d, J=7.5 Hz, 1H), 7.61 (d, J=7.6 Hz, 1H), 7.50 (t, J=7.7 Hz, 1H), 5.29 (dd, J=13.4, 5.1 Hz, 1H), 4.49 (d, J=17.0 Hz, 1H), 4.39 (d, J=17.1 Hz, 1H), 4.17-4.15 (m, 2H), 3.72-3.63 (m, 10H), 3.20 (t, J=6.3 Hz, 2H), 2.96-2.90 (m, 1H), 2.90-2.82 (m, 1H), 2.50-2.44 (m, 1H), 2.28-2.22 (m, 1H). HRMS (ESI) m/z: calcd for $C_{21}H_{27}N_2O_8S^+$ [M+H]$^+$, 467.1483; found, 467.1467.

Intermediate Example 24

Preparation of 14-((2-(2,6-dioxopiperidin-3-yl)-1-oxoisoindolin-4-yl)thio)-3,6,9,12-tetraoxatetradecanoic acid (SIAIS1213135)

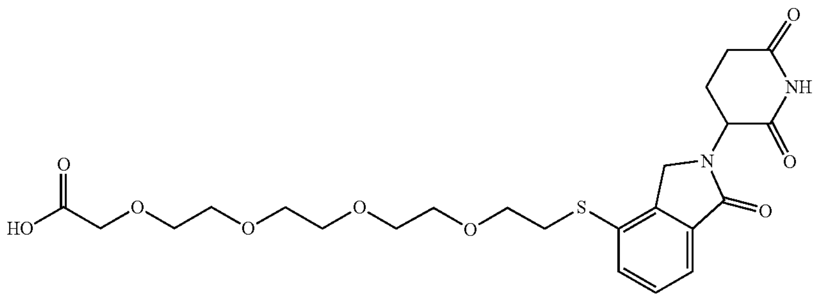 [SMILES: O=C(O)COCCOCCOCCOCCSc1cccc2c1CN(C1CCC(=O)NC1=O)C2=O]

The compound SIAIS1213135 was prepared according to the method of intermediate example 21, except that the p-toluenesulfonate-substituted substrate was tert-butyl 14-(tosyloxy)-3,6,9,12-tetraoxatetradecanoate. The target compound SIAIS1213135 was obtained as a light yellow oil (181 mg, yield 49%). $^1$H NMR (500 MHz, $CDCl_3$) δ 8.61 (s, 1H), 7.78 (dd, J=7.6, 0.7 Hz, 1H), 7.63 (dd, J=7.8, 0.8 Hz, 1H), 7.50 (t, J=7.0 Hz, 1H), 5.29 (dd, J=13.3, 5.1 Hz, 1H), 4.50 (d, J=17.0 Hz, 1H), 4.40 (d, J=16.9 Hz, 1H), 4.15 (s, 2H), 3.72-3.66 (m, 14H), 3.19 (t, J=6.6 Hz, 2H), 2.95-2.93 (m, 1H), 2.91-2.86 (m, 1H), 2.52-2.46 (m, 1H), 2.28-2.24 (m, 1H). HRMS (ESI) m/z: calcd for $C_{23}H_{31}N_2O_9S^+$ $[M+H]^+$, 511.1745; found, 511.1749.

Intermediate Example 25

Preparation of 17-((2-(2,6-dioxopiperidin-3-yl)-1-oxoisoindolin-4-yl)thio)-3,6,9,12,15-pentaoxaheptadecanoic acid (SIAIS1213137)

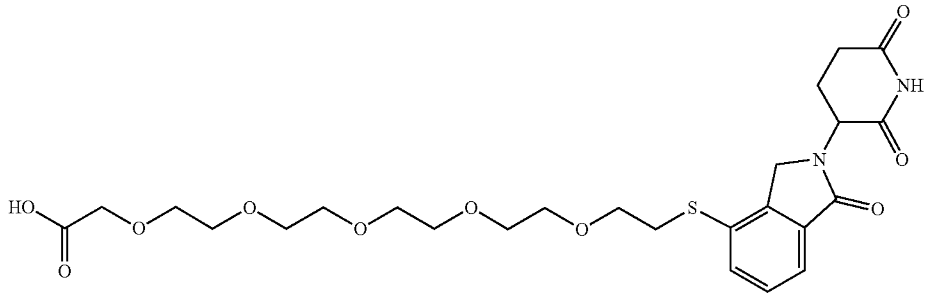 [SMILES: O=C(O)COCCOCCOCCOCCOCCSc1cccc2c1CN(C1CCC(=O)NC1=O)C2=O]

The compound SIAIS1213133 was prepared according to the method of intermediate example 21, except that the p-toluenesulfonate-substituted substrate was tert-butyl 17-(tosyloxy)-3,6,9,12,15-pentaoxaheptadecanoate. The target compound SIAIS1213133 was obtained as a light yellow oil (209 mg, yield 52%). $^1$H NMR (500 MHz, $CDCl_3$) δ 8.71 (s, 1H), 7.77 (d, J=7.0 Hz, 1H), 7.64 (dd, J=7.7, 0.7 Hz, 1H), 7.54-7.49 (m, 1H), 5.31 (dd, J=13.4, 5.1 Hz, 1H), 4.50 (d, J=17.0 Hz, 1H), 4.40 (d, J=17.0 Hz, 1H), 4.17 (s, 2H), 3.76-3.74 (m, 2H), 3.70-3.66 (m, 12H), 3.64-3.61 (m, 4H), 3.20 (t, J=6.5 Hz, 2H), 2.98-2.94 (m, 1H), 2.90-2.85 (m, 1H), 2.53-2.43 (m, 1H), 2.30-2.25 (m, 1H). HRMS (ESI) m/z: calcd for $C_{25}H_{35}N_2O_{10}S^+$ $[M+H]^+$, 569.1800; found, 569.1814.

Intermediate Example 26

Preparation of 2-((2-(2,6-dioxopiperidin-3-yl)-1-oxoisoindolin-4-yl)thio)acetic acid (SIAIS171090)

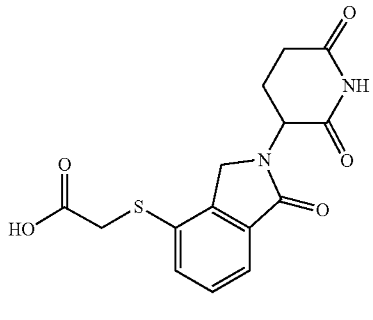 [SMILES: O=C(O)CSc1cccc2c1CN(C1CCC(=O)NC1=O)C2=O]

The compound SIAIS171090 was prepared according to the method of Scheme 8, except that the brominated substrate as the linker was tert-butyl 2-bromoacetate. The target compound SIAIS171090 was obtained as a white solid (77 mg, total yield of step 3: 64%). $^1$H NMR (500 MHz, DMSO) δ 12.88 (s, 1H), 11.00 (s, 1H), 7.68-7.45 (m, 3H), 5.15-5.13 (m, 1H), 4.32 (dd, J=56.2, 17.3 Hz, 2H), 3.94 (s, 2H), 2.95-2.91 (m, 1H), 2.63-2.59 (m, 1H), 2.49-2.39 (m, 1H), 2.08-1.92 (m, 1H). HRMS (ESI) m/z: calcd for $C_{15}H_{15}N_2O_5S^+$ $[M+H]^+$, 335.0696; found, 334.8134.

Intermediate Example 27

Preparation of 3-((2-(2,6-dioxopiperidin-3-yl)-1-oxoisoindolin-4-yl)thio)propanoic acid (SIAIS171086)

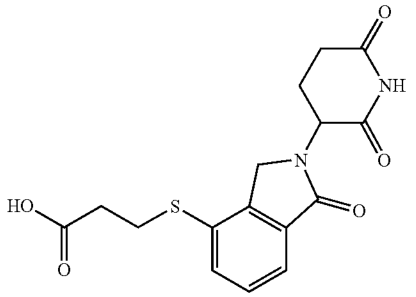 [SMILES: O=C(O)CCSc1cccc2c1CN(C1CCC(=O)NC1=O)C2=O]

The compound SIAIS171086 was prepared according to the method of intermediate example 26, except that the brominated substrate as the linker was tert-butyl 3-bromopropionate. The target compound SIAIS171086 was obtained as a white solid (40 mg, total yield of step 3: 32%). $^{1}$H NMR (500 MHz, DMSO) δ 10.99 (s, 1H), 7.70-7.55 (m, 3H), 5.13 (dd, J=13.3, 5.1 Hz, 1H), 4.40-4.18 (m, 2H), 3.24 (t, J=7.0 Hz, 2H), 2.95-2.87 (m, 1H), 2.63-2.53 (m, 3H), 2.47-2.34 (m, 1H), 2.05-1.95 (m, 1H). HRMS (ESI) m/z: calcd for $C_{16}H_{17}N_2O_5S^+$ [M+H]$^+$, 349.0853; found, 348.8166.

Intermediate Example 28

Preparation of 4-((2-(2,6-dioxopiperidin-3-yl)-1-oxoisoindolin-4-yl)thio)butanoic acid (SIAIS171089)

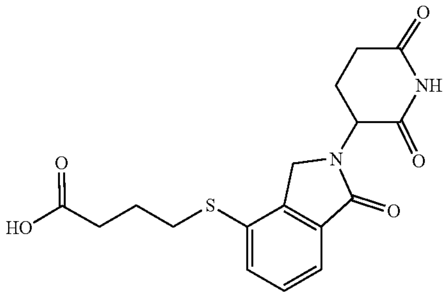 [SMILES: O=C(O)CCCSc1cccc2c1CN(C1CCC(=O)NC1=O)C2=O]

The compound SIAIS171089 was prepared according to the method of intermediate example 26, except that the brominated substrate as the linker was tert-butyl 4-bromobutyrate. The target compound SIAIS171089 was obtained as a white solid (50 mg, total yield of step 3: 38%). $^{1}$H NMR (500 MHz, DMSO) δ 12.15 (s, 1H), 10.99 (s, 1H), 7.71-7.49 (m, 3H), 5.13 (dd, J=13.3, 5.1 Hz, 1H), 4.41-4.18 (m, 2H), 3.10 (t, J=7.3 Hz, 2H), 2.92-2.88 (m, 1H), 2.61-2.59 (m, 1H), 2.49-2.42 (m, 1H), 2.38 (t, J=7.2 Hz, 2H), 2.05-1.96 (m, 1H), 1.84-1.74 (m, 2H). HRMS (ESI) m/z: calcd for $C_{17}H_{19}N_2O_5S^+$ [M+H]$^+$, 363.1009; found, 362.8160.

Intermediate Example 29

Preparation of 5-((2-(2,6-dioxopiperidin-3-yl)-1-oxoisoindolin-4-yl)thio)pentanoic acid (SIAIS171079)

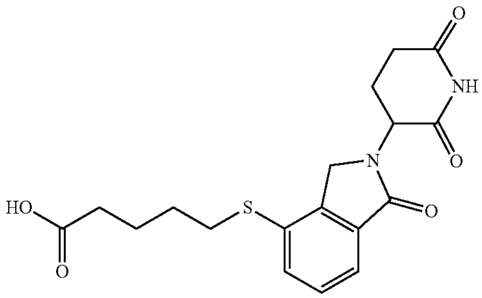 [SMILES: O=C(O)CCCCSc1cccc2c1CN(C1CCC(=O)NC1=O)C2=O]

The compound SIAIS171079 was prepared according to the method of intermediate example 26, except that the brominated substrate as the linker was tert-butyl 5-bromopentanoate. The target compound SIAIS171079 was obtained as a white solid (30 mg, total yield of step 3: 22%). $^{1}$H NMR (500 MHz, DMSO) δ 12.01 (s, 1H), 10.98 (s, 1H), 7.66-7.55 (m, 3H), 5.12 (dd, J=13.3, 5.1 Hz, 1H), 4.37-4.18 (m, 2H), 3.10-3.05 (m, 2H), 2.95-2.84 (m, 1H), 2.65-2.61 (m, 1H), 2.48-2.38 (m, 1H), 2.27-2.20 (m, 3H), 1.63-1.59 (m, 4H). HRMS (ESI) m/z: calcd for $C_{18}H_{21}N_2O_5S^+$ [M+H]$^+$, 377.1166; found, 376.8981.

Intermediate Example 30

Preparation of 6-((2-(2,6-dioxopiperidin-3-yl)-1-oxoisoindolin-4-yl)thio)hexanoic acid (SIAIS171091)

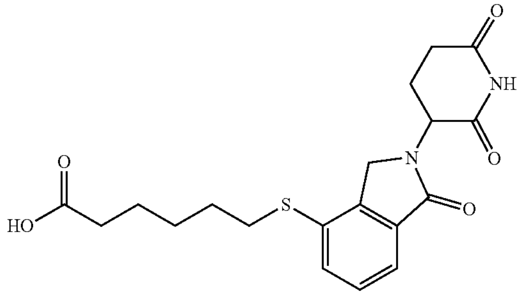 [SMILES: O=C(O)CCCCCSc1cccc2c1CN(C1CCC(=O)NC1=O)C2=O]

The compound SIAIS171091 was prepared according to the method of intermediate example 26, except that the brominated substrate as the linker was tert-butyl 6-bromohexanoate. The target compound SIAIS171091 was obtained as a white solid (75 mg, total yield of step 3: 53%). $^{1}$H NMR (500 MHz, DMSO) δ 11.98 (s, 1H), 10.98 (s, 1H), 7.59-7.52 (m, 3H), 5.12 (dd, J=13.4, 5.1 Hz, 1H), 4.26 (dd, J=40.9, 20.5 Hz, 2H), 3.07 (t, J=7.3 Hz, 2H), 2.96-2.84 (m, 1H), 2.64-2.60 (m, 1H), 2.48-2.39 (m, 1H), 2.19-2.15 (m, 2H), 2.02-2.00 (m, 1H), 1.70-1.35 (m, 6H). HRMS (ESI) m/z: calcd for $C_{19}H_{23}N_2O_5S^+$ [M+H]$^+$, 391.1322; found, 390.8150.

Intermediate Example 31

Preparation of 7-((2-(2,6-dioxopiperidin-3-yl)-1-oxoisoindolin-4-yl)thio)heptanoic acid (SIAIS171092)

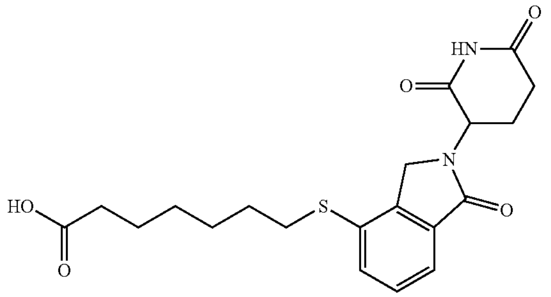 [SMILES: O=C(O)CCCCCCSc1cccc2c1CN(C1CCC(=O)NC1=O)C2=O]

The compound SIAIS171092 was prepared according to the method of intermediate example 26, except that the brominated substrate as the linker was tert-butyl 7-bromoheptanoate. The target compound SIAIS171092 was obtained as a white solid (79 mg, total yield of step 3: 54%).

$^1$H NMR (500 MHz, DMSO) δ 11.99 (s, 1H), 10.98 (s, 1H), 7.66-7.45 (m, 3H), 5.12 (dd, J=13.3, 5.1 Hz, 1H), 4.26 (dd, J=40.9, 20.5 Hz, 2H), 3.07 (t, J=7.3 Hz, 2H), 2.97-2.83 (m, 1H), 2.63-2.60 (m, 1H), 2.47-2.35 (m, 1H), 2.18 (t, J=7.3 Hz, 2H), 2.06-1.93 (m, 1H), 1.65-1.20 (m, 8H). HRMS (ESI) m/z: calcd for $C_{20}H_{25}N_2O_5S^+$ [M+H]$^+$, 405.1479; found, 404.8155.

Intermediate Example 32

Preparation of 4-(2-(2,6-dioxopiperidin-3-yl)-1-oxoisoindolin-4-yl)but-3-yn-1-yl methanesulfonate (SIAIS255120)

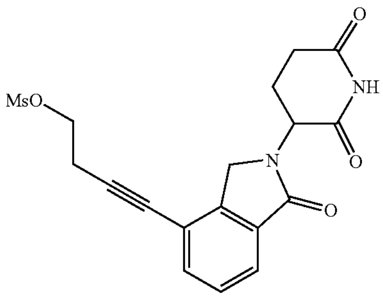 [SMILES: CS(=O)(=O)OCCC#Cc1cccc2c1CN(C1CCC(=O)NC1=O)C2=O]

According to Scheme 10, in step 1, the solution of 3-(4-bromo-1-oxoisoindolin-2-yl)piperidine-2,6-dione (0.50 g, 1.5 mmol) in 5 mL DMF was bubbled with argon gas for 5 min. To the mixture were sequentially added but-3-yn-1-ol (0.21 g, 3.0 mmol), $Pd(PPh_3)_2Cl_2$ (0.10 g, 0.15 mmol) and CuI (57 mg, 0.30 mmol) under stirring for 5 min, followed by addition of 2.5 mL of triethylamine. The mixture was heated to 80° C., and reacted overnight, and then cooled to room temperature. The reaction was quenched with 50 mL of water. The resulting mixture was extracted with ethyl acetate (3×50 mL). The organic phases were combined, washed with water (2×30 mL) and saturated brine (50 mL), dried over anhydrous sodium sulfate, and concentrated under reduced pressure to remove the solvents. The obtained crude product was subjected to a column chromatography (eluent (v/v): DCM/MeOH=5/1) to give an alcohol intermediate as light yellow solid (0.50 g).

In step 2, to a solution of the above intermediate in 15 mL of DCM were added triethylamine (0.44 g, 4.4 mmol) and Mesyl chloride (0.25 g, 2.2 mmol). The reaction system became clear, and reacted overnight. The reaction mixture was washed with saturated brine, rotary evaporated under reduced pressure to remove the solvents. The resulting residue was subjected to a column chromatography (eluent (v/v): DCM/MeOH=5/1) to give SIAIS255120 as light yellow solid (0.35 g). $^1$H NMR (500 MHz, DMSO-d6) δ 11.01 (s, 1H), 7.74 (dd, J=7.6, 1.0 Hz, 1H), 7.67 (dd, J=7.6, 1.0 Hz, 1H), 7.54 (t, J=7.6 Hz, 1H), 5.16 (dd, J=13.4, 5.1 Hz, 1H), 4.52-4.27 (m, 4H), 3.24 (s, 3H), 3.02-2.87 (m, 3H), 2.67-2.57 (m, 1H), 2.42 (qd, J=13.3, 4.4 Hz, 1H), 2.03 (m, 1H). HRMS (ESI) m/z: calcd for $C_{18}H_{19}N_2O_6S^+$ [M+H]$^+$, 391.0958; found, 391.0952.

Intermediate Example 33

Preparation of 5-(2-(2,6-dioxopiperidin-3-yl)-1-oxoisoindolin-4-yl)pent-4-yn-1-yl methanesulfonate (SIAIS255121)

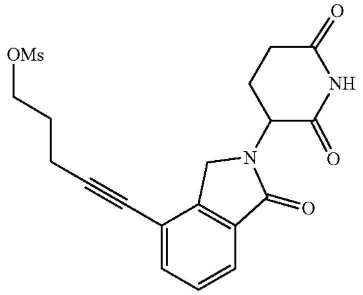 [SMILES: CS(=O)(=O)OCCCC#Cc1cccc2c1CN(C1CCC(=O)NC1=O)C2=O]

The compound SIAIS255121 was prepared according to the method of intermediate example 32, except that pent-4-yn-1-ol was used as the starting material. $^1$H NMR (500 MHz, DMSO-$d_6$) δ 11.00 (s, 1H), 7.72 (dd, J=7.6, 1.0 Hz, 1H), 7.66 (dd, J=7.8, 1.0 Hz, 1H), 7.53 (t, J=7.6 Hz, 1H), 5.15 (dd, J=13.3, 5.1 Hz, 1H), 4.48 (d, J=17.8 Hz, 1H), 4.38-4.28 (m, 3H), 3.20 (s, 3H), 3.00-2.86 (m, 1H), 2.61 in, 3H), 2.45 (dd, J=13.1, 4.5 Hz, 1H), 2.00 (m, 3H). HRMS (ESI) m/z: calcd for $C_{19}H_{21}N_2O_6S^+$ [M+H]$^+$, 405.1115; found, 405.1111.

Intermediate Example 34

Preparation of 6-(2-(2,6-dioxopiperidin-3-yl)-1-oxoisoindolin-4-yl)hex-5-yn-1-yl methanesulfonate (SIAIS255119)

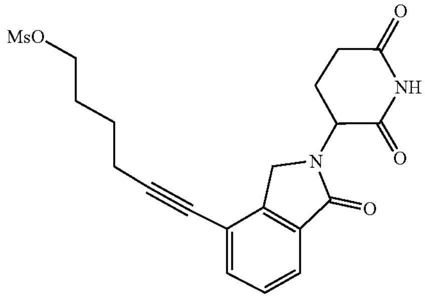 [SMILES: CS(=O)(=O)OCCCCC#Cc1cccc2c1CN(C1CCC(=O)NC1=O)C2=O]

The compound SIAIS255119 was prepared according to the method of intermediate example 32, except that hex-5-yn-1-ol was used as the starting material. $^1$H NMR (500 MHz, DMSO-$d_6$) δ 10.99 (s, 1H), 7.71 (dd, J=7.6, 1.1 Hz, 1H), 7.65 (dd, J=7.7, 1.0 Hz, 1H), 7.52 (t, J=7.6 Hz, 1H), 5.14 (dd, J=13.4, 5.1 Hz, 1H), 4.46 (d, J=17.7 Hz, 1H), 4.31 (d, J=17.7 Hz, 1H), 4.27 (t, J=6.4 Hz, 2H), 3.17 (s, 3H), 2.91 (m, 1H), 2.55 (m, 3H), 2.48-2.42 (m, 1H), 2.01 (m, 1H), 1.88-1.80 (m, 2H), 1.67 (m, 2H). HRMS (ESI) m/z: calcd for $C_{20}H_{23}N_2O_6S^+$ [M+HJ], 419.1271; found, 419.1270.

Intermediate Example 35

Preparation of 3-(4-((2-aminoethyl)thio)-1-oxoisoindolin-2-yl)piperidine-2,6-dione (SIAIS171123)

According to Scheme 11, in step 1, a 10 mL reaction flask was sequentially charged with the compound SIAIS171095

(0.36 mmol, 1 equiv), anhydrous DMF (2 mL) and anhydrous potassium carbonate (0.72 mmol, 2 equiv) with stirring at room temperature, followed by slow addition of the corresponding tert-butyl (2-bromoethyl)carbamate (0.43 mmol, 1.2 equiv). After the completion of addition, the mixture was stirred at room temperature for 1 h. After the starting materials were consumed, the crude product was separated by a reverse phase C18 column chromatography (eluent (v/v): acetonitrile/(water+0.05% TFA)=10%-100%), and the collected fractions were rotary evaporated under reduced pressure to remove the solvents. The resulting residue was lyophilized to give the Boc-protected alkylated intermediate product.

The corresponding intermediate compound obtained from step 1, dichloromethane (2 mL) and trifluoroacetic acid (2 mL) were sequentially added to a 10 mL reaction flask, and stirred at room temperature for 12 h, and then rotary evaporated under reduced pressure to remove the solvents. The resulting crude product was separated by a reverse phase C18 column chromatography (eluent (v/v): acetonitrile/(water+0.05% TFA)=10%-100%), and the collected fractions were rotary evaporated under reduced pressure to remove the solvents. The resulting residue was lyophilized to give the target product SIAIS171123 as white solid (68 mg, total yield of two steps 59%). $^1$H NMR (500 MHz, DMSO) δ 11.02 (s, 1H), 7.88 (s, 3H), 7.73 (dd, J=7.7, 0.8 Hz, 1H), 7.66 (dd, J=7.5, 0.7 Hz, 1H), 7.59 (t, J=7.6 Hz, 1H), 5.15 (dd, J=13.3, 5.1 Hz, 1H), 4.45-4.25 (m, 2H), 3.32-3.26 (m, 2H), 3.05-3.00 (m, 2H), 2.96-2.87 (m, 1H), 2.64-2.60 (m, 1H), 2.48-2.41 (m, 1H), 2.05-2.00 (m, 1H). HRMS (ESI) m/z: calcd for $C_{15}H_{18}N_3O_3S^+$ [M+H]$^+$, 320.1063; found, 320.1082.

Intermediate Example 36

Preparation of 3-(4-((3-aminopropyl)thio)-1-oxoisoindolin-2-yl)piperidine-2,6-dione (SIAIS171124)

The compound SIAIS171124 was prepared according to the method of intermediate example 35, except that the brominated substrate as the linker was tert-butyl (3-bromobutyl)carbamate. The target compound SIAIS171124 was obtained as a white solid (68 mg, total yield of two steps 56%). $^1$H NMR (500 MHz, DMSO) δ 11.00 (s, 1H), 7.75-7.67 (m, 4H), 7.63-7.49 (m, 2H), 5.14 (dd, J=13.3, 5.1 Hz, 1H), 4.43-4.16 (m, 2H), 3.22-3.11 (m, 2H), 2.97-2.85 (m, 3H), 2.67-2.56 (m, 1H), 2.48-2.40 (m, 1H), 2.05-1.95 (m, 1H), 1.91-1.77 (m, 2H). HRMS (ESI) m/z: calcd for $C_{16}H_{20}N_3O_3S^+$ [M+H]$^+$, 334.1220; found, 334.1213.

Intermediate Example 37

Preparation of 3-(4-((4-aminobutyl)thio)-1-oxoisoindolin-2-yl)piperidine-2,6-dione (SIAIS171131)

The compound SIAIS171131 was prepared according to the method of intermediate example 35, except that the brominated substrate as the linker was tert-butyl (4-bromobutyl)carbamate. The target compound SIAIS171131 was obtained as a light yellow solid (76 mg, total yield of two steps 60%). $^1$H NMR (500 MHz, DMSO) δ 10.99 (s, 1H), 7.81-7.47 (m, 6H), 5.13 (dd, J=13.3, 5.1 Hz, 1H), 4.25 (dd, J=31.3, 15.7 Hz, 2H), 3.20-3.03 (m, 2H), 2.96-2.85 (m, 1H), 2.85-2.80 (m, 2H), 2.63-2.60 (m, 1H), 2.46-2.30 (m, 1H), 2.06-1.94 (m, 1H), 1.71-1.56 (m, 4H). HRMS (ESI) m/z: calcd for $C_{17}H_{22}N_3O_3S^+$ [M+H]$^+$, 348.1376; found, 348.1381.

Intermediate Example 38

Preparation of 3-(4-((5-aminopentyl)thio)-1-oxoisoindolin-2-yl)piperidine-2,6-dione (SIAIS171132)

The compound SIAIS171132 was prepared according to the method of intermediate example 35, except that the brominated substrate as the linker was tert-butyl (5-bromopentyl)carbamate. The target compound SIAIS171132 was obtained as a light yellow solid (95 mg, total yield of two steps 73%). $^1$H NMR (500 MHz, DMSO) δ 11.00 (s, 1H), 7.85-7.45 (m, 6H), 5.21-5.07 (m, 1H), 4.42-4.16 (m, 2H), 3.16-3.05 (m, 2H), 2.92-2.85 (m, 1H), 2.84-2.71 (m, 2H), 2.64-2.60 (m, 1H), 2.45-2.40 (m, 1H), 2.07-1.93 (m, 1H), 1.66-1.58 (m, 2H), 1.54-1.50 (m, 2H), 1.49-1.44 (m, 2H). HRMS (ESI) m/z: calcd for $C_{18}H_{24}N_3O_3S^+$ [M+H]$^+$, 362.1533; found, 362.1537.

Intermediate Example 39

Preparation of 3-(4-((6-aminohexyl)thio)-1-oxoisoindolin-2-yl)piperidine-2,6-dione (SIAIS171134)

The compound SIAIS171134 was prepared according to the method of intermediate example 35, except that the brominated substrate as the linker was tert-butyl (6-bromohexyl)carbamate. The target compound SIAIS171134 was obtained as a light yellow solid (78 mg, total yield of two steps 57%). $^1$H NMR (500 MHz, DMSO) δ 11.00 (s, 1H), 7.84-7.43 (m, 6H), 5.16-5.13 (m, 1H), 4.30-4.15 (m, 2H), 3.14-3.03 (m, 2H), 2.97-2.88 (m, 1H), 2.82-2.72 (m, 2H), 2.62 (t, J=14.7 Hz, 1H), 2.49-2.39 (m, 1H), 2.06-1.96 (m, 1H), 1.68-1.56 (m, 2H), 1.51-1.46 (m, 2H), 1.45-1.37 (m, 2H), 1.36-1.28 (m, 2H). HRMS (ESI) m/z: calcd for $C_{19}H_{26}N_3O_3S^+$ [M+H]$^+$, 376.1689; found, 376.1702.

Intermediate Example 40

Preparation of 3-(4-((7-aminoheptyl)thio)-1-oxoisoindolin-2-yl)piperidine-2,6-dione (SIAIS171135)

The compound SIAIS171135 was prepared according to the method of intermediate example 35, except that the brominated substrate as the linker was tert-butyl (7-bromoheptyl)carbamate. The target compound SIAIS171135 was obtained as a white solid (100 mg, total yield of two steps 71%). $^1$H NMR (500 MHz, DMSO) δ 10.99 (s, 1H), 7.84-7.42 (m, 6H), 5.13 (dd, J=13.3, 5.1 Hz, 1H), 4.37-4.18 (m, 2H), 3.15-3.02 (m, 2H), 2.92-2.88 (m, 1H), 2.81-2.71 (m, 2H), 2.61 (t, J=14.8 Hz, 1H), 2.48-2.40 (m, 1H), 2.05-1.98 (m, 1H), 1.65-1.56 (m, 2H), 1.54-1.46 (m, 2H), 1.44-1.36 (m, 2H), 1.33-1.23 (m, 4H). HRMS (ESI) m/z: calcd for $C_{20}H_{28}N_3O_3S^+$ [M+H]$^+$, 390.1846; found, 390.1846.

Intermediate Example 41

Preparation of 3-(4-((8-aminooctyl)thio)-1-oxoisoindolin-2-yl)piperidine-2,6-dione (SIAIS171136)

The compound SIAIS171136 was prepared according to the method of intermediate example 35, except that the brominated substrate as the linker was tert-butyl (8-bromooctyl)carbamate. The target compound SIAIS171136 was obtained as a white solid (100 mg, total yield of two steps 68%). $^1$H NMR (500 MHz, DMSO) δ 10.99 (s, 1H), 7.75-7.47 (m, 6H), 5.13 (dd, J=13.3, 5.1 Hz, 1H), 4.28 (dd, J=70.1, 17.4 Hz, 2H), 3.13-3.00 (m, 2H), 2.98-2.84 (m, 1H), 2.78-2.74 (m, 2H), 2.64-2.59 (m, 1H), 2.47-2.38 (m, 1H), 2.06-1.93 (m, 1H), 1.68-1.54 (m, 2H), 1.52-1.48 (m, 2H), 1.45-1.34 (m, 2H), 1.30-1.20 (m, 6H). HRMS (ESI) m/z: calcd for $C_{21}H_{30}N_3O_{3S}^+$ [M+H]$^+$, 404.2002; found, 404.1996.

Intermediate Example 42

Preparation of 3-(4-((6-bromohexyl)thio)-1-oxoisoindolin-2-yl)piperidine-2,6-dione (SIAIS1216133)

Referring to Scheme 12, a 50 mL two-necked flask was sequentially charged with the compound SIAIS171095 (0.344 mmol, 1 equiv), potassium carbonate (0.688 mmol, 2 equiv), and DMF (5 mL), followed by evacuation and refilling with argon gas, and addition of 1,6-dibromohexane (0.413 mmol, 1.2 equiv). The mixture was stirred and reacted at room temperature for 1 h. After the reaction was complete, the mixture was filtered to remove the insoluble substance, and the filtrate was then subjected to a reverse phase C18 column chromatography (eluent (v/v): acetonitrile/(water)=10%-100%) for separation, and the collected fractions were concentrated under reduced pressure to remove the solvents, to give the corresponding target compound SIAIS1216133 (white solid, 339 mg, yield 38%). $^1$H NMR (500 MHz, DMSO) δ 11.01 (s, 1H), 7.63 (dd, J=7.5, 1.2 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.59 (d, J=17.4 Hz, 1H), 2.49-2.41 (m, 1H), 2.04-1.97 (m, 1H), 1.82-1.74 (m, 2H), 1.63-1.56 (m, 2H), 1.46-1.36 (m, 4H). HRMS (ESI) m/z: calcd for $C_{19}H_{24}BrN_2O_3S^+$ [M+H]$^+$, 439.0686; found, 439.0680.

Intermediate Example 43

Preparation of 2-(2,6-dioxopiperidin-3-yl)-4-((6-iodohexyl)amino)isoindoline-1,3-dione (SIAIS264018)

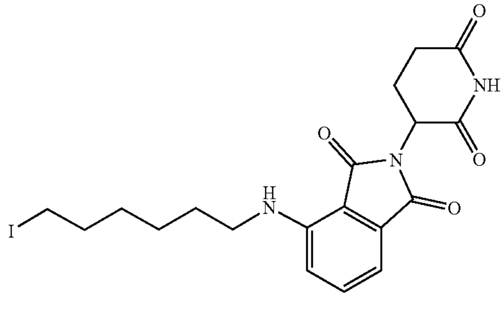 [SMILES: O=C1CCC(N2C(=O)c3cccc(NCCCCCCI)c3C2=O)C(=O)N1]

According to Scheme 13, in step 1, to the solution of 2-(2,6-dioxopiperidin-3-yl)-4-fluoroisoindolin-1,3-dione (16.8 mmol, 1 equiv) dissolve in 25 mL NMP were sequentially added 6-aminohexan-1-ol (16.8 mmol, 1.0 equiv) and DMF (25.2 mmol, 1.5 equiv). The mixture was heated and reacted at 90° C. for 4 h. After the reaction was complete, the reaction mixture was cooled to room temperature, and poured into saturated brine. The resulting mixture was extracted with ethyl acetate (4×50 mL). The organic phases were combined, washed with water (2×30 mL) and saturated brine (50 mL), dried over anhydrous sodium sulfate, and rotary evaporated under reduced pressure to remove the solvents. The obtained crude product was subjected to a column chromatography (eluent (v/v): petroleum ether/ethyl acetate=1:1) for purification, to give the intermediate. To a solution of the intermediate dissolved in 50 mL of tetrahydrofuran was added tetrabutylammonium fluoride (16.8 mmol). The resulting mixture was stirred at room temperature for 2 h. After the reaction was complete, to the mixture was added saturated brine (200 mL), followed by extraction with ethyl acetate (4×50 mL). The organic phases were combined, washed with water (2×30 mL) and saturated brine (50 mL), dried over anhydrous sodium sulfate, and rotary evaporated under reduced pressure to remove the solvents, to give the crude product (1.0 g) which was used directly in the next step.

In step 2, to the solution of the crude product from step 1 dissolved in 40 mL of mixed solvent (DCM/pyridine=3/1) were sequentially added triethylamine (0.52 mL, 3.8 mmol) and methanesulfonyl chloride (0.30 mL, 3.8 mmol). The mixture was heated to 40° C., and reacted for 2 h. After the reaction was complete, the mixture was washed with saturated brine, and rotary evaporated under reduced pressure to remove the solvents. The resulting residue was subjected to a column chromatography to give a yellow powder (m=0.80 g).

In step 3, to the solution of the crude product from step 2 dissolved in 10 mL of acetone was added sodium iodide (3.0 equiv). The mixture was heated to 60° C., and reacted for 24 h. After the conversion was complete, the mixture was cooled to room temperature, and diluted with 40 mL ethyl acetate. The resulting mixture was washed with saturated brine, dried over anhydrous sodium sulfate, and rotary evaporated under reduced pressure to remove the solvents, to give the product SIAIS264018 as a yellow solid which was used directly in the next step. $^1$H NMR (500 MHz, DMSO-$d_6$) δ 11.09 (s, 1H), 7.58 (dd, J=8.5, 7.0 Hz, 1H), 7.10 (d, J=8.6 Hz, 1H), 7.02 (d, J=7.0 Hz, 1H), 6.54 (t, J=5.9 Hz, 1H), 5.05 (dd, J=12.7, 5.4 Hz, 1H), 3.28 (q, J=6.7 Hz, 4H), 2.95-2.83 (m, 1H), 2.63-2.55 (m, 1H), 2.08 (d, J=4.9 Hz, 1H), 2.06-1.99 (m, 1H), 1.77 (t, J=7.0 Hz, 2H), 1.57 (t, J=7.1 Hz, 2H), 1.38 (p, J=5.0 Hz, 4H).

Intermediate Example 44

Preparation of Osimertinib Derivative SIAIS337051:

Osimertinib derivative (SIAIS337051) was prepared according to Scheme 16.

Scheme 16

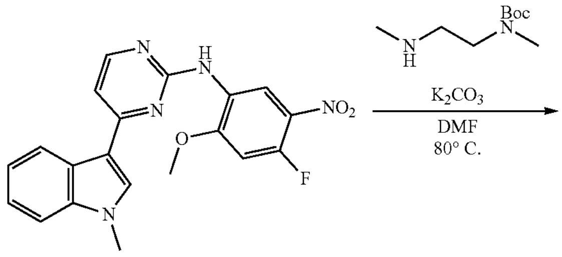

-continued

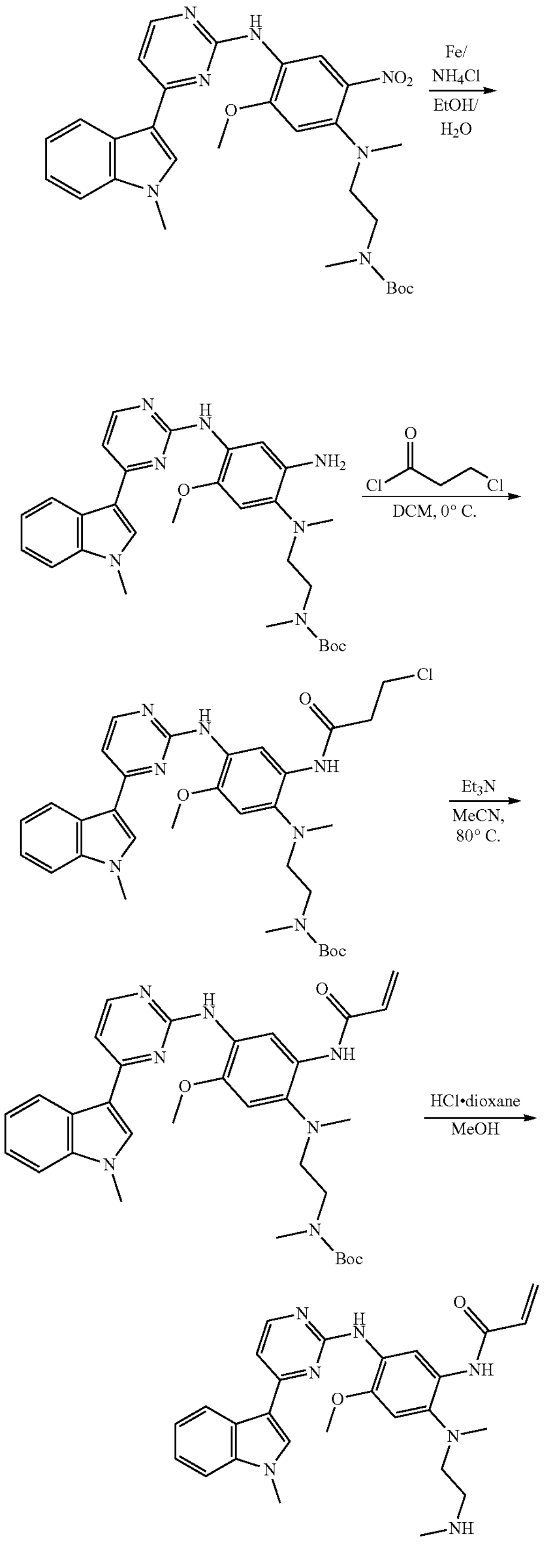

Preparation of N-(4-methoxy-2-(methyl(2-(methylamino)ethyl)amino)-5-((4-(1-methyl-1H-indol-3-yl)pyrimidin-2-yl)amino)phenyl)acrylamide (SIAIS337051)

Steps 1 and 2:

An egg-shaped flask was sequentially charged with N-(4-fluoro-2-methoxy-5-nitrophenyl)-4-(1-methyl-1H-indol-3-yl)pyrimidin-2-amine (1.18 g, 3 mmol), DMF (6 mL), tert-butyl methyl(2-(methylamino)ethyl)carbamate (677.8 mg, 3.6 mmol), and potassium carbonate (621.9 mg, 4.5 mmol) at room temperature, followed by evacuation and refilling with argon gas and reacting at 80° C. for 12 h. After the reaction was complete as monitored by TLC, the reaction was quenched with water. The mixture was extracted with ethyl acetate, and rotary evaporated. The resulting residue was subjected to a column chromatography (eluent (v/v): DCM:MeOH=30:1) for separation, to give a yellow solid (900 mg) which was used directly in the next step. To a solution of the obtained yellow solid dissolved in 20 mL of 75% ethanol were added iron powder (268.8 mg, 4.8 mmol) and ammonium chloride (342 mg, 6.4 mmol), followed by evacuation and refilling with argon gas and reacting at 80° C. for 3 h. After the reaction was complete as monitored by TLC, the mixture was filtered by a Buchner funnel. The filtrate cake was washed with a mixed solvent (dichloromethane:methanol=10:1). The filtrate was rotary evaporated, and the resulting residue was subjected to a column chromatography (eluent (v/v): DCM:MeOH=30:1) for separation, to give a yellow solid (780 mg, total yield of two steps 49%). HRMS (ESI) m/z: calcd for $C_{29}H_{36}N_7O_5^+$ $[M+H]^+$, 562.2772; found, 562.2771.

Steps 3 and 4:

A 100 mL clean egg-shaped flask was sequentially charged with the yellow solid obtained from the previous step (300 mg, 0.565 mmol), and DMF (5 mL), followed by addition of 3-chloropropanoyl chloride (60 μL, 0.633 mmol) with stirring at 0° C. The mixture was warmed up to room temperature, stirred and reacted at room temperature for 1 h. After the reaction was complete, the reaction was quenched with water. The resulting mixture was extracted with dichloromethane, washed with saturated brine, dried over anhydrous sodium sulfate, and rotary evaporated. The resulting residue was used directly in the next step. To a solution of the product obtained from the previous step (0.565 mmol) in 5 mL of acetonitrile was added triethylamine (171.2 mg, 1.695 mmol). The resulting mixture was reacted at 80° C. for 12 h. After the reaction was complete as monitored by LC-MS, the mixture was rotary evaporated, and the resulting residue was subjected to a silica gel column chromatography (eluent (v/v): dichloromethane/methanol=30:1) for separation, to give a yellow solid (280 mg, total yield of two steps 82%). HRMS (ESI) m/z: calcd for $C_{32}H_{40}N_7O_4^+$ $[M+H]^+$, 586.3136; found, 586.3133.

Step 5:

To a solution of the yellow solid obtained from the previous step dissolved in 2 mL of MeOH was added 4 mL of a solution of hydrochloric acid in dioxane (4M). The mixture was reacted at room temperature for 2 h. After the reaction was complete as monitored by LC-MS, the mixture was rotary evaporated, and the resulting residue was subjected to C18 reverse phase column chromatography (eluent: MeOH/water) for separation to give the SIAIS337051 as a yellow solid (228 mg, yield 99%). $^1H$ NMR (500 MHz, DMSO-$d_6$) δ 9.83 (s, 1H), 9.13 (s, 2H), 8.80 (s, 1H), 8.32 (d, J=89.5 Hz, 2H), 7.59 (d, J=8.2 Hz, 1H), 7.40 (d, J=6.6 Hz, 1H), 7.27 (dt, J=31.2, 7.7 Hz, 2H), 7.13 (dd, J=16.9, 10.2 Hz, 1H), 7.00 (s, 1H), 6.21 (d, J=16.9 Hz, 1H), 5.71 (d, J=10.3 Hz, 1H), 3.93 (s, 3H), 3.84 (s, 3H), 3.32 (d, J=5.6 Hz, 2H), 3.15 (q, J=6.0, 5.6 Hz, 2H), 2.64 (s, 3H), 2.58 (t, J=5.5 Hz, 3H). HRMS (ESI) m/z: calcd for $C_{27}H_{32}N_7O_2^+$ [M+H]$^+$, 486.2612; found, 486.2614.

Intermediate Example 45

Preparation of Dacomitinib Derivative C:

Referring to Scheme 1, Dacomitinib derivative B was prepared by using a method similar to that of Dacomitinib derivative A in Intermediate Example 1. The synthetic and structural characterization data of the intermediate are as follows:

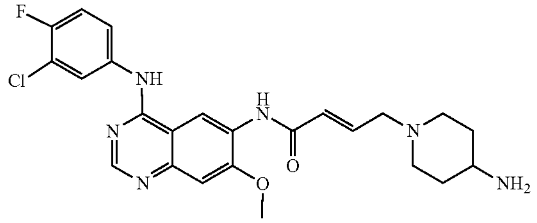 [SMILES: COc1cc2ncnc(Nc3ccc(F)c(Cl)c3)c2cc1NC(=O)/C=C/CN1CCC(N)CC1]

(E)-4-(4-aminopiperidin-1-yl)-N-(4-((3-chloro-4-fluorophenyl)amino)-7-methoxyquinazolin-6-yl)but-2-enamide (SIAIS249077). (yellow solid, 310 mg, total yield of two steps 73%) $^1$H NMR (500 MHz, MeOD) δ 9.19 (s, 1H), 8.70 (s, 1H), 7.94 (dd, J=6.7, 2.6 Hz, 1H), 7.69-7.63 (m, 1H), 7.36 (d, J=8.9 Hz, 1H), 7.32 (d, J=13.5 Hz, 1H), 7.06 (dt, J=14.7, 7.0 Hz, 1H), 6.81 (d, J=15.2 Hz, 1H), 4.16 (s, 3H), 3.92 (s, 1H), 3.59 (s, 1H), 3.08-2.99 (m, 1H), 2.26 (d, J=13.7 Hz, 2H), 2.19 (t, J=7.5 Hz, 1H), 2.09-1.98 (m, 2H), 1.65-1.58 (m, 1H), 1.32 (s, 2H). HRMS (ESI) m/z: calcd for $C_{24}H_{27}ClFN_6O_2^+$ [M+H]$^+$: 485.1863, found 485.1869.

Intermediate Example 46

Preparation of 9-(2-(2,6-dioxopiperidin-3-yl)-1-oxoisoindolin-4-yl)non-8-yn-1-yl methanesulfonate (SIAIS255127)

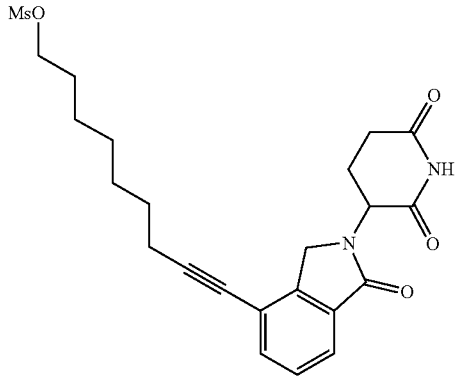 [SMILES: CS(=O)(=O)OCCCCCCCC#Cc1cccc2c1CN(C1CCC(=O)NC1=O)C2=O]

The compound SIAIS255127 was prepared according to the method of intermediate example 32, except that the non-8-yn-1-ol was used as the starting material. $^1$H NMR (500 MHz, DMSO) δ 11.00 (s, 1H), 7.70 (d, J=7.4 Hz, 1H), 7.63 (d, J=7.0 Hz, 1H), 7.52 (t, J=7.6 Hz, 1H), 5.14 (dd, J=13.3, 5.1 Hz, 1H), 4.44 (d, J=17.6 Hz, 1H), 4.30 (d, J=17.6 Hz, 1H), 4.18 (t, J=6.5 Hz, 2H), 3.15 (s, 3H), 2.91 (ddd, J=17.5, 13.7, 5.4 Hz, 1H), 2.63-2.57 (m, 1H), 2.47 (d, J=7.1 Hz, 2H), 2.46-2.40 (m, 1H), 2.02 (ddd, J=10.3, 5.1, 3.1 Hz, 1H), 1.66 (dd, J=13.5, 6.6 Hz, 2H), 1.61-1.53 (m, 2H), 1.47-1.40 (m, 2H), 1.40-1.33 (m, 4H). HRMS (ESI) m/z: calcd for $C_{23}H_{29}N_2O_6S^+$ [M+H]$^+$, 461.1741; found, 461.1740.

Intermediate Example 47

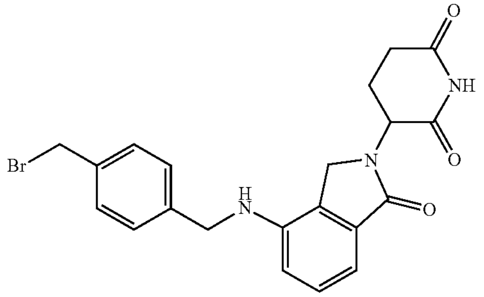 [SMILES: O=C1CCC(N2Cc3c(NCc4ccc(CBr)cc4)cccc3C2=O)C(=O)N1]

Preparation of 3-(4-((4-(bromomethyl)benzyl)amino)-1-oxoisoindolin-2-yl)piperidine-2,6-dione (SIAIS1221131)

A 50 mL egg-shaped flask was sequentially charged with Lenalidomide (1 mmol, 1 equiv), anhydrous N,N-dimethylformamide (10 mL) and DIPEA (3 mmol, 3 equiv), followed by addition of 1,4-bis(bromomethyl)benzene (2 mmol, 2 equiv) with stirring at room temperature. The mixture was stirred at 40° C. for 3 h. After the reaction was complete, the reaction mixture was filtered to remove the insoluble substance, and the filtrate was then directly subjected to a reverse phase C18 column chromatography (eluent (v/v): acetonitrile/water=10%-100%) for separation, and the collected fractions were concentrated under reduced pressure to remove the solvents, to give the corresponding product SIAIS1221131 as a yellow solid (235 mg, yield 53%). $^1$H NMR (500 MHz, DMSO) δ 11.02 (s, 1H), 7.38 (q, J=8.3 Hz, 4H), 7.20 (t, J=7.7 Hz, 2H), 6.93 (d, J=7.3 Hz, 1H), 6.62 (d, J=8.1 Hz, 1H), 5.12 (dd, J=13.3, 5.0 Hz, 1H), 4.68 (s, 2H), 4.39 (s, 2H), 4.32 (d, J=17.2 Hz, 1H), 4.20 (d, J=17.1 Hz, 1H), 2.97-2.89 (m, 1H), 2.63 (d, J=16.1 Hz, 1H), 2.38-2.27 (m, 1H), 2.09-2.01 (m, 1H). HRMS (ESI) m/z: calcd for $C_{21}H_{21}BrN_3O_3^+$ [M+H]$^+$, 442.0761; found, 442.0766.

Intermediate Example 48

Preparation of 2-((2-(2,6-dioxopiperidin-3-yl)-1-oxoisoindolin-4-yl)oxy)acetic acid (SIAIS1222121)

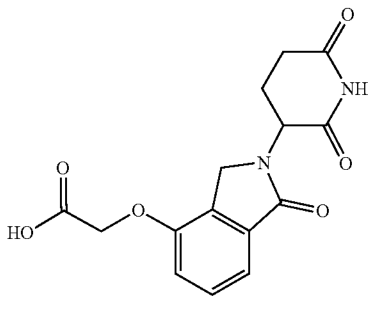

A 50 mL egg-shaped flask was sequentially charged with hydroxy-substituted lenalidomide (CAS No.: 1061604-41-8; 2 mmol, 1 equiv), acetonitrile (10 mL) and potassium carbonate (4 mmol, 2 equiv), followed by addition of tert-butyl 2-bromoacetate (2.4 mmol, 1.2 equiv) with stirring at room temperature. The mixture was reacted at 80° C. for 4 h. After the reaction was complete, the reaction mixture was concentrated under reduced pressure to remove acetonitrile. The resulting residue was dissolved in a small amount of DMSO, and subjected to a reverse phase C18 column chromatography (eluent (v/v): acetonitrile/water=10%-100%) for separation, and the collected fractions were concentrated under reduced pressure to remove the solvents, to give the corresponding tert-butyl ester intermediate compound. The corresponding tert-butyl ester intermediate compound, dichloromethane (1 mL) and trifluoroacetic acid (3 mL) were sequentially added to a 25 mL egg-shaped flask, and stirred at room temperature for 1 h, and then concentrated under reduced pressure to remove the solvents. The resulting residue was treated by addition of water and lyophilized to afford the corresponding target compound SIAIS1222121 (light yellow solid, 371 mg, yield 58%). $^1$H NMR (500 MHz, DMSO) δ 10.99 (s, 1H), 7.48 (t, J=7.6 Hz, 1H), 7.35 (d, J=7.6 Hz, 1H), 7.17 (d, J=8.2 Hz, 1H), 5.12 (dd, J=13.5, 4.9 Hz, 1H), 4.86 (s, 2H), 4.41 (d, J=17.5 Hz, 1H), 4.27 (d, J=17.4 Hz, 1H), 2.96-2.88 (m, 1H), 2.60 (d, J=17.1 Hz, 1H), 2.48-2.42 (m, 1H), 2.04-1.97 (m, 1H). HRMS (ESI) m/z: calcd for $C_{15}H_{15}N_2O_6^+$ [M+H]$^+$, 319.0925; found, 319.0928.

Intermediate Example 49

Preparation of 5-((2-(2,6-dioxopiperidin-3-yl)-1-oxoisoindolin-4-yl)oxy)pentanoic acid (SIAIS1222125)

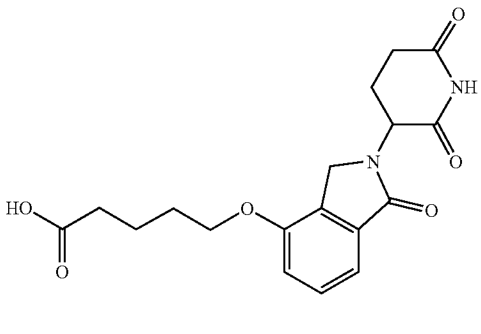

The compound SIAIS122212 was prepared according to the method of Intermediate Example 48, except that the brominated substrate as the linker was tert-butyl 5-bromopentanoate. The target compound SIAIS122212 was obtained as alight yellow solid (418 mg, yield: 59%). $^1$H NMR (500 MHz, DMSO) δ 10.97 (s, 1H), 7.48 (t, J=7.6 Hz, 1H), 7.31 (d, J=7.5 Hz, 1H), 7.24 (d, J=8.0 Hz, 1H), 5.11 (dd, J=13.3, 5.0 Hz, 1H), 4.37 (d, J=17.3 Hz, 1H), 4.23 (d, J=17.3 Hz, 1H), 4.13 (t, J=5.9 Hz, 2H), 2.96-2.87 (m, 1H), 2.59 (d, J=17.2 Hz, 1H), 2.49-2.42 (m, 1H), 2.30 (t, J=7.1 Hz, 2H), 2.02-1.95 (m, 1H), 1.79-1.75 (m, 2H), 1.73-1.64 (m, 2H). HRMS (ESI) m/z: calcd for $C_{18}H_{21}N_2O_6^+$ [M+H]$^+$, 361.1394; found, 361.1391.

Intermediate Example 50

Preparation of 6-((2-(2,6-dioxopiperidin-3-yl)-1-oxoisoindolin-4-yl)oxy)hexanoic acid (SIAIS1222149)

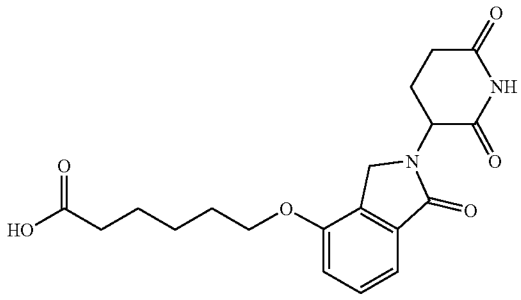 [SMILES: O=C(O)CCCCCOc1cccc2c1CN(C1CCC(=O)NC1=O)C2=O]

The compound SIAIS1222149 was prepared according to the method of Intermediate Example 48, except that the brominated substrate as the linker was tert-butyl 6-bromohexanoate. The target compound SIAIS1222149 was obtained as a light yellow solid (313 mg, yield: 42%). $^1$H NMR (500 MHz, DMSO) δ 10.97 (s, 1H), 7.48 (t, J=7.7 Hz, 1H), 7.31 (d, J=7.5 Hz, 1H), 7.24 (d, J=8.1 Hz, 1H), 5.11 (dd, J=13.3, 4.9 Hz, 1H), 4.38 (d, J=17.4 Hz, 1H), 4.23 (d, J=17.3 Hz, 1H), 4.11 (t, J=6.2 Hz, 2H), 2.97-2.87 (m, 1H), 2.59 (d, J=17.6 Hz, 1H), 2.49-2.40 (m, 1H), 2.24 (t, J=7.3 Hz, 2H), 2.03-1.96 (m, 1H), 1.79-1.72 (m, 2H), 1.61-1.54 (m, 2H), 1.50-1.41 (m, 2H). HRMS (ESI) m/z: calcd for $C_{19}H_{23}N_2O_6^+$ [M+H]$^+$, 375.1551; found, 375.1535.

Intermediate Example 51

Preparation of 7-((2-(2,6-dioxopiperidin-3-yl)-1-oxoisoindolin-4-yl)oxy)heptanoic acid (SIAIS1222151)

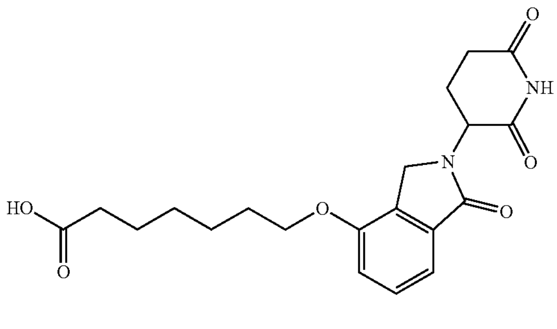 [SMILES: O=C(O)CCCCCCOc1cccc2c1CN(C1CCC(=O)NC1=O)C2=O]

The compound SIAIS1222151 was prepared according to the method of Intermediate Example 48, except that the brominated substrate as the linker was tert-butyl 7-bromoheptanoate. The target compound SIAIS1222151 was obtained as a light yellow solid (250 mg, yield: 32%). $^1$H NMR (500 MHz, DMSO) δ 10.97 (s, 1H), 7.48 (t, J=7.8 Hz, 1H), 7.31 (d, J=7.4 Hz, 1H), 7.24 (d, J=8.1 Hz, 1H), 5.11 (dd, J=13.2, 4.9 Hz, 1H), 4.38 (d, J=17.3 Hz, 1H), 4.23 (d, J=17.3 Hz, 1H), 4.11 (t, J=6.2 Hz, 211), 2.95-2.87 (m, 1H), 2.59 (d, J=18.3 Hz, 1H), 2.49-2.41 (m, 1H), 2.22 (t, J=7.3 Hz, 2H), 2.03-1.96 (m, 1H), 1.77-1.70 (m, 2H), 1.56-1.49

(m, 2H), 1.48-1.40 (m, 2H), 1.38-1.30 (m, 2H). HRMS (ESI) m/z: calcd for $C_{20}H_{25}N_2O_6^+$ [M+H]$^+$, 389.1707; found, 389.1702.

Intermediate Example 52

Preparation of 3-(4-((6-bromohexyl)oxy)-1-oxoisoindolin-2-yl)piperidine-2,6-dione (SIAIS1222127)

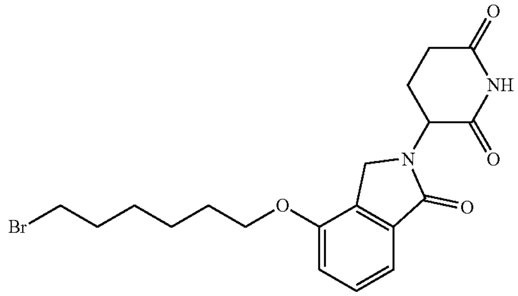 [SMILES: O=C1CCC(N2Cc3c(OCCCCCCBr)cccc3C2=O)C(=O)N1]

A 50 mL egg-shaped flask was sequentially charged with hydroxy-substituted lenalidomide (CAS No.: 1061604-41-8; 2 mmol, 1 equiv), acetonitrile (10 mL) and potassium carbonate (4 mmol, 2 equiv), followed by addition of 1,6-dibromohexane (4 mmol, 2 equiv) with stirring at room temperature. The mixture was reacted at 80° C. overnight. After the reaction was complete, the reaction mixture was concentrated under reduced pressure to remove acetonitrile. The resulting residue was dissolved in a small amount of DMSO, and subjected to a reverse phase C18 column chromatography (eluent (v/v): acetonitrile/water=10%-100%) for separation, and the collected fractions were concentrated under reduced pressure to remove the solvents, to give the corresponding target compound SIAIS1222127 (light yellow solid, 318 mg, yield 38%). $^1$H NMR (500 MHz, DMSO) δ 10.91 (s, 1H), 7.48 (t, J=7.8 Hz, 1H), 7.31 (d, J=7.4 Hz, 1H), 7.24 (d, J=8.1 Hz, 1H), 5.11 (dd, J=13.3, 5.0 Hz, 1H), 4.38 (d, J=17.4 Hz, 1H), 4.23 (d, J=17.3 Hz, 1H), 4.12 (t, J=6.2 Hz, 2H), 3.54 (t, J=6.6 Hz, 2H), 2.96-2.86 (m, 1H), 2.59 (d, J=17.4 Hz, 1H), 2.47-2.40 (m, 1H), 2.03-1.96 (m, 1H), 1.88-1.79 (m, 2H), 1.78-1.72 (m, 2H), 1.46 (s, 4H). HRMS (ESI) m/z: calcd for $C_{19}H_{24}BrN_2O_4^+$ [M+H]$^+$, 423.0914; found, 423.0913.

Examples of Compounds of the Present Invention

Example 1

Preparation of (E)-N-(4-((3-chloro-4-fluorophenyl)amino)-7-methoxyquinazolin-6-yl)-4-(4-(3-(2-((2-(2,6-dioxopiperidin-3-yl)-1,3-dioxoisoindolin-4-yl)amino)ethoxy)propanoyl)piperazin-1-yl)but-2-enamide (SIAIS249046)

Referring to Scheme 14, a reaction flask was sequentially charged with the corresponding EGFR inhibitor, i.e., Dacomitinib derivative A (0.02 mmol, 1 equiv), intermediate LM (SIAIS151001) (0.02 mmol, 1 equiv), HOAt (0.04 mmol, 2 equiv), EDCI (0.04 mmol, 2 equiv), 2 mL DMF, and NMM (0.2 mmol, 10 equiv) at room temperature, and the reaction mixture was reacted overnight. After the reaction was complete as monitored by TLC, the reaction mixture was filtered, and the filtrate was subjected to preparative HPLC (eluent (v/v): acetonitrile/(water+0.05% HCl)=10%-100%) for separation, and the collected fractions were rotary evaporated under reduced pressure to remove the acetonitrile. The resulting residue was lyophilized to give the final target compound (SIAIS249046). (yellow solid, 8.9 mg, yield 50%) $^1$H NMR (500 MHz, MeOD) δ 9.23 (s, 1H), 8.76 (s, 1H), 7.95 (dd, J=6.6, 2.5 Hz, 1H), 7.70-7.65 (m, 1H), 7.47 (s, 1H), 7.39 (t, J=8.9 Hz, 1H), 7.30 (s, 1H), 7.08-6.99 (m, 2H), 6.94 (d, J=6.9 Hz, 1H), 6.79 (d, J=15.2 Hz, 1H), 5.09 (dd, J=12.7, 5.5 Hz, 1H), 4.16 (s, 3H), 4.04 (d, J=6.5 Hz, 2H), 3.81 (s, 2H), 3.74 (d, J=5.1 Hz, 1H), 3.72 (d, J=5.2 Hz, 1H), 3.71-3.32 (m, 8H), 2.94-2.84 (m, 1H), 2.75-2.68 (m, 2H), 2.17-2.13 (m, 1H). HRMS (ESI) m/z: calcd for $C_{41}H_{42}ClFN_9O_8^+$ [M+H]$^+$, 842.2823; found, 842.2820.

Example 2

Preparation of (E)-N-(4-((3-chloro-4-fluorophenyl)amino)-7-methoxyquinazolin-6-yl)-4-(4-(3-(2-(2-((2-(2,6-dioxopiperidin-3-yl)-1,3-dioxoisoindolin-4-yl)amino)ethoxy)eth oxy)propanoyl)piperazin-1-yl)but-2-enamide (SIAIS262013)

Referring to the method of example 1, the target compound (SIAIS262013) was prepared by using Dacomitinib derivative A and intermediate LM (SIAIS151004). (yellow solid, 8.2 mg, yield 44%) $^1$H NMR (500 MHz, MeOD) δ 9.24 (s, 1H), 8.78 (s, 1H), 7.96 (dd, J=6.6, 2.5 Hz, 1H), 7.72-7.65 (m, 1H), 7.49 (s, 1H), 7.41 (t, J=8.9 Hz, 1H), 7.32 (s, 1H), 7.09-6.99 (m, 2H), 6.95 (d, J=6.9 Hz, 1H), 6.81 (d, J=15.2 Hz, 1H), 5.09 (dd, J=12.7, 5.5 Hz, 1H), 4.18 (s, 3H), 4.03 (d, J=6.5 Hz, 2H), 3.84 (s, 2H), 3.74 (d, J=5.1 Hz, 1H), 3.71 (d, J=5.2 Hz, 1H), 3.72-3.34 (m, 8H), 3.31-3.23 (m, 4H), 2.96-2.85 (m, 1H), 2.75-2.68 (m, 2H), 2.17-2.13 (m, 1H). HRMS (ESI) m/z: calcd for $C_{43}H_{46}ClFN_9O_9^+$ [M+H]$^+$, 886.3086; found, 886.3083.

Example 3

Preparation of (E)-N-(4-((3-chloro-4-fluorophenyl)amino)-7-methoxyquinazolin-6-yl)-4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)but-2-enamide (SIAIS249047)

Referring to the method of example 1, the target compound (SIAIS249047) was prepared by using Dacomitinib derivative A and intermediate LM (SIAIS151005). (yellow solid, 9.9 mg, yield 51%) $^1$H NMR (500 MHz, MeOD) δ 9.22 (s, 1H), 8.75 (s, 1H), 7.94 (dd, J=6.6, 2.5 Hz, 1H), 7.71-7.62 (m, 1H), 7.50-7.42 (m, 1H), 7.37 (t, J=8.9 Hz, 1H), 7.32 (s, 1H), 7.09-7.01 (m, 2H), 6.94 (d, J=7.0 Hz, 1H), 6.83 (d, J=15.2 Hz, 1H), 5.06 (dd, J=12.8, 5.5 Hz, 1H), 4.17 (s, 3H), 4.08 (d, J=7.1 Hz, 2H), 3.78-3.71 (m, 4H), 3.69-3.65 (m, 6H), 3.60 (d, J=3.3 Hz, 4H), 3.48 (t, J=5.0 Hz, 2H), 3.22-3.00 (m, 2H), 2.91-2.84 (m, 1H), 2.73-2.68 (m, 2H), 2.17-2.08 (m, 1H). HRMS (ESI) m/z: calcd for $C_{45}H_{50}ClFN_9O_{10}^+$ [M+H]$^+$, 930.3348; found, 930.3344.

Example 4

Preparation of (E)-N-(4-((3-chloro-4-fluorophenyl)amino)-7-methoxyquinazolin-6-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)but-2-enamide (SIAIS262014)

Referring to the method of example 1, the target compound (SIAIS262014) was prepared by using Dacomitinib derivative A and intermediate LM (SIAIS151006). (yellow solid, 10.1 mg, yield 49%) $^1$H NMR (500 MHz, MeOD) δ 9.19 (s, 1H), 8.73 (s, 1H), 7.93 (dd, J=6.6, 2.6 Hz, 1H), 7.68-7.64 (m, 1H), 7.43 (dd, J=8.5, 7.2 Hz, 1H), 7.37 (t, J=8.9 Hz, 1H), 7.30 (s, 1H), 7.04 (dd, J=15.1, 7.4 Hz, 1H), 6.98 (d, J=8.6 Hz, 1H), 6.90 (d, J=7.0 Hz, 1H), 6.85 (d, J=15.2 Hz, 1H), 5.07 (dd, J=12.6, 5.5 Hz, 1H), 4.16 (s, 3H), 4.12-4.04 (m, 2H), 3.73 (t, J=5.8 Hz, 6H), 3.67 (s, 2H), 3.65-3.57 (m, 8H), 3.46-3.43 (m, 2H), 2.91-2.86 (m, 2H), 2.79-2.72 (m, 2H), 2.72-2.63 (m, 1H), 2.14-2.10 (m, 1H). HRMS (ESI) m/z: calcd for $C_{47}H_{54}ClFN_9O_{11}^+$ [M+H]$^+$, 974.3610; found, 974.3612.

Example 5

Preparation of (E)-N-(4-((3-chloro-4-fluorophenyl) amino)-7-methoxyquinazolin-6-yl)-4-(4-(2-((2-(2,6-dioxopiperidin-3-yl)-1,3-dioxoisoindolin-4-yl) amino)acetyl)piperazin-1-yl)but-2-enamide (SIAIS219194)

Referring to the method of example 1, the target compound (SIAIS219194) was prepared by using Dacomitinib derivative A and intermediate LM (SIAIS151025). (yellow solid, 8.2 mg, yield 50%) $^1$H NMR (500 MHz, DMSO) δ 11.10 (s, 1H), 9.81 (s, 1H), 9.72 (s, 1H), 8.92 (s, 1H), 8.53 (s, 1H), 8.15-8.09 (m, 1H), 7.83-7.76 (m, 1H), 7.64-7.58 (m, 1H), 7.42 (t, J=9.1 Hz, 1H), 7.29 (s, 1H), 7.09 (d, J=4.2 Hz, 2H), 6.85-6.80 (m, 1H), 6.62 (d, J=15.3 Hz, 1H), 5.06 (dd, J=12.8, 5.4 Hz, 1H), 4.20 (d, J=4.1 Hz, 2H), 4.02 (s, 3H), 3.55 (d, J=16.3 Hz, 8H), 3.21 (d, J=5.8 Hz, 2H), 2.65-2.57 (m, 1H), 2.42 (s, 2H), 2.07-2.00 (m, 1H). HRMS (ESI) m/z: calcd for $C_{38}H_{35}ClFN_9O_7^+$ [M+H]$^+$, 783.2332; found, 783.2330.

Example 6

Preparation of (E)-N-(4-((3-chloro-4-fluorophenyl) amino)-7-methoxyquinazolin-6-yl)-4-(4-(3-((2-(2,6-dioxopiperidin-3-yl)-1,3-dioxoisoindolin-4-yl) amino)propanoyl)piperazin-1-yl)but-2-enamide (SIAIS262016)

Referring to the method of example 1, the target compound (SIAIS262016) was prepared by using Dacomitinib derivative A and intermediate LM (SIAIS151026). (yellow solid, 6.6 mg, yield 39%) $^1$H NMR (500 MHz, MeOD) δ 9.25 (s, 1H), 8.74 (s, 1H), 7.93 (dd, J=6.6, 2.6 Hz, 1H), 7.68-7.63 (m, 1H), 7.58 (dd, J=8.5, 7.2 Hz, 1H), 7.37 (t, J=8.9 Hz, 1H), 7.32 (s, 1H), 7.13 (d, J=8.6 Hz, 1H), 7.08-7.00 (m, 2H), 6.83 (d, J=15.3 Hz, 1H), 5.07 (dd, J=12.6, 5.5 Hz, 1H), 4.17 (d, J=5.4 Hz, 3H), 4.01. (d, J=7.1 Hz, 2H), 3.74-3.66 (m, 2H), 3.30 (s, 8H), 2.92-2.69 (m, 5H), 2.16-2.08 (m, 1H). HRMS (ESI) m/z: calcd for $C_{39}H_{37}ClFN_9O_7^+$ [M+H]$^+$, 797.2489; found, 797.2485.

Example 7

Preparation of (E)-N-(4-((3-chloro-4-fluorophenyl) amino)-7-methoxyquinazolin-6-yl)-4-(4-(4-((2-(2,6-dioxopiperidin-3-yl)-1,3-dioxoisoindolin-4-yl) amino)butanoyl)piperazin-1-yl)but-2-enamide (SIAIS249062)

Referring to the method of example 1, the target compound (SIAIS249062) was prepared by using Dacomitinib derivative A and intermediate LM (SIAIS151019). (yellow solid, 8.2 mg, yield 48%) $^1$H NMR (500 MHz, MeOD) δ 9.29 (s, 1H), 8.76 (s, 1H), 7.93 (dd, J=6.6, 2.5 Hz, 1H), 7.66 (dd, J=4.8, 2.7 Hz, 1H), 7.57 (dd, J=8.5, 7.2 Hz, 1H), 7.38 (t, J=8.9 Hz, 1H), 7.34 (s, 1H), 7.13 (d, J=8.5 Hz, 1H), 7.07 (dt, J=11.1, 5.7 Hz, 2H), 6.87 (d, J=15.2 Hz, 1H), 5.07 (dd, J=12.6, 5.4 Hz, 1H), 4.19 (s, 3H), 4.07 (d, J=7.1 Hz, 2H), 3.43 (t, J=6.2 Hz, 2H), 3.32-3.30 (m, 8H), 2.90-2.80 (m, 1H), 2.77-2.72 (m, 2H), 2.57 (s, 2H), 2.12 (d, J=5.2 Hz, 1H), 2.01 (d, J=10.9 Hz, 2H). HRMS (ESI) m/z: calcd for $C_{40}H_{39}ClFN_9O_7^+$ [M+H]$^+$, 811.2645; found, 811.2642.

Example 8

Preparation of (E)-N-(4-((3-chloro-4-fluorophenyl) amino)-7-methoxyquinazolin-6-yl)-4-(4-(5-((2-(2,6-dioxopiperidin-3-yl)-1,3-dioxoisoindolin-4-yl) amino)pentanoyl)piperazin-1-yl)but-2-enamide (SIAIS249048)的制备

Referring to the method of example 1, the target compound (SIAIS249048) was prepared by using Dacomitinib derivative A and intermediate LM (SIAIS151020). (yellow solid, 8.1 mg, yield 47%) $^1$H NMR (500 MHz, MeOD) δ 9.22 (s, 1H), 8.70 (s, 1H), 7.88 (dd, J=6.6, 2.5 Hz, 1H), 7.65-7.58 (m, 1H), 7.55-7.46 (m, 1H), 7.32 (t, J=8.9 Hz, 1H), 7.28 (s, 1H), 7.04-6.95 (m, 3H), 6.82 (d, J=15.2 Hz, 1H), 5.02 (dd, J=12.3, 5.0 Hz, 1H), 4.13 (s, 3H), 4.03 (d, J=7.0 Hz, 2H), 3.33 (d, J=8.4 Hz, 8H), 3.25-3.08 (m, 2H), 2.84-2.80 (m, 1H), 2.74-2.65 (m, 2H), 2.48 (s, 2H), 2.12-2.03 (m, 1H), 1.69 (s, 4H). HRMS (ESI) m/z: calcd for $C_{41}H_{41}ClFN_9O_7^+$ [M+H]$^+$, 825.2802; found, 825.2800.

Example 9

Preparation of (E)-N-(4-((3-chloro-4-fluorophenyl) amino)-7-methoxyquinazolin-6-yl)-4-(4-(6-((2-(2,6-dioxopiperidin-3-yl)-1,3-dioxoisoindolin-4-yl) amino)hexanoyl)piperazin-1-yl)but-2-enamide (SIAIS249049)

Referring to the method of example 1, the target compound (SIAIS249049) was prepared by using Dacomitinib derivative A and intermediate LM (SIAIS151027). (yellow solid, 8.3 mg, yield 47%) $^1$H NMR (500 MHz, MeOD) δ 9.26 (s, 1H), 8.75 (s, 1H), 7.93 (dd, J=6.6, 2.6 Hz, 1H), 7.68-7.63 (m, 1H), 7.53 (dd, J=8.5, 7.2 Hz, 1H), 7.37 (t, J=8.9 Hz, 1H), 7.33 (s, 1H), 7.07-7.02 (m, 3H), 6.88 (d, J=15.2 Hz, 1H), 5.06 (dd, J=12.6, 5.5 Hz, 1H), 4.18 (s, 3H), 4.10 (d, J=7.2 Hz, 2H), 3.92-3.32 (m, 8H), 3.18 (d, J=12.6 Hz, 2H), 2.89-2.85 (m, 1H), 2.76-2.67 (m, 2H), 2.48 (t, J=7.2 Hz, 2H), 2.13-2.08 (m, 1H), 1.74-1.65 (m, 4H), 1.49-1.46 (m, 2H). HRMS (ESI) m/z: calcd for $C_{42}H_{43}ClFN_9O_7^+$ [M+H]$^+$, 839.2958; found, 839.2955.

Example 10

Preparation of (E)-N-(4-((3-chloro-4-fluorophenyl) amino)-7-methoxyquinazolin-6-yl)-4-(4-(7-((2-(2,6-dioxopiperidin-3-yl)-1,3-dioxoisoindolin-4-yl) amino)heptanoyl)piperazin-1-yl)but-2-enamide (SIAIS262015)

Referring to the method of example 1, the target compound (SIAIS262015) was prepared by using Dacomitinib derivative A and intermediate LM (SIAIS151086). (yellow solid, 8.9 mg, yield 50%) $^1$H NMR (500 MHz, MeOD) δ 9.27 (s, 1H), 8.75 (s, 1H), 7.93 (dd, J=6.6, 2.6 Hz, 1H), 7.68-7.63 (m, 1H), 7.54 (dd, J=8.6, 7.1 Hz, 1H), 7.38 (t, J=8.9 Hz, 1H), 7.32 (s, 1H), 7.09-7.01 (m, 3H), 6.87 (d, J=15.2 Hz, 1H), 5.06 (dd, J=12.5, 5.5 Hz, 1H), 4.18 (s, 3H), 4.07 (d, J=7.0 Hz, 2H), 3.38-3.31 (m, 8H), 2.88-2.84 (m, 1H), 2.77-2.68 (m, 2H), 2.44 (t, J=7.5 Hz, 2H), 2.16-2.07 (m, 1H), 1.68-1.63 (m, 4H), 1.51-1.42 (m, 4H), 1.33-1.28 (m, 2H). HRMS (ESI) m/z: calcd for $C_{43}H_{45}ClFN_9O_7^+$ $[M+H]^+$, 853.3115; found, 853.3111.

Example 11

Preparation of (E)-N-(4-((3-chloro-4-fluorophenyl) amino)-7-methoxyquinazolin-6-yl)-4-(4-(2-((2-(2,6-dioxopiperidin-3-yl)-1-oxoisoindolin-4-yl)amino) acetyl)piperazin-1-yl)but-2-enamide (SIAIS249056)

Referring to the method of example 1, the target compound (SIAIS249056) was prepared by using Dacomitinib derivative A and intermediate LM (SIAIS1204057). (yellow solid, 7.1 mg, yield 44%) $^1H$ NMR (500 MHz, MeOD) δ 9.28 (d, J=6.8 Hz, 1H), 8.76 (s, 1H), 7.95-7.91 (m, 1H), 7.68-7.63 (m, 1H), 7.43-7.31 (m, 3H), 7.15 (dd, J=7.5, 4.7 Hz, 1H), 7.07-7.02 (m, 1H), 6.93-6.82 (m, 2H), 5.21 (dd, J=13.3, 5.2 Hz, 1H), 4.82-4.29 (m, 4H), 4.19 (s, 3H), 4.12 (t, J=7.7 Hz, 2H), 3.73-3.32 (m, 8H), 3.23-3.08 (m, 2H), 2.98-2.89 (m, 1H), 2.80 (d, J=18.4 Hz, 1H), 2.58-2.44 (m, 1H), 2.21 (d, J=10.3 Hz, 1H). HRMS (ESI) m/z: calcd for $C_{38}H_{37}ClFN_9O_6^+$ $[M+H]^+$, 769.2539; found, 769.2535.

Example 12

Preparation of (E)-N-(4-((3-chloro-4-fluorophenyl) amino)-7-methoxyquinazolin-6-yl)-4-(4-(4-((2-(2,6-dioxopiperidin-3-yl)-1-oxoisoindolin-4-yl)amino) butanoyl)piperazin-1-yl)but-2-enamide (SIAIS249057)

Referring to the method of example 1, the target compound (SIAIS249057) was prepared by using Dacomitinib derivative A and intermediate LM (SIAIS1204085). (yellow solid, 8.2 mg, yield 49%) $^1H$ NMR (500 MHz, MeOD) δ 9.27 (d, J=5.4 Hz, 1H), 8.75 (s, 1H), 7.93 (dd, J=6.6, 2.5 Hz, 1H), 7.67-7.63 (m, 1H), 7.53 (dd, J=9.7, 5.7 Hz, 1H), 7.47 (d, J=7.4 Hz, 1H), 7.37 (t, J=8.9 Hz, 1H), 7.34 (d, J=11.2 Hz, 1H), 7.28 (d, J=7.8 Hz, 1H), 7.08-6.98 (m, 1H), 6.85 (d, J=15.2 Hz, 1H), 5.17 (d, J=8.6 Hz, 1H), 4.74-4.46 (m, 2H), 4.19 (s, 3H), 4.03 (d, J=6.5 Hz, 2H), 3.62 (d, J=45.4 Hz, 2H), 3.46 (t, J=6.0 Hz, 2H), 3.34-3.31 (m, 8H), 3.14 (d, J=29.1 Hz, 2H), 2.98-2.84 (m, 1H), 2.79 (d, J=15.3 Hz, 1H), 2.68-2.47 (m, 2H), 2.29-2.17 (m, 1H), 2.05 (d, J=6.0 Hz, 1H). HRMS (ESI) m/z: calcd for $C_{40}H_{41}ClFN_9O_6^+$ $[M+H]^+$, 797.2852; found, 797.2851.

Example 13

Preparation of (E)-N-(4-((3-chloro-4-fluorophenyl) amino)-7-methoxyquinazolin-6-yl)-4-(4-(5-((2-(2,6-dioxopiperidin-3-yl)-1-oxoisoindolin-4-yl)amino) pentanoyl)piperazin-1-yl)but-2-enamide (SIAIS249058)

Referring to the method of example 1, the target compound (SIAIS249058) was prepared by using Dacomitinib derivative A and intermediate LM (SIAIS1210133). (yellow solid, 8.5 mg, yield 50%) $^1H$ NMR (500 MHz, MeOD) δ 9.29 (s, 1H), 8.76 (s, 1H), 7.93 (dd, J=6.6, 2.6 Hz, 1H), 7.66 (ddd, J=8.9, 4.1, 2.7 Hz, 1H), 7.58 (d, J=4.4 Hz, 2H), 7.38 (dd, J=12.1, 5.7 Hz, 2H), 7.34 (s, 1H), 7.06 (dt, J=14.3, 7.1 Hz, 1H), 6.88 (d, J=15.2 Hz, 1H), 5.20 (dd, J=13.1, 5.0 Hz, 1H), 4.62 (d, J=17.2 Hz, 1H), 4.55 (d, J=17.2 Hz, 1H), 4.19 (s, 3H), 4.09 (d, J=7.1 Hz, 2H), 3.60 (s, 2H), 3.44 (t, J=6.9 Hz, 2H), 3.31 (d, J=1.6 Hz, 8H), 2.97-2.86 (m, 1H), 2.80 (d, J=17.5 Hz, 1H), 2.54 (d, J=8.6 Hz, 2H), 2.22 (d, J=10.6 Hz, 1H), 1.87-1.71 (m, 4H). HRMS (ESI) m/z: calcd for $C_{41}H_{43}ClFN_9O_6^+$ $[M+H]^+$, 811.3009; found, 811.3007.

Example 14

Preparation of (E)-N-(4-((3-chloro-4-fluorophenyl) amino)-7-methoxyquinazolin-6-yl)-4-(4-(6-((2-(2,6-dioxopiperidin-3-yl)-1-oxoisoindolin-4-yl)amino) hexanoyl)piperazin-1-yl)but-2-enamide (SIAIS249059)

Referring to the method of example 1, the target compound (SIAIS249059) was prepared by using Dacomitinib derivative A and intermediate LM (SIAIS1204061). (yellow solid, 8.7 mg, yield 50%) $^1H$ NMR (500 MHz, MeOD) δ 9.27 (s, 1H), 8.75 (s, 1H), 7.93 (dd, J=6.6, 2.5 Hz, 1H), 7.68-7.57 (m, 3H), 7.44 (d, J=7.4 Hz, 1H), 7.36 (dd, J=17.4, 8.5 Hz, 2H), 7.12-7.02 (m, 1H), 6.89 (d, J=15.2 Hz, 1H), 5.20 (dd, J=13.2, 4.8 Hz, 1H), 4.64 (d, J=17.2 Hz, 1H), 4.57 (d, J=17.2 Hz, 1H), 4.18 (s, 3H), 4.10 (d, J=7.0 Hz, 2H), 3.63 (d, J=37.0 Hz, 2H), 3.42 (t, J=7.3 Hz, 2H), 3.31-3.11 (m, 8H), 2.98-2.76 (m, 2H), 2.60-2.44 (m, 3H), 2.27-2.17 (m, 1H), 1.88-1.63 (m, 4H), 1.58-1.45 (m, 2H). HRMS (ESI) m/z: calcd for $C_{42}H_{45}ClFN_9O_6^+$ $[M+H]^+$, 825.3165; found, 825.3163.

Example 15

Preparation of (E)-N-(4-((3-chloro-4-fluorophenyl) amino)-7-methoxyquinazolin-6-yl)-4-(4-(7-((2-(2,6-dioxopiperidin-3-yl)-1-oxoisoindolin-4-yl)amino) heptanoyl)piperazin-1-yl)but-2-enamide (SIAIS249060)

Referring to the method of example 1, the target compound (SIAIS249060) was prepared by using Dacomitinib derivative A and intermediate LM (SIAIS1204063). (yellow solid, 8.3 mg, yield 47%) $^1H$ NMR (500 MHz, MeOD) δ 9.28 (s, 1H), 8.75 (s, 1H), 7.93 (dd, J=6.6, 2.6 Hz, 1H), 7.68-7.64 (m, 1H), 7.40 (dt, J=17.8, 8.3 Hz, 2H), 7.33 (s, 1H), 7.26 (d, J=7.5 Hz, 1H), 7.09-7.02 (m, 2H), 6.88 (d, J=15.2 Hz, 1H), 5.17 (dd, J=13.3, 5.1 Hz, 1H), 4.43 (d, J=17.0 Hz, 1H), 4.37 (d, J=17.0 Hz, 1H), 4.09 (d, J=7.2 Hz, 2H), 3.57 (s, 2H), 3.31 (d, J=1.6 Hz, 8H), 2.95-2.88 (m, 1H), 2.83-2.75 (m, 1H), 2.59-2.38 (m, 3H), 2.23-2.18 (m, 1H), 1.69-1.64 (m, 4H), 1.52-1.39 (m, 4H). HRMS (ESI) m/z: calcd for $C_{43}H_{47}ClFN_9O_6^+$ $[M+H]^+$, 839.3322; found, 839.3322.

Example 16

Preparation of (E)-N-(4-((3-chloro-4-fluorophenyl) amino)-7-methoxyquinazolin-6-yl)-4-(4-(2-((2-(2,6-dioxopiperidin-3-yl)-1,3-dioxoisoindolin-4-yl)thio) acetyl)piperazin-1-yl)but-2-enamide (SIAIS249034)

Referring to the method of example 1, the target compound (SIAIS249034) was prepared by using Dacomitinib derivative A and intermediate LM (SIAIS151045). (yellow solid, 8.2 mg, yield 49%) $^1H$ NMR (500 MHz, DMSO) δ 11.13 (s, 1H), 10.13 (s, 1H), 9.10 (s, 1H), 8.80 (s, 1H), 8.02

(d, J=4.9 Hz, 1H), 7.82-7.77 (m, 2H), 7.74-7.62 (m, 3H), 7.52 (t, J=9.0 Hz, 1H), 7.38 (s, 1H), 6.94 (s, 1H), 6.80 (d, J=15.8 Hz, 1H), 5.14-5.09 (m, 1H), 4.35 (s, 2H), 4.07 (s, 3H), 3.55-3.50 (m, 4H), 3.25-3.11 (m, 4H), 2.92-2.86 (m, 2H), 2.60 (d, J=17.4 Hz, 2H), 2.10-1.96 (m, 2H). HRMS (ESI) m/z: calcd for $C_{38}H_{35}ClFN_8O_7S^+$ [M+H]), 801.2016; found, 801.2013.

Example 17

Preparation of (E)-N-(4-((3-chloro-4-fluorophenyl)amino)-7-methoxyquinazolin-6-yl)-4-(4-(3-((2-(2,6-dioxopiperidin-3-yl)-1,3-dioxoisoindolin-4-yl)thio)propanoyl)piperazin-1-yl)but-2-enamide (SIAIS249035)

Referring to the method of example 1, the target compound (SIAIS249035) was prepared by using Dacomitinib derivative A and intermediate LM (SIAIS151138). (yellow solid, 9.1 mg, yield 53%) $^1$H NMR (500 MHz, DMSO) δ 8.43 (s, 1H), 7.94 (s, 1H), 7.12 (s, 1H), 6.92 (d, J=17.4 Hz, 4H), 6.83 (d, J=25.9 Hz, 2H), 6.56 (t, J=8.8 Hz, 1H), 6.50 (s, 1H), 6.31-6.20 (m, 1H), 6.04 (d, J=15.5 Hz, 1H), 4.35-4.29 (m, 1H), 3.37 (s, 3H), 3.26 (s, 2H), 2.62-2.55 (m, 8H), 2.09-2.05 (m, 4H), 1.96-1.91 (m, 4H). HRMS (ESI) m/z: calcd for $C_{39}H_{37}ClFN_8O_7S^+$ [M+H]$^+$, 815.2173; found, 815.2170.

Example 18

Preparation of (E)-N-(4-((3-chloro-4-fluorophenyl)amino)-7-methoxyquinazolin-6-yl)-4-(4-(4-((2-(2,6-dioxopiperidin-3-yl)-1,3-dioxoisoindolin-4-yl)thio)butanoyl)piperazin-1-yl)but-2-enamide (SIAIS249036)

Referring to the method of example 1, the target compound (SIAIS249036) was prepared by using Dacomitinib derivative A and intermediate LM (SIAIS151139B). (yellow solid, 7.4 mg, yield 42%) $^1$H NMR (500 MHz, DMSO) δ 11.61 (s, 1H), 11.12 (s, 1H), 10.16 (s, 1H), 9.13 (s, 1H), 8.84 (s, 1H), 8.00 (dd, J=6.6, 2.3 Hz, 1H), 7.86 (d, J=8.2 Hz, 1H), 7.80 (t, J=7.7 Hz, 1H), 7.72-7.66 (m, 1H), 7.64 (d, J=7.2 Hz, 1H), 7.53 (t, J=9.1 Hz, 1H), 7.41 (s, 1H), 6.96 (dd, J=14.7, 7.4 Hz, 1H), 6.80 (d, J=15.3 Hz, 1H), 5.11 (dd, J=12.9, 5.4 Hz, 1H), 4.07 (s, 3H), 3.99 (s, 2H), 3.16-3.11 (m, 8H), 2.99-2.83 (m, 2H), 2.65-2.53 (m, 4H), 2.07-1.96 (m, 2H), 1.91 (s, 2H). HRMS (ESI) m/z: calcd for $C_{40}H_{39}ClFN_8O_7S^+$ [M+H]$^+$, 829.2329; found, 829.2329.

Example 19

Preparation of (E)-N-(4-((3-chloro-4-fluorophenyl)amino)-7-methoxyquinazolin-6-yl)-4-(4-(5-((2-(2,6-dioxopiperidin-3-yl)-1,3-dioxoisoindolin-4-yl)thio)pentanoyl)piperazin-1-yl)but-2-enamide (SIAIS249037)

Referring to the method of example 1, the target compound (SIAIS249037) was prepared by using Dacomitinib derivative A and intermediate LM (SIAIS151140B). (yellow solid, 8.5 mg, yield 48%) $^1$H NMR (500 MHz, DMSO) δ 11.75 (s, 1H), 11.12 (s, 1H), 10.16 (s, 1H), 9.13 (s, 1H), 8.84 (s, 1H), 8.00 (dd, J=6.7, 2.4 Hz, 1H), 7.82-7.73 (m, 2H), 7.73-7.66 (m, 1H), 7.63 (d, J=6.9 Hz, 1H), 7.53 (t, J=9.0 Hz, 1H), 7.43 (s, 1H), 7.03-6.93 (m, 1H), 6.79 (d, J=15.4 Hz, 1H), 5.11 (dd, J=12.8, 5.4 Hz, 1H), 4.07 (s, 3H), 3.98 (s, 2H), 3.27-3.00 (m, 8H), 2.95-2.83 (m, 2H), 2.65-2.55 (m, 2H), 2.44 (s, 2H), 2.09-1.95 (m, 2H), 1.70 (s, 4H). HRMS (ESI) m/z: calcd for $C_{41}H_{41}ClFN_8O_7S^+$ [M+H]$^+$, 843.2486; found, 843.2483.

Example 20

Preparation of (E)-N-(4-((3-chloro-4-fluorophenyl)amino)-7-methoxyquinazolin-6-yl)-4-(4-(6-((2-(2,6-dioxopiperidin-3-yl)-1,3-dioxoisoindolin-4-yl)thio)hexanoyl)piperazin-1-yl)but-2-enamide (SIAIS249038)

Referring to the method of example 1, the target compound (SIAIS249038) was prepared by using Dacomitinib derivative A and intermediate LM (SIAIS151141B). (yellow solid, 8.9 mg, yield 49%) $^1$H NMR (500 MHz, DMSO) δ 11.62 (s, 1H), 11.12 (s, 1H), 10.15 (s, 1H), 9.12 (s, 1H), 8.83 (s, 1H), 8.00 (dd, J=6.8, 2.4 Hz, 1H), 7.81-7.73 (m, 2H), 7.73-7.66 (m, 1H), 7.63 (d, J=7.0 Hz, 1H), 7.52 (t, J=9.1 Hz, 1H), 7.41 (s, 1H), 6.98-6.84 (m, 1H), 6.79 (d, J=15.5 Hz, 1H), 5.11 (dd, J=12.9, 5.4 Hz, 1H), 4.07 (s, 3H), 3.99 (s, 2H), 3.16-3.09 (m, 8H), 2.97-2.82 (m, 2H), 2.60-2.53 (m, 2H), 2.38 (t, J=7.2 Hz, 2H), 2.04-1.99 (m, 2H), 1.71-1.66 (m, 2H), 1.55 (d, J=7.2 Hz, 2H), 1.49-1.44 (m, 2H). HRMS (ESI) m/z: calcd for $C_{42}H_{43}ClFN_8O_7S^+$ [M+H]$^+$, 857.2642; found, 857.2640.

Example 21

Preparation of (E)-N-(4-((3-chloro-4-fluorophenyl)amino)-7-methoxyquinazolin-6-yl)-4-(4-(7-((2-(2,6-dioxopiperidin-3-yl)-1,3-dioxoisoindolin-4-yl)thio)heptanoyl)piperazin-1-yl)but-2-enamide (SIAIS249039)

Referring to the method of example 1, the target compound (SIAIS249039) was prepared by using Dacomitinib derivative A and intermediate LM (SIAIS151142B). (yellow solid, 9.1 mg, yield 50%) $^1$H NMR (500 MHz, DMSO) δ 11.79-11.41 (m, 1H), 11.12 (s, 1H), 10.12 (s, 1H), 9.09 (s, 1H), 8.79 (s, 1H), 8.03 (s, 1H), 7.81-7.70 (m, 3H), 7.63 (d, J=7.0 Hz, 1H), 7.51 (t, J=9.0 Hz, 1H), 7.41 (s, 1H), 6.94 (s, 1H), 6.78 (d, J=14.9 Hz, 1H), 5.11 (dd, J=12.9, 5.4 Hz, 1H), 4.06 (s, 3H), 3.97 (s, 2H), 3.14-3.08 (m, 8H), 2.94-2.83 (m, 2H), 2.66-2.54 (m, 2H), 2.36 (t, J=7.0 Hz, 2H), 2.05-1.99 (m, 2H), 1.67 (dd, J=14.6, 7.2 Hz, 2H), 1.54-1.42 (m, 4H), 1.36-1.32 (m, 2H). HRMS (ESI) m/z: calcd for $C_{43}H_{45}ClFN_8O_7S^+$ [M+H]$^+$, 871.2799; found, 871.2797.

Example 22

Preparation of (E)-N-(4-((3-chloro-4-fluorophenyl)amino)-7-methoxyquinazolin-6-yl)-4-(4-(2-(2-((2-(2,6-dioxopiperidin-3-yl)-1,3-dioxoisoindolin-4-yl)thio)ethoxy)acetyl)piperazin-1-yl)but-2-enamide (SIAIS219192)

Referring to the method of example 1, the target compound (SIAIS219192) was prepared by using Dacomitinib derivative A and intermediate LM (SIAIS1204137). (yellow solid, 9.5 mg, yield 54%) $^1$H NMR (500 MHz, MeOD) δ 9.20 (s, 1H), 8.76 (d, J=4.8 Hz, 1H), 7.94 (dd, J=6.6, 2.6 Hz, 1H), 7.72 (dd, J=12.5, 7.9 Hz, 2H), 7.69-7.64 (m, 1H), 7.55 (t, J=5.4 Hz, 1H), 7.37 (t, J=8.9 Hz, 1H), 7.32 (s, 1H), 7.17-7.10 (m, 1H), 6.88 (d, J=15.2 Hz, 1H), 5.11 (dd, J=12.8, 5.5 Hz, 1H), 4.40-4.36 (m, 2H), 4.22-4.07 (m, 8H), 3.89-

3.84 (m, 2H), 3.66 (s, 2H), 3.19-3.17 (m, 2H), 2.91-2.85 (m, 1H), 2.75-2.70 (m, 2H), 2.16-2.09 (m, 1H). HRMS (ESI) m/z: calcd for $C_{40}H_{39}ClFN_8O_8S^+$ [M+H]$^+$, 845.2279; found, 845.2275.

Example 23

Preparation of (E)-N-(4-((3-chloro-4-fluorophenyl) amino)-7-methoxyquinazolin-6-yl)-4-(4-(2-(2-(2-((2-(2,6-dioxopiperidin-3-yl)-1,3-dioxoisoindolin-4-yl) thio)ethoxy)ethoxy)acetyl)piperazin-1-yl)but-2-enamide (SIAIS262005)

Referring to the method of example 1, the target compound (SIAIS262005) was prepared by using Dacomitinib derivative A and intermediate LM (SIAIS1204139). (yellow solid, 9.1 mg, yield 49%) $^1$H NMR (500 MHz, DMSO) δ 11.12 (s, 1H), 10.12 (s, 1H), 9.11 (s, 1H), 8.83 (s, 1H), 8.01 (s, 1H), 7.80-7.74 (m, 2H), 7.70 (s, 1H), 7.61 (d, J=6.0 Hz, 1H), 7.53 (s, 1H), 7.36 (s, 1H), 6.94 (s, 1H), 6.79 (d, J=14.0 Hz, 1H), 5.12 (dd, J=12.9, 5.4 Hz, 1H), 4.22 (d, J=15.0 Hz, 2H), 4.07 (s, 3H), 4.02 (s, 2H), 3.73 (t, J=6.3 Hz, 2H), 3.55-3.50 (m, 10H), 3.09 (s, 4H), 2.92-2.86 (m, 1H), 2.64-2.55 (m, 2H), 2.09-2.01 (m, 1H). HRMS (ESI) m/z: calcd for $C_{42}H_{43}ClFN_8O_9S^+$ [M+H]$^+$, 889.2541; found, 889.2543.

Example 24

Preparation of (E)-N-(4-((3-chloro-4-fluorophenyl) amino)-7-methoxyquinazolin-6-yl)-4-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl) but-2-enamide (SIAIS262006)

Referring to the method of example 1, the target compound (SIAIS262006) was prepared by using Dacomitinib derivative A and intermediate LM (SIAIS1204141). (yellow solid, 9.7 mg, yield 49%) $^1$H NMR (500 MHz, DMSO) δ 11.44-11.23 (m, 1H), 11.12 (s, 1H), 10.13 (s, 1H), 9.10 (s, 1H), 8.82 (s, 1H), 8.01 (s, 1H), 7.80-7.74 (m, 2H), 7.69 (s, 1H), 7.62 (dd, J=5.9, 2.0 Hz, 1H), 7.52 (t, J=8.9 Hz, 1H), 7.37 (s, 1H), 6.93 (s, 1H), 6.79 (d, J=14.8 Hz, 1H), 5.11 (dd, J=12.9, 5.4 Hz, 1H), 4.20 (d, J=16.9 Hz, 2H), 4.07 (s, 3H), 4.01 (s, 2H), 3.71 (t, J=6.3 Hz, 2H), 3.58-3.53 (m, 8H), 3.34 (t, J=6.3 Hz, 6H), 3.07 (s, 4H), 2.93-2.84 (m, 1H), 2.66-2.57 (m, 2H), 2.09-2.02 (m, 1H). HRMS (ESI) m/z: calcd for $C_{44}H_{47}ClFN_8O_{10}S^+$ [M+H]$^+$, 933.2803; found, 933.2800.

Example 25

Preparation of (E)-N-(4-((3-chloro-4-fluorophenyl) amino)-7-methoxyquinazolin-6-yl)-4-(4-(14-((2-(2,6-dioxopiperidin-3-yl)-1,3-dioxoisoindolin-4-yl) thio)-3,6,9,12-tetraoxatetradecanoyl)piperazin-1-yl) but-2-enamide (SIAIS262007)

Referring to the method of example 1, the target compound (SIAIS262007) was prepared by using Dacomitinib derivative A and intermediate LM (SIAIS1204147). (yellow solid, 10.1 mg, yield 49%) $^1$H NMR (500 MHz, DMSO) δ 11.72-11.32 (m, 1H), 11.12 (s, 1H), 10.16 (s, 1H), 9.14 (s, 1H), 8.85 (s, 1H), 8.00 (s, 1H), 7.79-7.74 (m, 2H), 7.68 (s, 1H), 7.62 (dd, J=5.5, 2.4 Hz, 1H), 7.53 (t, J=9.1 Hz, 1H), 7.39 (s, 1H), 6.96 (s, 1H), 6.80 (d, J=15.1 Hz, 1H), 5.11 (dd, J=12.9, 5.4 Hz, 1H), 4.20 (d, J=20.5 Hz, 2H), 4.07 (s, 3H), 4.01 (s, 2H), 3.70 (t, J=6.3 Hz, 2H), 3.59-3.50 (m, 14H), 3.34 (t, J=6.3 Hz, 4H), 3.03 (d, J=50.8 Hz, 4H), 2.92-2.88 (m, 1H), 2.64-2.53 (m, 2H), 2.09-2.01 (m, 1H). HRMS (ESI) m/z: calcd for $C_{46}H_{51}ClFN_8O_{11}S^+$ [M+H]$^+$, 977.3065; found, 977.3061.

Example 26

Preparation of (E)-N-(4-((3-chloro-4-fluorophenyl) amino)-7-methoxyquinazolin-6-yl)-4-(4-(17-((2-(2,6-dioxopiperidin-3-yl)-1,3-dioxoisoindolin-4-yl) thio)-3,6,9,12,15-pentaoxaheptadecanoyl)piperazin-1-yl)but-2-enamide (SIAIS262008)

Referring to the method of example 1, the target compound (SIAIS262008) was prepared by using Dacomitinib derivative A and intermediate LM (SIAIS1204149). (yellow solid, 11.5 mg, yield 54%) $^1$H NMR (500 MHz, DMSO) δ 11.89 (s, 1H), 11.12 (s, 1H), 10.17 (s, 1H), 9.15 (s, 1H), 8.86 (s, 1H), 7.99 (dd, J=6.8, 2.5 Hz, 1H), 7.79-7.74 (m, 2H), 7.69-7.66 (m, 1H), 7.65-7.60 (m, 1H), 7.53 (td, J=9.0, 3.2 Hz, 1H), 7.45 (s, 1H), 7.02-6.94 (m, 1H), 6.80 (d, J=15.3 Hz, 1H), 5.11 (dd, J=12.9, 5.4 Hz, 1H), 4.21 (s, 2H), 4.07 (s, 3H), 4.00 (d, J=9.4 Hz, 2H), 3.70 (t, J=6.3 Hz, 2H), 3.61-3.51 (m, 18H), 3.33 (t, J=6.3 Hz, 4H), 3.06 (d, J=41.3 Hz, 4H), 2.91-2.86 (m, 1H), 2.62-2.52 (m, 2H), 2.08-1.99 (m, 1H). HRMS (ESI) m/z: calcd for $C_{48}H_{55}ClFN_8O_{12}S^+$ [M+H]$^+$, 1021.3327; found, 1021.3324.

Example 27

Preparation of (E)-N-(4-((3-chloro-4-fluorophenyl) amino)-7-methoxyquinazolin-6-yl)-4-(4-(2-((2-(2,6-dioxopiperidin-3-yl)-1-oxoisoindolin-4-yl)thio) acetyl)piperazin-1-yl)but-2-enamide (SIAIS219185)

Referring to the method of example 1, the target compound (SIAIS219185) was prepared by using Dacomitinib derivative A and intermediate LM (SIAIS171090). (yellow solid, 8.1 mg, yield 49%) $^1$H NMR (500 MHz, MeOD) δ 9.27 (s, 1H), 8.75 (s, 1H), 7.93 (dd, J=6.6, 2.6 Hz, 1H), 7.82-7.77 (m, 2H), 7.74 (d, J=7.5 Hz, 1H), 7.68-7.62 (m, 1H), 7.56 (t, J=7.7 Hz, 1H), 7.44 (d, J=8.1 Hz, 1H), 7.37 (t, J=8.9 Hz, 1H), 7.32 (s, 1H), 7.05-7.00 (m, 1H), 6.86 (d, J=15.2 Hz, 1H), 5.18 (dd, J=13.3, 5.2 Hz, 1H), 4.56 (d, J=17.5 Hz, 1H), 4.49 (d, J=17.4 Hz, 1H), 4.18 (s, 3H), 4.16-4.12 (m, 2H), 4.08 (d, J=5.9 Hz, 2H), 4.03 (d, J=5.4 Hz, 2H), 3.77-3.53 (m, 6H), 2.94-2.87 (m, 1H), 2.82-2.76 (m, 1H), 2.58-2.52 (m, 1H), 2.21-2.17 (m, 1H). HRMS (ESI) m/z: calcd for $C_{38}H_{37}ClFN_8O_6S^+$ [M+H]$^+$, 787.2224; found, 787.2221.

Example 28

Preparation of (E)-N-(4-((3-chloro-4-fluorophenyl) amino)-7-methoxyquinazolin-6-yl)-4-(4-(3-((2-(2,6-dioxopiperidin-3-yl)-1-oxoisoindolin-4-yl)thio)propanoyl)piperazin-1-yl)but-2-enamide (SIAIS219186)

Referring to the method of example 1, the target compound (SIAIS219186) was prepared by using Dacomitinib derivative A and intermediate LM (SIAIS171086). (yellow solid, 8.5 mg, yield 51%) $^1$H NMR (500 MHz, MeOD) δ 9.27 (s, 1H), 8.75 (s, 1H), 7.93 (dd, J=6.6, 2.6 Hz, 1H), 7.74-7.68 (m, 2H), 7.69-7.64 (m, 1H), 7.56 (t, J=7.7 Hz, 1H), 7.37 (t, J=8.9 Hz, 1H), 7.32 (s, 1H), 7.08-7.00 (m, 1H), 6.84 (d, J=15.2 Hz, 1H), 5.19 (dd, J=13.4, 5.1 Hz, 1H), 4.49 (d, J=17.4 Hz, 1H), 4.43 (d, J=17.4 Hz, 1H), 4.18 (s, 3H), 4.02 (d, J=6.8 Hz, 2H), 3.96-3.32 (m, 8H), 3.17 (s, 2H), 2.95-2.90 (m, 1H), 2.83-2.76 (m, 3H), 2.56-2.52 (m, 1H), 2.21-2.18 (m, 1H). HRMS (ESI) m/z: calcd for $C_{39}H_{39}ClFN_8O_6S^+$ $[M+H]^+$, 801.2380; found, 801.2381.

Example 29

Preparation of (E)-N-(4-((3-chloro-4-fluorophenyl) amino)-7-methoxyquinazolin-6-yl)-4-(4-(4-((2-(2,6-dioxopiperidin-3-yl)-1-oxoisoindolin-4-yl)thio)butanoyl)piperazin-1-yl)but-2-enamide (SIAIS219187)

Referring to the method of example 1, the target compound (SIAIS219187) was prepared by using Dacomitinib derivative A and intermediate LM (SIAIS171089). (yellow solid, 9.0 mg, yield 53%) $^1H$ NMR (500 MHz, MeOD) δ 9.29 (s, 1H), 8.76 (s, 1H), 7.94 (dd, J=6.6, 2.6 Hz, 1H), 7.72 (d, J=7.7 Hz, 1H), 7.70-7.64 (m, 2H), 7.55 (t, J=7.7 Hz, 1H), 7.38 (t, J=8.9 Hz, 1H), 7.33 (s, 1H), 7.07-7.02 (m, 1H), 6.87 (d, J=15.2 Hz, 1H), 5.18 (dd, J=13.3, 5.1 Hz, 1H), 4.49 (d, J=17.4 Hz, 1H), 4.46-4.40 (m, 1H), 4.19 (s, 3H), 4.06 (d, J=7.0 Hz, 2H), 3.72-3.62 (m, 2H), 3.59-3.49 (m, 2H), 3.25-3.08 (m, 5H), 2.94-2.86 (m, 2H), 2.83-2.74 (m, 1H), 2.62-2.50 (m, 3H), 2.21-2.14 (m, 1H), 1.97-1.93 (m, 2H). HRMS (ESI) m/z: calcd for $C_{40}H_{41}ClFN_8O_6S^+$ $[M+H]^+$, 815.2537; found, 815.2535.

Example 30

Preparation of (E)-N-(4-((3-chloro-4-fluorophenyl) amino)-7-methoxyquinazolin-6-yl)-4-(4-(5-((2-(2,6-dioxopiperidin-3-yl)-1-oxoisoindolin-4-yl)thio)pentanoyl)piperazin-1-yl)but-2-enamide (SIAIS219188)

Referring to the method of example 1, the target compound (SIAIS219188) was prepared by using Dacomitinib derivative A and intermediate LM (SIAIS171079). (yellow solid, 8.8 mg, yield 51%) $^1H$ NMR (500 MHz, MeOD) δ 9.28 (s, 1H), 8.75 (s, 1H), 7.94 (dd, J=6.6, 2.6 Hz, 1H), 7.68-7.63 (m, 3H), 7.53 (t, J=7.7 Hz, 1H), 7.38 (t, J=8.9 Hz, 1H), 7.32 (s, 1H), 7.09-7.03 (m, 1H), 6.85 (d, J=15.2 Hz, 1H), 5.17 (dd, J=13.4, 5.1 Hz, 1H), 4.48 (d, J=17.4 Hz, 1H), 4.43 (d, J=17.4 Hz, 1H), 4.18 (s, 3H), 4.02 (s, 2H), 3.15-3.10 (m, 8H), 2.96-2.85 (m, 1H), 2.82-2.76 (m, 1H), 2.57-2.52 (m, 1H), 2.45 (t, J=7.1 Hz, 2H), 2.22-2.15 (m, 2H), 2.04 (s, 1H), 1.77-1.68 (m, 4H). HRMS (ESI) m/z: calcd for $C_{41}H_{43}ClFN_8O_6S^+$ $[M+H]^+$, 829.2693; found, 829.2690.

Example 31

Preparation of (E)-N-(4-((3-chloro-4-fluorophenyl) amino)-7-methoxyquinazolin-6-yl)-4-(4-(6-((2-(2,6-dioxopiperidin-3-yl)-1-oxoisoindolin-4-yl)thio) hexanoyl)piperazin-1-yl)but-2-enamide (SIAIS219189)

Referring to the method of example 1, the target compound (SIAIS219189) was prepared by using Dacomitinib derivative A and intermediate LM (SIAIS171091). (yellow solid, 9.1 mg, yield 51%) $^1H$ NMR (500 MHz, MeOD) δ 9.26 (s, 1H), 8.75 (s, 1H), 7.93 (dd, J=6.6, 2.6 Hz, 1H), 7.68-7.63 (m, 3H), 7.53 (t, J=7.7 Hz, 1H), 7.38 (t, J=8.9 Hz, 1H), 7.32 (s, 1H), 7.09-7.03 (m, 1H), 6.87 (d, J=15.3 Hz, 1H), 5.17 (dd, J=13.3, 5.2 Hz, 1H), 4.50-4.44 (m, 1H), 4.42 (d, J=17.3 Hz, 1H), 4.18 (s, 3H), 4.05 (d, J=7.2 Hz, 2H), 3.34-3.30 (m, 8H), 3.09-3.05 (m, 2H), 2.95-2.88 (m, 1H), 2.79-2.74 (m, 1H), 2.57-2.52 (m, 1H), 2.38 (t, J=7.3 Hz, 2H), 2.22-2.14 (m, 1H), 1.66-1.62 (m, 4H), 1.53-1.49 (m, 2H). HRMS (ESI) m/z: calcd for $C_{42}H_{45}ClFN_8O_6S^+$ $[M+H]^+$, 843.2850; found, 843.2852.

Example 32

Preparation of (E)-N-(4-((3-chloro-4-fluorophenyl) amino)-7-methoxyquinazolin-6-yl)-4-(4-(7-((2-(2,6-dioxopiperidin-3-yl)-1-oxoisoindolin-4-yl)thio)heptanoyl)piperazin-1-yl)but-2-enamide (SIAIS219190)

Referring to the method of example 1, the target compound (SIAIS219190) was prepared by using Dacomitinib derivative A and intermediate LM (SIAIS171092). (yellow solid, 8.9 mg, yield 49%) $^1H$ NMR (500 MHz, MeOD) δ 9.26 (s, 1H), 8.74 (s, 1H), 7.93 (dd, J=6.6, 2.6 Hz, 1H), 7.67-7.62 (m, 3H), 7.52 (t, J=7.7 Hz, 1H), 7.37 (t, J=8.9 Hz, 1H), 7.32 (s, 1H), 7.05 (dd, J=14.9, 7.4 Hz, 1H), 6.86 (d, J=15.2 Hz, 1H), 5.17 (dd, J=13.4, 5.2 Hz, 1H), 4.49-4.43 (m, 1H), 4.40 (d, J=17.3 Hz, 1H), 4.18 (s, 3H), 4.04 (d, J=7.0 Hz, 2H), 3.31 (d, J=1.6 Hz, 8H), 3.10-3.02 (m, 2H), 2.92-2.88 (m, 1H), 2.82-2.74 (m, 1H), 2.57-2.52 (m, 1H), 2.39 (t, J=7.5 Hz, 2H), 2.22-2.14 (m, 1H), 1.71-1.63 (m, 2H), 1.59-1.55 (m, 2H), 1.49-1.44 (m, 2H), 1.39-1.34 (m, 2H). HRMS (ESI) m/z: calcd for $C_{43}H_{47}ClFN_8O_6S^+$ $[M+H]^+$, 857.3006; found, 857.3003.

Example 33

Preparation of (E)-N-(4-((3-chloro-4-fluorophenyl) amino)-7-methoxyquinazolin-6-yl)-4-(4-(2-(2-((2-(2,6-dioxopiperidin-3-yl)-1-oxoisoindolin-4-yl)thio) ethoxy)acetyl)piperazin-1-yl)but-2-enamide (SIAIS219193)

Referring to the method of example 1, the target compound (SIAIS219193) was prepared by using Dacomitinib derivative A and intermediate LM (SIAIS1213129). (yellow solid, 9.1 mg, yield 52%) $^1H$ NMR (500 MHz, MeOD) δ 9.29 (s, 1H), 8.76 (s, 1H), 7.94 (dd, J=6.6, 2.6 Hz, 1H), 7.72 (d, J=7.7 Hz, 1H), 7.70-7.61 (m, 2H), 7.52 (dd, J=10.0, 5.3 Hz, 1H), 7.38 (t, J=8.9 Hz, 1H), 7.32 (s, 1H), 7.07 (dt, J=14.8, 7.2 Hz, 1H), 6.86 (d, J=15.2 Hz, 1H), 5.17 (dd, J=13.1, 5.1 Hz, 1H), 4.51 (d, J=17.5 Hz, 1H), 4.47 (d, J=8.0 Hz, 1H), 4.21 (d, J=5.0 Hz, 2H), 4.18 (s, 3H), 4.09-4.05 (m, 2H), 3.74 (dd, J=10.6, 4.8 Hz, 2H), 3.35-3.31 (m, 8H), 3.26 (dd, J=13.1, 6.9 Hz, 2H), 2.91-2.86 (m, 1H), 2.83-2.76 (m, 1H), 2.58-2.54 (m, 1H), 2.25-2.17 (m, 1H). HRMS (ESI) m/z: calcd for $C_{40}H_{41}ClFN_8O_7S^+$ $[M+H]^+$, 831.2486; found, 831.2482.

Example 34

Preparation of (E)-N-(4-((3-chloro-4-fluorophenyl) amino)-7-methoxyquinazolin-6-yl)-4-(4-(2-(2-(2-((2-(2,6-dioxopiperidin-3-yl)-1-oxoisoindolin-4-yl)thio) ethoxy)ethoxy)acetyl)piperazin-1-yl)but-2-enamide (SIAIS262001)

Referring to the method of example 1, the target compound (SIAIS262001) was prepared by using Dacomitinib derivative A and intermediate LM (SIAIS1213131). (yellow solid, 9.2 mg, yield 50%) $^1H$ NMR (500 MHz, DMSO) δ 11.50 (s, 1H), 10.99 (s, 1H), 10.15 (s, 1H), 9.13 (s, 1H), 8.85 (s, 1H), 8.00 (d, J=6.8 Hz, 1H), 7.69 (d, J=7.7 Hz, 2H), 7.59-7.51 (m, 3H), 7.39 (s, 1H), 7.00-6.92 (m, 1H), 6.80 (d, J=15.4 Hz, 1H), 5.13 (dd, J=13.3, 5.2 Hz, 1H), 4.37 (d, J=17.4 Hz, 1H), 4.24 (d, J=17.5 Hz, 1H), 4.20 (d, J=9.9 Hz, 2H), 4.07 (s, 3H), 4.01 (s, 2H), 3.63 (t, J=6.4 Hz, 2H), 3.52 (d, J=34.2 Hz, 8H), 3.26 (t, J=6.1 Hz, 2H), 3.17-2.92 (m, 4H), 2.93-2.88 (m, 1H), 2.65-2.58 (m, 1H), 2.47-2.43 (m, 1H), 2.05-1.99 (m, 1H). HRMS (ESI) m/z: calcd for $C_{42}H_{45}ClFN_8O_8S^+$ [M+H]$^+$, 875.2748; found, 875.2744.

Example 35

Preparation of (E)-N-(4-((3-chloro-4-fluorophenyl) amino)-7-methoxyquinazolin-6-yl)-4-(4-(2-(2-(2-(2-((2-(2,6-dioxopiperidin-3-yl)-1-oxoisoindolin-4-yl) thio)ethoxy)ethoxy)ethoxy)acetyl)piperazin-1-yl) but-2-enamide (SIAIS262002)

Referring to the method of example 1, the target compound (SIAIS262002) was prepared by using Dacomitinib derivative A and intermediate LM (SIAIS1213133). (yellow solid, 10.2 mg, yield 53%) $^1H$ NMR (500 MHz, DMSO) δ 10.99 (s, 1H), 10.15 (s, 1H), 9.13 (s, 1H), 8.85 (s, 1H), 8.00 (dd, J=6.8, 2.5 Hz, 1H), 7.71-7.65 (m, 2H), 7.59-7.51 (m, 3H), 7.41 (s, 1H), 7.03-6.93 (m, 1H), 6.80 (d, J=15.4 Hz, 1H), 5.12 (dd, J=13.3, 5.1 Hz, 1H), 4.37 (d, J=17.4 Hz, 1H), 4.25-4.21 (m, 1H), 4.21 (s, 2H), 4.07 (s, 3H), 4.02-3.95 (m, 2H), 3.61 (d, J=6.3 Hz, 2H), 3.57-3.52 (m, 8H), 3.25 (t, J=6.0 Hz, 2H), 3.05 (s, 4H), 2.95-2.88 (m, 1H), 2.60 (t, J=15.9 Hz, 1H), 2.48-2.42 (m, 1H), 2.05-1.98 (m, 1H). HRMS (ESI) m/z: calcd for $C_{44}H_{49}ClFN_8O_9S^+$ [M+H]$^+$, 919.3010; found, 919.3012.

Example 36

Preparation of (E)-N-(4-((3-chloro-4-fluorophenyl) amino)-7-methoxyquinazolin-6-yl)-4-(4-(14-((2-(2,6-dioxopiperidin-3-yl)-1-oxoisoindolin-4-yl)thio)-3,6,9,12-tetraoxatetradecan-1-oyl)piperazin-1-yl)but-2-enamide (SIAIS262003)

Referring to the method of example 1, the target compound (SIAIS262003) was prepared by using Dacomitinib derivative A and intermediate LM (SIAIS1213135). (yellow solid, 10.3 mg, yield 51%) $^1H$ NMR (500 MHz, DMSO) δ 11.54 (s, 1H), 10.99 (s, 1H), 10.15 (s, 1H), 9.13 (s, 1H), 8.84 (s, 1H), 8.00 (d, J=7.0 Hz, 1H), 7.70-7.67 (m, 2H), 7.56 (ddd, J=18.6, 5.8, 2.8 Hz, 3H), 6.96 (dd, J=15.1, 7.0 Hz, 11H), 6.80 (d, J=15.3 Hz, 1H), 5.15-5.11 (m, 1H), 4.37 (d, J=12.5 Hz, 1H), 4.23 (d, J=13.4 Hz, 1H), 4.19 (d, J=14.0 Hz, 2H), 4.07 (s, 3H), 4.01 (s, 2H), 3.63-3.61 (m, 2H), 3.54-3.51 (m, 8H), 3.26-3.25 (m, 2H), 3.08 (s, 4H), 2.93-2.88 (m, 1H), 2.59 (d, J=16.1 Hz, 1H), 2.45-2.41 (m, 1H), 2.02-2.00 (m, 1H). HRMS (ESI) m/z: calcd for $C_{46}H_{53}ClFN_8O_{10}S^+$ [M+H]$^+$, 963.3272; found, 963.3270.

Example 37

Preparation of (E)-N-(4-((3-chloro-4-fluorophenyl) amino)-7-methoxyquinazolin-6-yl)-4-(4-(17-((2-(2,6-dioxopiperidin-3-yl)-1-oxoisoindolin-4-yl)thio)-3,6,9,12,15-pentaoxaheptadecan-1-oyl)piperazin-1-yl) but-2-enamide (SIAIS262004)

Referring to the method of example 1, the target compound (SIAIS262004) was prepared by using Dacomitinib derivative A and intermediate LM (SIAIS1213137). (yellow solid, 11.2 mg, yield 53%) $^1H$ NMR (500 MHz, DMSO) δ 11.25 (s, 1H), 10.99 (s, 1H), 10.18 (s, 1H), 9.16 (s, 1H), 8.87 (s, 1H), 8.02-7.96 (m, 1H), 7.70-7.66 (m, 2H), 7.55 (tdd, J=12.9, 7.0, 3.5 Hz, 3H), 7.45 (d, J=2.0 Hz, 1H), 6.99 (dt, J=14.4, 7.1 Hz, 1H), 6.80 (d, J=15.3 Hz, 1H), 5.12 (dd, J=13.3, 5.1 Hz, 1H), 4.37 (dd, J=17.4, 4.1 Hz, 1H), 4.26-4.22 (m, 1H), 4.23-4.16 (m, 2H), 4.08 (d, J=1.9 Hz, 3H), 4.01 (t, J=5.5 Hz, 2H), 3.73-3.69 (m, 1H), 3.69-3.64 (m, 1H), 3.64-3.60 (m, 2H), 3.58-3.52 (m, 10H), 3.28-3.24 (m, 2H), 3.23-2.95 (m, 4H), 2.91 (ddd, J=13.6, 11.1, 5.5 Hz, 1H), 2.65-2.56 (m, 1H), 2.44 (d, J=13.1 Hz, 1H), 2.03-1.98 (m, 1H). HRMS (ESI) m/z: calcd for $C_{48}H_{57}ClFN_8O_{11}S^+$ [M+H]$^+$, 1007.3535; found, 1007.3533.

Example 38

Preparation of (2S,4R)-1-((S)-2-(3-(2-(3-(4-((E)-4-((4-((3-chloro-4-fluorophenyl)amino)-7-methoxyquinazolin-6-yl)amino)-4-oxobut-2-en-1-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide (SIAIS249045)

Referring to the method of example 1, the target compound (SIAIS249045) was prepared by using Dacomitinib derivative A and intermediate LM (SIAIS151002). (white solid, 11.1 mg, yield 49%) $^1H$ NMR (500 MHz, MeOD) δ 9.84 (s, 1H), 9.27 (s, 1H), 8.76 (s, 1H), 7.92 (dd, J=6.6, 2.6 Hz, 1H), 7.68-7.63 (m, 1H), 7.53 (dt, J=16.8, 6.5 Hz, 5H), 7.37 (dd, J=15.8, 6.9 Hz, 2H), 7.08 (dd, J=14.9, 7.4 Hz, 1H), 6.89 (d, J=15.2 Hz, 1H), 4.65 (s, 1H), 4.61-4.55 (m, 2H), 4.51 (d, J=12.2 Hz, 2H), 4.43 (s, 1H), 4.18 (s, 3H), 4.12 (d, J=7.1 Hz, 2H), 3.90 (d, J=11.1 Hz, 1H), 3.83-3.72 (m, 7H), 3.62 (t, J=9.1 Hz, 7H), 2.62-2.51 (m, 8H), 2.26-2.22 (m, 1H), 2.09-2.05 (m, 1H), 1.34-1.29 (m, 2H), 1.04 (s, 9H). HRMS (ESI) m/z: calcd for $C_{53}H_{65}ClFN_{10}O_9S^+$ [M+H]$^+$, 1071.4324; found, 1071.4321.

Example 39

Preparation of (2S,4R)-1-((S)-2-(4-(4-((E)-4-((4-((3-chloro-4-fluorophenyl)amino)-7-methoxyquinazolin-6-yl)amino)-4-oxobut-2-en-1-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide (SIAIS249041)

Referring to the method of example 1, the target compound (SIAIS249041) was prepared by using Dacomitinib derivative A and intermediate LM (SIAIS074011). (white solid, 10.2 mg, yield 49%) $^1H$ NMR (500 MHz, MeOD) δ 9.83 (s, 1H), 9.27 (s, 1H), 8.76 (s, 1H), 7.93 (dd, J=6.6, 2.5 Hz, 1H), 7.68-7.63 (m, 1H), 7.54 (dt, J=8.2, 3.5 Hz, 5H), 7.38 (d, J=8.9 Hz, 1H), 7.12-7.05 (m, 1H), 6.90 (d, J=15.0 Hz, 1H), 4.62-4.48 (m, 6H), 4.39 (dd, J=15.8, 6.1 Hz, 2H), 4.19 (s, 3H), 4.12 (d, J=6.9 Hz, 2H), 3.89 (d, J=11.0 Hz, 1H), 3.80 (dd, J=10.9, 3.7 Hz, 1H), 3.69-3.55 (m, 3H), 2.78-2.48 (m, 10H), 2.29-2.20 (m, 2H), 2.12-1.97 (m, 2H), 1.03 (s, 9H). HRMS (ESI) m/z: calcd for $C_{49}H_{57}ClFN_{10}O_7S^+$ [M+H]$^+$, 983.3799; found, 983.3795.

Example 40

Preparation of (2S,4R)-1-((S)-2-(6-(4-((E)-4-((4-((3-chloro-4-fluorophenyl)amino)-7-methoxyquinazolin-6-yl)amino)-4-oxobut-2-en-1-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide (SIAIS249042)

Referring to the method of example 1, the target compound (SIAIS249042) was prepared by using Dacomitinib derivative A and intermediate LM (SIAIS074013). (white solid, 10.8 mg, yield 51%) $^1$H NMR (500 MHz, MeOD) δ 9.61 (s, 1H), 9.27 (s, 1H), 8.76 (s, 1H), 7.92 (dd, J=6.6, 2.6 Hz, 1H), 7.65 (ddd, J=8.8, 4.1, 2.6 Hz, 1H), 7.56-7.48 (m, 4H), 7.38 (t, J=8.9 Hz, 1H), 7.34 (s, 1H), 7.07 (dd, J=14.9, 7.4 Hz, 1H), 6.89 (d, J=15.3 Hz, 1H), 4.63 (s, 1H), 4.57 (dd, J=14.8, 6.0 Hz, 2H), 4.51 (d, J=12.2 Hz, 2H), 4.41 (d, J=15.7 Hz, 1H), 4.19 (s, 3H), 4.10 (d, J=7.2 Hz, 2H), 3.91 (d, J=11.0 Hz, 1H), 3.80 (dd, J=10.9, 3.8 Hz, 1H), 3.75-3.48 (m, 3H), 2.56 (s, 3H), 2.48 (d, J=3.1 Hz, 2H), 2.36-2.31 (m, 2H), 2.25-2.20 (m, 1H), 2.09-2.05 (m, 1H), 1.69-1.62 (m, 4H), 1.04 (s, 9H). HRMS (ESI) m/z: calcd for $C_{51}H_{61}ClFN_{10}O_7S^+$ [M+H]$^+$, 1011.4112; found, 1011.4110.

Example 41

Preparation of (2S,4R)-1-((S)-2-(8-(4-((E)-4-((4-((3-chloro-4-fluorophenyl)amino)-7-methoxyquinazolin-6-yl)amino)-4-oxobut-2-en-1-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide (SIAIS249043)

Referring to the method of example 1, the target compound (SIAIS249043) was prepared by using Dacomitinib derivative A and intermediate LM (SIAIS074015). (white solid, 10.8 mg, yield 49%) $^1$H NMR (500 MHz, MeOD) δ 9.86 (s, 1H), 9.27 (s, 1H), 8.76 (s, 1H), 7.93 (dd, J=6.6, 2.6 Hz, 1H), 7.66 (ddd, J=8.9, 4.1, 2.7 Hz, 1H), 7.54 (dd, J=23.3, 8.2 Hz, 4H), 7.39 (d, J=8.9 Hz, 1H), 7.35 (d, J=6.7 Hz, 1H), 7.10-7.06 (m, 1H), 6.89 (d, J=15.2 Hz, 1H), 4.64 (s, 1H), 4.59-4.48 (m, 3H), 4.41 (d, J=15.7 Hz, 1H), 4.19 (s, 3H), 4.11 (d, J=7.1 Hz, 2H), 3.91 (d, J=11.0 Hz, 1H), 3.82-3.78 (m, 1H), 2.59 (s, 3H), 2.46 (t, J=7.5 Hz, 2H), 2.33-2.20 (m, 3H), 2.09-2.05 (m, 1H), 1.66-1.57 (m, 4H), 1.03 (s, 9H). HRMS (ESI) m/z: calcd for $C_{53}H_{65}ClFN_{10}O_7S^+$ [M+H]$^+$, 1039.4425; found, 1039.4423.

Example 42

Preparation of (E)-N-(4-((3-chloro-4-fluorophenyl)amino)-7-methoxyquinazolin-6-yl)-4-(4-(4-(6-((2-(2,6-dioxopiperidin-3-yl)-1,3-dioxoisoindolin-4-yl)thio)hexanoyl)piperazin-1-yl)piperidin-1-yl)but-2-enamide (SIAIS262032)

Referring to the method of example 1, the target compound (SIAIS262032) was prepared by using Dacomitinib derivative B and intermediate LM (SIAIS151141B). (yellow solid, 8.1 mg, yield 48%) $^1$H NMR (500 MHz, MeOD) δ 9.27 (s, 1H), 8.75 (s, 1H), 7.93 (dd, J=6.5, 2.5 Hz, 1H), 7.76-7.69 (m, 2H), 7.67-7.63 (m, 1H), 7.63-7.57 (m, 1H), 7.38 (t, J=8.9 Hz, 1H), 7.32 (s, 1H), 7.05 (dd, J=14.8, 7.3 Hz, 1H), 6.87 (d, J=15.2 Hz, 1H), 5.13 (dd, J=12.7, 5.4 Hz, 1H), 4.18 (s, 3H), 4.07 (d, J=6.4 Hz, 2H), 3.92 (s, 2H), 3.77 (d, J=12.3 Hz, 2H), 3.60 (s, 2H), 3.41-3.36 (m, 5H), 3.22 (s, 2H), 3.15 (t, J=7.1 Hz, 2H), 2.87 (t, J=8.7 Hz, 1H), 2.80-2.68 (m, 2H), 2.55-2.42 (m, 4H), 2.22 (d, J=10.3 Hz, 2H), 2.18-2.10 (m, 1H), 1.85-1.76 (m, 2H), 1.74-1.64 (m, 2H), 1.58 (d, J=6.9 Hz, 2H). HRMS (ESI) m/z: calcd for $C_{47}H_{52}ClFN_9O_7S^+$ [M+H]$^+$, 940.3377; found, 940.3374.

Example 43

Preparation of (E)-N-(4-((3-chloro-4-fluorophenyl)amino)-7-methoxyquinazolin-6-yl)-4-(4-(4-(7-((2-(2,6-dioxopiperidin-3-yl)-1,3-dioxoisoindolin-4-yl)thio)heptanoyl)piperazin-1-yl)piperidin-1-yl)but-2-enamide (SIAIS262033)

Referring to the method of example 1, the target compound (SIAIS262033) was prepared by using Dacomitinib derivative B and intermediate LM (SIAIS151142B). (yellow solid, 8.4 mg, yield 49%) $^1$H NMR (500 MHz, MeOD) δ 9.26 (s, 1H), 8.75 (s, 1H), 7.93 (dd, J=6.6, 2.6 Hz, 1H), 7.74-7.68 (m, 2H), 7.68-7.64 (m, 1H), 7.60 (dd, J=6.8, 1.0 Hz, 1H), 7.38 (t, J=8.9 Hz, 1H), 7.32 (s, 1H), 7.10-7.02 (m, 11H), 6.87 (d, J=15.1 Hz, 1H), 5.16-5.12 (m, 1H), 4.18 (d, J=6.0 Hz, 3H), 4.08 (d, J=6.4 Hz, 2H), 3.92 (s, 2H), 3.77 (d, J=11.9 Hz, 2H), 3.61 (s, 2H), 3.45-3.42 (m, 5H), 3.22 (s, 2H), 3.13 (t, J=7.1 Hz, 2H), 2.90-2.86 (m, 1H), 2.76-2.72 (m, 2H), 2.52-2.42 (m, 4H), 2.22 (d, J=12.3 Hz, 2H), 2.18-2.11 (m, 1H), 1.81-1.73 (m, 2H), 1.66-1.62 (m, 2H), 1.58-1.53 (m, 2H), 1.47-1.42 (m, 2H). HRMS (ESI) m/z: calcd for $C_{48}H_{54}ClFN_9O_7S^+$ [M+H]$^+$, 954.3534; found, 954.3532.

Example 44

Preparation of (E)-N-(4-((3-chloro-4-fluorophenyl)amino)-7-methoxyquinazolin-6-yl)-4-(4-(4-(2-((2-(2,6-dioxopiperidin-3-yl)-1-oxoisoindolin-4-yl)thio)acetyl)piperazin-1-yl)piperidin-1-yl)but-2-enamide (SIAIS262034)

Referring to the method of example 1, the target compound (SIAIS262034) was prepared by using Dacomitinib derivative B and intermediate LM (SIAIS171090). (yellow solid, 6.5 mg, yield 42%) $^1$H NMR (500 MHz, MeOD) δ 9.28 (s, 1H), 8.75 (s, 1H), 7.93 (dd, J=6.6, 2.6 Hz, 1H), 7.83 (d, J=7.7 Hz, 1H), 7.76 (d, J=7.5 Hz, 1H), 7.70-7.63 (m, 1H), 7.58 (t, J=7.7 Hz, 1H), 7.38 (t, J=8.9 Hz, 1H), 7.32 (s, 1H), 7.07 (dt, J=14.6, 7.1 Hz, 1H), 6.88 (d, J=15.3 Hz, 1H), 5.17 (dd, J=13.3, 5.1 Hz, 1H), 4.57 (d, J=17.6 Hz, 1H), 4.50 (d, J=11.6 Hz, 1H), 4.18 (s, 3H), 4.12-3.98 (m, 4H), 3.78 (d, J=11.7 Hz, 2H), 3.58 (s, 2H), 3.38 (d, J=65.5 Hz, 5H), 3.20 (d, J=27.5 Hz, 4H), 2.93-2.87 (m, 1H), 2.82-2.78 (m, 1H), 2.59-2.54 (m, 1H), 2.42 (s, 1H), 2.21-2.18 (m, 4H). HRMS (ESI) m/z: calcd for $C_{43}H_{46}ClFN_9O_6S^+$ [M+H]$^+$, 870.2959; found, 870.2955.

Example 45

Preparation of (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)thio)hexanoyl)piperazin-1-yl)piperidin-1-yl)but-2-enamide (SIAIS262035)

Referring to the method of example 1, the target compound (SIAIS262035) was prepared by using Dacomitinib derivative B and intermediate LM (SIAIS171091). (yellow solid, 8.3 mg, yield 50%) $^1$H NMR (500 MHz, MeOD) δ 9.27 (s, 1H), 8.75 (s, 1H), 7.93 (dd, J=6.6, 2.6 Hz, 1H), 7.69-7.63 (m, 3H), 7.54 (t, J=7.6 Hz, 1H), 7.38 (t, J=8.9 Hz, 1H), 7.33 (s, 1H), 7.11-7.01 (m, 1H), 6.88 (d, J=15.1 Hz, 1H), 5.17 (dd, J=13.3, 5.1 Hz, 1H), 4.48 (d, J=17.3 Hz, 1H), 4.42 (d, J=17.4 Hz, 1H), 4.19 (s, 3H), 4.09 (s, 2H), 3.79 (d, J=10.9 Hz, 2H), 3.63 (d, J=12.1 Hz, 2H), 3.50-3.32 (m, 5H), 3.27-3.21 (m, 2H), 3.20-3.01 (m, 4H), 2.94-2.90 (m, 1H), 2.84-2.77 (m, 1H), 2.62-2.54 (m, 1H), 2.50 (d, J=10.6 Hz, 2H), 2.39 (t, J=7.2 Hz, 2H), 2.30-2.15 (m, 3H), 1.69-1.65 (m, 2H), 1.65-1.58 (m, 2H), 1.56-1.47 (m, 2H). HRMS (ESI) m/z: calcd for $C_{47}H_{54}ClFN_9O_6S^+$ [M+H]$^+$, 926.3585; found, 926.3581.

Example 46

Preparation of (E)-N-(4-((3-chloro-4-fluorophenyl) amino)-7-methoxyquinazolin-6-yl)-4-(4-(4-(2-((2-(2, 6-dioxopiperidin-3-yl)-1,3-dioxoisoindolin-4-yl) amino)acetyl)piperazin-1-yl)piperidin-1-yl)but-2-enamide (SIAIS262036)

Referring to the method of example 1, the target compound (SIAIS262036) was prepared by using Dacomitinib derivative B and intermediate LM (SIAIS151025). (yellow solid, 7.4 mg, yield 47%) $^1$H NMR (500 MHz, MeOD) δ 9.25 (s, 1H), 8.74 (s, 1H), 7.93 (dd, J=6.6, 2.5 Hz, 1H), 7.68-7.63 (m, 1H), 7.55-7.49 (m, 1H), 7.37 (t, J=8.9 Hz, 1H), 7.29 (s, 1H), 7.09 (dd, J=18.4, 7.4 Hz, 2H), 6.99 (d, J=8.5 Hz, 1H), 6.88 (d, J=15.1 Hz, 1H), 5.08 (dd, J=12.7, 5.5 Hz, 1H), 4.26 (s, 2H), 4.18 (s, 3H), 4.10 (s, 2H), 3.81 (d, J=11.7 Hz, 2H), 3.68 (s, 1H), 3.39-3.36 (m, 8H), 3.26 (d, J=12.3 Hz, 2H), 2.88 (m, 1H), 2.75-2.70 (m, 2H), 2.54-2.51 (s, 2H), 2.30 (s, 2H), 2.17-2.07 (m, 1H). HRMS (ESI) m/z: calcd for $C_{43}H_{45}ClFN_{10}O_7^+$ [M+H]$^+$, 867.3140; found, 867.3141.

Example 47

Preparation of (E)-N-(4-((3-chloro-4-fluorophenyl) amino)-7-methoxyquinazolin-6-yl)-4-(4-(4-(7-((2-(2, 6-dioxopiperidin-3-yl)-1,3-dioxoisoindolin-4-yl) amino)heptanoyl)piperazin-1-yl)piperidin-1-yl)but-2-enamide (SIAIS262037)

Referring to the method of example 1, the target compound (SIAIS262037) was prepared by using Dacomitinib derivative B and intermediate LM (SIAIS151086). (yellow solid, 9.1 mg, yield 54%) $^1$H NMR (500 MHz, MeOD) δ 9.27 (s, 1H), 8.75 (d, J=2.4 Hz, 1H), 7.96-7.90 (m, 1H), 7.68-7.61 (m, 1H), 7.56 (dd, J=10.9, 4.7 Hz, 1H), 7.38 (dd, J=10.1, 7.7 Hz, 1H), 7.32 (d, J=2.1 Hz, 1H), 7.05 (t, J=7.4 Hz, 3H), 6.88 (d, J=15.6 Hz, 1H), 5.09-5.05 (m, 1H), 4.18 (d, J=2.1 Hz, 3H), 4.09 (s, 2H), 3.79 (d, J=10.9 Hz, 2H), 3.65 (s, 2H), 3.35 (d, J=5.0 Hz, 9H), 3.24 (s, 2H), 2.85 (dd, J=13.3, 4.7 Hz, 1H), 2.73 (t, J=13.9 Hz, 2H), 2.49-2.44 (m, 4H), 2.24 (s, 2H), 2.17-2.07 (m, 1H), 1.68-1.65 (m, 4H), 1.46 (s, 4H). HRMS (ESI) m/z: calcd for $C_{48}H_{55}ClFN_{10}O_7^+$ [M+H]$^+$, 937.3922; found, 937.3920.

Example 48

Preparation of (E)-N-(4-((3-chloro-4-fluorophenyl) amino)-7-methoxyquinazolin-6-yl)-4-(4-(4-(3-(2-(2, 6-dioxopiperidin-3-yl)-1-oxoisoindolin-4-yl)propanoyl)piperazin-1-yl)piperidin-1-yl)but-2-enamide (SIAIS262052)

Referring to the method of example 1, the target compound (SIAIS262052) was prepared by using Dacomitinib derivative B and intermediate LM (SIAIS172147). (yellow solid, 8.6 mg, yield 55%) $^1$H NMR (500 MHz, MeOD) δ 9.27 (s, 1H), 8.75 (d, J=2.4 Hz, 1H), 7.96-7.90 (m, 1H), 7.68-7.61 (m, 1H), 7.56 (dd, J=10.9, 4.7 Hz, 1H), 7.38 (dd, J=10.1, 7.7 Hz, 1H), 7.32 (d, J=2.1 Hz, 1H), 7.05 (t, J=7.4 Hz, 3H), 6.88 (d, J=15.6 Hz, 1H), 5.09-5.05 (m, 1H), 4.18 (d, J=2.1 Hz, 3H), 4.09 (s, 2H), 3.79 (d, J=10.9 Hz, 2H), 3.65 (s, 2H), 3.35 (d, J=5.0 Hz, 9H), 3.24 (s, 2H), 2.85 (dd, J=13.3, 4.7 Hz, 1H), 2.73 (t, J=13.9 Hz, 2H), 2.49-2.44 (m, 4H), 2.24 (s, 2H), 2.17-2.07 (m, 1H), 1.68-1.65 (m, 4H), 1.46 (s, 4H). HRMS (ESI) m/z: calcd for $C_{44}H_{48}ClFN_9O_6^+$ [M+H]$^+$, 852.3395; found, 852.3391.

Example 49

Preparation of 4-((2-(3-(4-((4-((3,4-dichloro-2-fluorophenyl)amino)-7-methoxyquinazolin-6-yl)oxy) piperidin-1-yl)-3-oxopropoxy)ethyl)amino)-2-(2,6-dioxopiperidin-3-yl)isoindoline-1,3-dione (SIAIS249029)

Referring to the method of example 1, the target compound (SIAIS249029) was prepared by using Poziotinib derivative A and intermediate LM (SIAIS151001). (yellow solid, 9.7 mg, yield 52%) $^1$H NMR (500 MHz, MeOD) δ 8.72 (s, 1H), 7.98 (s, 1H), 7.57-7.51 (m, 3H), 7.21 (s, 1H), 7.06 (d, J=8.6 Hz, 1H), 6.94 (d, J=7.1 Hz, 1H), 4.99 (dd, J=12.6, 5.5 Hz, 1H), 4.06 (s, 3H), 3.86-3.81 (m, 2H), 3.75-3.70 (m, 2H), 3.59-3.39 (m, 5H), 2.90-2.55 (m, 6H), 2.15-2.00 (m, 4H), 1.84-1.78 (m, 2H). HRMS (ESI) m/z: calcd for $C_{38}H_{37}Cl_2FN_7O_8^+$ [M+H]$^+$, 808.2059; found, 808.2059.

Example 50

Preparation of 4-((2-(2-(3-(4-((4-((3,4-dichloro-2-fluorophenyl)amino)-7-methoxyquinazolin-6-yl)oxy) piperidin-1-yl)-3-oxopropoxy)ethoxy)ethyl)amino)-2-(2,6-dioxopiperidin-3-yl)isoindoline-1,3-dione (SIAIS249030)

Referring to the method of example 1, the target compound (SIAIS249030) was prepared by using Poziotinib derivative A and intermediate LM (SIAIS151004). (yellow solid, 9.5 mg, yield 48%) $^1$H NMR (500 MHz, MeOD) δ 8.70 (s, 1H), 7.95 (d, J=6.9 Hz, 1H), 7.59-7.52 (m, 2H), 7.47-7.42 (m, 1H), 7.22 (d, J=2.0 Hz, 1H), 7.00 (t, J=8.5 Hz, 1H), 6.91 (d, J=7.1 Hz, 1H), 5.03 (dd, J=8.3, 4.3 Hz, 1H), 4.07 (d, J=2.1 Hz, 3H), 3.99 (d, J=8.6 Hz, 1H), 3.93-3.86 (m, 1H), 3.78 (t, J=5.8 Hz, 2H), 3.71 (t, J=5.3 Hz, 2H), 3.67-3.63 (m, 4H), 3.57-3.43 (m, 5H), 2.88-2.58 (m, 6H), 2.18-2.02 (m, 4H). HRMS (ESI) m/z: calcd for $C_{40}H_{41}Cl_2FN_7O_9^+$ [M+H]$^+$, 852.2321; found, 852.2317.

Example 51

Preparation of 4-((2-(2-(2-(3-(4-((4-((3,4-dichloro-2-fluorophenyl)amino)-7-methoxyquinazolin-6-yl) oxy)piperidin-1-yl)-3-oxopropoxy)ethoxy)ethoxy) ethyl)amino)-2-(2,6-dioxopiperidin-3-yl)isoindoline-1,3-dione (SIAIS249031)

Referring to the method of example 1, the target compound (SIAIS249031) was prepared by using Poziotinib derivative A and intermediate LM (SIAIS151005). (yellow solid, 11.0 mg, yield 53%) H NMR (500 MHz, MeOD) δ 8.70 (s, 1H), 7.98 (d, J=3.5 Hz, 1H), 7.55 (q, J=9.0 Hz, 2H), 7.48 (t, J=7.8 Hz, 1H), 7.24 (s, 1H), 7.02 (dd, J=8.6, 3.9 Hz, 1H), 6.96 (d, J=7.1 Hz, 1H), 5.04 (dd, J=12.8, 5.3 Hz, 1H), 4.09 (d, J=6.5 Hz, 3H), 3.97-3.85 (m, 2H), 3.76 (t, J=5.4 Hz, 2H), 3.71 (t, J=5.2 Hz, 2H), 3.65 (s, 1H), 3.62-3.54 (m, 4H), 3.46 (dd, J=8.1, 5.0 Hz, 2H), 2.90-2.80 (m, 1H), 2.77-2.62 (m, 5H), 2.18-2.03 (m, 4H), 1.94 (s, 1H), 1.81 (d, J=8.9 Hz, 1H). HRMS (ESI) m/z: calcd for $C_{42}H_{45}Cl_2FN_7O_{10}^+$ [M+H]$^+$, 896.2584; found, 896.2581.

Example 52

Preparation of 4-((15-(4-((4-((3,4-dichloro-2-fluorophenyl)amino)-7-methoxyquinazolin-6-yl)oxy)piperidin-1-yl)-15-oxo-3,6,9,12-tetraoxapentadecyl)amino)-2-(2,6-dioxopiperidin-3-yl)isoindoline-1,3-dione (SIAIS249032)

Referring to the method of example 1, the target compound (SIAIS249032) was prepared by using Poziotinib derivative A and intermediate LM (SIAIS151006). (yellow solid, 11.2 mg, yield 52%) $^1$H NMR (500 MHz, MeOD) δ 8.70 (s, 1H), 8.00 (d, J=3.8 Hz, 1H), 7.58-7.54 (m, 2H), 7.54-7.47 (m, 1H), 7.25 (s, 1H), 7.07-7.02 (m, 1H), 7.03-6.96 (m, 1H), 5.03 (dd, J=12.7, 5.4 Hz, 1H), 4.09 (s, 3H), 3.97-3.87 (m, 2H), 3.76 (t, J=6.2 Hz, 2H), 3.71 (t, J=5.0 Hz, 2H), 3.62-3.56 (m, 15H), 3.46 (t, J=4.1 Hz, 2H), 2.90-2.80 (m, 1H), 2.78-2.66 (m, 4H), 2.19-2.05 (m, 3H), 1.94 (s, 1H), 1.83 (d, J=8.8 Hz, 1H). HRMS (ESI) m/z: calcd for $C_{44}H_{49}Cl_2FN_7O_{11}^+$ [M+H]$^+$, 940.2846; found, 940.2841.

Example 53

Preparation of 4-((18-(4-((4-((3,4-dichloro-2-fluorophenyl)amino)-7-methoxyquinazolin-6-yl)oxy)piperidin-1-yl)-18-oxo-3,6,9,12,15-pentaoxaoctadecyl)amino)-2-(2,6-dioxopiperidin-3-yl)isoindoline-1,3-dione (SIAIS249033)

Referring to the method of example 1, the target compound (SIAIS249033) was prepared by using Poziotinib derivative A and intermediate LM (SIAIS151007). (yellow solid, 11.4 mg, yield 50%) $^1$H NMR (500 MHz, MeOD) δ 8.69 (s, 1H), 7.98 (d, J=11.8 Hz, 1H), 7.59-7.53 (m, 2H), 7.49 (dd, J=15.6, 8.2 Hz, 1H), 7.24 (d, J=4.0 Hz, 1H), 7.04-6.95 (m, 2H), 5.03 (dd, J=12.9, 5.4, Hz, 1H), 4.08 (s, 3H), 3.89 (d, J=4.1 Hz, 2H), 3.76 (t, J=6.2 Hz, 2H), 3.71 (t, J=5.1 Hz, 2H), 3.69-3.48 (m, 19H), 3.47-3.42 (m, 2H), 2.91-2.80 (m, 1H), 2.77-2.66 (m, 4H), 2.19-2.06 (m, 3H), 1.97 (d, J=19.9 Hz, 1H), 1.84 (s, 1H). HRMS (ESI) m/z: calcd for $C_{46}H_{53}Cl_2FN_7O_{12}^+$ [M+H]$^+$, 984.3108; found, 984.3102.

Example 54

Preparation of 4-((2-(4-((4-((3,4-dichloro-2-fluorophenyl)amino)-7-methoxyquinazolin-6-yl)oxy)piperidin-1-yl)-2-oxoethyl)amino)-2-(2,6-dioxopiperidin-3-yl)isoindoline-1,3-dione (SIAIS219177)

Referring to the method of example 1, the target compound (SIAIS219177) was prepared by using Poziotinib derivative A and intermediate LM (SIAIS151025). (yellow solid, 8.6 mg, yield 50%) $^1$H NMR (500 MHz, MeOD) δ 8.71 (s, 1H), 8.05 (s, 1H), 7.63 (t, J=8.7 Hz, 2H), 7.58-7.50 (m, 3H), 7.28 (s, 1H), 5.15 (dd, J=13.2, 4.6 Hz, 1H), 4.46 (d, J=17.3 Hz, 1H), 4.40 (d, J=17.3 Hz, 1H), 4.09 (s, 3H), 3.95-3.79 (m, 2H), 3.54 (d, J=9.3 Hz, 2H), 3.36 (s, 1H), 3.11-3.04 (m, 2H), 2.94-2.84 (m, 1H), 2.77 (dd, J=15.4, 2.2 Hz, 1H), 2.58-2.46 (m, 1H), 2.42 (t, J=7.6 Hz, 2H), 2.18 (dt, J=12.8, 6.5 Hz, 1H), 2.14-2.02 (m, 2H), 1.93-1.79 (m, 2H), 1.68 (dt, J=14.7, 7.2 Hz, 2H), 1.63-1.58 (m, 2H), 1.55-1.45 (m, 2H), 1.42-1.38 (m, 2H). HRMS (ESI) m/z: calcd for $C_{35}H_{31}Cl_2FN_7O_7^+$ [M+H]$^+$, 750.1641; found, 750.1638.

Example 55

Preparation of 4-((4-(4-((4-((3,4-dichloro-2-fluorophenyl)amino)-7-methoxyquinazolin-6-yl)oxy)piperidin-1-yl)-4-oxobutyl)amino)-2-(2,6-dioxopiperidin-3-yl)isoindoline-1,3-dione (SIAIS219179)

Referring to the method of example 1, the target compound (SIAIS219179) was prepared by using Poziotinib derivative A and intermediate LM (SIAIS151019). (yellow solid, 9.2 mg, yield 51%) $^1$H NMR (500 MHz, MeOD) δ 8.71 (s, 1H), 8.05 (s, 1H), 7.63 (t, J=8.7 Hz, 2H), 7.58-7.50 (m, 3H), 7.28 (s, 1H), 5.15 (dd, J=13.2, 4.6 Hz, 1H), 4.46 (d, J=17.3 Hz, 1H), 4.40 (d, J=17.3 Hz, 1H), 4.09 (s, 3H), 3.95-3.79 (m, 2H), 3.54 (d, J=9.3 Hz, 2H), 3.36 (s, 1H), 3.11-3.04 (m, 2H), 2.94-2.84 (m, 1H), 2.77 (dd, J=15.4, 2.2 Hz, 1H), 2.58-2.46 (m, 1H), 2.42 (t, J=7.6 Hz, 2H), 2.18 (dt, J=12.8, 6.5 Hz, 1H), 2.14-2.02 (m, 2H), 1.93-1.79 (m, 2H), 1.68 (dt, J=14.7, 7.2 Hz, 2H), 1.63-1.58 (m, 2H), 1.55-1.45 (m, 2H), 1.42-1.38 (m, 2H). HRMS (ESI) m/z: calcd for $C_{37}H_{35}Cl_2FN_7O_7^+$ [M+H]$^+$, 778.1954; found, 778.1950.

Example 56

Preparation of 4-((5-(4-((4-((3,4-dichloro-2-fluorophenyl)amino)-7-methoxyquinazolin-6-yl)oxy)piperidin-1-yl)-5-oxopentyl)amino)-2-(2,6-dioxopiperidin-3-yl)isoindoline-1,3-dione (SIAIS219180)

Referring to the method of example 1, the target compound (SIAIS219180) was prepared by using Poziotinib derivative A and intermediate LM (SIAIS151020). (yellow solid, 9.7 mg, yield 53%) $^1$H NMR (500 MHz, MeOD) δ 8.71 (s, 1H), 8.05 (s, 1H), 7.63 (t, J=8.7 Hz, 2H), 7.58-7.50 (m, 3H), 7.28 (s, 1H), 5.15 (dd, J=13.2, 4.6 Hz, 1H), 4.46 (d, J=17.3 Hz, 1H), 4.40 (d, J=17.3 Hz, 1H), 4.09 (s, 3H), 3.95-3.79 (m, 2H), 3.54 (d, J=9.3 Hz, 2H), 3.36 (s, 1H), 3.11-3.04 (m, 2H), 2.94-2.84 (m, 1H), 2.77 (dd, J=15.4, 2.2 Hz, 1H), 2.58-2.46 (m, 1H), 2.42 (t, J=7.6 Hz, 2H), 2.18 (dt, J=12.8, 6.5 Hz, 1H), 2.14-2.02 (m, 2H), 1.93-1.79 (m, 2H), 1.68 (dt, J=14.7, 7.2 Hz, 2H), 1.63-1.58 (m, 2H), 1.55-1.45 (m, 2H), 1.42-1.38 (m, 2H). HRMS (ESI) m/z: calcd for $C_{38}H_{37}Cl_2FN_7O_7^+$ [M+H]$^+$, 792.2110; found, 792.2113.

Example 57

Preparation of 4-((6-(4-((4-((3,4-dichloro-2-fluorophenyl)amino)-7-methoxyquinazolin-6-yl)oxy)piperidin-1-yl)-6-oxohexyl)amino)-2-(2,6-dioxopiperidin-3-yl)isoindoline-1,3-dione (SIAIS219181)

Referring to the method of example 1, the target compound (SIAIS219181) was prepared by using Poziotinib derivative A and intermediate LM (SIAIS151027). (yellow solid, 9.3 mg, yield 50%) $^1$H NMR (500 MHz, MeOD) δ 8.71 (s, 1H), 8.05 (s, 1H), 7.63 (t, J=8.7 Hz, 2H), 7.58-7.50 (m, 3H), 7.28 (s, 1H), 5.15 (dd, J=13.2, 4.6 Hz, 1H), 4.46 (d, J=17.3 Hz, 1H), 4.40 (d, J=17.3 Hz, 1H), 4.09 (s, 3H), 3.95-3.79 (m, 2H), 3.54 (d, J=9.3 Hz, 2H), 3.36 (s, 1H), 3.11-3.04 (m, 2H), 2.94-2.84 (m, 1H), 2.77 (dd, J=15.4, 2.2 Hz, 1H), 2.58-2.46 (m, 1H), 2.42 (t, J=7.6 Hz, 2H), 2.18 (dt, J=12.8, 6.5 Hz, 1H), 2.14-2.02 (m, 2H), 1.93-1.79 (m, 2H), 1.68 (dt, J=14.7, 7.2 Hz, 2H), 1.63-1.58 (m, 2H), 1.55-1.45 (m, 2H), 1.42-1.38 (m, 2H). HRMS (ESI) m/z: calcd for $C_{39}H_{39}Cl_2FN_7O_7^+$ [M+H]$^+$, 806.2267; found, 806.2262.

Example 58

Preparation of 4-((2-(4-((4-((3,4-dichloro-2-fluorophenyl)amino)-7-methoxyquinazolin-6-yl)oxy)piperidin-1-yl)-2-oxoethyl)thio)-2-(2,6-dioxopiperidin-3-yl)isoindoline-1,3-dione (SIAIS249014)

Referring to the method of example 1, the target compound (SIAIS249014) was prepared by using Poziotinib derivative A and intermediate LM (SIAIS151045). (yellow solid, 6.7 mg, yield 38%) $^1H$ NMR (500 MHz, MeOD) δ 8.69 (s, 1H), 8.06 (s, 1H), 7.87 (d, J=8.1 Hz, 1H), 7.75 (t, J=7.7 Hz, 1H), 7.67 (d, J=7.3 Hz, 1H), 7.58-7.52 (m, 2H), 7.29 (s, 1H), 5.13 (dd, J=12.7, 5.5 Hz, 1H), 4.20 (s, 2H), 4.10 (s, 3H), 4.00-3.87 (m, 2H), 3.73-3.60 (m, 2H), 3.33 (s, 1H), 2.89-2.85 (m, 1H), 2.78-2.69 (m, 2H), 2.29-2.20 (m, 1H), 2.17-1.99 (m, 3H), 1.88-1.83 (m, 1H). HRMS (ESI) m/z: calcd for $C_{35}H_{30}Cl_2FN_6O_7S^+$ $[M+H]^+$, 767.1252; found, 767.1250.

Example 59

Preparation of 4-((3-(4-((4-((3,4-dichloro-2-fluorophenyl)amino)-7-methoxyquinazolin-6-yl)oxy)piperidin-1-yl)-3-oxopropyl)thio)-2-(2,6-dioxopiperidin-3-yl)isoindoline-1,3-dione (SIAIS249015)

Referring to the method of example 1, the target compound (SIAIS249015) was prepared by using Poziotinib derivative A and intermediate LM (SIAIS151138B). (yellow solid, 6.9 mg, yield 38%) $^1H$ NMR (500 MHz, MeOD) δ 8.70 (s, 1H), 8.05 (s, 1H), 7.76 (d, J=6.0 Hz, 2H), 7.66-7.61 (m, 1H), 7.58-7.52 (m, 2H), 7.28 (s, 1H), 5.12 (dd, J=9.0, 3.7 Hz, 1H), 4.09 (s, 3H), 3.94-3.87 (m, 1H), 3.82 (d, J=3.8 Hz, 1H), 3.66-3.59 (m, 1H), 3.59-3.50 (m, 1H), 3.43 (t, J=7.0 Hz, 2H), 3.33 (s, 1H), 2.91 (t, J=6.9 Hz, 2H), 2.89-2.81 (m, 1H), 2.76-2.72 (m, 2H), 2.16-2.05 (m, 3H), 1.92-1.82 (m, 2H). HRMS (ESI) m/z: calcd for $C_{36}H_{32}Cl_2FN_6O_7S^+$ $[M+H]^+$, 781.1409; found, 781.1405.

Example 60

Preparation of 4-((4-(4-((4-((3,4-dichloro-2-fluorophenyl)amino)-7-methoxyquinazolin-6-yl)oxy)piperidin-1-yl)-4-oxobutyl)thio)-2-(2,6-dioxopiperidin-3-yl)isoindoline-1,3-dione (SIAIS249016)

Referring to the method of example 1, the target compound (SIAIS249016) was prepared by using Poziotinib derivative A and intermediate LM (SIAIS151139B). (yellow solid, 5.7 mg, yield 31%) $^1H$ NMR (500 MHz, MeOD) δ 8.71 (d, J=1.9 Hz, 1H), 8.03 (d, J=2.8 Hz, 1H), 7.83 (d, J=8.2 Hz, 1H), 7.75 (t, J=7.7 Hz, 1H), 7.60 (t, J=7.5 Hz, 1H), 7.56-7.52 (m, 2H), 7.29 (s, 1H), 5.11 (dd, J=8.7, 3.9 Hz, 1H), 5.08 (dd, J=8.8, 4.0 Hz, 1H), 4.10 (s, 3H), 3.94 (d, J=12.9 Hz, 1H), 3.83 (s, 1H), 3.58-3.54 (m, 2H), 3.28-3.15 (m, 2H), 2.92-2.82 (m, 1H), 2.80-2.61 (m, 4H), 2.19-2.01 (m, 5H), 1.84 (s, 2H). HRMS (ESI) m/z: calcd for $C_{37}H_{34}Cl_2FN_6O_7S^+$ $[M+H]^+$, 795.1565; found, 795.1561.

Example 61

Preparation of 4-((5-(4-((4-((3,4-dichloro-2-fluorophenyl)amino)-7-methoxyquinazolin-6-yl)oxy)piperidin-1-yl)-5-oxopentyl)thio)-2-(2,6-dioxopiperidin-3-yl)isoindoline-1,3-dione (SIAIS249017)

Referring to the method of example 1, the target compound (SIAIS249017) was prepared by using Poziotinib derivative A and intermediate LM (SIAIS151140B). (yellow solid, 8.5 mg, yield 46%) $^1H$ NMR (500 MHz, MeOD) δ 8.70 (s, 1H), 8.04 (s, 1H), 7.76-7.71 (m, 2H), 7.60 (dd, J=6.0, 1.8 Hz, 1H), 7.58-7.51 (m, 2H), 7.28 (s, 1H), 5.10 (dd, J=12.6, 5.5 Hz, 1H), 4.10 (s, 3H), 3.95-3.83 (m, 2H), 3.63-3.53 (m, 2H), 3.33 (s, 1H), 3.18 (t, J=6.5 Hz, 2H), 2.92-2.79 (m, 1H), 2.78-2.64 (m, 2H), 2.53 (t, J=6.8 Hz, 2H), 2.22-2.02 (m, 4H), 1.92 (d, J=17.1 Hz, 1H), 1.85-1.82 (m, 4H). HRMS (ESI) m/z: calcd for $C_{38}H_{36}Cl_2FN_6O_7S^+$ $[M+H]^+$, 809.1722; found, 809.1720.

Example 62

Preparation of 4-((6-(4-((4-((3,4-dichloro-2-fluorophenyl)amino)-7-methoxyquinazolin-6-yl)oxy)piperidin-1-yl)-6-oxohexyl)thio)-2-(2,6-dioxopiperidin-3-yl)isoindoline-1,3-dione (SIAIS249018)

Referring to the method of example 1, the target compound (SIAIS249018) was prepared by using Poziotinib derivative A and intermediate LM (SIAIS151141B). (yellow solid, 6.5 mg, yield 34%) $^1H$ NMR (500 MHz, MeOD) δ 8.70 (s, 1H), 8.03 (s, 1H), 7.75-7.69 (m, 2H), 7.59 (d, J=6.6 Hz, 1H), 7.58-7.53 (m, 2H), 7.28 (s, 1H), 5.12-5.08 (m, 1H), 4.10 (s, 3H), 3.95-3.83 (m, 2H), 3.61-3.52 (m, 2H), 3.29-3.25 (m, 1H), 3.15 (t, J=7.2 Hz, 2H), 2.87-2.82 (m, 1H), 2.77-2.69 (m, 2H), 2.48 (t, J=7.4 Hz, 2H), 2.18-2.00 (m, 4H), 1.92 (d, J=18.2 Hz, 1H), 1.83-1.79 (m, 2H), 1.71-1.67 (m, 2H), 1.62-1.57 (m, 2H). HRMS (ESI) m/z: calcd for $C_{39}H_{38}Cl_2FN_6O_7S^+$ $[M+H]^+$, 823.1878; found, 823.1870.

Example 63

Preparation of 4-((7-(4-((4-((3,4-dichloro-2-fluorophenyl)amino)-7-methoxyquinazolin-6-yl)oxy)piperidin-1-yl)-7-oxoheptyl)thio)-2-(2,6-dioxopiperidin-3-yl)isoindoline-1,3-dione (SIAIS249019)

Referring to the method of example 1, the target compound (SIAIS249019) was prepared by using Poziotinib derivative A and intermediate LM (SIAIS151142B). (yellow solid, 9.0 mg, yield 47%) $^1H$ NMR (500 MHz, MeOD) δ 8.70 (s, 1H), 8.03 (s, 1H), 7.75-7.68 (m, 3H), 7.58 (d, J=7.3 Hz, 1H), 7.55 (s, 1H), 7.28 (s, 1H), 5.12-5.09 (m, 1H), 4.09 (s, 3H), 3.92-3.88 (m, 2H), 3.60-3.53 (m, 2H), 3.15-3.11 (m, 3H), 2.91-2.80 (m, 2H), 2.75-2.68 (m, 2H), 2.48-2.44 (m, 2H), 2.30 (t, J=7.4 Hz, 1H), 2.18-2.03 (m, 4H), 1.91 (s, 1H), 1.79-1.75 (m, 2H), 1.68-1.63 (m, 2H), 1.59-1.55 (m, 2H), 1.47-1.43 (m, 2H). HRMS (ESI) m/z: calcd for $C_{40}H_{40}Cl_2FN_6O_7S^+$ $[M+H]^+$, 837.2035; found, 837.2031.

Example 64

Preparation of 3-(4-((2-(4-((4-((3,4-dichloro-2-fluorophenyl)amino)-7-methoxyquinazolin-6-yl)oxy)piperidin-1-yl)-2-oxoethyl)thio)-1-oxoisoindolin-2-yl)piperidine-2,6-dione (SIAIS219164)

Referring to the method of example 1, the target compound (SIAIS219164) was prepared by using Poziotinib derivative A and intermediate LM (SIAIS17109). (yellow solid, 8.4 mg, yield 48%) $^1H$ NMR (500 MHz, MeOD) δ 8.69 (s, 1H), 8.02 (d, J=2.3 Hz, 1H), 7.80 (dd, J=7.7, 2.1 Hz, 1H), 7.74 (d, J=7.5 Hz, 1H), 7.55 (q, J=8.9 Hz, 3H), 7.27 (s, 1H), 5.20-5.15 (m, 1H), 4.57 (dd, J=17.5, 2.7 Hz, 1H), 4.50 (dd, J=17.3, 3.7 Hz, 1H), 4.10 (s, 3H), 4.00 (t, J=9.9 Hz, 2H), 3.85-3.81 (m, 2H), 3.62-3.51 (m, 2H), 3.35 (s, 1H), 2.97-

2.87 (m, 1H), 2.78 (d, J=17.5 Hz, 1H), 2.55-2.51 (m, 1H), 2.23-2.16 (m, 1H), 2.06 (s, 2H), 1.88-1.84 (m, 2H). HRMS (ESI) m/z: calcd for $C_{35}H_{32}Cl_2FN_6O_6S^+$ [M+H]$^+$, 753.1460; found, 753.1455.

Example 65

Preparation of 3-(4-((3-(4-((4-((3,4-dichloro-2-fluorophenyl)amino)-7-methoxyquinazolin-6-yl)oxy)piperidin-1-yl)-3-oxopropyl)thio)-1-oxoisoindolin-2-yl)piperidine-2,6-dione (SIAIS219165)

Referring to the method of example 1, the target compound (SIAIS219165) was prepared by using Poziotinib derivative A and intermediate LM (SIAIS171086). (yellow solid, 9.4 mg, yield 53%) $^1$H NMR (500 MHz, MeOD) δ 8.70 (s, 1H), 8.01 (d, J=3.1 Hz, 1H), 7.75-7.70 (m, 1H), 7.68 (d, J=7.5 Hz, 1H), 7.58-7.53 (m, 3H), 7.27 (s, 1H), 5.17 (dd, J=13.2, 5.0 Hz, 1H), 4.49 (d, J=16.9 Hz, 1H), 4.44 (d, J=16.8 Hz, 1H), 4.09 (s, 3H), 3.88 (s, 1H), 3.78-3.75 (m, 1H), 3.57-3.53 (m, 1H), 3.46 (d, J=10.0 Hz, 1H), 3.40-3.33 (m, 3H), 2.94-2.86 (m, 1H), 2.81-2.76 (m, 3H), 2.60-2.47 (m, 1H), 2.23-2.15 (m, 1H), 2.05 (s, 2H), 1.83 (s, 2H). HRMS (ESI) m/z: calcd for $C_{36}H_{34}Cl_2FN_6O_6S^+$ [M+H]$^+$, 767.1616; found, 767.1611.

Example 66

Preparation of 3-(4-((4-(4-((4-((3,4-dichloro-2-fluorophenyl)amino)-7-methoxyquinazolin-6-yl)oxy)piperidin-1-yl)-4-oxobutyl)thio)-1-oxoisoindolin-2-yl)piperidine-2,6-dione (SIAIS219166)

Referring to the method of example 1, the target compound (SIAIS219166) was prepared by using Poziotinib derivative A and intermediate LM (SIAIS171089). (yellow solid, 9.7 mg, yield 54%) $^1$H NMR (500 MHz, MeOD) δ 8.71 (d, J=2.4 Hz, 1H), 7.99 (d, J=4.3 Hz, 1H), 7.71 (d, J=8.3 Hz, 1H), 7.69-7.63 (m, 1H), 7.60-7.53 (m, 3H), 7.27 (d, J=3.4 Hz, 1H), 5.13 (dd, J=14.7, 5.1 Hz, 1H), 4.48 (d, J=12.8 Hz, 1H), 4.42 (d, J=12.8 Hz, 1H), 4.10 (d, J=1.6 Hz, 3H), 3.88 (s, 1H), 3.73 (t, J=20.2 Hz, 1H), 3.58-3.41 (m, 2H), 3.18-3.15 (m, 3H), 2.95-2.84 (m, 1H), 2.81-2.74 (m, 1H), 2.64-2.50 (m, 3H), 2.19-2.15 (m, 1H), 2.05-1.94 (m, 4H), 1.81 (s, 2H). HRMS (ESI) m/z: calcd for $C_{37}H_{36}Cl_2FN_6O_6S^+$ [M+H]$^+$, 781.1773; found, 781.1770.

Example 67

Preparation of 3-(4-((5-(4-((4-((3,4-dichloro-2-fluorophenyl)amino)-7-methoxyquinazolin-6-yl)oxy)piperidin-1-yl)-5-oxopentyl)thio)-1-oxoisoindolin-2-yl)piperidine-2,6-dione (SIAIS219167)

Referring to the method of example 1, the target compound (SIAIS219167) was prepared by using Poziotinib derivative A and intermediate LM (SIAIS171079). (yellow solid, 9.2 mg, yield 50%) $^1$H NMR (500 MHz, MeOD) δ 8.71 (s, 1H), 8.01 (d, J=6.7 Hz, 1H), 7.65 (dd, J=14.9, 6.9 Hz, 2H), 7.58-7.54 (m, 3H), 7.28 (s, 1H), 5.14 (dd, J=13.4, 5.1 Hz, 1H), 4.48 (d, J=17.3 Hz, 1H), 4.41 (d, J=17.3 Hz, 1H), 4.10 (s, 3H), 3.92-3.76 (m, 2H), 3.59-3.47 (m, 2H), 3.34 (s, 1H), 3.19-3.04 (m, 2H), 2.94-2.82 (m, 1H), 2.81-2.77 (m, 1H), 2.57-2.42 (m, 3H), 2.22-2.14 (m, 1H), 2.08-1.72 (m, 8H). HRMS (ESI) m/z: calcd for $C_{38}H_{38}Cl_2FN_6O_6S^+$ [M+H]$^+$, 795.1929; found, 795.1925.

Example 68

Preparation of 3-(4-((6-(4-((4-((3,4-dichloro-2-fluorophenyl)amino)-7-methoxyquinazolin-6-yl)oxy)piperidin-1-yl)-6-oxohexyl)thio)-1-oxoisoindolin-2-yl)piperidine-2,6-dione (SIAIS219168)

Referring to the method of example 1, the target compound (SIAIS219168) was prepared by using Poziotinib derivative A and intermediate LM (SIAIS171091). (yellow solid, 10.1 mg, yield 54%) $^1$H NMR (500 MHz, MeOD) δ 8.71 (s, 1H), 8.04 (s, 1H), 7.68-7.62 (m, 2H), 7.59-7.50 (m, 3H), 7.28 (s, 1H), 5.18-5.11 (m, 1H), 4.47 (d, J=17.3 Hz, 1H), 4.41 (d, J=17.4 Hz, 1H), 4.09 (s, 3H), 3.87-3.81 (m, 2H), 3.53-3.50 (m, 2H), 3.33 (s, 1H), 3.12-3.04 (m, 2H), 2.93-2.83 (m, 1H), 2.79-2.75 (m, 1H), 2.55-2.50 (m, 1H), 2.41 (t, J=7.3 Hz, 2H), 2.23-2.14 (m, 1H), 2.07 (s, 2H), 1.87-1.81 (m, 2H), 1.69-1.65 (m, 4H), 1.55-1.49 (m, 2H). HRMS (ESI) m/z: calcd for $C_{39}H_{40}Cl_2FN_6O_6S^+$ [M+H]$^+$, 809.2086; found, 809.2084.

Example 69

Preparation of 3-(4-((7-(4-((4-((3,4-dichloro-2-fluorophenyl)amino)-7-methoxyquinazolin-6-yl)oxy)piperidin-1-yl)-7-oxoheptyl)thio)-1-oxoisoindolin-2-yl)piperidine-2,6-dione (SIAIS219169)

Referring to the method of example 1, the target compound (SIAIS219169) was prepared by using Poziotinib derivative A and intermediate LM (SIAIS171092). (yellow solid, 9.8 mg, yield 52%) $^1$H NMR (500 MHz, MeOD) δ 8.71 (s, 1H), 8.05 (s, 1H), 7.63 (t, J=8.7 Hz, 2H), 7.58-7.50 (m, 3H), 7.28 (s, 1H), 5.15 (dd, J=13.2, 4.6 Hz, 1H), 4.46 (d, J=17.3 Hz, 1H), 4.40 (d, J=17.3 Hz, 1H), 4.09 (s, 3H), 3.95-3.79 (m, 2H), 3.54 (d, J=9.3 Hz, 2H), 3.36 (s, 1H), 3.11-3.04 (m, 2H), 2.94-2.84 (m, 1H), 2.77 (dd, J=15.4, 2.2 Hz, 1H), 2.58-2.46 (m, 1H), 2.42 (t, J=7.6 Hz, 2H), 2.18 (dt, J=12.8, 6.5 Hz, 1H), 2.14-2.02 (m, 2H), 1.93-1.79 (m, 2H), 1.68 (dt, J=14.7, 7.2 Hz, 2H), 1.63-1.58 (m, 2H), 1.55-1.45 (m, 2H), 1.42-1.38 (m, 2H). HRMS (ESI) m/z: calcd for $C_{40}H_{41}Cl_2FN_6O_6S^+$ [M+H]$^+$, 823.2242; found, 823.2238.

Example 70

Preparation of (2S,4R)-1-((S)-2-(2-(2-(2-(4-((4-((3,4-dichloro-2-fluorophenyl)amino)-7-methoxyquinazolin-6-yl)oxy)piperidin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide (SIAIS249024)

Referring to the method of example 1, the target compound (SIAIS249024) was prepared by using Poziotinib derivative A and intermediate LM (SIAIS151010). (white solid, 11.2 mg, yield 48%) $^1$H NMR (500 MHz, MeOD) δ 9.65 (s, 1H), 8.70 (s, 1H), 8.16 (d, J=18.4 Hz, 1H), 7.56-7.48 (m, 6H), 7.29 (d, J=4.3 Hz, 1H), 4.96 (s, 1H), 4.69 (s, 1H), 4.56 (dd, J=19.5, 11.0 Hz, 2H), 4.49 (s, 2H), 4.44-4.35 (m, 3H), 4.23-4.05 (m, 6H), 3.94-3.74 (m, 8H), 3.57 (d, J=7.5 Hz, 2H), 2.59-2.56 (m, 1H), 2.55 (s, 3H), 2.28-2.16 (m, 2H), 2.13-2.02 (m, 2H), 1.89-1.84 (m, 2H), 1.03 (s, 9H). HRMS (ESI) m/z: calcd for $C_{48}H_{56}Cl_2FN_8O_9S^+$ [M+H]$^+$, 1009.3247; found, 1009.3243.

Example 71

Preparation of (2S,4R)-1-((S)-2-(3-(2-(3-(4-((4-((3,4-dichloro-2-fluorophenyl)amino)-7-methoxyquinazolin-6-yl)oxy)piperidin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide (SIAIS249025)

Referring to the method of example 1, the target compound (SIAIS249025) was prepared by using Poziotinib derivative A and intermediate LM (SIAIS151002). (white solid, 12.1 mg, yield 51%) $^1$H NMR (500 MHz, MeOD) δ 9.50 (s, 1H), 8.70 (s, 1H), 8.14 (d, J=3.5 Hz, 1H), 7.55-7.46 (m, 6H), 7.30 (s, 1H), 4.96 (d, J=3.3 Hz, 1H), 4.64 (s, 1H), 4.56 (dd, J=18.3, 11.0 Hz, 3H), 4.49 (s, 1H), 4.38 (d, J=15.7 Hz, 1H), 4.09 (s, 3H), 3.92 (dd, J=33.3, 9.7 Hz, 3H), 3.78-3.73 (m, 6H), 3.65-3.50 (m, 8H), 2.73 (dd, J=13.3, 6.6 Hz, 2H), 2.61-2.49 (m, 6H), 2.24-2.18 (m, 2H), 2.15-2.03 (m, 2H), 1.97-1.77 (m, 2H), 1.03 (s, 9H). HRMS (ESI) m/z: calcd for $C_{50}H_{60}Cl_2FN_8O_9S^+$ $[M+H]^+$, 1037.3560; found, 1037.3555.

Example 72

Preparation of (2S,4R)-1-((S)-2-(tert-butyl)-16-(4-((4-((3,4-dichloro-2-fluorophenyl)amino)-7-methoxyquinazolin-6-yl)oxy)piperidin-1-yl)-4,16-dioxo-7,10,13-trioxa-3-azahexadecan-1-oyl)-4-hydroxy-N-(4-(4-methylthiazol-5-yl)benzyl)pyrrolidine-2-carboxamide (SIAIS249026)

Referring to the method of example 1, the target compound (SIAIS249026) was prepared by using Poziotinib derivative A and intermediate LM (SIAIS151003). (white solid, 12.4 mg, yield 50%) $^1$H NMR (500 MHz, MeOD) δ 9.47 (s, 1H), 8.71 (s, 1H), 8.14 (s, 1H), 7.55-7.46 (m, 6H), 7.30 (s, 1H), 4.95 (s, 1H), 4.64 (s, 1H), 4.60-4.51 (m, 3H), 4.49 (s, 1H), 4.38 (d, J=15.7 Hz, 1H), 4.09 (s, 3H), 3.96 (d, J=3.9 Hz, 1H), 3.89 (d, J=10.9 Hz, 2H), 3.82-3.70 (m, 6H), 3.67-3.57 (m, 12H), 2.77-2.69 (m, 2H), 2.61-2.48 (m, 6H), 2.25-2.15 (m, 2H), 2.14-2.05 (m, 2H), 1.91-1.86 (m, 2H), 1.03 (s, 9H). HRMS (ESI) m/z: calcd for $C_{52}H_{64}Cl_2FN_8O_{10}S^+$ $[M+H]^+$, 1081.3822; found, 1081.3820.

Example 73

Preparation of (2S,4R)-1-((S)-2-(tert-butyl)-19-(4-((4-((3,4-dichloro-2-fluorophenyl)amino)-7-methoxyquinazolin-6-yl)oxy)piperidin-1-yl)-4,19-dioxo-7,10,13,16-tetraoxa-3-azanonadecan-1-oyl)-4-hydroxy-N-(4-(4-methylthiazol-5-yl)benzyl)pyrrolidine-2-carboxamide (SIAIS249027)

Referring to the method of example 1, the target compound (SIAIS249027) was prepared by using Poziotinib derivative A and intermediate LM (SIAIS151008). (white solid, 12.1 mg, yield 47%) $^1$H NMR (500 MHz, MeOD) δ 9.53 (s, 1H), 8.71 (s, 1H), 8.15 (s, 1H), 7.55-7.46 (m, 6H), 7.31 (s, 1H), 4.99-4.93 (m, 1H), 4.64 (s, 1H), 4.60-4.52 (m, 2H), 4.49 (s, 1H), 4.38 (d, J=15.7 Hz, 1H), 4.09 (s, 3H), 3.98 (s, 1H), 3.88 (d, J=10.7 Hz, 2H), 3.82-3.70 (m, 6H), 3.62 (d, J=6.3 Hz, 16H), 2.78-2.65 (m, 2H), 2.62-2.53 (m, 5H), 2.51-2.45 (m, 1H), 2.28-2.15 (m, 2H), 2.15-2.05 (m, 2H), 1.98-1.78 (m, 2H), 1.03 (s, 9H). HRMS (ESI) m/z: calcd for $C_{54}H_{68}Cl_2FN_8O_{11}S^+$ $[M+H]^+$, 1125.4084; found, 1125.4081.

Example 74

Preparation of (2S,4R)-1-((S)-2-(tert-butyl)-22-(4-((4-((3,4-dichloro-2-fluorophenyl)amino)-7-methoxyquinazolin-6-yl)oxy)piperidin-1-yl)-4,22-dioxo-7,10,13,16,19-pentaoxa-3-azadocosan-1-oyl)-4-hydroxy-N-(4-(4-methylthiazol-5-yl)benzyl)pyrrolidine-2-carboxamide (SIAIS249028)

Referring to the method of example 1, the target compound (SIAIS249028) was prepared by using Poziotinib derivative A and intermediate LM (SIAIS151009). (white solid, 13.1 mg, yield 49%) $^1$H NMR (500 MHz, MeOD) δ 9.23 (s, 1H), 8.71 (s, 1H), 8.16 (s, 1H), 7.57-7.43 (m, 6H), 7.31 (s, 1H), 5.00-4.94 (m, 1H), 4.64 (s, 1H), 4.61-4.47 (m, 4H), 4.37 (d, J=15.6 Hz, 1H), 4.10 (d, J=9.6 Hz, 3H), 4.01-3.95 (m, 1H), 3.88 (d, J=11.0 Hz, 2H), 3.83-3.70 (m, 6H), 3.66-3.56 (m, 22H), 2.75-2.69 (m, 2H), 2.61-2.54 (m, 1H), 2.52-2.45 (m, 5H), 2.24-2.16 (m, 2H), 2.09-2.04 (m, 2H), 1.96-1.90 (m, 1H), 1.84-1.79 (m, 1H). HRMS (ESI) m/z: calcd for $C_{56}H_{72}Cl_2FN_8O_{12}S^+$ $[M+H]^+$, 1169.4346; found, 1169.4341.

Example 75

Preparation of (2S,4R)-1-((S)-2-(4-(4-((4-((3,4-dichloro-2-fluorophenyl)amino)-7-methoxyquinazolin-6-yl)oxy)piperidin-1-yl)-4-oxobutanamido)-3,3-dimethylbutanoyl)-4-hydroxy-N-(4-(4-methylthiazol-5-yl)benzyl)pyrrolidine-2-carboxamide (SIAIS249020)

Referring to the method of example 1, the target compound (SIAIS249020) was prepared by using Poziotinib derivative A and intermediate LM (SIAIS074011). (white solid, 7.7 mg, yield 35%) $^1$H NMR (500 MHz, MeOD) δ 9.24 (d, J=3.2 Hz, 1H), 8.71 (d, J=2.6 Hz, 1H), 8.05 (s, 1H), 7.58-7.54 (m, 2H), 7.50 (d, J=8.2 Hz, 2H), 7.45 (d, J=8.2 Hz, 2H), 7.28 (s, 1H), 4.91 (s, 1H), 4.61 (d, J=2.0 Hz, 1H), 4.56 (dd, J=18.6, 10.6 Hz, 2H), 4.49 (s, 1H), 4.38 (d, J=15.5 Hz, 1H), 4.09 (t, J=5.2 Hz, 3H), 3.89 (d, J=10.2 Hz, 3H), 3.80 (dd, J=11.0, 3.9 Hz, 1H), 3.59 (d, J=9.8 Hz, 2H), 2.79-2.70 (m, 2H), 2.69-2.61 (m, 1H), 2.57 (dd, J=14.1, 7.4 Hz, 1H), 2.52 (d, J=8.1 Hz, 3H), 2.26-2.14 (m, 2H), 2.12-2.05 (m, 2H), 1.94 (s, 1H), 1.84 (s, 1H), 1.04 (s, 9H). HRMS (ESI) m/z: calcd for $C_{46}H_{52}Cl_2FN_8O_7S^+$ $[M+H]^+$, 949.3035; found, 949.3032.

Example 76

Preparation of (2S,4R)-1-((S)-2-(6-(4-((4-((3,4-dichloro-2-fluorophenyl)amino)-7-methoxyquinazolin-6-yl)oxy)piperidin-1-yl)-6-oxohexanamido)-3,3-dimethylbutanoyl)-4-hydroxy-N-(4-(4-methylthiazol-5-yl)benzyl)pyrrolidine-2-carboxamide (SIAIS249021)

Referring to the method of example 1, the target compound (SIAIS249021) was prepared by using Poziotinib derivative A and intermediate LM (SIAIS074013). (white solid, 8.1 mg, yield 36%) $^1$H NMR (500 MHz, MeOD) δ 9.32 (s, 1H), 8.71 (s, 1H), 8.05 (s, 1H), 7.58-7.53 (m, 2H), 7.50 (d, J=8.4 Hz, 2H), 7.46 (dd, J=10.9, 5.8 Hz, 2H), 7.28

(s, 1H), 4.91 (s, 1H), 4.63 (d, J=3.9 Hz, 1H), 4.60-4.52 (m, 2H), 4.49 (s, 1H), 4.37 (d, J=15.6 Hz, 1H), 4.09 (s, 3H), 3.90 (d, J=11.1 Hz, 3H), 3.80 (dd, J=10.9, 3.9 Hz, 1H), 3.62-3.53 (m, 2H), 2.53 (d, J=9.0 Hz, 3H), 2.48 (d, J=6.7 Hz, 2H), 2.38-2.32 (m, 2H), 2.23-2.18 (m, 2H), 2.09-2.06 (m, 2H), 1.90 (d, J=51.0 Hz, 2H), 1.69-1.64 (m, 4H), 1.04 (s, 9H). HRMS (ESI) m/z: calcd for $C_{48}H_{56}Cl_2FN_8O_7S^+$ [M+H]$^+$, 977.3348; found, 977.3343.

Example 77

Preparation of (2S,4R)-1-((S)-2-(8-(4-((4-((3,4-dichloro-2-fluorophenyl)amino)-7-methoxyquinazolin-6-yl)oxy)piperidin-1-yl)-8-oxooctanamido)-3,3-dimethylbutanoyl)-4-hydroxy-N-(4-(4-methylthiazol-5-yl)benzyl)pyrrolidine-2-carboxamide (SIAIS249022)

Referring to the method of example 1, the target compound (SIAIS249022) was prepared by using Poziotinib derivative A and intermediate LM (SIAIS074015). (white solid, 9.7 mg, yield 42%) $^1$H NMR (500 MHz, MeOD) δ 9.36 (s, 1H), 8.71 (s, 1H), 8.07 (s, 1H), 7.58-7.53 (m, 2H), 7.53-7.49 (m, 2H), 7.46 (t, J=6.5 Hz, 2H), 7.28 (s, 1H), 4.92 (s, 1H), 4.63 (s, 1H), 4.60-4.47 (m, 3H), 4.38 (d, J=15.6 Hz, 1H), 4.09 (s, 3H), 3.90 (q, J=17.7 Hz, 3H), 3.80 (dd, J=11.0, 3.9 Hz, 1H), 3.57 (dd, J=11.1, 6.7 Hz, 2H), 2.52 (s, 3H), 2.47-2.42 (m, 2H), 2.34-2.14 (m, 4H), 2.12-2.05 (m, 2H), 1.96-1.80 (m, 2H), 1.69-1.60 (m, 4H), 1.43-1.35 (m, 4H), 1.03 (s, 9H). HRMS (ESI) m/z: calcd for $C_{50}H_{60}Cl_2FN_8O_7S^+$ [M+H]$^+$, 1005.3661; found, 1005.3656.

Example 78

Preparation of (2S,4R)-1-((S)-2-(10-(4-((4-((3,4-dichloro-2-fluorophenyl)amino)-7-methoxyquinazolin-6-yl)oxy)piperidin-1-yl)-10-oxodecanamido)-3,3-dimethylbutanoyl)-4-hydroxy-N-(4-(4-methylthiazol-5-yl)benzyl)pyrrolidine-2-carboxamide (SIAIS249023)

Referring to the method of example 1, the target compound (SIAIS249023) was prepared by using Poziotinib derivative A and intermediate LM (SIAIS074019). (white solid, 10.8 mg, yield 45%) $^1$H NMR (500 MHz, MeOD) δ 9.31 (s, 1H), 8.71 (s, 1H), 8.08 (d, J=3.8 Hz, 1H), 7.59-7.54 (m, 2H), 7.51 (q, J=5.6 Hz, 2H), 7.46 (t, J=7.0 Hz, 2H), 7.29 (s, 1H), 4.92 (dd, J=6.9, 3.5 Hz, 1H), 4.64 (s, 1H), 4.61-4.48 (m, 3H), 4.42-4.35 (m, 1H), 4.10 (s, 3H), 3.95-3.84 (m, 3H), 3.80 (dd, J=10.9, 3.8 Hz, 1H), 3.62-3.52 (m, 2H), 2.56-2.52 (m, 3H), 2.49-2.41 (m, 2H), 2.33-2.15 (m, 4H), 2.11-2.07 (m, 2H), 1.94-1.77 (m, 2H), 1.61 (d, J=6.2 Hz, 4H), 1.35 (s, 8H), 1.03 (s, 9H). HRMS (ESI) m/z: calcd for $C_{52}H_{64}Cl_2FN_8O_7S^+$ [M+H]$^+$, 1033.3974; found, 1033.3971.

Example 79

Preparation of 4-((2-(4-(3-((4-((3-chloro-4-fluorophenyl)amino)-7-methoxyquinazolin-6-yl)oxy)propyl)piperazin-1-yl)-2-oxoethyl)thio)-2-(2,6-dioxopiperidin-3-yl)isoindoline-1,3-dione (SIAIS184164)

Referring to the method of example 1, the target compound (SIAIS184164) was prepared by using Gefitinib derivative A and intermediate LM (SIAIS151045). (yellow solid, 6.9 mg, yield 40%) $^1$H NMR (500 MHz, MeOD) δ 8.74 (s, 1H), 8.08 (d, J=3.5 Hz, 1H), 8.00-7.96 (m, 1H), 7.96 (s, 1H), 7.80-7.75 (m, 1H), 7.73 (s, 1H), 7.72-7.67 (m, 1H), 7.38 (t, J=8.9 Hz, 1H), 7.27 (s, 1H), 5.14 (dd, J=12.6, 5.6 Hz, 1H), 4.42 (d, J=5.6 Hz, 2H), 4.10 (t, J=3.4 Hz, 3H), 3.74 (s, 2H), 3.50 (s, 2H), 3.29-2.95 (m, 8H), 2.89-2.82 (m, 1H), 2.76-2.71 (m, 2H), 2.45 (s, 2H), 2.15 (s, 1H). HRMS (ESI) m/z: calcd for $C_{37}H_{36}ClFN_7O_7S^+$ [M+H]$^+$, 776.2064; found, 776.2061.

Example 80

Preparation of 4-((4-(4-(3-((4-((3-chloro-4-fluorophenyl)amino)-7-methoxyquinazolin-6-yl)oxy)propyl)piperazin-1-yl)-4-oxobutyl)thio)-2-(2,6-dioxopiperidin-3-yl)isoindoline-1,3-dione (SIAIS184165)

Referring to the method of example 1, the target compound (SIAIS184165) was prepared by using Gefitinib derivative A and intermediate LM (SIAIS151139B). (yellow solid, 7.8 mg, yield 43%) $^1$H NMR (500 MHz, MeOD) δ 8.73 (s, 1H), 8.09 (s, 1H), 7.98 (dd, J=6.6, 2.6 Hz, 1H), 7.82 (d, J=8.0 Hz, 1H), 7.77-7.74 (m, 1H), 7.70 (ddd, J=9.0, 4.1, 2.6 Hz, 1H), 7.62 (d, J=7.0 Hz, 1H), 7.37 (t, J=8.9 Hz, 1H), 7.26 (s, 1H), 5.11 (dd, J=12.6, 5.4 Hz, 1H), 4.42 (t, J=5.6 Hz, 2H), 4.09 (s, 3H), 3.82-3.58 (m, 2H), 3.49 (t, J=7.5 Hz, 2H), 3.30-3.20 (m, 8H), 2.88-2.82 (m, 1H), 2.75-2.64 (m, 4H), 2.49-2.41 (m, 2H), 2.17-2.06 (m, 3H). HRMS (ESI) m/z: calcd for $C_{39}H_{40}ClFN_7O_7S^+$ [M+H]$^+$, 804.2377; found, 804.2374.

Example 81

Preparation of 4-((6-(4-(3-((4-((3-chloro-4-fluorophenyl)amino)-7-methoxyquinazolin-6-yl)oxy)propyl)piperazin-1-yl)-6-oxohexyl)thio)-2-(2,6-dioxopiperidin-3-yl)isoindoline-1,3-dione (SIAIS184166)

Referring to the method of example 1, the target compound (SIAIS184166) was prepared by using Gefitinib derivative A and intermediate LM (SIAIS151141B). (yellow solid, 9.5 mg, yield 51%) H NMR (500 MHz, MeOD) δ 8.74 (s, 1H), 8.11 (s, 1H), 7.98 (dd, J=6.6, 2.6 Hz, 1H), 7.75-7.68 (m, 3H), 7.59 (dd, J=6.7, 1.3 Hz, 1H), 7.37 (t, J=8.9 Hz, 1H), 7.26 (s, 1H), 5.11 (dd, J=12.7, 5.5 Hz, 1H), 4.43 (t, J=5.5 Hz, 2H), 4.09 (s, 3H), 3.73 (d, J=40.0 Hz, 2H), 3.50 (t, J=7.3 Hz, 2H), 3.31-3.01 (m, 8H), 2.89-2.83 (m, 1H), 2.78-2.67 (m, 2H), 2.48-2.43 (m, 4H), 2.18-2.09 (m, 1H), 1.86-1.78 (m, 2H), 1.77-1.67 (m, 2H), 1.61-1.58 (m, 2H). HRMS (ESI) m/z: calcd for $C_{41}H_{44}ClFN_7O_7S^+$ [M+H]$^+$, 832.2690; found, 832.2687.

Example 82

Preparation of 4-((2-(2-(4-(3-((4-((3-chloro-4-fluorophenyl)amino)-7-methoxyquinazolin-6-yl)oxy)propyl)piperazin-1-yl)-2-oxoethoxy)ethyl)thio)-2-(2,6-dioxopiperidin-3-yl)isoindoline-1,3-dione (SIAIS184168)

Referring to the method of example 1, the target compound (SIAIS184168) was prepared by using Gefitinib derivative A and intermediate LM (SIAIS1204137). (yellow solid, 8.2 mg, yield 45%) $^1$H NMR (500 MHz, MeOD) δ 8.73 (s, 1H), 8.05 (s, 1H), 8.02-7.97 (m, 1H), 7.71 (dd, J=10.3, 3.7 Hz, 3H), 7.57 (s, 1H), 7.39-7.35 (m, 1H), 7.22 (s, 1H), 5.08 (dd, J=12.6, 5.4 Hz, 1H), 4.45-4.41 (m, 4H), 4.08 (s, 3H), 3.93-3.90 (m, 2H), 3.56-3.53 (m, 4H), 3.38-3.34 (m, 8H), 2.84-2.75 (m, 1H), 2.69-2.65 (m, 2H), 2.46 (s, 2H), 2.11 (d, J=5.2 Hz, 1H). HRMS (ESI) m/z: calcd for $C_{39}H_{40}ClFN_7O_8S^+$ [M+H]$^+$, 820.2326; found, 820.2321.

Example 83

Preparation of 4-((2-(2-(2-(2-(4-(3-((4-((3-chloro-4-fluorophenyl)amino)-7-methoxyquinazolin-6-yl)oxy)propyl)piperazin-1-yl)-2-oxoethoxy)ethoxy)ethoxy)ethyl)thio)-2-(2,6-dioxopiperidin-3-yl)isoindoline-1,3-dione (SIAIS184169)

Referring to the method of example 1, the target compound (SIAIS184169) was prepared by using Gefitinib derivative A and intermediate LM (SIAIS1204141). (yellow solid, 9.1 mg, yield 45%) $^1$H NMR (500 MHz, MeOD) δ 8.71 (s, 1H), 8.01-7.95 (m, 2H), 7.73-7.67 (m, 2H), 7.64 (s, 1H), 7.48 (dd, J=6.0, 2.0 Hz, 1H), 7.37 (dd, J=8.9, 3.4 Hz, 1H), 7.20 (s, 1H), 5.12-5.08 (m, 1H), 4.41-4.37 (m, 2H), 4.37-4.25 (m, 2H), 4.07 (s, 3H), 3.84 (t, J=6.0 Hz, 2H), 3.72-3.61 (m, 14H), 3.56-3.47 (m, 4H), 3.05 (s, 1H), 2.89-2.83 (m, 1H), 2.78-2.60 (m, 3H), 2.45 (s, 2H), 2.15-2.08 (m, 1H). HRMS (ESI) m/z: calcd for $C_{43}H_{48}ClFN_7O_{10}S^+$ [M+H]$^+$, 908.2850; found, 908.2846.

Example 84

Preparation of 4-((17-(4-(3-((4-((3-chloro-4-fluorophenyl)amino)-7-methoxyquinazolin-6-yl)oxy)propyl)piperazin-1-yl)-17-oxo-3,6,9,12,15-pentaoxaheptadecyl)thio)-2-(2,6-dioxopiperidin-3-yl)isoindoline-1,3-dione (SIAIS184170)

Referring to the method of example 1, the target compound (SIAIS184170) was prepared by using Gefitinib derivative A and intermediate LM (SIAIS1204149). (yellow solid, 9.2 mg, yield 41%) $^1$H NMR (500 MHz, MeOD) δ 8.72 (s, 1H), 8.06 (s, 1H), 7.98 (dt, J=6.0, 3.0 Hz, 1H), 7.73-7.70 (m, 1H), 7.68 (dd, J=7.1, 4.7 Hz, 2H), 7.56-7.51 (m, 1H), 7.39-7.33 (m, 1H), 7.23 (s, 1H), 5.10 (dd, J=12.7, 5.5 Hz, 1H), 4.41 (dd, J=11.5, 5.9 Hz, 2H), 4.39-4.27 (m, 2H), 4.08 (s, 3H), 3.80 (t, J=6.1 Hz, 2H), 3.69-3.60 (m, 18H), 3.57-3.41 (m, 4H), 3.37-3.32 (m, 2H), 3.29 (s, 2H), 3.26-3.04 (m, 2H), 2.89-2.83 (m, 1H), 2.79-2.63 (m, 2H), 2.50-2.42 (m, 2H), 2.17-2.09 (m, 1H). HRMS (ESI) m/z: calcd for $C_{47}H_{56}ClFN_7O_{12}S^+$ [M+H]$^+$, 996.3375; found, 996.3371.

Example 85

Preparation of 3-(4-((2-(4-(3-((4-((3-chloro-4-fluorophenyl)amino)-7-methoxyquinazolin-6-yl)oxy)propyl)piperazin-1-yl)-2-oxoethyl)thio)-1-oxoisoindolin-2-yl)piperidine-2,6-dione (SIAIS184184)

Referring to the method of example 1, the target compound (SIAIS184184) was prepared by using Gefitinib derivative A and intermediate LM (SIAIS171090). (yellow solid, 6.7 mg, yield 39%) $^1$H NMR (500 MHz, MeOD) δ 8.44 (s, 1H), 8.00 (dd, J=6.7, 2.5 Hz, 1H), 7.78 (d, J=7.8 Hz, 1H), 7.75-7.73 (m, 2H), 7.69-7.64 (m, 1H), 7.55 (t, J=7.6 Hz, 1H), 7.26 (t, J=8.9 Hz, 1H), 7.18 (s, 1H), 5.17 (dd, J=13.3, 5.1 Hz, 1H), 4.55 (d, J=17.6 Hz, 1H), 4.48 (d, J=17.3 Hz, 1H), 4.25 (d, J=6.0 Hz, 2H), 4.00 (s, 3H), 3.57 (d, J=5.4 Hz, 2H), 3.53 (d, J=3.7 Hz, 2H), 3.35-3.30 (m, 8H), 2.92-2.88 (m, 1H), 2.81-2.76 (m, 1H), 2.58-2.51 (m, 1H), 2.21-2.17 (m, 1H), 2.08 (d, J=7.2 Hz, 2H). HRMS (ESI) m/z: calcd for $C_{37}H_{38}ClFN_7O_6S^+$ [M+H]$^+$, 762.2271; found, 762.2268.

Example 86

Preparation of 3-(4-((4-(4-(3-((4-((3-chloro-4-fluorophenyl)amino)-7-methoxyquinazolin-6-yl)oxy)propyl)piperazin-1-yl)-4-oxobutyl)thio)-1-oxoisoindolin-2-yl)piperidine-2,6-dione (SIAIS184185)

Referring to the method of example 1, the target compound (SIAIS184185) was prepared by using Gefitinib derivative A and intermediate LM (SIAIS171089). (yellow solid, 7.2 mg, yield 41%) $^1$H NMR (500 MHz, MeOD) δ 8.46 (s, 1H), 8.02-7.98 (m, 1H), 7.75 (s, 1H), 7.68 (dd, J=19.3, 7.6 Hz, 3H), 7.54 (t, J=7.7 Hz, 1H), 7.27 (t, J=8.9 Hz, 1H), 7.19 (s, 1H), 5.18-5.14 (m, 1H), 4.48 (d, J=17.3 Hz, 1H), 4.42 (d, J=17.2 Hz, 1H), 4.25 (t, J=5.8 Hz, 2H), 4.01 (s, 31H), 3.69-3.65 (m, 2H), 3.60-3.36 (m, 8H), 3.15-3.10 (m, 2H), 2.89-2.84 (m, 1H), 2.79-2.75 (m, 1H), 2.65 (s, 2H), 2.55 (d, J=7.0 Hz, 1H), 2.19 (s, 1H), 2.11 (s, 2H), 1.95 (t, J=7.1 Hz, 2H). HRMS (ESI) m/z: calcd for $C_{39}H_{42}ClFN_7O_6S^+$ [M+H]$^+$, 790.2584; found, 790.2581.

Example 87

Preparation of 3-(4-((6-(4-(3-((4-((3-chloro-4-fluorophenyl)amino)-7-methoxyquinazolin-6-yl)oxy)propyl)piperazin-1-yl)-6-oxohexyl)thio)-1-oxoisoindolin-2-yl)piperidine-2,6-dione (SIAIS184186)

Referring to the method of example 1, the target compound (SIAIS184186) was prepared by using Gefitinib derivative A and intermediate LM (SIAIS171091). (yellow solid, 8.2 mg, yield 45%) $^1$H NMR (500 MHz, MeOD) δ 8.45 (s, 1H), 8.00 (d, J=6.7 Hz, 1H), 7.74 (s, 1H), 7.65 (dd, J=19.0, 8.2 Hz, 3H), 7.52 (t, J=7.7 Hz, 1H), 7.26 (t, J=8.9 Hz, 1H), 7.18 (s, 1H), 5.17-5.13 (m, 1H), 4.46 (d, J=17.6 Hz, 1H), 4.40 (d, J=17.2 Hz, 1H), 4.24 (t, J=5.9 Hz, 2H), 4.00 (s, 3H), 3.79-3.65 (m, 2H), 3.63-3.33 (m, 8H), 3.07 (d, J=3.5 Hz, 2H), 2.92-2.86 (m, 1H), 2.79-2.75 (m, 1H), 2.60 (t, J=7.3 Hz, 2H), 2.38 (d, J=7.2 Hz, 1H), 2.22-2.08 (m, 3H), 1.71-1.67 (m, 2H), 1.65-1.59 (m, 2H), 1.58-1.49 (m, 2H). HRMS (ESI) m/z: calcd for $C_{41}H_{46}ClFN_7O_6S^+$ [M+H]$^+$, 818.2897; found, 818.2893.

Example 88

Preparation of 3-(4-((2-(4-(1-(3-((4-((3-chloro-4-fluorophenyl)amino)-7-methoxyquinazolin-6-yl)oxy)propyl)piperidin-4-yl)piperazin-1-yl)-2-oxoethyl)thio)-1-oxoisoindolin-2-yl)piperidine-2,6-dione (SIAIS262085)

Referring to the method of example 1, the target compound (SIAIS262085) was prepared by using Gefitinib derivative B and intermediate LM (SIAIS171090). (yellow solid, 10.1 mg, yield 43%) $^1$H NMR (500 MHz, MeOD) δ 8.74 (s, 1H), 8.12 (s, 1H), 7.98 (dd, J=6.6, 2.6 Hz, 1H), 7.83 (d, J=7.7 Hz, 1H), 7.78 (d, J=7.5 Hz, 1H), 7.75-7.68 (m, 1H), 7.58 (t, J=7.7 Hz, 1H), 7.37 (t, J=8.9 Hz, 1H), 7.26 (s, 1H), 5.18 (dd, J=13.4, 5.1 Hz, 1H), 4.57 (d, J=17.5 Hz, 1H), 4.50 (dd, J=14.7, 4.1 Hz, 1H), 4.43 (t, J=5.5 Hz, 2H), 4.11 (s, 3H), 3.99-3.91 (m, 5H), 3.58-3.52 (m, 4H), 3.30-3.13 (m, 8H), 2.94-2.87 (m, 1H), 2.81-2.77 (m, 1H), 2.61-2.51 (m, 1H), 2.45 (s, 3H), 2.29-2.14 (m, 4H). HRMS (ESI) m/z: calcd for $C_{42}H_{47}ClFN_8O_6S^+$ [M+H]$^+$, 845.3006; found, 845.3001, Example 89

Preparation of 3-(4-((5-(4-(1-(3-((4-((3-chloro-4-fluorophenyl)amino)-7-methoxyquinazolin-6-yl)oxy)propyl)piperidin-4-yl)piperazin-1-yl)-5-oxopentyl)thio)-1-oxoisoindolin-2-yl)piperidine-2,6-dione (SIAIS262086)

Referring to the method of example 1, the target compound (SIAIS262086) was prepared by using Gefitinib derivative B and intermediate LM (SIAIS171079). (yellow solid, 11.2 mg, yield 45%) $^1$H NMR (500 MHz, MeOD) δ 8.74 (s, 1H), 8.11 (s, 1H), 7.98 (dd, J=6.6, 2.6 Hz, 1H), 7.75-7.68 (m, 1H), 7.66 (t, J=7.0 Hz, 2H), 7.54 (t, J=7.7 Hz, 1H), 7.37 (t, J=8.9 Hz, 1H), 7.26 (s, 1H), 5.17 (dd, J=13.3, 5.1 Hz, 1H), 4.48 (d, J=17.3 Hz, 1H), 4.46-4.39 (m, 3H), 4.11 (s, 3H), 3.92 (d, J=12.6 Hz, 2H), 3.60 (s, 2H), 3.45-3.41 (m, 5H), 3.18-3.11 (m, 8H), 2.94-2.89 (m, 1H), 2.81-2.76 (m, 1H), 2.57-2.43 (m, 7H), 2.24-2.18 (m, 3H), 1.79-1.71 (m, 4H). HRMS (ESI) m/z: calcd for $C_{45}H_{53}ClFN_8O_6S^+$ [M+H]$^+$, 887.3476; found, 887.3471.

Example 90

Preparation of 3-(4-((6-(4-(1-(3-((4-((3-chloro-4-fluorophenyl)amino)-7-methoxyquinazolin-6-yl)oxy)propyl)piperidin-4-yl)piperazin-1-yl)-6-oxohexyl)thio)-1-oxoisoindolin-2-yl)piperidine-2,6-dione (SIAIS262087)

Referring to the method of example 1, the target compound (SIAIS262087) was prepared by using Gefitinib derivative B and intermediate LM (SIAIS171091). (yellow solid, 11.3 mg, yield 45%) $^1$H NMR (500 MHz, MeOD) δ 8.74 (s, 1H), 8.02 (s, 1H), 7.96-7.93 (m, 1H), 7.69-7.64 (m, 3H), 7.54 (t, J=7.7 Hz, 1H), 7.37 (t, J=8.9 Hz, 1H), 7.27 (s, 1H), 5.17 (dd, J=13.3, 5.2 Hz, 1H), 4.48 (d, J=17.4 Hz, 1H), 4.42 (d, J=14.3 Hz, 1H), 4.39 (t, J=3.9 Hz, 2H), 4.10 (s, 3H), 3.85 (d, J=49.3 Hz, 6H), 3.45 (d, J=7.2 Hz, 2H), 3.30-3.12 (m, 6H), 3.11-3.02 (m, 2H), 2.96-2.86 (m, 1H), 2.82-2.77 (m, 1H), 2.59-2.50 (m, 1H), 2.49-2.36 (m, 6H), 2.22-2.13 (m, 3H), 1.71-1.58 (m, 4H), 1.55-1.51 (m, 2H). HRMS (ESI) m/z: calcd for $C_{46}H_{55}ClFN_8O_6S^+$ [M+H]$^+$, 901.3632; found, 901.3632.

Example 91

Preparation of N-(4-((3-chloro-4-fluorophenyl)amino)-7-(((S)-tetrahydrofuran-3-yl)oxy)quinazolin-6-yl)-2-((2-(2,6-dioxopiperidin-3-yl)-1,3-dioxoisoindolin-4-yl)thio)acetamide (SIAIS184093)

Referring to the method of example 1, the target compound (SIAIS184093) was prepared by using Afatinib derivative A and intermediate LM (SIAIS151045). (white solid, 12.2 mg, yield 43%) $^1$H NMR (500 MHz, MeOD) δ 9.16 (s, 1H), 8.72 (s, 1H), 7.90 (dd, J=6.6, 2.6 Hz, 1H), 7.80 (d, J=7.9 Hz, 1H), 7.75 (t, J=7.6 Hz, 1H), 7.68 (d, J=7.2 Hz, 1H), 7.66-7.60 (m, 1H), 7.36 (t, J=8.9 Hz, 1H), 7.21 (s, 11H), 5.29 (s, 1H), 5.16 (dd, J=12.5, 5.5 Hz, 1H), 4.26 (s, 2H), 4.02 (qd, J=10.7, 4.1 Hz, 2H), 3.89-3.82 (m, 2H), 2.92-2.85 (m, 1H), 2.79-2.70 (m, 2H), 2.37 (dd, J=14.0, 8.0 Hz, 1H), 2.14 (dd, J=13.1, 6.1 Hz, 2H). HRMS (ESI) m/z: calcd for $C_{33}H_{27}ClFN_6O_7S^+$ [M+H]$^+$, 705.1329; found, 705.1326.

Example 92

Preparation of N-(4-((3-chloro-4-fluorophenyl)amino)-7-(((S)-tetrahydrofuran-3-yl)oxy)quinazolin-6-yl)-4-((2-(2,6-dioxopiperidin-3-yl)-1,3-dioxoisoindolin-4-yl)thio)butanamide (SIAIS184094)

Referring to the method of example 1, the target compound (SIAIS184094) was prepared by using Afatinib derivative A and intermediate LM (SIAIS151139B). (white solid, 13.6 mg, yield 46%) $^1$H NMR (500 MHz, MeOD) δ 9.07 (s, 1H), 8.73 (s, 1H), 7.94 (dd, J=6.6, 2.4 Hz, 1H), 7.79 (d, J=8.3 Hz, 1H), 7.74 (t, J=7.6 Hz, 1H), 7.68-7.63 (m, 1H), 7.62 (d, J=7.0 Hz, 1H), 7.37 (t, J=8.9 Hz, 1H), 7.22 (s, 11H), 5.32 (s, 1H), 5.08 (dd, J=12.7, 5.3 Hz, 1H), 4.18 (d, J=10.3 Hz, 1H), 4.04 (dd, J=13.3, 7.3 Hz, 2H), 3.91 (dt, J=13.2, 6.6 Hz, 1H), 2.85-2.78 (m, 3H), 2.76-2.66 (m, 2H), 2.48-242 (m, 1H), 2.29 (s, 1H), 2.25-2.17 (m, 2H), 2.10 (s, 1H). HRMS (ESI) m/z: calcd for $C_{35}H_{31}ClFN_6O_7S^+$ [M+H]$^+$, 733.1642; found, 733.1640.

Example 93

Preparation of N-(4-((3-chloro-4-fluorophenyl)amino)-7-(((S)-tetrahydrofuran-3-yl)oxy)quinazolin-6-yl)-6-((2-(2,6-dioxopiperidin-3-yl)-1,3-dioxoisoindolin-4-yl)thio)hexanamide (SIAIS184095)

Referring to the method of example 1, the target compound (SIAIS184095) was prepared by using Afatinib derivative A and intermediate LM (SIAIS151141B). (white solid, 14.1 mg, yield 46%) $^1$H NMR (500 MHz, MeOD) δ 9.05 (s, 1H), 8.72 (s, 1H), 7.93 (dd, J=6.6, 2.6 Hz, 1H), 7.71-7.67 (m, 2H), 7.67-7.64 (m, 1H), 7.56-7.52 (m, 1H), 7.37 (t, J=8.9 Hz, 1H), 7.23 (s, 1H), 5.33 (d, J=4.6 Hz, 1H), 5.09 (dd, J=12.8, 5.4 Hz, 1H), 4.19 (d, J=10.6 Hz, 1H), 4.11-4.02 (m, 2H), 3.94-3.88 (m, 1H), 3.16 (t, J=7.0 Hz, 2H), 2.87-2.83 (m, 1H), 2.77-2.66 (m, 2H), 2.64-2.59 (m, 2H), 2.47-2.43 (m, 1H), 2.33-2.24 (m, 1H), 2.15-2.08 (m, 1H), 1.87-1.82 (m, 4H), 1.69-1.64 (m, 2H). HRMS (ESI) m/z: calcd for $C_{37}H_{35}ClFN_6O_7S^+$ [M+H]$^+$, 761.1955; found, 761.1952.

Example 94

Preparation of N-(4-((3-chloro-4-fluorophenyl)amino)-7-(((S)-tetrahydrofuran-3-yl)oxy)quinazolin-6-yl)-2-(2-((2-(2,6-dioxopiperidin-3-yl)-1,3-dioxoisoindolin-4-yl)thio)ethoxy)acetamide (SIAIS184152)

Referring to the method of example 1, the target compound (SIAIS184152) was prepared by using Afatinib derivative A and intermediate LM (SIAIS1204137). (white solid, 8.8 mg, yield 44%) $^1$H NMR (500 MHz, $CDCl_3$) δ 9.34 (d, J=5.8 Hz, 2H), 9.08 (s, 1H), 8.73 (d, J=24.1 Hz, 1H), 8.64 (s, 1H), 7.97 (s, 1H), 7.86 (s, 1H), 7.55 (s, 3H), 7.42 (d, J=10.7 Hz, 1H), 7.21 (t, J=8.4 Hz, 1H), 5.31 (s, 1H), 4.97 (s, 1H), 4.18-4.12 (m, 2H), 4.06 (s, 2H), 3.93-3.74 (m, 2H), 3.29 (s, 2H), 2.85-2.78 (m, 3H), 2.63-2.57 (m, 1H), 2.21-2.15 (m, 3H), 1.47-1.42 (m, 1H). HRMS (ESI) m/z: calcd for $C_{35}H_{31}ClFN_6O_8S^+$ [M+H]$^+$, 749.1591; found, 749.1588.

Example 95

Preparation of N-(4-((3-chloro-4-fluorophenyl)amino)-7-(((S)-tetrahydrofuran-3-yl)oxy)quinazolin-6-yl)-2-(2-(2-((2-(2,6-dioxopiperidin-3-yl)-1,3-dioxoisoindolin-4-yl)thio)ethoxy)ethoxy)acetamide (SIAIS184153)

Referring to the method of example 1, the target compound (SIAIS184153) was prepared by using Afatinib derivative A and intermediate LM (SIAIS1204139). (white solid, 10.5 mg, yield 50%) $^1$H NMR (500 MHz, $CDCl_3$) δ 9.33 (d, J=5.8 Hz, 2H), 9.07 (s, 1H), 8.71 (d, J=24.1 Hz, 1H), 8.62 (s, 1H), 7.96 (s, 1H), 7.85 (s, 1H), 7.53 (s, 3H), 7.40 (d, J=10.7 Hz, 1H), 7.20 (t, J=8.4 Hz, 1H), 5.29 (s, 1H), 4.96 (s, 1H), 4.14 (d, J=15.7 Hz, 2H), 4.04 (s, 2H), 3.90-3.72 (m, 6H), 3.28 (s, 2H), 2.83-2.78 (m, 3H), 2.61-2.55 (m, 1H), 2.19-2.14 (m, 3H), 1.45-1.40 (m, 1H). HRMS (ESI) m/z: calcd for $C_{37}H_{35}ClFN_6O_9S^+$ $[M+H]^+$, 793.1853; found, 793.1851.

Example 96

Preparation of N-(4-((3-chloro-4-fluorophenyl)amino)-7-(((S)-tetrahydrofuran-3-yl)oxy)quinazolin-6-yl)-2-(2-(2-(2-((2-(2,6-dioxopiperidin-3-yl)-1,3-dioxoisoindolin-4-yl)thio)ethoxy)ethoxy)ethoxy)acetamide (SIAIS184154)

Referring to the method of example 1, the target compound (SIAIS184154) was prepared by using Afatinib derivative A and intermediate LM (SIAIS1204141). (white solid, 9.9 mg, yield 44%) $^1$H NMR (500 MHz, $CDCl_3$) δ 9.78 (s, 1H), 9.41 (d, J=2.7 Hz, 1H), 9.20 (s, 1H), 9.09 (s, 1H), 8.57 (s, 1H), 8.02 (s, 1H), 7.86-7.77 (m, 1H), 7.61-7.49 (m, 2H), 7.46-7.43 (m, 2H), 7.17 (dd, J=14.7, 8.5 Hz, 1H), 5.25 (s, 1H), 5.05-4.93 (m, 1H), 4.23 (s, 2H), 4.09 (dd, J=31.1, 9.7 Hz, 2H), 3.94-3.74 (m, 8H), 3.69 (d, J=8.8 Hz, 4H), 3.21 (s, 2H), 2.88-2.83 (m, 1H), 2.83-2.72 (m, 2H), 2.54 (s, 1H), 2.17-2.12 (m, 2H). HRMS (ESI) m/z: calcd for $C_{39}H_{39}ClFN_6O_{10}S^+$ $[M+H]^+$, 837.2115; found, 837.2112.

Example 97

Preparation of N-(4-((3-chloro-4-fluorophenyl)amino)-7-(((S)-tetrahydrofuran-3-yl)oxy)quinazolin-6-yl)-14-((2-(2,6-dioxopiperidin-3-yl)-1,3-dioxoisoindolin-4-yl)thio)-3,6,9,12-tetraoxatetradecan-1-amide (SIAIS184155)

Referring to the method of example 1, the target compound (SIAIS184155) was prepared by using Afatinib derivative A and intermediate LM (SIAIS1204147). (white solid, 9.8 mg, yield 42%) $^1$H NMR (500 MHz, $CDCl_3$) δ 9.66 (s, 1H), 9.41 (s, 1H), 9.23 (s, 1H), 9.09 (s, 1H), 8.59 (s, 1H), 8.05 (s, 1H), 7.83 (s, 1H), 7.57 (d, J=4.7 Hz, 2H), 7.53-7.46 (m, 2H), 7.18 (td, J=8.6, 3.9 Hz, 1H), 5.25 (s, 1H), 5.04-4.93 (m, 1H), 4.24 (s, 2H), 4.09 (dd, J=24.2, 12.7 Hz, 2H), 3.95-3.76 (m, 8H), 3.71-3.64 (m, 8H), 3.24 (s, 2H), 2.88-2.84 (m, 1H), 2.83-2.71 (m, 2H), 2.53 (s, 1H), 2.19-2.14 (m, 2H). HRMS (ESI) m/z: calcd for $C_{41}H_{43}ClFN_6O_{11}S^+$ $[M+H]^+$, 881.2378; found, 881.2375.

Example 98

Preparation of N-(4-((3-chloro-4-fluorophenyl)amino)-7-(((S)-tetrahydrofuran-3-yl)oxy)quinazolin-6-yl)-17-((2-(2,6-dioxopiperidin-3-yl)-1,3-dioxoisoindolin-4-yl)thio)-3,6,9,12,15-pentaoxaheptadecan-1-amide (SIAIS184156)

Referring to the method of example 1, the target compound (SIAIS184156) was prepared by using Afatinib derivative A and intermediate LM (SIAIS1204149). (white solid, 10.2 mg, yield 41%) $^1$H NMR (500 MHz, $CDCl_3$) δ 9.66 (s, 1H), 9.41 (s, 1H), 9.33 (s, 1H), 9.13 (s, 1H), 8.59 (s, 1H), 8.02 (s, 1H), 7.82 (d, J=5.2 Hz, 1H), 7.66-7.49 (m, 4H), 7.15 (t, J=8.6 Hz, 1H), 5.26 (s, 1H), 5.05-4.93 (m, 1H), 4.24 (s, 2H), 4.09-4.03 (m, 2H), 3.91-3.72 (m, 8H), 3.70-3.59 (m, 12H), 3.24 (d, J=5.7 Hz, 2H), 2.90-2.78 (m, 2H), 2.54 (s, 1H), 2.18-2.13 (m, 2H). HRMS (ESI) m/z: calcd for $C_{43}H_{47}ClFN_6O_{12}S^+$ $[M+H]^+$, 925.2640; found, 925.2636.

Example 99

Preparation of N-(4-((3-chloro-4-fluorophenyl)amino)-7-(((S)-tetrahydrofuran-3-yl)oxy)quinazolin-6-yl)-3-((2-(2,6-dioxopiperidin-3-yl)-1-oxoisoindolin-4-yl)thio)propanamide (SIAIS1210085)

Referring to the method of example 1, the target compound (SIAIS1210085) was prepared by using Afatinib derivative A and intermediate LM (SIAIS171086). (yellow solid, 9.9 mg, yield 53%) $^1$H NMR (500 MHz, MeOD) δ 9.02 (s, 1H), 8.70 (s, 1H), 7.91 (dd, J=6.6, 2.5 Hz, 1H), 7.67 (t, J=6.7 Hz, 1H), 7.63-7.60 (m, 2H), 7.54-7.50 (m, 1H), 7.33 (dd, J=11.1, 6.7 Hz, 1H), 7.23 (s, 1H), 5.35-5.30 (m, 1H), 5.17-5.13 (m, 1H), 4.45 (d, J=17.2 Hz, 1H), 4.41 (d, J=17.2 Hz, 1H), 4.14 (dd, J=10.5, 4.0 Hz, 1H), 4.05-4.01 (m, 2H), 3.91-3.88 (m, 1H), 3.18 (t, J=7.2 Hz, 2H), 2.95-2.83 (m, 2H), 2.77-2.74 (m, 2H), 2.51-2.46 (m, 2H), 2.29-2.21 (m, 1H), 2.17-2.12 (m, 1H). HRMS (ESI) m/z: calcd for $C_{34}H_{31}ClFN_6O_6S^+$ $[M+H]^+$, 705.1693; found, 705.1691.

Example 100

Preparation of N-(4-((3-chloro-4-fluorophenyl)amino)-7-(((S)-tetrahydrofuran-3-yl)oxy)quinazolin-6-yl)-4-((2-(2,6-dioxopiperidin-3-yl)-1-oxoisoindolin-4-yl)thio)butanamide (SIAIS1210087)

Referring to the method of example 1, the target compound (SIAIS1210087) was prepared by using Afatinib derivative A and intermediate LM (SIAIS171089). (yellow solid, 10.3 mg, yield 54%) $^1$H NMR (500 MHz, MeOD) δ 9.04 (s, 1H), 8.71 (s, 1H), 7.93 (dd, J=6.6, 2.5 Hz, 1H), 7.69 (t, J=6.7 Hz, 1H), 7.65-7.62 (m, 2H), 7.56-7.50 (m, 1H), 7.35 (dd, J=11.1, 6.7 Hz, 1H), 7.24 (s, 1H), 5.36-5.31 (m, 1H), 5.18-5.14 (m, 1H), 4.46 (d, J=17.2 Hz, 1H), 4.42 (d, J=17.2 Hz, 1H), 4.16 (dd, J=10.5, 4.0 Hz, 1H), 4.06-4.01 (m, 2H), 3.93-3.90 (m, 1H), 3.20 (t, J=7.2 Hz, 2H), 2.96-2.84 (m, 2H), 2.78-2.75 (m, 2H), 2.52-2.47 (m, 2H), 2.30-2.22 (m, 1H), 2.19-2.14 (m, 1H), 2.13-2.07 (m, 2H). HRMS (ESI) m/z: calcd for $C_{35}H_{33}ClFN_6O_6S^+$ $[M+H]^+$, 719.1849; found, 719.1846.

Example 101

Preparation of N-(4-((3-chloro-4-fluorophenyl)amino)-7-(((S)-tetrahydrofuran-3-yl)oxy)quinazolin-6-yl)-6-((2-(2,6-dioxopiperidin-3-yl)-1-oxoisoindolin-4-yl)thio)hexanamide (SIAIS1210089)

Referring to the method of example 1, the target compound (SIAIS1210089) was prepared by using Afatinib derivative A and intermediate LM (SIAIS171091). (yellow solid, 11.1 mg, yield 56%) $^1$H NMR (500 MHz, MeOD) δ 8.95 (d, J=8.6 Hz, 1H), 8.68 (s, 1H), 7.95 (dd, J=6.6, 2.6 Hz, 1H), 7.67-7.62 (m, 2H), 7.58 (dd, J=6.8, 5.4 Hz, 1H), 7.48 (dd, J=10.0, 4.5 Hz, 1H), 7.34 (dd, J=9.2, 8.6 Hz, 1H), 7.22 (d, J=1.0 Hz, 1H), 5.31 (d, J=4.6 Hz, 1H), 5.16 (dd, J=9.5, 3.9 Hz, 1H), 4.46-4.41 (m, 1H), 4.38 (d, J=17.3 Hz, 1H), 4.17 (t, J=10.6 Hz, 1H), 4.08-4.00 (m, 2H), 3.92-3.88 (m, 1H), 3.09 (dt, J=7.0, 4.5 Hz, 2H), 2.91-2.87 (m, 1H), 2.79-2.73 (m, 1H), 2.57-2.53 (m, 2H), 2.51-2.46 (m, 2H), 2.27-2.23 (m, 1H), 2.21-2.11 (m, 1H), 1.80-1.70 (m, 4H), 1.62-1.57 (m, 2H). HRMS (ESI) m/z: calcd for $C_{37}H_{37}ClFN_6O_6S^+$ [M+H]$^+$, 747.2162; found, 747.2161.

Example 102

Preparation of (E)-N-(4-((3-chloro-4-fluorophenyl) amino)-7-methoxyquinazolin-6-yl)-4-(4-(4-(5-(2-(2, 6-dioxopiperidin-3-yl)-1-oxoisoindolin-4-yl)pent-4-yn-1-yl)piperazin-1-yl)piperidin-1-yl)but-2-enamide (SIAIS262050)

According to Scheme 9, to a solution of Dacomitinib derivative B (20 mg, 0.036 mmol) dissolved in 2 mL of DMF was sequentially added SIAIS255121 (17.5 mg, 0.0432 mmol), NaI (10.8 mg, 0.072 mmol), and $K_2CO_3$ (10 mg, 0.072 mmol), and the reaction mixture was heated to 50° C. and reacted overnight. The reaction was quenched with 0.10 mL of water. The resulting mixture was subjected to preparative HPLC (eluent (v/v): acetonitrile/(water+0.05% HCl)=10%-100%) for separation, and the collected fractions were rotary evaporated under reduced pressure to remove the acetonitrile and most of the water. The resulting residue was lyophilized to give the final target compound (SIAIS262050). (yellow solid, 12.1 mg, yield 39%) $^1$H NMR (500 MHz, MeOD) δ 9.26 (s, 1H), 8.74 (s, 1H), 7.91 (dd, J=6.6, 2.6 Hz, 1H), 7.74 (d, J=7.4 Hz, 1H), 7.67-7.62 (m, 2H), 7.50 (t, J=7.6 Hz, 1H), 7.36 (t, J=8.9 Hz, 1H), 7.32 (s, 1H), 7.11-7.02 (m, 1H), 6.86 (d, J=15.5 Hz, 1H), 5.20 (dd, J=13.2, 5.2 Hz, 1H), 4.57 (d, J=17.6 Hz, 1H), 4.51 (d, J=17.6 Hz, 1H), 4.19 (s, 3H), 4.06 (s, 2H), 3.72 (s, 5H), 3.60-3.37 (m, 8H), 3.16 (d, J=13.9 Hz, 2H), 2.97-2.88 (m, 1H), 2.77 (d, J=15.6 Hz, 1H), 2.63-2.58 (m, 3H), 2.38 (s, 2H), 2.24-2.16 (m, 1H), 2.11-1.99 (m, 2H), 1.77-1.71 (n, 2H). HRMS (ESI) m/z: calcd for $C_{46}H_{50}ClFN_9O_5^+$ [M+H]$^+$, 862.3602; found, 862.3601.

Example 103

Preparation of (E)-N-(4-((3-chloro-4-fluorophenyl) amino)-7-methoxyquinazolin-6-yl)-4-(4-(4-(6-(2-(2, 6-dioxopiperidin-3-yl)-1-oxoisoindolin-4-yl)hex-5-yn-1-yl)piperazin-1-yl)piperidin-1-yl)but-2-enamide (SIAIS262051)

Referring to the method of example 102, the target compound (SIAIS262051) was prepared by using Dacomitinib derivative B and intermediate LM (SIAIS255119). (yellow solid, 12.8 mg, yield 41%) $^1$H NMR (500 MHz, MeOD) δ 9.27 (s, 1H), 8.76 (s, 1H), 7.93 (dd, J=6.6, 2.6 Hz, 1H), 7.75 (d, J=7.4 Hz, 1H), 7.68-7.62 (m, 2H), 7.51 (t, J=7.6 Hz, 1H), 7.38 (t, J=8.9 Hz, 1H), 7.33 (s, 1H), 7.10-7.02 (m, 1H), 6.87 (d, J=15.5 Hz, 1H), 5.21 (dd, J=13.2, 5.2 Hz, 1H), 4.58 (d, J=17.6 Hz, 1H), 4.52 (d, J=17.6 Hz, 1H), 4.19 (s, 3H), 4.08 (s, 2H), 3.74 (s, 5H), 3.61-3.37 (m, 8H), 3.18 (d, J=13.9 Hz, 2H), 2.98-2.88 (m, 1H), 2.79 (d, J=15.6 Hz, 1H), 2.63-2.59 (m, 3H), 2.39 (s, 2H), 2.25-2.16 (m, 1H), 2.12-1.99 (m, 4H), 1.79-1.71 (m, 2H). HRMS (ESI) m/z: calcd for $C_{47}H_{52}ClFN_9O_5^+$ [M+H]$^+$, 876.3758; found, 876.3755.

Example 104

Preparation of 3-(4-(5-(4-(1-(3-((4-((3-chloro-4-fluorophenyl)amino)-7-methoxyquinazolin-6-yl)oxy) propyl)piperidin-4-yl)piperazin-1-yl)pent-1-yn-1-yl)-1-oxoisoindolin-2-yl)piperidine-2,6-dione (SIAIS262089)

Referring to the method of example 102, the target compound (SIAIS262089) was prepared by using Gefitinib derivative B and intermediate LM (SIAIS255121). (yellow solid, 13.1 mg, yield 41%) $^1$H NMR (500 MHz, MeOD) δ 8.74 (s, 1H), 8.12 (s, 1H), 7.98 (s, 1H), 7.77 (d, J=8.0 Hz, 1H), 7.70 (s, 1H), 7.65 (d, J=7.2 Hz, 1H), 7.53 (d, J=7.5 Hz, 1H), 7.37 (t, J=8.5 Hz, 1H), 7.26 (s, 1H), 5.20 (d, J=7.1 Hz, 1H), 4.56 (s, 1H), 4.51 (d, J=17.5 Hz, 1H), 4.42 (s, 2H), 4.10 (s, 3H), 3.83 (d, J=11.2 Hz, 2H), 3.75-3.32 (m, 13H), 3.15 (d, J=12.9 Hz, 2H), 2.93 (s, 1H), 2.81-2.77 (m, 1H), 2.68 (s, 2H), 2.55 (s, 1H), 2.44 (s, 2H), 2.28 (s, 2H), 2.18-2.13 (m, 3H), 2.02 (s, 2H). HRMS (ESI) m/z: calcd for $C_{45}H_{51}ClFN_8O_5^+$ [M+H]$^+$, 837.3649; found, 837.3644.

Example 105

Preparation of 3-(4-(6-(4-(1-(3-((4-((3-chloro-4-fluorophenyl)amino)-7-methoxyquinazolin-6-yl)oxy) propyl)piperidin-4-yl)piperazin-1-yl)hex-1-yn-1-yl)-1-oxoisoindolin-2-yl)piperidine-2,6-dione (SIAIS262090)

Referring to the method of example 102, the target compound (SIAIS262090) was prepared by using Gefitinib derivative B and intermediate LM (SIAIS255119). (yellow solid, 13.1 mg, yield 41%) $^1$H NMR (500 MHz, MeOD) δ 8.74 (s, 1H), 8.11 (s, 1H), 7.97 (dd, J=6.6, 2.6 Hz, 1H), 7.76 (d, J=7.9 Hz, 1H), 7.71 (dd, J=7.9, 3.7 Hz, 1H), 7.64 (d, J=6.9 Hz, 1H), 7.51 (t, J=7.7 Hz, 1H), 7.37 (t, J=8.9 Hz, 1H), 7.26 (s, 1H), 5.20 (dd, J=13.3, 5.2 Hz, 1H), 4.56 (d, J=17.4 Hz, 1H), 4.50 (d, J=17.4 Hz, 1H), 4.42 (t, J=5.7 Hz, 2H), 4.10 (s, 3H), 3.85 (d, J=11.7 Hz, 2H), 3.55-3.40 (m, 5H), 3.28-3.04 (m, 8H), 2.95-2.90 (m, 1H), 2.79 (d, J=15.6 Hz, 1H), 2.64-2.51 (m, 3H), 2.43 (s, 2H), 2.29 (d, J=7.1 Hz, 2H), 2.20 (s, 1H), 1.99 (s, 4H), 1.75 (d, J=7.7 Hz, 2H), 1.60 (s, 2H). HRMS (ESI) m/z: calcd for $C_{46}H_{53}ClFN_8O_5^+$ [M+H]$^+$, 851.3806; found, 851.3802.

Example 106

Preparation of (E)-N-(4-((3-chloro-4-fluorophenyl) amino)-7-methoxyquinazolin-6-yl)-4-(4-(4-(6-((2-(2, 6-dioxopiperidin-3-yl)-1-oxoisoindolin-4-yl)thio) hexyl)piperazin-1-yl)piperidin-1-yl)but-2-enamide (SIAIS262065)

Referring to the method of example 102, the target compound (SIAIS262065) was prepared by using Dacomitinib derivative B and intermediate LM (SIAIS1216133). (yellow solid, 11.2 mg, yield 45%). $^1$H NMR (500 MHz, MeOD) δ 9.27 (s, 1H), 8.76 (s, 1H), 7.93 (dd, J=6.6, 2.6 Hz, 1H), 7.66 (dt, J=8.7, 4.3 Hz, 3H), 7.54 (t, J=7.7 Hz, 1H), 7.38 (t, J=8.9 Hz, 1H), 7.33 (s, 1H), 7.06 (dt, J=14.7, 7.2 Hz, 1H), 6.88 (d, J=15.4 Hz, 1H), 5.18 (dd, J=13.4, 5.2 Hz, 1H), 4.47 (d, J=17.3 Hz, 1H), 4.45-4.39 (m, 1H), 4.18 (d, J=5.9

Hz, 3H), 4.08 (d, J=6.0 Hz, 2H), 3.76 (s, 2H), 3.75-3.35 (m, 8H), 3.18 (s, 4H), 3.08 (dq, J=13.2, 6.3 Hz, 3H), 2.97-2.88 (m, 1H), 2.80 (ddd, J=17.7, 4.6, 2.4 Hz, 1H), 2.60-2.51 (m, 1H), 2.43 (s, 2H), 2.23-2.07 (m, 3H), 1.79-1.66 (m, 4H), 1.57-1.51 (m, 2H), 1.42 (dd, J=14.7, 7.3 Hz, 2H). HRMS (ESI) m/z: calcd for $C_{47}H_{56}ClFN_9O_5S^+$ $[M+H]^+$, 912.3792; found, 912.3790.

Example 107

Preparation of (E)-N-(4-((3-chloro-4-fluorophenyl) amino)-7-methoxyquinazolin-6-yl)-4-(4-(4-(6-((2-(2, 6-dioxopiperidin-3-yl)-1,3-dioxoisoindolin-4-yl) amino)hexyl)piperazin-1-yl)piperidin-1-yl)but-2-enamide (SIAIS262072)

Referring to the method of example 102, the target compound (SIAIS262072) was prepared by using Dacomitinib derivative B and intermediate LM (SIAIS264018). (yellow solid, 10.8 mg, yield 44%). $^1$H NMR (500 MHz, MeOD) δ 9.27 (s, 1H), 8.75 (s, 1H), 7.92 (dd, J=6.6, 2.6 Hz, 1H), 7.67-7.63 (m, 1H), 7.58-7.54 (m, 1H), 7.38 (t, J=8.9 Hz, 1H), 7.33 (s, 1H), 7.05 (q, J=8.3 Hz, 3H), 6.87 (d, J=15.1 Hz, 1H), 5.07 (dd, J=12.6, 5.7 Hz, 1H), 4.18 (s, 3H), 4.07 (s, 2H), 3.74 (s, 4H), 3.39 (dd, J=26.0, 19.4 Hz, 5H), 3.19 (s, 4H), 2.85 (dd, J=13.0, 4.4 Hz, 1H), 2.78-2.69 (m, 2H), 2.38 (s, 2H), 2.13-2.03 (m, 3H), 1.80 (s, 2H), 1.71 (dd, J=14.0, 6.7 Hz, 2H), 1.49 (d, J=9.3 Hz, 4H). HRMS (ESI) m/z: calcd for $C_{47}H_{55}ClFN_{10}O_6^+$ $[M+H]^+$, 909.3973; found, 909.3971.

Example 108

Preparation of N-(4-((3-chloro-4-fluorophenyl) amino)-7-(3-(4-(2-((2-(2,6-dioxopiperidin-3-yl)-1-oxoisoindolin-4-yl)thio)acetyl)piperazin-1-yl) propoxy)quinazolin-6-yl)acrylamide (SIAIS262121)

Referring to the method of example 1, the target compound (SIAIS262121) was prepared by using Caneritinib derivative A and intermediate LM (SIAIS171090). (yellow solid, 6.8 mg, yield 40%). $^1$H NMR (500 MHz, MeOD) δ 9.14 (s, 1H), 8.75 (s, 1H), 7.95 (dd, J=6.6, 2.5 Hz, 1H), 7.83 (d, J=7.7 Hz, 1H), 7.76 (d, J=7.6 Hz, 1H), 7.68-7.63 (m, 1H), 7.58 (t, J=7.6 Hz, 1H), 7.39-7.33 (m, 2H), 6.79 (dd, J=17.0, 10.3 Hz, 1H), 6.51 (d, J=16.9 Hz, 1H), 5.90 (d, J=11.0 Hz, 1H), 5.18 (dd, J=13.3, 5.1 Hz, 1H), 4.55 (s, 1H), 4.48 (dd, J=14.6, 8.9 Hz, 4H), 4.02 (d, J=17.2 Hz, 2H), 3.60 (s, 4H), 3.45 (s, 4H), 2.93-2.88 (m, 1H), 2.78 (s, 1H), 2.58-2.51 (m, 1H), 2.46 (s, 2H), 2.19 (d, J=7.7 Hz, 1H). HRMS (ESI) m/z: calcd for $C_{39}H_{39}ClFN_8O_6S^+$ $[M+H]^+$, 801.2380; found, 801.2381.

Example 109

Preparation of N-(4-((3-chloro-4-fluorophenyl) amino)-7-(3-(4-(5-((2-(2,6-dioxopiperidin-3-yl)-1-oxoisoindolin-4-yl)thio)pentanoyl)piperazin-1-yl) propoxy)quinazolin-6-yl)acrylamide (SIAIS262122)

Referring to the method of example 1, the target compound (SIAIS262122) was prepared by using Caneritinib derivative A and intermediate LM (SIAIS171079). (yellow solid, 7.1 mg, yield 40%). $^1$H NMR (500 MHz, MeOD) δ 9.11 (s, 1H), 8.74 (s, 1H), 7.95 (dd, J=6.6, 2.6 Hz, 1H), 7.69-7.64 (m, 3H), 7.53 (d, J=7.6 Hz, 1H), 7.37 (t, J=8.9 Hz, 1H), 7.34 (s, 1H), 6.75 (dd, J=16.9, 10.3 Hz, 1H), 6.51 (dd, J=16.9, 1.5 Hz, 1H), 5.90 (dd, J=10.2, 1.5 Hz, 1H), 5.15 (dd, J=13.4, 5.1 Hz, 1H), 4.48 (dd, J=11.5, 5.8 Hz, 3H), 4.41 (d, J=17.3 Hz, 1H), 3.64 (s, 4H), 3.45 (s, 2H), 3.23-2.97 (m, 6H), 2.93-2.86 (m, 1H), 2.79 (dd, J=10.0, 7.6 Hz, 1H), 2.54 (dd, J=13.1, 4.8 Hz, 1H), 2.46 (t, J=7.1 Hz, 4H), 2.21-2.16 (m, 1H), 1.74 (dd, J=23.6, 6.9 Hz, 4H). HRMS (ESI) m/z: calcd for $C_{42}H_{45}ClFN_8O_6S^+$ $[M+H]^+$, 843.2850; found, 843.2853.

Example 110

Preparation of N-(4-((3-chloro-4-fluorophenyl) amino)-7-(3-(4-(6-((2-(2,6-dioxopiperidin-3-yl)-1-oxoisoindolin-4-yl)thio)hexanoyl)piperazin-1-yl) propoxy)quinazolin-6-yl)acrylamide (SIAIS262123)

Referring to the method of example 1, the target compound (SIAIS262123) was prepared by using Caneritinib derivative A and intermediate LM (SIAIS171091). (yellow solid, 8.2 mg, yield 46%). $^1$H NMR (500 MHz, MeOD) δ 9.14 (s, 1H), 8.75 (s, 1H), 7.95 (dd, J=6.6, 2.6 Hz, 1H), 7.69-7.63 (m, 3H), 7.54 (t, J=7.6 Hz, 1H), 7.38 (t, J=8.9 Hz, 1H), 7.35 (s, 1H), 6.78 (dd, J=17.0, 10.2 Hz, 1H), 6.51 (d, J=16.8 Hz, 1H), 5.91 (d, J=10.4 Hz, 1H), 5.18-5.13 (m, 1H), 4.47 (dd, J=11.2, 5.3 Hz, 3H), 4.42 (d, J=17.3 Hz, 1H), 3.63 (d, J=30.6 Hz, 4H), 3.46 (s, 2H), 3.09 (ddd, J=22.7, 18.4, 16.1 Hz, 6H), 2.95-2.85 (m, 1H), 2.78 (d, J=15.2 Hz, 1H), 2.55 (dd, J=13.2, 4.7 Hz, 1H), 2.50 (d, J=9.4 Hz, 2H), 2.40 (t, J=7.2 Hz, 2H), 2.19 (d, J=7.9 Hz, 1H), 1.68 (dd, J=14.5, 7.1 Hz, 2H), 1.61 (dd, J=14.6, 7.4 Hz, 2H), 1.52 (d, J=7.3 Hz, 2H). HRMS (ESI) m/z: calcd for $C_{43}H_{47}ClFN_8O_6S^+$ $[M+H]^+$, 857.3006; found, 857.3002.

Example 111

Preparation of N-(4-((3-chloro-4-fluorophenyl) amino)-7-(3-(4-(2-((2-(2,6-dioxopiperidin-3-yl)-1,3-dioxoisoindolin-4-yl)amino)acetyl)piperazin-1-yl) propoxy)quinazolin-6-yl)acrylamide (SIAIS262124)

Referring to the method of example 1, the target compound (SIAIS262124) was prepared by using Caneritinib derivative A and intermediate LM (SIAIS151025). (yellow solid, 7.3 mg, yield 44%). $^1$H NMR (500 MHz, MeOD) δ 9.10 (s, 1H), 8.73 (s, 1H), 7.95 (dd, J=6.5, 2.5 Hz, 1H), 7.68-7.63 (m, 1H), 7.57 (d, J=8.5 Hz, 1H), 7.39-7.33 (m, 2H), 7.11 (d, J=7.0 Hz, 1H), 7.03 (d, J=8.4 Hz, 1H), 6.76 (dd, J=17.0, 10.3 Hz, 1H), 6.51 (dd, J=16.9, 1.5 Hz, 1H), 5.91 (dd, J=10.3, 1.5 Hz, 1H), 5.10-5.06 (m, 1H), 4.48 (t, J=5.8 Hz, 2H), 4.29 (s, 2H), 3.62 (d, J=21.2 Hz, 4H), 3.47 (d, J=18.1 Hz, 4H), 3.17 (s, 2H), 2.84 (dd, J=13.0, 7.8 Hz, 1H), 2.74 (dd, J=18.5, 5.6 Hz, 3H), 2.50-2.47 (m, 1H), 2.13 (d, J=5.1 Hz, 1H). HRMS (ESI) m/z: calcd for $C_{39}H_{38}ClFN_9O_7^+$ $[M+H]^+$, 798.2561; found, 798.2564.

Example 112

Preparation of N-(4-((3-chloro-4-fluorophenyl) amino)-7-(3-(4-(6-((2-(2,6-dioxopiperidin-3-yl)-1,3-dioxoisoindolin-4-yl)amino)hexanoyl)piperazin-1-yl)propoxy)quinazolin-6-yl)acrylamide (SIAIS262125)

Referring to the method of example 1, the target compound (SIAIS262125) was prepared by using Caneritinib derivative A and intermediate LM (SIAIS151027). (yellow solid, 7.9 mg, yield 44%). $^1$H NMR (500 MHz, MeOD) δ 9.08 (s, 1H), 8.73 (s, 1H), 7.95 (d, J=3.9 Hz, 1H), 7.65 (s, 1H), 7.55 (d, J=8.2 Hz, 1H), 7.37 (t, J=8.9 Hz, 1H), 7.33 (s, 1H), 7.08-7.02 (m, 2H), 6.72 (dd, J=16.9, 10.7 Hz, 1H), 6.51 (d, J=16.9 Hz, 1H), 5.90 (d, J=10.6 Hz, 1H), 5.05 (d, J=11.9 Hz, 1H), 4.46 (s, 2H), 4.28-4.08 (m, 2H), 3.58 (s, 4H), 3.45 (s, 4H), 3.14-3.02 (m, 2H), 2.84 (d, J=13.8 Hz, 1H), 2.72-2.68 (m, 2H), 2.48 (d, J=6.9 Hz, 4H), 2.11 (s, 1H), 1.70 (s, 4H), 1.50 (s, 2H). HRMS (ESI) m/z: calcd for $C_{43}H_{46}ClFN_9O_7^+$ [M+H]$^+$, 854.3187; found, 854.3182.

Example 113

Preparation of N-(4-((3-chloro-4-fluorophenyl)amino)-7-(3-(4-(7-((2-(2,6-dioxopiperidin-3-yl)-1,3-dioxoisoindolin-4-yl)amino)heptanoyl)piperazin-1-yl)propoxy)quinazolin-6-yl)acrylamide (SIAIS262126)

Referring to the method of example 1, the target compound (SIAIS262126) was prepared by using Caneritinib derivative A and intermediate LM (SIAIS151086). (yellow solid, 7.6 mg, yield 42%). $^1$H NMR (500 MHz, MeOD) δ 9.12 (s, 1H), 8.74 (s, 1H), 7.95 (dd, J=6.6, 2.4 Hz, 1H), 7.68-7.63 (m, 1H), 7.59-7.53 (m, 1H), 7.37 (t, J=8.8 Hz, 1H), 7.34 (s, 1H), 7.05 (t, J=8.0 Hz, 2H), 6.75 (dd, J=16.9, 10.2 Hz, 1H), 6.51 (d, J=17.7 Hz, 1H), 5.91 (d, J=10.5 Hz, 1H), 5.07-5.03 (m, 1H), 4.47 (t, J=5.5 Hz, 2H), 3.60 (s, 4H), 3.45 (s, 4H), 3.17 (s, 4H), 2.85 (d, J=13.4 Hz, 1H), 2.72 (t, J=13.1 Hz, 2H), 2.52-2.42 (m, 4H), 2.13-2.08 (m, 1H), 1.73-1.62 (m, 4H), 1.46 (s, 4H). HRMS (ESI) m/z: calcd for $C_{44}H_{48}ClFN_9O_7^+$ [M+H]$^+$, 868.3344; found, 868.3341.

Example 114

Preparation of N-(4-((3-chloro-4-fluorophenyl)amino)-7-(3-(4-(3-(2-(2-((2-(2,6-dioxopiperidin-3-yl)-1,3-dioxoisoindolin-4-yl)amino)ethoxy)ethoxy)propanoyl)piperazin-1-yl)propoxy)quinazolin-6-yl)acrylamide (SIAIS262127)

Referring to the method of example 1, the target compound (SIAIS262127) was prepared by using Caneritinib derivative A and intermediate LM (SIAIS151004). (yellow solid, 8.5 mg, yield 45%). $^1$H NMR (500 MHz, MeOD) δ 9.06 (s, 1H), 8.70 (s, 1H), 7.95 (dd, J=6.7, 2.6 Hz, 1H), 7.67 (dd, J=7.2, 4.5 Hz, 1H), 7.48-7.43 (m, 1H), 7.38 (t, J=8.9 Hz, 1H), 7.27 (s, 1H), 7.00 (d, J=8.5 Hz, 1H), 6.91 (d, J=7.2 Hz, 1H), 6.73 (dd, J=16.9, 10.3 Hz, 1H), 6.55-6.48 (m, 1H), 5.93-5.89 (m, 1H), 5.06 (dd, J=12.8, 5.5 Hz, 3H), 4.38 (s, 2H), 3.81-3.56 (m, 12H), 3.44 (d, J=11.5 Hz, 8H), 2.89-2.81 (m, 2H), 2.75 (d, J=7.4 Hz, 2H), 2.67 (d, J=13.4 Hz, 1H), 2.44 (s, 2H), 2.11 (s, 1H). HRMS (ESI) m/z: calcd for $C_{44}H_{48}ClFN_9O_9^+$ [M+H]$^+$, 900.3242; found, 900.3241.

Example 115

Preparation of (2S,4R)-1-((S)-2-(5-(4-(3-((6-acrylamido-4-((3-chloro-4-fluorophenyl)amino)quinazolin-7-yl)oxy)propyl)piperazin-1-yl)-5-oxopentanamido)-3,3-dimethylbutanoyl)-4-hydroxy-N-(4-(4-methylthiazol-5-yl)benzyl)pyrrolidine-2-carboxamide (SIAIS262128)

Referring to the method of example 1, the target compound (SIAIS262128) was prepared by using Caneritinib derivative A and intermediate LM (SIAIS074012). (yellow solid, 10.3 mg, yield 48%). $^1$H NMR (500 MHz, MeOD) δ 9.40 (d, J=10.0 Hz, 1H), 9.17 (s, 1H), 8.76 (s, 1H), 7.94 (dd, J=6.6, 2.6 Hz, 1H), 7.68-7.63 (m, 1H), 7.51 (t, J=7.7 Hz, 2H), 7.46 (d, J=8.3 Hz, 2H), 7.39-7.35 (m, 2H), 6.85 (dd, J=16.9, 10.3 Hz, 1H), 6.51 (dd, J=16.9, 1.5 Hz, 1H), 5.90 (dd, J=10.3, 1.5 Hz, 1H), 4.58 (dd, J=13.6, 5.6 Hz, 2H), 4.50 (dd, J=12.6, 7.2 Hz, 4H), 4.41-4.36 (m, 1H), 4.22 (s, 1H), 3.91 (d, J=11.0 Hz, 1H), 3.81 (dd, J=11.0, 3.8 Hz, 1H), 3.66 (d, J=35.5 Hz, 3H), 3.51 (s, 2H), 3.18 (d, J=12.4 Hz, 2H), 2.55-2.49 (m, 5H), 2.46 (t, J=7.5 Hz, 2H), 2.29-2.23 (m, 3H), 2.11-2.05 (m, 1H), 1.66-1.59 (m, 4H), 1.41-1.35 (m, 4H), 1.04 (s, 9H). HRMS (ESI) m/z: calcd for $C_{51}H_{61}ClFN_{10}O_7S^+$ [M+H]$^+$, 1011.4112; found, 1011.4114.

Example 116

Preparation of N-(4-((3-chloro-4-fluorophenyl)amino)-7-(3-(4-(6-(2-(2,6-dioxopiperidin-3-yl)-3-oxoisoindolin-1-yl)hex-5-yn-1-yl)piperazin-1-yl)propoxy)quinazolin-6-yl)acrylamide (SIAIS262131)

Referring to the method of example 102, the target compound (SIAIS262131) was prepared by using Caneritinib derivative A and intermediate LM (SIAIS255119). (yellow solid, 9.4 mg, yield 38%). $^1$H NMR (500 MHz, MeOD) δ 9.18 (s, 1H), 8.76 (s, 1H), 7.94 (dd, J=6.6, 2.6 Hz, 1H), 7.76 (d, J=7.1 Hz, 1H), 7.68-7.62 (m, 2H), 7.51 (t, J=7.6 Hz, 1H), 7.38 (t, J=8.9 Hz, 1H), 7.35 (s, 1H), 6.81 (dd, J=16.8, 10.4 Hz, 1H), 6.51 (dd, J=16.9, 1.5 Hz, 1H), 5.90 (dd, J=10.2, 1.5 Hz, 1H), 5.21 (dd, J=13.3, 5.2 Hz, 1H), 4.56 (s, 1H), 4.52 (d, J=12.1 Hz, 1H), 4.49 (d, J=5.9 Hz, 2H), 3.75 (s, 4H), 3.65-3.38 (m, 8H), 2.95-2.87 (m, 1H), 2.80 (dd, J=15.3, 12.9 Hz, 1H), 2.63 (t, J=6.7 Hz, 2H), 2.60-2.53 (m, 1H), 2.46 (s, 2H), 2.22-2.15 (m, 1H), 2.03 (d, J=7.9 Hz, 2H), 1.76 (dd, J=14.7, 7.3 Hz, 2H). HRMS (ESI) m/z: calcd for $C_{43}H_{45}ClFN_8O_5^+$ [M+H]$^+$, 807.3180; found, 807.3177.

Example 117

Preparation of N-(4-((3-chloro-4-fluorophenyl)amino)-7-(3-(4-(6-((2-(2,6-dioxopiperidin-3-yl)-1,3-dioxoisoindolin-4-yl)amino)hexyl)piperazin-1-yl)propoxy)quinazolin-6-yl)acrylamide (SIAIS262182)

Referring to the method of example 102, the target compound (SIAIS262182) was prepared by using Caneritinib derivative A and intermediate LM (SIAIS264018). (yellow solid, 12.1 mg, yield 46%). $^1$H NMR (500 MHz, DMSO) δ 11.09 (s, 1H), 9.94 (s, 1H), 9.16 (s, 1H), 8.87 (s, 1H), 7.99 (d, J=5.9 Hz, 11H), 7.68 (dd, J=7.5, 4.2 Hz, 1H), 7.59 (dd, J=8.4, 7.2 Hz, 1H), 7.54 (t, J=9.0 Hz, 1H), 7.43 (s, 1H), 7.11 (d, J=8.6 Hz, 1H), 7.03 (d, J=7.0 Hz, 1H), 6.94 (s, 1H), 6.55 (s, 1H), 6.37 (d, J=16.9 Hz, 1H), 5.86 (d, J=11.1 Hz, 1H), 5.05 (dd, J=12.8, 5.4 Hz, 1H), 4.38 (s, 2H), 3.73 (d, J=47.0 Hz, 6H), 3.22 (d, J=102.4 Hz, 10H), 2.89-2.83 (m, 1H), 2.64-2.52 (m, 2H), 2.36 (s, 2H), 2.07-1.98 (m, 1H), 1.72 (s, 2H), 1.67-1.56 (m, 2H), 1.38 (s, 4H). HRMS (ESI) m/z: calcd for $C_{43}H_{48}ClFN_9O_6^+$ [M+H]$^+$, 840.3395; found, 840.3392.

Example 118

Preparation of N-(4-((3-chloro-4-fluorophenyl)amino)-7-(3-(4-(4-(2-((2-(2,6-dioxopiperidin-3-yl)-1-oxoisoindolin-4-yl)thio)acetyl)piperazin-1-yl)piperidin-1-yl)propoxy)quinazolin-6-yl)acrylamide (SIAIS262174)

Referring to the method of example 1, the target compound (SIAIS262174) was prepared by using Caneritinib derivative B and intermediate LM (SIAIS171090). (yellow solid, 6.8 mg, yield 44%). $^{1}$H NMR (500 MHz, MeOD) δ 9.17 (s, 1H), 8.75 (s, 1H), 7.93 (dd, J=6.6, 2.6 Hz, 1H), 7.69-7.64 (m, 2H), 7.53 (t, J=7.6 Hz, 1H), 7.34 (dd, J=11.7, 6.0 Hz, 2H), 6.85-6.82 (m, 1H), 6.50 (d, J=16.9 Hz, 1H), 5.91 (d, J=10.3 Hz, 1H), 5.16 (dd, J=13.4, 5.1 Hz, 1H), 4.46 (dd, J=11.5, 5.9 Hz, 3H), 4.41 (d, J=17.3 Hz, 1H), 3.87 (d, J=12.0 Hz, 2H), 3.66 (s, 2H), 3.56-3.43 (m, 4H), 3.25 (t, J=12.5 Hz, 4H), 3.17-3.06 (m, 3H), 2.95-2.85 (m, 1H), 2.76 (d, J=15.5 Hz, 1H), 2.60-2.44 (m, 7H), 2.26 (d, J=12.5 Hz, 2H), 2.21-2.16 (m, 1H). HRMS (ESI) m/z: calcd for $C_{44}H_{48}ClFN_9O_6S^+$ [M+H]$^+$, 884.3115; found; 884.3119.

Example 119

Preparation of N-(4-((3-chloro-4-fluorophenyl)amino)-7-(3-(4-(4-(5-((2-(2,6-dioxopiperidin-3-yl)-1-oxoisoindolin-4-yl)thio)pentanoyl)piperazin-1-yl)piperidin-1-yl)propoxy)quinazolin-6-yl)acrylamide (SIAIS262175)

Referring to the method of example 1, the target compound (SIAIS262175) was prepared by using Caneritinib derivative B and intermediate LM (SIAIS171079). (yellow solid, 7.1 mg, yield 44%). $^{1}$H NMR (500 MHz, MeOD) δ 9.18 (s, 1H), 8.76 (s, 1H), 7.94 (dd, J=6.6, 2.6 Hz, 1H), 7.69-7.65 (m, 2H), 7.54 (t, J=7.6 Hz, 1H), 7.37 (dd, J=11.7, 6.0 Hz, 2H), 6.85 (dd, J=16.8, 10.3 Hz, 1H), 6.51 (d, J=16.9 Hz, 1H), 5.91 (d, J=10.3 Hz, 1H), 5.17 (dd, J=13.4, 5.1 Hz, 1H), 4.48 (dd, J=11.5, 5.9 Hz, 3H), 4.42 (d, J=17.3 Hz, 1H), 3.87 (d, J=12.0 Hz, 2H), 3.68 (s, 2H), 3.56-3.40 (m, 4H), 3.24 (t, J=12.5 Hz, 4H), 3.17-3.04 (m, 3H), 2.97-2.87 (m, 1H), 2.79 (d, J=15.5 Hz, 1H), 2.60-2.44 (m, 7H), 2.28 (d, J=12.5 Hz, 2H), 2.22-2.16 (m, 1H), 1.83-1.68 (m, 4H), 1.45-1.32 (m, 2H). HRMS (ESI) m/z: calcd for $C_{47}H_{54}ClFN_9O_6S^+$ [M+H]$^+$, 926.3585; found, 926.3583.

Example 120

Preparation of N-(4-((3-chloro-4-fluorophenyl)amino)-7-(3-(4-(4-(6-((2-(2,6-dioxopiperidin-3-yl)-1-oxoisoindolin-4-yl)thio)hexanoyl)piperazin-1-yl)piperidin-1-yl)propoxy)quinazolin-6-yl)acrylamide (SIAIS262176)

Referring to the method of example 1, the target compound (SIAIS262176) was prepared by using Caneritinib derivative B and intermediate LM (SIAIS171091). (yellow solid, 7.5 mg, yield 45%). $^{1}$H NMR (500 MHz, MeOD) δ 9.17 (s, 1H), 8.76 (s, 1H), 7.94 (dd, J=6.6, 2.6 Hz, 1H), 7.67 (dd, J=7.7, 2.9 Hz, 2H), 7.54 (t, J=7.6 Hz, 1H), 7.38 (t, J=8.9 Hz, 1H), 7.34 (s, 1H), 6.82 (dd, J=16.9, 10.3 Hz, 1H), 6.52 (dd, J=16.9, 1.4 Hz, 1H), 5.95-5.88 (m, 1H), 5.18 (dd, J=13.1, 5.0 Hz, 1H), 4.48 (dd, J=11.5, 6.0 Hz, 3H), 4.42 (d, J=17.3 Hz, 1H), 3.86 (d, J=11.1 Hz, 2H), 3.44 (dd, J=33.3, 26.1 Hz, 8H), 3.30-3.14 (m, 4H), 3.08 (ddd, J=19.6, 13.2, 6.3 Hz, 3H), 2.91 (dd, J=21.7, 9.2 Hz, 1H), 2.79 (d, J=15.7 Hz, 1H), 2.60-2.44 (m, 5H), 2.39 (t, J=7.0 Hz, 2H), 2.19 (dd, J=15.9, 10.9 Hz, 3H), 1.67 (dd, J=15.0, 7.2 Hz, 2H), 1.61 (dd, J=14.8, 7.3 Hz, 2H), 1.56-1.49 (m, 2H). HRMS (ESI) m/z: calcd for $C_{48}H_{56}ClFN_9O_6S^+$ [M+H]$^+$, 940.3741; found, 940.3739.

Example 121

Preparation of N-(4-((3-chloro-4-fluorophenyl)amino)-7-(3-(4-(4-(2-((2-(2,6-dioxopiperidin-3-yl)-1,3-dioxoisoindolin-4-yl)amino)acetyl)piperazin-1-yl)piperidin-1-yl)propoxy)quinazolin-6-yl)acrylamide (SIAIS262177)

Referring to the method of example 1, the target compound (SIAIS262177) was prepared by using Caneritinib derivative B and intermediate LM (SIAIS151025). (yellow solid, 6.4 mg, yield 41%). $^{1}$H NMR (500 MHz, MeOD) δ 9.17 (s, 1H), 8.75 (s, 1H), 7.94 (dd, J=6.6, 2.6 Hz, 1H), 7.69-7.63 (m, 1H), 7.62-7.54 (m, 1H), 7.38 (t, J=8.9 Hz, 1H), 7.34 (s, 1H), 7.11 (d, J=7.1 Hz, 1H), 7.03 (d, J=8.5 Hz, 1H), 6.81 (dd, J=16.9, 10.3 Hz, 1H), 6.52 (d, J=16.9 Hz, 1H), 5.91 (d, J=11.6 Hz, 1H), 5.08 (dd, J=12.6, 5.5 Hz, 1H), 4.49 (t, J=5.5 Hz, 2H), 4.29 (s, 2H), 3.88 (d, J=10.5 Hz, 2H), 3.62-3.58 (m, 8H), 3.29-2.95 (m, 5H), 2.86 (dd, J=13.5, 5.7 Hz, 1H), 2.80-2.68 (m, 2H), 2.51 (s, 4H), 2.25 (s, 2H), 2.16-2.09 (m, 1H). HRMS (ESI) m/z: calcd for $C_{44}H_{47}ClFN_{10}O_7^+$ [M+H]$^+$, 881.3296; found, 881.3296.

Example 122

Preparation of N-(4-((3-chloro-4-fluorophenyl)amino)-7-(3-(4-(4-(6-((2-(2,6-dioxopiperidin-3-yl)-1,3-dioxoisoindolin-4-yl)amino)hexanoyl)piperazin-1-yl)piperidin-1-yl)propoxy)quinazolin-6-yl)acrylamide (SIAIS262178)

Referring to the method of example 1, the target compound (SIAIS262178) was prepared by using Caneritinib derivative B and intermediate LM (SIAIS151027). (yellow solid, 7.8 mg, yield 47%). $^{1}$H NMR (500 MHz, MeOD) δ 9.17 (s, 1H), 8.76 (s, 1H), 7.94 (dd, J=6.6, 2.6 Hz, 1H), 7.69-7.62 (m, 1H), 7.59-7.54 (m, 1H), 7.38 (t, J=8.9 Hz, 1H), 7.35 (s, 1H), 7.06 (t, J=7.7 Hz, 1H), 6.83 (dd, J=16.8, 10.4 Hz, 1H), 6.52 (d, J=16.9 Hz, 1H), 5.91 (d, J=11.8 Hz, 1H), 5.07 (dd, J=12.6, 5.5 Hz, 1H), 4.49 (s, 2H), 3.87 (s, 2H), 3.71-3.35 (m, 12H), 3.21 (d, J=10.6 Hz, 5H), 2.85 (d, J=8.6 Hz, 1H), 2.73 (t, J=14.4 Hz, 2H), 2.55-2.45 (m, 4H), 2.27 (s, 2H), 2.12 (s, 1H), 1.74-1.67 (m, 2H), 1.51 (d, J=7.3 Hz, 2H), 1.41-1.33 (m, 2H). HRMS (ESI) m/z: calcd for $C_{48}H_{55}ClFN_{10}O_7^+$ [M+H]$^+$, 937.3922; found, 937.3926.

Example 123

Preparation of N-(4-((3-chloro-4-fluorophenyl)amino)-7-(3-(4-(4-(7-((2-(2,6-dioxopiperidin-3-yl)-1,3-dioxoisoindolin-4-yl)amino)heptanoyl)piperazin-1-yl)piperidin-1-yl)propoxy)quinazolin-6-yl)acrylamide (SIAIS262179)

Referring to the method of example 1, the target compound (SIAIS262179) was prepared by using Caneritinib derivative B and intermediate LM (SIAIS151086). (yellow solid, 8.2 mg, yield 49%). $^{1}$H NMR (500 MHz, MeOD) δ 9.17 (s, 1H), 8.75 (s, 1H), 7.97-7.92 (m, 1H), 7.68-7.61 (m, 1H), 7.59-7.53 (m, 1H), 7.37 (dd, J=15.8, 6.9 Hz, 2H), 7.07-7.04 (m, 1H), 6.82 (s, 1H), 6.51 (d, J=17.0 Hz, 1H), 5.91 (dd, J=10.3, 1.5 Hz, 1H), 5.07 (dd, J=12.1, 6.0 Hz, 1H), 4.49 (s, 2H), 3.84 (s, 2H), 3.72-3.32 (m, 12H), 3.18 (d, J=15.7 Hz, 5H), 2.85 (dd, J=13.3, 4.8 Hz, 1H), 2.78-2.67 (m, 2H), 2.47 (d, J=23.2 Hz, 4H), 2.31-2.17 (m, 2H), 2.15-2.08

(m, 1H), 1.73-1.60 (m, 4H), 1.45 (d, J=13.6 Hz, 4H). HRMS (ESI) i/z: calcd for $C_{49}H_{57}ClFN_{10}O_7^+$ $[M+H]^+$, 951.4079; found, 951.4075.

Example 124

Preparation of N-(4-((3-chloro-4-fluorophenyl) amino)-7-(3-(4-(4-(6-((2-(2,6-dioxopiperidin-3-yl)-1-oxoisoindolin-4-yl)thio)hexyl)piperazin-1-yl)piperidin-1-yl)propoxy)quinazolin-6-yl)acrylamide (SIAIS262180)

Referring to the method of example 102, the target compound (SIAIS262180) was prepared by using Canertinib derivative B and intermediate LM (SIAIS1216133). (yellow solid, 11.2 mg, yield 46%). $^1$H NMR (500 MHz, MeOD) δ 9.17 (s, 1H), 8.76 (s, 1H), 7.94 (dd, J=6.6, 2.6 Hz, 1H), 7.67-7.65 (m, 2H), 7.54 (t, J=7.6 Hz, 1H), 7.38 (dd, J=12.3, 5.4 Hz, 2H), 6.84 (dd, J=16.9, 10.3 Hz, 1H), 6.52 (dd, J=16.9, 1.3 Hz, 1H), 5.91 (dd, J=10.3, 1.4 Hz, 1H), 5.18 (dd, J=13.3, 5.2 Hz, 1H), 4.48 (dd, J=13.2, 7.4 Hz, 3H), 4.44-4.39 (m, 1H), 3.83 (d, J=12.5 Hz, 2H), 3.76-3.34 (m, 10H), 3.19 (t, J=12.2 Hz, 4H), 3.09-3.04 (m, 3H), 2.96-2.88 (m, 1H), 2.84-2.76 (m, 1H), 2.55-2.51 (m, 3H), 2.40 (d, J=12.8 Hz, 2H), 2.19-2.15 (m, 3H), 1.78-1.67 (m, 4H), 1.53 (d, J=7.3 Hz, 2H), 1.41 (dt, J=13.8, 7.2 Hz, 2H). HRMS (ESI) m/z: calcd for $C_{48}H_{58}ClFN_9O_5S^+$ $[M+H]^+$, 926.3949; found, 926.3953.

Example 125

Preparation of N-(4-((3-chloro-4-fluorophenyl) amino)-7-(3-(4-(4-(6-((2-(2,6-dioxopiperidin-3-yl)-1,3-dioxoisoindolin-4-yl)amino)hexyl)piperazin-1-yl) piperidin-1-yl)propoxy)quinazolin-6-yl)acrylamide (SIAIS262183)

Referring to the method of example 102, the target compound (SIAIS262183) was prepared by using Canertinib derivative B and intermediate LM (SIAIS264018). (yellow solid, 12.2 mg, yield 50%). $^1$H NMR (500 MHz, MeOD) δ 9.17 (s, 1H), 8.76 (s, 1H), 7.94 (dd, J=6.5, 2.5 Hz, 1H), 7.66-7.61 (m, 1H), 7.56 (dd, J=8.5, 7.1 Hz, 1H), 7.40-7.34 (m, 2H), 7.06 (t, J=7.4 Hz, 2H), 6.84 (dd, J=16.9, 10.0 Hz, 1H), 6.52 (d, J=16.9 Hz, 1H), 5.91 (d, J=11.7 Hz, 1H), 5.07 (dd, J=12.6, 5.5 Hz, 1H), 4.48 (t, J=5.6 Hz, 2H), 3.80 (s, 2H), 3.43-3.41 (m, 8H), 3.18 (d, J=13.1 Hz, 4H), 2.88-2.83 (m, 1H), 2.77-2.69 (m, 2H), 2.50 (s, 2H), 2.34 (s, 2H), 2.16-2.08 (m, 3H), 1.80 (s, 2H), 1.76-1.70 (m, 2H), 1.50 (d, J=10.7 Hz, 4H). HRMS (ESI) m/z: calcd for $C_{48}H_{57}ClFN_{10}O_6^+$ $[M+H]^+$, 923.4130; found, 923.4143.

Example 126

Preparation of 2-(4-((4-((3-chloro-4-fluorophenyl) amino)-7-methoxyquinazolin-6-yl)oxy)piperidin-1-yl)-N-(2-((2-(2,6-dioxopiperidin-3-yl)-1-oxoisoindolin-4-yl)thio)ethyl)acetamide (SIAIS293047)

Referring to the method of example 1, the target compound (SIAIS293047) was prepared by using Gefitinib derivative C and intermediate LM (SIAIS171123). (yellow solid, 7.6 mg, yield 45%). $^1$H NMR (500 MHz, MeOD) δ 8.73 (s, 1H), 8.31 (s, 1H), 8.00 (dd, J=6.6, 2.6 Hz, 1H), 7.78 (dd, J=7.8, 0.8 Hz, 1H), 7.72 (s, 1H), 7.66 (s, 1H), 7.56 (t, J=7.7 Hz, 1H), 7.36 (t, J=8.9 Hz, 1H), 7.28 (s, 1H), 5.17 (d, J=8.4 Hz, 1H), 5.01 (s, 1H), 4.53 (d, J=17.4 Hz, 1H), 4.47

(d, J=17.5 Hz, 1H), 4.11 (d, J=9.7 Hz, 3H), 3.90 (q, J=15.5 Hz, 2H), 3.58-3.50 (m, 2H), 3.49-3.33 (m, 4H), 3.29-3.21 (m, 2H), 2.90 (ddd, J=17.0, 12.7, 4.5 Hz, 1H), 2.83-2.74 (m, 1H), 2.52 (dt, J=13.1, 8.4 Hz, 1H), 2.39-2.17 (m, 4H), 2.04 (s, 1H). HRMS (ESI) m/z: calcd for $C_{37}H_{38}ClFN_7O_6S^+$ $[M+H]^+$, 762.2271; found, 762.2266.

Example 127

Preparation of 2-(4-((4-((3-chloro-4-fluorophenyl) amino)-7-methoxyquinazolin-6-yl)oxy)piperidin-1-yl)-N-(3-((2-(2,6-dioxopiperidin-3-yl)-1-oxoisoindolin-4-yl)thio)propyl)acetamide (SIAIS293048)

Referring to the method of example 1, the target compound (SIAIS293048) was prepared by using Gefitinib derivative C and intermediate LM (SIAIS171124). (yellow solid, 8.1 mg, yield 47%). $^1$H NMR (500 MHz, MeOD) δ 8.74 (s, 1H), 8.33 (s, 1H), 7.99 (dd, J=6.6, 2.6 Hz, 1H), 7.72 (ddd, J=8.9, 4.1, 2.7 Hz, 1H), 7.68 (d, J=7.6 Hz, 1H), 7.64 (d, J=7.3 Hz, 1H), 7.52 (t, J=7.7 Hz, 1H), 7.36 (t, J=8.9 Hz, 1H), 7.28 (s, 1H), 5.17 (d, J=9.5 Hz, 1H), 5.04 (s, 1H), 4.50 (s, 1H), 4.45 (d, J=17.4 Hz, 1H), 4.09 (s, 3H), 3.99 (s, 2H), 3.67-3.34 (m, 6H), 3.20 (ddd, J=15.2, 14.2, 9.6 Hz, 2H), 3.10 (t, J=7.2 Hz, 2H), 2.95-2.85 (m, 1H), 2.82-2.75 (m, 1H), 2.53 (ddd, J=26.5, 13.3, 4.7 Hz, 1H), 2.32 (s, 2H), 2.22-2.16 (m, 1H), 1.93-1.83 (m, 2H). HRMS (ESI) m/z: calcd for $C_{38}H_{40}ClFN_7O_6S^+$ $[M+H]^+$, 776.2428; found, 776.2424.

Example 128

Preparation of 2-(4-((4-((3-chloro-4-fluorophenyl) amino)-7-methoxyquinazolin-6-yl)oxy)piperidin-1-yl)-N-(4-((2-(2,6-dioxopiperidin-3-yl)-1-oxoisoindolin-4-yl)thio)butyl)acetamide (SIAIS293049)

Referring to the method of example 1, the target compound (SIAIS293049) was prepared by using Gefitinib derivative C and intermediate LM (SIAIS171131). (yellow solid, 8.4 mg, yield 48%). $^1$H NMR (500 MHz, MeOD) δ 8.74 (s, 1H), 8.31 (s, 1H), 7.99 (dd, J=6.6, 2.6 Hz, 1H), 7.74-7.71 (m, 1H), 7.67 (d, J=7.2 Hz, 1H), 7.60 (s, 1H), 7.52 (t, J=7.6 Hz, 1H), 7.36 (t, J=8.9 Hz, 1H), 7.28 (s, 1H), 5.15 (s, 1H), 5.03 (s, 1H), 4.45 (s, 1H), 4.41 (d, J=17.6 Hz, 1H), 4.10 (s, 3H), 3.95 (s, 2H), 3.82-3.33 (m, 6H), 3.29 (s, 2H), 3.17-3.04 (m, 2H), 2.94-2.85 (m, 1H), 2.78-2.74 (m, 1H), 2.53 (dt, J=17.9, 10.9 Hz, 1H), 2.31 (s, 2H), 2.18-2.13 (m, 1H), 1.69 (s, 4H). HRMS (ESI) m/z: calcd for $C_{39}H_{42}ClFN_7O_6S^+$ $[M+H]^+$, 790.2584; found, 790.2581.

Example 129

Preparation of 2-(4-((4-((3-chloro-4-fluorophenyl) amino)-7-methoxyquinazolin-6-yl)oxy)piperidin-1-yl)-N-(6-((2-(2,6-dioxopiperidin-3-yl)-1-oxoisoindolin-4-yl)thio)hexyl)acetamide (SIAIS293050)

Referring to the method of example 1, the target compound (SIAIS293050) was prepared by using Gefitinib derivative C and intermediate LM (SIAIS171134). (yellow solid, 8.7 mg, yield 48%). $^1$H NMR (500 MHz, MeOD) δ 8.73 (s, 1H), 8.35 (s, 1H), 8.00 (dd, J=6.6, 2.4 Hz, 1H), 7.74 (s, 1H), 7.65-7.59 (m, 2H), 7.54-7.48 (m, 1H), 7.36 (t, J=8.9 Hz, 1H), 7.27 (s, 1H), 5.16 (dd, J=13.4, 5.1 Hz, 1H), 5.08 (s, 1H), 4.45 (d, J=17.3 Hz, 1H), 4.38 (d, J=17.3 Hz, 1H), 4.10 (s, 3H), 4.00 (s, 2H), 3.60 (dd, J=43.0, 36.5 Hz, 4H), 3.31-3.22 (m, 4H), 3.12-3.01 (m, 2H), 2.91 (ddd, J=17.4, 14.3, 7.5 Hz, 1H), 2.84-2.75 (m, 1H), 2.56-2.46 (m, 1H), 2.33 (s, 2H), 2.21-2.14 (m, 1H), 1.69-1.60 (m, 2H), 1.52 (dt, J=18.4, 5.4 Hz, 4H), 1.37 (dt, J=15.7, 8.0 Hz, 2H). HRMS (ESI) m/z: calcd for $C_{41}H_{46}ClFN_7O_6S^+$ [M+H]$^+$, 818.2897; found, 818.2892.

Example 130

Preparation of 2-(4-((4-((3-chloro-4-fluorophenyl)amino)-7-methoxyquinazolin-6-yl)oxy)piperidin-1-yl)-N-(7-((2-(2,6-dioxopiperidin-3-yl)-1-oxoisoindolin-4-yl)thio)heptyl)acetamide (SIAIS293051)

Referring to the method of example 1, the target compound (SIAIS293051) was prepared by using Gefitinib derivative C and intermediate LM (SIAIS171135). (yellow solid, 8.5 mg, yield 46%). $^1$H NMR (500 MHz, MeOD) δ 8.72 (s, 1H), 8.31-8.21 (m, 1H), 7.99 (s, 1H), 7.72 (s, 1H), 7.61 (d, J=7.6 Hz, 2H), 7.53-7.48 (m, 1H), 7.36 (t, J=8.9 Hz, 1H), 7.26 (s, 1H), 5.16 (dd, J=13.3, 5.2 Hz, 1H), 5.03 (s, 1H), 4.44 (d, J=17.3 Hz, 1H), 4.38 (d, J=17.2 Hz, 1H), 4.09 (s, 3H), 4.00 (s, 2H), 3.46 (dd, J=10.8, 9.1 Hz, 6H), 3.25 (t, J=7.1 Hz, 2H), 3.08-3.03 (m, 2H), 2.90 (m, 1H), 2.82-2.76 (m, 1H), 2.55-2.48 (m, 1H), 2.34 (s, 2H), 2.19 (t, J=7.5 Hz, 1H), 1.64 (dd, J=14.8, 7.2 Hz, 2H), 1.52 (d, J=6.6 Hz, 2H), 1.46 (s, 2H), 1.33 (s, 4H). HRMS (ESI) m/z: calcd for $C_{42}H_{48}ClFN_7O_6S^+$ [M+H]$^+$, 832.3054; found, 832.3052.

Example 131

Preparation of 2-(4-((4-((3-chloro-4-fluorophenyl)amino)-7-methoxyquinazolin-6-yl)oxy)piperidin-1-yl)-N-(8-((2-(2,6-dioxopiperidin-3-yl)-1-oxoisoindolin-4-yl)thio)octyl)acetamide (SIAIS293052)

Referring to the method of example 1, the target compound (SIAIS293052) was prepared by using Gefitinib derivative C and intermediate LM (SIAIS171136). (yellow solid, 9.1 mg, yield 49%). $^1$H NMR (500 MHz, MeOD) δ 8.72 (s, 1H), 8.35 (s, 1H), 8.00 (dd, J=6.6, 2.6 Hz, 1H), 7.73 (s, 1H), 7.64-7.60 (m, 2H), 7.53-7.48 (m, 1H), 7.36 (t, J=8.9 Hz, 1H), 7.27 (s, 1H), 5.16 (dd, J=13.3, 5.2 Hz, 1H), 5.08 (s, 1H), 4.44 (d, J=17.3 Hz, 1H), 4.38 (d, J=17.3 Hz, 1H), 4.10 (s, 3H), 4.01 (s, 2H), 3.95-3.32 (m, 6H), 3.24 (dd, J=13.0, 5.9 Hz, 2H), 3.11-3.01 (m, 2H), 2.94-2.86 (m, 1H), 2.78 (m, 1H), 2.52 (dt, J=13.4, 8.6 Hz, 1H), 2.34 (s, 2H), 2.20-2.16 (m, 1H), 1.70-1.63 (m, 2H), 1.56-1.44 (m, 4H), 1.39-1.31 (m, 6H). HRMS (ESI) m/z: calcd for $C_{43}H_{50}ClFN_7O_6S^+$ [M+H]$^+$, 846.3210; found, 846.3217.

Example 132

Preparation of 2-(4-((4-((3-chloro-2-fluorophenyl)amino)-7-methoxyquinazolin-6-yl)oxy)piperidin-1-yl)-N-(4-((2-(2,6-dioxopiperidin-3-yl)-1-oxoisoindolin-4-yl)thio)butyl)acetamide (SIAIS293067)

Referring to the method of example 1, the target compound (SIAIS293067) was prepared by using Sapitinib derivative A and intermediate LM (SIAIS171131). (yellow solid, 9.1 mg, yield 49%). $^1$H NMR (500 MHz, MeOD) δ 8.70 (d, J=5.0 Hz, 1H), 8.40-8.26 (m, 1H), 7.69-7.62 (m, 2H), 7.53 (s, 3H), 7.31 (d, J=13.9 Hz, 2H), 5.14 (s, 1H), 4.42 (dd, J=30.2, 16.1 Hz, 2H), 4.11 (d, J=14.3 Hz, 3H), 3.97 (d, J=7.6 Hz, 2H), 3.67-3.36 (m, 5H), 3.09 (s, 2H), 2.95-2.84 (m, 1H), 2.78 (d, J=16.3 Hz, 1H), 2.58-2.43 (m, 2H), 2.33 (s, 2H), 2.18 (s, 1H), 2.09 (s, 1H), 1.70 (s, 4H). HRMS (ESI) m/z: calcd for $C_{39}H_{42}ClFN_7O_6S^+$ [M+H]$^+$, 790.2584; found, 790.2582.

Example 133

Preparation of 2-(4-((4-((3-chloro-2-fluorophenyl)amino)-7-methoxyquinazolin-6-yl)oxy)piperidin-1-yl)-N-(6-((2-(2,6-dioxopiperidin-3-yl)-1-oxoisoindolin-4-yl)thio)hexyl)acetamide (SIAIS293068)

Referring to the method of example 1, the target compound (SIAIS293068) was prepared by using Sapitinib derivative A and intermediate LM (SIAIS171134). (yellow solid, 9.1 mg, yield 49%). $^1$H NMR (500 MHz, MeOD) δ 8.70 (s, 1H), 8.30 (d, J=51.9 Hz, 1H), 7.62 (d, J=7.5 Hz, 2H), 7.55 (d, J=7.2 Hz, 3H), 7.31 (s, 2H), 5.15 (s, 1H), 4.45 (d, J=18.1 Hz, 1H), 4.39 (d, J=17.6 Hz, 1H), 4.11 (s, 3H), 4.00 (s, 2H), 3.81-3.42 (m, 5H), 3.05 (s, 2H), 2.90 (s, 1H), 2.78 (d, J=18.1 Hz, 1H), 2.52 (s, 1H), 2.34 (s, 2H), 2.22-1.90 (m, 3H), 1.75-1.71 (m, 2H), 1.50 (s, 4H), 1.36-1.32 (m, 4H). HRMS (ESI) m/z: calcd for $C_{41}H_{46}ClFN_7O_6S^+$ [M+H]$^+$, 818.2897; found, 818.2895.

Example 134

Preparation of 2-(4-((4-((3-chloro-2-fluorophenyl)amino)-7-methoxyquinazolin-6-yl)oxy)piperidin-1-yl)-N-(7-((2-(2,6-dioxopiperidin-3-yl)-1-oxoisoindolin-4-yl)thio)heptyl)acetamide (SIAIS293069)

Referring to the method of example 1, the target compound (SIAIS293069) was prepared by using Sapitinib derivative A and intermediate LM (SIAIS171135). (yellow solid, 9.1 mg, yield 49%). $^1$H NMR (500 MHz, MeOD) δ 8.69 (s, 1H), 8.23 (s, 1H), 7.63 (d, J=7.6 Hz, 2H), 7.53 (dq, J=14.8, 7.4 Hz, 3H), 7.32-7.27 (m, 2H), 5.17 (dd, J=13.2, 5.0 Hz, 1H), 4.45 (d, J=17.4 Hz, 1H), 4.39 (d, J=17.2 Hz, 1H), 4.11 (s, 3H), 4.00 (s, 2H), 3.48 (dd, J=57.2, 32.1 Hz, 5H), 3.24 (t, J=7.0 Hz, 2H), 3.10-3.01 (m, 2H), 2.94-2.87 (m, 1H), 2.79 (d, J=16.0 Hz, 1H), 2.60-2.45 (m, 2H), 2.36 (s, 2H), 2.20-2.07 (m, 2H), 1.69-1.62 (m, 2H), 1.50 (dd, J=18.8, 11.8 Hz, 4H), 1.35 (s, 4H). HRMS (ESI) m/z: calcd for $C_{42}H_{48}ClFN_7O_6S^+$ [M+H]$^+$, 832.3054; found, 832.3044.

Example 135

Preparation of 2-(4-((4-((3-chloro-2-fluorophenyl)amino)-7-methoxyquinazolin-6-yl)oxy)piperidin-1-yl)-N-(8-((2-(2,6-dioxopiperidin-3-yl)-1-oxoisoindolin-4-yl)thio)octyl)acetamide (SIAIS293070)

Referring to the method of example 1, the target compound (SIAIS293070) was prepared by using Sapitinib derivative A and intermediate LM (SIAIS171136). (yellow solid, 9.1 mg, yield 49%). $^1$H NMR (500 MHz, MeOD) δ 8.67 (s, 1H), 8.21 (s, 1H), 7.62 (d, J=7.6 Hz, 2H), 7.53-7.48 (m, 3H), 7.33-7.27 (m, 2H), 5.18 (dd, J=13.2, 5.0 Hz, 1H), 4.46 (d, J=17.4 Hz, 1H), 4.36 (d, J=17.2 Hz, 1H), 4.10 (s, 3H), 4.00 (s, 2H), 3.47-3.43 (m, 5H), 3.23 (t, J=7.0 Hz, 2H), 3.10-3.01 (m, 2H), 2.93-2.87 (m, 1H), 2.77 (d, J=16.0 Hz, 1H), 2.60-2.46 (m, 2H), 2.34 (s, 2H), 2.21-2.07 (m, 2H), 1.68-1.62 (m, 2H), 1.50-1.44 (m, 4H), 1.35 (s, 4H). HRMS (ESI) m/z: calcd for $C_{43}H_{50}ClFN_7O_6S^+$ [M+H]$^+$, 846.3210; found, 846.3212.

Example 136

Preparation of N-(2-((2-(2-((2-(2,6-dioxopiperidin-3-yl)-1-oxoisoindolin-4-yl)thio)-N-methylacetamido)ethyl)(methyl)amino)-4-methoxy-5-((4-(1-methyl-1H-indol-3-yl)pyrimidin-2-yl)amino)phenyl)acrylamide (SIAIS337052)

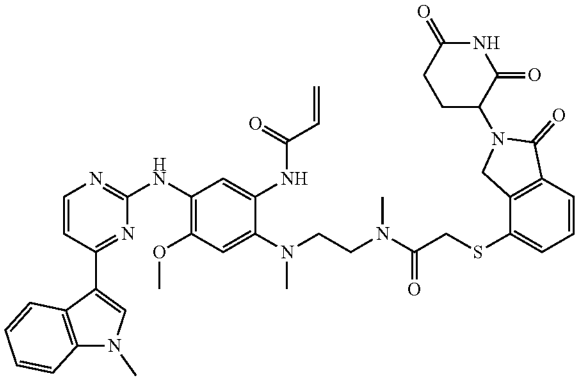 [SMILES: C=CC(=O)Nc1cc(Nc2nccc(-c3cn(C)c4ccccc34)n2)c(OC)cc1N(C)CCN(C)C(=O)CSc1cccc2c1CN(C1CCC(=O)NC1=O)C2=O]

Referring to the method of example 1, the target compound (SIAIS337052) was prepared by using Osimertinib derivative SIAIS337051 and intermediate LM (SIAIS171090). (yellow solid, 9.2 mg, yield 45%). $^1$H NMR (500 MHz, DMSO-$d_6$) δ 10.98 (d, J=7.0 Hz, 1H), 9.28 (s, 1H), 8.82 (s, 1H), 8.22 (s, 2H), 7.66 (d, J=7.7 Hz, 1H), 7.58 (t, J=9.4 Hz, 2H), 7.50 (dt, J=15.4, 7.7 Hz, 1H), 7.44-7.38 (m, 1H), 7.30 (s, 1H), 7.19 (s, 1H), 7.05 (d, J=38.4 Hz, 1H), 6.69 (dt, J=19.8, 9.5 Hz, 1H), 6.19 (d, J=17.1 Hz, 1H), 5.69 (d, J=10.3 Hz, 1H), 5.12 (dd, J=13.4, 5.2 Hz, 1H), 4.39 (d, J=17.5 Hz, 1H), 4.25 (d, J=17.3 Hz, 1H), 4.11 (s, 2H), 3.93 (s, 3H), 3.82 (s, 3H), 3.50 (d, J=7.1 Hz, 4H), 3.03 (s, 2H), 2.90 (t, J=13.8 Hz, 1H), 2.84-2.74 (m, 4H), 2.59 (s, 1H), 2.43 (s, 1H), 2.02-1.96 (m, 1H). HRMS (ESI) m/z: calcd for $C_{42}H_{44}N_9O_6S^+$ [M+H]$^+$, 802.3130; found, 802.3132.

Example 137

Preparation of N-(2-((2-(3-((2-(2,6-dioxopiperidin-3-yl)-1-oxoisoindolin-4-yl)thio)-N-methylpropanamido)ethyl)(methyl)amino)-4-methoxy-5-((4-(1-methyl-1H-indol-3-yl)pyrimidin-2-yl)amino)phenyl)acrylamide (SIAIS337053)

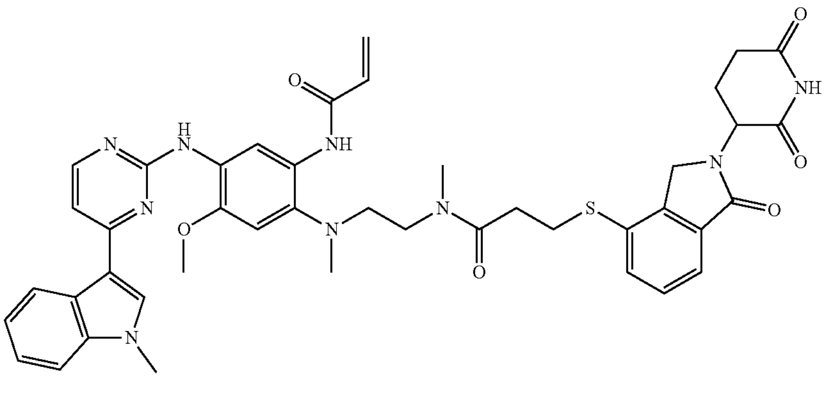 [SMILES: C=CC(=O)Nc1cc(Nc2nccc(-c3cn(C)c4ccccc34)n2)c(OC)cc1N(C)CCN(C)C(=O)CCSc1cccc2c1CN(C1CCC(=O)NC1=O)C2=O]

Referring to the method of example 1, the target compound (SIAIS337053) was prepared by using Osimertinib derivative SIAIS337051 and intermediate LM (SIAIS171086). (yellow solid, 9.7 mg, yield 44%). $^1$H NMR (500 MHz, DMSO-$d_6$) δ 10.98 (s, 1H), 9.25 (s, 1H), 8.82 (s, 1H), 8.22 (s, 2H), 7.57 (ddt, J=26.7, 15.6, 8.4 Hz, 4H), 7.41 (d, J=6.7 Hz, 1H), 7.29 (d, J=8.6 Hz, 1H), 7.19 (s, 1H), 7.02 (d, J=22.5 Hz, 1H), 6.70 (dd, J=16.9, 9.9 Hz, 1H), 6.19 (d, J=17.0 Hz, 1H), 5.71 (d, J=10.8 Hz, 1H), 5.11 (dd, J=13.4, 6.0 Hz, 1H), 4.32 (d, J=17.1 Hz, 1H), 4.19 (d, J=8.6 Hz, 1H), 3.93 (s, 3H), 3.84 (s, 3H), 3.52-3.38 (m, 4H), 3.23 (d, J=8.0 Hz, 2H), 3.13 (s, 1H), 2.86 (s, 3H), 2.80 (d, J=6.5 Hz, 3H), 2.71-2.61 (m, 3H), 2.40 (s, 1H), 1.98 (s, 1H). HRMS (ESI) m/z: calcd for $C_{43}H_{46}N_9O_6S^+$ [M+H]$^+$, 816.3286; found, 816.3277.

Example 138

Preparation of N-(2-((2-acrylamido-5-methoxy-4-((4-(1-methyl-1H-indol-3-yl)pyrimidin-2-yl)amino)phenyl)(methyl)amino)ethyl)-4-((2-(2,6-dioxopiperidin-3-yl)-1-oxoisoindolin-4-yl)thio)-N-methylbutanamide (SIAIS337054)

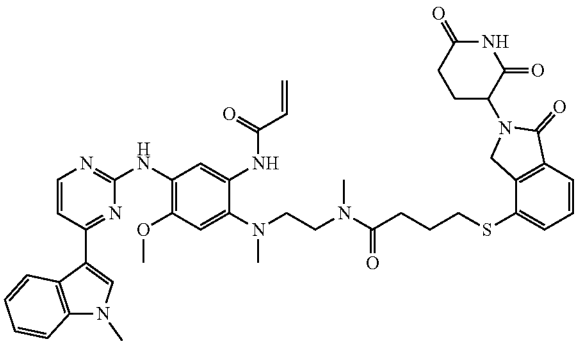 [SMILES: C=CC(=O)Nc1cc(Nc2nccc(-c3cn(C)c4ccccc34)n2)c(OC)cc1N(C)CCN(C)C(=O)CCCSc1cccc2c1CN(C1CCC(=O)NC1=O)C2=O]

Referring to the method of example 1, the target compound (SIAIS337054) was prepared by using Osimertinib derivative SIAIS337051 and intermediate LM (SIAIS171089). (yellow solid, 9.5 mg, yield 51%). $^1$H NMR (500 MHz, DMSO-$d_6$) δ 10.98 (s, 1H), 9.32 (s, 1H), 8.81 (s, 1H), 8.22 (s, 2H), 7.65 (d, J=7.5 Hz, 1H), 7.58-7.52 (m, 3H), 7.40 (t, J=6.2 Hz, 1H), 7.29 (d, J=8.2 Hz, 1H), 7.18 (s, 1H), 7.07 (s, 1H), 6.75-6.63 (m, 1H), 6.24-6.15 (m, 1H), 5.70 (d, J=10.3 Hz, 1H), 5.11 (dd, J=12.9, 6.3 Hz, 1H), 4.34 (d, J=17.3 Hz, 1H), 4.20 (d, J=17.3 Hz, 1H), 3.93 (s, 3H), 3.83 (s, 3H), 3.49 (d, J=6.9 Hz, 4H), 3.16-3.09 (m, 2H), 3.00 (s, 1H), 2.89 (s, 3H), 2.80 (s, 3H), 2.43-2.33 (m, 3H), 2.01-1.98 (m, 1H), 1.84-1.72 (m, 2H). HRMS (ESI) m/z: calcd for $C_{44}H_{48}N_9O_6S^+$ [M+H]$^+$, 830.3443; found, 830.3441.

Example 139

Preparation of N-(2-((2-acrylamido-5-methoxy-4-((4-(1-methyl-1H-indol-3-yl)pyrimidin-2-yl)amino)phenyl)(methyl)amino)ethyl)-5-((2-(2,6-dioxopiperidin-3-yl)-1-oxoisoindolin-4-yl)thio)-N-methylpentanamide (SIAIS337055)

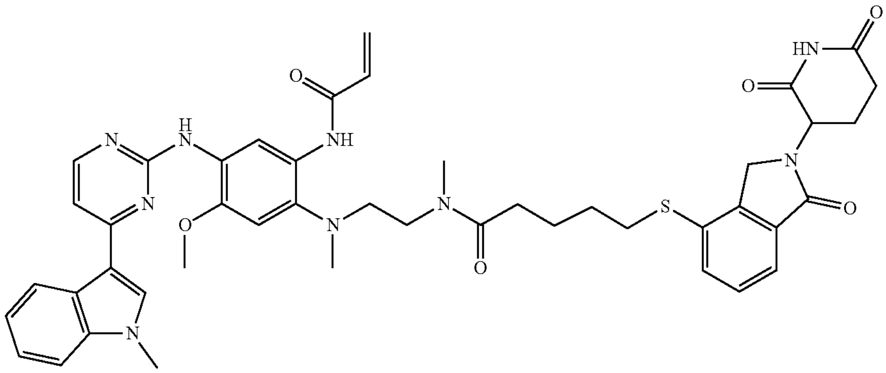 [SMILES: C=CC(=O)Nc1cc(Nc2nccc(-c3cn(C)c4ccccc34)n2)c(OC)cc1N(C)CCN(C)C(=O)CCCCSc1cccc2c1CN(C1CCC(=O)NC1=O)C2=O]

Referring to the method of example 1, the target compound (SIAIS337055) was prepared by using Osimertinib derivative SIAIS337051 and intermediate LM (SIAIS171079). (yellow solid, 9.9 mg, yield 48%). $^1$H NMR (500 MHz, DMSO-$d_6$) δ 10.99 (s, 1H), 9.28 (s, 1H), 8.82 (s, 1H), 8.23 (s, 2H), 7.64 (d, J=7.5 Hz, 1H), 7.58-7.53 (m, 3H), 7.41 (t, J=6.2 Hz, 1H), 7.28 (d, J=8.2 Hz, 1H), 7.18 (s, 1H), 7.08 (s, 1H), 6.76-6.63 (m, 1H), 6.25-6.15 (m, 1H), 5.71 (d, J=10.3 Hz, 1H), 5.13 (dd, J=12.9, 6.3 Hz, 1H), 4.36 (d, J=17.3 Hz, 1H), 4.22 (d, J=17.3 Hz, 1H), 3.95 (s, 3H), 3.84 (s, 3H), 3.51-3.47 (m, 4H), 3.17-3.09 (m, 2H), 3.01 (s, 1H), 2.89 (s, 3H), 2.82 (s, 3H), 2.44-2.33 (m, 3H), 2.02-1.99 (m, 1H), 1.86-1.72 (m, 4H). HRMS (ESI) m/z: calcd for $C_{45}H_{50}N_9O_6S^+$ [M+H]$^+$, 844.3599; found, 844.3601.

Example 140

Preparation of N-(2-((2-acrylamido-5-methoxy-4-((4-(1-methyl-1H-indol-3-yl)pyrimidin-2-yl)amino)phenyl)(methyl)amino)ethyl)-6-((2-(2,6-dioxopiperidin-3-yl)-1-oxoisoindolin-4-yl)thio)-N-methylhexanamide (SIAIS337056)

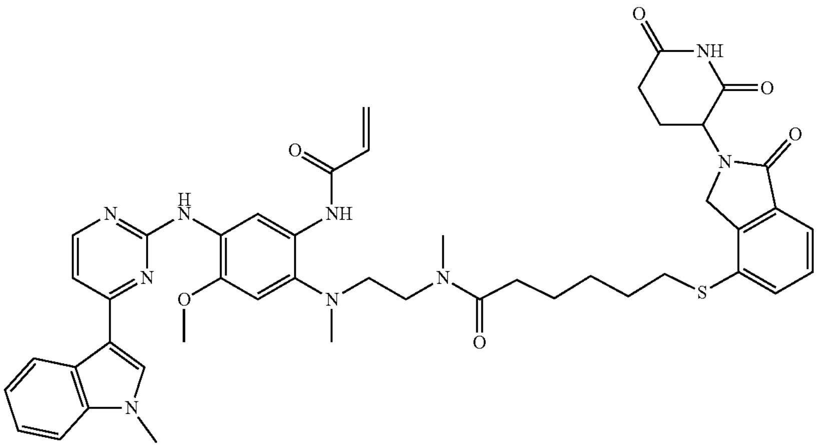 [SMILES: C=CC(=O)Nc1cc(Nc2nccc(-c3cn(C)c4ccccc34)n2)c(OC)cc1N(C)CCN(C)C(=O)CCCCCSc1cccc2c1CN(C1CCC(=O)NC1=O)C2=O]

Referring to the method of example 1, the target compound (SIAIS337056) was prepared by using Osimertinib derivative SIAIS337051 and intermediate LM (SIAIS171091). (yellow solid, 9.3 mg, yield 43%). $^1$H NMR (500 MHz, DMSO-$d_6$) δ 10.97 (s, 1H), 9.25 (s, 1H), 8.84 (s, 1H), 8.25 (s, 2H), 7.66 (d, J=7.5 Hz, 1H), 7.56-7.53 (m, 3H), 7.42 (t, J=6.2 Hz, 1H), 7.29 (d, J=8.2 Hz, 1H), 7.16 (s, 1H), 7.05 (s, 1H), 6.77-6.63 (m, 1H), 6.24-6.15 (m, 1H), 5.72 (d, J=10.3 Hz, 1H), 5.14 (dd, J=12.9, 6.3 Hz, 1H), 4.35 (d, J=17.3 Hz, 1H), 4.24 (d, J=17.3 Hz, 1H), 3.97 (s, 3H), 3.85 (s, 3H), 3.51-3.46 (m, 4H), 3.18-3.11 (m, 2H), 3.04 (s, 1H), 2.88 (s, 3H), 2.83 (s, 3H), 2.45-2.33 (m, 3H), 2.03-1.99 (m, 1H), 1.88-1.71 (m, 6H). HRMS (ESI) m/z: calcd for $C_{46}H_{52}N_9O_6S^+$ [M+H]$^+$, 858.3756; found, 858.3759.

Example 141

Preparation of N-(2-((2-acrylamido-5-methoxy-4-((4-(1-methyl-1H-indol-3-yl)pyrimidin-2-yl)amino)phenyl)(methyl)amino)ethyl)-7-((2-(2,6-dioxopiperidin-3-yl)-1-oxoisoindolin-4-yl)thio)-N-methylheptanamide (SIAIS337057)

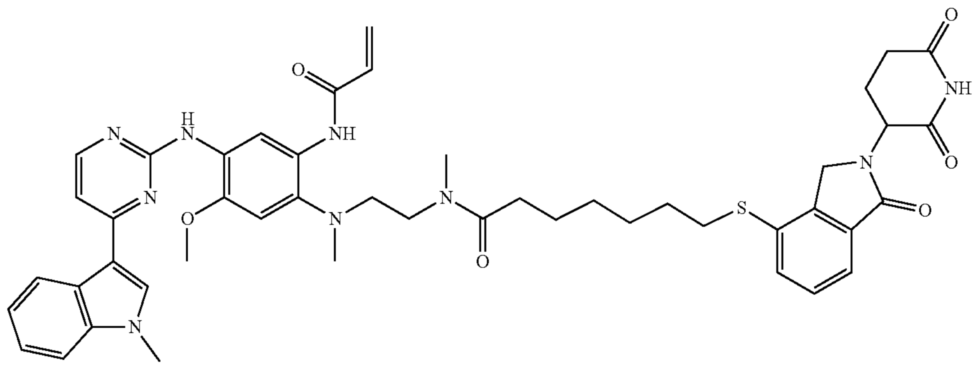 [SMILES: C=CC(=O)Nc1cc(Nc2nccc(-c3cn(C)c4ccccc34)n2)c(OC)cc1N(C)CCN(C)C(=O)CCCCCCSc1cccc2c1CN(C1CCC(=O)NC1=O)C2=O]

Referring to the method of example 1, the target compound (SIAIS337057) was prepared by using Osimertinib derivative SIAIS337051 and intermediate LM (SIAIS171092). (yellow solid, 8.8 mg, yield 43%). $^1$H NMR (500 MHz, DMSO-$d_6$) δ 10.99 (s, 1H), 9.26 (s, 1H), 8.84 (s, 1H), 8.26 (s, 2H), 7.68 (d, J=7.5 Hz, 1H), 7.57-7.53 (m, 3H), 7.43 (t, J=6.2 Hz, 1H), 7.28 (d, J=8.2 Hz, 1H), 7.15 (s, 1H), 7.07 (s, 1H), 6.79-6.63 (m, 1H), 6.26-6.15 (m, 1H), 5.71 (d, J=10.3 Hz, 1H), 5.14 (dd, J=12.9, 6.3 Hz, 1H), 4.36 (d, J=17.3 Hz, 1H), 4.25 (d, J=17.3 Hz, 1H), 3.98 (s, 3H), 3.86 (s, 3H), 3.52-3.46 (m, 4H), 3.19-3.11 (m, 2H), 3.05 (s, 1H), 2.89 (s, 3H), 2.84 (s, 3H), 2.46-2.33 (m, 3H), 2.04-1.98 (m, 1H), 1.89-1.71 (m, 8H). HRMS (ESI) m/z: calcd for $C_{47}H_{54}N_9O_6S^+$ [M+H]$^+$, 872.3912; found, 872.3904.

Example 142

Preparation of N-(2-((2-acrylamido-5-methoxy-4-((4-(1-methyl-1H-indol-3-yl)pyrimidin-2-yl)amino)phenyl)(methyl)amino)ethyl)-9-((2-(2,6-dioxopiperidin-3-yl)-1-oxoisoindolin-4-yl)thio)-N-methylnonanamide (SIAIS337059)

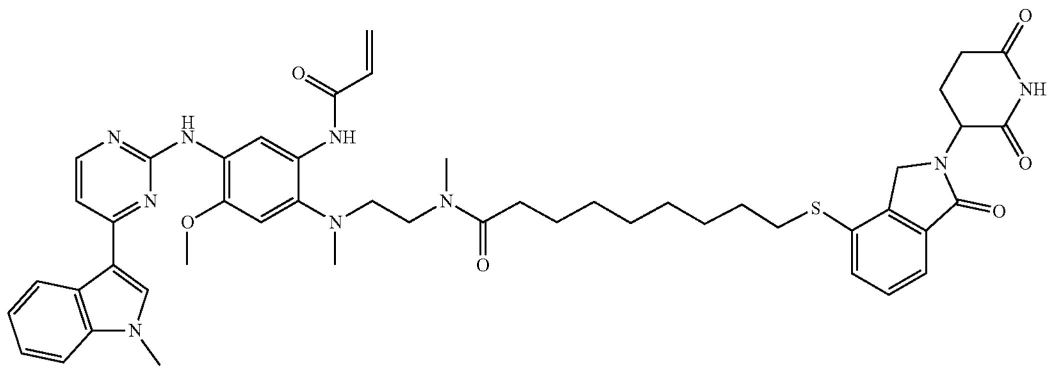 [SMILES: C=CC(=O)Nc1cc(Nc2nccc(-c3cn(C)c4ccccc34)n2)c(OC)cc1N(C)CCN(C)C(=O)CCCCCCCCSc1cccc2c1CN(C1CCC(=O)NC1=O)C2=O]

Referring to the method of example 1, the target compound (SIAIS337059) was prepared by using Osimertinib derivative SIAIS337051 and intermediate LM (SIAIS299138). (yellow solid, 7.9 mg, yield 38%). 1H NMR (500 MHz, DMSO-$d_6$) δ 10.97 (s, 1H), 9.25 (s, 1H), 8.83 (s, 1H), 8.25 (s, 2H), 7.67 (d, J=7.5 Hz, 1H), 7.58-7.53 (m, 3H), 7.42-7.40 (m, 1H), 7.26 (d, J=8.2 Hz, 1H), 7.14 (s, 1H), 7.09 (s, 1H), 6.77-6.63 (m, 1H), 6.28-6.15 (m, 1H), 5.72 (d, J=10.3 Hz, 1H), 5.16 (dd, J=12.9, 6.3 Hz, 1H), 4.33 (d, J=17.3 Hz, 1H), 4.23 (d, J=17.3 Hz, 1H), 3.97 (s, 3H), 3.84 (s, 3H), 3.55-3.46 (m, 4H), 3.18-3.11 (m, 2H), 3.06 (s, 1H), 2.87 (s, 3H), 2.83 (s, 3H), 2.48-2.33 (m, 3H), 2.02-1.98 (m, 1H), 1.86-1.70 (m, 10H). HRMS (ESI) m/z: calcd for $C_{49}H_{58}N_9O_6S^+$ $[M+H]^+$, 900.4225; found, 900.4217.

Example 143

Preparation of N-(2-((2-acrylamido-5-methoxy-4-((4-(1-methyl-1H-indol-3-yl)pyrimidin-2-yl)amino)phenyl)(methyl)amino)ethyl)-10-((2-(2,6-dioxopiperidin-3-yl)-1-oxoisoindolin-4-yl)thio)-N-methyldecanamide (SIAIS337060)

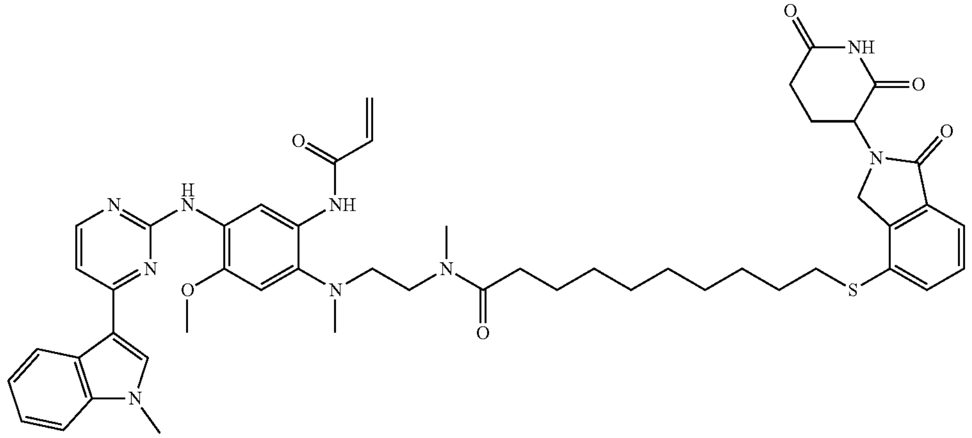 [SMILES: C=CC(=O)Nc1cc(Nc2nccc(-c3cn(C)c4ccccc34)n2)c(OC)cc1N(C)CCN(C)C(=O)CCCCCCCCCSc1cccc2c1CN(C1CCC(=O)NC1=O)C2=O]

Referring to the method of example 1, the target compound (SIAIS337060) was prepared by using Osimertinib derivative SIAIS337051 and intermediate LM (SIAIS299135). (yellow solid, 9.5 mg, yield 42%). $^1H$ NMR (500 MHz, DMSO-$d_6$) δ 10.99 (s, 1H), 9.26 (s, 1H), 8.85 (s, 1H), 8.27 (s, 2H), 7.68 (d, J=7.5 Hz, 1H), 7.59-7.53 (m, 3H), 7.46-7.40 (m, 1H), 7.25 (d, J=8.2 Hz, 1H), 7.13 (s, 1H), 7.08 (s, 1H), 6.79-6.63 (m, 1H), 6.26-6.15 (m, 1H), 5.71 (d, J=10.3 Hz, 1H), 5.13 (dd, J=12.9, 6.3 Hz, 1H), 4.34 (d, J=17.3 Hz, 1H), 4.25 (d, J=17.3 Hz, 1H), 3.98 (s, 3H), 3.83 (s, 3H), 3.57-3.46 (m, 4H), 3.19-3.13 (m, 2H), 3.08 (s, 1H), 2.88 (s, 3H), 2.85 (s, 3H), 2.49-2.33 (m, 3H), 2.03-1.99 (m, 1H), 1.87-1.70 (m, 12H). HRMS (ESI) m/z: calcd for $C_{50}H_{60}N_9O_6S^+$ $[M+H]^+$, 914.4382; found, 914.4386.

Example 144

Preparation of N-(2-((2-acrylamido-5-methoxy-4-((4-(1-methyl-1H-indol-3-yl)pyrimidin-2-yl)amino)phenyl)(methyl)amino)ethyl)-11-((2-(2,6-dioxopiperidin-3-yl)-1-oxoisoindolin-4-yl)thio)-N-methylundecanamide (SIAIS337061)

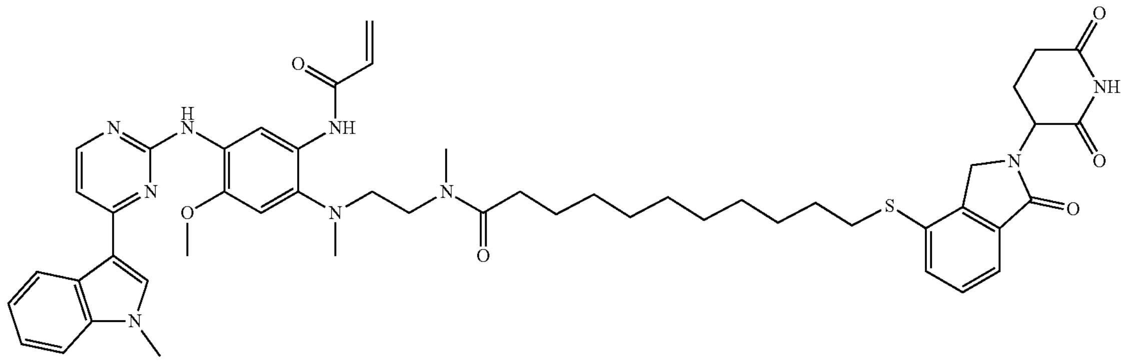 [SMILES: C=CC(=O)Nc1cc(Nc2nccc(-c3cn(C)c4ccccc34)n2)c(OC)cc1N(C)CCN(C)C(=O)CCCCCCCCCCSc1cccc2c1CN(C1CCC(=O)NC1=O)C2=O]

Referring to the method of example 1, the target compound (SIAIS337061) was prepared by using Osimertinib derivative SIAIS337051 and intermediate LM (SIAIS122009). (yellow solid, 9.7 mg, yield 43%). $^1$H NMR (500 MHz, DMSO-$d_6$) δ 10.98 (s, 1H), 9.25 (s, 1H), 8.84 (s, 1H), 8.27 (s, 2H), 7.69 (d, J=7.5 Hz, 1H), 7.58-7.53 (m, 3H), 7.48-7.40 (m, 1H), 7.27 (d, J=8.2 Hz, 1H), 7.14 (s, 1H), 7.09 (s, 1H), 6.79-6.65 (m, 1H), 6.28-6.15 (m, 1H), 5.72 (d, J=10.3 Hz, 1H), 5.15 (dd, J=12.9, 6.3 Hz, 1H), 4.35 (d, J=17.3 Hz, 1H), 4.26 (d, J=17.3 Hz, 1H), 3.99 (s, 3H), 3.85 (s, 3H), 3.59-3.46 (m, 4H), 3.19-3.12 (m, 2H), 3.08 (s, 1H), 2.89 (s, 3H), 2.87 (s, 3H), 2.49-2.36 (m, 3H), 2.04-2.00 (m, 1H), 1.89-1.70 (m, 14H). HRMS (ESI) m/z: calcd for $C_{51}H_{62}N_9O_6S^+$ [M+H]$^+$, 928.4538; found, 928.4544.

Example 145

Preparation of N-(2-((2-(2-(2-((2-(2,6-dioxopiperidin-3-yl)-1-oxoisoindolin-4-yl)thio)ethoxy)-N-methylacetamido)ethyl)(methyl)amino)-4-methoxy-5-((4-(1-methyl-1H-indol-3-yl)pyrimidin-2-yl)amino)phenyl)acrylamide (SIAIS337074)

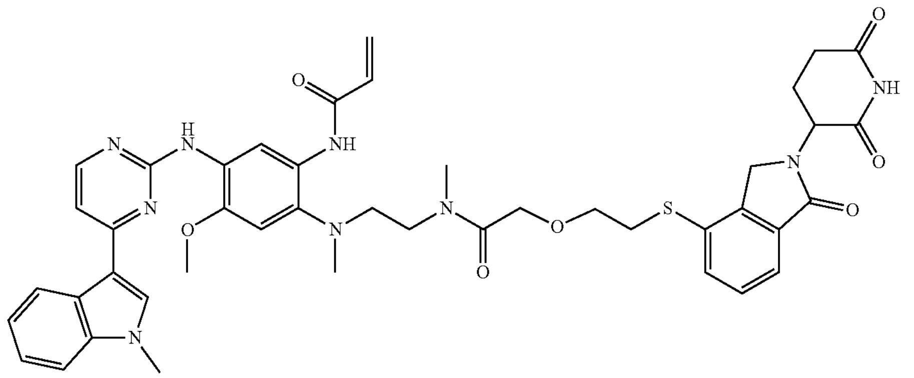 [SMILES: C=CC(=O)Nc1cc(Nc2nccc(-c3cn(C)c4ccccc34)n2)c(OC)cc1N(C)CCN(C)C(=O)COCCSc1cccc2c1CN(C1CCC(=O)NC1=O)C2=O]

Referring to the method of example 1, the target compound (SIAIS337074) was prepared by using Osimertinib derivative SIAIS337051 and intermediate LM (SIAIS1213129). (yellow solid, 9.8 mg, yield 44%). $^1$H NMR (500 MHz, Methanol-$d_4$) δ 8.58 (s, 1H), 8.13-8.01 (m, 2H), 7.56-7.25 (m, 8H), 7.15 (s, 1H), 6.61 (d, J=11.8 Hz, 1H), 6.49 (d, J=16.8 Hz, 1H), 5.93 (d, J=9.7 Hz, 1H), 5.17 (dd, J=13.2, 5.0 Hz, 1H), 4.39-4.26 (m, 4H), 3.98 (d, J=8.6 Hz, 3H), 3.89 (s, 3H), 3.75-3.55 (m, 8H), 3.07 (d, J=19.0 Hz, 6H), 2.87-2.79 (m, 1H), 2.74-2.70 (m, 1H), 2.43-2.39 (m, 1H), 2.09 (s, 1H). HRMS (ESI) m/z: calcd for $C_{44}H_{48}N_9O_7S^+$ [M+H]$^+$, 846.3392; found, 846.3395.

Example 146

Preparation of N-(2-((2-(2-(2-(2-((2-(2,6-dioxopiperidin-3-yl)-1-oxoisoindolin-4-yl)thio)ethoxy)ethoxy)-N-methylacetamido)ethyl)(methyl)amino)-4-methoxy-5-((4-(1-methyl-1H-indol-3-yl)pyrimidin-2-yl)amino)phenyl)acrylamide (SIAIS337075)

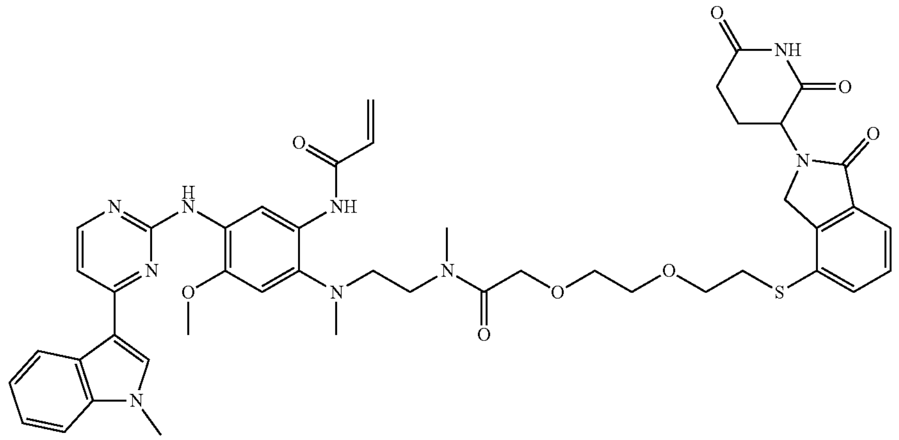 [SMILES: C=CC(=O)Nc1cc(Nc2nccc(-c3cn(C)c4ccccc34)n2)c(OC)cc1N(C)CCN(C)C(=O)COCCOCCSc1cccc2c1CN(C1CCC(=O)NC1=O)C2=O]

Referring to the method of example 1, the target compound (SIAIS337075) was prepared by using Osimertinib derivative SIAIS337051 and intermediate LM (SIAIS1213131). (yellow solid, 8.8 mg, yield 41%). $^1$H NMR (500 MHz, Methanol-$d_4$) δ 8.59 (s, 1H), 8.14-8.01 (m, 2H), 7.58-7.25 (m, 8H), 7.17 (s, 1H), 6.60 (d, J=11.8 Hz, 1H), 6.48 (d, J=16.8 Hz, 1H), 5.92 (d, J=9.7 Hz, 1H), 5.16 (dd, J=13.2, 5.0 Hz, 1H), 4.37-4.25 (m, 4H), 3.97 (d, J=8.6 Hz, 3H), 3.88 (s, 3H), 3.74-3.52 (m, 12H), 3.05 (d, J=19.0 Hz, 6H), 2.86-2.78 (m, 1H), 2.73-2.70 (m, 1H), 2.42-2.39 (m, 1H), 2.07 (s, 1H). HRMS (ESI) m/z: calcd for $C_{46}H_{52}N_9O_8S^+$ [M+H]$^+$, 890.3654; found, 890.3658.

Example 147

Preparation of N-(2-((14-((2-(2,6-dioxopiperidin-3-yl)-1-oxoisoindolin-4-yl)thio)-3-methyl-4-oxo-6,9,12-trioxa-3-azatetradecyl)(methyl)amino)-4-methoxy-5-((4-(1-methyl-1H-indol-3-yl)pyrimidin-2-yl)amino)phenyl)acrylamide (SIAIS337076)

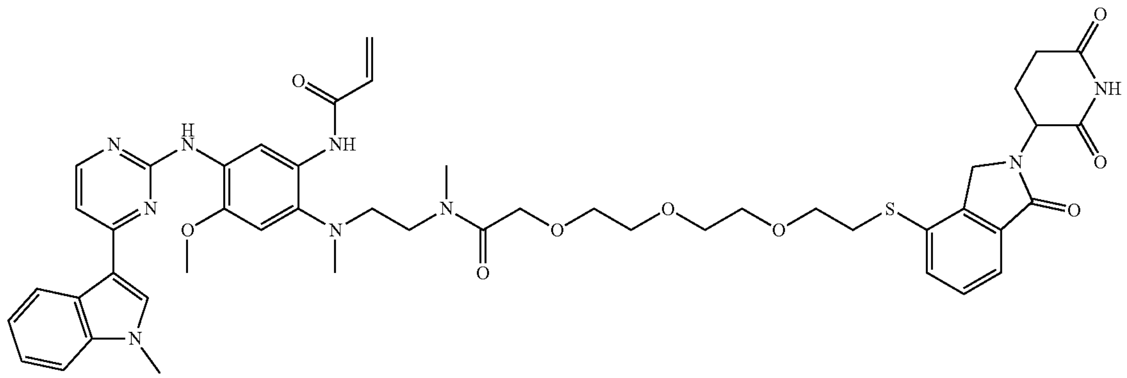 [SMILES: C=CC(=O)Nc1cc(Nc2nccc(-c3cn(C)c4ccccc34)n2)c(OC)cc1N(C)CCN(C)C(=O)COCCOCCOCCSc1cccc2c1CN(C1CCC(=O)NC1=O)C2=O]

Referring to the method of example 1, the target compound (SIAIS337076) was prepared by using Osimertinib derivative SIAIS337051 and intermediate LM (SIAIS1213133). (yellow solid, 10.1 mg, yield 39%). $^1$H NMR (500 MHz, Methanol-$d_4$) δ 8.60 (s, 1H), 8.15-8.02 (m, 2H), 7.59-7.25 (m, 8H), 7.19 (s, 1H), 6.61 (d, J=11.8 Hz, 1H), 6.50 (d, J=16.8 Hz, 1H), 5.94 (d, J=9.7 Hz, 1H), 5.18 (dd, J=13.2, 5.0 Hz, 1H), 4.38-4.22 (m, 4H), 3.98 (d, J=8.6 Hz, 3H), 3.92 (s, 3H), 3.76-3.52 (m, 16H), 3.07 (d, J=19.0 Hz, 6H), 2.87-2.79 (m, 1H), 2.71 (d, J=17.7 Hz, 1H), 2.43-2.40 (m, 1H), 2.08 (s, 1H). HRMS (ESI) m/z: calcd for $C_{48}H_{56}N_9O_9S^+$ [M+H]$^+$, 934.3916; found, 934.3919.

Example 148

Preparation of N-(2-((2-acrylamido-5-methoxy-4-((4-(1-methyl-1H-indol-3-yl)pyrimidin-2-yl)amino)phenyl)(methyl)amino)ethyl)-14-((2-(2,6-dioxopiperidin-3-yl)-1-oxoisoindolin-4-yl)thio)-N-methyl-3,6,9,12-tetraoxatetradecanamide (SIAIS337077)

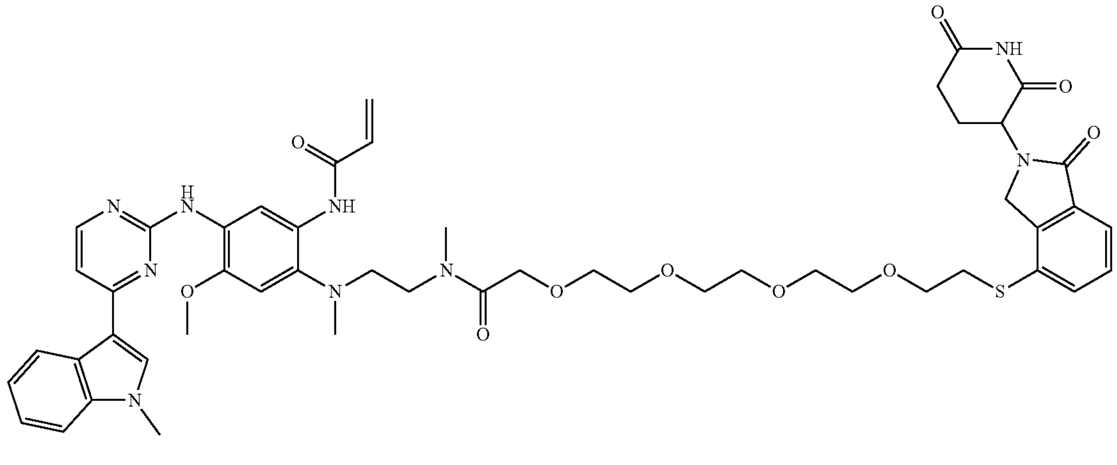 [SMILES: C=CC(=O)Nc1cc(Nc2nccc(-c3cn(C)c4ccccc34)n2)c(OC)cc1N(C)CCN(C)C(=O)COCCOCCOCCOCCSc1cccc2c1CN(C1CCC(=O)NC1=O)C2=O]

Referring to the method of example 1, the target compound (SIAIS337077) was prepared by using Osimertinib derivative SIAIS337051 and intermediate LM (SIAIS1213135). (yellow solid, 10.9 mg, yield 43%). $^1$H NMR (500 MHz, Methanol-$d_4$) δ 8.62 (s, 1H), 8.17-8.02 (m, 2H), 7.61-7.26 (m, 8H), 7.21 (s, 1H), 6.63 (d, J=11.8 Hz, 1H), 6.51 (d, J=16.8 Hz, 1H), 5.96 (d, J=9.7 Hz, 1H), 5.17 (dd, J=13.2, 5.0 Hz, 1H), 4.39-4.24 (m, 4H), 3.99 (d, J=8.6 Hz, 3H), 3.94 (s, 3H), 3.78-3.52 (m, 20H), 3.09-3.05 (m, 6H), 2.88-2.79 (m, 1H), 2.72 (d, J=17.7 Hz, 1H), 2.45-2.41 (m, 1H), 2.09 (s, 1H). HRMS (ESI) m/z: calcd for $C_{50}H_{60}N_9O_{10}S^+$ [M+H]$^+$, 978.4178; found, 978.4172.

Example 149

Preparation of N-(2-((2-acrylamido-5-methoxy-4-((4-(1-methyl-1H-indol-3-yl)pyrimidin-2-yl)amino)phenyl)(methyl)amino)ethyl)-17-((2-(2,6-dioxopiperidin-3-yl)-1-oxoisoindolin-4-yl)thio)-N-methyl-3,6,9,12,15-pentaoxaheptadecanamide (SIAIS337078)

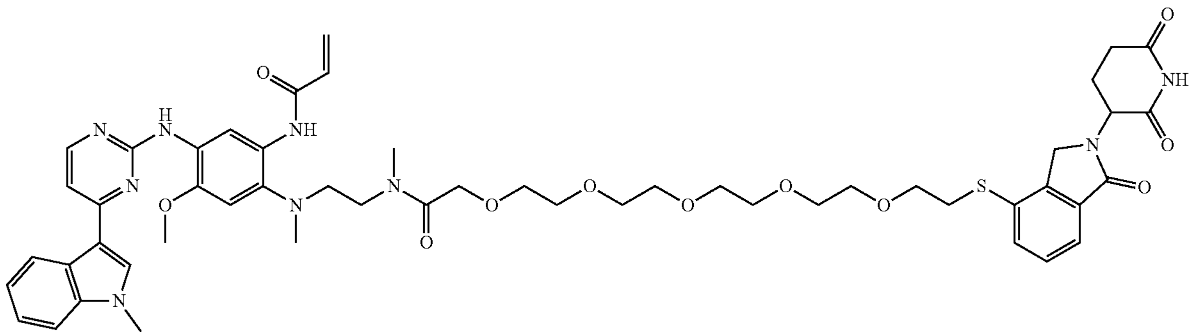 [SMILES: C=CC(=O)Nc1cc(Nc2nccc(-c3cn(C)c4ccccc34)n2)c(OC)cc1N(C)CCN(C)C(=O)COCCOCCOCCOCCOCCSc1cccc2c1CN(C1CCC(=O)NC1=O)C2=O]

Referring to the method of example 1, the target compound (SIAIS337078) was prepared by using Osimertinib derivative SIAIS337051 and intermediate LM (SIAIS1213137). (yellow solid, 9.9 mg, yield 34%). $^1$H NMR (500 MHz, Methanol-$d_4$) δ 8.61 (s, 1H), 8.16-8.02 (m, 2H), 7.60-7.31 (m, 8H), 7.22 (s, 1H), 6.62 (d, J=11.8 Hz, 1H), 6.50 (d, J=16.8 Hz, 1H), 5.95 (d, J=9.7 Hz, 1H), 5.16 (dd, J=13.2, 5.0 Hz, 1H), 4.38-4.27 (m, 4H), 3.98 (d, J=8.6 Hz, 3H), 3.93 (s, 3H), 3.77-3.52 (m, 24H), 3.08-3.05 (m, 6H), 2.87-2.79 (m, 1H), 2.73 (d, J=17.7 Hz, 1H), 2.45-2.41 (m, 1H), 2.08 (s, 1H). HRMS (ESI) m/z: calcd for $C_{52}H_{64}N_9O_{11}S^+$ [M+H]$^+$, 1022.4441; found, 1022.4437.

Example 150

Preparation of N-(2-((2-((3-((2-(2,6-dioxopiperidin-3-yl)-1-oxoisoindolin-4-yl)thio)propyl)(methyl)amino)ethyl)(methyl)amino)-4-methoxy-5-((4-(1-methyl-1H-indol-3-yl)pyrimidin-2-yl)amino)phenyl)acrylamide (SIAIS337079)

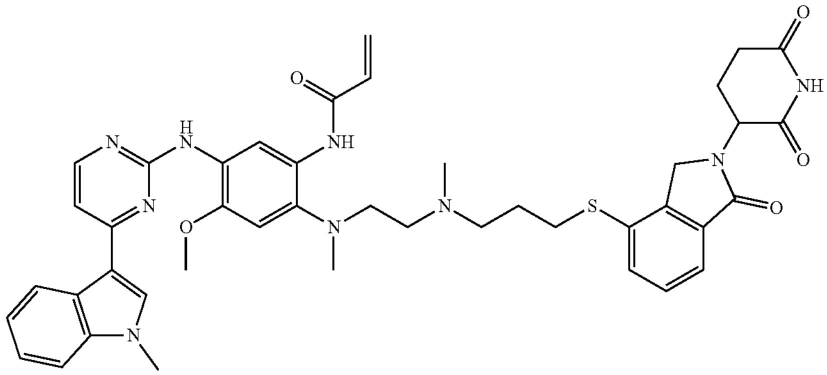 [SMILES: C=CC(=O)Nc1cc(Nc2nccc(-c3cn(C)c4ccccc34)n2)c(OC)cc1N(C)CCN(C)CCCSc1cccc2c1CN(C1CCC(=O)NC1=O)C2=O]

Referring to the method of example 1, the target compound (SIAIS337079) was prepared by using Osimertinib derivative SIAIS337051 and intermediate LM (SIAIS213132). (yellow solid, 9.8 mg, yield 46%). $^1$H NMR (500 MHz, Methanol-$d_4$) δ 8.52 (s, 1H), 8.26 (s, 1H), 8.12-7.95 (m, 2H), 7.50 (d, J=34.1 Hz, 2H), 7.41 (d, J=6.5 Hz, 1H), 7.37-7.25 (m, 4H), 7.05 (d, J=10.1 Hz, 1H), 6.55 (d, J=10.3 Hz, 1H), 6.48 (d, J=10.5 Hz, 1H), 5.85 (d, J=10.0 Hz, 1H), 5.13 (dd, J=13.2, 5.0 Hz, 1H), 4.47 (d, J=17.4 Hz, 1H), 4.35 (d, J=17.2 Hz, 1H), 4.01 (s, 3H), 3.97 (s, 3H), 3.55-3.49 (m, 4H), 3.23-3.21 (m, 2H), 2.95 (s, 3H), 2.87-2.85 (m, 3H), 2.83 (s, 3H), 2.75-2.69 (m, 1H), 2.31-2.19 (m, 1H), 2.07-1.93 (m, 3H). HRMS (ESI) m/z: calcd for $C_{43}H_{48}N_9O_5S^+$ [M+H]$^+$, 802.3494; found, 802.3493.

Example 151

Preparation of N-(2-((2-((5-((2-(2,6-dioxopiperidin-3-yl)-1-oxoisoindolin-4-yl)thio)pentyl)(methyl)amino)ethyl)(methyl)amino)-4-methoxy-5-((4-(1-methyl-1H-indol-3-yl)pyrimidin-2-yl)amino)phenyl)acrylamide (SIAIS337081)

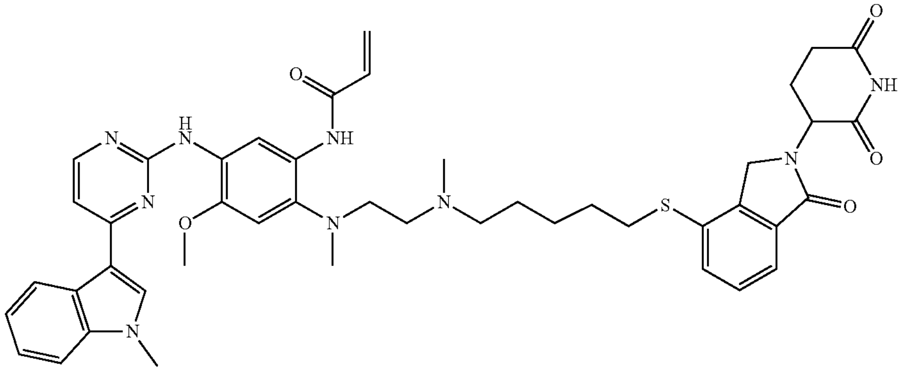 [SMILES: C=CC(=O)Nc1cc(Nc2nccc(-c3cn(C)c4ccccc34)n2)c(OC)cc1N(C)CCN(C)CCCCCSc1cccc2c1CN(C1CCC(=O)NC1=O)C2=O]

Referring to the method of example 1, the target compound (SIAIS337081) was prepared by using Osimertinib derivative SIAIS337051 and intermediate LM (SIAIS213135). (yellow solid, 9.7 mg, yield 43%). $^1$H NMR (500 MHz, Methanol-$d_4$) δ 8.42 (d, J=11.4 Hz, 1H), 8.28 (s, 1H), 7.96 (d, J=39.8 Hz, 2H), 7.64 (d, J=7.5 Hz, 1H), 7.52 (s, 2H), 7.27 (s, 3H), 7.11 (d, J=34.9 Hz, 2H), 6.52 (s, 2H), 5.87 (s, 11H), 5.18 (dd, J=13.2, 5.0 Hz, 1H), 4.46 (d, J=17.4 Hz, 1H), 4.36 (d, J=17.2 Hz, 1H), 4.08 (s, 31H), 3.98 (s, 3H), 3.55-3.49 (m, 4H), 3.28-3.23 (m, 2H), 2.95 (s, 3H), 2.86-2.82 (m, 3H), 2.80 (s, 3H), 2.75-2.69 (m, 1H), 2.36-2.17 (m, 1H), 2.09-1.95 (m, 7H). HRMS (ESI) m/z: calcd for $C_{45}H_{52}N_9O_5S^+$ [M+H]$^+$, 830.3807; found, 830.3803.

Example 152

Preparation of N-(2-((2-((6-((2-(2,6-dioxopiperidin-3-yl)-1-oxoisoindolin-4-yl)thio)hexyl)(methyl)amino)ethyl)(methyl)amino)-4-methoxy-5-((4-(1-methyl-1H-indol-3-yl)pyrimidin-2-yl)amino)phenyl)acrylamide (SIAIS337082)

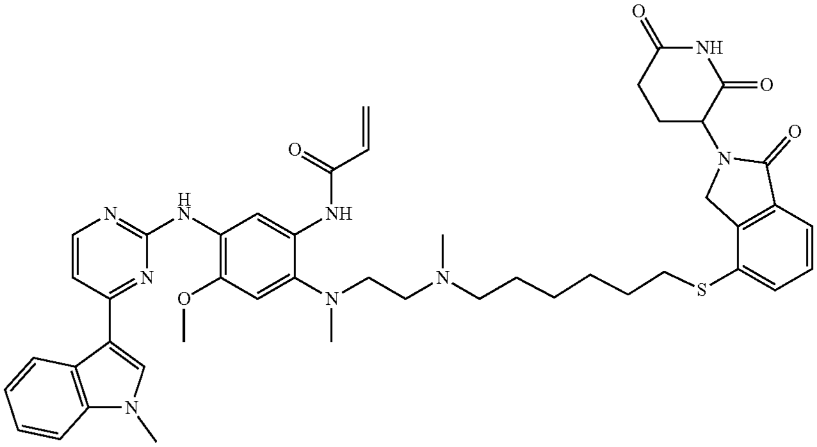 [SMILES: C=CC(=O)Nc1cc(Nc2nccc(-c3cn(C)c4ccccc34)n2)c(OC)cc1N(C)CCN(C)CCCCCCSc1cccc2c1CN(C1CCC(=O)NC1=O)C2=O]

Referring to the method of example 1, the target compound (SIAIS337082) was prepared by using Osimertinib derivative SIAIS337051 and intermediate LM (SIAIS1216133). (yellow solid, 9.9 mg, yield 47%). $^1$H NMR (500 MHz, Methanol-$d_4$) δ 8.47 (d, J=13.6 Hz, 1H), 8.31 (s, 1H), 8.05-8.01 (m, 2H), 7.54 (d, J=11.4 Hz, 2H), 7.35-7.31 (m, 5H), 7.07 (s, 1H), 6.58 (s, 1H), 6.48 (d, J=17.2 Hz, 1H), 5.85 (s, 1H), 5.17 (dd, J=13.2, 5.0 Hz, 1H), 4.45 (d, J=17.4 Hz, 1H), 4.35 (d, J=17.2 Hz, 1H), 4.01 (s, 3H), 3.96 (s, 3H), 3.53-3.46 (m, 4H), 3.26-3.21 (m, 2H), 2.93 (s, 3H), 2.85-2.82 (m, 3H), 2.79 (s, 3H), 2.74-2.62 (m, 1H), 2.34-2.15 (m, 1H), 2.06-1.93 (m, 9H). HRMS (ESI) m/z: calcd for $C_{46}H_{54}N_9O_5S^+$ [M+H]$^+$, 844.3963; found, 844.3967.

Example 153

Preparation of N-(2-((2-((7-((2-(2,6-dioxopiperidin-3-yl)-1-oxoisoindolin-4-yl)thio)heptyl)(methyl)amino)ethyl)(methyl)amino)-4-methoxy-5-((4-(1-methyl-1H-indol-3-yl)pyrimidin-2-yl)amino)phenyl)acrylamide (SIAIS337083)

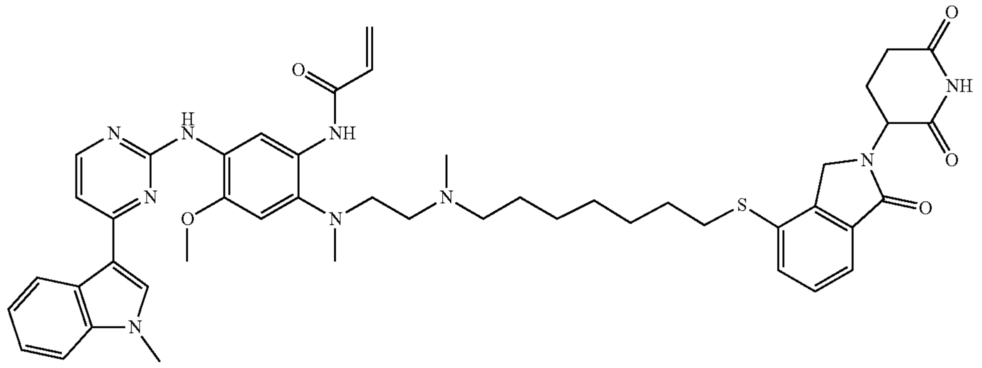 [SMILES: C=CC(=O)Nc1cc(Nc2nccc(-c3cn(C)c4ccccc34)n2)c(OC)cc1N(C)CCN(C)CCCCCCCSc1cccc2c1CN(C1CCC(=O)NC1=O)C2=O]

Referring to the method of example 1, the target compound (SIAIS337083) was prepared by using Osimertinib derivative SIAIS337051 and intermediate LM (SIAIS1216135). (yellow solid, 8.7 mg, yield 35%). $^1$H NMR (500 MHz, Methanol-$d_4$) δ 8.62 (d, J=14.0 Hz, 1H), 8.48 (s, 1H), 8.24 (s, 1H), 8.14 (t, J=7.7 Hz, 1H), 7.73-7.64 (m, 2H), 7.56-7.40 (m, 4H), 7.23 (s, 1H), 6.83-6.71 (m, 1H), 6.65 (d, J=16.9 Hz, 1H), 6.02 (d, J=10.4 Hz, 1H), 5.22 (dd, J=13.2, 5.0 Hz, 1H), 4.48 (d, J=17.4 Hz, 1H), 4.37 (d, J=17.2 Hz, 1H), 4.09 (s, 3H), 3.99 (s, 3H), 3.59-3.48 (m, 4H), 3.29-3.25 (m, 2H), 2.98 (s, 3H), 2.87-2.85 (m, 3H), 2.83 (s, 3H), 2.79-2.68 (m, 1H), 2.37-2.15 (m, 1H), 2.09-1.96 (m, 1H). HRMS (ESI) m/z: calcd for $C_{47}H_{56}N_9O_5S^+$ [M+H]$^+$, 858.4120; found, 858.4122.

Example 154

Preparation of N-(2-((2-((8-((2-(2,6-dioxopiperidin-3-yl)-1-oxoisoindolin-4-yl)thio)octyl)(methyl)amino)ethyl)(methyl)amino)-4-methoxy-5-((4-(1-methyl-1H-indol-3-yl)pyrimidin-2-yl)amino)phenyl)acrylamide (SIAIS337084)

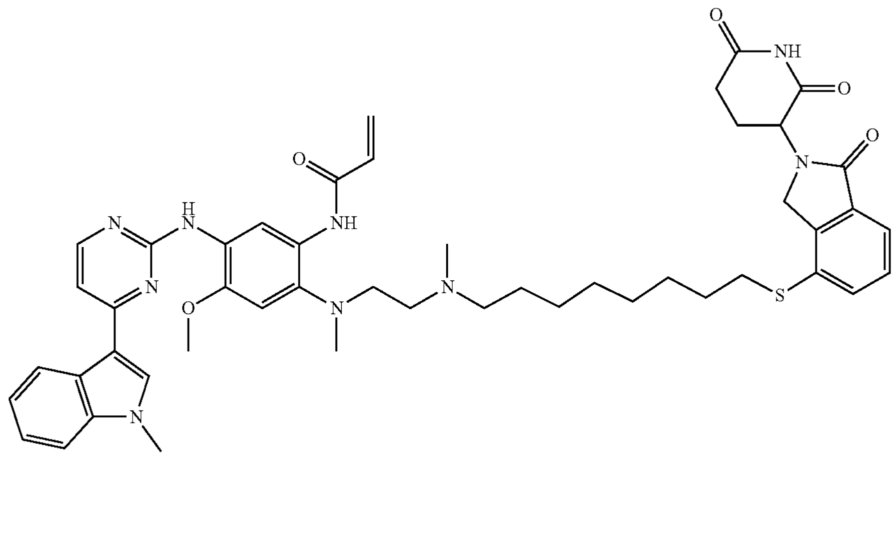 [SMILES: C=CC(=O)Nc1cc(Nc2nccc(-c3cn(C)c4ccccc34)n2)c(OC)cc1N(C)CCN(C)CCCCCCCCSc1cccc2c1CN(C1CCC(=O)NC1=O)C2=O]

Referring to the method of example 1, the target compound (SIAIS337084) was prepared by using Osimertinib derivative SIAIS337051 and intermediate LM (SIAIS1216137). (yellow solid, 9.4 mg, yield 43%). $^{1}H$ NMR (500 MHz, Methanol-$d_4$) δ 8.52 (s, 1H), 8.34 (s, 1H), 8.03 (s, 1H), 7.98 (d, J=2.1 Hz, 1H), 7.61 (d, J=7.0 Hz, 1H), 7.54 (d, J=8.4 Hz, 1H), 7.45 (d, J=9.4 Hz, 1H), 7.42 (dd, J=8.2, 1.9 Hz, 2H), 7.37 (d, J=6.2 Hz, 1H), 7.34-7.26 (m, 2H), 7.08 (s, 1H), 6.66-6.57 (m, 1H), 6.49 (d, J=16.9 Hz, 1H), 5.87 (d, J=10.0 Hz, 1H), 5.16 (dd, J=13.2, 5.0 Hz, 1H), 4.42 (d, J=17.4 Hz, 1H), 4.33 (d, J=17.2 Hz, 1H), 4.05 (s, 3H), 3.95 (s, 3H), 3.56-3.46 (m, 4H), 3.25-3.25 (m, 2H), 2.94 (s, 3H), 2.87-2.85 (m, 3H), 2.81 (s, 3H), 2.77-2.68 (m, 1H), 2.35-2.17 (m, 1H), 2.07-1.96 (m, 13H). HRMS (ESI) m/z: calcd for $C_{48}H_{58}N_9O_5S^+$ [M+H]$^+$, 872.4276; found, 872.4278.

Example 155

Preparation of N-(2-((2-((9-((2-(2,6-dioxopiperidin-3-yl)-1-oxoisoindolin-4-yl)thio)nonyl)(methyl)amino)ethyl)(methyl)amino)-4-methoxy-5-((4-(1-methyl-1H-indol-3-yl)pyrimidin-2-yl)amino)phenyl)acrylamide (SIAIS337085)

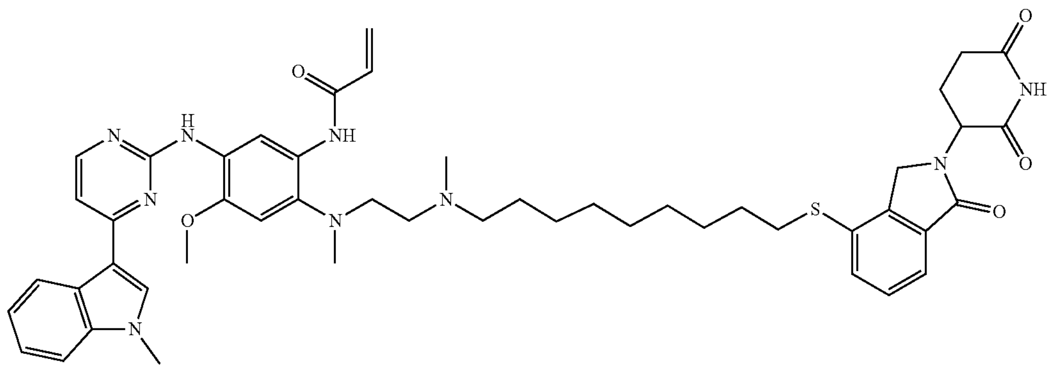 [SMILES: C=CC(=O)Nc1cc(Nc2nccc(-c3cn(C)c4ccccc34)n2)c(OC)cc1N(C)CCN(C)CCCCCCCCCSc1cccc2c1CN(C1CCC(=O)NC1=O)C2=O]

Referring to the method of example 1, the target compound (SIAIS337085) was prepared by using Osimertinib derivative SIAIS337051 and intermediate LM (SIAIS1220059). (yellow solid, 9.3 mg, yield 46%). $^1$H NMR (500 MHz, Methanol-$d_4$) δ 8.51 (d, J=15.2 Hz, 1H), 8.35 (s, 1H), 8.04 (s, 2H), 7.56 (d, J=27.2 Hz, 3H), 7.45-7.25 (m, 5H), 7.09 (s, 1H), 6.61 (d, J=12.3 Hz, 1H), 6.50 (d, J=16.8 Hz, 1H), 5.88 (d, J=10.3 Hz, 1H), 5.16 (dd, J=13.2, 5.0 Hz, 1H), 4.45 (d, J=17.4 Hz, 1H), 4.34 (d, J=17.2 Hz, 1H), 4.03 (s, 3H), 3.93 (s, 3H), 3.57-3.46 (m, 4H), 3.27-3.28 (m, 2H), 2.93 (s, 3H), 2.86-2.82 (m, 3H), 2.80 (s, 3H), 2.75-2.68 (m, 1H), 2.34-2.16 (m, 1H), 2.08-1.96 (m, 15H). HRMS (ESI) m/z: calcd for $C_{49}H_{60}N_9O_5S^+$ [M+H]$^+$, 886.4433; found, 886.4431.

Example 156

Preparation of N-(2-((2-((10-((2-(2,6-dioxopiperidin-3-yl)-1-oxoisoindolin-4-yl)thio)decyl)(methyl)amino)ethyl)(methyl)amino)-4-methoxy-5-((4-(1-methyl-1H-indol-3-yl)pyrimidin-2-yl)amino)phenyl)acrylamide (SIAIS337086)

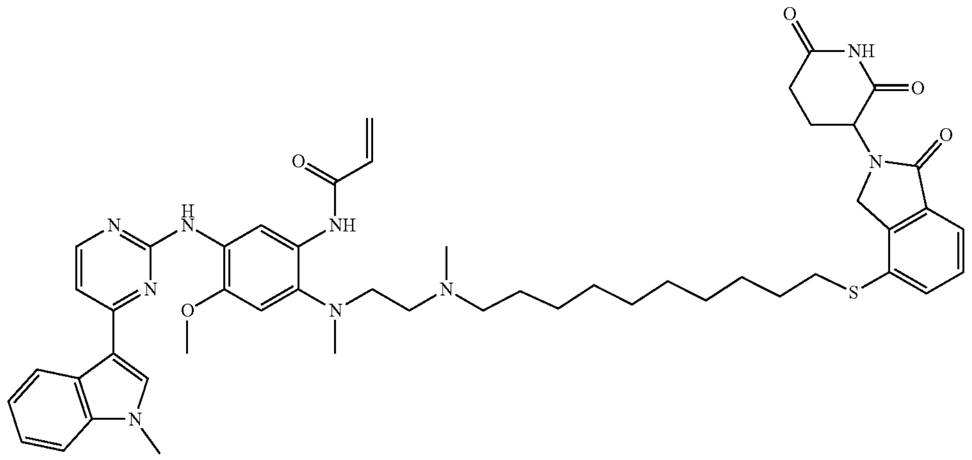 [SMILES: C=CC(=O)Nc1cc(Nc2nccc(-c3cn(C)c4ccccc34)n2)c(OC)cc1N(C)CCN(C)CCCCCCCCCCSc1cccc2c1CN(C1CCC(=O)NC1=O)C2=O]

Referring to the method of example 1, the target compound (SIAIS337086) was prepared by using Osimertinib derivative SIAIS337051 and intermediate LM (SIAIS1220013). (yellow solid, 9.8 mg, yield 47%). $^1$H NMR (500 MHz, MeOD) δ 8.53 (d, J=15.2 Hz, 1H), 8.37 (s, 1H), 8.05 (s, 2H), 7.57 (d, J=27.2 Hz, 3H), 7.46-7.25 (m, 5H), 7.08 (s, 1H), 6.60 (d, J=12.3 Hz, 1H), 6.48 (d, J=16.8 Hz, 1H), 5.87 (d, J=10.3 Hz, 1H), 5.13 (dd, J=13.2, 5.0 Hz, 1H), 4.42 (d, J=17.4 Hz, 1H), 4.33 (d, J=17.2 Hz, 1H), 4.01 (s, 3H), 3.92 (s, 3H), 3.56-3.43 (m, 4H), 3.25-3.21 (m, 2H), 2.91 (s, 3H), 2.85-2.82 (m, 3H), 2.80 (s, 3H), 2.74-2.68 (m, 1H), 2.32-2.16 (m, 1H), 2.08-1.96 (m, 17H). HRMS (ESI) m/z: calcd for $C_{50}H_{62}N_9O_5S^+$ [M+H]$^+$, 900.4589; found, 900.4586.

Example 157

Preparation of N-(2-((2-((11-((2-(2,6-dioxopiperidin-3-yl)-1-oxoisoindolin-4-yl)thio)undecyl)(methyl)amino)ethyl)(methyl)amino)-4-methoxy-5-((4-(1-methyl-1H-indol-3-yl)pyrimidin-2-yl)amino)phenyl)acrylamide (SIAIS337087)

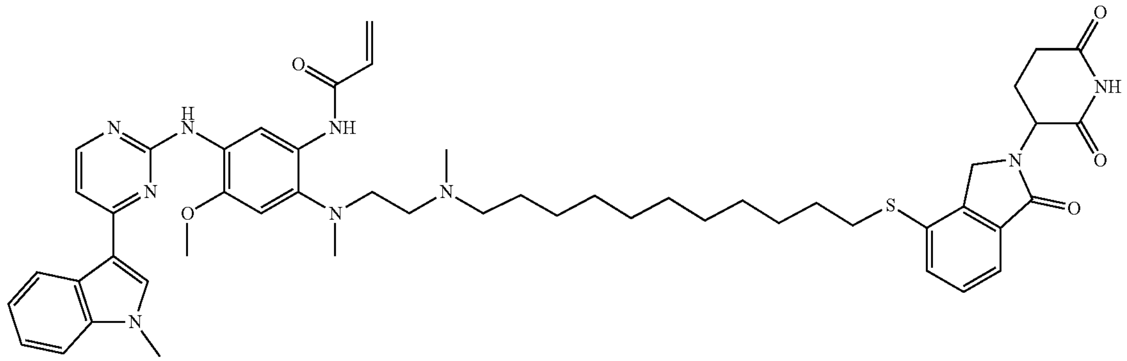 [SMILES: C=CC(=O)Nc1cc(Nc2nccc(-c3cn(C)c4ccccc34)n2)c(OC)cc1N(C)CCN(C)CCCCCCCCCCCSc1cccc2c1CN(C1CCC(=O)NC1=O)C2=O]

Referring to the method of example 1, the target compound (SIAIS337087) was prepared by using Osimertinib derivative SIAIS337051 and intermediate LM (SIAIS1220015). (yellow solid, 8.7 mg, yield 42%). $^1$H NMR (500 MHz, Methanol-$d_4$) δ 8.53 (s, 1H), 8.33 (s, 1H), 8.03 (s, 2H), 7.60 (d, J=7.4 Hz, 1H), 7.52 (d, J=7.3 Hz, 2H), 7.46 (t, J=7.8 Hz, 1H), 7.39 (d, J=6.9 Hz, 1H), 7.28 (dt, J=27.3, 7.4 Hz, 2H), 7.06 (s, 1H), 6.59 (dd, J=16.9, 10.0 Hz, 1H), 6.48 (d, J=17.0 Hz, 1H), 5.85 (d, J=10.2 Hz, 1H), 5.17-5.12 (m, 1H), 4.37 (t, J=5.6 Hz, 2H), 4.00 (s, 3H), 3.94 (s, 3H), 3.57-3.42 (m, 3H), 3.11 (q, J=7.3 Hz, 3H), 2.92 (dd, J=17.1, 4.2 Hz, 5H), 2.81 (d, J=1.5 Hz, 3H), 2.76 (d, J=17.3 Hz, 1H), 2.49 (t, J=6.7 Hz, 1H), 2.20-2.11 (m, 1H), 2.03 (d, J=6.7 Hz, 1H), 1.55 (s, 4H), 1.30 (s, 4H), 1.08 (d, J=35.9 Hz, 10H). HRMS (ESI) m/z: calcd for $C_{51}H_{64}N_9O_5S^+$ [M+H]$^+$, 914.4746; found, 914.4743.

Example 158

Preparation of N-(2-((2-((4-(((2-(2,6-dioxopiperidin-3-yl)-1-oxoisoindolin-4-yl)thio)methyl)benzyl)(methyl)amino)ethyl)(methyl)amino)-4-methoxy-5-((4-(1-methyl-1H-indol-3-yl)pyrimidin-2-yl)amino)phenyl)acrylamide (SIAIS337088)

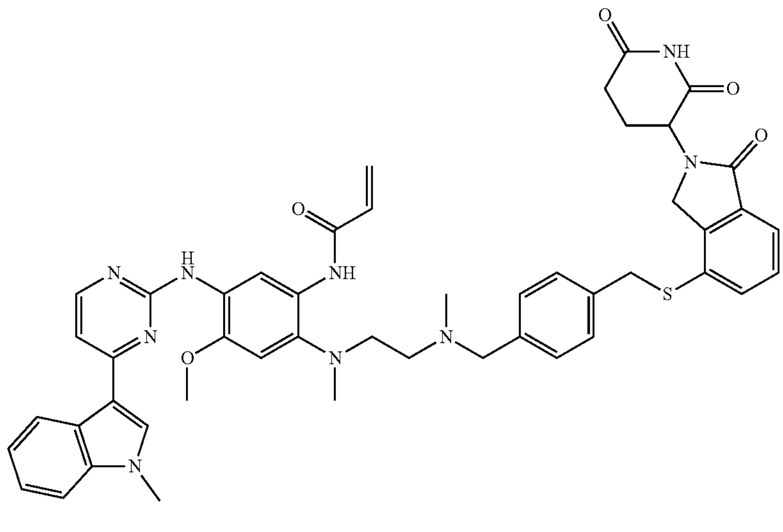 [SMILES: C=CC(=O)Nc1cc(Nc2nccc(-c3cn(C)c4ccccc34)n2)c(OC)cc1N(C)CCN(C)Cc1ccc(CSc2cccc3c2CN(C2CCC(=O)NC2=O)C3=O)cc1]

Referring to the method of example 1, the target compound (SIAIS337088) was prepared by using Osimertinib derivative SIAIS337051 and intermediate LM (SIAIS1220141). (yellow solid, 9.8 mg, yield 43%). $^{1}$H NMR (500 MHz, Methanol-$d_4$) δ 8.58 (s, 1H), 8.57-8.47 (m, 1H), 8.05-7.94 (m, 1H), 7.87 (d, J=7.0 Hz, 1H), 7.59 (d, J=7.9 Hz, 1H), 7.44-7.31 (m, 4H), 7.25 (d, J=7.9 Hz, 3H), 7.18 (d, J=7.8 Hz, 1H), 7.12 (d, J=7.7 Hz, 1H), 7.07 (t, J=7.6 Hz, 1H), 6.69-6.54 (m, 2H), 6.38 (d, J=10.1 Hz, 1H), 5.96 (d, J=9.0 Hz, 1H), 5.06-4.93 (m, 1H), 4.64-4.55 (m, 1H), 4.15 (d, J=12.8 Hz, 1H), 4.12-4.05 (m, 1H), 4.02 (d, J=5.1 Hz, 3H), 3.98-3.77 (m, 3H), 3.68 (d, J=5.0 Hz, 3H), 3.58 (d, J=14.6 Hz, 1H), 3.42 (d, J=13.3 Hz, 1H), 3.07 (s, 3H), 2.99 (d, J=13.4 Hz, 1H), 2.89-2.82 (m, 1H), 2.74 (d, J=3.3 Hz, 4H), 2.23-2.10 (m, 1H). HRMS (ESI) m/z: calcd for $C_{48}H_{50}N_9O_5S^+$ [M+H]$^+$, 864.3650; found, 864.3653.

Example 159

Preparation of N-(2-((2-((5-(2-(2,6-dioxopiperidin-3-yl)-1-oxoisoindolin-4-yl)pent-4-yn-1-yl)(methyl)amino)ethyl)(methyl)amino)-4-methoxy-5-((4-(1-methyl-1H-indol-3-yl)pyrimidin-2-yl)amino)phenyl)acrylamide (SIAIS337089)

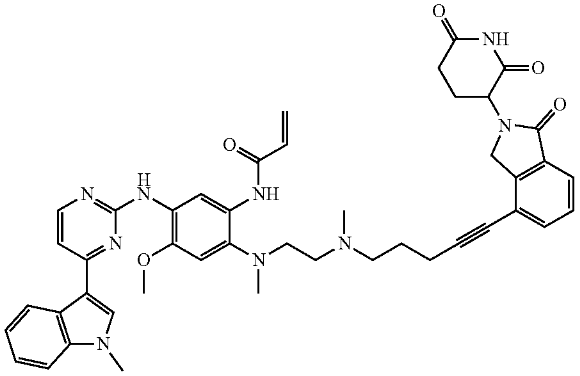 [SMILES: C=CC(=O)Nc1cc(Nc2nccc(-c3cn(C)c4ccccc34)n2)c(OC)cc1N(C)CCN(C)CCCC#Cc1cccc2c1CN(C1CCC(=O)NC1=O)C2=O]

Referring to the method of example 1, the target compound (SIAIS337089) was prepared by using Osimertinib derivative SIAIS337051 and intermediate LM (SIAIS255121). (yellow solid, 9.5 mg, yield 40%). $^{1}$H NMR (500 MHz, Methanol-$d_4$) δ 8.46 (d, J=15.7 Hz, 1H), 8.28 (s, 1H), 8.08-8.00 (m, 2H), 7.96-7.85 (m, 1H), 7.60 (dd, J=15.1, 7.3 Hz, 1H), 7.56-7.47 (m, 1H), 7.37-7.25 (m, 4H), 7.07 (d, J=9.4 Hz, 1H), 6.67-6.57 (m, 1H), 6.48 (d, J=16.9 Hz, 1H), 5.84 (d, J=10.1 Hz, 1H), 5.03 (d, J=17.4 Hz, 1H), 4.25-4.11 (m, 1H), 4.05 (s, 3H), 3.95 (s, 3H), 3.76 (d, J=14.6 Hz, 1H), 3.65 (s, 1H), 3.51 (d, J=12.5 Hz, 1H), 3.26 (s, 4H), 2.98 (s, 3H), 2.86 (d, J=13.8 Hz, 1H), 2.80 (d, J=6.6 Hz, 3H), 2.72 (d, J=14.2 Hz, 1H), 2.37 (s, 2H), 2.27-2.18 (m, 1H), 1.91 (s, 3H). HRMS (ESI) m/z: calcd for $C_{45}H_{48}N_9O_5^+$ [M+H]$^+$, 794.3773; found, 794.3775.

Example 160

Preparation of N-(2-((2-((5-(2-(2,6-dioxopiperidin-3-yl)-1-oxoisoindolin-4-yl)pent-4-yn-1-yl)(methyl)amino)ethyl)(methyl)amino)-4-methoxy-5-((4-(1-methyl-1H-indol-3-yl)pyrimidin-2-yl)amino)phenyl)acrylamide (SIAIS337090)

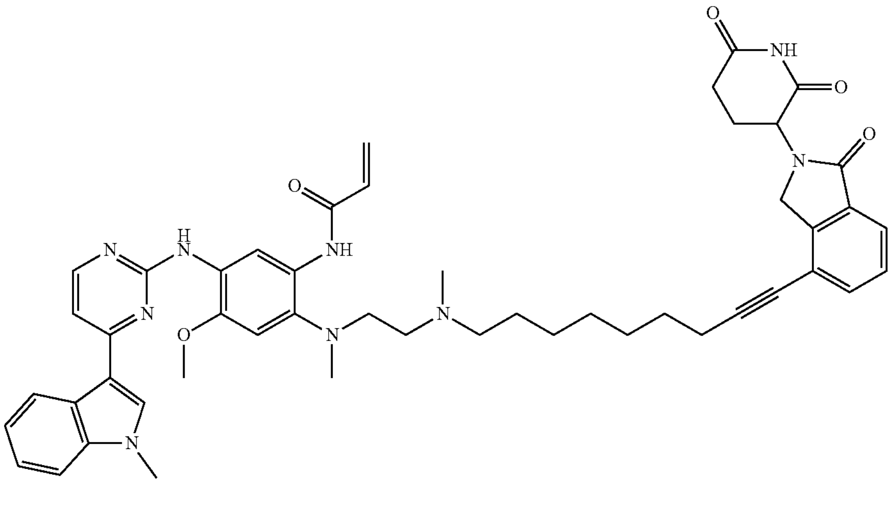 [SMILES: C=CC(=O)Nc1cc(Nc2nccc(-c3cn(C)c4ccccc34)n2)c(OC)cc1N(C)CCN(C)CCCCCCCC#Cc1cccc2c1CN(C1CCC(=O)NC1=O)C2=O]

Referring to the method of example 1, the target compound (SIAIS337090) was prepared by using Osimertinib derivative SIAIS337051 and intermediate LM (SIAIS255127). (yellow solid, 8.7 mg, yield 33%). $^1H$ NMR (500 MHz, Methanol-$d_4$) δ 8.44 (d, J=18.1 Hz, 1H), 8.31 (s, 1H), 8.11-7.99 (m, 2H), 7.70-7.63 (m, 1H), 7.44-7.41 (m, 3H), 7.33-7.27 (m, 3H), 7.07 (d, J=5.6 Hz, 1H), 6.64 (t, J=13.5 Hz, 11H), 6.47 (d, J=16.8 Hz, 1H), 5.84 (d, J=10.1 Hz, 1H), 5.10 (s, 1H), 4.26 (d, J=10.9 Hz, 2H), 4.01 (s, 3H), 3.98 (s, 1H), 3.86 (s, 3H), 3.73 (d, J=13.6 Hz, 1H), 3.49-3.44 (m, 2H), 3.22-3.09 (m, 3H), 2.91 (s, 3H), 2.81 (s, 3H), 2.77-2.65 (m, 1H), 2.36-2.31 (m, 3H), 2.04 (s, 1H), 1.61 (s, 2H), 1.41 (s, 2H), 1.28-1.22 (m, 6H). HRMS (ESI) m/z: calcd for $C_{49}H_{56}N_9O_5^+$ [M+H]$^+$, 850.4399; found, 850.4394.

Example 161

Preparation of (E)-N-(4-((3-chloro-4-fluorophenyl)amino)-7-methoxyquinazolin-6-yl)-4-(4-(4-(5-((2-(2,6-dioxopiperidin-3-yl)-1-oxoisoindolin-4-yl)thio)pentyl)piperazin-1-yl)piperidin-1-yl)but-2-enamide (SIAIS262064)

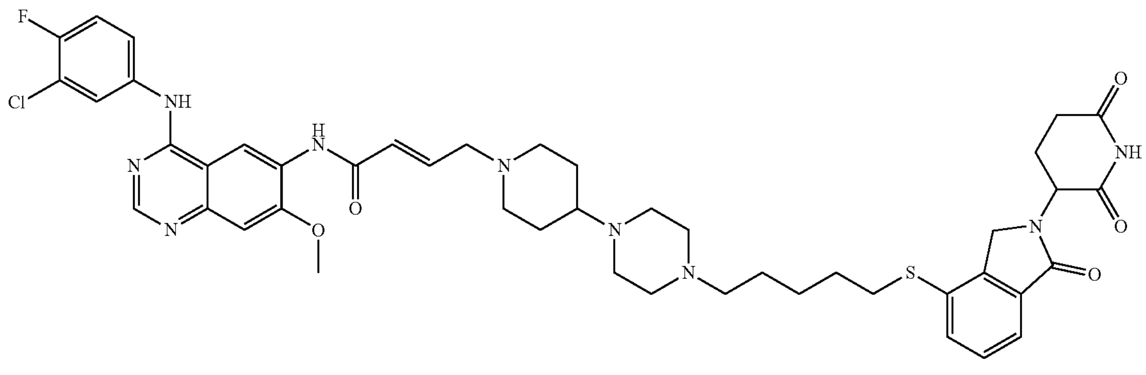 [SMILES: COc1cc2ncnc(Nc3ccc(F)c(Cl)c3)c2cc1NC(=O)/C=C/CN1CCC(N2CCN(CCCCCSc3cccc4c3CN(C3CCC(=O)NC3=O)C4=O)CC2)CC1]

Referring to the method of example 1, the target compound (SIAIS262064) was prepared by using Dacomitinib derivative B and intermediate LM (SIAIS213135). (yellow solid, 8.9 mg, yield 35%). HRMS (ESI) m/z: calcd for $C_{46}H_{54}ClFN_9O_5S^+$ [M+H]$^+$, 898.3636; found, 898.3631.

Example 162

Preparation of (E)-N-(4-((3-chloro-4-fluorophenyl)amino)-7-methoxyquinazolin-6-yl)-4-(4-(4-(5-((2-(2,6-dioxopiperidin-3-yl)-1,3-dioxoisoindolin-4-yl)amino)pentyl)piperazin-1-yl)piperidin-1-yl)but-2-enamide (SIAIS262071)

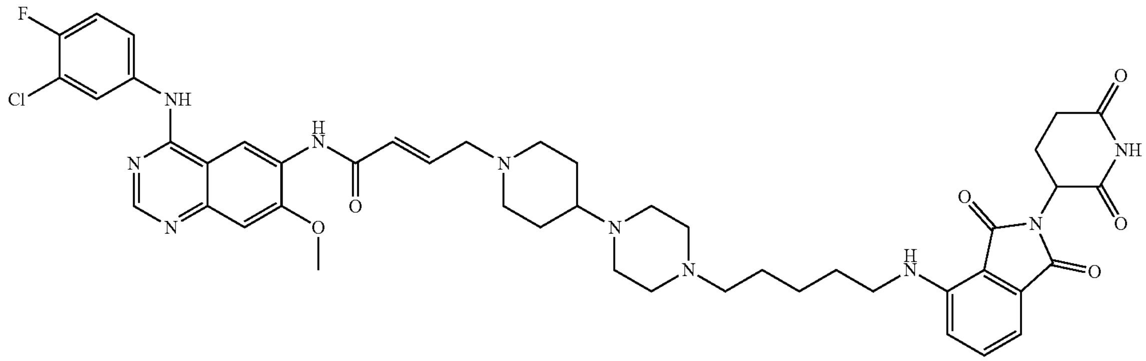 [SMILES: COc1cc2ncnc(Nc3ccc(F)c(Cl)c3)c2cc1NC(=O)/C=C/CN1CCC(N2CCN(CCCCCNc3cccc4c3C(=O)N(C3CCC(=O)NC3=O)C4=O)CC2)CC1]

Referring to the method of example 1, the target compound (SIAIS262071) was prepared by using Dacomitinib derivative B and intermediate LM (SIAIS264009). (yellow solid, 9.5 mg, yield 41%). HRMS (ESI) m/z: calcd for $C_{46}H_{53}ClFN_{10}O_6^+$ [M+H]$^+$, 895.3817; found, 895.3815.

Example 163

Preparation of (E)-N-(4-((3-chloro-4-fluorophenyl)amino)-7-methoxyquinazolin-6-yl)-4-(4-(2-((2-(2,6-dioxopiperidin-3-yl)-1-oxoisoindolin-4-yl)thio)acetamido)piperidin-1-yl)but-2-enamide (SIAIS262110)

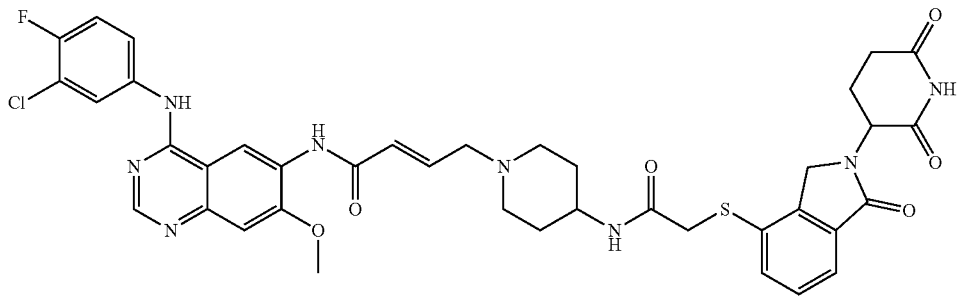 [SMILES: COc1cc2ncnc(Nc3ccc(F)c(Cl)c3)c2cc1NC(=O)/C=C/CN1CCC(NC(=O)CSc2cccc3c2CN(C2CCC(=O)NC2=O)C3=O)CC1]

Referring to the method of example 1, the target compound (SIAIS262110) was prepared by using Dacomitinib derivative C and intermediate LM (SIAIS171090). (yellow solid, 9.2 mg, yield 48%). HRMS (ESI) m/z: calcd for $C_{39}H_{39}ClFN_8O_6^+$ [M+H]$^+$, 801.2380; found, 801.2389.

Example 164

Preparation of (E)-N-(4-((3-chloro-4-fluorophenyl)amino)-7-methoxyquinazolin-6-yl)-4-(4-(4-((2-(2,6-dioxopiperidin-3-yl)-1-oxoisoindolin-4-yl)thio)butanamido)piperidin-1-yl)but-2-enamide (SIAIS262112)

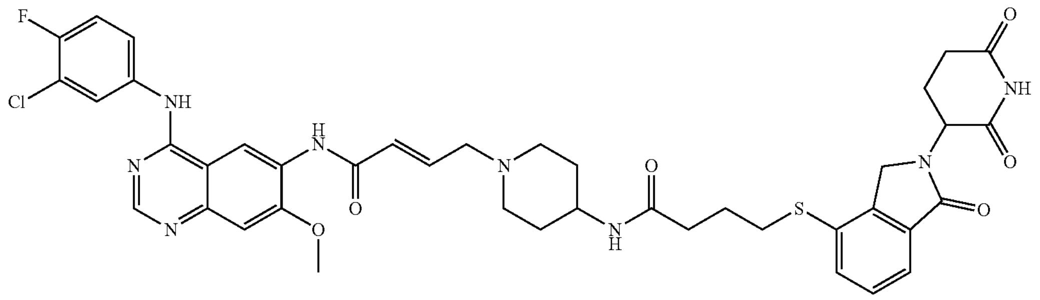 [SMILES: COc1cc2ncnc(Nc3ccc(F)c(Cl)c3)c2cc1NC(=O)/C=C/CN1CCC(NC(=O)CCCSc2cccc3c2CN(C2CCC(=O)NC2=O)C3=O)CC1]

Referring to the method of example 1, the target compound (SIAIS262112) was prepared by using Dacomitinib derivative C and intermediate LM (SIAIS171089). (yellow solid, 9.5 mg, yield 49%). HRMS (ESI) m/z: calcd for $C_{41}H_{43}ClFN_8O_6^+$ [M+H]$^+$, 829.2693; found, 829.2697.

Example 165

Preparation of (E)-N-(1-(4-((4-((3-chloro-4-fluorophenyl)amino)-7-methoxyquinazolin-6-yl)amino)-4-oxobut-2-en-1-yl)piperidin-4-yl)-5-((2-(2,6-dioxopiperidin-3-yl)-1-oxoisoindolin-4-yl)thio)pentanamide (SIAIS262113)

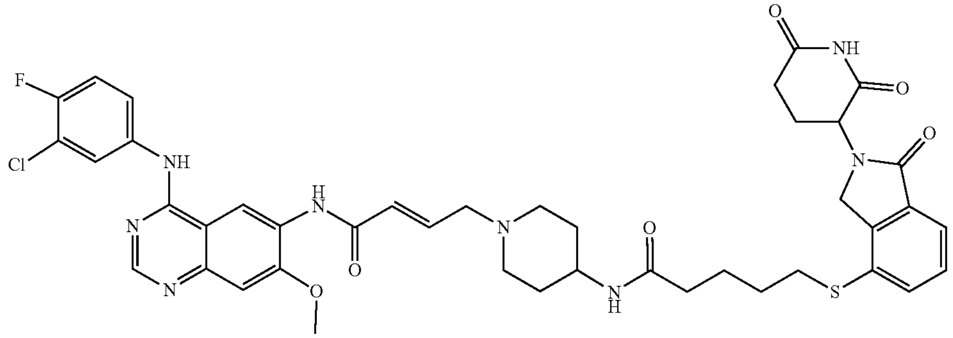 [SMILES: COc1cc2ncnc(Nc3ccc(F)c(Cl)c3)c2cc1NC(=O)/C=C/CN1CCC(NC(=O)CCCCSc2cccc3c2CN(C2CCC(=O)NC2=O)C3=O)CC1]

Referring to the method of example 1, the target compound (SIAIS262113) was prepared by using Dacomitinib derivative C and intermediate LM (SIAIS171079). (yellow solid, 9.3 mg, yield 46%). HRMS (ESI) m/z: calcd for $C_{42}H_{45}ClFN_8O_6^+$ [M+H]$^+$, 843.2850; found, 843.2844.

Example 166

Preparation of (E)-N-(1-(4-((4-((3-chloro-4-fluorophenyl)amino)-7-methoxyquinazolin-6-yl)amino)-4-oxobut-2-en-1-yl)piperidin-4-yl)-6-((2-(2,6-dioxopiperidin-3-yl)-1-oxoisoindolin-4-yl)thio)hexanamide (SIAIS262114)

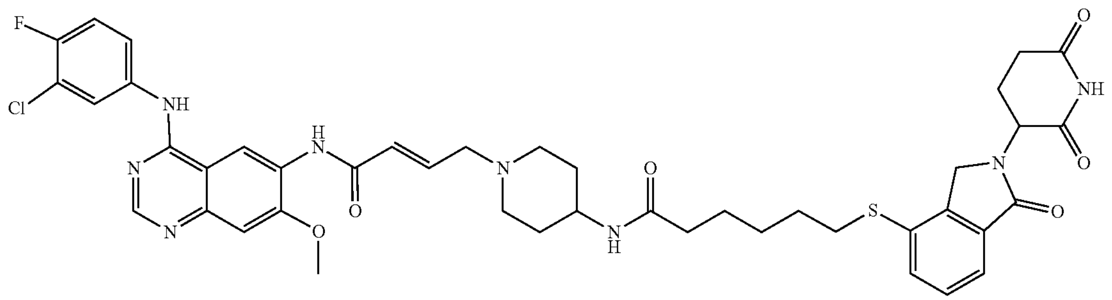 [SMILES: COc1cc2ncnc(Nc3ccc(F)c(Cl)c3)c2cc1NC(=O)/C=C/CN1CCC(NC(=O)CCCCCSc2cccc3c2CN(C2CCC(=O)NC2=O)C3=O)CC1]

Referring to the method of example 1, the target compound (SIAIS262114) was prepared by using Dacomitinib derivative C and intermediate LM (SIAIS171091). (yellow solid, 9.6 mg, yield 45%). HRMS (ESI) m/z: calcd for $C_{43}H_{47}ClFN_8O_6^+$ [M+H]$^+$, 857.3006; found, 857.3009.

Example 167

Preparation of (E)-N-(1-(4-((4-((3-chloro-4-fluorophenyl)amino)-7-methoxyquinazolin-6-yl)amino)-4-oxobut-2-en-1-yl)piperidin-4-yl)-7-((2-(2,6-dioxopiperidin-3-yl)-1-oxoisoindolin-4-yl)thio)heptanamide (SIAIS262115)

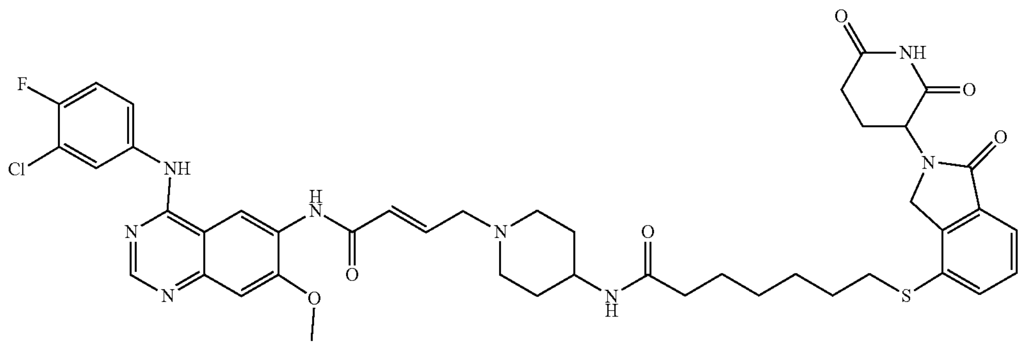 [SMILES: COc1cc2ncnc(Nc3ccc(F)c(Cl)c3)c2cc1NC(=O)/C=C/CN1CCC(NC(=O)CCCCCCSc2cccc3c2CN(C2CCC(=O)NC2=O)C3=O)CC1]

Referring to the method of example 1, the target compound (SIAIS262115) was prepared by using Dacomitinib derivative C and intermediate LM (SIAIS171092). (yellow solid, 9.8 mg, yield 43%). HRMS (ESI) m/z: calcd for $C_{44}H_{49}ClFN_8O_6^+$ [M+H]$^+$, 871.3163; found, 871.3167.

Example 168

Preparation of (E)-N-(4-((3-chloro-4-fluorophenyl) amino)-7-methoxyquinazolin-6-yl)-4-(4-((5-(2-(2,6-dioxopiperidin-3-yl)-1-oxoisoindolin-4-yl)pent-4-yn-1-yl)amino)piperidin-1-yl)but-2-enamide (SIAIS262116)

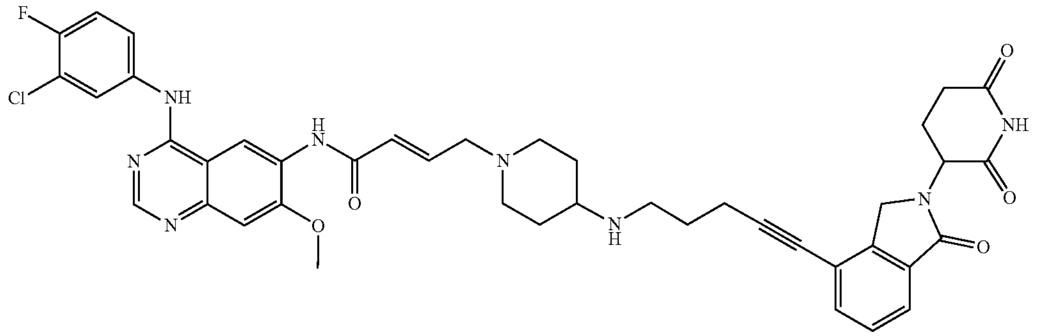 [SMILES: COc1cc2ncnc(Nc3ccc(F)c(Cl)c3)c2cc1NC(=O)/C=C/CN1CCC(NCCCC#Cc2cccc3c2CN(C2CCC(=O)NC2=O)C3=O)CC1]

Referring to the method of example 1, the target compound (SIAIS262116) was prepared by using Dacomitinib derivative C and intermediate LM (SIAIS255121). (yellow solid, 8.4 mg, yield 45%). HRMS (ESI) m/z: calcd for $C_{42}H_{43}ClFN_8O_5^+$ [M+H]$^+$, 793.3023; found, 793.3028.

Example 169

Preparation of (E)-N-(4-((3-chloro-4-fluorophenyl) amino)-7-methoxyquinazolin-6-yl)-4-(4-((6-(2-(2,6-dioxopiperidin-3-yl)-1-oxoisoindolin-4-yl)hex-5-yn-1-yl)amino)piperidin-1-yl)but-2-enamide (SIAIS262117)

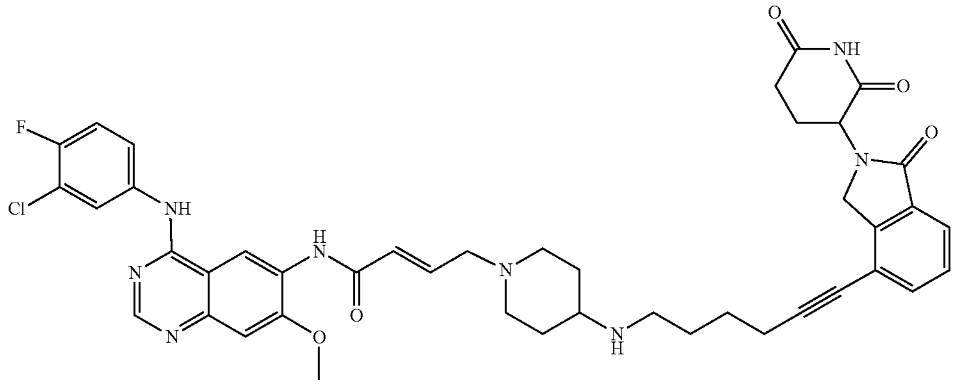 [SMILES: COc1cc2ncnc(Nc3ccc(F)c(Cl)c3)c2cc1NC(=O)/C=C/CN1CCC(NCCCCC#Cc2cccc3c2CN(C2CCC(=O)NC2=O)C3=O)CC1]

Referring to the method of example 1, the target compound (SIAIS262117) was prepared by using Dacomitinib derivative C and intermediate LM (SIAIS255119). (yellow solid, 8.4 mg, yield 45%). HRMS (ESI) m/z: calcd for $C_{43}H_{45}ClFN_8O_5^+$ [M+H]$^+$, 807.3180; found, 807.3183.

Example 170

Preparation of (E)-N-(1-(4-((4-((3-chloro-4-fluorophenyl)amino)-7-methoxyquinazolin-6-yl)amino)-4-oxobut-2-en-1-yl)piperidin-4-yl)-11-((2-(2,6-dioxopiperidin-3-yl)-1-oxoisoindolin-4-yl)thio) undecanamide (SIAIS262118)

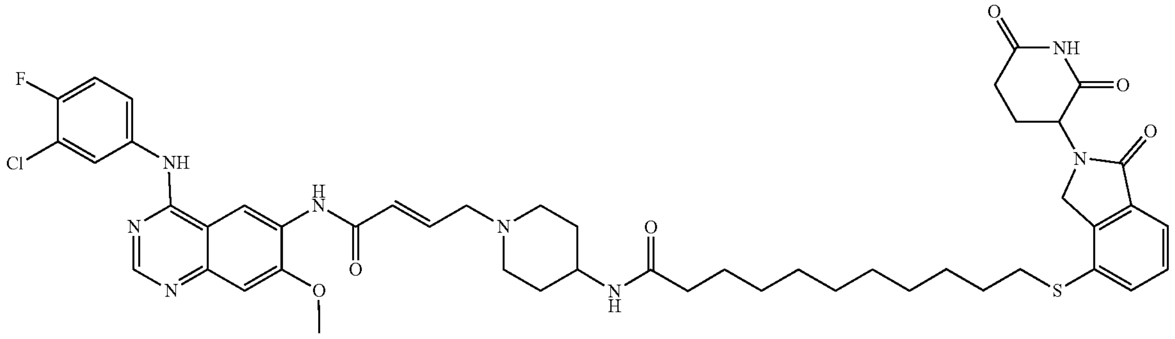 [SMILES: COc1cc2ncnc(Nc3ccc(F)c(Cl)c3)c2cc1NC(=O)/C=C/CN1CCC(NC(=O)CCCCCCCCCCSc2cccc3c2CN(C2CCC(=O)NC2=O)C3=O)CC1]

Referring to the method of example 1, the target compound (SIAIS262118) was prepared by using Dacomitinib derivative C and intermediate LM (SIAIS1220099). (yellow solid, 9.6 mg, yield 35%). HRMS (ESI) m/z: calcd for $C_{48}H_{57}ClFN_8O_6^+$ [M+H]$^+$, 927.3789; found, 927.3784.

Example 171

Preparation of (E)-N-(4-((3-chloro-4-fluorophenyl) amino)-7-methoxyquinazolin-6-yl)-4-(4-(4-(4-(((2-(2,6-dioxopiperidin-3-yl)-1-oxoisoindolin-4-yl)thio) methyl)benzyl)piperazin-1-yl)piperidin-1-yl)but-2-enamide (SIAIS337021)

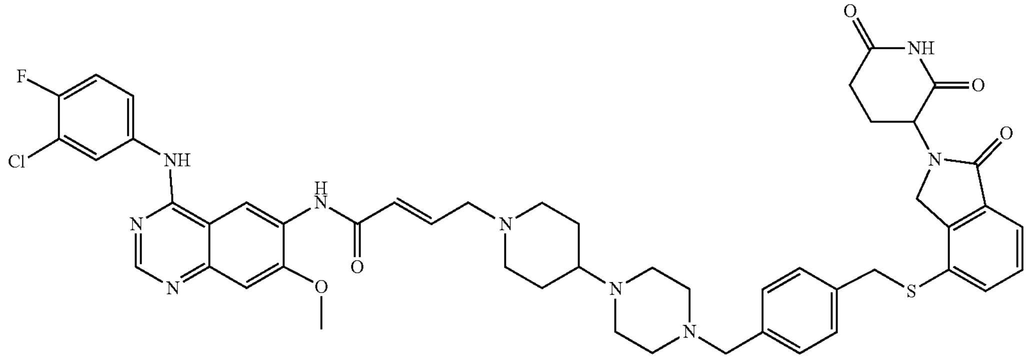 [SMILES: COc1cc2ncnc(Nc3ccc(F)c(Cl)c3)c2cc1NC(=O)/C=C/CN1CCC(N2CCN(Cc3ccc(CSc4cccc5c4CN(C4CCC(=O)NC4=O)C5=O)cc3)CC2)CC1]

Referring to the method of example 1, the target compound (SIAIS337021) was prepared by using Dacomitinib derivative B and intermediate LM (SIAIS1220141). (yellow solid, 9.4 mg, yield 32%). HRMS (ESI) m/z: calcd for $C_{49}H_{52}ClFN_9O_5S^+$ [M+H]$^+$, 932.3479; found, 932.3474.

Example 172

Preparation of (E)-N-(4-((3-chloro-4-fluorophenyl) amino)-7-methoxyquinazolin-6-yl)-4-(4-(4-(4-(((2-(2,6-dioxopiperidin-3-yl)-1-oxoisoindolin-4-yl) amino)methyl)benzyl)piperazin-1-yl)piperidin-1-yl) but-2-enamide (SIAIS337024)

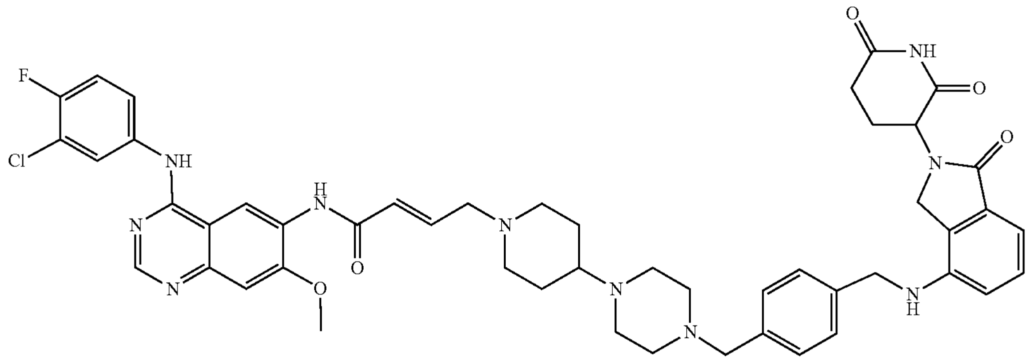 [SMILES: COc1cc2ncnc(Nc3ccc(F)c(Cl)c3)c2cc1NC(=O)/C=C/CN1CCC(N2CCN(Cc3ccc(CNc4cccc5c4CN(C4CCC(=O)NC4=O)C5=O)cc3)CC2)CC1]

Referring to the method of example 1, the target compound (SIAIS337024) was prepared by using Dacomitinib derivative B and intermediate LM (SIAIS1221131). (yellow solid, 9.1 mg, yield 33%). HRMS (ESI) m/z: calcd for $C_{49}H_{53}ClFN_{10}O_5^+$ [M+H]$^+$, 915.3867; found, 915.3864.

Example 173

Preparation of (E)-N-(4-((3-chloro-4-fluorophenyl) amino)-7-methoxyquinazolin-6-yl)-4-(4-(4-(2-((2-(2,6-dioxopiperidin-3-yl)-1-oxoisoindolin-4-yl)oxy) acetyl)piperazin-1-yl)piperidin-1-yl)but-2-enamide (SIAIS337025)

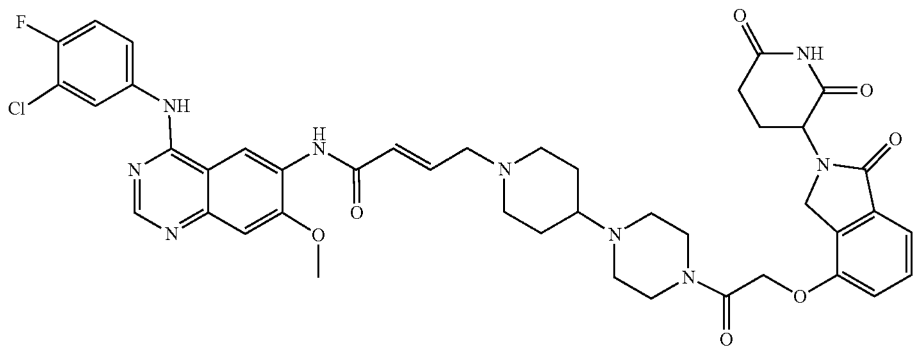 [SMILES: COc1cc2ncnc(Nc3ccc(F)c(Cl)c3)c2cc1NC(=O)/C=C/CN1CCC(N2CCN(C(=O)COc3cccc4c3CN(C3CCC(=O)NC3=O)C4=O)CC2)CC1]

Referring to the method of example 1, the target compound (SIAIS337025) was prepared by using Dacomitinib derivative B and intermediate LM (SIAIS1222121). (yellow solid, 9.7 mg, yield 45%). HRMS (ESI) m/z: calcd for $C_{43}H_{46}ClFN_9O_7^+$ [M+H]$^+$, 854.3187; found, 854.3181.

Example 174

Preparation of (E)-N-(4-((3-chloro-4-fluorophenyl) amino)-7-methoxyquinazolin-6-yl)-4-(4-(4-(5-((2-(2, 6-dioxopiperidin-3-yl)-1-oxoisoindolin-4-yl)oxy) pentanoyl)piperazin-1-yl)piperidin-1-yl)but-2-enamide (SIAIS337026)

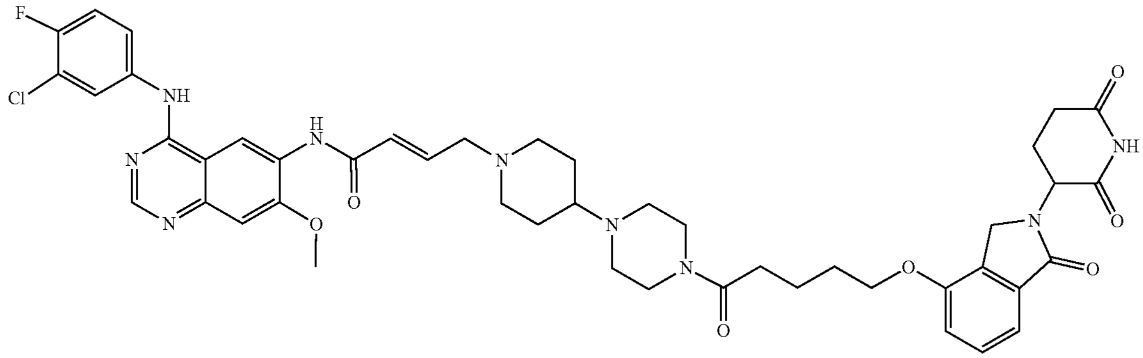 [SMILES: COc1cc2ncnc(Nc3ccc(F)c(Cl)c3)c2cc1NC(=O)/C=C/CN1CCC(N2CCN(C(=O)CCCCOc3cccc4c3CN(C3CCC(=O)NC3=O)C4=O)CC2)CC1]

Referring to the method of example 1, the target compound (SIAIS337026) was prepared by using Dacomitinib derivative B and intermediate LM (SIAIS1222125). (yellow solid, 9.3 mg, yield 42%). HRMS (ESI) m/z: calcd for $C_{46}H_{52}ClFN_9O_7^+$ [M+H]$^+$, 896.3657; found, 896.3651.

Example 175

Preparation of (E)-N-(4-((3-chloro-4-fluorophenyl) amino)-7-methoxyquinazolin-6-yl)-4-(4-(4-(6-((2-(2, 6-dioxopiperidin-3-yl)-1-oxoisoindolin-4-yl)oxy) hexanoyl)piperazin-1-yl)piperidin-1-yl)but-2-enamide (SIAIS337027)

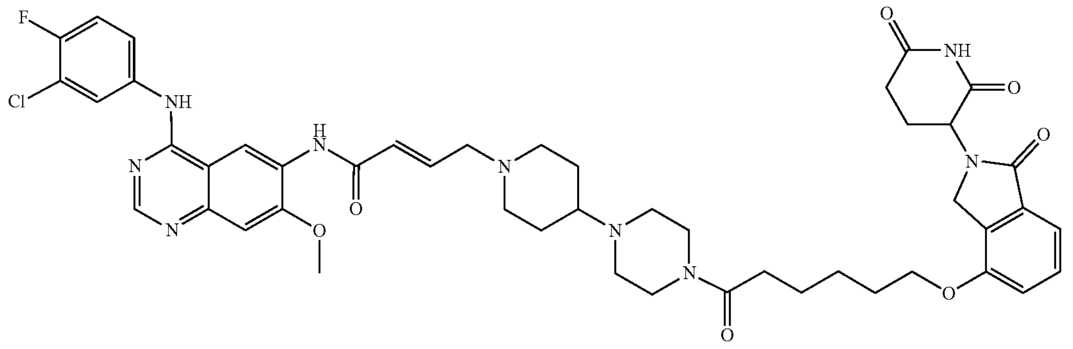 [SMILES: COc1cc2ncnc(Nc3ccc(F)c(Cl)c3)c2cc1NC(=O)/C=C/CN1CCC(N2CCN(C(=O)CCCCCOc3cccc4c3CN(C3CCC(=O)NC3=O)C4=O)CC2)CC1]

Referring to the method of example 1, the target compound (SIAIS337027) was prepared by using Dacomitinib derivative B and intermediate LM (SIAIS1222149). (yellow solid, 8.8 mg, yield 39%). HRMS (ESI) m/z: calcd for $C_{47}H_{54}ClFN_9O_7^+$ [M+H]$^+$, 910.3813; found, 910.3811.

Example 176

Preparation of (E)-N-(4-((3-chloro-4-fluorophenyl)amino)-7-methoxyquinazolin-6-yl)-4-(4-(4-(7-((2-(2,6-dioxopiperidin-3-yl)-1-oxoisoindolin-4-yl)oxy)heptanoyl)piperazin-1-yl)piperidin-1-yl)but-2-enamide (SIAIS337028)

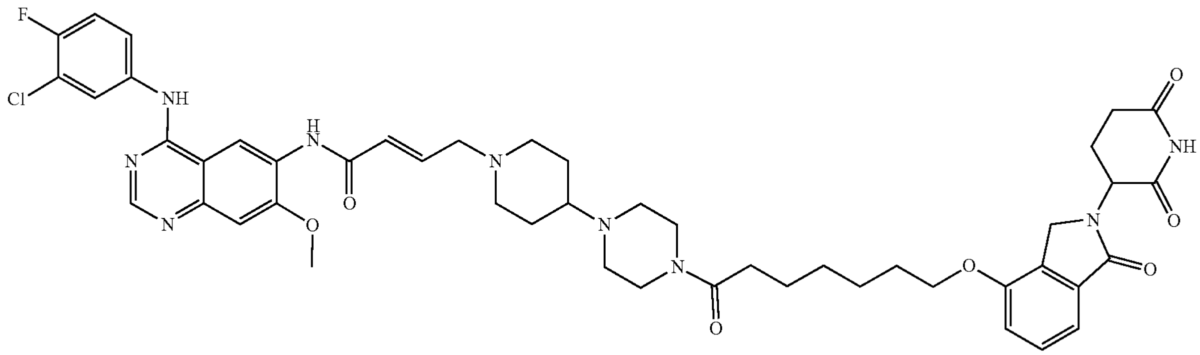 [SMILES: COc1cc2ncnc(Nc3ccc(F)c(Cl)c3)c2cc1NC(=O)/C=C/CN1CCC(N2CCN(C(=O)CCCCCCOc3cccc4c3CN(C3CCC(=O)NC3=O)C4=O)CC2)CC1]

Referring to the method of example 1, the target compound (SIAIS337028) was prepared by using Dacomitinib derivative B and intermediate LM (SIAIS1222151). (yellow solid, 8.6 mg, yield 34%). HRMS (ESI) m/z: calcd for $C_{48}H_{56}ClFN_9O_7^+$ [M+H]$^+$, 924.3970; found, 924.3974.

Example 177

Preparation of (E)-N-(4-((3-chloro-4-fluorophenyl)amino)-7-methoxyquinazolin-6-yl)-4-(4-(4-(6-((2-(2,6-dioxopiperidin-3-yl)-1-oxoisoindolin-4-yl)oxy)hexyl)piperazin-1-yl)piperidin-1-yl)but-2-enamide (SIAIS337029)

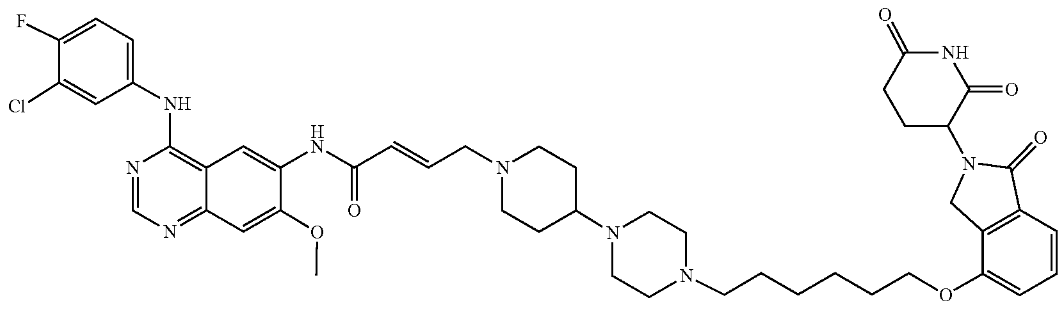 [SMILES: COc1cc2ncnc(Nc3ccc(F)c(Cl)c3)c2cc1NC(=O)/C=C/CN1CCC(N2CCN(CCCCCCOc3cccc4c3CN(C3CCC(=O)NC3=O)C4=O)CC2)CC1]

Referring to the method of example 1, the target compound (SIAIS337029) was prepared by using Dacomitinib derivative B and intermediate LM (SIAIS1222127). (yellow solid, 8.2 mg, yield 31%). HRMS (ESI) m/z: calcd for $C_{47}H_{56}ClFN_9O_6^+$ [M+H]$^+$, 896.4021; found, 896.4029.

Example 178

Preparation of (E)-N-(4-((3-chloro-4-fluorophenyl) amino)-7-methoxyquinazolin-6-yl)-4-(4-(4-(6-((2-(2, 6-dioxopiperidin-3-yl)-1-oxoisoindolin-4-yl)amino) hexanoyl)piperazin-1-yl)piperidin-1-yl)but-2-enamide (SIAIS337035)

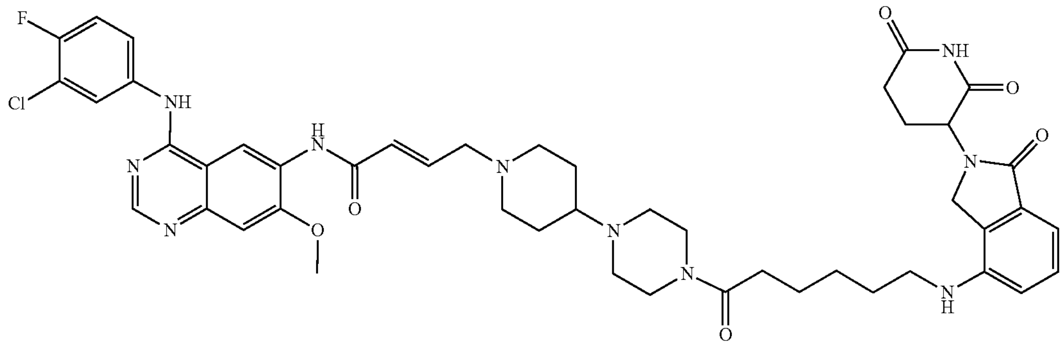 [SMILES: COc1cc2ncnc(Nc3ccc(F)c(Cl)c3)c2cc1NC(=O)/C=C/CN1CCC(N2CCN(C(=O)CCCCCNc3cccc4c3CN(C3CCC(=O)NC3=O)C4=O)CC2)CC1]

Referring to the method of example 1, the target compound (SIAIS337035) was prepared by using Dacomitinib derivative B and intermediate LM (SIAIS1204061). (yellow solid, 8.5 mg, yield 42%). HRMS (ESI) m/z: calcd for $C_{47}H_{55}ClFN_{10}O_6^+$ [M+H]$^+$, 909.3973; found, 909.3978.

Example 179

Preparation of (E)-N-(4-((3-chloro-4-fluorophenyl) amino)-7-methoxyquinazolin-6-yl)-4-(4-(4-(7-((2-(2, 6-dioxopiperidin-3-yl)-1-oxoisoindolin-4-yl)amino) heptanoyl)piperazin-1-yl)piperidin-1-yl)but-2-enamide (SIAIS337036)

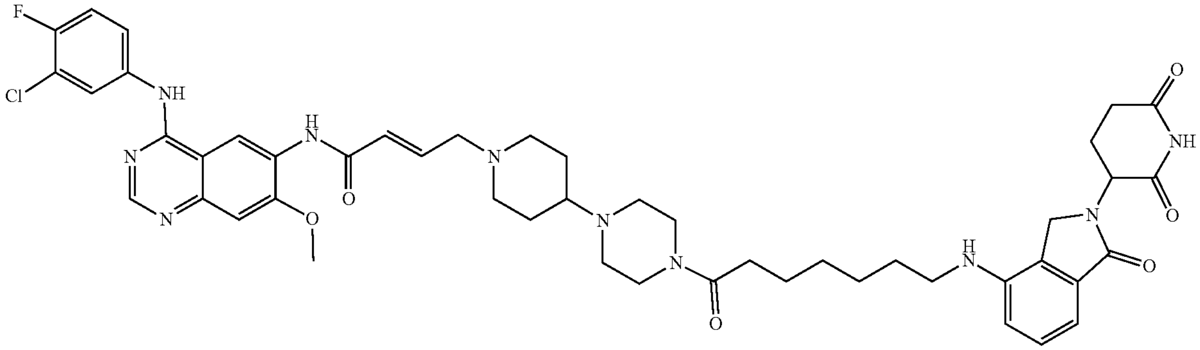 [SMILES: COc1cc2ncnc(Nc3ccc(F)c(Cl)c3)c2cc1NC(=O)/C=C/CN1CCC(N2CCN(C(=O)CCCCCCNc3cccc4c3CN(C3CCC(=O)NC3=O)C4=O)CC2)CC1]

Referring to the method of example 1, the target compound (SIAIS337036) was prepared by using Dacomitinib derivative B and intermediate LM (SIAIS1204063). (yellow solid, 8.7 mg, yield 43%). HRMS (ESI) m/z: calcd for $C_{48}H_{57}ClFN_{10}O_6^+$ [M+H]$^+$, 923.4130; found, 923.4128.

Example 180

Preparation of (E)-N-(4-((3-chloro-4-fluorophenyl)amino)-7-methoxyquinazolin-6-yl)-4-(4-(4-(10-((2-(2,6-dioxopiperidin-3-yl)-1-oxoisoindolin-4-yl)thio)decanoyl)piperazin-1-yl)piperidin-1-yl)but-2-enamide (SIAIS337037)

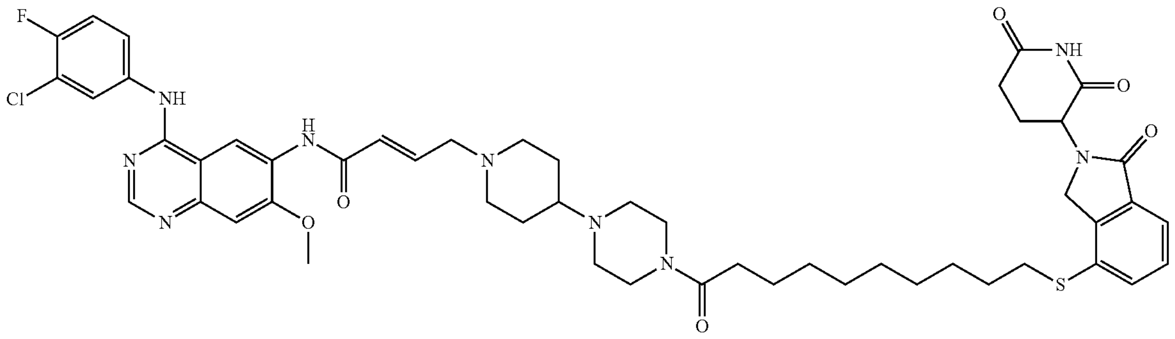 [SMILES: COc1cc2ncnc(Nc3ccc(F)c(Cl)c3)c2cc1NC(=O)/C=C/CN1CCC(N2CCN(C(=O)CCCCCCCCCSc3cccc4c3CN(C3CCC(=O)NC3=O)C4=O)CC2)CC1]

Referring to the method of example 1, the target compound (SIAIS337037) was prepared by using Dacomitinib derivative B and intermediate LM (SIAIS299135). (yellow solid, 8.9 mg, yield 41%). HRMS (ESI) m/z: calcd for $C_{51}H_{62}ClFN_9O_6S^+$ [M+H]$^+$, 982.4211; found, 982.4218.

Example 181

Preparation of (E)-N-(4-((3-chloro-4-fluorophenyl)amino)-7-methoxyquinazolin-6-yl)-4-(4-(4-(11-((2-(2,6-dioxopiperidin-3-yl)-1-oxoisoindolin-4-yl)thio)undecanoyl)piperazin-1-yl)piperidin-1-yl)but-2-enamide (SIAIS337038)

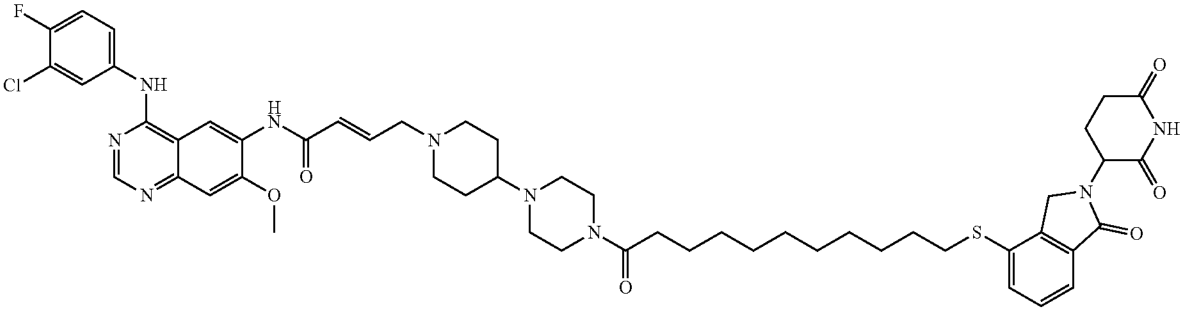 [SMILES: COc1cc2ncnc(Nc3ccc(F)c(Cl)c3)c2cc1NC(=O)/C=C/CN1CCC(N2CCN(C(=O)CCCCCCCCCCSc3cccc4c3CN(C3CCC(=O)NC3=O)C4=O)CC2)CC1]

Referring to the method of example 1, the target compound (SIAIS337038) was prepared by using Dacomitinib derivative B and intermediate LM (SIAIS1220099). (yellow solid, 9.3 mg, yield 46%). HRMS (ESI) m/z: calcd for $C_{52}H_{64}ClFN_9O_6S^+$ [M+H]$^+$, 996.4367; found, 996.4362.

Example 182

Preparation of (E)-N-(4-((3-chloro-4-fluorophenyl)amino)-7-methoxyquinazolin-6-yl)-4-(4-(4-(10-((2-(2,6-dioxopiperidin-3-yl)-1-oxoisoindolin-4-yl)thio)decyl)piperazin-1-yl)piperidin-1-yl)but-2-enamide (SIAIS337039)

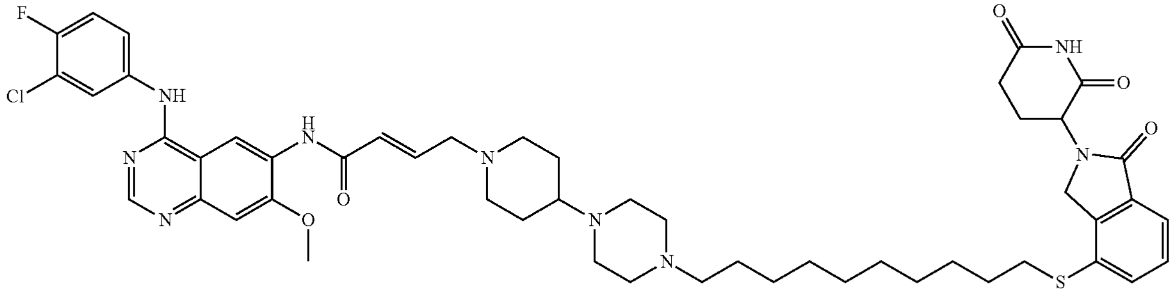 [SMILES: COc1cc2ncnc(Nc3ccc(F)c(Cl)c3)c2cc1NC(=O)/C=C/CN1CCC(N2CCN(CCCCCCCCCCSc3cccc4c3CN(C3CCC(=O)NC3=O)C4=O)CC2)CC1]

Referring to the method of example 1, the target compound (SIAIS337039) was prepared by using Dacomitinib derivative B and intermediate LM (SIAIS1220013). (yellow solid, 9.8 mg, yield 47%). HRMS (ESI) m/z: calcd for $C_{51}H_{64}ClFN_9O_5S^+$ [M+H]$^+$, 968.4418; found, 968.4418.

Example 183

Preparation of (E)-N-(4-((3-chloro-4-fluorophenyl)amino)-7-methoxyquinazolin-6-yl)-4-(4-(4-(11-((2-(2,6-dioxopiperidin-3-yl)-1-oxoisoindolin-4-yl)thio)undecyl)piperazin-1-yl)piperidin-1-yl)but-2-enamide (SIAIS337040)

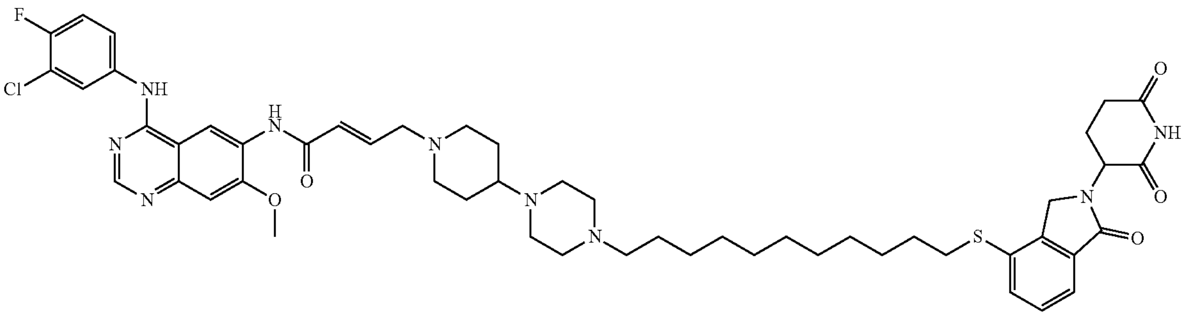 [SMILES: COc1cc2ncnc(Nc3ccc(F)c(Cl)c3)c2cc1NC(=O)/C=C/CN1CCC(N2CCN(CCCCCCCCCCCSc3cccc4c3CN(C3CCC(=O)NC3=O)C4=O)CC2)CC1]

Referring to the method of example 1, the target compound (SIAIS337040) was prepared by using Dacomitinib derivative B and intermediate LM (SIAIS1220015). (yellow solid, 9.9 mg, yield 43%). HRMS (ESI) m/z: calcd for $C_{52}H_{66}ClFN_9O_5S^+$ [M+H]+, 982.4575; found, 982.4575.

Example 184

Preparation of (2S,4R)-1-((S)-19-(4-(3-((6-acrylamido-4-((3-chloro-4-fluorophenyl)amino)quinazolin-7-yl)oxy)propyl)piperazin-1-yl)-2-(tert-butyl)-4,19-dioxo-7,10,13,16-tetraoxa-3-azanonadecanoyl)-4-hydroxy-N-(4-(4-methylthiazol-5-yl)benzyl)pyrrolidine-2-carboxamide (SIAIS262130)

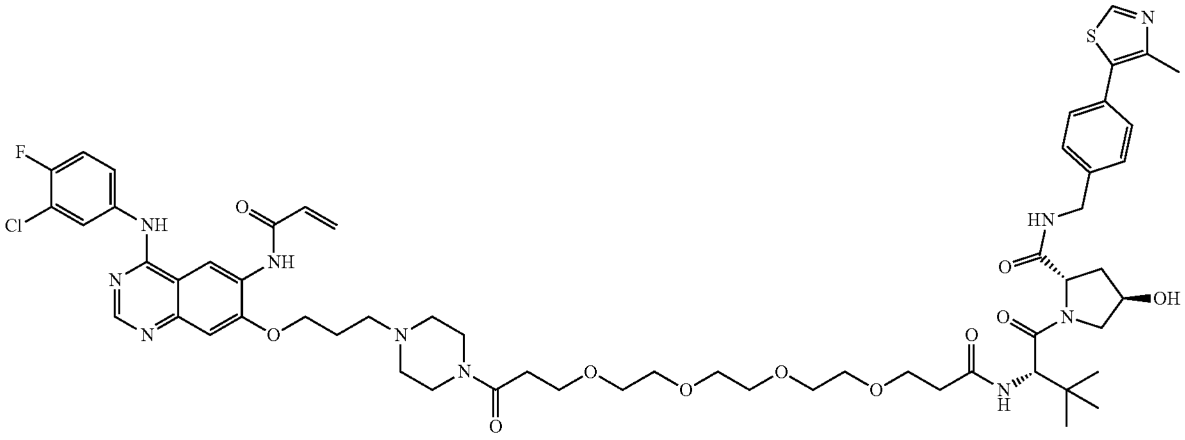 [SMILES: C=CC(=O)Nc1cc2c(Nc3ccc(F)c(Cl)c3)ncnc2cc1OCCCN1CCN(C(=O)CCOCCOCCOCCOCCC(=O)N[C@H](C(=O)N2C[C@H](O)C[C@H]2C(=O)NCc2ccc(-c3scnc3C)cc2)C(C)(C)C)CC1]

Referring to the method of example 1, the target compound (SIAIS262130) was prepared by using Caneritinib derivative A and intermediate LM (SIAIS151008). (white solid, 10.8 mg, yield 36%). HRMS (ESI) m/z: calcd for $C_{58}H_{75}ClFN_{10}O_{11}S^+$ [M+H]+, 1173.5005; found, 1173.5001.

Example 185

Preparation of (E)-N-(4-((3-chloro-4-fluorophenyl)amino)-7-methoxyquinazolin-6-yl)-4-(4-(2-((2-(2,6-dioxopiperidin-3-yl)-1,3-dioxoisoindolin-4-yl)amino)acetamido)piperidin-1-yl)but-2-enamide (SIAIS249081)

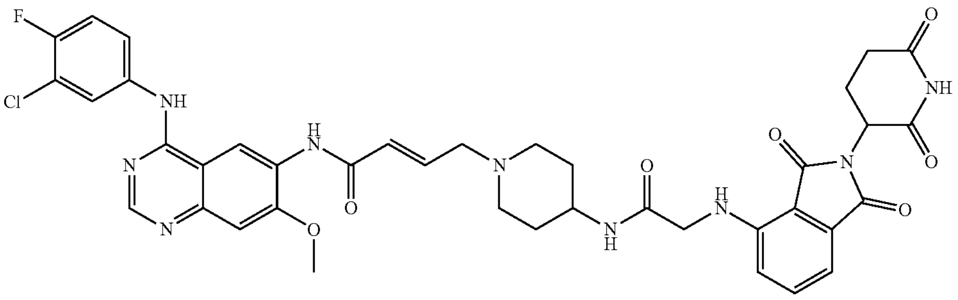

Referring to the method of example 1, the target compound (SIAIS249081) was prepared by using Dacomitinib derivative B and intermediate LM (SIAIS151025). (yellow solid, 8.6 mg, yield 54%). $^1$H NMR (500 MHz, Methanol-$d_4$) δ 9.09 (s, 1H), 8.61 (s, 1H), 7.97 (dd, J=6.7, 2.6 Hz, 1H), 7.66 (ddd, J=8.9, 4.1, 2.5 Hz, 1H), 7.57 (dd, J=8.5, 7.1 Hz, 1H), 7.33-7.27 (m, 2H), 7.13 (d, J=7.1 Hz, 1H), 7.00 (dd, J=14.9, 7.5 Hz, 1H), 6.89 (d, J=8.4 Hz, 1H), 6.81 (d, J=15.1 Hz, 1H), 5.08 (dd, J=12.6, 5.5 Hz, 1H), 4.13 (s, 3H), 4.03 (s, 2H), 3.99 (d, J=7.2 Hz, 1H), 3.61-3.56 (m, 1H), 3.23-3.16 (m, 1H), 2.86 (ddd, J=17.8, 14.3, 5.2 Hz, 1H), 2.79-2.67 (m, 2H), 2.23-2.03 (m, 4H), 1.88-1.78 (m, 2H), 1.65-1.58 (m, 1H), 1.39-1.35 (m, 2H). HRMS (ESI) m/z: calcd for $C_{39}H_{38}ClFN_9O_7^+$ [M+H]$^+$, 798.2561; found, 798.2563.

Example 186

Preparation of (E)-N-(4-((3-chloro-4-fluorophenyl)amino)-7-methoxyquinazolin-6-yl)-4-(4-(3-((2-(2,6-dioxopiperidin-3-yl)-1,3-dioxoisoindolin-4-yl)amino)propanamido)piperidin-1-yl)but-2-enamide (SIAIS249082)

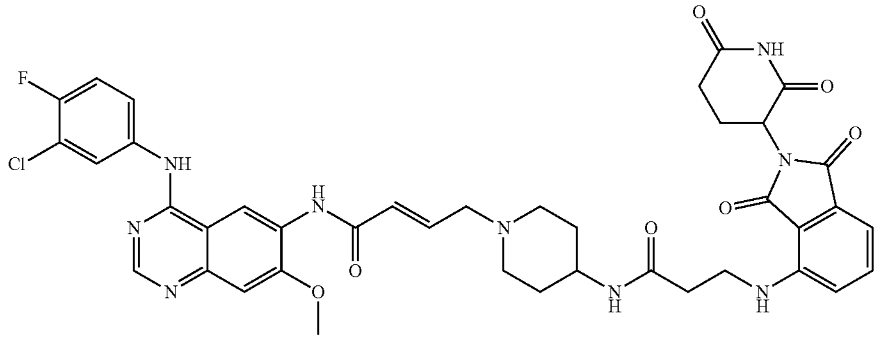 [SMILES: COc1cc2ncnc(Nc3ccc(F)c(Cl)c3)c2cc1NC(=O)/C=C/CN1CCC(NC(=O)CCNc2cccc3c2C(=O)N(C2CCC(=O)NC2=O)C3=O)CC1]

Referring to the method of example 1, the target compound (SIAIS249082) was prepared by using Dacomitinib derivative B and intermediate LM (SIAIS151026). (yellow solid, 9.6 mg, yield 56%). $^1$H NMR (500 MHz, Methanol-$d_4$) δ 9.24 (s, 1H), 8.62 (s, 1H), 7.99 (dd, J=6.7, 2.6 Hz, 1H), 7.74-7.67 (m, 1H), 7.59 (dd, J=8.6, 7.1 Hz, 1H), 7.36-7.26 (m, 2H), 7.15 (d, J=8.6 Hz, 1H), 7.06 (dd, J=14.6, 7.5 Hz, 2H), 6.80 (d, J=15.2 Hz, 1H), 5.10 (dd, J=12.3, 5.3 Hz, 1H), 4.14 (s, 3H), 3.98 (d, J=7.0 Hz, 2H), 3.90 (s, 1H), 3.75-3.66 (m, 1H), 3.09 (s, 1H), 2.94-2.82 (m, 1H), 2.80-2.69 (m, 2H), 2.58-2.51 (m, 2H), 2.22-2.03 (m, 4H), 1.65-1.58 (m, 2H), 1.38-1.28 (m, 3H). HRMS (ESI) m/z: calcd for $C_{40}H_{40}ClFN_9O_7^+$ [M+H]$^+$, 812.2718; found, 812.2713.

Example 187

Preparation of (E)-N-(4-((3-chloro-4-fluorophenyl)amino)-7-methoxyquinazolin-6-yl)-4-(4-(4-((2-(2,6-dioxopiperidin-3-yl)-1,3-dioxoisoindolin-4-yl)amino)butanamido)piperidin-1-yl)but-2-enamide (SIAIS249083)

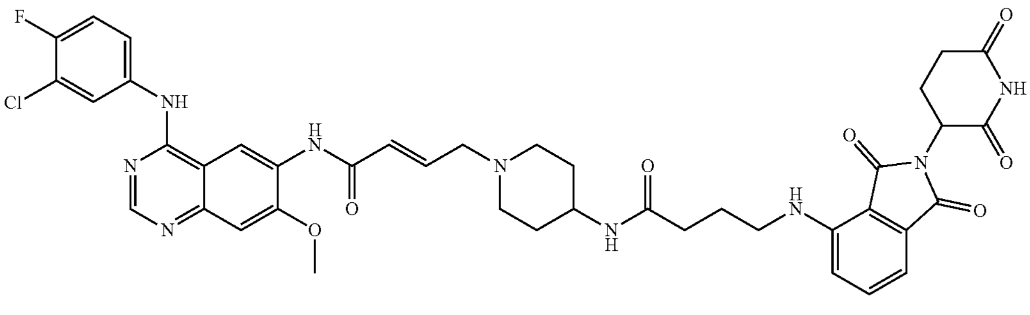

Referring to the method of example 1, the target compound (SIAIS249083) was prepared by using Dacomitinib derivative B and intermediate LM (SIAIS151019). (yellow solid, 8.7 mg, yield 51%). $^1$H NMR (500 MHz, Methanol-$d_4$) δ 9.24 (s, 1H), 8.66 (s, 1H), 7.97 (dd, J=6.7, 2.7 Hz, 1H), 7.68 (ddd, J=8.9, 4.2, 2.7 Hz, 1H), 7.56 (dd, J=8.6, 7.1 Hz, 1H), 7.37-7.28 (m, 2H), 7.09 (d, J=8.5 Hz, 1H), 7.04 (dd, J=7.3, 4.0 Hz, 1H), 6.82 (d, J=15.2 Hz, 1H), 5.07 (dd, J=12.5, 5.4 Hz, 1H), 4.15 (s, 3H), 4.00 (d, J=7.2 Hz, 2H), 3.81-3.75 (m, 1H), 3.59-3.48 (m, 1H), 3.47-3.42 (m, 2H), 3.23-3.14 (m, 1H), 2.91-2.85 (m, 1H), 2.75 (dt, J=14.3, 3.1 Hz, 2H), 2.31 (d, J=8.4 Hz, 2H), 2.13-2.08 (m, 1H), 2.13-2.01 (m, 4H), 1.7-1.59 (m, 2H), 1.38-1.29 (m, 2H). HRMS (ESI) m/z: calcd for $C_{41}H_{42}ClFN_9O_7^+$ [M+H]$^+$, 826.2874; found, 826.2870.

Example 188

Preparation of (E)-N-(1-(4-((4-((3-chloro-4-fluorophenyl)amino)-7-methoxyquinazolin-6-yl)amino)-4-oxobut-2-en-1-yl)piperidin-4-yl)-6-((2-(2,6-dioxopiperidin-3-yl)-1,3-dioxoisoindolin-4-yl)amino) hexanamide (SIAIS249084)

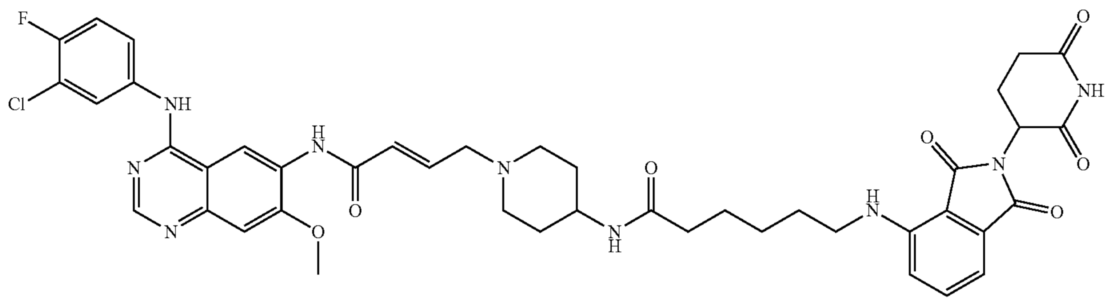

Referring to the method of example 1, the target compound (SIAIS249084) was prepared by using Dacomitinib derivative B and intermediate LM (SIAIS151020). (yellow solid, 11.1 mg, yield 65%). $^1$H NMR (500 MHz, Methanol-$d_4$) δ 9.17 (s, 1H), 8.64 (s, 1H), 7.98 (s, 1H), 7.68 (s, 1H), 7.55 (s, 1H), 7.32 (dd, J=19.0, 6.5 Hz, 2H), 7.1-7.00 (m, 3H), 6.82 (d, J=15.1 Hz, 1H), 5.07 (dd, J=12.5, 5.4 Hz, 1H), 4.15 (s, 3H), 4.00 (s, 1H), 3.62-3.5 (m, 1H), 3.21-3.15 (m, 1H), 2.84 (d, J=17.2 Hz, 1H), 2.75-2.71 (m, 2H), 2.28-2.18 (m, 2H), 2.09-1.99 (m, 4H), 1.72-1.68 (m, 4H), 1.63-1.58 (m, 1H) 1.48-1.38 (m, 2H), 1.35-1.28 (m, 4H). HRMS (ESI) m/z: calcd for $C_{43}H_{46}ClFN_9O_7^+$ [M+H]$^+$, 854.3187; found, 854.3189.

Example 189

Preparation of (E)-N-(1-(4-((4-((3-chloro-4-fluorophenyl)amino)-7-methoxyquinazolin-6-yl)amino)-4-oxobut-2-en-1-yl)piperidin-4-yl)-7-((2-(2,6-dioxopiperidin-3-yl)-1,3-dioxoisoindolin-4-yl)amino) heptanamide (SIAIS249085)

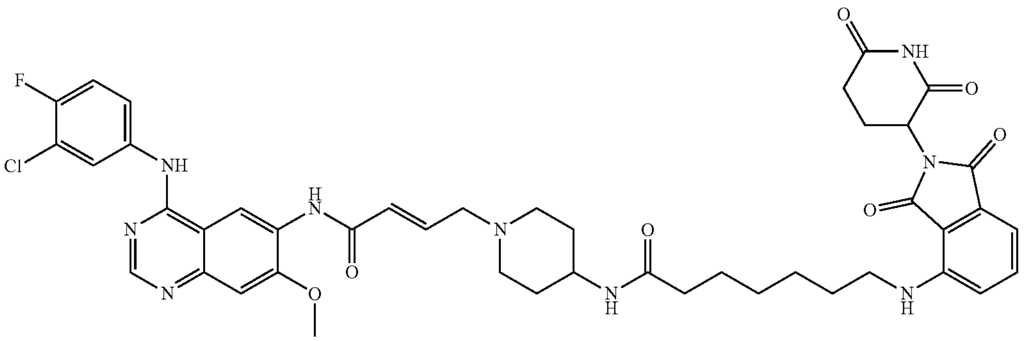

Referring to the method of example 1, the target compound (SIAIS249085) was prepared by using Dacomitinib derivative B and intermediate LM (SIAIS151086). (yellow solid, 10.6 mg, yield 59%). $^1$H NMR (500 MHz, Methanol-$d_4$) δ 9.15 (s, 1H), 8.65 (s, 1H), 7.96 (dd, J=6.6, 2.6 Hz, 1H), 7.66 (ddd, J=8.9, 4.2, 2.6 Hz, 1H), 7.54 (dd, J=8.6, 7.1 Hz, 1H), 7.36-7.29 (m, 2H), 7.03 (dd, J=7.9, 2.6 Hz, 2H), 7.00 (t, J=7.4 Hz, 1H), 6.83 (d, J=15.2 Hz, 1H), 5.05 (dd, J=12.4, 5.5 Hz, 1H), 4.15 (s, 3H), 4.01 (d, J=7.2 Hz, 2H), 4.00-3.96 (m, 1H), 3.61-3.58 (m, 1H), 3.19-3.15 (m, 1H), 2.91-2.80 (m, 1H), 2.80-2.65 (m, 2H), 2.20 (q, J=7.6 Hz, 2H), 2.15-2.07 (m, 4H), 1.69-1.60 (m, 5H), 1.48-1.31 (m, 8H). HRMS (ESI) m/z: calcd for $C_{44}H_{48}ClFN_9O_7^+$ [M+H]$^+$, 868.3344; found, 868.3341.

Example 190

Preparation of (E)-N-(4-((3-chloro-4-fluorophenyl)amino)-7-methoxyquinazolin-6-yl)-4-(4-(3-(2-(2-((2-(2,6-dioxopiperidin-3-yl)-1,3-dioxoisoindolin-4-yl)amino)ethoxy)ethoxy)propanamido)piperidin-1-yl)but-2-enamide (SIAIS249086)

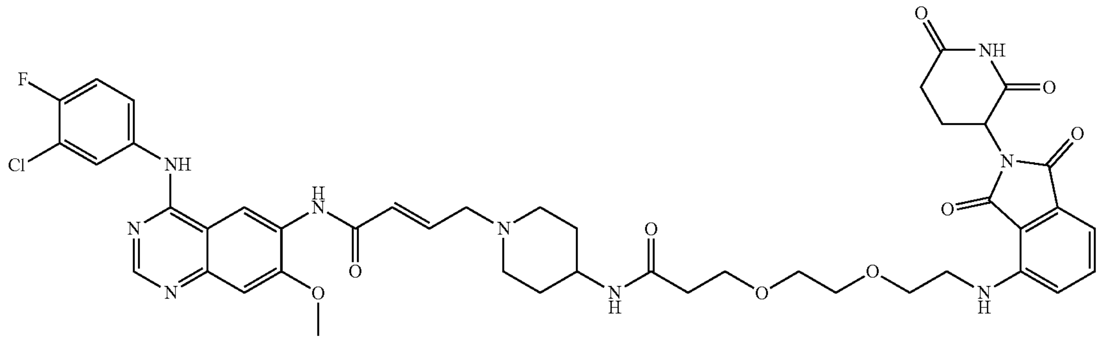 [SMILES: COc1cc2ncnc(Nc3ccc(F)c(Cl)c3)c2cc1NC(=O)/C=C/CN1CCC(NC(=O)CCOCCOCCNc2cccc3c2C(=O)N(C2CCC(=O)NC2=O)C3=O)CC1]

Referring to the method of example 1, the target compound (SIAIS249086) was prepared by using Dacomitinib derivative B and intermediate LM (SIAIS151004). (yellow solid, 10.2 mg, yield 54%) $^1$H NMR (500 MHz, Methanol-$d_4$) δ 9.17 (s, 1H), 8.68 (s, 1H), 7.95 (dd, J=6.7, 2.6 Hz, 1H), 7.69-7.64 (m, 1H), 7.57-7.50 (m, 1H), 7.33 (dd, J=19.2, 10.3 Hz, 2H), 7.09 (d, J=8.5 Hz, 1H), 7.09-6.98 (m, 2H), 6.81 (d, J=15.2 Hz, 1H), 5.07 (dd, J=12.4, 5.5 Hz, 1H), 4.15 (s, 3H), 4.00 (d, J=7.2 Hz, 2H), 3.98-3.91 (m, 1H), 3.73 (dt, J=8.2, 5.7 Hz, 5H), 3.66-3.60 (m, 4H), 3.49 (t, J=5.3 Hz, 2H), 3.22-3.07 (m, 1H), 2.91-2.77 (m, 1H), 2.78-2.65 (m, 2H), 2.48-2.36 (m, 2H), 2.2-2.15 (m, 3H), 1.83-1.80 (m, 2H), 1.65-1.62 (m, 1H), 1.37-1.31 (m, 2H). HRMS (ESI) m/z: calcd for $C_{44}H_{48}ClFN_9O_9^+$ [M+H]$^+$, 900.3242; found, 900.3241.

Example 191

Preparation of 4-(4-(3-((6-acrylamido-4-((3-chloro-4-fluorophenyl)amino)quinazolin-7-yl)oxy)propyl)piperazin-1-yl)-N-(2-(2-((2-(2,6-dioxopiperidin-3-yl)-1,3-dioxoisoindolin-4-yl)amino)ethoxy)ethyl)-4-oxobutanamide (SIAIS249099)

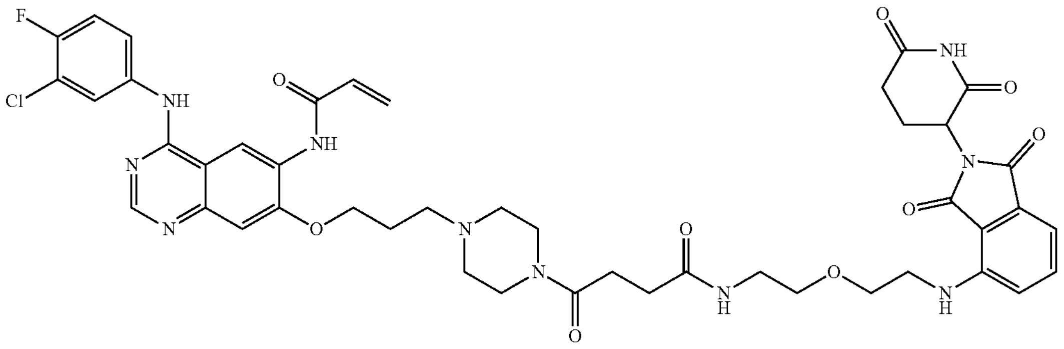 [SMILES: C=CC(=O)Nc1cc2c(Nc3ccc(F)c(Cl)c3)ncnc2cc1OCCCN1CCN(C(=O)CCC(=O)NCCOCCNc2cccc3c2C(=O)N(C2CCC(=O)NC2=O)C3=O)CC1]

Referring to the method of example 1, the target compound (SIAIS249099) was prepared by using Caneritinib derivative A and intermediate LM (SIAIS164118). (yellow solid, 10.1 mg, yield 56%). HRMS (ESI) m/z: calcd for $C_{45}H_{49}ClFN_{10}O_9^+$ [M+H]$^+$, 927.3351; found, 927.3353.

Example 192

Preparation of 4-(4-(3-((6-acrylamido-4-((3-chloro-4-fluorophenyl)amino)quinazolin-7-yl)oxy)propyl) piperazin-1-yl)-N-(2-((2-(2,6-dioxopiperidin-3-yl)-1,3-dioxoisoindolin-4-yl)amino)ethyl)-4-oxobutanamide (SIAIS249100)

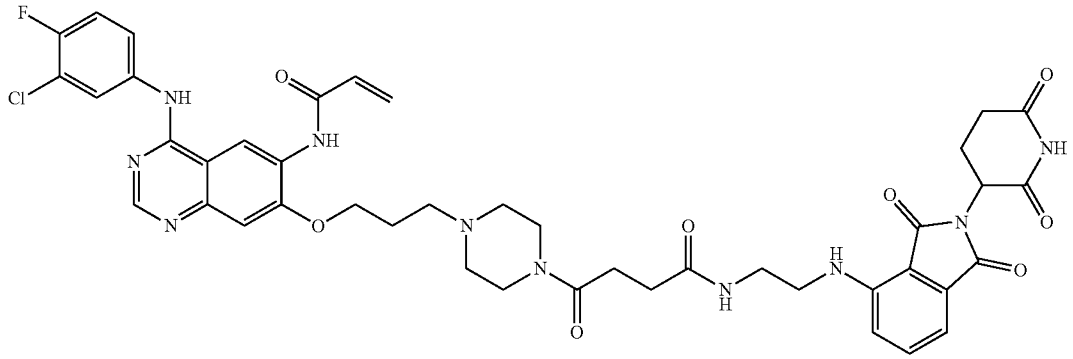 [SMILES: C=CC(=O)Nc1cc2c(Nc3ccc(F)c(Cl)c3)ncnc2cc1OCCCN1CCN(C(=O)CCC(=O)NCCNc2cccc3c2C(=O)N(C2CCC(=O)NC2=O)C3=O)CC1]

Referring to the method of example 1, the target compound (SIAIS249100) was prepared by using Caneritinib derivative A and intermediate LM (SIAIS164119). (yellow solid, 9.6 mg, yield 59%). $^1$H NMR (500 MHz, Methanol-$d_4$) δ 9.14 (s, 1H), 8.74 (s, 1H), 7.94 (dd, J=6.6, 2.6 Hz, 1H), 7.69-7.63 (mz, 1H), 7.54 (dd, J=8.6, 7.1 Hz, 1H), 7.42-7.33 (m, 2H), 7.12 (d, J=8.6 Hz, 1H), 7.02 (d, J=7.1 Hz, 1H), 6.78 (dd, J=16.9, 10.3 Hz, 1H), 6.51 (dd, J=16.9, 1.6 Hz, 1H), 5.90 (dd, J=10.2, 1.6 Hz, 1H), 5.05 (dd, J=12.7, 5.5 Hz, 2H), 4.48 (t, J=5.9 Hz, 2H), 3.71-3.61 (m, 3H), 3.52-3.40 (m, 6H), 2.93-2.82 (m, 1H), 2.77-2.66 (m, 4H), 2.70-2.63 (m, 6H), 2.13-2.05 (m, 1H), 2.05-2.01 (m, 1H), 1.39-1.36 (m, 2H). HRMS (ESI) m/z: calcd for $C_{43}H_{45}ClFN_{10}O_8^+$ [M+H]$^+$, 883.3089; found, 883.3081.

Example 193
Preparation of (2S,4R)-1-((S)-2-(3-(4-(3-(4-(3-((6-acrylamido-4-((3-chloro-4-fluorophenyl)amino)quinazolin-7-yl)oxy)propyl)piperazin-1-yl)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide (SIAIS249101)
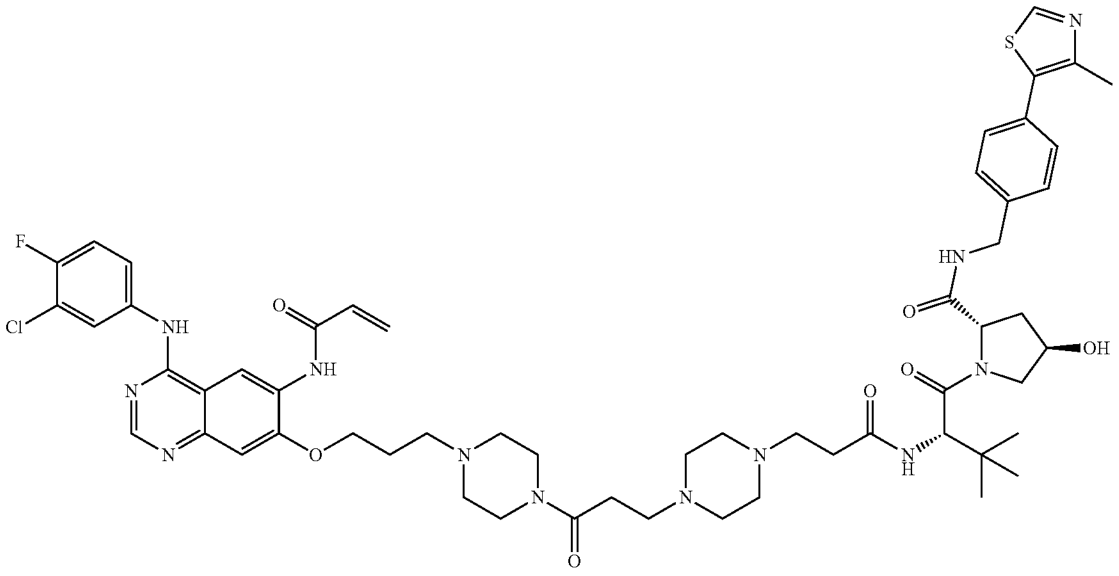 [SMILES: C=CC(=O)Nc1cc2c(Nc3ccc(F)c(Cl)c3)ncnc2cc1OCCCN1CCN(C(=O)CCN2CCN(CCC(=O)N[C@H](C(=O)N3C[C@H](O)C[C@H]3C(=O)NCc3ccc(-c4scnc4C)cc3)C(C)(C)C)CC2)CC1]

Referring to the method of example 1, the target compound (SIAIS249101) was prepared by using Caneritinib derivative A and intermediate LM (SIAIS1213011). (white solid, 8.2 mg, yield 37%). HRMS (ESI) m/z: calcd for $C_{56}H_{71}ClFN_{12}O_7S^+$ $[M+H]^+$, 1109.4956; found, 1109.4951.

Example 194

Preparation of (2S,4R)-1-((S)-2-(3-(4-(3-(4-(3-((6-acrylamido-4-((3-chloro-4-fluorophenyl)amino)quinazolin-7-yl)oxy)propyl)piperazin-1-yl)-3-oxopropyl)phenyl)propanamido)-3,3-dimethylbutanoyl)-4-hydroxy-N-(4-(4-methylthiazol-5-yl)benzyl)pyrrolidine-2-carboxamide (SIAIS249102)

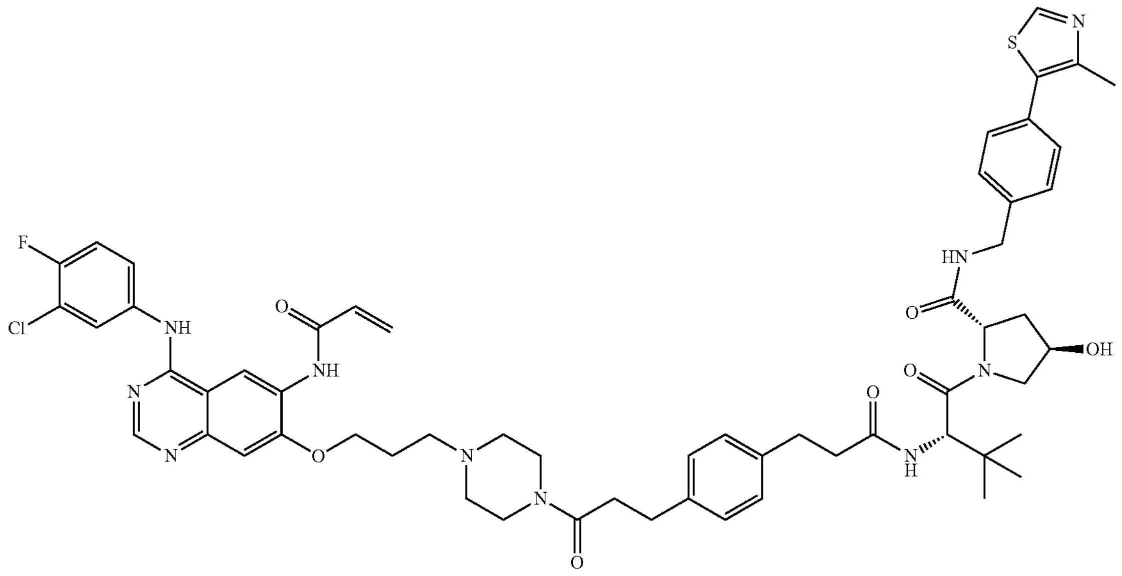 [SMILES: C=CC(=O)Nc1cc2c(Nc3ccc(F)c(Cl)c3)ncnc2cc1OCCCN1CCN(C(=O)CCc2ccc(CCC(=O)N[C@H](C(=O)N3C[C@H](O)C[C@H]3C(=O)NCc3ccc(-c4scnc4C)cc3)C(C)(C)C)cc2)CC1]

Referring to the method of example 1, the target compound (SIAIS249102) was prepared by using Caneritinib derivative A and intermediate LM (SIAIS1213061). (white solid, 12 mg, yield 55%). $^1$H NMR (500 MHz, Methanol-$d_4$) δ 9.16 (s, 1H), 9.12 (s, 1H), 8.75 (s, 1H), 7.93 (dd, J=6.6, 2.7 Hz, 1H), 7.7-7.64 (m, 1H), 7.47 (d, J=8.3 Hz, 1H), 7.42 (d, J=8.2 Hz, 2H), 7.37 (d, J=3.2 Hz, 2H), 7.15 (s, 4H), 6.84 (dd, J=16.9, 10.3 Hz, 1H), 6.50 (dd, J=16.9, 1.6 Hz, 1H), 5.89 (dd, J=10.3, 1.6 Hz, 1H), 4.61-4.53 (m, 3H), 4.51-4.46 (m, 2H), 4.37 (d, J=15.5 Hz, 1H), 4.09 (s, 1H), 3.89 (d, J=11.0 Hz, 1H), 3.78 (dd, J=10.9, 4.0 Hz, 1H), 3.45-3.40 (m, 3H), 3.30-3.19 (m, 1H), 2.94-2.82 (m, 5H), 2.79-2.72 (m, 3H), 2.64-2.53 (m, 3H), 2.49 (s, 3H), 2.28-2.17 (m, 1H), 2.12-1.99 (m, 1H), 1.29 (s, 2H), 0.96 (s, 9H). HRMS (ESI) m/z: calcd for $C_{58}H_{67}ClFN_{10}O_7S^+$ [M+H]$^+$, 1101.4582; found, 1101.4580.

Example 195

Preparation of (E)-N-(4-((3-chloro-4-fluorophenyl) amino)-7-methoxyquinazolin-6-yl)-4-(4-(4-(4-((2-(2-((2-(2,6-dioxopiperidin-3-yl)-1,3-dioxoisoindolin-4-yl)amino)ethoxy)ethyl)amino)-4-oxobutanoyl) piperazin-1-yl)piperidin-1-yl)but-2-enamide (SIAIS249103)

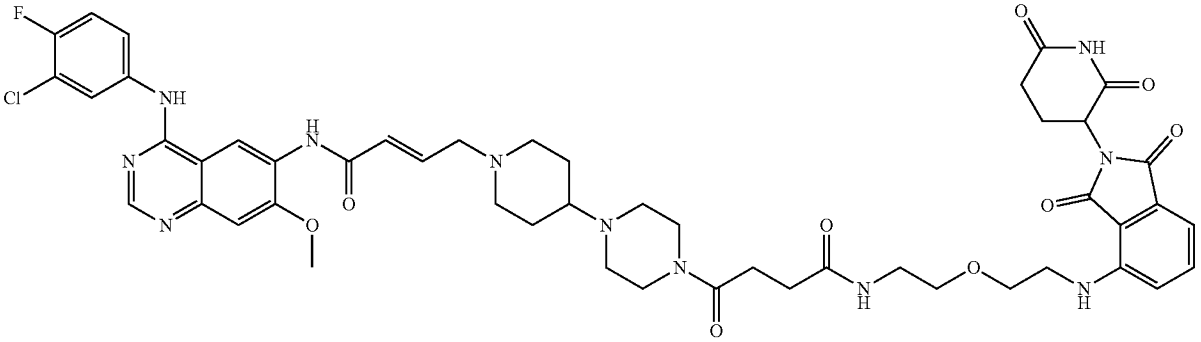 [SMILES: COc1cc2ncnc(Nc3ccc(F)c(Cl)c3)c2cc1NC(=O)/C=C/CN1CCC(N2CCN(C(=O)CCC(=O)NCCOCCNc3cccc4c3C(=O)N(C3CCC(=O)NC3=O)C4=O)CC2)CC1]

Referring to the method of example 1, the target compound (SIAIS249103) was prepared by using Dacomitinib derivative C and intermediate LM (SIAIS164118). (yellow solid, 11.6 mg, yield 64%). $^1$H NMR (500 MHz, Methanol-$d_4$) δ 9.27 (s, 1H), 8.75 (s, 1H), 7.92 (dd, J=6.7, 2.6 Hz, 1H), 7.64-7.68 (m, 1H), 7.60-7.55 (m, 1H), 7.37 (t, J=8.9 Hz, 1H), 7.32 (s, 1H), 7.11-7.02 (m, 3H), 6.87 (d, J=15.1 Hz, 1H), 5.09 (dd, J=12.1, 5.4 Hz, 1H), 4.18 (s, 3H), 4.08 (s, 2H), 3.79 (d, J=12.6 Hz, 2H), 3.72 (dt, J=9.0, 5.1 Hz, 3H), 3.67-3.63 (m, 2H), 3.58 (t, J=5.2 Hz, 2H), 3.53 (dt, J=6.0, 2.6 Hz, 2H), 3.49 (t, J=5.1 Hz, 2H), 3.48-3.38 (m, 3H), 3.26-3.18 (m, 1H), 2.89-2.82 (m, 1H), 2.79-2.70 (m, 3H), 2.70-2.45 (m, 6H), 2.28-2.17 (m, 2H), 2.15-2.10 (m, 2H), 1.38-1.32 (m, 2H). HRMS (ESI) m/z: calcd for $C_{49}H_{56}ClFN_{11}O_9^+$ [M+H]$^+$, 996.3930; found, 996.3931.

Example 196

Preparation of (E)-N-(4-((3-chloro-4-fluorophenyl) amino)-7-methoxyquinazolin-6-yl)-4-(4-(4-(4-((2-((2-(2,6-dioxopiperidin-3-yl)-1,3-dioxoisoindolin-4-yl)amino)ethyl)amino)-4-oxobutanoyl)piperazin-1-yl)piperidin-1-yl)but-2-enamide (SIAIS249104)

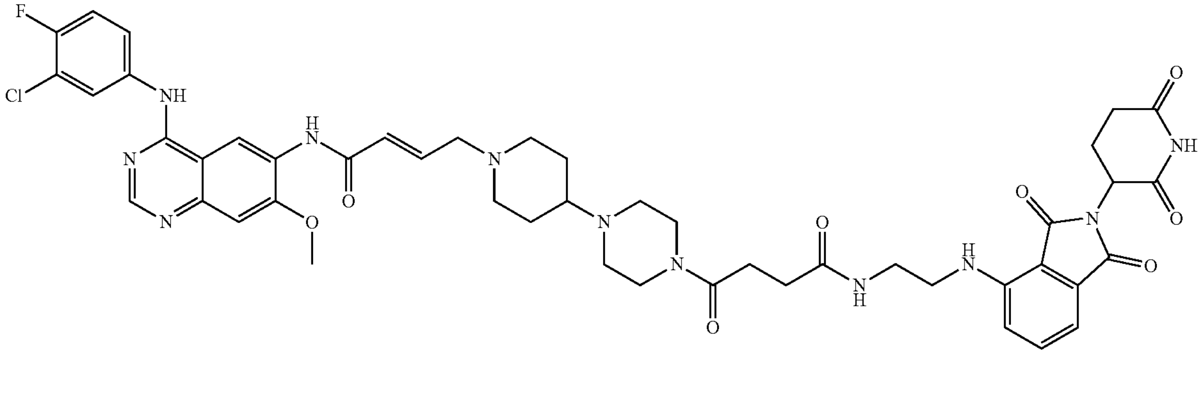 [SMILES: COc1cc2ncnc(Nc3ccc(F)c(Cl)c3)c2cc1NC(=O)/C=C/CN1CCC(N2CCN(C(=O)CCC(=O)NCCNc3cccc4c3C(=O)N(C3CCC(=O)NC3=O)C4=O)CC2)CC1]

Referring to the method of example 1, the target compound (SIAIS249104) was prepared by using Dacomitinib derivative C and intermediate LM (SIAIS164119). (yellow solid, 11.8 mg, yield 70%). $^1$H NMR (500 MHz, Methanol-$d_4$) δ 9.26 (s, 1H), 8.74 (s, 1H), 7.93 (dd, J=6.6, 2.6 Hz, 1H), 7.68-7.63 (m, 1H), 7.56 (dd, J=8.6, 7.1 Hz, 1H), 7.37 (t, J=8.9 Hz, 1H), 7.32 (s, 1H), 7.13 (d, J=8.6 Hz, 1H), 7.08-7.02 (m, 2H), 6.86 (d, J=15.2 Hz, 1H), 5.07 (dd, J=12.7, 5.5 Hz, 1H), 4.18 (s, 3H), 4.05 (s, 2H), 3.75 (s, 2H), 3.50-3.41 (m, 8H), 3.22-3.12 (m, 3H), 2.92-2.86 (m, 1H), 2.78-2.58 (m, 5H), 2.55-2.41 (m, 4H), 2.25-2.15 (m, 2H), 2.14-2.09 (m, 2H), 1.35-1.30 (m, 2H). HRMS (ESI) m/z: calcd for $C_{47}H_{52}ClFN_{11}O_8$+ $[M+H]^+$, 952.3667; found, 952.3665.

Example 197

Preparation of (2S,4R)-1-((S)-2-(3-(4-(3-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide (SIAIS249105)

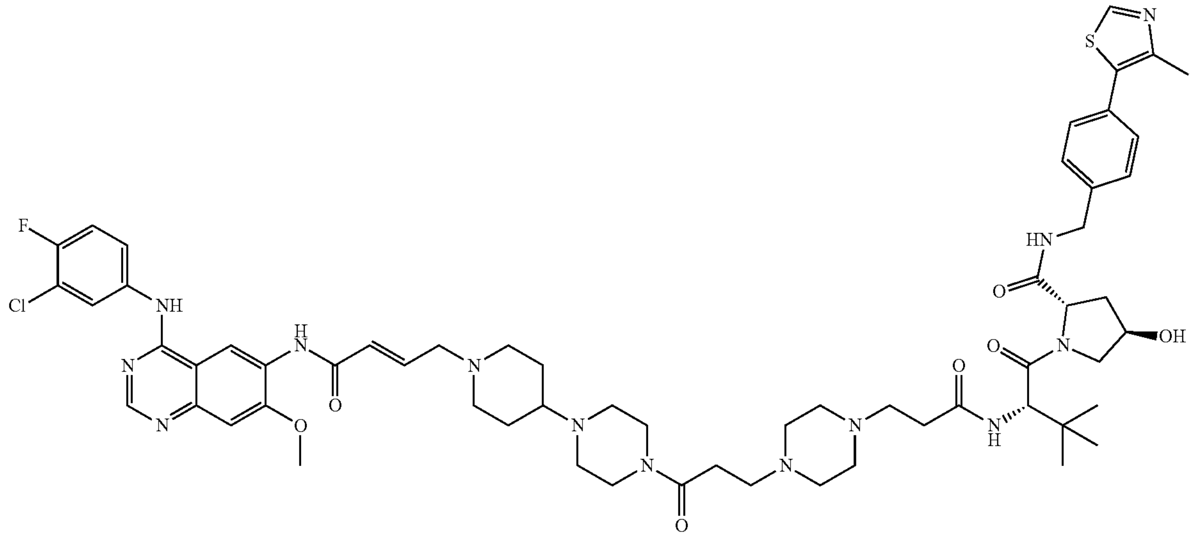 [SMILES: COc1cc2ncnc(Nc3ccc(F)c(Cl)c3)c2cc1NC(=O)/C=C/CN1CCC(N2CCN(C(=O)CCN3CCN(CCC(=O)N[C@H](C(=O)N4C[C@H](O)C[C@H]4C(=O)NCc4ccc(-c5scnc5C)cc4)C(C)(C)C)CC3)CC2)CC1]

Referring to the method of example 1, the target compound (SIAIS249105) was prepared by using Dacomitinib derivative C and intermediate LM (SIAIS1213011). (white solid, 12.1 mg, yield 57%). $^1$H NMR (500 MHz, Methanol-$d_4$) δ 9.53 (s, 1H), 9.26 (s, 1H), 8.75 (s, 1H), 7.92 (dd, J=6.6, 2.6 Hz, 1H), 7.70-7.65 (m, 1H), 7.57-7.51 (m, 2H), 7.50-7.44 (m, 2H), 7.40-7.32 (m, 2H), 7.07 (dt, J=14.8, 7.2 Hz, 1H), 6.89 (d, J=15.2 Hz, 1H), 4.67-4.46 (m, 5H), 4.39 (dd, J=15.8, 2.0 Hz, 1H), 4.18 (s, 3H), 4.10 (s, 2H), 3.97 (d, J=11.0 Hz, 2H), 3.88-3.45 (m, 24H), 3.28-3.20 (m, 2H), 2.91-2.87 (m, 2H), 2.55 (s, 3H), 2.33-2.16 (m, 3H), 2.12-1.98 (m, 1H), 1.32-1.28 (m, 2H), 1.06 (s, 9H). HRMS (ESI) m/z: calcd for $C_{60}H_{78}ClFN_{13}O_7S^+$ [M+H]$^+$, 1178.5535; found, 1178.5531.

Example 198

Preparation of (2S,4R)-1-((S)-2-(3-(4-(3-(4-(1-((E)-4-((4-((3-chloro-4-fluorophenyl)amino)-7-methoxyquinazolin-6-yl)amino)-4-oxobut-2-en-1-yl)piperidin-4-yl)piperazin-1-yl)-3-oxopropyl)phenyl)propanamido)-3,3-dimethylbutanoyl)-4-hydroxy-N-(4-(4-methylthiazol-5-yl)benzyl)pyrrolidine-2-carboxamide (SIAIS249106)

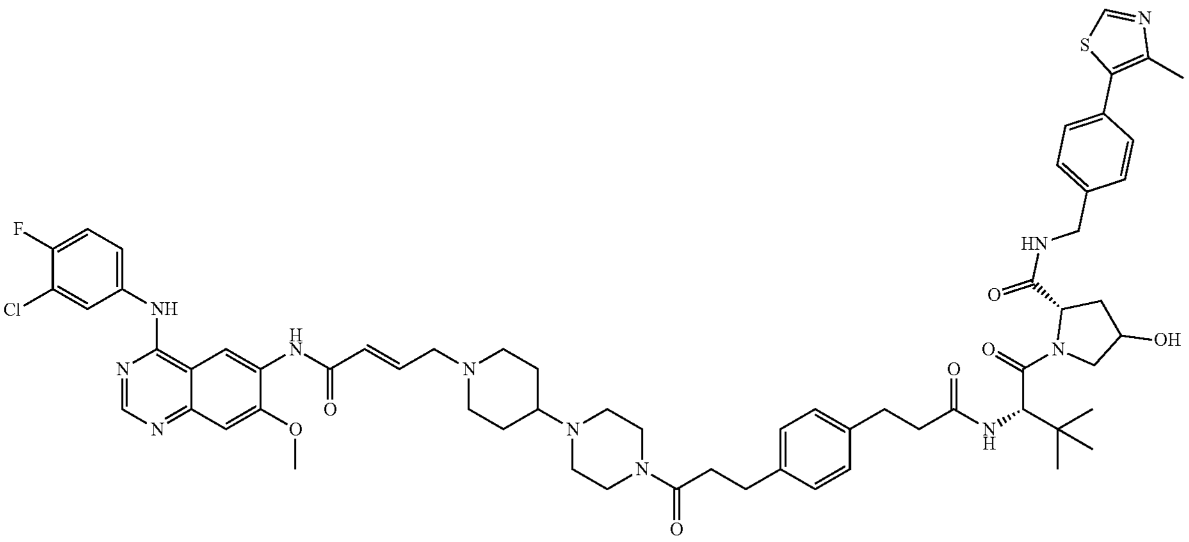 [SMILES: COc1cc2ncnc(Nc3ccc(F)c(Cl)c3)c2cc1NC(=O)/C=C/CN1CCC(N2CCN(C(=O)CCc3ccc(CCC(=O)N[C@H](C(=O)N4CC(O)C[C@H]4C(=O)NCc4ccc(-c5scnc5C)cc4)C(C)(C)C)cc3)CC2)CC1]

Referring to the method of example 1, the target compound (SIAIS249106) was prepared by using Dacomitinib derivative C and intermediate LM (SIAIS1213061). (white solid, 13 mg, yield 56%). $^1$H NMR (500 MHz, Methanol-$d_4$) δ 9.26 (s, 1H), 9.14 (s, 1H), 8.75 (s, 1H), 7.92 (dt, J=6.6, 2.8 Hz, 1H), 7.68-7.62 (m, 1H), 7.49-7.45 (m, 2H), 7.44-7.41 (m, 1H), 7.39-7.31 (m, 2H), 7.15 (s, 3H), 7.07 (dt, J=14.7, 7.1 Hz, 1H), 6.88 (d, J=15.2 Hz, 1H), 4.65-4.45 (m, 4H), 4.38 (d, J=15.6 Hz, 1H), 4.18 (s, 3H), 4.09 (s, 2H), 3.89 (d, J=11.0 Hz, 1H), 3.79 (dd, J=10.9, 4.0 Hz, 3H), 3.62 (d, J=12.1 Hz, 2H), 3.29-3.16 (m, 4H), 2.92-2.81 (m, 5H), 2.73 (d, J=7.7 Hz, 2H), 2.63-2.53 (m, 2H), 2.49 (s, 3H), 2.48-2.45 (m, 1H), 2.29-2.16 (m, 3H), 2.13-2.00 (m, 1H), 1.37-1.27 (m, 3H), 0.97 (s, 9H), 0.95-0.83 (m, 2H). HRMS (ESI) m/z: calcd for $C_{62}H_{74}ClFN11O_7S+$ [M+H]$^+$, 1170.5160; found, 1170.5161.

Biological Activity Assay

Materials:

- Halt protease and phosphatase inhibitors (Thermo Fisher)
- Cell TITER BLUE detection kit (Promega)
- Cell TITER GLO detection kit (Promega)
- Cell counting kit-8 (CCK-8; WST) (Dojindo)
- RPMI1640 (GIBICO)
- Fetal bovine serum (GIBICO)
- Penicillin-Streptomycin (GIBICO)
- SuperSignal West Pico Chemiluminescent Substrate (Thermo Fisher)
- SuperSignal West Femto Maximum Sensitivity Substrate (Thermo Fisher)
- Cycloheximide (Sigma)

Antibodies

Most of the antibodies used for the following assays were purchased from Cell Signaling Technology Company, such as EGFR (#4267S) etc; and α-tubulin and GAPDH were purchased from Abcam Company.

Cell Culture

The cell lines with abnormal EGFR expression used are as follows:

HCC827 cells (EGFR Exon19 del, non-small cell lung cancer cells);

PC9 cells (EGFR Exon 19 del, non-small cell lung cancer cells);

PC9BracA1 (EGFR Exon 19 del+T790M, non-small cell lung cancer cells)

H1975 (EGFR Exon T790M+L858R mutation, non-small cell lung cancer cell line)

BT474 cells (HER2 positive breast cancer cells)

The tumor cell lines used were routinely cultured in an incubator with 5% $CO_2$ at 37° C.

HCC827 and H1975 cells were purchased from ATCC. Sources of PC9 and PC9BracA1 cells can be found in articles (Song, 2015) and (Chmielecki, 2011). The medium for non-small cell lung cancer cell lines is RPMI1640 supplemented with 10% FCS and Penicillin-Streptomycin. BT474 Breast cancer cells were cultured in RPMI1640 supplemented with 10% FCS, Insulin and Penicillin-Streptomycin. The cells used were identified as correct cells by STR cells, and were negative for mycoplasma through routine inspections.

Construction of EGFR triple mutant cell line PC9 DCT (Dell9+T790M+C797S): The cDNA expressing human EGFR was cloned into pLVX vector, and exon 19 deletion mutation (746-750) and T790M mutation were introduced by point mutation and C797S mutation. Transferred into PC9 cells by lentiviral packaging. Cells stably expressing EGFR triple mutations were obtained by fluorescence screening.

Generation of EGFR Triple Mutant Cell Line PC9 DCT (Del19+T790M+C797S):

The cDNA sequence expressing human EGFR was cloned into a pLVX vector ($GFP^+$), and then introduce the EGFR exon 19 deletion (746-750), exon 20 T790M and C797S mutations by were generated by site-directed mutagenesis. The PC9 cells were infected with lentivirus containing the indicated EGFR mutations, and the cells stably expressing EGFR triple mutation were obtained by fluorescence screening.

Western Blotting Assay

Cancer cells were planted in 12-well-plate at the density of 0.15 million cells per well with 1 mL RPMI1640 completed culture medium. Compounds with different concentrations (DMSO as a solution system, and 1 μL of compounds of different concentrations was added to 1 mL of the cell culture medium) were added to the cells planted one day before. 16 hours after treated, the medium was discarded and the cells were washed with precooled PBS. The cells were placed on ice and treated with RIPA protein lysis buffer containing halt protease and phosphatase inhibitor. After centrifugation at 10000 rpm at 4° C. for 10 minutes, the supernatant was collected. The same amount of proteins were added into 4×SDS loading buffer and heated at 95° C. for 5 minutes for denaturation, and the samples were stored at −20° C. after denaturation, or directly conducted protein electrophoresis. The 4-20% gradient preformed Electrophoretic gels were purchased from Kingsy. The electrophoresis tank and related components were purchased from Bio-rad company, and the electrophoresis condition was isobaric 120V for 2 hours. PVDF membrane was used for the transmembrane, and the whole transmembrane process was carried out on ice with a constant current of 0.4 amperes for an hour. The membrane was blocked with 5% skimmed milk dilution with TBST buffer. Refer to the corresponding antibody instructions for the specific steps of immunoblotting.

Cells Viability Assays

All of the half inhibitory concentrations ($IC_{50}$) of these compounds of the present invention were determined with WST reagent from Fuyuan Biotec Company. The specific experiment procedures are as follows: Cancer cells were planted in 96-well-plate at the density of 3 000 cells per well with 100 μL RPMI1640 completed culture medium. In the next day, compounds with indicated concentrations were added to the cells, DMSO was used as the negative control and the EGFR TKIs were used to treat cells as the positive groups. After 72 hours drug treatment, cell viability was measured by using the WST reagent following the instructions. The growth inhibition curve of the compounds on cells were plotted by Prism GraphPad, and the compounds $IC_{50}$ calculated from it. The specific results are shown in the tables.

Results

1. Studies on Dacomitinib-Based Compounds of the Present Invention 1.1 Studies on Cell Growth Inhibition Abilities of the Compounds of the Present Invention in EGFR Positive Cell Lines.

The concentration-dependent assays were taken to determine the anti-tumor activity of these indicated compounds in HCC827 and PC9 cell lines, both of which have the EGFR Exon 19 deletion mutation, sensitive to EGFR inhibitors. The cells were treated with the gradient concentration of these compounds (the maximum concentration: 10 μM; 3-fold dilution ratio, 10 concentration gradients) for 72 hours and then incubated with the WST (CCK8) reagent to determine the cell viability. The results are shown as follows:

As shown in Table 1, all of the dacomitinib-based compounds of the present invention can inhibit the cell growth of HCC827 or PC9 cells well. The $IC_{50}$ values of some compounds of the present invention are close to which of dacomitinib on HCC827 cells (0.5 nM), for instance, the $IC_{50}$ of SIAIS262033 is about 1.0 nM. The cell killing effect of dacomitinib on PC9 cells ($IC_{50}$: 0.4 nM) is higher than that of the dacomitinib derivatives we synthesized, while some of the compounds of the present invention have the similar efficacy as dacomitinib, such as SIAIS249059 with the $IC_{50}$ 1.2 nM on PC9 cells.

Moreover, the cell viability assays were taken on H1975 cells as well, and the results indicated that these compounds of the present invention also showed cell proliferation inhibition effect in H1975 and the detailed results are shown in Table 2.

TABLE 1

The $IC_{50}$ values of the dacomitinib-based compounds of the present invention on the cell lines of lung adenocarcinoma with EGFR sensitive mutations (half inhibitory cencerntration)

| Compounds | cell lines of lung adenocarcinoma | $IC_{50}$ (nM) |
|---|---|---|
| dacomitinib | HCC827 (Exon19 Del) | 0.5 |
| Dacomitinib derivative A | HCC827 (Exon19 Del) | 4.0 |
| SIAIS219185 | HCC827 (Exon19 Del) | 15.7 |
| SIAIS219186 | HCC827 (Exon19 Del) | 6.0 |
| SIAIS219187 | HCC827 (Exon19 Del) | 6.7 |
| SIAIS219188 | HCC827 (Exon19 Del) | 3.1 |

TABLE 1-continued

The $IC_{50}$ values of the dacomitinib-based compounds of the present invention on the cell lines of lung adenocarcinoma with EGFR sensitive mutations (half inhibitory cencerntration)

| Compounds | cell lines of lung adenocarcinoma | $IC_{50}$ (nM) |
|---|---|---|
| SIAIS219189 | HCC827 (Exon19 Del) | 3.8 |
| SIAIS219190 | HCC827 (Exon19 Del) | 18.6 |
| SIAIS219192 | HCC827 (Exon19 Del) | 16.4 |
| SIAIS219193 | HCC827 (Exon19 Del) | 2.2 |
| SIAIS219194 | HCC827 (Exon19 Del) | 5.3 |
| SIAIS249034 | HCC827 (Exon19 Del) | 23.0 |
| SIAIS249035 | HCC827 (Exon19 Del) | 10.0 |
| SIAIS249036 | HCC827 (Exon19 Del) | 8.1 |
| SIAIS249037 | HCC827 (Exon19 Del) | 6.6 |
| SIAIS249038 | HCC827 (Exon19 Del) | 4.7 |
| SIAIS249039 | HCC827 (Exon19 Del) | 5.2 |
| SIAIS249046 | HCC827 (Exon19 Del) | 3.4 |
| SIAIS249047 | HCC827 (Exon19 Del) | 23.6 |
| SIAIS249048 | HCC827 (Exon19 Del) | 3.2 |
| SIAIS249049 | HCC827 (Exon19 Del) | 4.6 |
| SIAIS249056 | HCC827 (Exon19 Del) | 7.3 |
| SIAIS249057 | HCC827 (Exon19 Del) | 11.5 |
| SIAIS249058 | HCC827 (Exon19 Del) | 5.5 |
| SIAIS249059 | HCC827 (Exon19 Del) | 11.1 |
| SIAIS249060 | HCC827 (Exon19 Del) | 11.5 |
| SIAIS249062 | HCC827 (Exon19 Del) | 3.7 |
| SIAIS262001 | HCC827 (Exon19 Del) | 26.9 |
| SIAIS262002 | HCC827 (Exon19 Del) | 26.1 |
| SIAIS262003 | HCC827 (Exon19 Del) | 104.3 |
| SIAIS262004 | HCC827 (Exon19 Del) | 7.2 |
| SIAIS262005 | HCC827 (Exon19 Del) | 66.9 |
| SIAIS262006 | HCC827 (Exon19 Del) | 35.5 |
| SIAIS262007 | HCC827 (Exon19 Del) | 26.0 |
| SIAIS262008 | HCC827 (Exon19 Del) | 46.6 |
| SIAIS262013 | HCC827 (Exon19 Del) | 35.8 |
| SIAIS262014 | HCC827 (Exon19 Del) | 39.5 |
| SIAIS262015 | HCC827 (Exon19 Del) | 3.0 |
| SIAIS262016 | HCC827 (Exon19 Del) | 4.5 |
| SIAIS249041 | HCC827 (Exon19 Del) | 38.3 |
| SIAIS249042 | HCC827 (Exon19 Del) | 31.3 |
| SIAIS249043 | HCC827 (Exon19 Del) | 19.3 |
| SIAIS249045 | HCC827 (Exon19 Del) | 41.9 |
| Dacomitinib derivative | HCC827 (Exon19 Del) | 2.9 |
| SIAIS262032 | HCC827 (Exon19 Del) | 3.3 |
| SIAIS262033 | HCC827 (Exon19 Del) | 1.0 |
| SIAIS262034 | HCC827 (Exon19 Del) | 3.6 |
| SIAIS262035 | HCC827 (Exon19 Del) | 2.2 |
| SIAIS262036 | HCC827 (Exon19 Del) | 2.4 |
| SIAIS262037 | HCC827 (Exon19 Del) | 1.6 |
| SIAIS262050 | HCC827 (Exon19 Del) | 0.8 |
| SIAIS262051 | HCC827 (Exon19 Del) | 2.5 |
| SIAIS262052 | HCC827 (Exon19 Del) | 1.4 |
| SIAIS249077 | HCC827 (Exon19 Del) | 20 |
| SIAIS249081 | HCC827 (Exon19 Del) | 12 |
| SIAIS249082 | HCC827 (Exon19 Del) | 6 |
| SIAIS249083 | HCC827 (Exon19 Del) | 5 |
| SIAIS249084 | HCC827 (Exon19 Del) | 3 |
| SIAIS249085 | HCC827 (Exon19 Del) | 3 |
| SIAIS249086 | HCC827 (Exon19 Del) | 17 |
| SIAIS262110 | HCC827 (Exon19 Del) | 20 |
| SIAIS262112 | HCC827 (Exon19 Del) | 14 |
| SIAIS262113 | HCC827 (Exon19 Del) | 49 |
| SIAIS262114 | HCC827 (Exon19 Del) | 4 |
| SIAIS262115 | HCC827 (Exon19 Del) | 4 |
| SIAIS262116 | HCC827 (Exon19 Del) | 11 |
| SIAIS262117 | HCC827 (Exon19 Del) | 16 |
| SIAIS262118 | HCC827 (Exon19 Del) | 3 |
| SIAIS249103 | HCC827 (Exon19 Del) | 12.8 |
| SIAIS249104 | HCC827 (Exon19 Del) | 18.2 |
| SIAIS249105 | HCC827 (Exon19 Del) | 54.3 |
| SIAIS249106 | HCC827 (Exon19 Del) | 16.2 |
| SIAIS262065 | HCC827 (Exon19 Del) | 3.1 |
| SIAIS262071 | HCC827 (Exon19 Del) | 5.9 |
| SIAIS262072 | HCC827 (Exon19 Del) | 16.9 |
| SIAIS337021 | HCC827 (Exon19 Del) | 1.3 |
| SIAIS337024 | HCC827 (Exon19 Del) | 1.1 |

TABLE 1-continued

The $IC_{50}$ values of the dacomitinib-based compounds of the present invention on the cell lines of lung adenocarcinoma with EGFR sensitive mutations (half inhibitory cencerntration)

| Compounds | cell lines of lung adenocarcinoma | $IC_{50}$ (nM) |
|---|---|---|
| SIAIS337025 | HCC827 (Exon19 Del) | 5.6 |
| SIAIS337026 | HCC827 (Exon19 Del) | 0.5 |
| SIAIS337027 | HCC827 (Exon19 Del) | 1.1 |
| SIAIS337028 | HCC827 (Exon19 Del) | 0.9 |
| SIAIS337029 | HCC827 (Exon19 Del) | 0.3 |
| SIAIS337035 | HCC827 (Exon19 Del) | 4.3 |
| SIAIS337036 | HCC827 (Exon19 Del) | 0.7 |
| SIAIS337037 | HCC827 (Exon19 Del) | 0.3 |
| SIAIS337038 | HCC827 (Exon19 Del) | 0.3 |
| SIAIS337039 | HCC827 (Exon19 Del) | 5.7 |
| SIAIS337040 | HCC827 (Exon19 Del) | 26.8 |
| SIAIS249103 | HCC827 (Exon19 Del) | 12.8 |
| SIAIS249104 | HCC827 (Exon19 Del) | 18.2 |
| SIAIS249105 | HCC827 (Exon19 Del) | 54.3 |
| SIAIS249106 | HCC827 (Exon19 Del) | 16.2 |
| dacomitinib | PC9 (Exon19 Del) | 0.4 |
| Dacomitinib derivative A | PC9 (Exon19 Del) | 9.7 |
| SIAIS219185 | PC9 (Exon19 Del) | 23.3 |
| SIAIS219186 | PC9 (Exon19 Del) | 21.7 |
| SIAIS219187 | PC9 (Exon19 Del) | 33.3 |
| SIAIS219188 | PC9 (Exon19 Del) | 25.1 |
| SIAIS219189 | PC9 (Exon19 Del) | 9.2 |
| SIAIS219190 | PC9 (Exon19 Del) | 7.2 |
| SIAIS219192 | PC9 (Exon19 Del) | 8.9 |
| SIAIS219193 | PC9 (Exon19 Del) | 43.6 |
| SIAIS219194 | PC9 (Exon19 Del) | 4.0 |
| SIAIS249034 | PC9 (Exon19 Del) | 167 |
| SIAIS249035 | PC9 (Exon19 Del) | 56.5 |
| SIAIS249036 | PC9 (Exon19 Del) | 47.7 |
| SIAIS249037 | PC9 (Exon19 Del) | 28.7 |
| SIAIS249038 | PC9 (Exon19 Del) | 22.9 |
| SIAIS249039 | PC9 (Exon19 Del) | 18.7 |
| SIAIS249046 | PC9 (Exon19 Del) | 57 |
| SIAIS249048 | PC9 (Exon19 Del) | 10.3 |
| SIAIS249049 | PC9 (Exon19 Del) | 16.0 |
| SIAIS249056 | PC9 (Exon19 Del) | 4.0 |
| SIAIS249057 | PC9 (Exon19 Del) | 7.8 |
| SIAIS249058 | PC9 (Exon19 Del) | 9.9 |
| SIAIS249059 | PC9 (Exon19 Del) | 1.2 |
| SIAIS249060 | PC9 (Exon19 Del) | 16 |
| SIAIS249062 | PC9 (Exon19 Del) | 10 |
| SIAIS262001 | PC9 (Exon19 Del) | 53 |
| SIAIS262002 | PC9 (Exon19 Del) | 78 |
| SIAIS262004 | PC9 (Exon19 Del) | 15 |
| SIAIS262005 | PC9 (Exon19 Del) | 84 |
| SIAIS262006 | PC9 (Exon19 Del) | 73 |
| SIAIS262007 | PC9 (Exon19 Del) | 84 |
| SIAIS262013 | PC9 (Exon19 Del) | 28 |
| SIAIS262014 | PC9 (Exon19 Del) | 128 |
| SIAIS262015 | PC9 (Exon19 Del) | 12 |
| SIAIS262016 | PC9 (Exon19 Del) | 112 |
| SIAIS249041 | PC9 (Exon19 Del) | 99 |
| SIAIS249043 | PC9 (Exon19 Del) | 70.6 |
| SIAIS249045 | PC9 (Exon19 Del) | 691 |
| Dacomitinib derivative | PC9 (Exon19 Del) | 2.3 |
| SIAIS262032 | PC9 (Exon19 Del) | 43.5 |
| SIAIS262033 | PC9 (Exon19 Del) | 3.8 |
| SIAIS262034 | PC9 (Exon19 Del) | 11.3 |
| SIAIS262035 | PC9 (Exon19 Del) | 6.1 |
| SIAIS262036 | PC9 (Exon19 Del) | 6.7 |
| SIAIS262037 | PC9 (Exon19 Del) | 2.1 |
| SIAIS262050 | PC9 (Exon19 Del) | 9.9 |
| SIAIS262051 | PC9 (Exon19 Del) | 2.5 |
| SIAIS262052 | PC9 (Exon19 Del) | 1.3 |
| SIAIS249077 | PC9 (Exon19 Del) | 0.8 |
| SIAIS249081 | PC9 (Exon19 Del) | 32.6 |
| SIAIS249082 | PC9 (Exon19 Del) | 6.1 |
| SIAIS249083 | PC9 (Exon19 Del) | 2.9 |
| SIAIS249084 | PC9 (Exon19 Del) | 0.6 |
| SIAIS249085 | PC9 (Exon19 Del) | 7.9 |

TABLE 1-continued

The $IC_{50}$ values of the dacomitinib-based compounds of the present invention on the cell lines of lung adenocarcinoma with EGFR sensitive mutations (half inhibitory cencerntration)

| Compounds | cell lines of lung adenocarcinoma | $IC_{50}$ (nM) |
|---|---|---|
| SIAIS249086 | PC9 (Exon19 Del) | 34.2 |
| SIAIS262110 | PC9 (Exon19 Del) | 73.0 |
| SIAIS262112 | PC9 (Exon19 Del) | 42.5 |
| SIAIS262113 | PC9 (Exon19 Del) | 3.9 |
| SIAIS262114 | PC9 (Exon19 Del) | 11.9 |
| SIAIS262115 | PC9 (Exon19 Del) | 7.2 |
| SIAIS262116 | PC9 (Exon19 Del) | 3.3 |
| SIAIS262117 | PC9 (Exon19 Del) | 31.2 |
| SIAIS262118 | PC9 (Exon19 Del) | 3.8 |
| SIAIS249103 | PC9 (Exon19 Del) | 20.4 |
| SIAIS249104 | PC9 (Exon19 Del) | 37.6 |
| SIAIS249105 | PC9 (Exon19 Del) | 60.5 |
| SIAIS249106 | PC9 (Exon19 Del) | 50.1 |
| SIAIS262065 | PC9 (Exon19 Del) | 185 |
| SIAIS337021 | PC9 (Exon19 Del) | 74 |
| SIAIS337024 | PC9 (Exon19 Del) | 13 |
| SIAIS337025 | PC9 (Exon19 Del) | 36 |
| SIAIS337026 | PC9 (Exon19 Del) | 8.6 |
| SIAIS337027 | PC9 (Exon19 Del) | 13.2 |
| SIAIS337028 | PC9 (Exon19 Del) | 20.3 |
| SIAIS337029 | PC9 (Exon19 Del) | 28.4 |
| SIAIS337035 | PC9 (Exon19 Del) | 6.3 |
| SIAIS337036 | PC9 (Exon19 Del) | 1.3 |
| SIAIS337037 | PC9 (Exon19 Del) | 0.7 |
| SIAIS337038 | PC9 (Exon19 Del) | 1.6 |
| SIAIS337039 | PC9 (Exon19 Del) | 19.7 |
| SIAIS249103 | PC9 (Exon19 Del) | 20.4 |
| SIAIS249104 | PC9 (Exon19 Del) | 37.6 |
| SIAIS249105 | PC9 (Exon19 Del) | 60.5 |
| SIAIS249106 | PC9 (Exon19 Del) | 50.1 |

TABLE 2

The $IC_{50}$ of Dacomitinib-based compounds of the present invention on the cell lines of lung adenocarcinoma with EGFR sensitive mutations (half inhibitory cencerntration)

| Cell lines | Compounds | $IC_{50}$ (nM) |
|---|---|---|
| H1975 (L858R + T790M) | Dacomitinib | 833.5 |
| H1975 (L858R + T790M) | SIAIS249081 | 114.3 |
| H1975 (L858R + T790M) | SIAIS249085 | 951.8 |
| H1975 (L858R + T790M) | SIAIS262115 | 550.5 |
| H1975 (L858R + T790M) | SIAIS262118 | 298.7 |
| H1975 (L858R + T790M) | SIAIS262034 | 828.2 |
| H1975 (L858R + T790M) | SIAIS262035 | 513.9 |
| H1975 (L858R + T790M) | SIAIS262036 | 511.0 |
| PC9Brac1(Ex19del + T790M) | Dacomitinib | 674 |
| PC9Brac1(Ex19del + T790M) | SIAIS249083 | 435 |
| PC9Brac1(Ex19del + T790M) | SIAIS249084 | 434 |
| PC9Brac1(Ex19del + T790M) | SIAIS249085 | 481 |
| PC9Brac1(Ex19del + T790M) | SIAIS262115 | 488 |
| PC9Brac1(Ex19del + T790M) | SIAIS262118 | 205 |
| PC9Brac1(Ex19del + T790M) | SIAIS262021 | 953.9 |
| PC9Brac1(Ex19del + T790M) | SIAIS262032 | 437.6 |
| PC9Brac1(Ex19del + T790M) | SIAIS262035 | 491.4 |
| PC9Brac1(Ex19del + T790M) | SIAIS262036 | 260.4 |

1.2 Studies on the Decrease of EGFR Protein Level Caused by the Dacomitinib-Based Compounds of the Present Invention The degradation efficacy of the dacomitinib-based compounds on EGFR was determined in HCC827 and H1975 cell lines, which harboring EGFR Exon 19del and EGFR L858R+T790M mutations respectively.

Dacomitinib with gradient concentrations (1, 10, 50, 100, 500 nM) were used to treat HCC827 cells for 16 hours, then the western blot assay was taken to estimate the EGFR levels of the cell lysates in each group. As shown in FIG. 1, dacomitinib couldn't degrade EGFR even at the high concentration of 500 nM.

Figure 2:
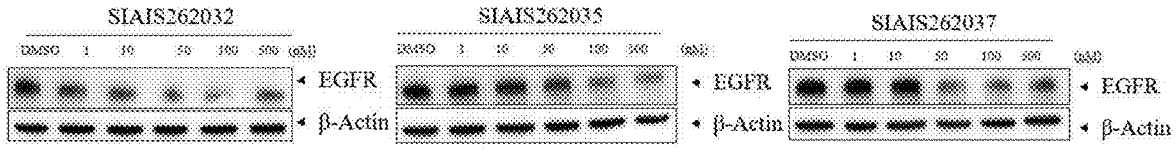
FIG. 2 shows the study on the compounds of the present invention based on dacomitinib derivative B (lung cancer cell line H1975).

As shown in FIG. 1 and FIG. 2, the dacomitinib derivative A-based and the dacomitinib derivative B-based compounds of the present invention could cause EGFR degradation with the drug concentration increased in H1975 cells.

In FIG. 2, concentration-dependent degradation assays were performed on non-small cell lung cancer cell line H1975 (T790M-mutant cell line, the most common mutation type of first-generation EGFR inhibitors). The results showed that the compounds of the present invention also showed good EGFR degradation effect in H1975 cells. Compounds SIAIS262032, SIAIS262035 and SIAIS262037, with strong cell proliferation inhibitory ability, showed obvious EGFR degradation efficacy in H1975 cells. The $DC_{50}$ of compounds SIAIS262032 and SIAIS262037 are both about 50 nM, which provides great potential for drug development to overcome drug resistance caused by EGFR T790M mutation.

2. Studies on Poziotinib-Based Compounds of the Present Invention 2.1 Studies on Cell Proliferation Inhibitory Efficacy of the Compounds of the Present Invention on EGFR Mutant Cell Lines The cell viability assays were taken to determine the anti-tumor activity of these indicated compounds of the present invention in HCC827 and PC9 cell lines, both of which have the EGFR Exon 19 deletion mutation, sensitive to EGFR inhibitors. The cells were treated with the gradient concentration of these compounds (the maximum concentration: 10 μM; 3-fold dilution ratio, 10 concentration gradients) for 72 hours and then incubated with the WST (CCK8) reagent to determine the cell viability. The results are shown as Table 3.

All poziotinib-based compounds of the present invention can inhibit the cell proliferation of HCC827 and PC9 cells well (Table 3). The $IC_{50}$ values of the compounds we synthesized are close to which of poziotinib on HCC827 cells (0.5 nM).

TABLE 3

The $IC_{50}$ of Poziotinib-based compounds of the present invention on the cell lines of lung adenocarcinoma (half inhibitory cencerntration)

| Cell lines | Compounds | $IC_{50}$ (nM) |
|---|---|---|
| HCC827(Exon19 Del) | Poziotinib | 0.5 |
| HCC827(Exon19 Del) | Poziotinib derivative A (SIAIS219149) | 7.1 |
| HCC827(Exon19 Del) | SIAIS249029 | 80 |
| HCC827(Exon19 Del) | SIAIS249030 | 6.3 |
| HCC827(Exon19 Del) | SIAIS249031 | 28.2 |
| HCC827(Exon19 Del) | SIAIS249032 | 11.0 |
| HCC827(Exon19 Del) | SIAIS249033 | 13.0 |
| HCC827(Exon19 Del) | SIAIS219177 | 8.2 |
| HCC827(Exon19 Del) | SIAIS219179 | 20.2 |
| HCC827(Exon19 Del) | SIAIS219180 | 26.7 |
| HCC827(Exon19 Del) | SIAIS219181 | 23.1 |
| HCC827(Exon19 Del) | SIAIS249014 | 51 |
| HCC827(Exon19 Del) | SIAIS249015 | 46 |
| HCC827(Exon19 Del) | SIAIS249016 | 29 |
| HCC827(Exon19 Del) | SIAIS249017 | 23 |
| HCC827(Exon19 Del) | SIAIS249018 | 13.3 |

TABLE 3-continued

The $IC_{50}$ of Poziotinib-based compounds of the present invention on the cell lines of lung adenocarcinoma (half inhibitory cencerntration)

| Cell lines | Compounds | $IC_{50}$ (nM) |
|---|---|---|
| HCC827(Exon19 Del) | SIAIS249019 | 38 |
| HCC827(Exon19 Del) | SIAIS219164 | 33 |
| HCC827(Exon19 Del) | SIAIS219165 | 23 |
| HCC827(Exon19 Del) | SIAIS219166 | 30 |
| HCC827(Exon19 Del) | SIAIS219167 | 31 |
| HCC827(Exon19 Del) | SIAIS219168 | 40 |
| HCC827(Exon19 Del) | SIAIS219169 | 38 |
| HCC827(Exon19 Del) | SIAIS249024 | 174 |
| HCC827(Exon19 Del) | SIAIS249025 | 158 |
| HCC827(Exon19 Del) | SIAIS249026 | 266 |
| HCC827(Exon19 Del) | SIAIS249027 | 400 |
| HCC827(Exon19 Del) | SIAIS249028 | 240 |
| HCC827(Exon19 Del) | SIAIS249020 | 75.5 |
| HCC827(Exon19 Del) | SIAIS249021 | 75.4 |
| HCC827(Exon19 Del) | SIAIS249022 | 40 |
| HCC827(Exon19 Del) | SIAIS249023 | 49 |
| PC9 (Exon 19 Del) | Poziotinib | <0.1 |
| PC9 (Exon 19 Del) | Poziotinib derivative A (SIAIS219149) | 17 |
| PC9 (Exon 19 Del) | SIAIS219165 | 3 |
| PC9 (Exon 19 Del) | SIAIS219177 | 38 |
| PC9 (Exon 19 Del) | SIAIS249015 | 130 |

3. Studies on Gefitinib and Sapitinib-Based Compounds of the Present Invention 1.1 Studies on Cell Proliferation Inhibitory Effect of the Compounds of the Present Invention in EGFR Positive Cell Lines.

The cell viability assays were taken to determine the anti-tumor activity of these indicated compounds in HCC827 cells with the EGFR Exon 19 deletion mutation, which is sensitive to EGFR inhibitors. The cells were treated with the gradient concentration of these compounds (the maximum concentration: 10 μM; 3-fold dilution ratio, 10 concentration gradients) for 72 hours and then incubated with the WST reagent to determine the cell viability. The experiments were repeated more than 3 times and the results are shown as Table 4.

The cell proliferation inhibitory efficacy of gefitinib derivatives A or B-based PROTAD compounds of the present invention on HCC827 cells is weaker than that of gefitinib with the $IC_{50}$ 4.8 nM, while the gefitinib derivative C-based PROTAD compounds could inhibit the HCC827 cell growth well, for instance the SIAIS293052 has the similar cell killing capacity as gefitinib. All of the sapitinib (AZD8931)—based compounds could inhibit cell proliferation well, such as SIAIS293067 which is better than sapitinib on cell killing.

TABLE 4

The $IC_{50}$ values of Gefitinib and Sapitinib-based PROTAD compounds on the lung adenocarcinoma cell lines (half inhibitory cencerntration)

| Cell lines | Compounds | $IC_{50}$ (nM) |
|---|---|---|
| HCC827(Exon19 Del) | Gefitinib | 6 |
| HCC827(Exon19 Del) | Gefitinib derivative A (SIAIS184161) | 10 |
| HCC827(Exon19 Del) | SIAIS184164 | 47 |
| HCC827(Exon19 Del) | SIAIS184165 | 58 |
| HCC827(Exon19 Del) | SIAIS184166 | 80 |
| HCC827(Exon19 Del) | SIAIS184168 | 43 |
| HCC827(Exon19 Del) | SIAIS184169 | 22 |
| HCC827(Exon19 Del) | SIAIS184170 | 186 |
| HCC827(Exon19 Del) | SIAIS184184 | 100 |
| HCC827(Exon19 Del) | SIAIS184185 | 113 |
| HCC827(Exon19 Del) | SIAIS184186 | 124 |
| HCC827(Exon19 Del) | Gefitinib derivative C (SIAIS293033) | 575 |
| HCC827(Exon19 Del) | SIAIS293047 | 12 |
| HCC827(Exon19 Del) | SIAIS293048 | 23 |
| HCC827(Exon19 Del) | SIAIS293049 | 2.8 |
| HCC827(Exon19 Del) | SIAIS293050 | 1.5 |
| HCC827(Exon19 Del) | SIAIS293051 | 6.5 |
| HCC827(Exon19 Del) | SIAIS293052 | 0.25 |
| HCC827(Exon19 Del) | SIAIS262080 | 41 |
| HCC827(Exon19 Del) | SIAIS262085 | 145 |
| HCC827(Exon19 Del) | SIAIS262086 | 59 |
| HCC827(Exon19 Del) | SIAIS262087 | 31 |
| HCC827(Exon19 Del) | SIAIS262089 | 102 |
| HCC827(Exon19 Del) | SIAIS262090 | 47 |
| PC9 (Exon19 Del) | Gefitinib | 97 |
| PC9 (Exon19 Del) | SIAIS184166 | 692 |
| PC9 (Exon19 Del) | SIAIS184168 | 317 |
| PC9 (Exon19 Del) | SIAIS184169 | 318 |
| HCC827(Exon19 Del) | Sapitinib (AZD8931) | 0.4 |
| HCC827(Exon19 Del) | SIAIS293067 | 0.3 |
| HCC827(Exon19 Del) | SIAIS293068 | 1.2 |
| HCC827(Exon19 Del) | SIAIS293069 | 9.4 |
| HCC827(Exon19 Del) | SIAIS293070 | 14.0 |

4. Studies on Afatinib-Based Compounds of the Present Invention

The cell viability assays were taken to determine the anti-tumor activity of these indicated compounds in HCC827 cells with the EGFR Exon 19 deletion mutation, which is sensitive to EGFR inhibitors. The cells were treated with the gradient concentration of these compounds (the maximum concentration: 10 μM; 3-fold dilution ratio, 10 concentration gradients) for 72 hours and then incubated with the WST reagent to determine the cell viability. The results are shown as Table 5.

All series of afatinib derivative-based compounds of the present invention could inhibit the proliferation of HCC827 cells obviously (Table 5), and the inhibitory efficacies were similar as that of afatinib with the $IC_{50}$ of 1.1 nM.

TABLE 5

The $IC_{50}$ values of Afatinib-based PROTAD compounds of the present invention on the lung adenocarcinoma cell lines (half inhibitory cencerntration)

| Cell lines | Compounds | $IC_{50}$ (nM) |
|---|---|---|
| HCC827(Exon19 Del) | Afatinib | 1.1 |
| HCC827(Exon19 Del) | Afatinib derivative A (SIAIS184181) | 8 |
| HCC827(Exon19 Del) | SIAIS184093 | 86.2 |
| HCC827(Exon19 Del) | SIAIS184094 | 104.6 |
| HCC827(Exon19 Del) | SIAIS184095 | 174.2 |
| HCC827(Exon19 Del) | SIAIS184152 | 131 |
| HCC827(Exon19 Del) | SIAIS184153 | 315.8 |
| HCC827(Exon19 Del) | SIAIS184154 | 249.6 |

TABLE 5-continued

The $IC_{50}$ values of Afatinib-based PROTAD compounds of the present invention on the lung adenocarcinoma cell lines (half inhibitory cencerntration)

| Cell lines | Compounds | $IC_{50}$ (nM) |
|---|---|---|
| HCC827(Exon19 Del) | SIAIS184155 | 79 |
| HCC827(Exon19 Del) | SIAIS184156 | 977.7 |
| HCC827(Exon19 Del) | SIAIS1210085 | 481.3 |
| HCC827(Exon19 Del) | SIAIS1210087 | 237.8 |
| HCC827(Exon19 Del) | SIAIS1210089 | 159.5 |

5. Studies on Canertinib-Based Compounds of the Present Invention 5.1 Studies on Cell Proliferation Inhibitory Effect of the Compounds of the Present Invention in EGFR Positive Cell Lines.

The cell viability assays were taken to determine the anti-tumor activity of these indicated compounds in HCC827 and PC9 cell lines, both of which have the EGFR Exon 19 deletion mutation, sensitive to EGFR inhibitors. The cells were treated with the gradient concentration of these compounds (the maximum concentration: 10 μM; 3-fold dilution ratio, 10 concentration gradients) for 72 hours and then incubated with the WST reagent to determine the cell viability. The results are shown as Table 6.

All of the canertinib-based compounds of the present invention can inhibit the cell proliferation of HCC827 and PC9 cells well (Table 6). The $IC_{50}$ values of canertinib on HCC827 and PC9 cells are 0.7 nM and 0.9 nM, respectively, and the canertinib-based PROTAD compounds of the present invention showed the inhibitory effect equivalent to that of canertinib, for instance, the half-inhibition concentration of SIAIS262125 in HCC827 cells is 0.3 nM.

The cell viability assays were also taken to determine the cell proliferation inhibitory ability of these compounds in H1975 and PC9Brcal NSCLC cell lines, both of which have the acquired EGFR T790M drug resistance mutation against the $1^{st}$ generation EGFR TKIs. The results reflected that these compounds of the present invention could inhibit the cell proliferation of H1975 and PC9Brcal cells well (Table 7), and most of the PROTAD compounds showed greater capacity in cell growth inhibition than canertinib. The $IC_{50}$ values of SIAIS262125 and SIAIS262182 on H1975 cell are less than 25 nM, which means that the development of degradation agents to overcome T790M mutation is promising.

TABLE 6

The $IC_{50}$ values of Canertinib-based PROTAD compounds of the present invention on the lung adenocarcinoma cell lines (half inhibitory cencerntration)

| | $IC_{50}$ (nM) | |
|---|---|---|
| Compounds | HCC827(Exon19 Del) | PC9(Exon19 Del) |
| Caneritinib | 0.7 | 0.9 |
| Caneritinib derivative A (SIAIS293064) | 4.5 | not tested |
| Caneritinib derivative B (SIAIS249183) | 15.9 | 13.9 |
| SIAIS249092 | 4.5 | 1.1 |
| SIAIS249099 | 11.8 | 29.7 |
| SIAIS249100 | 41 | 88.5 |
| SIAIS249101 | 70 | 58.5 |

TABLE 6-continued

The $IC_{50}$ values of Canertinib-based PROTAD compounds of the present invention on the lung adenocarcinoma cell lines (half inhibitory cencerntration)

| | $IC_{50}$ (nM) | |
|---|---|---|
| Compounds | HCC827(Exon19 Del) | PC9(Exon19 Del) |
| SIAIS249102 | 25.2 | 16 |
| SIAIS262121 | 9.3 | 43.4 |
| SIAIS262122 | 4.1 | 23.1 |
| SIAIS262123 | 2 | 8.3 |
| SIAIS262124 | 10.3 | 2.6 |
| SIAIS262125 | 0.3 | 1.3 |
| SIAIS262126 | 2.5 | 2.3 |
| SIAIS262127 | 6.4 | 9.7 |
| SIAIS262128 | 14.3 | 15.9 |
| SIAIS262130 | 47.2 | 179.1 |
| SIAIS262131 | 1.2 | 29.3 |
| SIAIS262182 | 1.4 | 11.1 |
| SIAIS249153 | 28.6 | 69.9 |
| SIAIS262174 | 11 | 16.7 |
| SIAIS262175 | 6.7 | 17 |
| SIAIS262176 | 3.3 | 15.8 |
| SIAIS262177 | 5.7 | 3.4 |
| SIAIS262178 | 5.2 | 0.4 |
| SIAIS262179 | 2.5 | 10.3 |
| SIAIS262180 | 4.2 | 10.2 |

TABLE 7

The $IC_{50}$ values of Canertinib-based PROTAD compounds of the present invention on the lung adenocarcinoma cell lines (half inhibitory cencerntration)

| | $IC_{50}$ (nM) | |
|---|---|---|
| Compounds | H1975 (L858R + T790M) | PC9Brca1 (Ex19del + T790M |
| Caneritinib | 110 | 1163 |
| SIAIS249092 | 25 | 160 |
| SIAIS262122 | 97 | 474 |
| SIAIS262123 | 143 | 380 |
| SIAIS262124 | 413 | 419 |
| SIAIS262125 | 15 | 79 |
| SIAIS262126 | 20 | 85 |
| SIAIS262127 | 468 | 423 |
| SIAIS262131 | 45 | 216 |
| SIAIS262182 | 12 | 192 |
| SIAIS249153 | 102 | 755 |
| SIAIS262174 | 287 | 267 |
| SIAIS262175 | 430 | NA |
| SIAIS262176 | 67 | 472 |
| SIAIS262177 | 654 | 209 |
| SIAIS262178 | 38 | 69 |
| SIAIS262179 | 43 | 181 |
| SIAIS262180 | 24 | 570 |
| SIAIS262183 | 250 | 1058 |

NA: not available 5.2 Studies on the Decrease of EGFR Level Caused by the Canertinib-Based PROTAD Compounds of the Present Invention The degradation efficacy of the canertinib-based compounds on EGFR was determined in H1975 cells with the EGFR L858R+T790M mutation.

Figure 3:
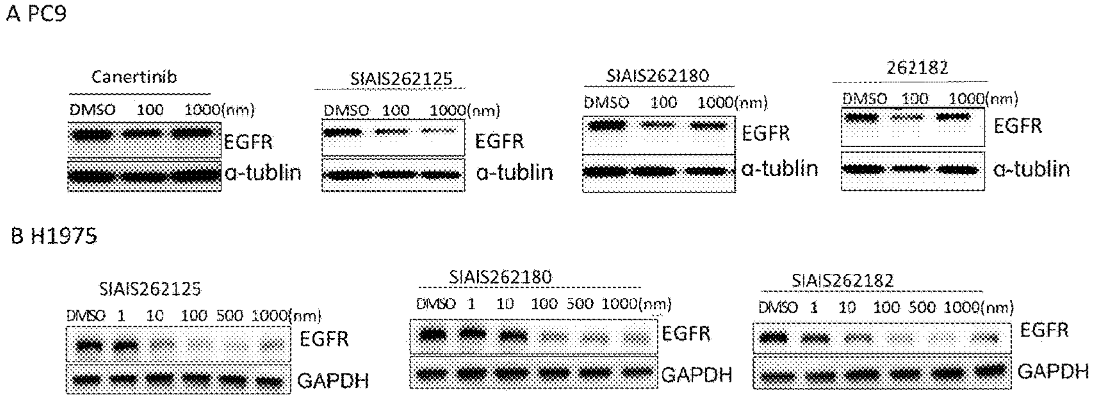
FIG. 3 shows the study on the compounds of the present invention based on Canertinib derivatives A and B (lung cancer cell lines PC9 and H1975).

The H1975 cells were treated with the PROTADs with different concentrations (1, 10, 50, 100, 500 nM) for 16 hours, and then the western blot assay was taken to estimate the EGFR levels of the cell lysates in each group. As shown in FIG. 3, the compounds, SIAIS262125, SIAIS262180, SIAIS262182 with strong cell proliferation inhibitory ability, showed obvious EGFR degradation efficacy in H1975 cells, which means that the degradation of EGFR is important for killing tumor cells. The $DC_{50}$ of SIAIS262125 and SIAIS262182 are both less than 10 nM, much better than canertinib, which provides great potential for drug development to overcome drug resistance caused by EGFR T790M mutation.

Figure 4:
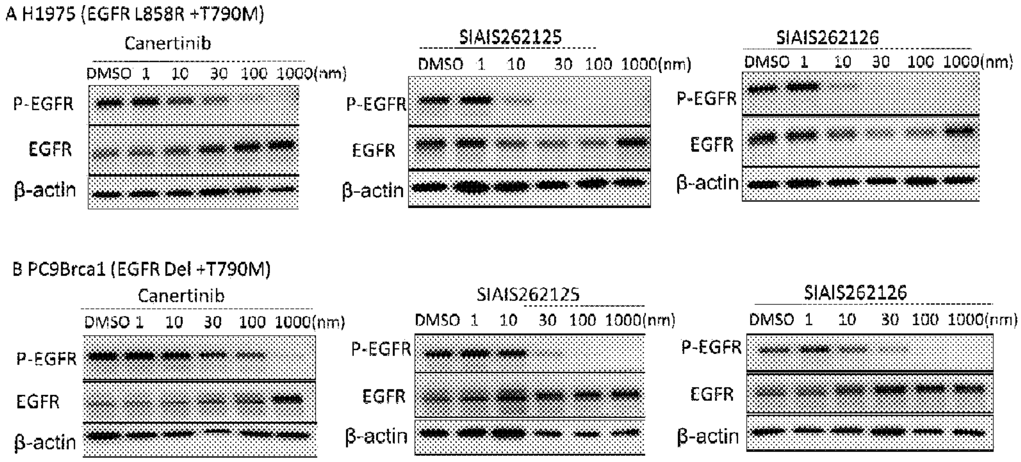
FIG. 4 shows that the inhibitory activity of the compounds of the present invention on the phosphorylation level of EGFR is superior over that of small molecule inhibitors (lung cancer cell lines H1975 and PC9Brc1).
Figure 5:
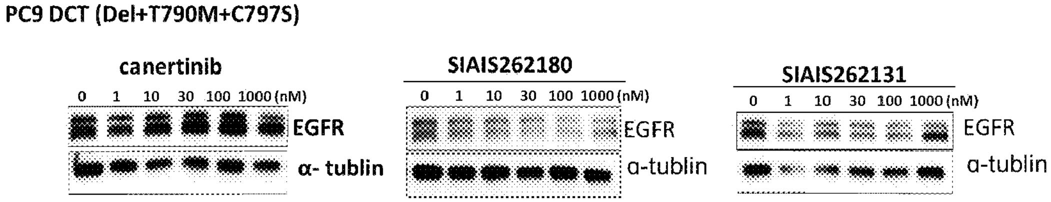
FIG. 5 shows the degradation ability of the compounds of the present invention on the EGFR protein with three mutations (PC9DCT (Del19+T790M+C797S) cell line).

Moreover, the effect on EGFR phosphorylation level caused by the compounds of the present invention was also studied (FIG. 4). The results showed that the inhibition capacity on the EGFR phosphorylation level of the PROTADs is much better than that of canertinib.

6. Studies on Osimertinib-Based PROTAD Compounds of the Present Invention 6.1 Studies on Cell Proliferation Inhibitory Effect of the Compounds of the Present Invention in Lung Adenocarcinoma Cell Lines.

The cell viability assays were taken to determine the anti-tumor activity of these indicated compounds in HCC827, PC9, H1975 and PC9Bracl cell lines, which have the EGFR Exon 19 deletion mutation, sensitive to EGFR inhibitors. The cells were treated with the gradient concentration of these compounds (the maximum concentration: 10 μM; 3-fold dilution ratio, 10 concentration gradients) for 72 hours and then incubated with the WST reagent to determine the cell viability. The results are shown as Table 8.

TABLE 8

The $IC_{50}$ values of Osimertinib-based PROTAD compounds of the present invention on the lung adenocarcinoma cell lines (half inhibitory cencerntration)

| Compounds | Cell lines | $IC_{50}$ (nM) |
|---|---|---|
| Osimertinib | HCC827 | 0.36 |
| SIAIS337051 | HCC827 | 1.0 |
| SIAIS337052 | HCC827 | 352.6 |
| SIAIS337055 | HCC827 | 460.8 |
| SIAIS337056 | HCC827 | 113.8 |
| SIAIS337057 | HCC827 | 47.7 |
| SIAIS337059 | HCC827 | 46.7 |
| SIAIS337060 | HCC827 | 121.5 |
| SIAIS337061 | HCC827 | 352.6 |
| SIAIS337074 | HCC827 | 3 |
| SIAIS337075 | HCC827 | 170 |
| SIAIS337076 | HCC827 | 10 |
| SIAIS337077 | HCC827 | 36 |
| SIAIS337078 | HCC827 | 125 |
| SIAIS337079 | HCC827 | 879 |
| SIAIS337080 | HCC827 | 770 |
| SIAIS337081 | HCC827 | 184 |
| SIAIS337082 | HCC827 | 8 |
| SIAIS337083 | HCC827 | 46 |
| SIAIS337084 | HCC827 | 353 |
| SIAIS337085 | HCC827 | 6 |
| SIAIS337086 | HCC827 | 3 |
| SIAIS337087 | HCC827 | 91 |
| SIAIS337088 | HCC827 | 5 |
| SIAIS337089 | HCC827 | 15 |
| SIAIS337090 | HCC827 | 9 |
| Osimertinib | PC9 | 4 |
| SIAIS337051 | PC9 | 2 |
| SIAIS337074 | PC9 | 91 |
| SIAIS337076 | PC9 | 459 |
| SIAIS337079 | PC9 | 373 |
| SIAIS337080 | PC9 | 103 |
| SIAIS337081 | PC9 | 134 |
| SIAIS337082 | PC9 | 89 |
| SIAIS337083 | PC9 | 512 |
| SIAIS337084 | PC9 | 271 |
| SIAIS337085 | PC9 | 143 |
| SIAIS337086 | PC9 | 64 |
| SIAIS337087 | PC9 | 320 |
| SIAIS337088 | PC9 | 302 |
| SIAIS337089 | PC9 | 82 |
| SIAIS337090 | PC9 | 161 |

TABLE 8-continued

The $IC_{50}$ values of Osimertinib-based PROTAD compounds of the present invention on the lung adenocarcinoma cell lines (half inhibitory cencerntration)

| Compounds | Cell lines | $IC_{50}$ (nM) |
|---|---|---|
| Osimertinib | H1975 | 2 |
| SIAIS337051 | H1975 | 1 |
| SIAIS337057 | H1975 | 21 |
| SIAIS337060 | H1975 | 171 |
| SIAIS337074 | H1975 | 145 |
| SIAIS337076 | H1975 | 187 |
| SIAIS337079 | H1975 | 70 |
| SIAIS337080 | H1975 | 34 |
| SIAIS337081 | H1975 | 18 |
| SIAIS337082 | H1975 | 55 |
| SIAIS337083 | H1975 | 494 |
| SIAIS337085 | H1975 | 462 |
| SIAIS337086 | H1975 | 203 |
| SIAIS337087 | H1975 | 242 |
| SIAIS337088 | H1975 | 239 |
| SIAIS337089 | H1975 | 16 |
| SIAIS337090 | H1975 | 117 |
| Osimertinib | Pc9Brc1 | 354 |
| SIAIS337051 | Pc9Brc1 | 479 |
| SIAIS337056 | Pc9Brc1 | 973 |
| SIAIS337074 | Pc9Brc1 | 238 |
| SIAIS337076 | Pc9Brc1 | 303 |
| SIAIS337079 | Pc9Brc1 | 366 |
| SIAIS337080 | Pc9Brc1 | 520 |
| SIAIS337081 | Pc9Brc1 | 207 |
| SIAIS337082 | Pc9Brc1 | 218 |
| SIAIS337083 | Pc9Brc1 | 676 |
| SIAIS337084 | Pc9Brc1 | 686 |
| SIAIS337085 | Pc9Brc1 | 239 |
| SIAIS337086 | Pc9Brc1 | 194 |
| SIAIS337087 | Pc9Brc1 | 598 |
| SIAIS337088 | Pc9Brc1 | 662 |
| SIAIS337089 | Pc9Brc1 | 107 |
| SIAIS337090 | Pc9Brc1 | 413 |

7. Studies on the Anti-Tumor Capacity of the PROTAD Compounds of the Present Invention in Cells with EGFR Tertiary Drug Resistance Mutations.

The cell viability assays were taken to determine the anti-tumor activity of these indicated compounds in PC9 cells, which overexpressed Exon 19del+T790M+C797S triple mutant EGFR. The results showed that the poziotinib-based PROTADs could inhibit the PC9 drug resistant cells proliferation much better than the poziotinib derivative.

The degradation efficacy of some of the PROTAD compounds of the present invention on EGFR was determined in PC9 cells harboring EGFR triple mutations (19del+T790M+C797S). The results reflected that these compounds of the present invention could degrade the mutant EGFR effectively, suggesting that these PROTADs have great anti-tumor efficacy in drug resistant PC9 cells with EGFR triple mutations.

TABLE 9

The $IC_{50}$ values of Canertinib-based PROTAD compounds of the present invention on the adenocarcinoma cell lines with EGFR triple mutations (half inhibitory cencerntration)

| Cell lines | Compounds | $IC_{50}$ (nM) |
|---|---|---|
| PC9(Del + T790M + C797S) | Poziotinib derivative A (SIAIS219149) | 5.2 |

TABLE 9-continued

The $IC_{50}$ values of Canertinib-based PROTAD compounds of the present invention on the adenocarcinoma cell lines with EGFR triple mutations (half inhibitory cencerntration)

| Cell lines | Compounds | $IC_{50}$ (nM) |
|---|---|---|
| PC9(Del + T790M + C797S) | SIAIS219164 | 4.8 |
| PC9(Del + T790M + C797S) | SIAIS219165 | 4.6 |
| PC9(Del + T790M + C797S) | SIAIS219166 | 4.6 |
| PC9(Del + T790M + C797S) | SIAIS219167 | 4.1 |
| PC9(Del + T790M + C797S) | SIAIS219168 | 2.9 |
| PC9(Del + T790M + C797S) | SIAIS219169 | 3.6 |
| PC9(Del + T790M + C797S) | SIAIS219177 | 2.4 |
| PC9(Del + T790M + C797S) | SIAIS219179 | 3.9 |
| PC9(Del + T790M + C797S) | SIAIS219180 | 3.3 |
| PC9(Del + T790M + C797S) | SIAIS219181 | 3.8 |
| PC9(Del + T790M + C797S) | SIAIS249014 | 1.8 |
| PC9(Del + T790M + C797S) | SIAIS249015 | 4.7 |
| PC9(Del + T790M + C797S) | SIAIS249016 | 1.5 |
| PC9(Del + T790M + C797S) | SIAIS249017 | 2.2 |

8. Studies on the Anti-Tumor Capacity of the PROTAD Compound of the Present Invention in HER2 Positive Breast Cancer Cells The cell viability assays were taken to determine the anti-tumor activity of these indicated compounds in BT474 cells, which can overexpress HER2 protein. The cells were treated with the gradient concentration of these compounds (the maximum concentration: 10 μM; 3-fold dilution ratio, 10 concentration gradients) for 72 hours and then incubated with the CCK8 reagent to determine the cell viability. The results are shown in Table 10. Some of these PROTADs displayed better antineoplastic activity than the relative EGFR TKIs, such as compound SIAIS262125 etc.

Figure 6:
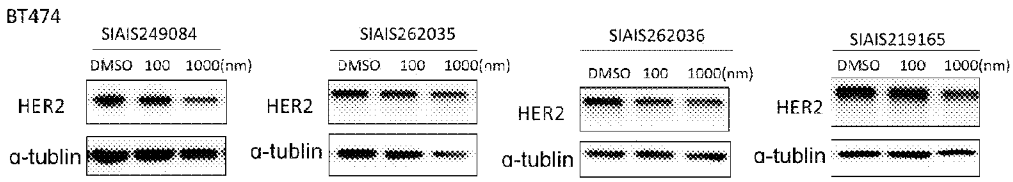
FIG. 6 shows the study of the compounds of the present invention on breast cancer cell line (BT474 cell line).

Meanwhile, the HER2 levels in BT474 cells treated with the compounds of the present invention were determined and the results indicated that these compounds of the present invention have the ability of HER2 degradation at high concentrations (FIG. 6).

TABLE 10

The $IC_{50}$ values of Canertinib-based PROTAD compounds of the present invention on the lung adenocarcinoma cell lines (half inhibitory cencerntration)

| Cell line | Compounds | $IC_{50}$ (nM) |
|---|---|---|
| BT474 | poziotinib | <0.1 |
| BT474 | SIAIS219149 | 81.2 |
| BT474 | SIAIS219165 | 2.7 |
| BT474 | SIAIS219177 | 35.9 |
| BT474 | SIAIS249015 | 87.0 |
| BT474 | Caneri tinib | 17.5 |
| BT474 | SIAIS249092 | 1.2 |
| BT474 | SIAIS249099 | 35.6 |
| BT474 | SIAIS249102 | 3.8 |
| BT474 | SIAIS262121 | 5.3 |
| BT474 | SIAIS262122 | 48.0 |
| BT474 | SIAIS262123 | 48.9 |
| BT474 | SIAIS262124 | 16.4 |
| BT474 | SIAIS262125 | 9.6 |
| BT474 | SIAIS262126 | 17.6 |
| BT474 | SIAIS262128 | 42.1 |
| BT474 | SIAIS262131 | 5.1 |
| BT474 | SIAIS262182 | 5.0 |
| BT474 | Canertinib B | NA |
| BT474 | SIAIS249153 | 15.3 |
| BT474 | SIAIS262174 | 28.2 |
| BT474 | SIAIS262175 | 22.5 |
| BT474 | SIAIS262176 | 1.4 |

TABLE 10-continued

The $IC_{50}$ values of Canertinib-based PROTAD compounds of the present invention on the lung adenocarcinoma cell lines (half inhibitory cencerntration)

| Cell line | Compounds | $IC_{50}$ (nM) |
|---|---|---|
| BT474 | SIAIS262177 | 8.2 |
| BT474 | SIAIS262178 | 2.1 |
| BT474 | SIAIS262179 | 14.6 |
| BT474 | SIAIS262180 | 4.4 |
| BT474 | SIAIS262183 | 11.9 |
| BT474 | Dacomitinib derivative SIAIS262021 | 32.6 |
| BT474 | SIAIS262033 | 0.7 |
| BT474 | SIAIS262035 | 2.1 |
| BT474 | SIAIS262036 | 0.3 |
| BT474 | SIAIS262037 | 0.9 |
| BT474 | SIAIS249077 | 12.35 |
| BT474 | SIAIS249082 | 52.48 |
| BT474 | SIAIS249083 | 64.93 |
| BT474 | SIAIS249084 | 6.077 |
| BT474 | SIAIS249085 | 39.29 |
| BT474 | SIAIS262113 | 67.72 |
| BT474 | SIAIS262114 | 89.98 |
| BT474 | SIAIS262115 | 33.66 |
| BT474 | SIAIS262116 | 82.99 |
| BT474 | SIAIS262117 | 483.7 |
| BT474 | SIAIS262118 | 63.16 |
| BT474 | SIAIS262064 | 1.846 |
| BT474 | SIAIS337024 | 51.46 |

NA: Not available

In summary, the PROTAD compounds of the present invention can effectively overcomes the various shortcomings in the prior small molecular targeted therapy on lung cancers and has high industrial utilization value.

The basic principles, main features and advantages of the present disclosure are shown and described above. Those skilled in the art should understand that the present disclosure is not limited by the foregoing embodiments, and they can make various changes, substitutions and alterations herein without departing from the spirit and scope of the present disclosure. These changes, substitutions and alterations fall within the scope of the present disclosure. The claimed scope of the present disclosure is defined by the appended claims and their equivalents.

The invention claimed is:

1. A bifunctional compound of Formula I,

Formula I

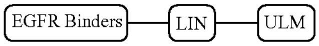

or a pharmaceutically acceptable salt, an isomer, or a solvate thereof, wherein the isomer is selected from: enantiomers, diastereisomers, or cis-trans isomers, wherein:

(i) the EGFR Binders represents a group shown by the following formula:

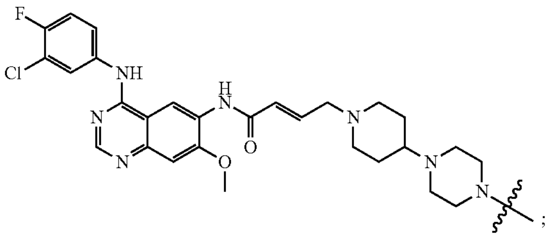 [SMILES: *N1CCN(C2CCN(C/C=C/C(=O)Nc3cc4c(Nc5ccc(F)c(Cl)c5)ncnc4cc3OC)CC2)CC1]

ULM represents:

Formula II

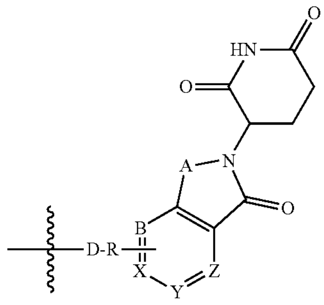

wherein A represents —$CH_2$— or —(C═O)—;

B, X, Y, and Z each independently represent CH;

R represents —S—, —$CH_2$—, —NH—, —O— or ethynylene;

D is absent; and

LIN represents a linking group covalently bonded to the EGFR Binders and ULM, and represents: —W—$(CH_2)_2$—, —W—$(CH_2)_3$—, —W—$(CH_2)_4$—, —W—$(CH_2)_5$—, —W—$(CH_2)_6$—, —W—$(CH_2)_7$—, —W—$(CH_2)_8$—, —W—$(CH_2)_9$—, —W—$(CH_2)_{10}$—, —W—$(CH_2)_{11}$—, —W—$(CH_2)_{12}$—, —W—$(CH_2)_{13}$—, —W—$(CH_2)_{14}$—, or —W—$(CH_2)_{15}$—, wherein W represents —(C═O)—, or W is absent;

or (ii) the EGFR Binders represents a group shown by the following formula:

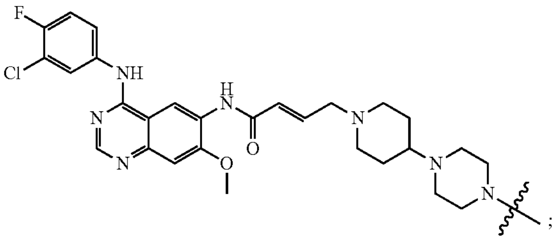 [SMILES: *N1CCN(C2CCN(C/C=C/C(=O)Nc3cc4c(Nc5ccc(F)c(Cl)c5)ncnc4cc3OC)CC2)CC1]

ULM represents:

Formula II

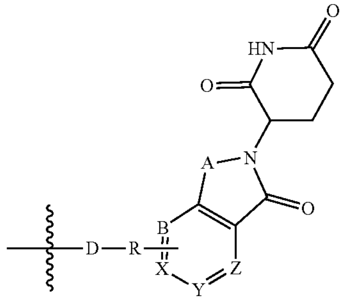

wherein A represents —$CH_2$— or —(C═O)—;

B, X, Y, and Z each independently represent CH;

R represents —S—, —$CH_2$—, —NH—, —O— or ethynylene;

D is absent; and

LIN represents a linking group covalently bonded to the EGFR Binders and ULM, and represents: —$CH_2$-phenylene-$CH_2$—;

or (iii) the EGFR Binders represents a group shown by the following formula:

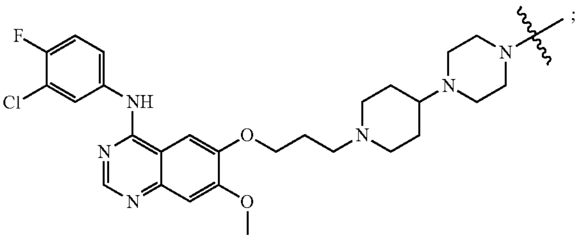 [SMILES: *N1CCN(C2CCN(CCCOc3cc4c(Nc5ccc(F)c(Cl)c5)ncnc4cc3OC)CC2)CC1]

ULM represents:

Formula II

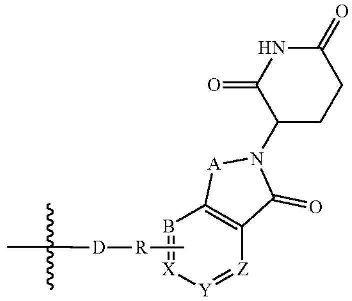

wherein A represents —$CH_2$— or —(C═O)—;

B, X, Y, and Z each independently represent CH;

R represents —S— or ethynylene;

D is absent; and

LIN represents a linking group covalently bonded to the EGFR Binders and ULM, and represents: —W—$(CH_2)_2$—, —W—$(CH_2)_3$—, —W—$(CH_2)_4$—, —W—$(CH_2)_5$—, —W—$(CH_2)_6$—, —W—$(CH_2)_7$—, —W—$(CH_2)_8$—, —W—$(CH_2)_9$—, —W—$(CH_2)_{10}$—, —W—$(CH_2)_{11}$—, —W—$(CH_2)_{12}$—, —W—$(CH_2)_{13}$—, —W—$(CH_2)_{14}$—, or —W—$(CH_2)_{15}$—, wherein W represents —(C═O)—, or W is absent;

or (iv) the EGFR Binders represents a group shown by the following formula:

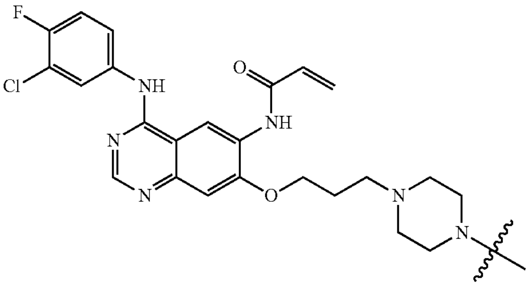

or

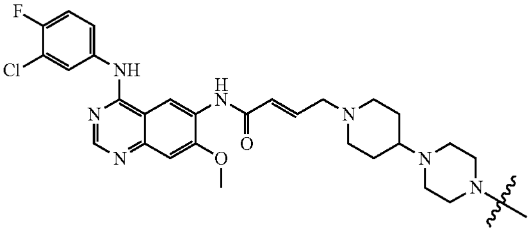

;

ULM represents:

Formula II

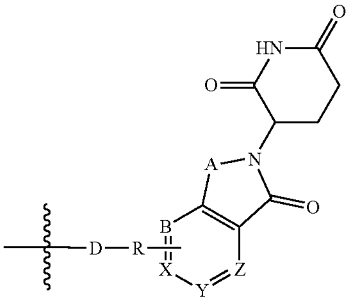

wherein A represents $-CH_2-$ or $-(C{=}O)-$;

B, X, Y, and Z each independently represent CH;

R represents —S—, —NH— or ethynylene;

D is absent; and

LIN represents a linking group covalently bonded to the EGFR Binders and ULM, and represents: $-W-(CH_2)_2-$, $-W-(CH_2)_3-$, $-W-(CH_2)_4-$, $-W-(CH_2)_5-$, $-W-(CH_2)_6-$, $-W-(CH_2)_7-$, $-W-(CH_2)_8-$, $-W-(CH_2)_9-$, $-W-(CH_2)_{10}-$, $-W-(CH_2)_{11}-$, $-W-(CH_2)_{12}-$, $-W-(CH_2)_{13}-$, $-W-(CH_2)_{14}-$, or $-W-(CH_2)_{15}-$, wherein W represents $-(C{=}O)-$, or W is absent.

2. The bifunctional compound of claim 1, or a pharmaceutically acceptable salt, an isomer, or a solvate thereof, wherein the bifunctional compound is a bifunctional compound according to (i), wherein in (i), the ULM represents a group selected from ones shown by the following formulas:

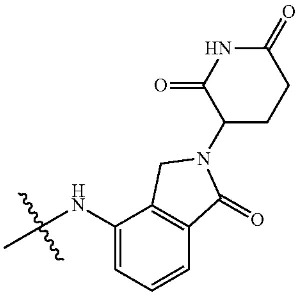

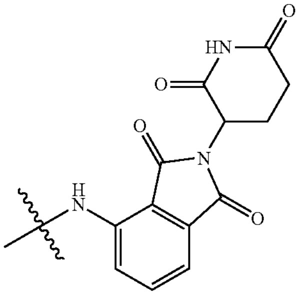

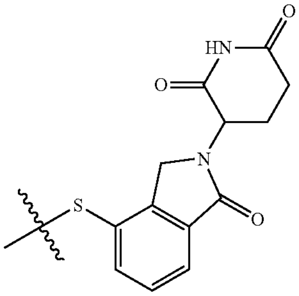

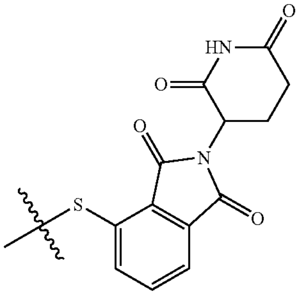

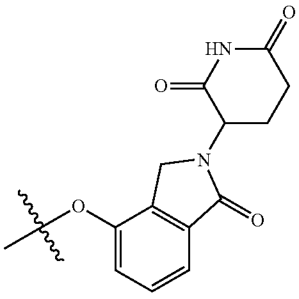

-continued
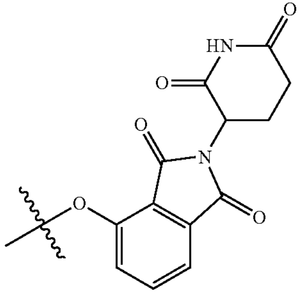
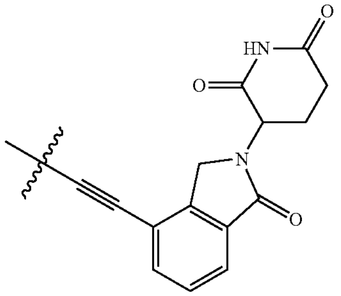
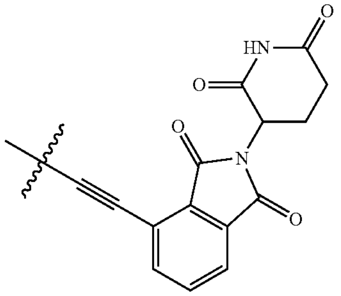
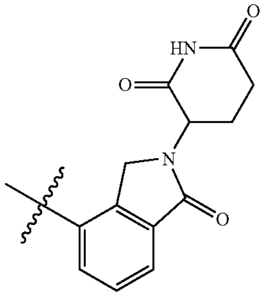
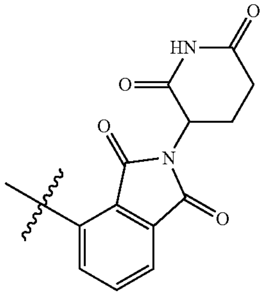
-continued
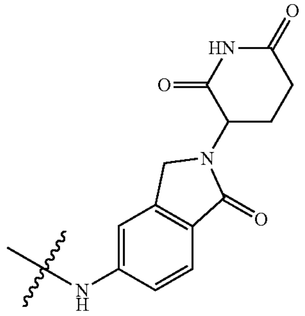
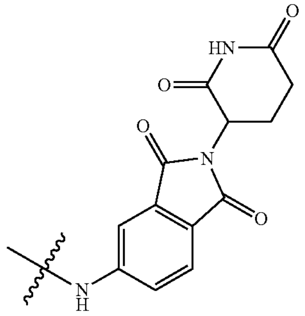
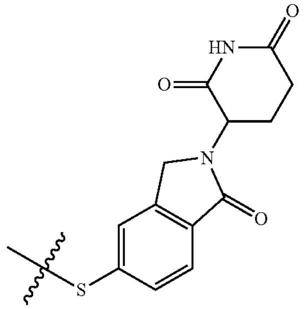
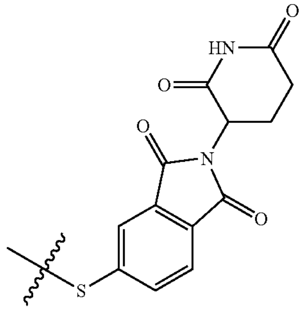
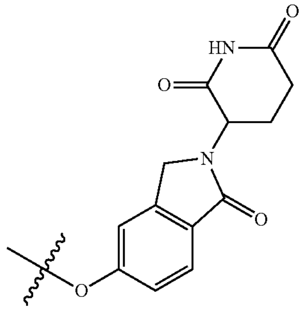

-continued

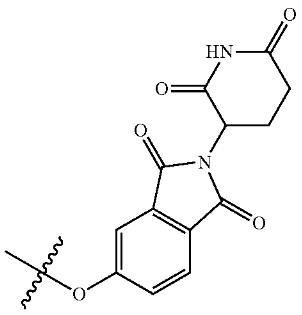

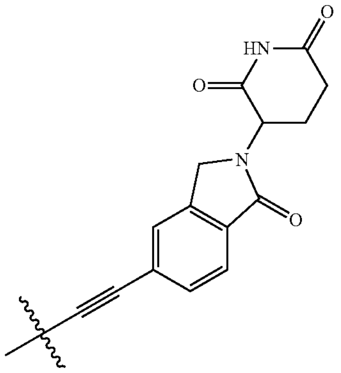

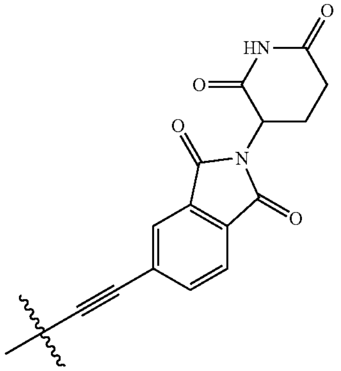

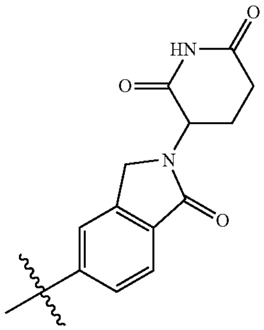

-continued

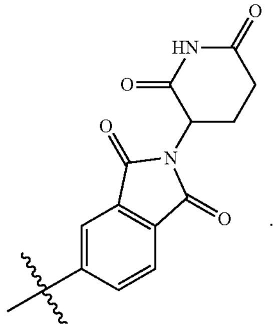

.

3. The bifunctional compound of claim 1, or a pharmaceutically acceptable salt, an isomer, or a solvate thereof, wherein the bifunctional compound is a bifunctional compound according to (ii).

4. The bifunctional compound of claim 3, or a pharmaceutically acceptable salt, an isomer, or a solvate thereof, wherein in (ii), the ULM represents a group selected from ones shown by the following formulas:

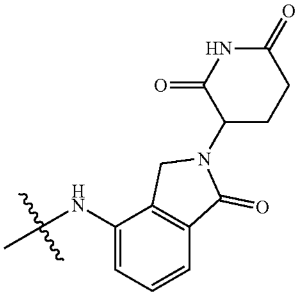

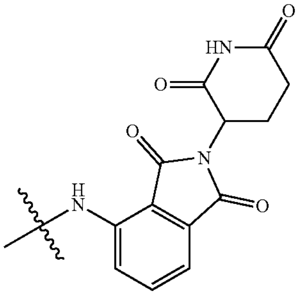

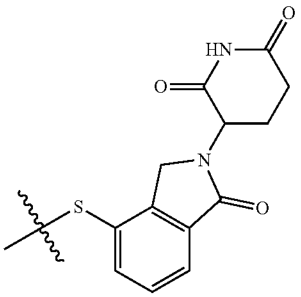

-continued
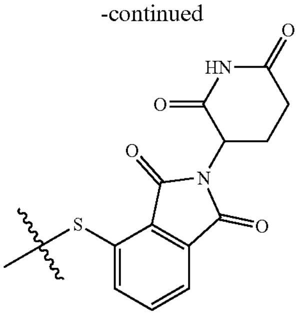
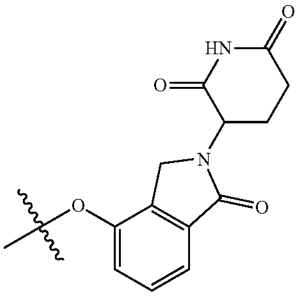
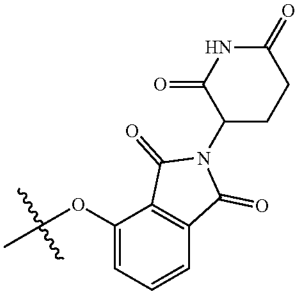
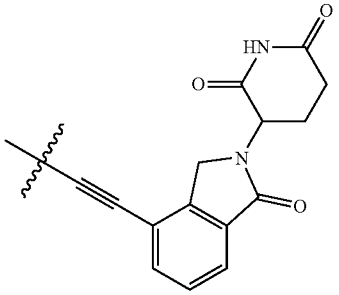
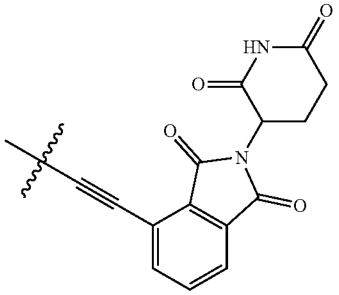
-continued
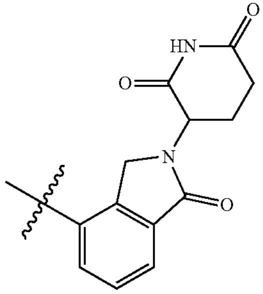
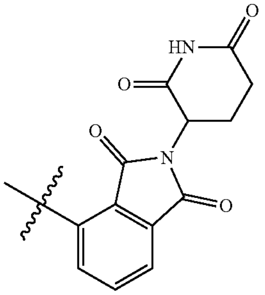
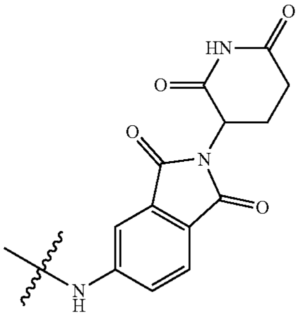
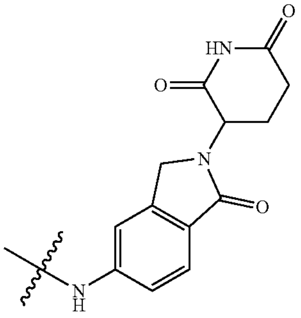
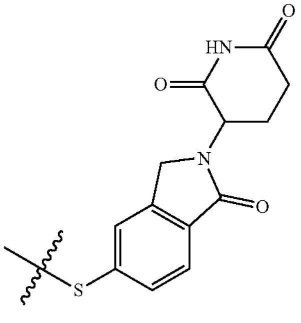
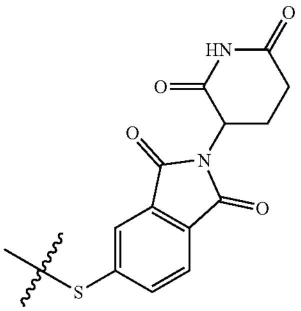

-continued

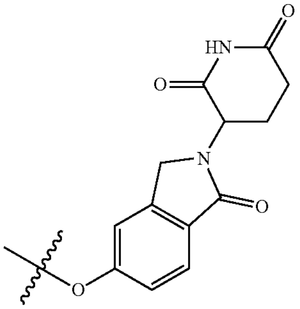

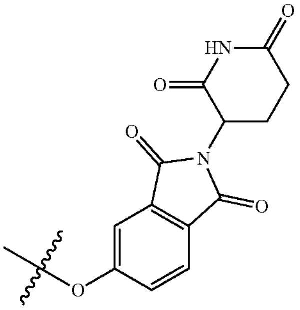

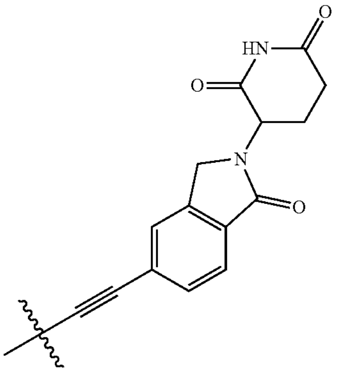

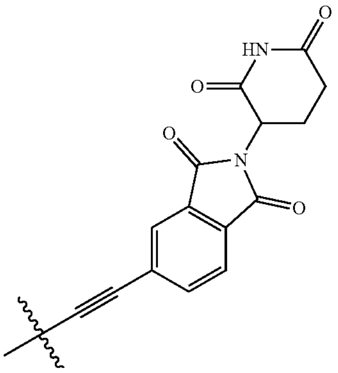

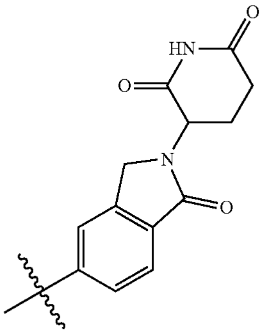

-continued

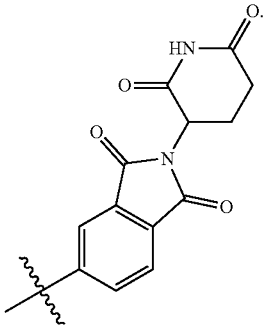

5. The bifunctional compound of claim 1, or a pharmaceutically acceptable salt, an isomer, or a solvate thereof, wherein the bifunctional compound is a bifunctional compound according to (iii).

6. The bifunctional compound of claim 5, or a pharmaceutically acceptable salt, an isomer, or a solvate thereof, wherein in (iii), the ULM represents a group selected from ones shown by the following formulas:

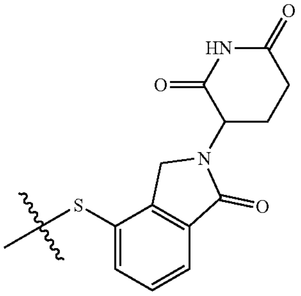

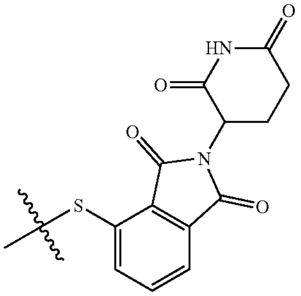

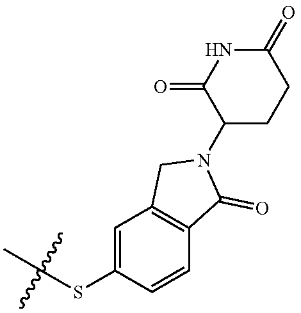

-continued

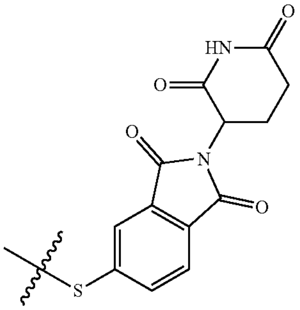

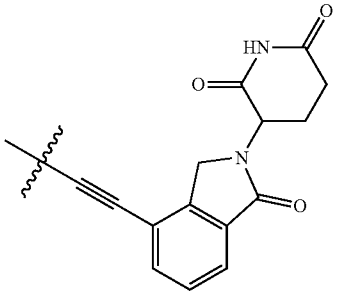

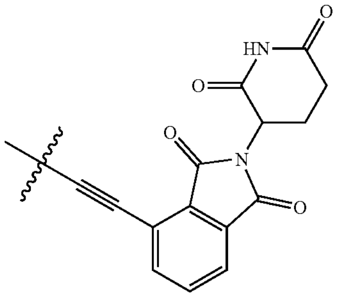

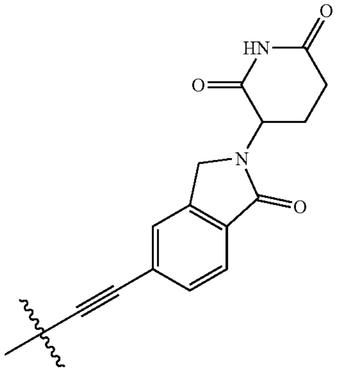

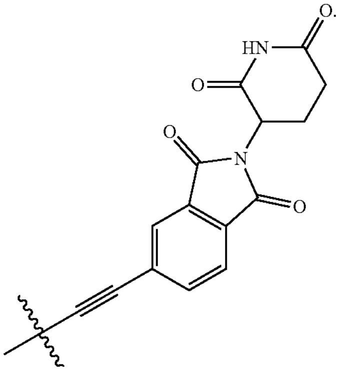

7. The bifunctional compound of claim 1, or a pharmaceutically acceptable salt, an isomer, or a solvate thereof, wherein the bifunctional compound is a bifunctional compound according to (iv).

8. The bifunctional compound of claim 7, or a pharmaceutically acceptable salt, an isomer, or a solvate thereof, wherein in (iv), the ULM represents a group selected from ones shown by the following formulas:

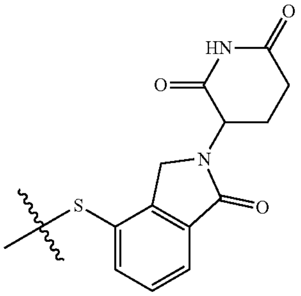

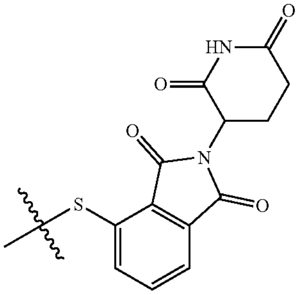

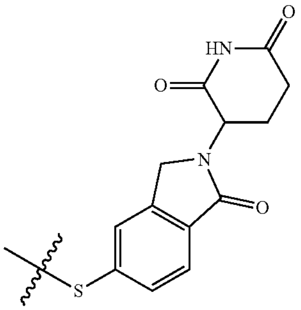

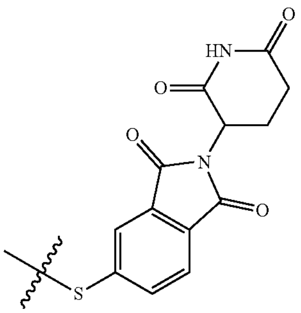

-continued
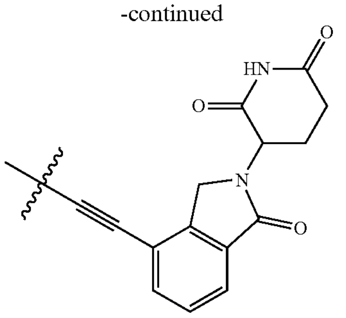
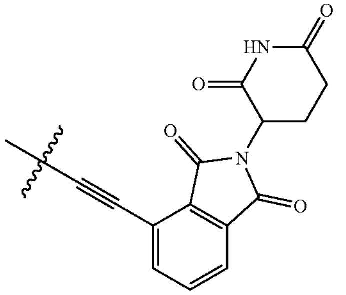
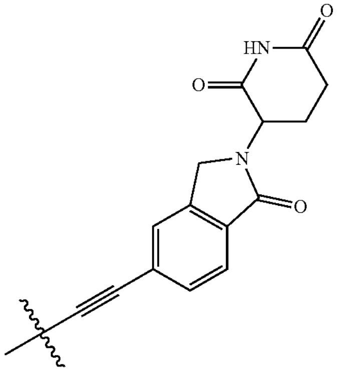
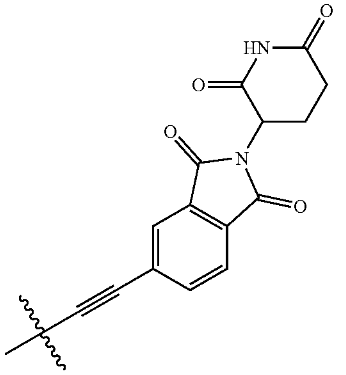
-continued
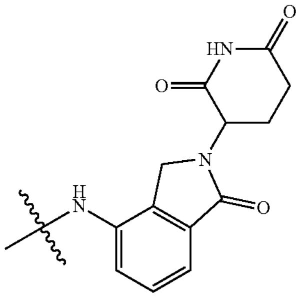
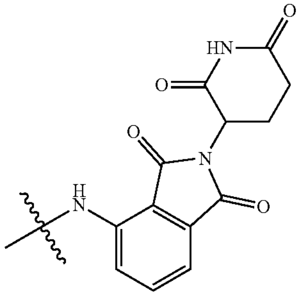
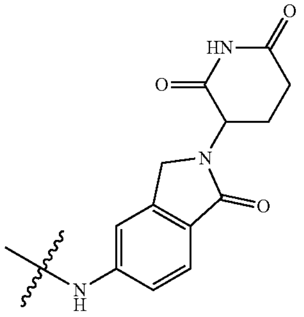
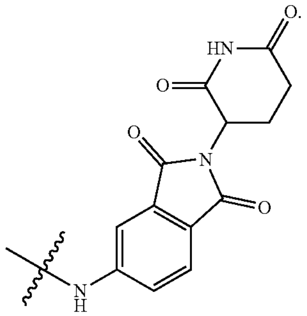 [SMILES: *Nc1ccc2c(c1)C(=O)N(C1CCC(=O)NC1=O)C2=O]
9. The bifunctional compound of claim 1, or a pharmaceutically acceptable salt, an isomer, or a solvate thereof, wherein the bifunctional compound is selected from:
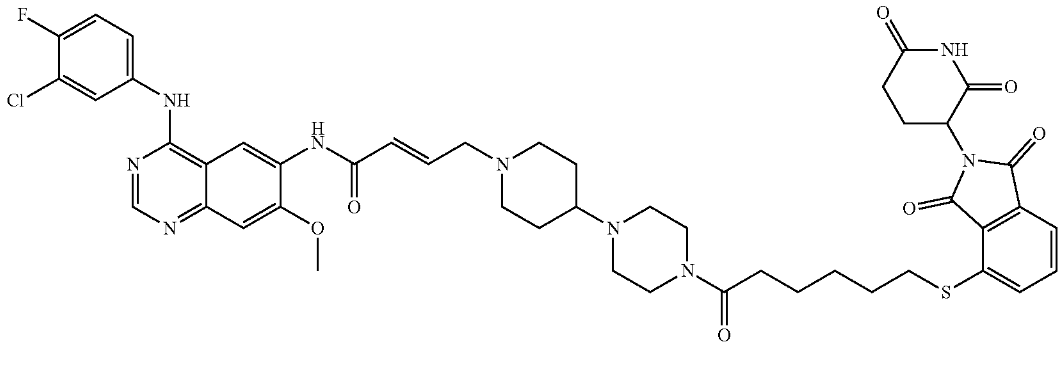

-continued
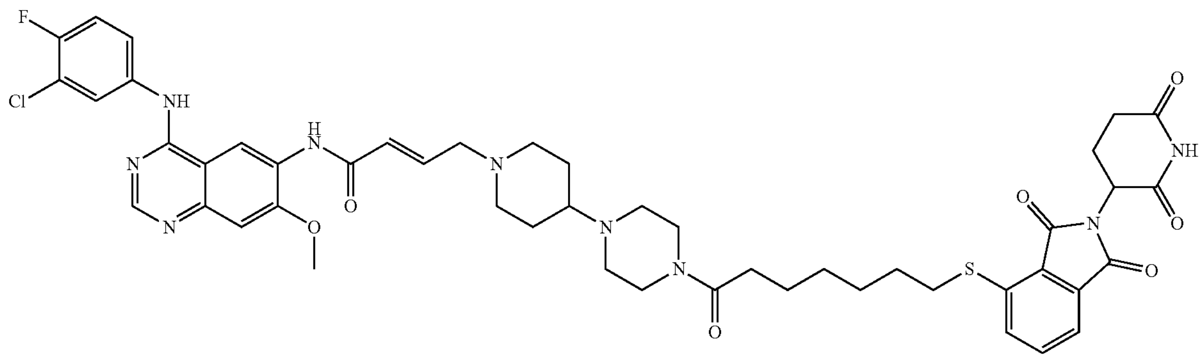
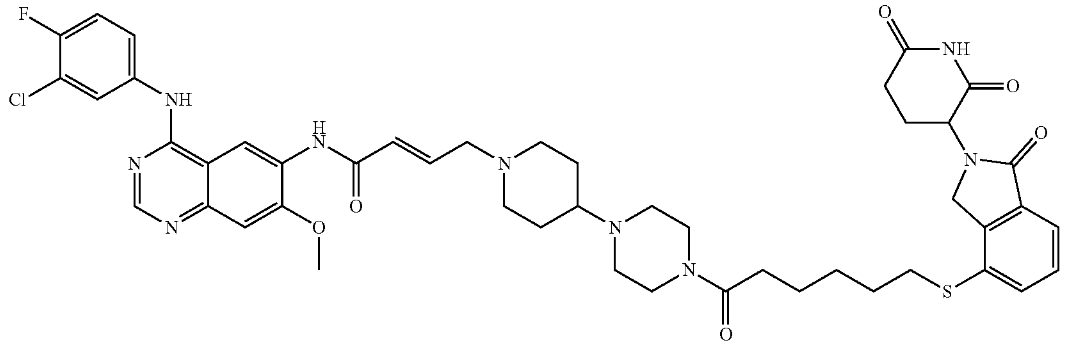
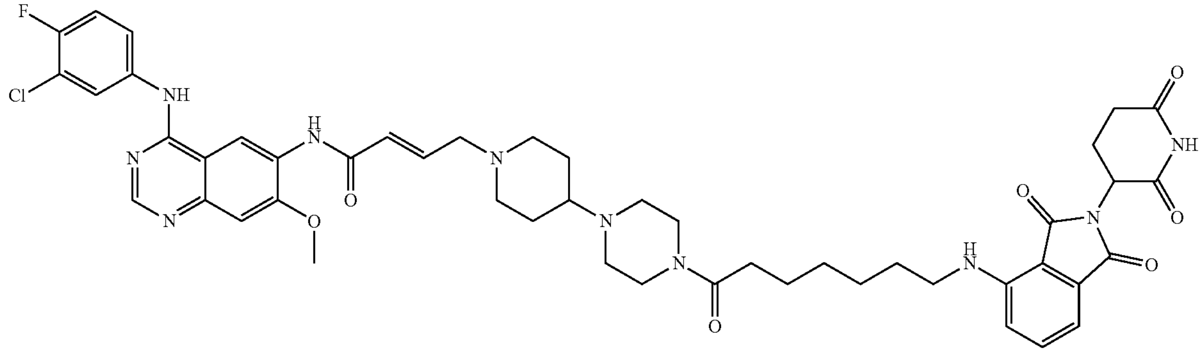
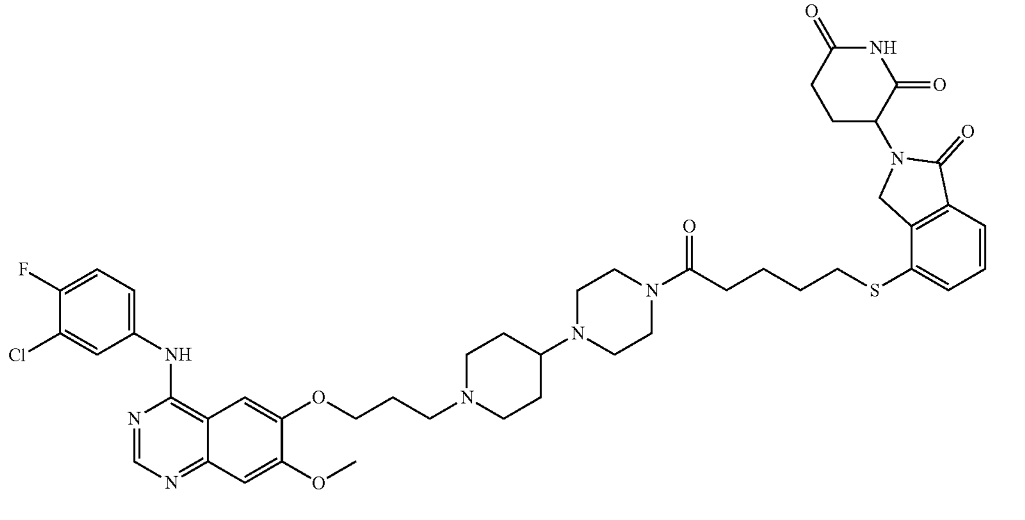

-continued
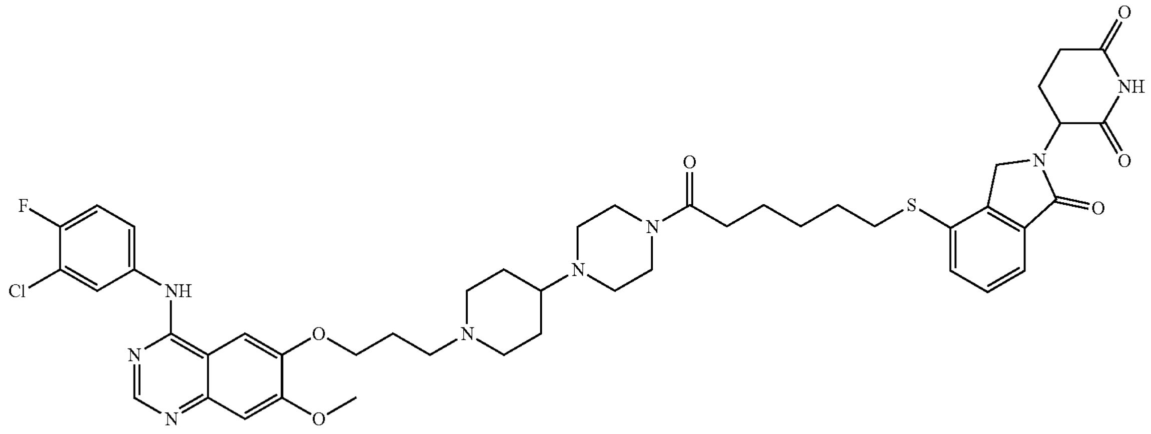
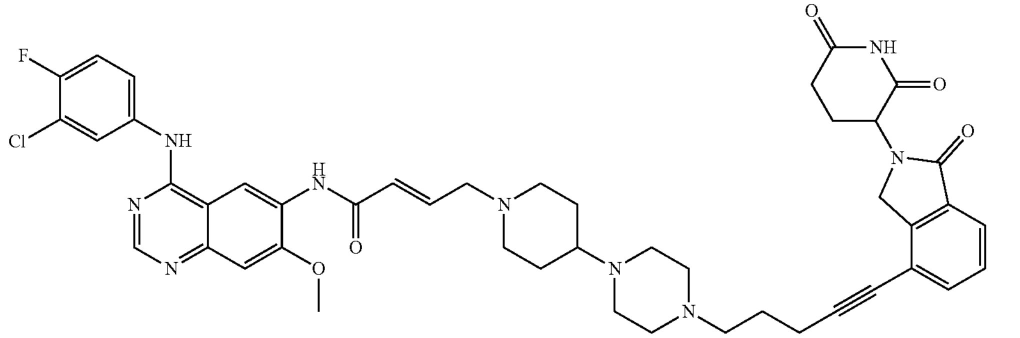
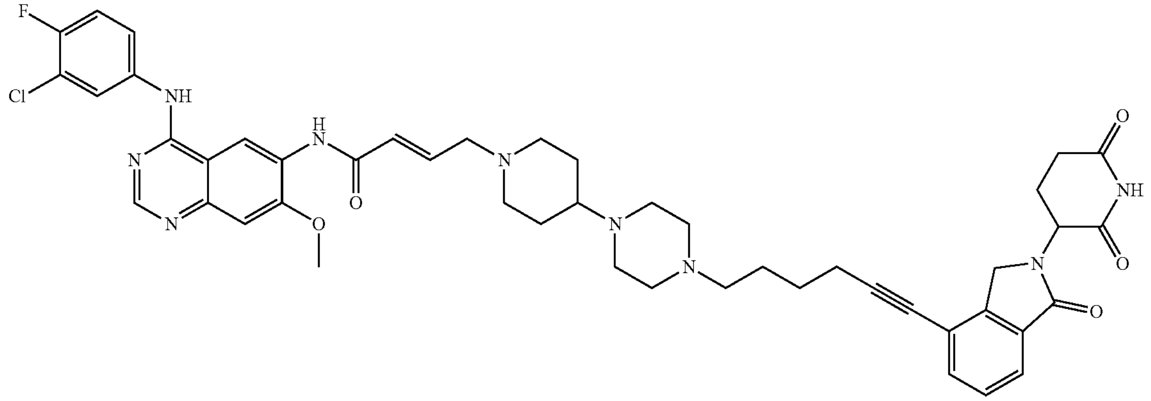
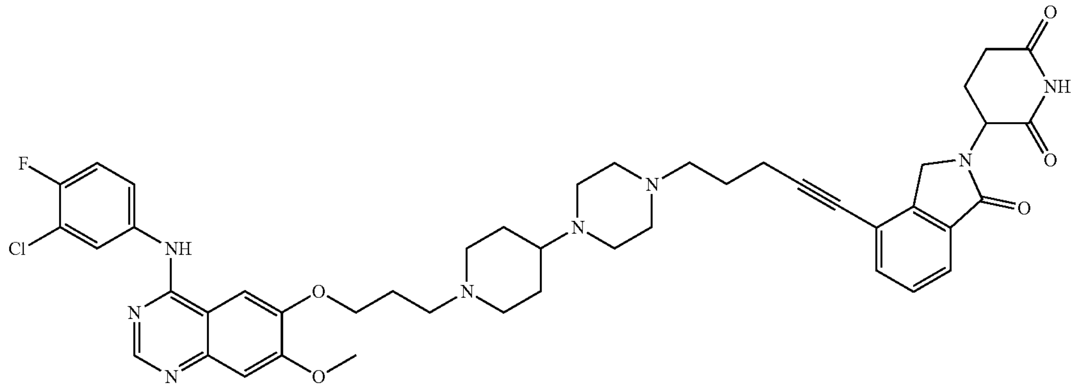

-continued
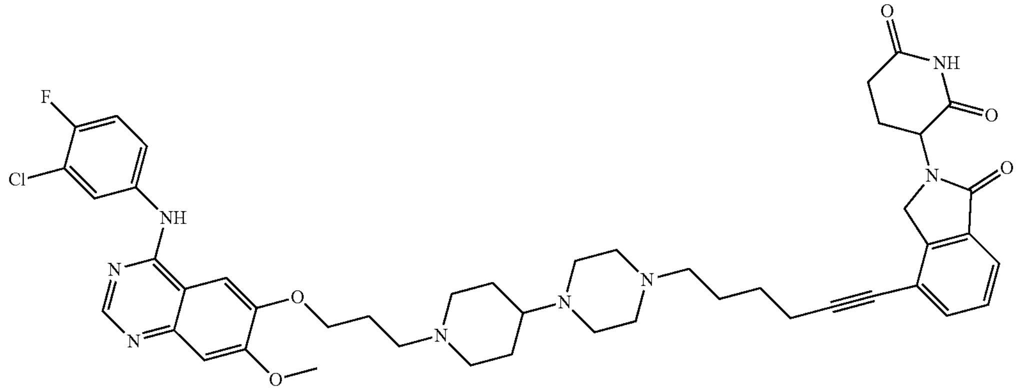
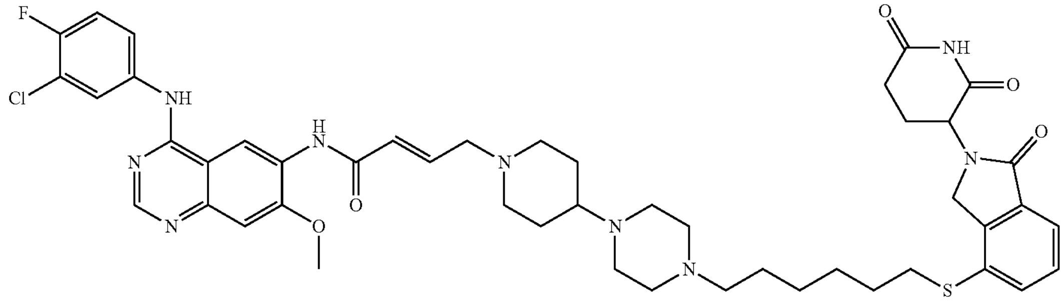
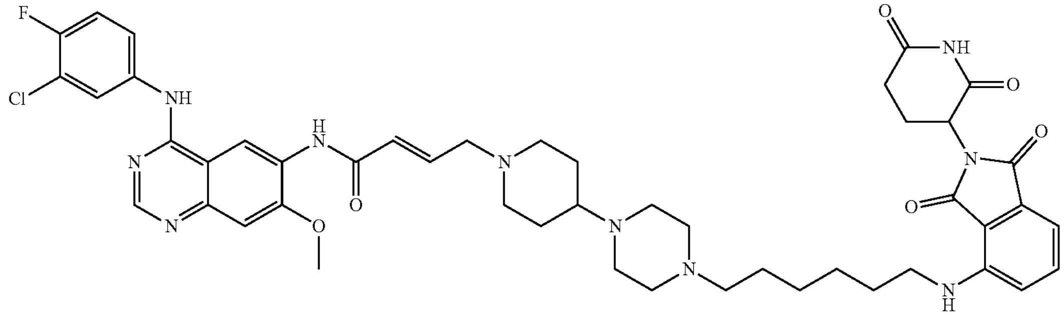
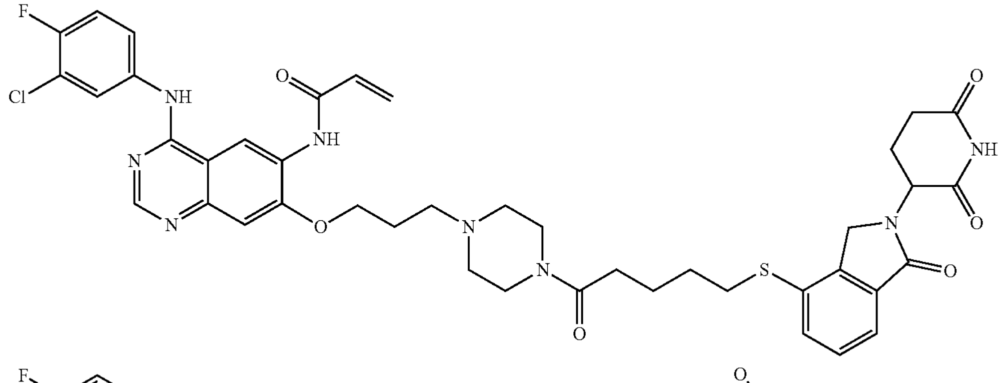
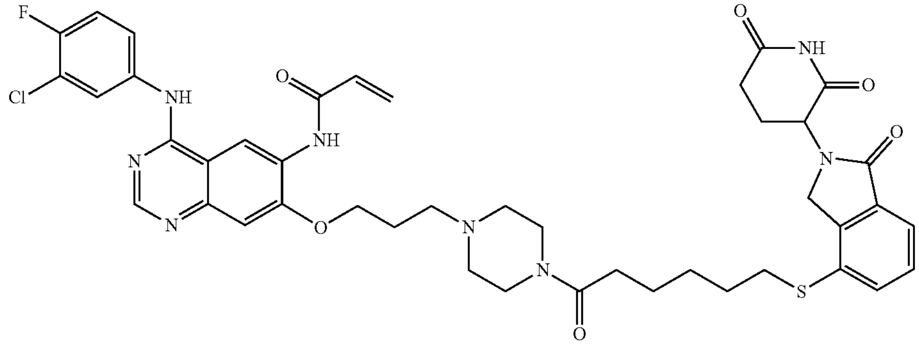

-continued
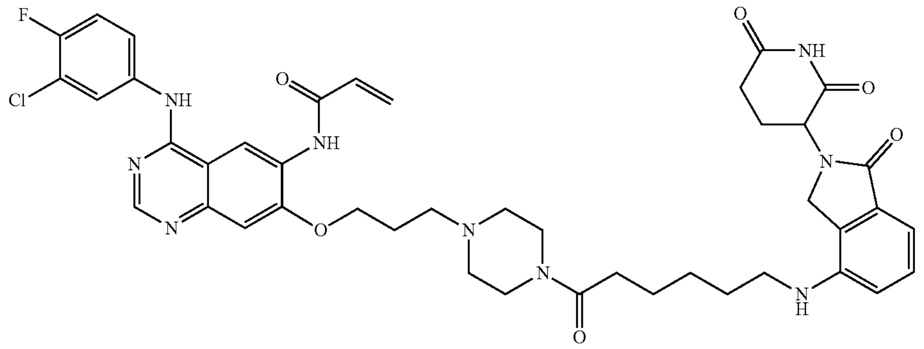
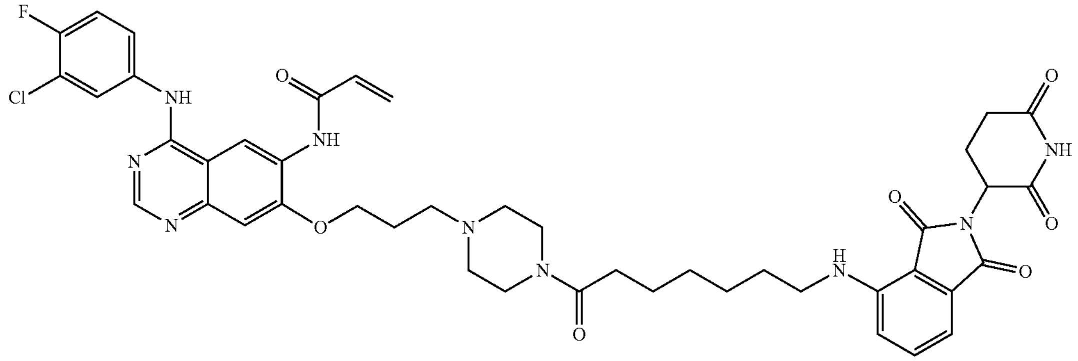
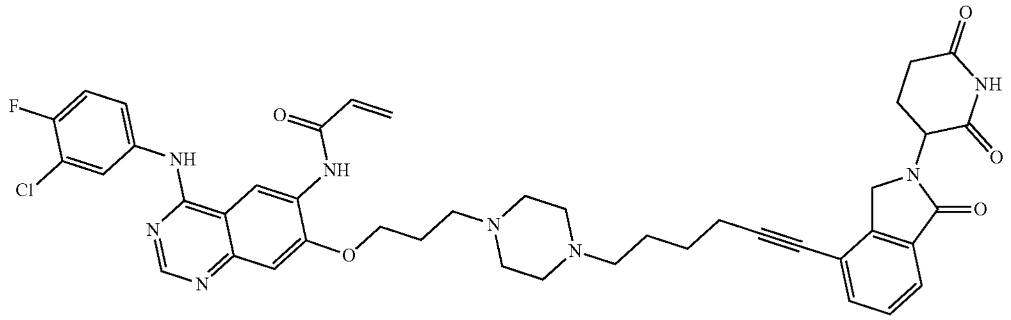
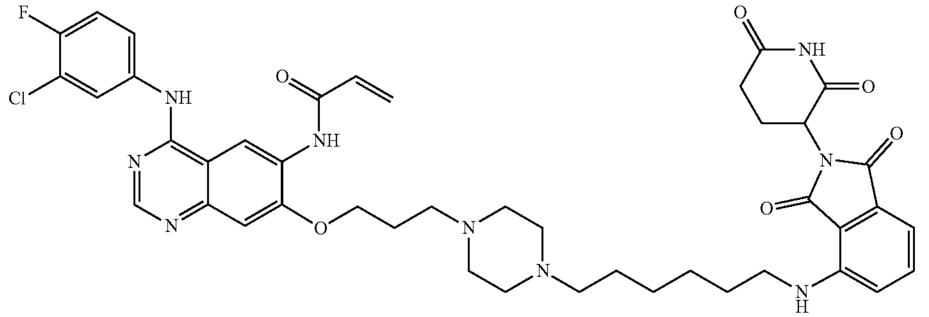
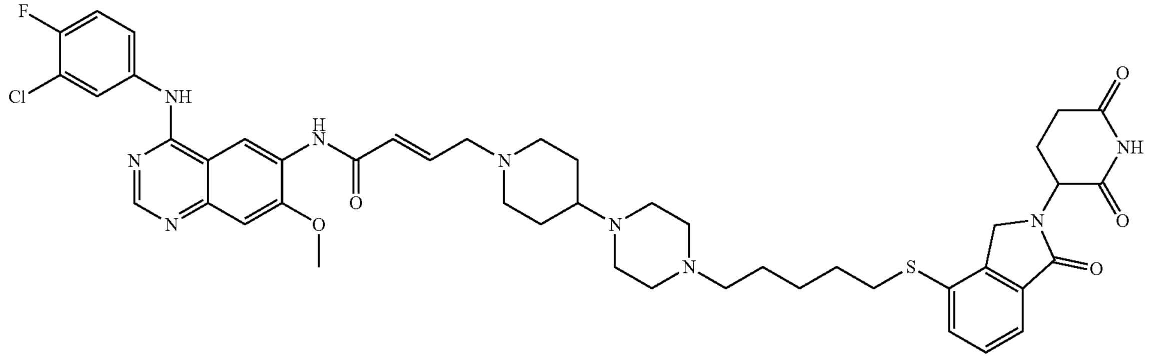

-continued
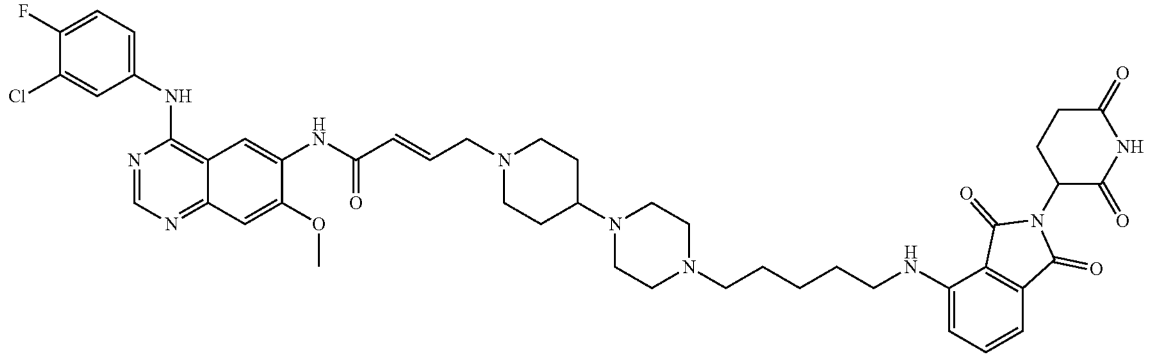
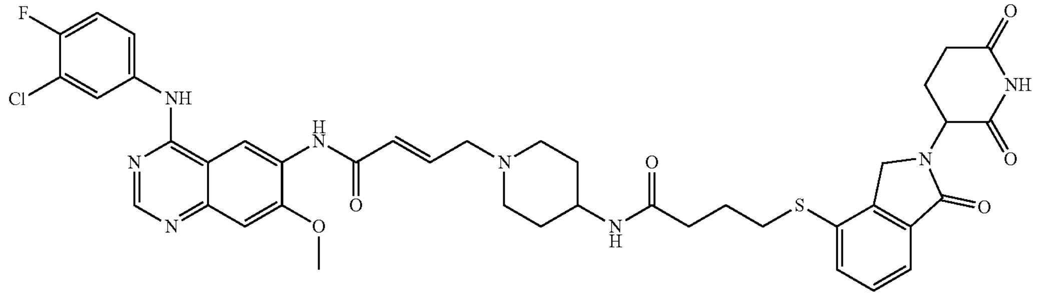
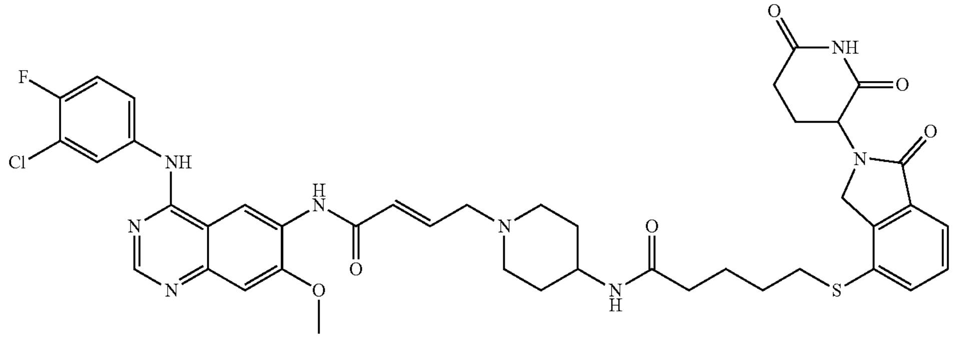
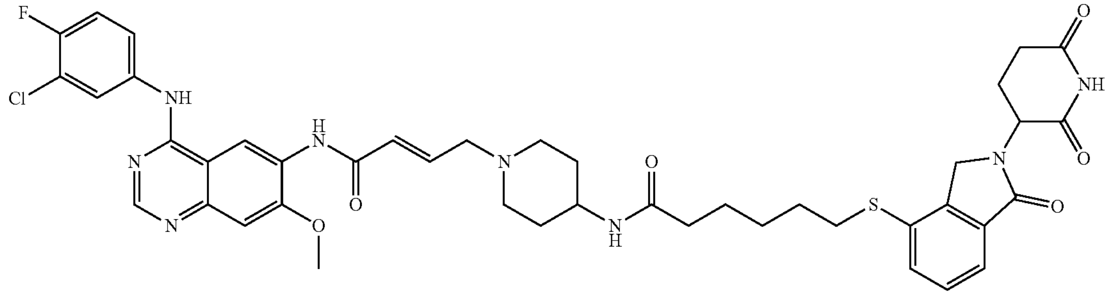
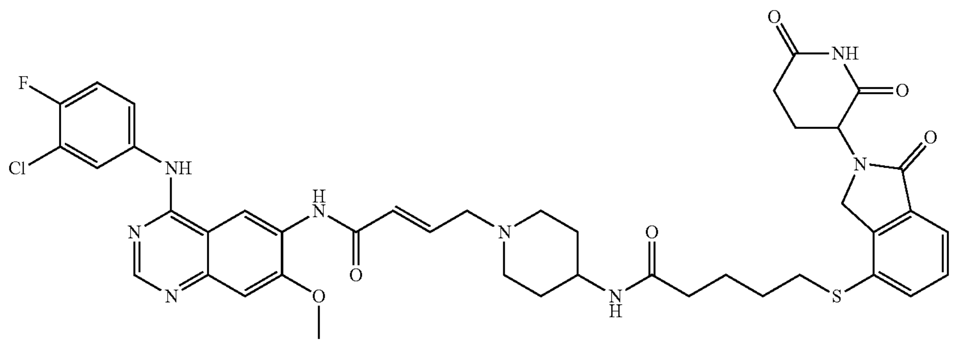

-continued
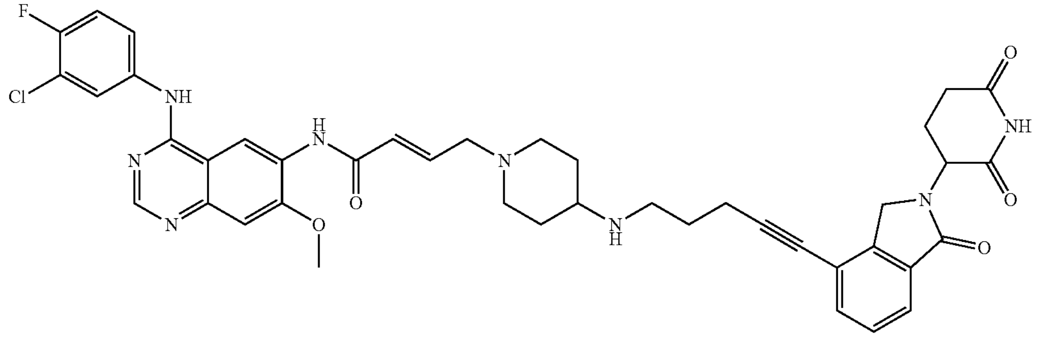
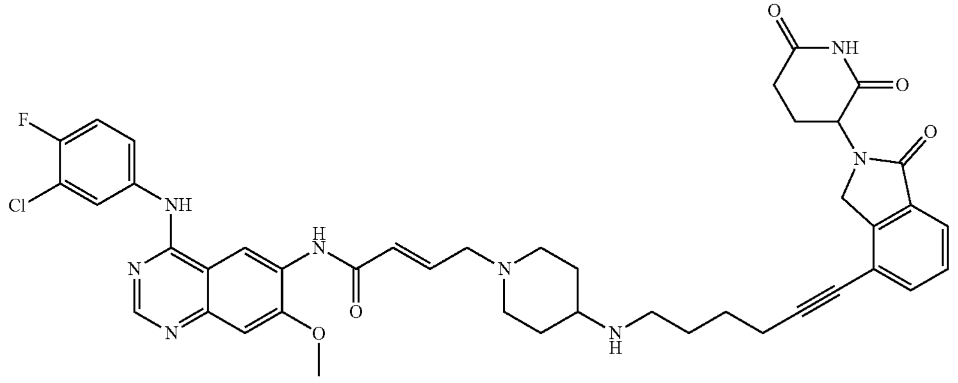
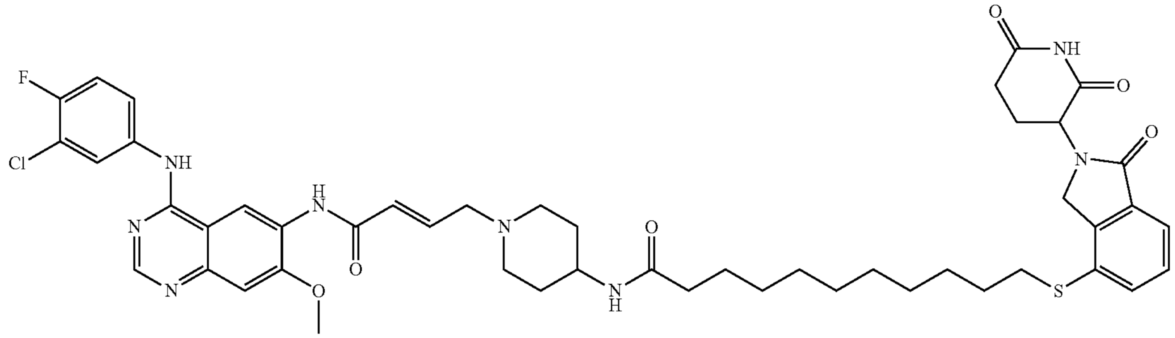
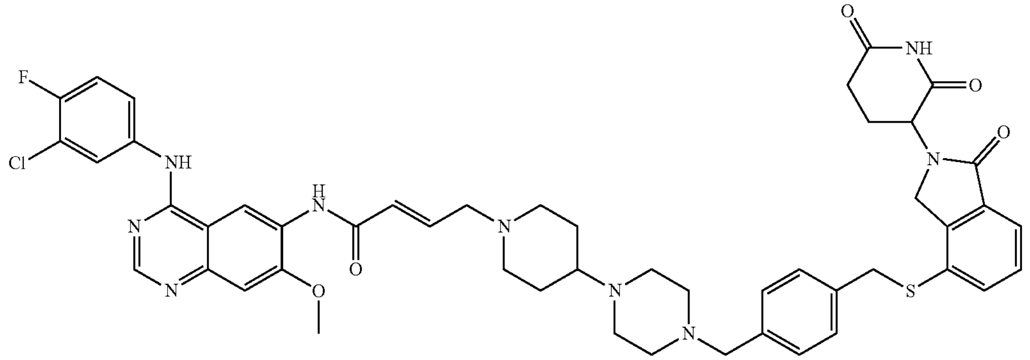

-continued
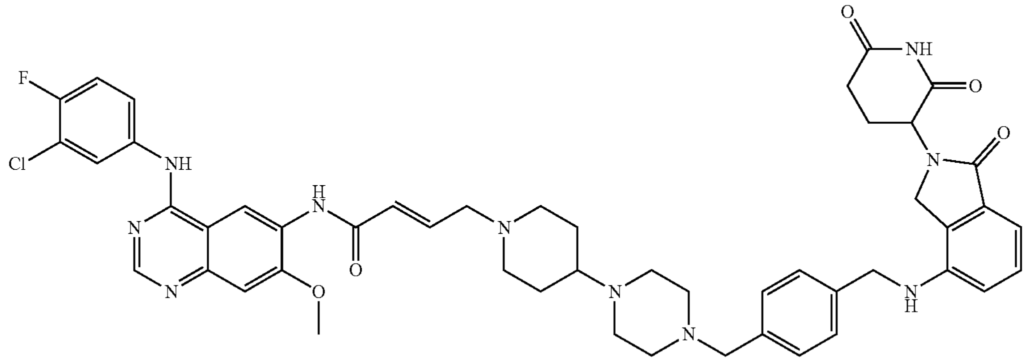
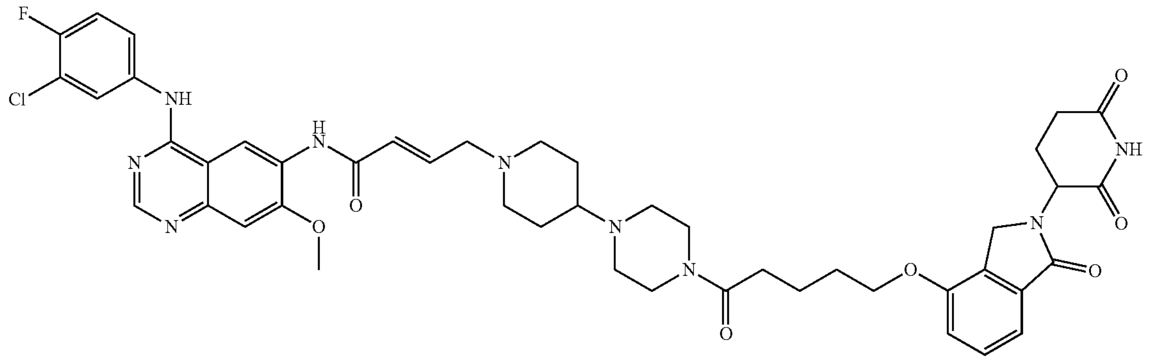
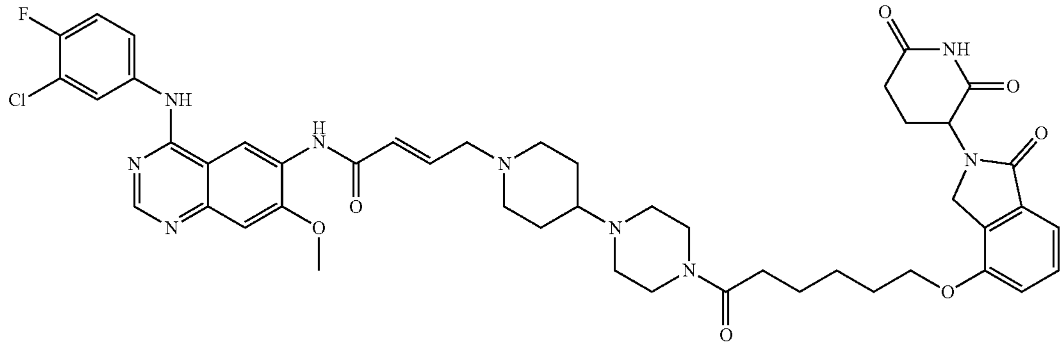
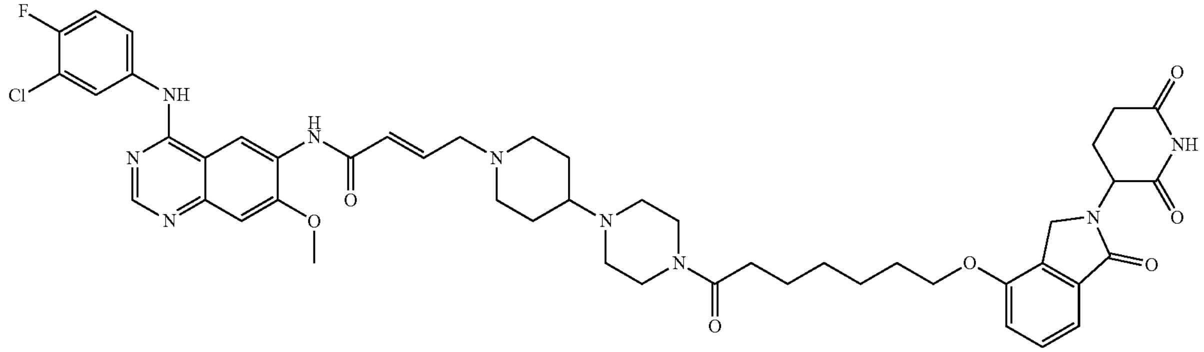
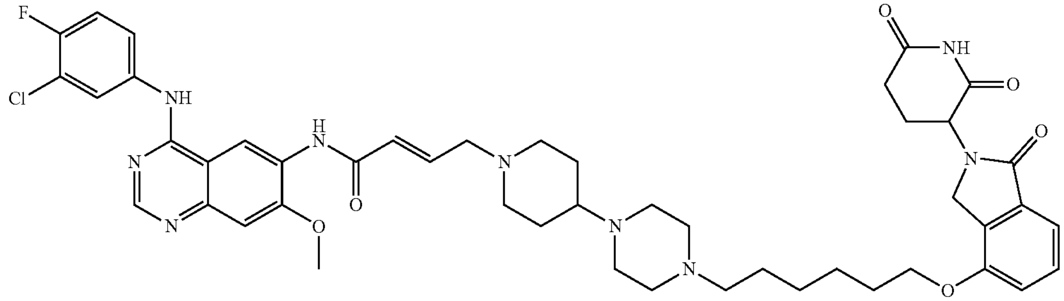

-continued
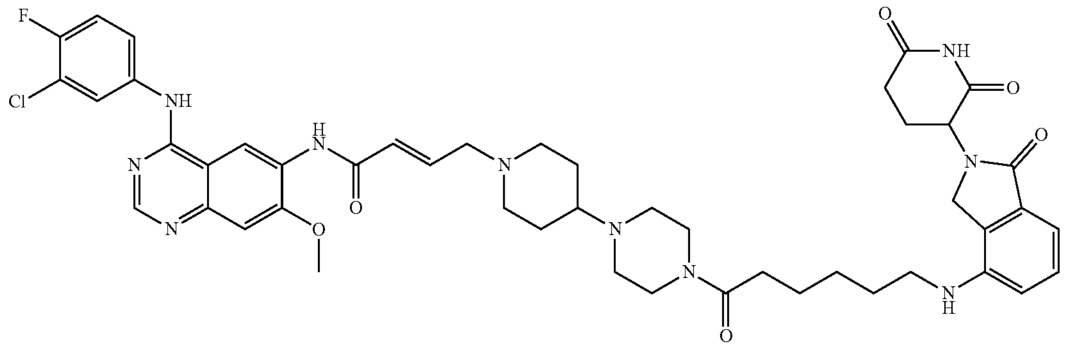
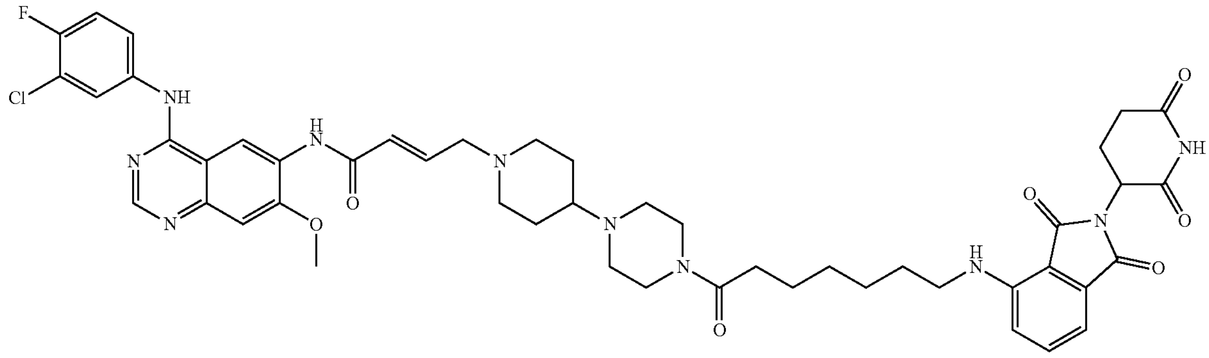
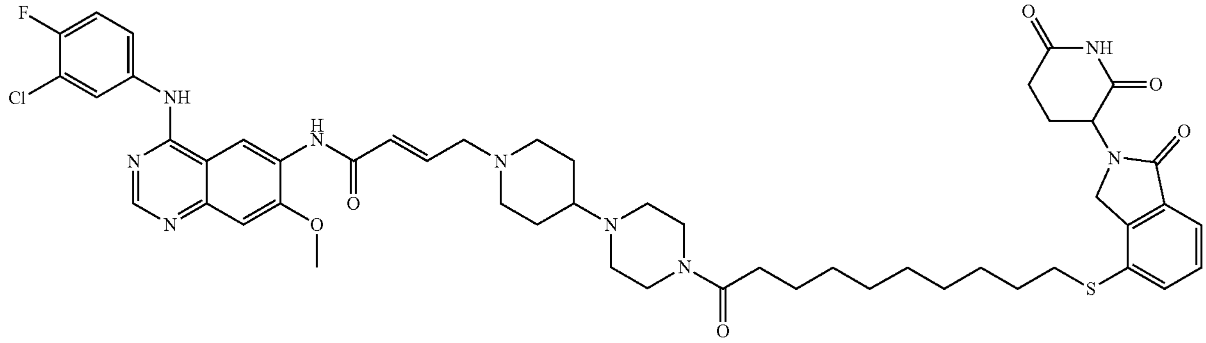
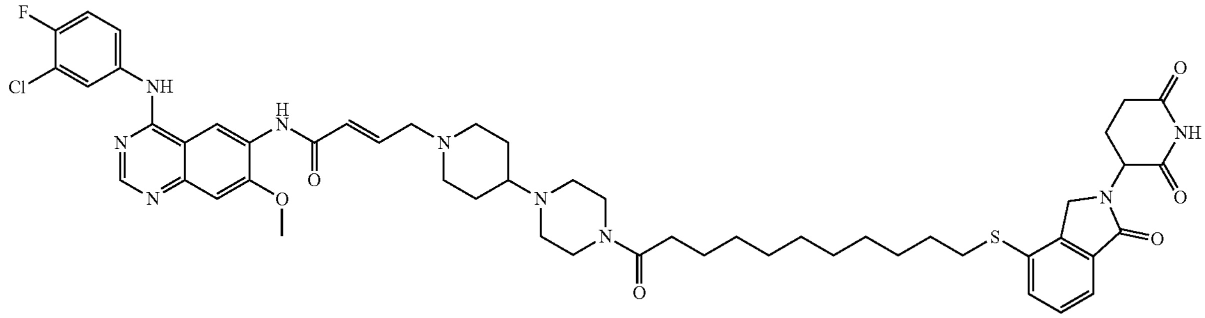
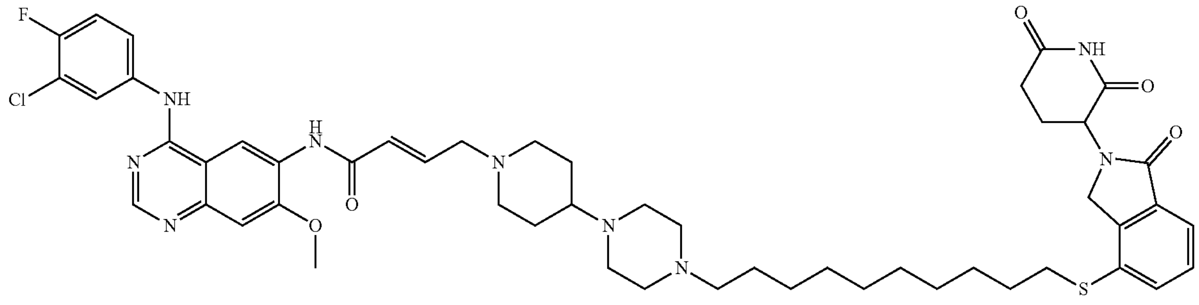

-continued
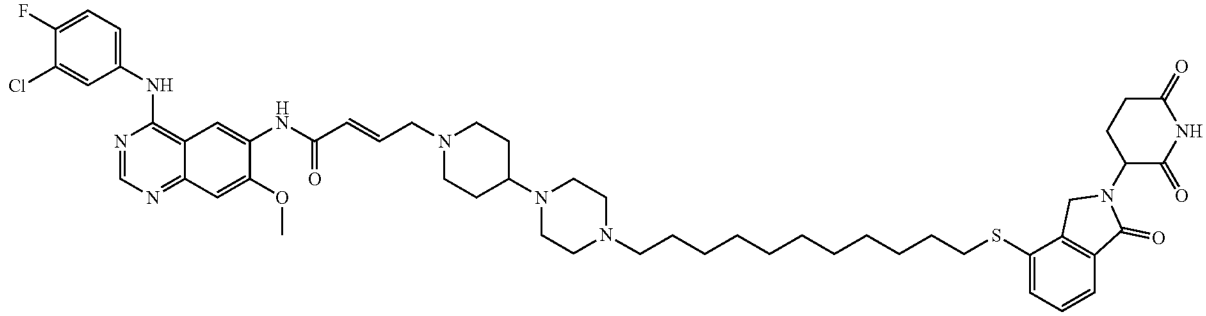
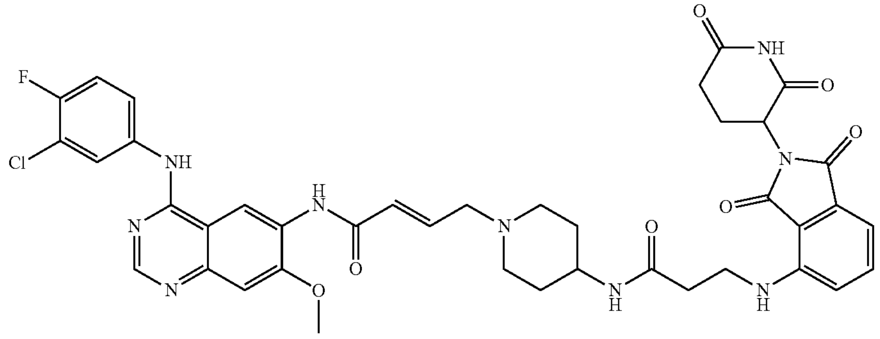
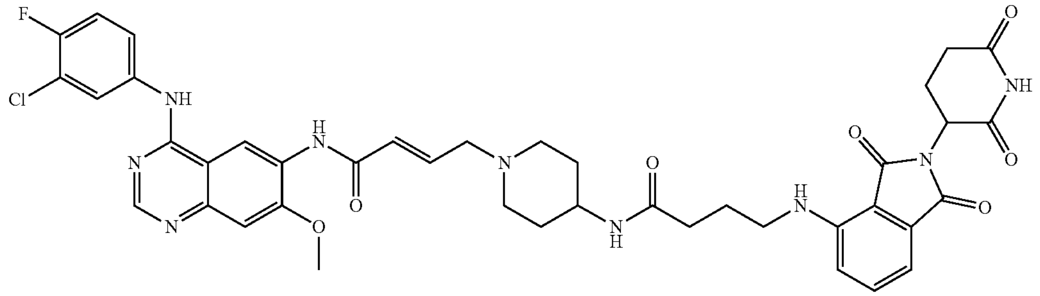
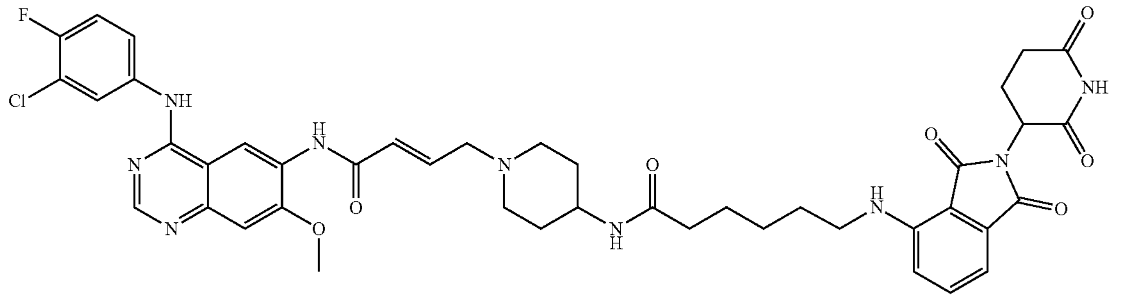
and
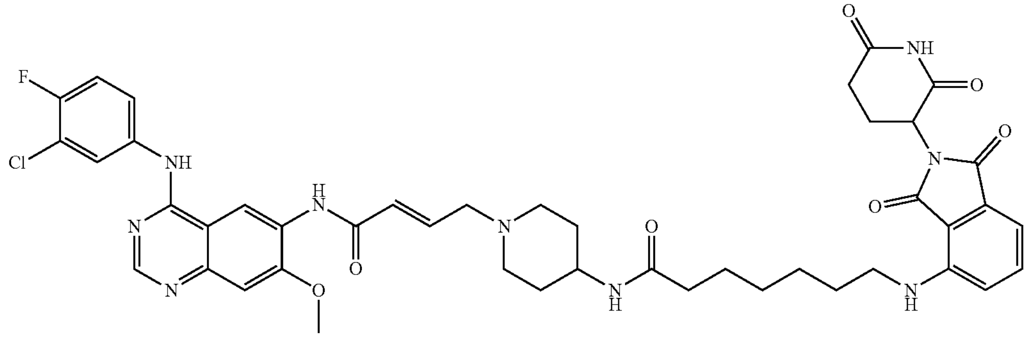
.

10. The bifunctional compound of claim 1, or a pharmaceutically acceptable salt, an isomer, or a solvate thereof, wherein the bifunctional compound is a bifunctional compound according to (i).

11. A pharmaceutical composition comprising the bifunctional compound of claim 1 or a pharmaceutically acceptable salt, an isomer, or a solvate thereof, and at least one pharmaceutically acceptable carrier, an additive, an adjuvant, or an excipient.

12. A method for regulating epidermal growth factor receptor (EGFR) and/or its mutants, comprising administering to an individual a therapeutically effective amount of the bifunctional compound of claim 1 or a pharmaceutically acceptable salt thereof, or a pharmaceutical composition comprising the bifunctional compound or pharmaceutically acceptable salt thereof.

13. A method for treating receptor tyrosine kinase (RTK)-associated diseases, comprising administering to an individual a therapeutically effective amount of the bifunctional compound of claim 1 or a pharmaceutically acceptable salt thereof, or a pharmaceutical composition comprising the bifunctional compound or pharmaceutically acceptable salt thereof.

14. A method for treating EGFR-dependent associated diseases, comprising administering to an individual a therapeutically effective amount of the bifunctional compound of claim 1 for a pharmaceutically acceptable salt thereof, or a pharmaceutical composition comprising the bifunctional compound or pharmaceutically acceptable salt thereof.

15. A method for treating one or more diseases selected from tumors, myeloid tumors, or solid tumors, cancers, leukemia, lymphoma, colorectal cancer, brain cancer, bone cancer, epithelial cell-derived tumors (epithelial cancers), basal cell carcinoma, adenocarcinoma, gastrointestinal cancer, lip cancer, oral cancer, esophageal cancer, small intestine cancer, gastric cancer, colon cancer, liver cancer, bladder cancer, pancreatic cancer, ovarian cancer, cervical cancer, lung cancer, breast cancer, skin cancer, squamous cell and/or basal cell carcinoma, prostate cancer, glioma, glioblastoma, renal cell carcinoma and other cancers known to affect systemic epithelial cells, chronic granulocytic leukemia (CML), acute myeloid leukemia (AML) and acute promyelocytic leukemia (APL), comprising administering to an individual a therapeutically effective amount of the bifunctional compound or a pharmaceutically acceptable salt thereof of claim 1, or a pharmaceutical composition comprising the bifunctional compound or pharmaceutically acceptable salt thereof.

16. The method of claim 14, wherein the EGFR-dependent associated diseases are EGFR overexpression- or high EGFR activity-associated diseases.

* * * * *